US011224364B2

(12) United States Patent
Jones et al.

(10) Patent No.: US 11,224,364 B2
(45) Date of Patent: Jan. 18, 2022

(54) INGESTIBLE DEVICE AND ASSOCIATED METHODS

(71) Applicant: Progenity Inc., San Diego, CA (US)

(72) Inventors: Ryan Elliott Jones, Providenciales (TC); Hamilton Roger Tang, Los Altos, CA (US); Rachel Ellen Gerver, Oakland, CA (US); Mitchell Lawrence Jones, La Jolla, CA (US)

(73) Assignee: Progenity, Inc., San Diego, CA (US)

( * ) Notice: Subject to any disclaimer, the term of this patent is extended or adjusted under 35 U.S.C. 154(b) by 507 days.

(21) Appl. No.: 15/844,427

(22) Filed: Dec. 15, 2017

(65) Prior Publication Data

US 2018/0168490 A1 Jun. 21, 2018

Related U.S. Application Data

(60) Provisional application No. 62/572,341, filed on Oct. 13, 2017, provisional application No. 62/570,411, (Continued)

(51) Int. Cl.
A61B 5/1455 (2006.01)
A61B 5/1459 (2006.01)
(Continued)

(52) U.S. Cl.
CPC ........ *A61B 5/1459* (2013.01); *A61B 1/00009* (2013.01); *A61B 1/041* (2013.01); *A61B 1/043* (2013.01); *A61B 5/002* (2013.01); *A61B 5/065* (2013.01); *A61B 5/073* (2013.01); *A61B 5/1455* (2013.01); *A61B 5/14507* (2013.01); *A61B 5/14542* (2013.01); *A61B 5/14546* (2013.01); *A61B 5/14556* (2013.01); *A61B 5/4222* (2013.01); *A61B 5/4255* (2013.01); *A61B 5/4845* (2013.01); *A61B 5/4866* (2013.01); *A61B 5/6861* (2013.01); *A61B 5/7257* (2013.01); *A61B 5/7275* (2013.01); *A61B 5/7282* (2013.01); *A61B 5/742* (2013.01); *A61M 31/005* (2013.01); *A61B 5/0071* (2013.01); *A61B 5/0075* (2013.01); *A61B 5/024* (2013.01); *A61B 5/0531* (2013.01); *A61B 5/1126* (2013.01); (Continued)

(58) Field of Classification Search
None
See application file for complete search history.

(56) References Cited

U.S. PATENT DOCUMENTS 7,460,896 B2 * 12/2008 Iddan .................... A61B 1/041
600/339
2002/0128559 A1 9/2002 Zigler
(Continued)

OTHER PUBLICATIONS

Ankri et al., "New optical method for enhanced detection of colon cancer by capsule endoscopy", Nanoscale, vol. 5, No. 20, p. 9806, 2013.
(Continued)

*Primary Examiner* — Marjan Fardanesh
(74) *Attorney, Agent, or Firm* — Procopio Cory Hargreaves and Savitch LLP

(57) ABSTRACT

An ingestible device is disclosed which can produce spectral data of one or more analytes, as well as associated methods for characterizing the gastrointestinal tract of a subject which contains such analytes. Related kits and systems are also disclosed.

35 Claims, 132 Drawing Sheets

Related U.S. Application Data filed on Oct. 10, 2017, provisional application No. 62/434,797, filed on Dec. 15, 2016.

(51) Int. Cl.

| | |
|---|---|
| *A61B 5/06* | (2006.01) |
| *A61B 5/00* | (2006.01) |
| *A61B 5/145* | (2006.01) |
| *A61B 1/00* | (2006.01) |
| *A61B 1/04* | (2006.01) |
| *A61B 5/07* | (2006.01) |
| *A61M 31/00* | (2006.01) |
| *A61B 5/024* | (2006.01) |
| *A61B 5/0531* | (2021.01) |
| *A61B 5/11* | (2006.01) |
| *A61B 34/20* | (2016.01) |
| *A61B 10/00* | (2006.01) |

(52) U.S. Cl.
CPC ....... *A61B 5/14503* (2013.01); *A61B 5/14535* (2013.01); *A61B 5/14539* (2013.01); *A61B 5/4238* (2013.01); *A61B 5/4848* (2013.01); *A61B 5/6873* (2013.01); *A61B 5/6898* (2013.01); *A61B 2010/0061* (2013.01); *A61B 2034/2065* (2016.02); *A61B 2560/0233* (2013.01); *A61B 2560/0242* (2013.01); *A61B 2560/0247* (2013.01); *A61B 2560/0252* (2013.01); *A61B 2560/0475* (2013.01); *A61B 2562/0233* (2013.01); *A61B 2562/046* (2013.01)

(56) References Cited

U.S. PATENT DOCUMENTS

| | | |
|---|---|---|
| 2009/0124853 A1 | 5/2009 | Gono |
| 2010/0249546 A1 | 9/2010 | White |
| 2011/0125031 A1 | 5/2011 | Blit |
| 2013/0172672 A1* | 7/2013 | Iddan ............... A61B 1/041 600/109 |
| 2014/0249546 A1 | 9/2014 | Shvartsberg et al. |
| 2014/0296666 A1 | 10/2014 | Rabinovitz |
| 2018/0168488 A1 | 6/2018 | Jones et al. |
| 2018/0168489 A1 | 6/2018 | Jones et al. |

OTHER PUBLICATIONS

Decruyenaere et al., "Faecal near-infrared reflectance spectroscopy (NIRS) compared with other techniques for estimating thedigestibility and dry matter intake of lactating grazing dairy cows", Animal Feed Science and Technology, vol. 173, No. 3, pp. 220-234, 2012.

International Search Report and Written Opinion in International Application No. PCT/US2017/066768, dated May 22, 2018, 21 pages.

International Search Report and Written Opinion in International Application No. PCT/US2017/066844, dated May 22, 2018, 22 pages.

International Search Report and Written Opinion in International Application No. PCT/US2017/066873, dated May 29, 2018, 22 pages.

Invitation to Pay Additional Fees in International Application No. PCT/US2017/066768, dated Mar. 23, 2018, 17 pages.

Invitation to Pay Additional Fees in International Application No. PCT/US2017/066844, dated Mar. 23, 2018, 18 pages.

Invitation to Pay Additional Fees in International Application No. PCT/US2017/066873, dated Mar. 23, 2018, 19 pages.

Lu et al., "Spectral-spatial classification for noninvasive cancer detection using hyperspectral imaging", J. of Biomedical Optics, vol. 19, No. 10, p. 106004, 2014.

U.S. Office Action in U.S. Appl. No. 15/844,349, dated Dec. 23, 2019, 12 pages.

U.S. Office Action in U.S. Appl. No. 15/844,381, dated Dec. 23, 2019, 9 pages.

* cited by examiner

Personal Data

| | |
|---|---|
| Age | 43 |
| Sex | F |
| Weight | 198 |
| Height | 6'2" |
| BMI | 24 |
| Race | Caucasian |
| Country | United States |
| Diabetic | No |
| married | No |
| Diabets | No |
| Member | 1/29/16 |
| Capsules | 3 |

Goals

| | |
|---|---|
| Weight | 125 |
| BMI | 20 |
| Body fat | 25% |
| Lean Muscle | Med |
| Diabets | Better Control |
| Sleep | Improve |
| Satiety/Hunger | Improve |
| Endurance | High |
| Regularity | Improve |

Quick Select

Groups/Social/Challenges

| Groups | Social | Challenges |
|---|---|---|
| ☒ Diabetes | ☒ Family | ☒ Family |
| ☒ Obesity | ☒ Work | ☒ Work |
| ☒ Cancer | ☒ Work out | ☒ School |
| ☒ Elderly | ☒ School | ☒ Charity |
| ☒ IBS | | |
| ☒ Epilepsy | | |
| ☒ Vegan | | |

Base Meal

| | |
|---|---|
| Capsule | v1.1 |
| Meal Type | Base |
| Date | 2/2/16 |
| Time | 8:11 AM |
| Place | San Francisco |

Estimated Profile
- Total
- Carbs
- Proteins
- Fat
- Water

Anatomy

Learning's / Results / Report

| | |
|---|---|
| Transit time | 26 hours |
| Chewing | Sufficient |
| Gastric Emptying | 0.5 hours |
| Fiber | Low |
| Sleep | High impact (too close sleep) |
| Protein | 95% |
| Carbs | 80% |
| Fat | 80% |
| YOU PERSONALIZED DIET SELECTION | |

| Water/Hydration | Poor |
|---|---|
| Foods to avoid | Starch |
| Foods to eat | Protein/Fiber |
| Satiety/Hunger | Low |
| Allergies | Low |
| Impact weight rank | 7.5 |
| Metabolism | Med |
| | High |

FIG. 6

| Normal Lunch | | | |
|---|---|---|---|
| Capsule | v1.1 | Transit time | 26 hours | Water/Hydration | Average |
| Meal type | Normal Lunch | Chewing | Not sufficient | Foods to avoid | Starch |
| Date | 5/20/16 | Gastric Emptying | 1.5 hours | Foods to eat | Protein/Fiber |
| Time | 12:11 PM | Fiber | Low | Satiety/Hunger | Low |
| Place | New York | Sleep | High impact | Allergies | High (check gluten) |
| | | Protein | 95% | Impact weight rank | 7.5 |
| | | Carbs | 80% | Metabolism | Med |
| | | Fat | 80% | Diabetes risk | High |
| | | YOU PERSONALIZED DIET SELECTION | | | |

| High Protein/Low Fat Dinner | | | |
|---|---|---|---|
| Capsule | v1.2 | Transit time | 23 hours | Water/Hydration | Good |
| Meal type | High Protein | Chewing | Not sufficient | Foods to avoid | Starch |
| Date | 3/27/16 | Gastric Emptying | 0.5 hours | Foods to eat | Protein/Fiber |
| Time | 12:11 PM | Fiber | High | Satiety/Hunger | Low |
| Place | New York | Sleep | Low impact | | |

FIG. 6 (Cont.)

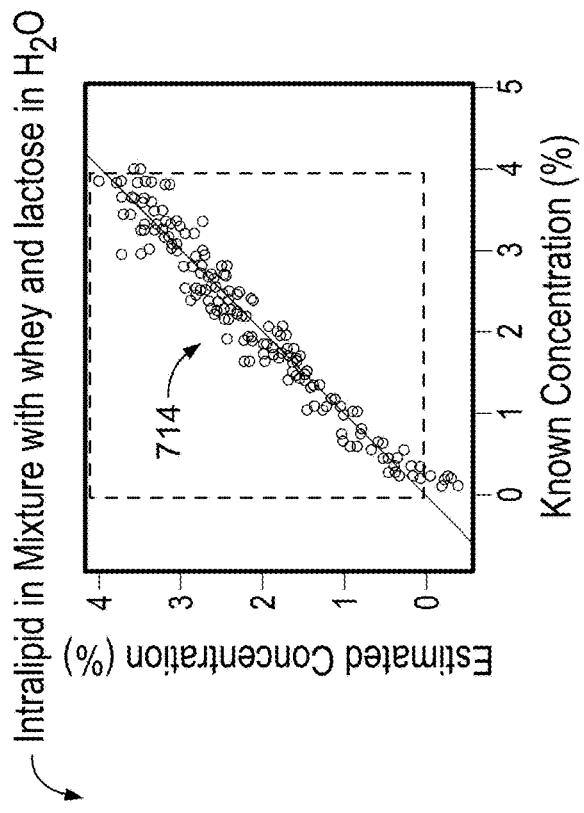
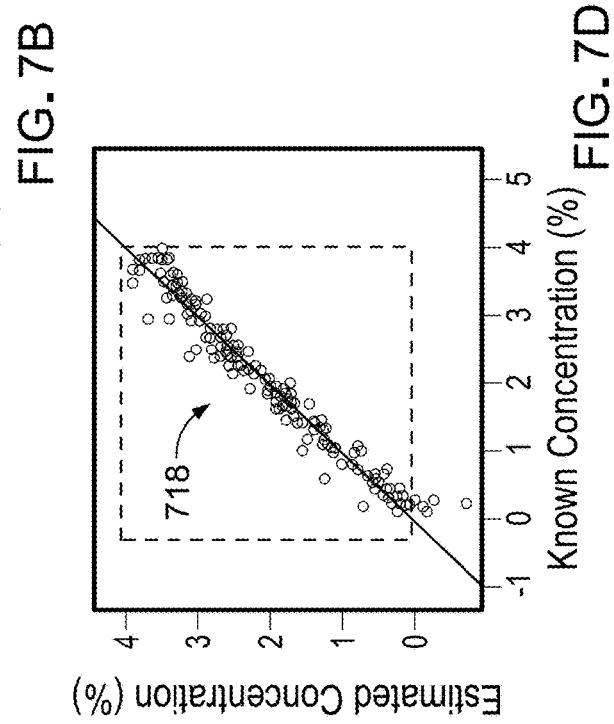
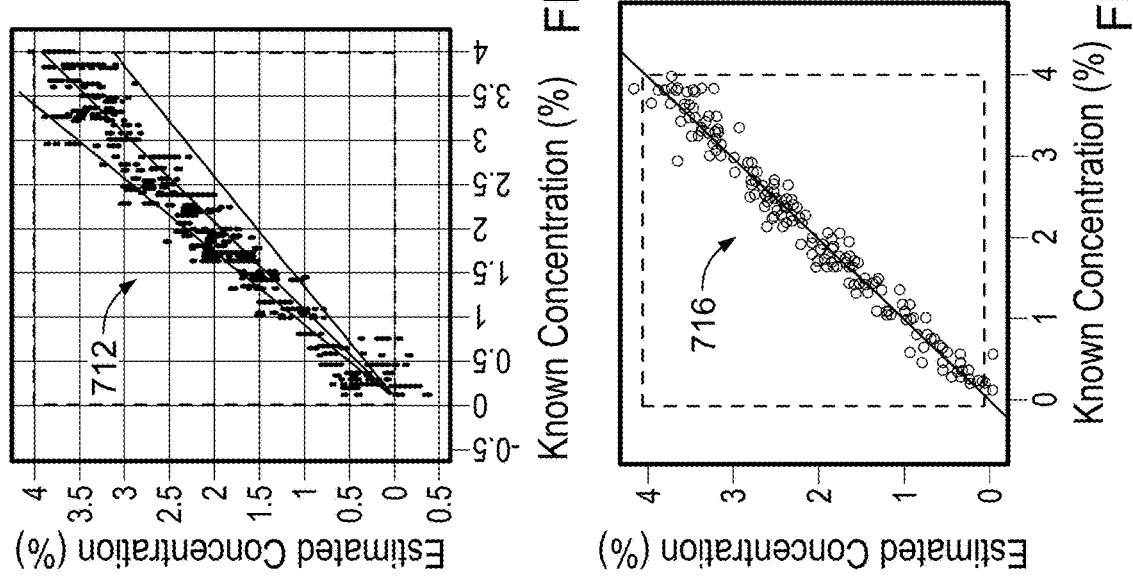
FIG. 7A  FIG. 7B  FIG. 7C  FIG. 7D

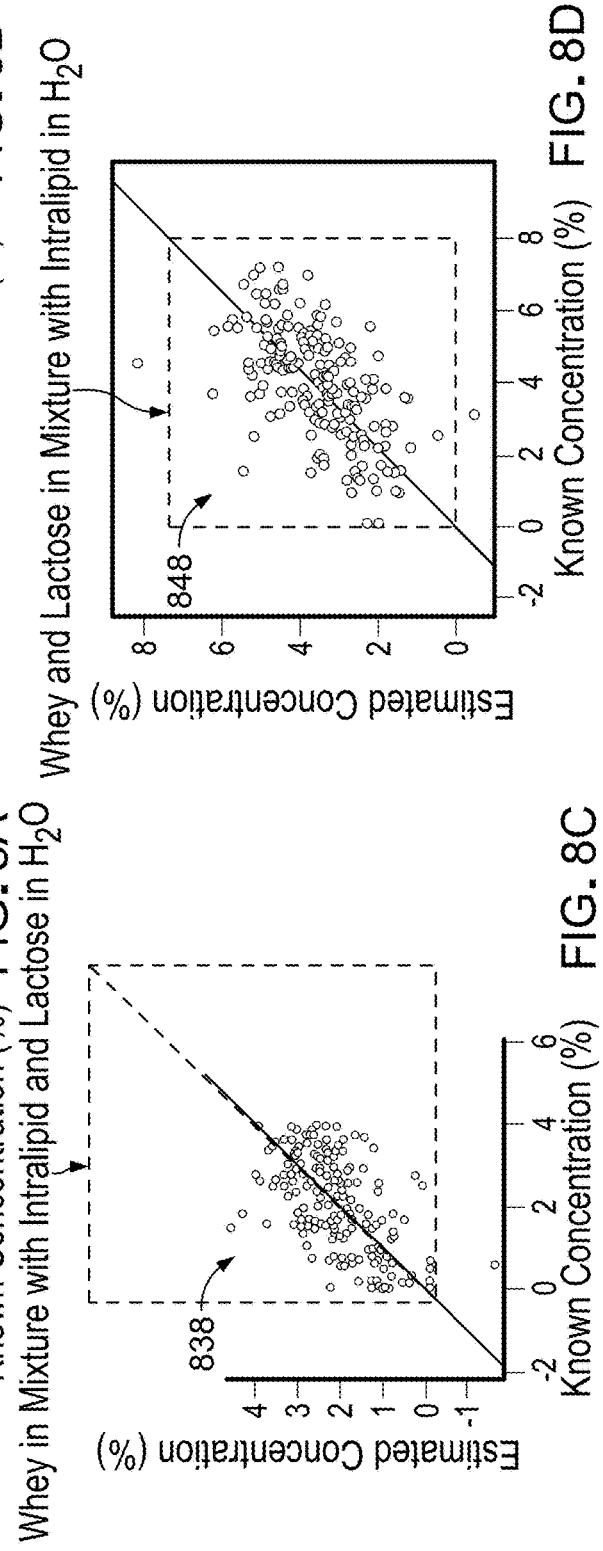
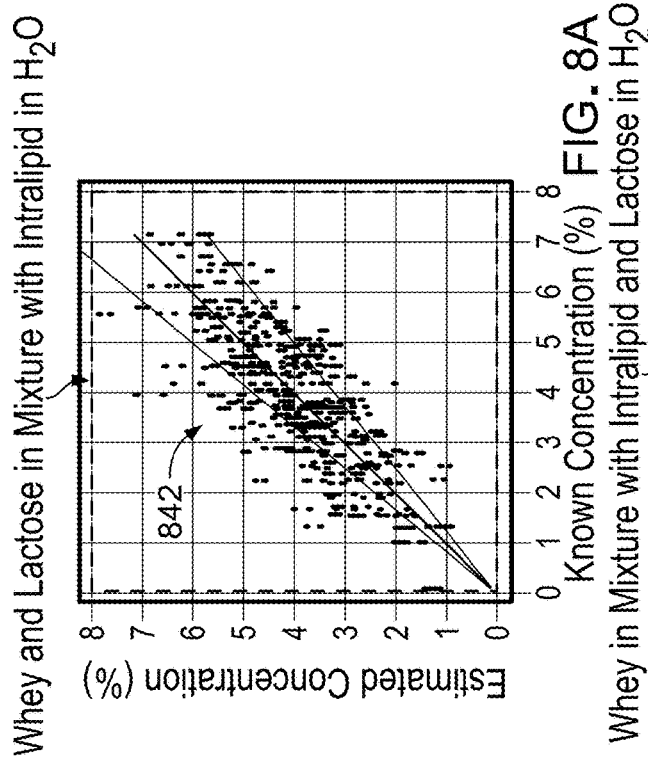

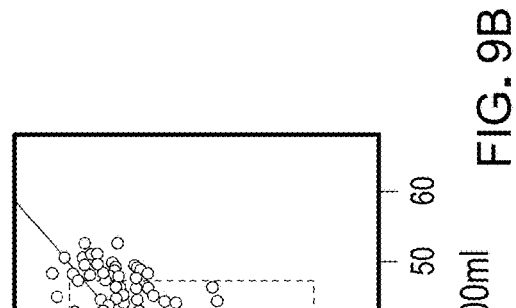
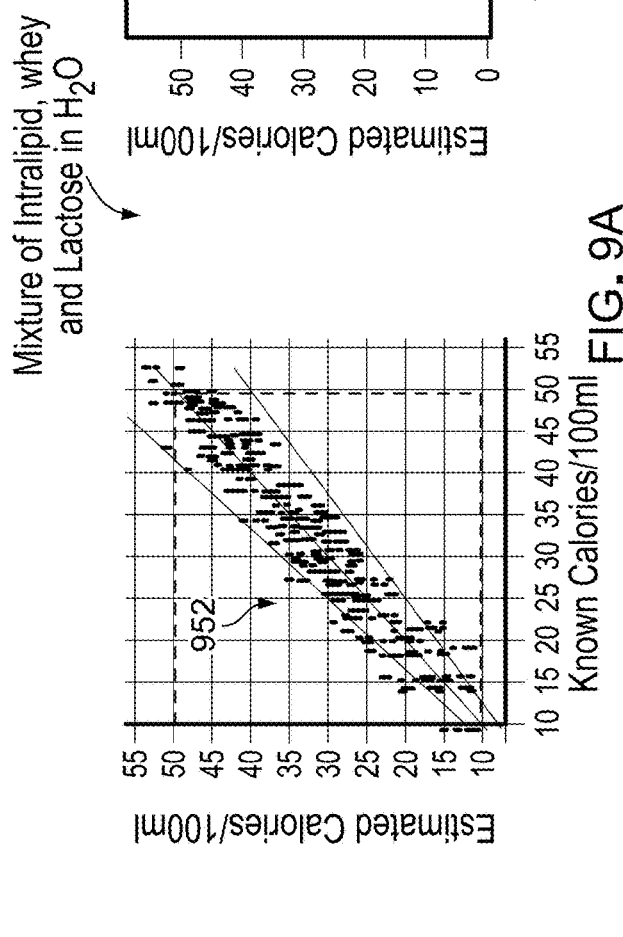
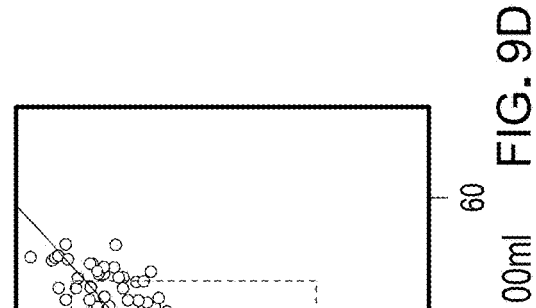
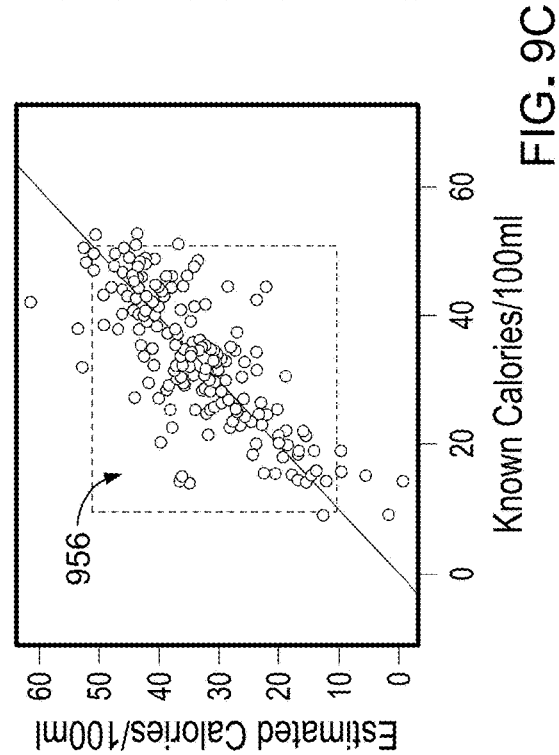
FIG. 9A
FIG. 9B
FIG. 9C
FIG. 9D

Ibuprofen in H₂O

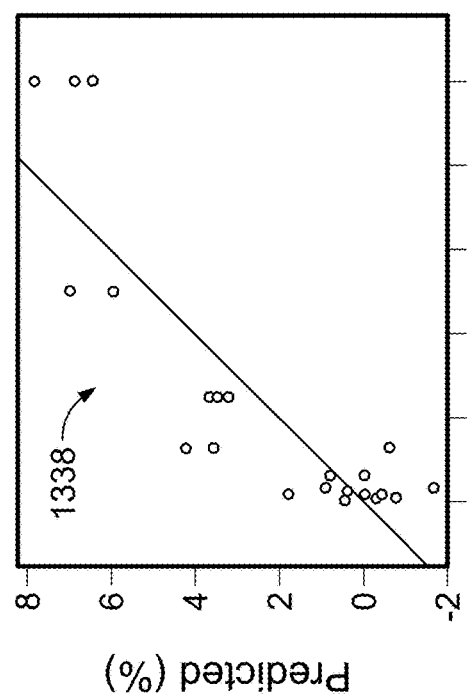
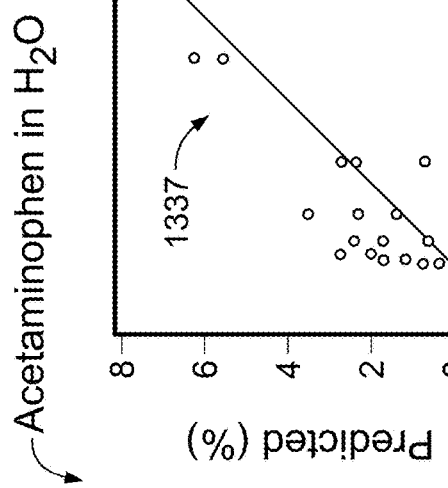
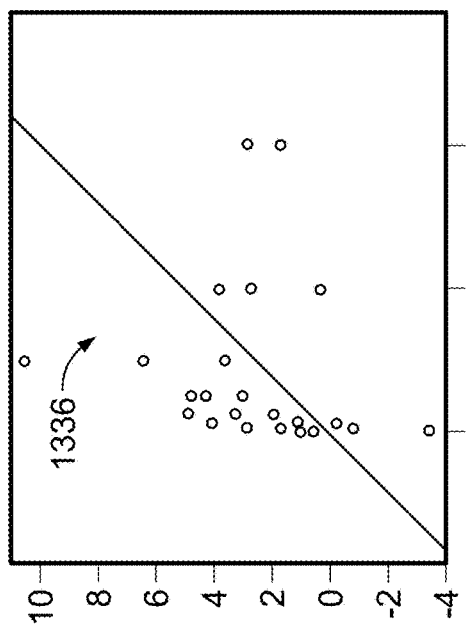
FIG. 41A
FIG. 41B
FIG. 41C
FIG. 41D

IgM in $H_2O$

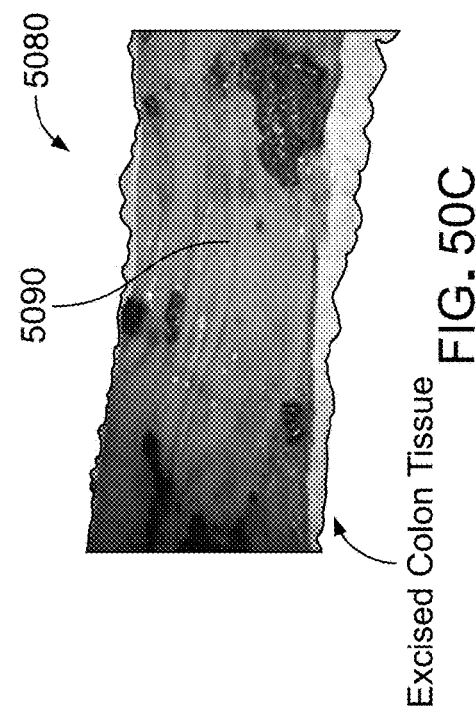
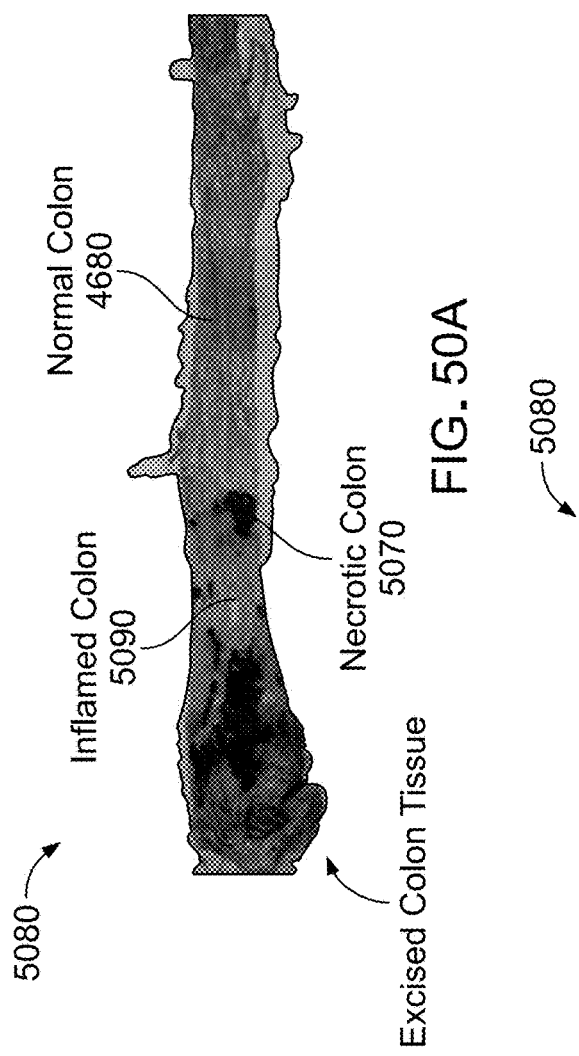
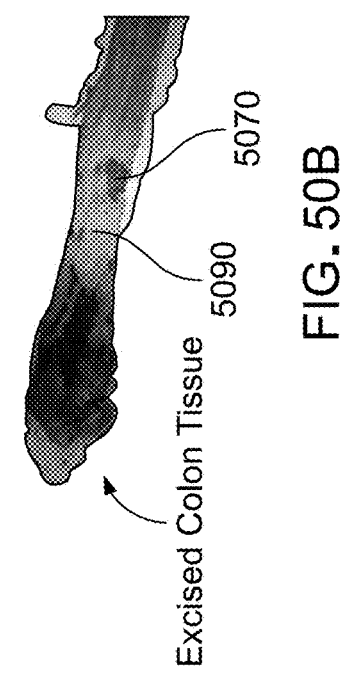

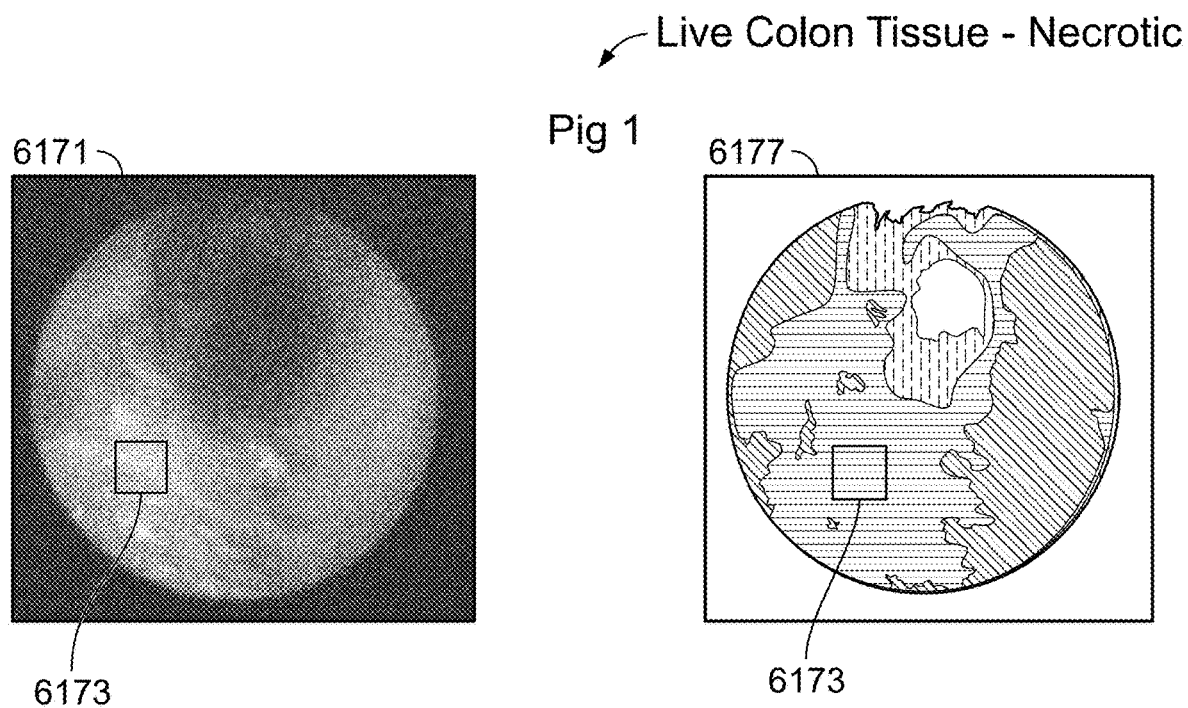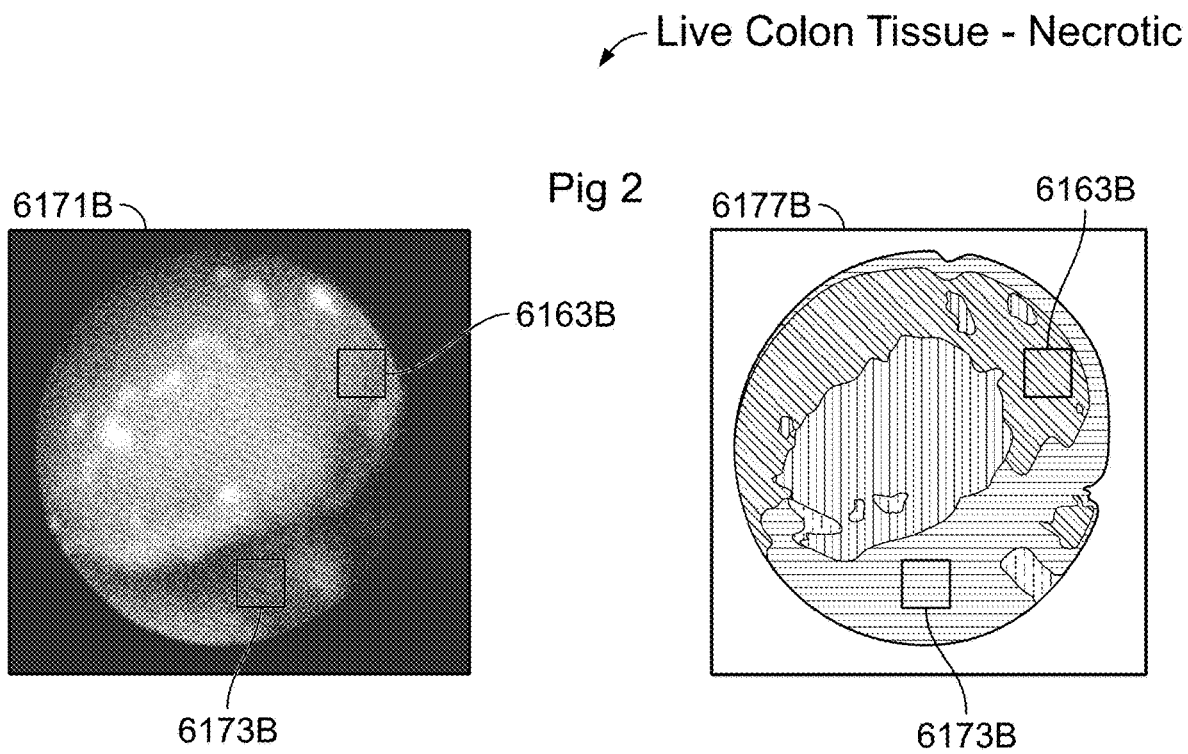
FIG. 61

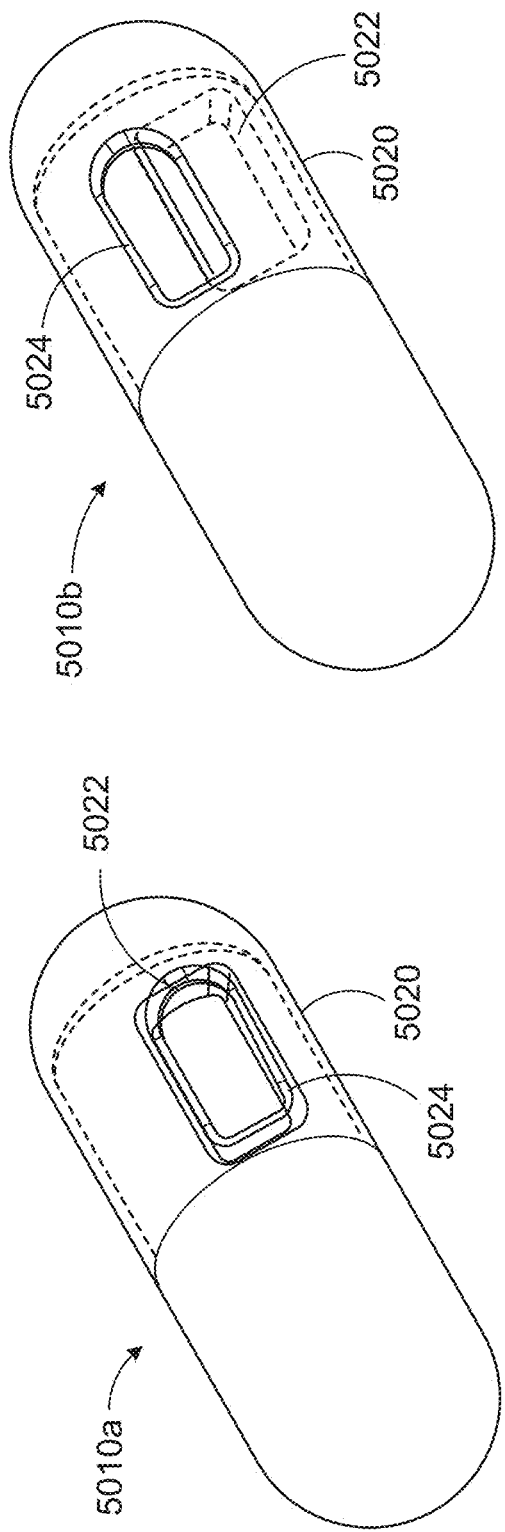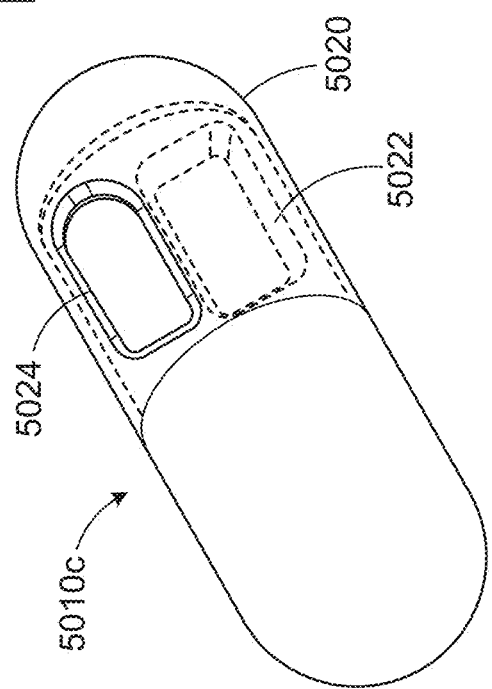

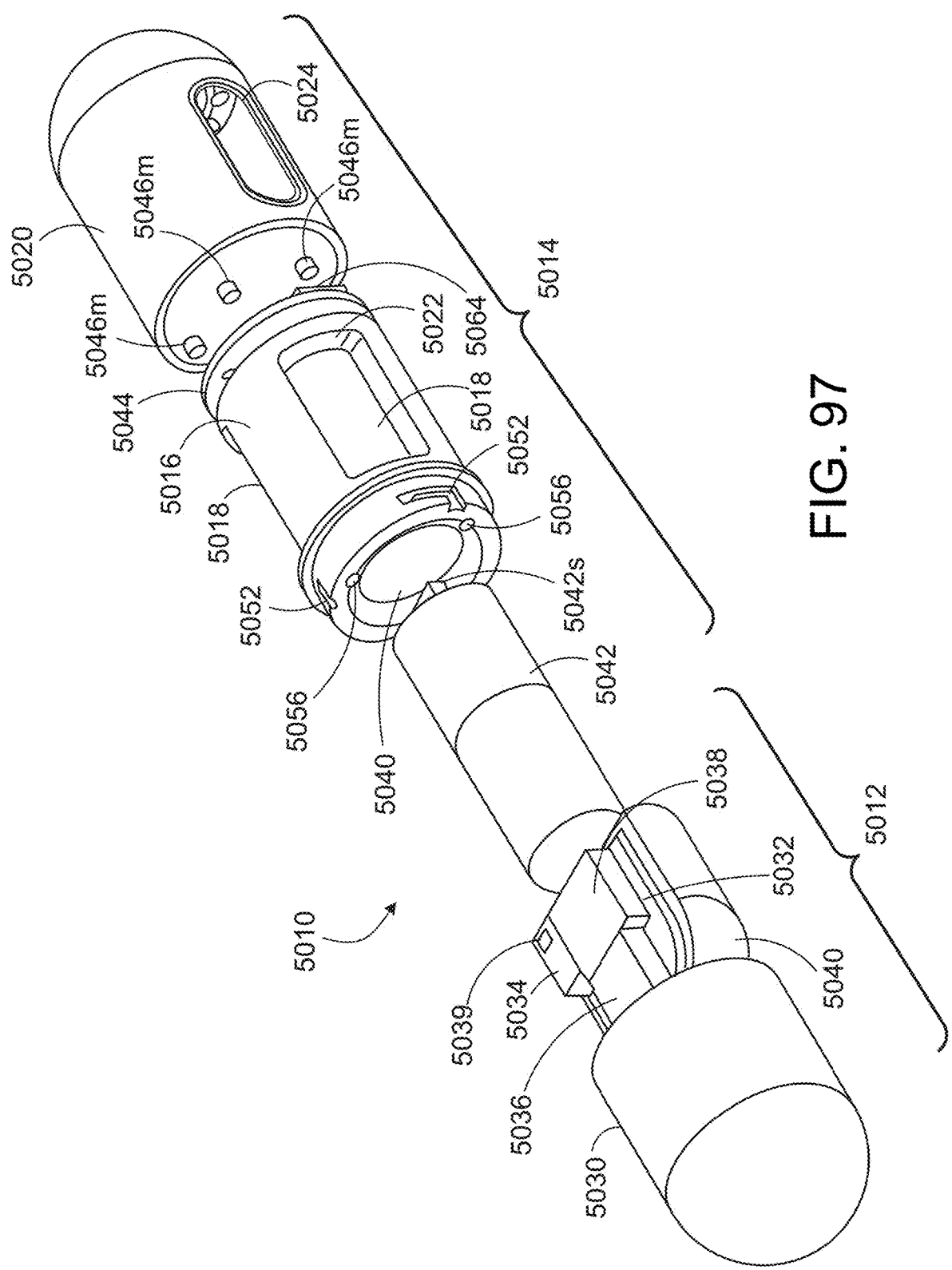

INGESTIBLE DEVICE AND ASSOCIATED METHODS

CROSS-REFERENCE TO RELATED APPLICATIONS

This application claims priority to the following U.S. Patent Applications: U.S. Ser. No. 62/434,797, entitled "Ingestible Device and Associated Methods," and filed on Dec. 15, 2016; U.S. Ser. No. 62/570,411, entitled "Ingestible Device and Associated Methods," and filed Oct. 10, 2017; and U.S. Ser. No. 62/572,341, entitled "Ingestible Device and Associated Methods," and filed Oct. 13, 2017.

INCORPORATION BY REFERENCE

This application incorporates by reference the following U.S. patent applications in their entirety: U.S. Ser. No. 62/434,797, entitled "Ingestible Device and Associated Methods," and filed on Dec. 15, 2016; U.S. Ser. No. 62/570,411, entitled "Ingestible Device and Associated Methods," and filed Oct. 10, 2017; and U.S. Ser. No. 62/572,341, entitled "Ingestible Device and Associated Methods," and filed Oct. 13, 2017; U.S. Ser. No. 14/460,893, entitled "Ingestible Medical Device," and filed Aug. 15, 2014; U.S. Ser. No. 15/514,413, entitled "Electromechanical Pill Device with Localization Capabilities," and filed Mar. 24, 2017; U.S. Ser. No. 15/680,400, entitled "Systems and Methods for Obtaining Samples using Ingestible Devices," filed on Aug. 18, 2017; U.S. Ser. No. 15/680,430, entitled "Sampling Systems and Related Materials and Methods," filed on Aug. 18, 2017; U.S. Ser. No. 15/699,848, entitled "Electromechanical Ingestible Delivery of a Dispensable Substance," filed on Sep. 8, 2017; U.S. Ser. No. 62/480,187, entitled "Localization Systems and Methods for an Opto-electromechanical Pill Device," filed on Mar. 31, 2017; and U.S. Ser. No. 62/540,873, entitled "Localization Systems and Methods for an Ingestible Device," filed on Aug. 3, 2017.

FIELD

The disclosure relates to an ingestible device and, more specifically, to an ingestible device which can produce spectral data of one or more analytes within the gastrointestinal (GI) tract and/or of tissue of one or more regions of the GI tract, as well as associated methods, kits and systems.

BACKGROUND

The GI tract of a subject can contain information regarding a subject.

SUMMARY

The technology disclosed herein allows for rapid, real time assessment of information relating to a subject (e.g., information relating to the subject's GI tract). In some embodiments, the information can relate to the presence and/or quantity of an analyte of interest (e.g., an analyte of interest in the GI tract of a subject). In certain embodiments, the information can relate to the condition of tissue of the GI tract of a subject. In some embodiments, the information can relate to the location of the ingestible device in the GI tract of a subject. In some embodiments, the information can be used to develop a digestion profile of a subject. In certain embodiments, the technology can be implemented using an ingestible device that may be used to take one or more samples of a subject (e.g., one or more samples in one or more locations of the GI tract of the subject). In some embodiments, the technology can be implemented without the ingestible device collecting a sample of the GI tract of the subject. An ingestible device can be implemented in an autonomous fashion. For example, information can be exchanged between the ingestible device when present in the subject (in vivo) and outside the subject (ex vivo). In some embodiments, the information can be exchanged in real time. In certain embodiments, the technology can be used to help determine whether a subject has a given GI disorder. In some embodiments, the technology can be used to help determine a treatment protocol for a subject (e.g., a GI disorder treatment protocol for the subject). In certain embodiments, the technology can be used to determine a digestion profile for a subject. The spectroscopic techniques disclosed herein can be used individually or in any combination, as desired. In some embodiments, an ingestible device is configured such that different spectroscopic techniques are performed in different chambers (e.g., detection chambers) of an ingestible device, and/or without the use of chamber (e.g., via a hyperspectral camera). Optionally, multiple different spectroscopic methods may be used to provide complementary information regarding a subject (e.g., provide information relating to the subject's GI tract) and/or supplementary information regarding a subject (e.g., provide information relating to the subject's GI tract).

The disclosure generally provides an ingestible device configured to collect spectral data for one or more analytes (e.g., a therapeutic agent or a macronutrient) present in the GI tract of a subject and/or to collect spectral data characterize one or more regions of the GI tract of a subject. In some embodiments, the ingestible device includes one more spectrometers configured to generate the spectral data. Also described are associated kits, methods and/or systems for characterizing the GI tract of a subject. Some embodiments are directed to an ingestible device which can produce spectral data of one or more analytes present in the GI tract and/or regions of the GI tract. Certain embodiments are directed to associated methods for characterizing the GI tract of a subject which contains such analytes, as well as related kits and systems.

Generating spectral data at one or more wavelengths (e.g., pre-determined wavelengths) in accordance with the disclosure beneficially allows for the detection and/or quantitation, in vivo, of one or more particular analytes within a sample in the GI tract, and/or for the analysis of the condition of tissue of the GI tract, and/or to determine the location of the ingestible device within the GI tract (e.g., based on information regarding the tissue of the GI tract). For example, spectral data in the low NIR is suitable for detecting food and macronutrients, and spectral data in the high NIR is suitable for detecting features of human anatomy, physiology, pathophysiology and biology. Spectral data at longer wavelengths, e.g., 2500-16000 nm, is suitable for detecting chemical compounds and dissolved gases. In some embodiments, one or more of these observations is/are used to generate spectral data (e.g., hyperspectral data) for a sample. More generally, spectral data of a variety of different wavelengths can be used to analyze one or more analytes (e.g., one or more macronutrients, one or more drugs, one or more biomarkers, one or more antibiotics, one or more antibodies, one or more constituents of blood) present in the GI tract and/or tissue associated with one or more regions of the GI tract (e.g., in one or more of the mouth, throat, esophagus, stomach, small intestine (duodenum, jejunum, ileum), large intestine (ascending colon, transverse colon, and descending colon), rectum, anus, and sphincter, which can yield information relating to the location of the ingestible device within the GI tract of the subject (e.g., by analyzing the spectral data relating to the GI tract and comparing it to one or more spectral standards for GI tract tissue).

In some embodiments, spectral data is used to develop one or more digestion profiles of a subject, e.g., when the analyte(s) include one or more macronutrients. In certain embodiments, the spectral data is used to develop one or more drug absorbance profiles when the analyte(s) comprises a drug(s). In some embodiments, the spectra data is used to detect and/or measure a marker of a condition, e.g., when the analyte(s) include a marker (e.g., a biomarker) for the condition. In certain embodiments, the spectral data is used to detect bleeds into the GI tract, e.g., when the analyte(s) include one or more constituents of blood, such as, for example, hemoglobin or a blood cell (e.g., an erythrocyte). In some embodiments, the spectral data is used to determine the condition of GI tract tissue (e.g., via hyperspectral imaging). In some embodiments, the spectral data is used to determine the location of the ingestible device within the GI tract (e.g., by comparing spectral data for the tissue of the GI tract and to one or more spectral standards for tissue of the GI tract). Optionally, spectral data can be used in various combinations of such techniques to provide a multitude of different information about a given subject.

Generating spectral data at one or more pre-determined wavelengths allows for information to be obtained regarding the subject without necessarily identifying specific analytes. As an example, the spectral data gathered by the disclosed ingestible device is suitably used to search a database of spectral standards or digestion profiles, and it may be determined that similar spectral data is indicative of individuals with a vegetarian diet who have recently eaten a particular type of ingestible standard. As another example, the spectral data gathered by the disclosed ingestible device is suitably used to search a database of spectral standards, and it may be determined that similar spectral data is indicative of individuals (e.g., with a specific health condition) who have been administered (e.g., recently administered) a particular type of therapeutic agent (e.g., a drug or particular type of drug).

Spectral data associated with a drug may be used in accordance with the disclosed technologies to develop an absorption profile (e.g., as a function of time and/or location within the GI tract) and/or to predict the absorption of the therapeutic agent (e.g., drug) by the subject. Additionally or alternatively, spectral data associated with a therapeutic agent (e.g., drug) may be used in accordance with the disclosed technologies to determine whether a therapeutic agent may be beneficial or detrimental to a criteria selected by a user such as wanting to ameliorate, treat, or cure a certain condition. For example, a subject's therapeutic agent absorption profile may indicate that s/he is unable to absorb, and/or only partially absorb, and/or metabolize, and/or partially metabolize a given therapeutic agent or type of therapeutic agent (e.g., a drug described herein). Optionally, this information may be used to infer what dose of a particular therapeutic agent the subject will actually absorb if they are administered the particular therapeutic agent or a different therapeutic agent of the same or similar type. Such information can be used, for example, to determine a dosage of a particular therapeutic agent that may be considered safe and/or effective for a given subject.

Hyperspectral imaging may be advantageously used in the methods and devices described herein as the additional spatial dimensions allow for images to be analyzed in order to identify non-homogeneous samples and/or obtain spectra from different areas of the image such as to focus on liquid sample or particular matter such as food particles, etc. The results of this analysis may be beneficially included in the digestion profile for a subject, or may be used in conjunction with a digestion profile to infer information about the subject or provide recommendations for the subject. For example, spectral data may be used in accordance with the disclosed technologies to detect the presence of a particular chemical or macronutrient present within the sample over time, which suitably indicates the subject's ability to absorb and/or metabolize the chemical or macronutrient from the sample as it transits through the GI tract of the subject. More generally, hyperspectral imaging may be used for a broad range of analytes to be analyzed at multiple time points and/or at multiple locations, for example, throughout the GI tract.

An ingestible standard (e.g., a set meal or a predetermined composition of one or more macronutrients) may be used with the disclosed ingestible device in order to generate spectral data that is associated with the ingestible standard. One advantage of using an ingestible standard is to facilitate the comparison of spectral data and/or digestion profiles from the same individual or from different individuals. For example, the ingestible standard serves as a control and differences in the spectral data and/or digestion profiles for a subject having ingested the same ingestible standard may be ascribed to changes in the physiology of the GI tract rather than differences in the ingested material. As another example, the use of an ingestible standard also allows for the identification of individuals with similar GI tract characteristics based on similarities in their spectral data. Information on those individuals may then be beneficially used to inform or predict the characteristics of a subject.

The disclosed technologies can be used to produce a digestion profile indicative of the relative or total amount of one or more analytes in one or more samples. For example, the digestion profile indicates to a user the relative concentration of macronutrients in the stomach of the subject, or the total amount in grams of fat in the intestine of the subject. Data indicative of the presence of one or more analytes is gathered by the disclosed ingestible device at several points in time, and is advantageously used to determine how effectively the subject digests absorbs and/or metabolizes particular analytes. As an example, if the level of a particular macronutrient detected in the sample is reduced over time, it may indicate that the subject has absorbed and/or metabolized the macronutrient. As another example, if the level of a particular macronutrient detected in the sample is reduced more quickly over time compared to that of one or more other macronutrients, then the subject may have a higher rate of absorption of the particular macronutrient relative to the one or more other macronutrients (the subject may absorb and/or metabolize the particular macronutrient faster than the one or more other macronutrients).

Spectral data associated with an ingestible standard for a subject may be used in accordance with the disclosed technologies to predict the absorption of calories or macronutrients by the subject for the substance, or whether the substance may be beneficial or detrimental to a criteria selected by a user such as wanting to lose weight, gain weight, lose body fat, gain body fat, lose muscle mass, gain muscle mass, manage a medical condition, treat a medical condition, increase absorption of a macronutrient, decrease absorption of a macronutrient, absorb carbohydrates (e.g., carb loading for sports performance) or gain lean muscle.

For example, a subject's digestion profile may indicate that they are able to only partially digest certain types of vegetables, and this information may be used to infer how many calories and macronutrients the subject will actually absorb if they consume one of those types of vegetables.

In one aspect, provided herein is a device comprising a spectrometer configured to generate spectral data of a sample within the gastrointestinal (GI) tract of a subject in vivo, wherein the device is an ingestible device.

In some embodiments, the device comprises a communications unit configured to transmit data to and/or receive operating parameters from a base station.

In some embodiments, the device comprises a processing unit configured to generate a digestion profile for the subject based on the spectral data.

In some embodiments, the processing unit is within the device. In some embodiments, the device is configured to communicate with a processing unit within a base station that is external to the device. In some embodiments, the device and/or the base station comprises memory configured to store the spectral data and/or the digestion profile. In some embodiments, the processing unit is configured to compare the spectral data to one or more spectral standards to generate the digestion profile.

In some embodiments, the processing unit is configured to generate the digestion profile based on one or more inputs. In some embodiments, the one or more inputs comprises information relating to the subject.

In some embodiments, the information relating to the subject comprises at least one member selected from the group consisting of weight, height, sex, diet, physical activity level, a medical condition, a medication, a genetic profile, a phenotypic profile, an immune profile, body mass index (BMI), race, age, tobacco use, alcohol use, heart rate, pulse, place of residence, blood glucose level, adiposity, and a microbiome profile. In some embodiments, the medical condition comprises at least one member selected from the group consisting of cancer, a metabolic disease, diabetes, irritable bowel syndrome, an inflammatory bowel disease, short bowel syndrome, a malabsorption syndrome, a bile metabolism disorder, obesity, a pancreatic insufficiency, chronic pancreatitis, epilepsy, a protein malnutrition, an allergy, and Celiac disease.

In some embodiments, the one or more inputs comprise one or more criteria selected by a user. In some embodiments, the one or more criteria comprises an indication of one or more analytes, a desired outcome for the subject, or a combination thereof. In some embodiments, the desired outcome comprises at least one outcome selected from the group consisting of losing weight, gaining weight, losing body fat, gaining body fat, losing muscle mass, gaining muscle mass, managing a medical condition, treating a medical condition, increasing absorption of a macronutrient, and decreasing absorption of a macronutrient.

In some embodiments, the processing unit is configured to search a database comprising a plurality of digestion profiles and identify an individual or a plurality of individuals with digestion profiles similar to the digestion profile for the subject. In some embodiments, the processing unit is configured to display information regarding the individual or the plurality of individuals identified as having digestion profiles similar to the digestion profile for the subject. In some embodiments, the processing unit is configured to add information regarding the individual or of the plurality of individuals identified as having digestion profiles similar to the digestion profile for the subject.

In some embodiments, the processing unit is configured to transmit the spectral data to a server and receive the digestion profile for the subject from the server.

In some embodiments, the digestion profile for the subject is indicative of the presence or absence of one or more analytes in the sample. In some embodiments, the digestion profile for the subject is indicative of a relative or a total amount of one or more analytes in the sample. In some embodiments, the one or more analytes comprise at least one member selected from the group consisting of a macronutrient, a blood component, a salt, water, a fiber, bile, a ketone body, mucus, a bacterium, gastric juice, a therapeutic agent, a nutritional supplement, and an ingestible standard.

In some embodiments, the one or more analytes comprise at least one member selected from the group consisting of an alcohol, a carbohydrate, a protein, an amino acid, and a fat.

In some embodiments, the one or more analytes comprise a non-absorbed standard, an indigestible standard, or a non-absorbed indigestible standard.

In some embodiments, the amino acid is selected from the group consisting of histidine, isoleucine, leucine, lysine, methionine, phenylalanine, threonine, tryptophan, valine, arginine, cysteine, glutamine, glycine, proline, serine, tyrosine, alanine, asparagine, aspartic acid, glutamic acid, selenocysteine, and a combination thereof.

In some embodiments, the carbohydrate is selected from the group consisting of glucose, fructose, galactose, xylose, sucrose, lactose, maltose, trehalose, sorbitol, mannitol, altodextrin, maltotriose, raffinose, stachyose, a fructo-oligosaccharide, amylose, an amylopectin, a modified starch, a cellulose, a hemicellulose, a pectin, a gum, a mucilage, a hydrocolloid, and a combination thereof.

In some embodiments, the fat is selected from the group consisting of oleic acid, linoleic acid, α-linolenic acid, myristic acid, myristoleic acid, palmitic acid, palmitoleic acid, oleic acid, gadoleic acid, erucic acid, nervonic acid, α-linolenic acid, docosahexaenoic acid, eicosapentaenoic acid, elaidic acid, erucic acid, linoleic acid, linoelaidic acid, sapienic acid, stearic acid, vaccenic acid, lauric acid, eicosapentaenoic acid, docosahexaenoic acid, γ-linolenic acid, stearidonic acid, paullinic acid, gondoic acid, eruic acid, nervonic acid, docosohexanoic acid, docosatetraenoic acid, and conjugated linoleic acid, or a combination thereof.

In some embodiments, the alcohol comprises ethanol.

In some embodiments, the digestion profile is indicative of calories ingested by the subject, calories absorbed by the subject, the amount of one or more analytes ingested by the subject, the amount of one or more analytes absorbed by the subject, or a combination thereof. In some embodiments, the digestion profile is indicative of a lifestyle recommendation for the subject, a dietary recommendation for the subject, or a combination thereof. In some embodiments, the digestion profile is predictive of the effect of ingesting one or more substances by the subject.

In some embodiments, the one or more analytes comprise at least two different analytes.

In some embodiments, the device is configured to generate the spectral data at a predetermined region within the GI tract of the subject. In some embodiments, the predetermined region within the GI tract of the subject is selected from the group consisting of the mouth, the throat, the esophagus, the stomach, the small intestine, the proximal duodenum, the distal duodenum, the jejunum, the ileum, the descending colon, the ascending colon, transverse colon, the rectum, the sphincter, and the anus of the subject.

In some embodiments, the device is operable to generate the spectral data at a plurality of time points as the device travels through the GI tract of the subject.

In some embodiments, the processing unit is configured to generate a plurality of digestion profiles at a plurality of time points as the device travels through the GI tract of the subject.

In some embodiments, the spectrometer comprises at least one member selected from the group consisting of a light source, a photodetector, a dispersive element, a lens, and a filter.

In some embodiments, the spectrometer is configured to generate at least one member selected from the group consisting of absorbance spectral data, transmission spectral data, reflectance spectral data, Fourier transform spectral data, and Raman spectral data.

In some embodiments, the device comprises a plurality of spectrometers configured to generate different types of spectral data.

In some embodiments, the spectrometer comprises a light source and a photodetector defining a light path through a detection chamber.

In some embodiments, the sample is a fluid sample, and the device comprises one or more ports, valves and/or pumps to control transfer of the fluid sample from the GI tract into the detection chamber.

In some embodiments, the spectrometer comprises a light source and a photodetector positioned on the exterior of the device. In some embodiments, the light source is configured to transmit light radially towards an environment external to the device, and the photodetector is configured to detect a radial reflectance from the environment external to the device. In some embodiments, the light source is adjacent to the photodetector.

In some embodiments, the spectral data comprises at least one member selected from the group consisting of ultraviolet spectral data, visible spectral data, near-infrared (NIR) spectral data, and mid-infrared (MIR) spectral data. In some embodiments, the spectral data comprises NIR spectral data. In some embodiments, the NIR spectral data comprises absorbance or reflectance data at one or more wavelengths between 600 nm and 2600 nm. In some embodiments, the spectral data comprises MIR spectral data. In some embodiments, the MIR spectral data comprises absorbance or reflectance data at one or more wavelengths between 1500 nm and 5600 nm.

In some embodiments, the spectrometer comprises a 2-dimensional array of photodetectors. In some embodiments, the spectral data comprises hyperspectral data. In some embodiments, the spectrometer comprises a hyperspectral camera.

In some embodiments, the processing unit is configured to compare the hyperspectral data to one or more spectral standards to generate the digestion profile.

In some embodiments, the device comprises one or more environmental sensors for measuring environmental data external to the device. In some embodiments, the one or more environmental sensors comprises at least one member selected from the group consisting of a capacitance sensor, a temperature sensor, an impedance sensor, a pH level sensor, a heart rate sensor, acoustic sensor, reflected visible light sensor, image sensor, and a movement sensor. In some embodiments, the environmental sensor comprises a movement sensor, wherein the movement sensor comprises a step sensor. In some embodiments, the image sensor comprises a video camera.

In some embodiments, the processing unit is configured to generate the digestion profile based on the spectral data and the environmental data. In some embodiments, the processing unit is configured to compare the environmental data to one or more environmental data standards.

In some embodiments, the processing unit is configured to identify a location of the device within the GI tract of the subject based on the spectral data. In some embodiments, the processing unit is configured to identify a location of the device within the GI tract of the subject based on the spectral data, the environmental data, or a combination thereof. In some embodiments, the processing unit is configured to identify a location of the device within the GI tract of the subject based on reflected visible light.

In some embodiments, the device is configured to attach to the GI tract of the subject in vivo. In some embodiments, the device is configured to releasably attach to the GI tract of the subject at one or more predetermined locations. In some embodiments, the device is attachable to the GI tract of the subject using an adhesive, negative pressure, a fastener, or a combination thereof.

In some embodiments, the device is static within the GI tract relative to material passing through the GI tract of the subject and the spectrometer is configured to generate spectral data at predetermined time intervals.

In some embodiments, the device comprises a microcontroller configured to operate the spectrometer to generate the spectral data, and optionally wherein the processing unit is the microcontroller. In some embodiments, the microcontroller is configured to operate the one or more environmental sensors to generate the environmental data. In some embodiments, the microcontroller is configured to operate the spectrometer to generate the spectral data and/or environmental data based on the location of the device within the GI tract of the subject.

In some embodiments, the sample is a fluid sample within the GI tract of the subject. In some embodiments, the fluid sample does not comprise tissue from the GI tract of the subject.

In some embodiments, the device is in the shape of a capsule.

In some embodiments, the ingestible device, comprises: a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device has an opening between an interior of the ingestible device and an exterior of the ingestible device, and the ingestible device comprises: a chamber; and a multi-stage valve system in the interior of the ingestible device, wherein: the multi-stage valve system has first, second and third states, the first state of the multi-stage valve system is different from the second and third states of the multi-stage valve system; the second state of the multi-stage valve system is different from the first and third states of the multi-stage valve system; when the multi-stage valve system is in its first state, the opening prevents fluid communication between the interior of the ingestible device and the exterior of the ingestible device; when the multi-stage valve system is in its second state, the opening allows fluid communication between the interior of the ingestible device and the exterior of the ingestible device; and when the multi-stage valve system is in its third state, the opening prevents fluid communication between the interior of the ingestible device and the exterior of the ingestible device.

In some embodiments, the ingestible device has an opening between an interior of the ingestible device and an exterior of the ingestible device, and the ingestible device comprises: a chamber; and a multi-stage valve system in the interior of the ingestible device, wherein: the multi-stage valve system comprises: an actuator system comprising a first member; a trigger comprising a first peg and a first lip; a gate comprising a protrusion, and a gate leg having an opening; and a biasing system comprising first and second biasing members; when the multi-stage valve system is in a first stage: the first biasing member applies a force to the trigger so that the first peg contacts the first member; the first member opposes the force applied to the trigger by the first biasing member; the second biasing member applies a force to the gate so that the protrusion contacts the first lip; the first lip opposes the force applied to the gate by the second biasing member; and the opening in the gate leg is not aligned with the opening in the ingestible device.

In some embodiments, the ingestible device has an opening between an interior of the ingestible device and an exterior of the ingestible device, and the ingestible device comprises: a chamber; and a sampling system in the interior of the ingestible device, wherein: the sampling system comprises: a first absorbent member; and a second absorbent member different from the first absorbent member; and the sampling system is configured so that fluid that flows from the exterior of the ingestible device to the interior of the ingestible device enters the first absorbent member; and the sampling system is configured to allow fluid to flow from the first absorbent member to the second absorbent member.

In some embodiments, the device has an opening between an interior of the ingestible device and an exterior of the ingestible device, and the ingestible device comprises: a chamber; and a sampling system in the interior of the ingestible device configured to absorb a fluid that enters the interior of the ingestible device via the opening, the sampling system comprising an absorbent member and at least one preservative at least partially absorbed in the absorbent member.

In some embodiments, the ingestible device comprises: a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device comprises: a housing defined by a first end, a second end substantially opposite from the first end, a wall extending longitudinally from the first end to the second end, and an opening; a sampling chamber within the housing, wherein the sampling chamber contains an absorptive material; an inlet port connecting the opening in the housing to the sampling chamber; a single use sealing device positioned within the inlet port that seals the inlet port; and a heating element proximate to the single use sealing device, wherein: the heating element is configured to apply heat to the single use sealing device to unseal the inlet port and open the sampling chamber, and at least a portion of the absorptive material proximate to the inlet port is configured to expand when in contact with a sample and reseal the inlet port.

In some embodiments, the ingestible device comprises: a housing defined by a first end, a second end substantially opposite from the first end, a wall extending longitudinally from the first end to the second end, and an opening; a sampling chamber within the housing having an entry port and an exit port on an opposite end of the sampling chamber from the entry port, wherein the exit port is configured to allow gas to exit the chamber and prevent at least a portion of a sample from exiting the chamber; an inlet region connecting the opening in the housing to the entry port of the sampling chamber; and a moveable valve positioned to open and close the inlet region, wherein: the moveable valve in an open position allows the sample to enter the sampling chamber; and the moveable valve in a closed position prevents the sample from entering the sampling chamber.

In some embodiments, the device comprises one or more processing devices; and one more machine readable hardware storage devices storing instructions that are executable by the one or more processing devices to determine a location of the ingestible device in a region of a GI tract of a subject to an accuracy of at least 85%. In some embodiments, the device comprises one or more processing devices; and one more machine readable hardware storage devices storing instructions that are executable by the one or more processing devices to determine that the ingestible device is in the cecum of a subject to an accuracy of at least 70%.

In some embodiments, the device comprises one or more processing devices; and one more machine readable hardware storage devices storing instructions that are executable by the one or more processing devices to transmit data to a device capable of implementing the data to determine a location of the medical device in a region of a GI tract of a subject to an accuracy of at least 85%. In some embodiments, the device comprises one or more processing devices; and one more machine readable hardware storage devices storing instructions that are executable by the one or more processing devices to transmit data to an external device capable of implementing the data to determine that the ingestible device is in the cecum of subject to an accuracy of at least 70%.

In some embodiments, the device comprises first and second light sources, wherein the first light source is configured to emit light at a first wavelength, and the second light source is configured to emit light at a second wavelength different from the first wavelength. In some embodiments, the device comprises first and second detectors, wherein the first detector is configured to detect light at the first wavelength, and the second detector is configured to detect light at the second wavelength.

In one aspect, provided herein is a kit, comprising a device described herein and at least one ingestible standard, at least one detection agent, or a combination thereof. In some embodiments, the ingestible standard comprises a predetermined quantity of at least one macronutrient. In some embodiments, the at least one macronutrient is an alcohol, a carbohydrate, a protein, an amino acid, or a fat. In some embodiments, the ingestible standard is a set meal or a hydratable powdered formulation. In some embodiments, the ingestible standard comprises a non-absorbed marker, an indigestible marker, or a non-absorbed indigestible marker.

In some embodiments, the detection agent is configured to selectively bind to one or more analytes. In some embodiments, the detection agent comprises a fluorescent label. In some embodiments, the fluorescent label comprises Fast Green FCF dye (Green #3) or Brilliant Blue FCF (Blue #1) dye.

In one aspect, provided herein is a system, comprising an ingestible device which comprises a spectrometer configured to generate spectral data of a sample within the gastrointestinal (GI) tract of a subject in vivo; and a processing unit configured to generate a digestion profile for the subject based on the spectral data. In some embodiments, the system comprises a communications unit. In some embodiments, the system comprises memory configured to store the spectral data, the digestion profile for the subject, or a combination thereof. In some embodiments, the system is configured to generate a display to a user.

In some embodiments, the system comprises an interface configured to allow a user to configure the processing unit to generate the digestion profile for the subject based on one or more inputs. In some embodiments, the one or more inputs comprise information relating to the subject. In some embodiments, the information relating to the subject comprises at least one member selected from the group consisting of weight, height, sex, diet, physical activity level, a medical condition, a medication, a genetic profile, a phenotypic profile, an immune profile, body mass index (BMI), race, age, tobacco use, alcohol use, heart rate, pulse, place of residence, blood glucose level, adiposity, and a microbiome profile. In some embodiments, the information relating to the subject comprises at least one medical condition selected from the group consisting of cancer, a metabolic disease, diabetes, irritable bowel syndrome, an inflammatory bowel disease, short bowel syndrome, a malabsorption syndrome, a bile metabolism disorder, obesity, a pancreatic insufficiency, chronic pancreatitis, epilepsy, a protein malnutrition, an allergy, and Celiac disease.

In some embodiments, the one or more inputs comprise one or more criteria selected by the user. In some embodiments, the one or more criteria comprises an indication of one or more analytes, a desired outcome for the subject, or a combination thereof.

In some embodiments, the desired outcome comprises at least one outcome selected from the group consisting of losing weight, gaining weight, losing body fat, gaining body fat, losing muscle mass, gaining muscle mass, managing a medical condition, treating a medical condition, increasing absorption of a macronutrient, and decreasing absorption of a macronutrient.

In some embodiments, the processing unit is configured to compare the spectral data to one or more spectral standards to generate the digestion profile.

In some embodiments, the processing unit is configured to search a database comprising a plurality of digestion profiles and identify an individual or a plurality of individuals with digestion profiles similar to the digestion profile for the subject. In some embodiments, the processing unit is configured to display information regarding the individual or the plurality of individuals identified as having digestion profiles similar to the digestion profile for the subject. In some embodiments, the processing unit is configured to add information regarding the individual or the plurality of individuals identified as having digestion profiles similar to the digestion profile for the subject.

In some embodiments, the communications unit is configured to transmit data from the ingestible device to a base station and/or to transmit operating parameters from the base station to the ingestible device. In some embodiments, at least one member selected from the group consisting of the processing unit, memory, display and interface is within a base station. In some embodiments, the base station is a computer or a personal electronic device. In some embodiments, the personal electronic device is selected from the group consisting of a watch, a phone, a tablet, a fitness monitor, and a physical activity tracker.

In some embodiments, the processing unit is configured to transmit the spectral data to a server and to receive the digestion profile from the server.

In some embodiments, the ingestible device comprises a device described herein.

In one aspect, provided herein is a method, comprising obtaining spectral data of for at least one sample within the gastrointestinal (GI) tract of a subject in vivo; and using the spectral data to generate a digestive profile of the subject. In some embodiments, the method comprises using an ingestible device comprising a spectrometer to obtain the spectral data. In some embodiments, the method comprises administering the ingestible device to the subject.

In some embodiments, the method comprises administering to the subject an ingestible device comprising a spectrometer configured to generate the spectral data of the sample; operating the device to obtain spectral data for at least one sample within the GI tract of the subject; and generating a digestion profile for the subject based on the spectral data obtained by the device.

In some embodiments, the device is administered orally to the subject.

In some embodiments, the method comprises administering at least one ingestible standard, at least one detection agent, or a combination thereof, to the subject. In some embodiments, the at least one ingestible standard, the at least one detection agent, or a combination thereof, is administered to the subject before the device is administered to the subject. In some embodiments, the at least one ingestible standard, the at least one detection agent, or a combination thereof, is administered to the subject concurrently with the device. In some embodiments, the at least one ingestible standard, the at least one detection agent, or a combination thereof, is administered to the subject after the device is administered to the subject. In some embodiments, the ingestible standard comprises a predetermined quantity of at least one macronutrient. In some embodiments, the at least one macronutrient is an alcohol, a carbohydrate, a protein, an amino acid, or a fat. In some embodiments, the ingestible standard is a set meal or a hydratable powdered formulation. In some embodiments, the ingestible standard comprises a non-absorbed marker, an indigestible marker, or a non-absorbed indigestible marker.

In some embodiments, the detection agent is configured to selectively bind to one or more analytes. In some embodiments, the detection agent comprises a fluorescent label. In some embodiments, the fluorescent label comprises Fast Green FCF dye (Green #3) or Brilliant Blue FCF (Blue #1) dye.

In some embodiments, the ingestible standard, the detection agent, or a combination thereof, is administered to the subject within a time period of from about five minutes to about two hours from the administration of the ingestible device to the subject.

In some embodiments, the digestion profile for the subject is indicative of the presence or absence of one or more analytes in the sample. In some embodiments, the digestion profile for the subject is indicative of a relative or a total amount of one or more analytes in the sample. In some embodiments, the one or more analytes comprise at least one member selected from the group consisting of a macronutrient, a blood component, a salt, water, a fiber, bile, a ketone body, mucus, a bacterium, gastric juice, a therapeutic agent, a nutritional supplement, and an ingestible standard. In some embodiments, the one or more analytes comprise at least one member selected from the group consisting of an alcohol, a carbohydrate, a protein, an amino acid, and a fat. In some embodiments, the one or more analytes comprise a non-absorbed standard, an indigestible standard, or a non-absorbed indigestible standard.

In some embodiments, the amino acid is selected from the group consisting of histidine, isoleucine, leucine, lysine, methionine, phenylalanine, threonine, tryptophan, valine, arginine, cysteine, glutamine, glycine, proline, serine, tyrosine, alanine, asparagine, aspartic acid, glutamic acid, selenocysteine, and a combination thereof.

In some embodiments, the carbohydrate is selected from the group consisting of glucose, fructose, galactose, xylose, sucrose, lactose, maltose, trehalose, sorbitol, mannitol, altodextrin, maltotriose, raffinose, stachyose, a fructo-oligosaccharide, amylose, an amylopectin, a modified starch, a cellulose, a hemicellulose, a pectin, a gum, a mucilage, a hydrocolloid, and a combination thereof.

In some embodiments, the fat is selected from the group consisting of oleic acid, linoleic acid, α-linolenic acid, myristic acid, myristoleic acid, palmitic acid, palmitoleic acid, oleic acid, gadoleic acid, erucic acid, nervonic acid, α-linolenic acid, docosahexaenoic acid, eicosapentaenoic acid, elaidic acid, erucic acid, linoleic acid, linoelaidic acid, sapienic acid, stearic acid, vaccenic acid, lauric acid, eicosapentaenoic acid, docosahexaenoic acid, γ-linolenic acid, stearidonic acid, paullinic acid, gondoic acid, eruic acid, nervonic acid, docosohexanoic acid, docosatetraenoic acid, and conjugated linoleic acid, or a combination thereof.

In some embodiments, the alcohol comprises ethanol.

In some embodiments, the digestion profile is indicative of calories ingested by the subject, calories absorbed by the subject, the amount of one or more analytes ingested by the subject, the amount of one or more analytes absorbed by the subject, or a combination thereof.

In some embodiments, the digestion profile is indicative of a lifestyle recommendation for the subject, a dietary recommendation for the subject, or a combination thereof. In some embodiments, the digestion profile is predictive of the effect of ingesting one or more substances by the subject. In some embodiments, the one or more analytes comprise at least two different analytes.

In some embodiments, the method further comprises operating the device to obtain the spectral data at one or more predetermined regions within the GI tract of the subject. In some embodiments, the one or more predetermined regions are selected from the mouth, the throat, the esophagus, the stomach, the small intestine, the proximal duodenum, the distal duodenum, the jejunum, the ileum, the descending colon, the ascending colon, transverse colon, the rectum, the sphincter, and the anus of the subject. In some embodiments, the obtaining the spectral data at one or more predetermined regions within the GI tract comprises operating the spectrometer to obtain spectral data based on the identified location of the device within the GI tract of the subject. In some embodiments, the obtaining the spectral data at one or more predetermined regions within the GI tract comprises attaching the device to a predetermined location within the GI tract of the subject. In some embodiments, the predetermined location within the GI tract comprises at least one location selected from the group consisting of the stomach, proximal and distal duodenum, jejunum, ileum, descending colon, ascending colon and transverse colon.

In some embodiments, the method comprises, after attaching the device, operating the spectrometer to obtain spectral data at a plurality of time points as material flows past the device in the GI tract of the subject.

In some embodiments, the spectral data comprises at least one member selected from the group consisting of absorbance spectral data, transmission spectral data, reflectance spectral data, Fourier transform spectral data and/or Raman spectral data. In some embodiments, the spectral data comprises hyperspectral data. In some embodiments, the spectral data comprises one member selected from the group consisting of ultraviolet, visible, near-infrared (NIR) or mid-infrared (MIR) spectral data. In some embodiments, the spectral data comprises NIR spectral data at one or more wavelengths between 600 nm and 2600 nm. In some embodiments, the device comprises one or more environmental sensors, and the method further comprises measuring environmental data of the GI tract external to the device in the subject. In some embodiments, the environmental data comprises one member selected from the group consisting of capacitance data, temperature data, impedance data, pH level data, heart rate data, acoustic data, image data, and movement data.

In some embodiments, generating the digestive profile for the subject comprises comparing the spectral data to one or more standard spectra. In some embodiments, generating the digestive profile for the subject comprises receiving one or more inputs from a user and generating the digestion profile based on the one or more inputs.

In some embodiments, the one or more inputs comprise information related to the subject. In some embodiments, the information relating to the subject comprises at least one member selected from the group consisting of weight, height, sex, diet, physical activity level, a medical condition, a medication, a genetic profile, a phenotypic profile, an immune profile, body mass index (BMI), race, age, tobacco use, alcohol use, heart rate, pulse, place of residence, blood glucose level, adiposity, and a microbiome profile. In some embodiments, the medical condition comprises at least one member selected from the group consisting of cancer, a metabolic disease, diabetes, irritable bowel syndrome, an inflammatory bowel disease, short bowel syndrome, a malabsorption syndrome, a bile metabolism disorder, obesity, a pancreatic insufficiency, chronic pancreatitis, epilepsy, a protein malnutrition, an allergy, and Celiac disease. In some embodiments, the one or more inputs comprise one or more criteria selected by a user. In some embodiments, the one or more criteria comprises an indication of one or more analytes, a desired outcome for the subject, or a combination thereof.

In some embodiments, the desired outcome comprises at least one outcome selected from the group consisting of losing weight, gaining weight, losing body fat, gaining body fat, losing muscle mass, gaining muscle mass, managing a medical condition, treating a medical condition, increasing absorption of a macronutrient, and decreasing absorption of a macronutrient.

In some embodiments, the method comprises transmitting the spectral data from the ingestible device to a base station and/or transmitting operating parameters from the base station to the ingestible device. In some embodiments, the method comprises transmitting the spectral data from the base station to a server, wherein the server generates the digestion profile based on the spectral data. In some embodiments, the method comprises transmitting one or more inputs to the server, wherein the server generates the digestion profile based on the spectral data and the one or more inputs.

In some embodiments, the method comprises storing the spectral data and/or the digestion profile on computer-readable memory. In some embodiments, the computer-readable memory is on the base station or on a server.

In some embodiments, the method comprises obtaining the spectral data in multiple different wavelength ranges.

In some embodiments, the method comprises identifying the location of the device within the GI tract of the subject based on the spectral data and/or environmental data, and optionally, the method comprises operating the spectrometer to obtain spectral data based on the location of the device within the GI tract of the subject.

In some embodiments, the method comprises operating the spectrometer to produce a spectrum of radiation scattered by the sample within the GI tract; and generating the digestion profile comprises: accessing a plurality of spectra corresponding to samples having different concentrations of the ingestible standard and the detection agent; determining a concentration of the ingestible standard of the sample within the GI tract as the concentration corresponding to a spectrum from among the plurality of spectra that matches the produced spectrum; and quantifying absorption of the ingestible standard in the GI tract of the subject based on the determined concentration and, at least, on a combination of an initial concentration of the ingestible standard and an initial concentration of the detection agent. In some embodiments, the detection agent comprises a fluorescent label; and the ingestible standard comprises one or more macronutrients. In some embodiments, the quantifying the absorption of the ingestible standard is performed based on Equation (3).

In some embodiments, the method comprises orally administering an ingestible standard and/or detection agent to the subject, wherein: the ingestible standard within the GI tract is an unknown macronutrient; operating the spectrometer to obtain the spectral data comprises obtaining a spectrum of light scattered by the unknown macronutrient; and generating the digestion profile comprises: accessing a plurality of spectra corresponding to respective macronutrient; and identifying the unknown macronutrient as a particular nutrient corresponding to a spectrum from among the plurality of spectra that matches the obtained spectrum.

In some embodiments, the method comprises orally administering an ingestible standard and/or detection agent to the subject, wherein: operating the spectrometer to obtain the spectral data comprises obtaining a spectrum of light scattered by the ingestible standard comprising a first macronutrient; and generating the digestion profile comprises accessing a plurality of spectra corresponding to the ingestible standard having different concentrations of the first macronutrient, and determining a concentration of the first macronutrient of the ingestible standard within the GI tract as the concentration corresponding to a spectrum from among the plurality of spectra that matches the obtained spectrum.

In some embodiments, the sample is a mixture that comprises a protein having an unknown protein concentration, and a lipid having an unknown lipid concentration; and the method comprises operating the spectrometer to obtain the spectral data, wherein obtaining the spectral data comprises obtaining a mixture-absorbance value for a particular UV wavelength, and a spectrum of light that interacted with the mixture, such that the spectrum has a visible, NIR, and/or MIR spectral range; and wherein generating the digestion profile comprises: determining the unknown lipid concentration based on the spectrum, wherein the lipid corresponds to the first macronutrient; determining, from a mapping of lipid concentration to lipid-absorbance values for the particular UV wavelength, a lipid-absorbance value corresponding to the determined lipid concentration; determining a difference between the mixture-absorbance value for the particular wavelength and the determined lipid-absorbance value; and attributing the determined difference to a protein-absorbance value for the particular wavelength, and determining, from a mapping of protein concentration to protein-absorbance values for the particular wavelength, the unknown protein concentration as corresponding to the protein-absorbance value at the particular wavelength. In some embodiments, the sample comprises a mixture, wherein the mixture comprises a protein having an unknown concentration and a lipid having an unknown concentration; wherein the method comprises operating the spectrometer to obtain the spectral data comprises obtaining: a first spectrum of light that interacts with the mixture, such that the first spectrum has a UV spectral range; and a second spectrum of light that interacts with the mixture, such that the second spectrum is in the visible, NIR, and/or MIR spectral range; and generating the digestion profile comprises: determining the unknown lipid concentration based on the second spectrum, wherein the lipid corresponds to the first macronutrient; determining, over a target subrange of the UV wavelength range, a difference spectrum as the difference between the first spectrum and a pre-stored lipid spectrum that corresponds to the determined lipid concentration; identifying a pre-stored protein spectrum that best matches the determined difference spectrum, and attributing to the unknown protein concentration a value of protein concentration corresponding to the identified pre-stored protein spectrum.

In some embodiments, the method comprises orally administering an ingestible standard and/or detection agent to the subject, wherein the method comprises operating the spectrometer to obtain the spectral data, wherein obtaining the spectral data comprises obtaining a spectrum of light scattered by the ingestible standard having traces of blood; and generating the digestion profile comprises accessing a plurality of spectra corresponding to the ingestible standard having different blood concentrations; and determining a blood concentration of the ingestible standard within the GI tract as the concentration corresponding to a spectrum from among the plurality of spectra that matches the obtained spectrum.

In some embodiments, the method comprises orally administering an ingestible standard and/or detection agent to the subject, wherein the method comprises operating the spectrometer to obtain the spectral data, wherein obtaining the spectral data comprises obtaining a spectrum of light scattered by the ingestible standard having traces of bile; and generating the digestion profile comprises accessing a plurality of spectra corresponding to the ingestible standard having different bile concentrations; and determining bile concentration of the ingestible standard within the GI tract as the concentration corresponding to a spectrum from among the plurality of spectra that matches the obtained spectrum.

In some embodiments, the method comprises using the non-absorbed indigestible marker as a relative marker to determine an amount of analyte present in the GI tract. In some embodiments, separate spectra are obtained for at least some of the different wavelength ranges. In some embodiments, a first wavelength range is in the UV spectral range, and a second wavelength range is in a spectral range selected from the group consisting of a visible spectral range, a NIR spectral range, and a mid-IR spectral range.

In some embodiments, the method comprises using the obtained data to generate qualitative information about one or more contents of the GI tract of the subject. In some embodiments, the method comprises using the obtained data to generate quantitative information about one or more contents of the GI tract of the subject. In some embodiments, the method comprises using the obtained data to generate qualitative information about one or more analytes. In some embodiments, the method comprises using the obtained data to generate quantitative information about one or more analytes.

In one aspect, provided herein is a device, comprising a spectrometer configured to generate spectral data of a sample within the gastrointestinal (GI) tract of a subject in vivo, wherein the device is an ingestible device, and the spectral data comprises information useful to determine analyte information about the presence or absence of an analyte in the sample and/or an amount of the analyte in the sample. In some embodiments, the device comprises a communications unit configured to transmit data to and/or receive operating parameters from a base station. In some embodiments, the device comprises a processing unit configured to generate the analyte information based on the spectral data.

In some embodiments, the processing unit is within the device. In some embodiments, the device is configured to communicate with a processing unit within a base station that is external to the device. In some embodiments, the device and/or the base station comprises memory configured to store the spectral data and/or the analyte information. In some embodiments, the processing unit is configured to compare the spectral data to one or more spectral standards to generate the analyte information. In some embodiments, the processing unit is configured to generate subject information based on the analyte information and one or more inputs. In some embodiments, the one or more inputs comprises information relating to the subject.

In some embodiments, the information relating to the subject comprises at least one member selected from the group consisting of weight, height, sex, diet, physical activity level, a medical condition, a medication, a genetic profile, a phenotypic profile, an immune profile, body mass index (BMI), race, age, tobacco use, alcohol use, heart rate, pulse, place of residence, blood glucose level, adiposity, and a microbiome profile. In some embodiments, the medical condition comprises at least one member selected from the group consisting of cancer, a metabolic disease, diabetes, irritable bowel syndrome, an inflammatory bowel disease, short bowel syndrome, a malabsorption syndrome, a bile metabolism disorder, obesity, a pancreatic insufficiency, chronic pancreatitis, epilepsy, a protein malnutrition, an allergy, and Celiac disease.

In some embodiments, the one or more inputs comprise one or more criteria selected by a user. In some embodiments, the one or more criteria comprises an indication of a desired outcome for the subject, a status of the subject, or a combination thereof.

In some embodiments, the processing unit is configured to search a database comprising spectral standards for a plurality of analytes. In some embodiments, the processing unit is configured to display the analyte information. In some embodiments, the processing unit is configured to display the subject information. In some embodiments, the processing unit is configured to compare information regarding one or more of the spectral standards to the analyte information to determine the amount of analyte in the subject. In some embodiments, the processing unit is configured to transmit the spectral data to a server and receive the analyte information from the server.

In some embodiments, the analyte information is based on the presence or absence of the analyte in the sample. In some embodiments, the analyte information is based on a relative or a total amount of the analyte in the sample. In some embodiments, the analyte comprises a biomolecule, a constituent of blood, a microorganism, a therapeutic agent, a drug, a biomarker, a pesticide, a pollutant, a fragment thereof, or a metabolite thereof. In some embodiments, the analyte comprises a protein, an aptamer, a nucleic acid, an amino acid, a steroid, a polysaccharide, a carbohydrate, a fat, an alcohol, a ketone, or a metabolite.

In some embodiments, the protein is selected from the group consisting of an antibody, an affimer, a cytokine, a chemokine, an enzyme, a hormone, a cancer antigen, a tissue-specific antigen, a histone, an albumin, a globulin, a scleroprotein, a phosphoprotein, a mucoprotein, a chromoprotein, a lipoprotein, a nucleoprotein, a glycoprotein, a receptor, a membrane-anchored protein, a transmembrane protein, a secreted protein, a human leukocyte antigen (HLA), a blood clotting factor, a microbial protein, and fragments thereof.

In some embodiments, the metabolite is selected from the group consisting of serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof.

In some embodiments, the microorganism is a bacterium, a virus, a prion, a protozoan, a fungus, or a parasite.

In some embodiments, the therapeutic agent is selected from the group consisting of a GLP-1 analog, an opioid, a parathyroid hormone, human growth hormone, a somatostatin, a long lasting insulin, a cancer drug, a drug that provides long-term HIV pre-exposure prophylaxis, an immunosuppressant, a TNFα inhibitor, an IL-12/IL-23 inhibitor, an IL-6 receptor inhibitor, an integrin inhibitor, a toll-like receptor (TLR) agonist, a TLR antagonist, a SMAD7 inhibitor, a JAK inhibitor, an immunosuppressant, a live biotherapeutic, a carbohydrate sulfotransferase 15 (CHST15) inhibitor, an IL-1 inhibitor, an IL-13 inhibitor, an IL-10 receptor agonist, glatiramer acetate, a CD40/CD40L inhibitor, a CD3 inhibitor, a CD14 inhibitor, a CD20 inhibitor, a CD25 inhibitor, a CD28 inhibitor, a CD49 inhibitor, a CD89 inhibitor, and a chemokine/chemokine receptor inhibitor.

In some embodiments, the protein is selected from the group consisting of actin, arp2/3, collagen, coronin, dystrophin, elastin, F-spondin, fibronectin, keratin, myosin, nebulin, pikachurin, spectrin, tau, titin, tropomyosin, tubulin, albumins, alpha globulin, beta globulin, C1-inhibitor, C3-convertase, cadherin, carboxypeptidase, C-reactive protein, ependymin, Factor VIII, Factor XIII, fibrin, fibrinogen, gamma globulin, hemoglobin, IgA, IgD, IgE, IgG, IgM, integrin, myoglobin, NCAM, Protein C, Protein S, Protein Z, Protein Z-related protease inhibitor, selectin, serum albumin, serum Amyloid P Component, thrombin, Von Willebrand Factor, CFTR, C-myc, estrogen receptor, FOXP2, FOXP3, glucose transporter, glycophorin D, histones, hydrolases, muscarinic acetylcholine receptor, MyoD, nicotinic acetylcholine receptor, oxidoreductases, P53, potassium channel, rhodopsin, scramblase and transferases, TNFα, lipoteichoic acid (LTA), lipopolysaccharide (LPS), lipopolysaccharide binding protein (LBP), a cytokine, a chemokine, IL12/23, IL-6, IL-10, MADCAM, α4γ7 integrin, hepatocyte growth factor (HGF), epidermal growth factor (EGF), heparin-binding epidermal growth factor (HB-EGF), TGFβ, adalimumab, infliximab, certolizumab pegol, vedolizumab, natalizumab, golimumab, bevacizumab, cetuximab, and combinations thereof.

In some embodiments, the carbohydrate is selected from the group consisting of glucose, fructose, galactose, xylose, sucrose, lactose, maltose, trehalose, sorbitol, mannitol, altodextrin, maltotriose, raffinose, stachyose, a fructo-oligosaccharide, amylose, an amylopectin, a modified starch, a cellulose, a hemicellulose, a pectin, a gum, a mucilage, a hydrocolloid, and a combination thereof.

In some embodiments, the fat is selected from the group consisting of oleic acid, linoleic acid, α-linolenic acid, myristic acid, myristoleic acid, palmitic acid, palmitoleic acid, oleic acid, gadoleic acid, erucic acid, nervonic acid, α-linolenic acid, docosahexaenoic acid, eicosapentaenoic acid, elaidic acid, erucic acid, linoleic acid, linoelaidic acid, sapienic acid, stearic acid, vaccenic acid, lauric acid, eicosapentaenoic acid, docosahexaenoic acid, γ-linolenic acid, stearidonic acid, paullinic acid, gondoic acid, eruic acid, nervonic acid, docosohexanoic acid, docosatetraenoic acid, and conjugated linoleic acid, or a combination thereof.

In some embodiments, the alcohol comprises ethanol. In some embodiments, the amino acid comprises at least one member selected from the group consisting of histidine, isoleucine, leucine, lysine, methionine, phenylalanine, threonine, tryptophan, valine, arginine, cysteine, glutamine, glycine, proline, serine, tyrosine, alanine, asparagine, aspartic acid, glutamic acid and selenocysteine.

In some embodiments, the constituent of blood comprises hemoglobin or a blood cell.

In some embodiments, the analyte comprises a bile acid or a bile acid salt. In some embodiments, the analyte comprises an antibiotic.

In some embodiments, the analyte is associated with a disease, a disorder, or a pathogen.

In some embodiments, the analyte comprises acetoacetate, beta-hydroxybutyrate, acetone, or a combination thereof.

In some embodiments, the analyte information is indicative that the subject has or is at risk of developing a disease or disorder. In some embodiments, the analyte information is indicative of the amount of analyte ingested, absorbed, or metabolized by the subject.

In some embodiments, the device comprises a processing unit configured to generate a drug absorbance profile based on the spectral data. In some embodiments, the processing unit is within the device. In some embodiments, the device is configured to communicate with a processing unit within a base station that is external to the device. In some embodiments, the device and/or the base station comprises memory configured to store the spectral data and/or the drug absorbance profile. In some embodiments, the processing unit is configured to compare the spectral data to one or more spectral standards to generate the drug absorbance profile. In some embodiments, the processing unit is configured to generate the drug absorbance profile based on one or more inputs.

In some embodiments, the one or more inputs comprise information relating to the subject. In some embodiments, the information relating to the subject comprises at least one member selected from the group consisting of weight, height, sex, diet, physical activity level, a medical condition, a medication, a genetic profile, a phenotypic profile, an immune profile, body mass index (BMI), race, age, tobacco use, alcohol use, heart rate, pulse, place of residence, blood glucose level, adiposity, and a microbiome profile. In some embodiments, the medical condition comprises at least one member selected from the group consisting of cancer, a metabolic disease, diabetes, irritable bowel syndrome, an inflammatory bowel disease, short bowel syndrome, a malabsorption syndrome, a bile metabolism disorder, obesity, a pancreatic insufficiency, chronic pancreatitis, epilepsy, a protein malnutrition, an allergy, and Celiac disease.

In some embodiments, the one or more inputs comprise one or more criteria selected by a user. In some embodiments, the one or more criteria comprise an indication of one or more analytes, a desired outcome, or a combination thereof. In some embodiments, the desired outcome comprises at least one member selected from the group consisting of a safe dosage regimen of a therapeutic agent for the subject, an effective dosage regimen of a therapeutic agent for the subject, a response to therapy for the subject based on a determined presence of a biomarker in the GI tract of the subject, and a response to therapy based on a determined amount of a biomarker in the GI tract of the subject.

In some embodiments, the processing unit is configured to search a database comprising a plurality of drug absorbance profiles and identify an individual or a group of individuals with drug absorbance profiles similar to the drug absorbance profile for the subject. In some embodiments, the processing unit is configured to display information regarding the individual or the plurality of individuals identified as having drug absorbance profiles similar to the drug absorbance profile for the subject. In some embodiments, the processing unit is configured to add information regarding the individual or the plurality of individuals identified as having drug absorbance profiles similar to the digestion profile for the subject.

In some embodiments, the processing unit is configured to transmit the spectral data to a server and receive the drug absorbance profile for the subject from the server.

In some embodiments, the drug absorbance profile is indicative of the presence or absence of the analyte in the sample. In some embodiments, the drug absorbance profile is indicative of a relative or a total amount of the analyte in the sample. In some embodiments, the analyte comprises one or more therapeutic agents. In some embodiments, the one or more therapeutic agents comprise a GLP-1 analog, an opioid, a parathyroid hormone, human growth hormone, a somatostatin, a long lasting insulin, a cancer drug, a drug that provides long-term HIV pre-exposure prophylaxis, an immunosuppressant, a TNFα inhibitor, an IL-12/IL-23 inhibitor, an IL-6 receptor inhibitor, an integrin inhibitor, a toll-like receptor (TLR) agonist, a TLR antagonist, a SMAD7 inhibitor, a JAK inhibitor, an immunosuppressant, a live biotherapeutic, a carbohydrate sulfotransferase 15 (CHST15) inhibitor, an IL-1 inhibitor, an IL-13 inhibitor, an IL-10 receptor agonist, glatiramer acetate, a CD40/CD40L inhibitor, a CD3 inhibitor, a CD14 inhibitor, a CD20 inhibitor, a CD25 inhibitor, a CD28 inhibitor, a CD49 inhibitor, a CD89 inhibitor, or a chemokine/chemokine receptor inhibitor. In some embodiments, the one or more therapeutic agents comprise an analgesic drug, an antibiotic drug, an anticoagulant drug, an antidepressant drug, an anticancer drug, an antiepileptic drug, an anti-inflammatory drug, an antipsychotic drug, an antiviral drug, a sedative drug, or an antidiabetic drug. In some embodiments, the one or more therapeutic agents comprise a diuretic drug, a cholinergic drug, a dopaminergic drug, a GABAergic drug, or a serotonergic drug. In some embodiments, the one or more therapeutic agents comprise a 5-alpha-reductase inhibitor, an angiotensin II receptor antagonist, an ACE inhibitor, an alpha-adrenergic agonist, a beta blocker, a dopamine agonist, a dopamine antagonist, an incretin mimetic, a non-steroidal anti-inflammatory drug—cyclooxygenase inhibitor, a proton-pump inhibitor, a renin inhibitor, a selective glucocorticoid receptor modulator, a selective serotonin reuptake inhibitor, or a statin. In some embodiments, the one or more therapeutic agents comprise a β-lactam antibiotic, a benzodiazepine, a cardiac glycoside, a fibrate, or a thiazide diuretic. In some embodiments, the one or more therapeutic agents comprise at least one therapeutic agent selected from the group consisting of a TNFα inhibitor, an IL-6R inhibitor, an integrin inhibitor, a TLR3 agonist, a TLR agonist that binds and activates TLR4, a TLR agonist that binds and activates TLR5, a TLR agonist that binds and activates TLR7/8, a TLR agonist that binds and activates TLR9, a TLR agonist that is a bacterial or viral component, a SMAD7 inhibitor, a JAK inhibitor, a low molecular weight immunosuppressant, a corticosteroid, a cytostatic, a calcineurin inhibitor, an mTOR inhibitor, a CHST15 inhibitor, an IL-1 inhibitor, an IL-13 inhibitor, IL-10, an IL-10 agonist, a CD40/CD40L inhibitor, glatiramer acetate, and a stem cell.

In some embodiments, the device comprises a processing unit configured to generate biomarker data for the subject based on the spectral data. In some embodiments, the processing unit is within the device. In some embodiments, the device is configured to communicate with a processing unit within a base station that is external to the device. In some embodiments, the device and/or the base station comprises memory configured to store the spectral data and/or the biomarker data. In some embodiments, the processing unit is configured to compare the spectral data to one or more spectral standards to generate the biomarker data. In some embodiments, the processing unit is configured to generate the biomarker data based on one or more inputs.

In some embodiments, the one or more inputs comprise information relating to the subject. In some embodiments, the information relating to the subject comprises at least one member selected from the group consisting of weight, height, sex, diet, physical activity level, a medical condition, a medication, a genetic profile, a phenotypic profile, an immune profile, body mass index (BMI), race, age, tobacco use, alcohol use, heart rate, pulse, place of residence, blood glucose level, adiposity, and a microbiome profile. In some embodiments, the medical condition comprises at least one member selected from the group consisting of cancer, a metabolic disease, diabetes, irritable bowel syndrome, an inflammatory bowel disease, short bowel syndrome, a malabsorption syndrome, a bile metabolism disorder, obesity, a pancreatic insufficiency, chronic pancreatitis, epilepsy, a protein malnutrition, an allergy, and Celiac disease.

In some embodiments, the one or more inputs comprise one or more criteria selected by a user. In some embodiments, the one or more criteria comprise an indication of one or more analytes, a desired outcome, or a combination thereof. In some embodiments, the desired outcome comprises at least one member selected from the group consisting of a safe dosage regimen of a therapeutic agent for the subject, an effective dosage regimen of a therapeutic agent for the subject, a response to therapy for the subject based on a determined presence of a biomarker in the GI tract of the subject, and a response to therapy based on a determined amount of a biomarker in the GI tract of the subject. In some embodiments, the processing unit is configured to search a database comprising a plurality of biomarker data and identify an individual or a group of individuals with biomarker data similar to the biomarker data for the subject. In some embodiments, the processing unit is configured to display information regarding the individual or the plurality of individuals identified as having biomarker data similar to the biomarker data for the subject. In some embodiments, the processing unit is configured to add information regarding the individual or the plurality of individuals identified as having biomarker data similar to the biomarker data for the subject.

In some embodiments, the processing unit is configured to transmit the spectral data to a server and receive the biomarker data for the subject from the server. In some embodiments, the biomarker data is indicative of the presence or absence of the analyte in the sample, and the analyte comprises a biomarker. In some embodiments, the spectral data are spectral data corresponding to a biomarker. In some embodiments, the presence or absence of the one or more biomarkers is indicative of a disease, an infection, an environmental exposure, or a combination thereof.

In some embodiments, the one or more biomarkers comprise a biomarker for a GI disorder. In some embodiments, the one or more biomarkers comprise a biomarker selected from then group consisting of interferon-γ, IL-1α, IL-6, IL-22, IL-17A, TNFα, IL-2, memory cells (CD44$^+$ CD45RB$^-$CD4$^+$ cells), and α4γ7 integrin. In some embodiments, the one or more biomarkers comprise a biomarker selected from the group consisting of anti-glycan, anti-*Saccharomyces cerevisiae*, anti-laminaribioside, anti-chitobioside, anti-mannobioside, anti-laminarin, anti-chitin antibodies, anti-outer membrane porin C, anti-Cbir1 flagellin, anti-I2 antibody, autoantibodies targeting the exocrine pancreas, perinuclear anti-neutrophil antibody, and calprotectin. In some embodiments, the one or more biomarkers comprise a biomarker selected from the group consisting of phospho STAT 1, STAT 3, STAT 5, VEGF, VCAM, ICAM, and IL-6. In some embodiments, the one or more biomarkers comprise an immunoglobulin or a fragment thereof. In some embodiments, the immunoglobulin is selected from the group consisting of immunoglobulin M (IgM), immunoglobulin D (IgD), immunoglobulin G (IgG), immunoglobulin E (IgE), and immunoglobulin A (IgA).

In some embodiments, the biomarker is selected from the group consisting of group consisting of an anti-Fla1 antibody, anti-Fla2 antibody, anti-FlaA antibody, anti-FliC antibody, anti-FliC2 antibody, anti-FliC3 antibody, anti-YBaN1 antibody, anti-ECFliC antibody, anti-EcOFliC antibody, anti-SeFljB antibody, anti-CjFlaA antibody, anti-CjFlaB antibody, anti-SfFliC antibody, anti-CjCgtA antibody, anti-Cjdmh antibody, anti-CjGT-A antibody, anti-EcYidX antibody, anti-EcEra antibody, anti-EcFrvX antibody, anti-EcGabT antibody, anti-EcYedK antibody, anti-EcYbaN antibody, anti-EcYhgN antibody, anti-RtMaga antibody, anti-RbCpaF antibody, anti-RgPilD antibody, anti-LaFrc antibody, anti-LaEno antibody, anti-LjEFTu antibody, anti-BfOmpa antibody, anti-PrOmpA antibody, anti-Cp10bA antibody, anti-CpSpA antibody, anti-EfSant antibody, anti-LmOsp antibody, anti-SfET-2 antibody, anti-Cpatox antibody, anti-Cpbtox antibody, anti-EcSta2 antibody, anti-EcOStx2A antibody, anti-CjcdtB/C antibody, anti-CdTcdA/B antibody, and combinations thereof.

In some embodiments, the device is configured to generate the spectral data at a predetermined region within the GI tract of the subject. In some embodiments, the predetermined region within the GI tract of the subject is selected from the group consisting of the mouth, the throat, the esophagus, the stomach, the small intestine, the proximal duodenum, the distal duodenum, the jejunum, the ileum, the descending colon, the ascending colon, transverse colon, the rectum, the sphincter, and the anus of the subject.

In some embodiments, the device is operable to generate the spectral data at a plurality of time points as the device travels through the GI tract of the subject.

In some embodiments, the processing unit is configured to generate a plurality of digestion profiles at a plurality of time points as the device travels through the GI tract of the subject.

In some embodiments, the spectrometer comprises at least one member selected from the group consisting of a light source, a photodetector, a dispersive element, a lens, and a filter. In some embodiments, the spectrometer is configured to generate at least one member selected from the group consisting of absorbance spectral data, transmission spectral data, reflectance spectral data, Fourier transform spectral data, and Raman spectral data.

In some embodiments, the device comprises a plurality of spectrometers configured to generate different types of spectral data.

In some embodiments, the spectrometer comprises a light source and a photodetector defining a light path through a detection chamber.

In some embodiments, the sample is a fluid sample, and the device comprises one or more ports, valves and/or pumps to control transfer of the fluid sample from the GI tract into the detection chamber.

In some embodiments, the spectrometer comprises a light source and a photodetector positioned on the exterior of the device. In some embodiments, the light source is configured to transmit light radially towards an environment external to the device, and the photodetector is configured to detect a radial reflectance from the environment external to the device. In some embodiments, the light source is adjacent to the photodetector.

In some embodiments, the spectral data comprises at least one member selected from the group consisting of ultraviolet spectral data, visible spectral data, near-infrared (NIR) spectral data, and mid-infrared (MIR) spectral data. In some embodiments, the spectral data comprises NIR spectral data. In some embodiments, the NIR spectral data comprises absorbance or reflectance data at one or more wavelengths between 600 nm and 2600 nm. In some embodiments, the spectral data comprises MIR spectral data. In some embodiments, the MIR spectral data comprises absorbance or reflectance data at one or more wavelengths between 1500 nm and 5600 nm.

In some embodiments, the spectrometer comprises a 2-dimensional array of photodetectors. In some embodiments, the spectral data comprises hyperspectral data. In some embodiments, the spectrometer comprises a hyperspectral camera.

In some embodiments, the processing unit is configured to compare the hyperspectral data to one or more spectral standards.

In some embodiments, the device further comprises one or more environmental sensors for measuring environmental data external to the device. In some embodiments, the one or more environmental sensors comprises at least one member selected from the group consisting of a capacitance sensor, a temperature sensor, an impedance sensor, a pH level sensor, a heart rate sensor, acoustic sensor, reflected visible light sensor, image sensor, and a movement sensor. In some embodiments, the one or more environmental sensors comprises a movement sensor, wherein the movement sensor comprises a step sensor. In some embodiments, the image sensor comprises a video camera.

In some embodiments, the processing unit is configured to generate the digestion profile, the drug absorption profile, or the biomarker data based on the spectral data and the environmental data. In some embodiments, the processing unit is configured to compare the environmental data to one or more environmental data standards.

In some embodiments, the processing unit is configured to identify a location of the device within the GI tract of the subject based on the spectral data. In some embodiments, the processing unit is configured to identify a location of the device within the GI tract of the subject based on the spectral data, the environmental data, or a combination thereof. In some embodiments, the processing unit is configured to identify a location of the device within the GI tract of the subject based on reflected visible light.

In some embodiments, the device is configured to attach to the GI tract of the subject in vivo. In some embodiments, the device is configured to releasably attach to the GI tract of the subject at one or more predetermined locations. In some embodiments, the device is attachable to the GI tract of the subject using an adhesive, negative pressure, a fastener, or a combination thereof. In some embodiments, the device is static within the GI tract relative to material passing through the GI tract of the subject and the spectrometer is configured to generate spectral data at predetermined time intervals.

In some embodiments, the device comprises a microcontroller configured to operate the spectrometer to generate the spectral data, and optionally wherein the processing unit is the microcontroller. In some embodiments, the microcontroller is configured to operate the one or more environmental sensors to generate the environmental data. In some embodiments, the microcontroller is configured to operate the spectrometer to generate the spectral data and/or environmental data based on the location of the device within the GI tract of the subject.

In some embodiments, the sample is a fluid sample within the GI tract of the subject. In some embodiments, the fluid sample does not comprise tissue from the GI tract of the subject.

In some embodiments, the device is in the shape of a capsule.

In some embodiments, the ingestible device, comprises: a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device has an opening between an interior of the ingestible device and an exterior of the ingestible device, and the ingestible device comprises: a chamber; and a multi-stage valve system in the interior of the ingestible device, wherein: the multi-stage valve system has first, second and third states, the first state of the multi-stage valve system is different from the second and third states of the multi-stage valve system; the second state of the multi-stage valve system is different from the first and third states of the multi-stage valve system; when the multi-stage valve system is in its first state, the opening prevents fluid communication between the interior of the ingestible device and the exterior of the ingestible device; when the multi-stage valve system is in its second state, the opening allows fluid communication between the interior of the ingestible device and the exterior of the ingestible device; and when the multi-stage valve system is in its third state, the opening prevents fluid communication between the interior of the ingestible device and the exterior of the ingestible device.

In some embodiments, the ingestible device has an opening between an interior of the ingestible device and an exterior of the ingestible device, and the ingestible device comprises a chamber; and a multi-stage valve system in the interior of the ingestible device, wherein: the multi-stage valve system comprises an actuator system comprising a first member; a trigger comprising a first peg and a first lip; a gate comprising a protrusion, and a gate leg having an opening; and a biasing system comprising first and second biasing members; when the multi-stage valve system is in a first stage: the first biasing member applies a force to the trigger so that the first peg contacts the first member; the first member opposes the force applied to the trigger by the first biasing member; the second biasing member applies a force to the gate so that the protrusion contacts the first lip; the first lip opposes the force applied to the gate by the second biasing member; and the opening in the gate leg is not aligned with the opening in the ingestible device.

In some embodiments, the ingestible device has an opening between an interior of the ingestible device and an exterior of the ingestible device, and the ingestible device comprises a chamber; and a sampling system in the interior of the ingestible device, wherein: the sampling system comprises: a first absorbent member; and a second absorbent member different from the first absorbent member; and the sampling system is configured so that fluid that flows from the exterior of the ingestible device to the interior of the ingestible device enters the first absorbent member; and the sampling system is configured to allow fluid to flow from the first absorbent member to the second absorbent member.

In some embodiments, the device has an opening between an interior of the ingestible device and an exterior of the ingestible device, and the ingestible device comprises a chamber; and a sampling system in the interior of the ingestible device configured to absorb a fluid that enters the interior of the ingestible device via the opening, the sampling system comprising an absorbent member and at least one preservative at least partially absorbed in the absorbent member.

In some embodiments, the ingestible device comprises: a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device comprises: a housing defined by a first end, a second end substantially opposite from the first end, a wall extending longitudinally from the first end to the second end, and an opening; a sampling chamber within the housing, wherein the sampling chamber contains an absorptive material; an inlet port connecting the opening in the housing to the sampling chamber; a single use sealing device positioned within the inlet port that seals the inlet port; and a heating element proximate to the single use sealing device, wherein: the heating element is configured to apply heat to the single use sealing device to unseal the inlet port and open the sampling chamber, and at least a portion of the absorptive material proximate to the inlet port is configured to expand when in contact with a sample and reseal the inlet port.

In some embodiments, the ingestible device comprises: a housing defined by a first end, a second end substantially opposite from the first end, a wall extending longitudinally from the first end to the second end, and an opening; a sampling chamber within the housing having an entry port and an exit port on an opposite end of the sampling chamber from the entry port, wherein the exit port is configured to allow gas to exit the chamber and prevent at least a portion of a sample from exiting the chamber; an inlet region connecting the opening in the housing to the entry port of the sampling chamber; and a moveable valve positioned to open and close the inlet region, wherein: the moveable valve in an open position allows the sample to enter the sampling chamber; and the moveable valve in a closed position prevents the sample from entering the sampling chamber.

In some embodiments, the device comprises one or more processing devices; and one more machine readable hardware storage devices storing instructions that are executable by the one or more processing devices to determine a location of the ingestible device in a region of a GI tract of a subject to an accuracy of at least 85%.

In some embodiments, the device comprises one or more processing devices; and one more machine readable hardware storage devices storing instructions that are executable by the one or more processing devices to determine that the ingestible device is in the cecum of a subject to an accuracy of at least 70%.

In some embodiments, the device comprises one or more processing devices; and one more machine readable hardware storage devices storing instructions that are executable by the one or more processing devices to transmit data to a device capable of implementing the data to determine a location of the medical device in a region of a GI tract of a subject to an accuracy of at least 85%.

In some embodiments, the device comprises one or more processing devices; and one more machine readable hardware storage devices storing instructions that are executable by the one or more processing devices to transmit data to an external device capable of implementing the data to determine that the ingestible device is in the cecum of a subject to an accuracy of at least 70%.

In some embodiments, the device comprises first and second light sources, wherein the first light source is configured to emit light at a first wavelength, and the second light source is configured to emit light at a second wavelength different from the first wavelength. In some embodiments, the device comprises first and second detectors, wherein the first detector is configured to detect light at the first wavelength, and the second detector is configured to detect light at the second wavelength.

In one aspect, provided herein is a kit, comprising: a device provided herein; and at least one ingestible standard, at least one detection agent, or a combination thereof. In some embodiments, the ingestible standard comprises a predetermined quantity of at least one analyte or at least one therapeutic agent. In some embodiments, the detection agent is configured to selectively bind to one or more analytes. In some embodiments, the detection agent comprises a fluorescent label.

In some embodiments, the fluorescent label comprises Fast Green FCF dye (Green #3) or Brilliant Blue FCF (Blue #1) dye.

In one aspect, provided herein is a system, comprising: an ingestible device which comprises a spectrometer configured to generate spectral data of a sample within the gastrointestinal (GI) tract of a subject in vivo; and a processing unit configured to generate subject information about the subject, wherein the sample comprises an analyte, the spectral data comprises information useful to determine analyte information about the presence or absence of an analyte in the sample and/or an amount of the analyte in the sample, and the subject information is based on the spectral data. In some embodiments, the system comprises a communications unit. In some embodiments, the system comprises memory configured to store the spectral data, the subject information, or a combination thereof. In some embodiments, the system is configured to generate a display to a user.

In some embodiments, the system comprises an interface configured to allow a user to configure the processing unit to generate the subject information based on one or more inputs. In some embodiments, the one or more inputs comprise additional information relating to the subject. In some embodiments, the additional information relating to the subject comprises at least one member selected from the group consisting of weight, height, sex, diet, physical activity level, a medical condition, a medication, a genetic profile, a phenotypic profile, an immune profile, body mass index (BMI), race, age, tobacco use, alcohol use, heart rate, pulse, place of residence, blood glucose level, adiposity, and a microbiome profile. In some embodiments, the additional information relating to the subject comprises at least one medical condition selected from the group consisting of cancer, a metabolic disease, diabetes, irritable bowel syndrome, an inflammatory bowel disease, short bowel syndrome, a malabsorption syndrome, a bile metabolism disorder, obesity, a pancreatic insufficiency, chronic pancreatitis, epilepsy, a protein malnutrition, an allergy, and Celiac disease.

In some embodiments, the one or more inputs comprise one or more criteria selected by the user. In some embodiments, the one or more criteria comprises an indication of a desired outcome for the subject, a status of the subject, or a combination thereof. In some embodiments, the desired outcome comprises at least one member selected from the group consisting of a safe dosage regimen of a drug for the subject, an effective dosage regimen of a drug for the subject, a response to therapy for the subject based on a determined presence of a biomarker in the GI tract of the subject, and a response to therapy based on a determined amount of a biomarker in the GI tract of the subject.

In some embodiments, the processing unit is configured to search a database comprising spectral standards for a plurality of analytes. In some embodiments, the processing unit is configured to display the analyte information. In some embodiments, the processing unit is configured to compare information regarding one or more of the spectral standards to the analyte information to determine the amount of analyte in the subject.

In some embodiments, the subject information is based on the presence or absence of the analyte in the sample, and/or based on a relative amount or a total amount of the analyte in the sample.

In some embodiments, the communications unit is configured to transmit data from the ingestible device to a base station and/or to transmit operating parameters from the base station to the ingestible device. In some embodiments, at least one member selected from the group consisting of the processing unit, memory, display and interface is within a base station. In some embodiments, the base station is a computer or a personal electronic device. In some embodiments, the personal electronic device is selected from the group consisting of a watch, a phone, a tablet, a fitness monitor, and a physical activity tracker.

In some embodiments, the processing unit is configured to transmit the spectral data to a server and to receive the analyte information from the server.

In some embodiments, the ingestible device comprises a device as described herein.

In one aspect, provided herein is a method, comprising obtaining spectral data for at least one sample within the gastrointestinal (GI) tract of a subject in vivo, the spectral data comprising information about the presence or absence of an analyte in the sample and/or an amount of the analyte in the sample; and using the spectral data to determine subject information about the subject. In some embodiments, the method comprises using an ingestible device comprising a spectrometer to obtain the spectral data. In some embodiments, the method comprises administering the ingestible device to the subject.

In some embodiments, the method comprises administering to the subject an ingestible device comprising a spectrometer configured to generate the spectral data of the sample; operating the device to obtain spectral data for at least one sample within the GI tract of the subject; and generating a subject information for the subject based on the spectral data obtained by the device. In some embodiments, the device is administered orally to the subject.

In some embodiments, the method comprises administering at least one analyte, at least one detection agent, or a combination thereof, to the subject. In some embodiments, the at least one analyte, at least one detection agent, or a combination thereof, is administered to the subject before the device is administered to the subject. In some embodiments, the at least one analyte, at least one detection agent, or a combination thereof, is administered to the subject concurrently with the device. In some embodiments, the at least one analyte, at least one detection agent, or a combination thereof, is administered to the subject after the device is administered to the subject. In some embodiments, the method comprises administering a predetermined quantity of at least one analyte to the subject.

In some embodiments, the at least one analyte comprises a biomolecule, a constituent of blood, a microorganism, a therapeutic agent, a biomarker, a pesticide, a pollutant, a fragment thereof, or a metabolite thereof. In some embodiments, the at least one analyte comprises a protein, an aptamer, a nucleic acid, an amino acid, a steroid, a polysaccharide, a carbohydrate, a fat, an alcohol, a ketone, or a metabolite.

In some embodiments, the method comprises administering a non-absorbed marker, an indigestible marker, or a non-absorbed indigestible marker to the subject. In some embodiments, the detection agent is configured to selectively bind to one or more analytes. In some embodiments, the detection agent comprises an antibody. In some embodiments, the detection agent comprises an antibiotic.

In some embodiments, the subject information is indicative of the presence or absence of the analyte in the sample. In some embodiments, the subject information is indicative of a relative or a total amount of the analyte in the sample.

In some embodiments, the analyte comprises a biomolecule, a constituent of blood, a microorganism, a therapeutic agent, a biomarker, a pesticide, a pollutant, a fragment thereof, or a metabolite thereof. In some embodiments, the analyte comprises a protein, an aptamer, a nucleic acid, an amino acid, a steroid, a polysaccharide, a carbohydrate, a fat, an alcohol, a ketone, or a metabolite.

In some embodiments, the protein is selected from the group consisting of an antibody, an affimer, a cytokine, a chemokine, an enzyme, a hormone, a cancer antigen, a tissue-specific antigen, a histone, an albumin, a globulin, a scleroprotein, a phosphoprotein, a mucoprotein, a chromoprotein, a lipoprotein, a nucleoprotein, a glycoprotein, a receptor, a membrane-anchored protein, a transmembrane protein, a secreted protein, a human leukocyte antigen (HLA), a blood clotting factor, a microbial protein, and fragments thereof.

In some embodiments, the constituent of blood comprises hemoglobin or a blood cell.

In some embodiments, the metabolite is selected from the group consisting of serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof.

In some embodiments, the microorganism is a bacterium, a virus, a prion, a protozoan, a fungus, or a parasite.

In some embodiments, the therapeutic agent is selected from the group consisting of a GLP-1 analog, an opioid, a parathyroid hormone, human growth hormone, a somatostatin, a long lasting insulin, a cancer drug, a drug that provides long-term HIV pre-exposure prophylaxis, an immunosuppressant, a TNFα inhibitor, an IL-12/IL-23 inhibitor, an IL-6 receptor inhibitor, an integrin inhibitor, a toll-like receptor (TLR) agonist, a TLR antagonist, a SMAD7 inhibitor, a JAK inhibitor, an immunosuppressant, a live biotherapeutic, a carbohydrate sulfotransferase 15 (CHST15) inhibitor, an IL-1 inhibitor, an IL-13 inhibitor, an IL-10 receptor agonist, glatiramer acetate, a CD40/CD40L inhibitor, a CD3 inhibitor, a CD14 inhibitor, a CD20 inhibitor, a CD25 inhibitor, a CD28 inhibitor, a CD49 inhibitor, a CD89 inhibitor, and a chemokine/chemokine receptor inhibitor.

In some embodiments, the protein is selected from the group consisting of actin, arp2/3, collagen, coronin, dystrophin, elastin, F-spondin, fibronectin, keratin, myosin, nebulin, pikachurin, spectrin, tau, titin, tropomyosin, tubulin, albumins, alpha globulin, beta globulin, C1-inhibitor, C3-convertase, cadherin, carboxypeptidase, C-reactive protein, ependymin, Factor VIII, Factor XIII, fibrin, fibrinogen, gamma globulin, hemoglobin, IgA, IgD, IgE, IgG, IgM, integrin, myoglobin, NCAM, Protein C, Protein S, Protein Z, Protein Z-related protease inhibitor, selectin, serum albumin, serum Amyloid P Component, thrombin, Von Willebrand Factor, CFTR, C-myc, estrogen receptor, FOXP2, FOXP3, glucose transporter, glycophorin D, histones, hydrolases, muscarinic acetylcholine receptor, MyoD, nicotinic acetylcholine receptor, oxidoreductases, P53, potassium channel, rhodopsin, scramblase and transferases. TNFα, lipoteichoic acid (LTA), lipopolysaccharide (LPS), lipopolysaccharide binding protein (LBP), a cytokine, a chemokine, IL12/23, IL-6, IL-10, MADCAM, α4γ7 integrin, hepatocyte growth factor (HGF), epidermal growth factor (EGF), heparin-binding epidermal growth factor (HB-EGF), TGFβ, adalimumab, infliximab, certolizumab pegol, vedolizumab, natalizumab, golimumab, bevacizumab, cetuximab, and combinations thereof.

In some embodiments, the carbohydrate is selected from the group consisting of glucose, fructose, galactose, xylose, sucrose, lactose, maltose, trehalose, sorbitol, mannitol, altodextrin, maltotriose, raffinose, stachyose, a fructo-oligosaccharide, amylose, an amylopectin, a modified starch, a cellulose, a hemicellulose, a pectin, a gum, a mucilage, a hydrocolloid, and a combination thereof.

In some embodiments, the fat is selected from the group consisting of oleic acid, linoleic acid, α-linolenic acid, myristic acid, myristoleic acid, palmitic acid, palmitoleic acid, oleic acid, gadoleic acid, erucic acid, nervonic acid, α-linolenic acid, docosahexaenoic acid, eicosapentaenoic acid, elaidic acid, erucic acid, linoleic acid, linoelaidic acid, sapienic acid, stearic acid, vaccenic acid, lauric acid, eicosapentaenoic acid, docosahexaenoic acid, γ-linolenic acid, stearidonic acid, paullinic acid, gondoic acid, eruic acid, nervonic acid, docosohexanoic acid, docosatetraenoic acid, and conjugated linoleic acid, or a combination thereof.

In some embodiments, the alcohol comprises ethanol.

In some embodiments, the amino acid comprises at least one member selected from the group consisting of histidine, isoleucine, leucine, lysine, methionine, phenylalanine, threonine, tryptophan, valine, arginine, cysteine, glutamine, glycine, proline, serine, tyrosine, alanine, asparagine, aspartic acid, glutamic acid and selenocysteine.

In some embodiments, the analyte comprises acetoacetate, beta-hydroxybutyrate, acetone, or a combination thereof. In some embodiments, the analyte comprises a bile acid or a bile acid salt. In some embodiments, the analyte comprises an antibiotic. In some embodiments, the analyte is associated with a disease, a disorder, or a pathogen.

In some embodiments, the subject information is indicative that the subject has or is at risk of developing a disease or disorder. In some embodiments, the subject information is indicative of the amount of analyte ingested, absorbed, or metabolized by the subject.

In some embodiments, the analyte is an unknown therapeutic agent, and wherein the method further comprises operating the spectrometer to obtain the spectral data; the spectral data is obtained by obtaining a spectrum of light scattered by the unknown drug, and the subject information is determined by: accessing a plurality of spectra corresponding to different therapeutic agents, and identifying the unknown therapeutic agent corresponding to a spectrum from among the plurality of spectra that matches the obtained spectrum. In some embodiments, the unknown therapeutic agent is selected from the group consisting of a GLP-1 analog, an opioid, a parathyroid hormone, human growth hormone, a somatostatin, a long lasting insulin, a cancer drug, a drug that provides long-term HIV pre-exposure prophylaxis, an immunosuppressant, a TNFα inhibitor, an IL-12/IL-23 inhibitor, an IL-6 receptor inhibitor, an integrin inhibitor, a toll-like receptor (TLR) agonist, a TLR antagonist, a SMAD7 inhibitor, a JAK inhibitor, an immunosuppressant, a live biotherapeutic, a carbohydrate sulfotransferase 15 (CHST15) inhibitor, an IL-1 inhibitor, an IL-13 inhibitor, an IL-10 receptor agonist, glatiramer acetate, a CD40/CD40L inhibitor, a CD3 inhibitor, a CD14 inhibitor, a CD20 inhibitor, a CD25 inhibitor, a CD28 inhibitor, a CD49 inhibitor, a CD89 inhibitor, and a chemokine/chemokine receptor inhibitor, an anti-inflammatory drug, and an angiotensin converting enzyme (ACE) inhibitor.

In some embodiments, the method further comprises operating the spectrometer to obtain the spectral data, wherein the spectral data is obtained by obtaining a spectrum of light scattered by the analyte, and wherein the subject information is determined by: accessing a plurality of spectra corresponding to the analyte at different concentrations; and determining a concentration of the analyte as the concentration corresponding to the spectrum from among the plurality of spectra that matches the obtained spectrum. In some embodiments, the analyte comprises a biomolecule, a constituent of blood, a microorganism, a therapeutic agent, a biomarker, a pesticide, a pollutant, a protein, an aptamer, a nucleic acid, an amino acid, a steroid, a polysaccharide, a carbohydrate, a fat, an alcohol, a ketone, a fragment thereof, or a metabolite thereof. In some embodiments, the analyte comprises a therapeutic agent. In some embodiments, therapeutic agent is selected from the group consisting of a GLP-1 analog, an opioid, a parathyroid hormone, human growth hormone, a somatostatin, a long lasting insulin, a cancer drug, a drug that provides long-term HIV pre-exposure prophylaxis, an immunosuppressant, a TNFα inhibitor, an IL-12/IL-23 inhibitor, an IL-6 receptor inhibitor, an integrin inhibitor, a toll-like receptor (TLR) agonist, a TLR antagonist, a SMAD7 inhibitor, a JAK inhibitor, an immunosuppressant, a live biotherapeutic, a carbohydrate sulfotransferase 15 (CHST15) inhibitor, an IL-1 inhibitor, an IL-13 inhibitor, an IL-10 receptor agonist, glatiramer acetate, a CD40/CD40L inhibitor, a CD3 inhibitor, a CD14 inhibitor, a CD20 inhibitor, a CD25 inhibitor, a CD28 inhibitor, a CD49 inhibitor, a CD89 inhibitor, and a chemokine/chemokine receptor inhibitor, an anti-inflammatory drug, and an angiotensin converting enzyme (ACE) inhibitor. In some embodiments, the therapeutic agent is an anti-inflammatory drug or an ACE inhibitor. In some embodiments, the analyte comprises a protein. In some embodiments, the protein is selected from the group consisting of actin, arp2/3, collagen, coronin, dystrphin, elastin, F-spondin, fibronectin, keratin, myosin, nebulin, pikachurin, spectrin, tau, titin, tropomyosin, tubulin, albumins, alpha globulin, beta globulin, C1-inhibitor, C3-convertase, cadherin, carboxypeptidase, C-reactive protein, ependymin, Factor VIII, Factor XIII, fibrin, fibrinogen, gamma globulin, hemoglobin, IgA, IgD, IgE, IgG, IgM, integrin, myoglobin, NCAM, Protein C, Protein S, Protein Z, Protein Z-related protease inhibitor, selectin, serum albumin, serum Amyloid P Component, thrombin, Von Willebrand Factor, CFTR, C-myc, estrogen receptor, FOXP2, FOXP3, glucose transporter, glycophorin D, histones, hydrolases, muscarinic acetylcholine receptor, MyoD, nicotinic acetylcholine receptor, oxidoreductases, P53, potassium channel, rhodopsin, scramblase and transferases. TNFα, lipoteichoic acid (LTA), lipopolysaccharide (LPS), lipopolysaccharide binding protein (LBP), a cytokine, a chemokine, IL12/23, IL-6, IL-10, MADCAM, α4γ7 integrin, hepatocyte growth factor (HGF), epidermal growth factor (EGF), heparin-binding epidermal growth factor (HB-EGF), TGFβ, adalimumab, infliximab, certolizumab pegol, vedolizumab, natalizumab, golimumab, bevacizumab, cetuximab, and combinations thereof. In some embodiments, the protein is a serum protein. In some embodiments, the serum protein is an immunoglobulin or hemoglobin.

In one aspect, provided herein is a method, comprising obtaining spectral data for at least one sample within the gastrointestinal (GI) tract of a subject in vivo; and using the spectral data to generate a drug absorption profile of the subject. In some embodiments, the method comprises using an ingestible device comprising a spectrometer to obtain the spectral data. In some embodiments, the method comprises administering to the subject an ingestible device comprising a spectrometer configured to generate the spectral data of the sample; operating the device to obtain spectral data for at least one sample within the GI tract of the subject; and generating a drug absorption profile for the subject based on the spectral data obtained by the device.

In some embodiments, the device is administered orally to the subject.

In some embodiments, the drug absorption profile for the subject is indicative of the presence or absence of a therapeutic agent, a metabolite thereof, or a fragment thereof, in the sample. In some embodiments, the drug absorption profile for the subject is indicative of a relative or a total amount of therapeutic agent, a metabolite thereof, or a fragment thereof, in the sample. In some embodiments, the therapeutic agent is selected from the group consisting of a GLP-1 analog, an opioid, a parathyroid hormone, human growth hormone, a somatostatin, a long lasting insulin, a cancer drug, a drug that provides long-term HIV pre-exposure prophylaxis, an immunosuppressant, a TNFα inhibitor, an IL-12/IL-23 inhibitor, an IL-6 receptor inhibitor, an integrin inhibitor, a toll-like receptor (TLR) agonist, a TLR antagonist, a SMAD7 inhibitor, a JAK inhibitor, an immunosuppressant, a live biotherapeutic, a carbohydrate sulfotransferase 15 (CHST15) inhibitor, an IL-1 inhibitor, an IL-13 inhibitor, an IL-10 receptor agonist, glatiramer acetate, a CD40/CD40L inhibitor, a CD3 inhibitor, a CD14 inhibitor, a CD20 inhibitor, a CD25 inhibitor, a CD28 inhibitor, a CD49 inhibitor, a CD89 inhibitor, and a chemokine/chemokine receptor inhibitor. In some embodiments, the therapeutic agent is selected from the group consisting of an analgesic drug, an antibiotic drug, an anticoagulant drug, an antidepressant drug, an anticancer drug, an antiepileptic drug, an anti-inflammatory drug, an antipsychotic drug, an antiviral drug, a sedative drug, and an antidiabetic drug. In some embodiments, the therapeutic agent is selected from the group consisting of a diuretic drug, a cholinergic drug, a dopaminergic drug, a GABAergic drug, and a serotonergic drug. In some embodiments, the therapeutic agent is selected from the group consisting of a 5-alpha-reductase inhibitor, an angiotensin II receptor antagonist, an ACE inhibitor, an alpha-adrenergic agonist, a beta blocker, a dopamine agonist, a dopamine antagonist, an incretin mimetic, a nonsteroidal anti-inflammatory drug—cyclooxygenase inhibitor, a proton-pump inhibitor, a renin inhibitor, a selective glucocorticoid receptor modulator, a selective serotonin reuptake inhibitor, and a statin. In some embodiments, the therapeutic agent is selected from the group consisting of a β-lactam antibiotic, a benzodiazepine, a cardiac glycoside, a fibrate, and a thiazide diuretic. In some embodiments, the therapeutic agent is selected from the group consisting of a TNFα inhibitor, an IL-6R inhibitor, an integrin inhibitor, a TLR3 agonist, a TLR agonist that binds and activates TLR4, a TLR agonist that binds and activates TLR5, a TLR agonist that binds and activates TLR7/8, a TLR agonist that binds and activates TLR9, a TLR agonist that is a bacterial or viral component, a SMAD7 inhibitor, a JAK inhibitor, a low molecular weight immunosuppressant, a corticosteroid, a cytostatic, a calcineurin inhibitor, an mTOR inhibitor, a CHST15 inhibitor, an IL-1 inhibitor, an IL-13 inhibitor, IL-10, an IL-10 agonist, a CD40/CD40L inhibitor, glatiramer acetate, and a stem cell.

In some embodiments, the drug absorption profile is indicative of a safe dosage regimen of a therapeutic agent for the subject, an effective dosage regimen of a therapeutic agent for the subject, the ability of the subject to respond to therapy with a therapeutic agent, or a combination thereof. In some embodiments, the drug absorption profile is indicative of the amount of therapeutic agent ingested, absorbed, or metabolized by the subject.

In another aspect, provided herein is a method, comprising obtaining spectral data of for at least one sample within the gastrointestinal (GI) tract of a subject in vivo; and using the spectral data to generate biomarker data of the subject. In some embodiments, the method comprises using an ingestible device comprising a spectrometer to obtain the spectral data. In some embodiments, the method comprises administering to the subject an ingestible device comprising a spectrometer configured to generate the spectral data of the sample; operating the device to obtain spectral data for at least one sample within the GI tract of the subject; and generating biomarker data for the subject based on the spectral data obtained by the device. In some embodiments, the device is administered orally to the subject.

In some embodiments, the biomarker data for the subject is indicative of the presence or absence of one or more biomarkers in the sample. In some embodiments, the biomarker data for the subject is indicative of a relative or a total amount of one or more biomarkers in the sample. In some embodiments, the presence or absence of the one or more biomarkers is indicative of a disease, an infection, an environmental exposure, or a combination thereof.

In some embodiments, the one or more biomarkers comprise a biomarker for a GI disorder.

In some embodiments, the one or more biomarkers comprise a biomarker selected from then group consisting of interferon-γ, IL-1α, IL-6, IL-22, IL-17A, TNFα, IL-2, memory cells ($CD44^+CD45RB^-CD4^+$ cells), and α4γ7 integrin.

In some embodiments, the one or more biomarkers comprise a biomarker selected from the group consisting of anti-glycan, anti-*Saccharomyces cerevisiae*, anti-laminaribioside, anti-chitobioside, anti-mannobioside, anti-laminarin, anti-chitin antibodies, anti-outer membrane porin C, anti-Cbir1 flagellin, anti-12 antibody, autoantibodies targeting the exocrine pancreas, perinuclear anti-neutrophil antibody, and calprotectin.

In some embodiments, the one or more biomarkers comprise a biomarker selected from the group consisting of phospho STAT 1, STAT 3, STAT 5, VEGF, VCAM, ICAM, and IL-6.

In some embodiments, the one or more biomarkers comprise an immunoglobulin or a fragment thereof. In some embodiments, the immunoglobulin is selected from the group consisting of immunoglobulin M, immunoglobulin D, immunoglobulin G, immunoglobulin E, and immunoglobulin A.

In some embodiments, the biomarker data is indicative of the ability of the subject to respond to therapy with a therapeutic agent. In some embodiments, the method further comprises operating the device to obtain the spectral data at one or more predetermined regions within the GI tract of the subject. In some embodiments, the one or more predetermined regions are selected from the mouth, the throat, the esophagus, the stomach, the small intestine, the proximal duodenum, the distal duodenum, the jejunum, the ileum, the descending colon, the ascending colon, transverse colon, the rectum, the sphincter, and the anus of the subject.

In some embodiments, the obtaining the spectral data at one or more predetermined regions within the GI tract comprises operating the spectrometer to obtain spectral data based on the identified location of the device within the GI tract of the subject.

In some embodiments, the obtaining the spectral data at one or more predetermined regions within the GI tract comprises attaching the device to a predetermined region within the GI tract of the subject. In some embodiments, the predetermined region within the GI tract comprises at least one region selected from the group consisting of the stomach, proximal and distal duodenum, jejunum, ileum, descending colon, ascending colon and transverse colon. In some embodiments, the method comprises, after attaching the device, operating the spectrometer to obtain spectral data at a plurality of time points as material flows past the device in the GI tract of the subject.

In some embodiments, the spectral data comprises at least one member selected from the group consisting of absorbance spectral data, transmission spectral data, reflectance spectral data, Fourier transform spectral data and/or Raman spectral data.

In some embodiments, the spectral data comprises one member selected from the group consisting of ultraviolet, visible, near-infrared (NIR) or mid-infrared (MIR) spectral data. In some embodiments, the spectral data comprises NIR spectral data at one or more wavelengths between 600 nm and 2600 nm.

In some embodiments, the device comprises one or more environmental sensors, and the method further comprises measuring environmental data of the GI tract external to the device in the subject. In some embodiments, the environmental data comprises one member selected from the group consisting of capacitance data, temperature data, impedance data, pH level data, heart rate data, acoustic data, image data, and movement data.

In some embodiments, the method further comprises comparing the spectral data to one or more standard spectra. In some embodiments, generating the drug absorption profile for the subject comprises comparing the spectral data to one or more standard spectra. In some embodiments, generating the biomarker data for the subject comprises comparing the spectral data to one or more standard spectra.

In some embodiments, generating the drug absorption profile for the subject comprises receiving one or more inputs from a user and generating the drug absorption profile based on the one or more inputs. In some embodiments, generating the biomarker data for the subject comprises receiving one or more inputs from a user and generating the biomarker data based on the one or more inputs. In some embodiments, the one or more inputs comprise information related to the subject. In some embodiments, the information relating to the subject comprises at least one member selected from the group consisting of weight, height, sex, diet, physical activity level, a medical condition, a medication, a genetic profile, a phenotypic profile, an immune profile, body mass index (BMI), race, age, tobacco use, alcohol use, heart rate, pulse, place of residence, blood glucose level, adiposity, and a microbiome profile. In some embodiments, the medical condition comprises at least one member selected from the group consisting of cancer, a metabolic disease, diabetes, irritable bowel syndrome, an inflammatory bowel disease, short bowel syndrome, a malabsorption syndrome, a bile metabolism disorder, obesity, a pancreatic insufficiency, chronic pancreatitis, epilepsy, a protein malnutrition, an allergy, and Celiac disease.

In some embodiments, the one or more inputs comprise one or more criteria selected by a user. In some embodiments, the one or more criteria comprises an indication of one or more analytes, a desired outcome for the subject, or a combination thereof.

In some embodiments, the method comprises transmitting the spectral data from the ingestible device to a base station and/or transmitting operating parameters from the base station to the ingestible device.

In some embodiments, the method comprises transmitting the spectral data from the base station to a server, wherein the server generates the drug absorption profile based on the spectral data. In some embodiments, the method comprises transmitting one or more inputs to the server, wherein the server generates the drug absorption profile based on the spectral data and the one or more inputs.

In some embodiments, the method comprises transmitting the spectral data from the base station to a server, wherein the server generates the biomarker data based on the spectral data. In some embodiments, the method comprises transmitting one or more inputs to the server, wherein the server generates the biomarker data based on the spectral data and the one or more inputs.

In some embodiments, the method comprises storing the spectral data, the subject information, the drug absorption profile, the biomarker data, or a combination thereof, on computer-readable memory. In some embodiments, the computer-readable memory is on the base station or on a server.

In some embodiments, the method comprises obtaining the spectral data in multiple different wavelength ranges.

In one aspect, provided herein is a device, comprising a spectrometer configured to acquire spectral data of gastrointestinal (GI) tract tissue of a subject in vivo, wherein the device is an ingestible device.

In some embodiments, the spectrometer comprises a hyperspectral camera, and the spectral data comprise a hyperspectral image of the GI tract tissue. In some embodiments, the hyperspectral camera is configured to use the hyperspectral image to produce one or more spectra corresponding to the tissue.

In some embodiments, the device comprises a communications unit configured to transmit data to and/or receive operating parameters from a base station.

In some embodiments, the device comprises a processing unit configured to produce a GI tract tissue health profile for the GI tract tissue based on the one or more spectra. In some embodiments, the processing unit is within the device.

In some embodiments, the device is configured to communicate with a processing unit within a base station that is external to the device. In some embodiments, the device and/or the base station comprises memory configured to store the spectral data and/or the GI tract tissue health profile.

In some embodiments, the processing unit is configured: to access a plurality of reference spectra corresponding to tissue having a specific health condition or a specific oxygenation level; and to compare the one or more spectra produced from the hyperspectral image with the plurality of reference spectra to determine the health condition of the GI tract tissue. In some embodiments, the specific health condition comprises one or more of normal issue, inflamed tissue, scabbed tissue, and necrotic tissue. In some embodiments, the determination of the health condition of the GI tract tissue comprises: determining coefficients of a linear combinations of the plurality of reference spectra that match the one or more spectra produced from the hyperspectral image; and identifying the health condition of the GI tract tissue as a combination of health conditions corresponding to the determined coefficients. In some embodiments, the comparison comprises: comparing a magnitude of the one or more spectra with a magnitude of each reference spectrum within the plurality of reference spectra; and identifying the health condition of the GI tract tissue by matching the magnitude of the acquired spectrum to the magnitude of a reference spectrum corresponding to tissue having a specific health condition.

In some embodiments, the specific health condition comprises a specific oxygenation level of the GI tract tissue. In some embodiments, the oxygenation level is from about 1% to about 100%. In some embodiments, the oxygenation level is about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In some embodiments, the comparison comprises: comparing a spectral feature of the one or more spectra with a spectral feature of each reference spectrum within the plurality of reference spectra; and identifying the oxygenation level of the GI tract tissue by matching the spectral features of the one or more spectra to the spectral features of a reference spectrum corresponding to tissue having a specific oxygenation level.

In some embodiments, the spectrometer is configured to acquire a spectrum corresponding to a GI tract tissue. In some embodiments, the device further comprises a communications unit configured to transmit data to and/or receive operating parameters from a base station. In some embodiments, the device comprises a processing unit configured to produce a GI tract tissue health profile for the GI tract tissue based on the acquired spectrum. In some embodiments, the processing unit is configured: to access a plurality of reference spectra corresponding to tissue having a specific health condition; to compare a magnitude of the acquired spectrum with a magnitude of each reference spectrum within the plurality of reference spectra; and to determine the health condition of the GI tract tissue by matching the magnitude of the acquired spectrum to the magnitude of a reference spectrum corresponding to tissue having a specific health condition.

In some embodiments, the device is configured to generate the spectral data at a predetermined region within the GI tract of the subject. In some embodiments, the predetermined region within the GI tract is selected from the group consisting of the mouth, the throat, the esophagus, the stomach, the small intestine, the proximal duodenum, the distal duodenum, the jejunum, the ileum, the descending colon, the ascending colon, transverse colon, the rectum, the sphincter, and the anus. In some embodiments, the generating spectral data at one or more predetermined regions within the GI tract comprises identifying the location of the device within the GI tract of the subject based on the spectral data. In some embodiments, the spectrometer is configured to obtain spectral data by acquiring a spectrum of light reflected off tissue within the GI tract.

In some embodiments, the processer is configured to: access a plurality of reference spectra corresponding to tissue from specific regions of the GI tract; compare a magnitude of the acquired spectrum with a magnitude of each reference spectrum within the plurality of reference spectra; and identify the location of the device as a specific region of the GI tract by matching the magnitude of the acquired spectrum to the magnitude of a reference spectrum corresponding to tissue from the specific region of the GI tract. In some embodiments, the processer is configured to: access a plurality of reference spectra corresponding to tissue from specific regions of the GI tract; compare a spectral feature of the acquired spectrum with a spectral feature of each reference spectrum within the plurality of reference spectra; and identify the location of the device as a specific region of the GI tract by matching the spectral features of the acquired spectrum to the spectral features of a reference spectrum corresponding to tissue from the specific region of the GI tract. In some embodiments, the plurality of reference spectra corresponds to tissue from the mouth, the throat, the esophagus, the stomach, the small intestine, the proximal duodenum, the distal duodenum, the jejunum, the ileum, the descending colon, the ascending colon, transverse colon, the rectum, the sphincter, and the anus.

In some embodiments, the device is operable to generate the spectral data at a plurality of time points as the device travels through the GI tract of the subject.

In some embodiments, the processing unit is configured to generate a plurality of GI tract tissue health profiles at a plurality of time points as the device travels through the GI tract of the subject.

In some embodiments, the spectrometer comprises at least one member selected from the group consisting of a light source, a photodetector, a dispersive element, a lens, and a filter. In some embodiments, the spectrometer is configured to generate at least one member selected from the group consisting of absorbance spectral data, transmission spectral data, reflectance spectral data, Fourier transform spectral data, and Raman spectral data.

In some embodiments, the device comprises a plurality of spectrometers configured to generate different types of spectral data.

In some embodiments, the spectrometer comprises a light source and a photodetector positioned on the exterior of the device. In some embodiments, the light source is configured to transmit light radially towards an environment external to the device, and the photodetector is configured to detect a radial reflectance from the environment external to the device. In some embodiments, the light source is adjacent to the photodetector.

In some embodiments, the spectral data comprises at least one member selected from the group consisting of ultraviolet spectral data, visible spectral data, near-infrared (NIR) spectral data, and mid-infrared (MIR) spectral data. In some embodiments, the spectral data comprises NIR spectral data. In some embodiments, the NIR spectral data comprises absorbance or reflectance data at one or more wavelengths between 600 nm and 2600 nm. In some embodiments, the spectral data comprises MIR spectral data. In some embodiments, the MIR spectral data comprises absorbance or reflectance data at one or more wavelengths between 1500 nm and 5600 nm.

In some embodiments, the spectrometer comprises a 2-dimensional array of photodetectors.

In some embodiments, the device further comprises one or more environmental sensors for measuring environmental data external to the device. In some embodiments, the one or more environmental sensors comprises at least one member selected from the group consisting of a capacitance sensor, a temperature sensor, an impedance sensor, a pH level sensor, a heart rate sensor, acoustic sensor, reflected visible light sensor, image sensor, and a movement sensor. In some embodiments, the environmental sensor comprises a movement sensor, wherein the movement sensor comprises a step sensor. In some embodiments, the image sensor comprises a video camera. In some embodiments, the processing unit is configured to generate the digestion profile based on the spectral data and the environmental data. In some embodiments, the processing unit is configured to compare the environmental data to one or more environmental data standards.

In some embodiments, the processing unit is configured to identify a location of the device within the GI tract of the subject based on the spectral data. In some embodiments, the processing unit is configured to identify a location of the device within the GI tract of the subject based on the spectral data, the environmental data, or a combination thereof. In some embodiments, the processing unit is configured to identify a location of the device within the GI tract of the subject based on reflected visible light.

In some embodiments, the device is configured to attach to the GI tract of the subject in vivo. In some embodiments, the device is configured to releasably attach to the GI tract of the subject at one or more predetermined locations. In some embodiments, the device is attachable to the GI tract of the subject using an adhesive, negative pressure, a fastener, or a combination thereof. In some embodiments, the device is static within the GI tract relative to material passing through the GI tract of the subject and the spectrometer is configured to generate spectral data at predetermined time intervals.

In some embodiments, the device comprises a microcontroller configured to operate the spectrometer to generate the spectral data, and optionally wherein the processing unit is the microcontroller. In some embodiments, the microcontroller is configured to operate the one or more environmental sensors to generate the environmental data. In some embodiments, the microcontroller is configured to operate the spectrometer to generate the spectral data and/or environmental data based on the location of the device within the GI tract of the subject.

In some embodiments, the device is in the shape of a capsule.

In some embodiments, the ingestible device, comprises: a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device has an opening between an interior of the ingestible device and an exterior of the ingestible device, and the ingestible device comprises: a chamber; and a multi-stage valve system in the interior of the ingestible device, wherein: the multi-stage valve system has first, second and third states, the first state of the multi-stage valve system is different from the second and third states of the multi-stage valve system; the second state of the multi-stage valve system is different from the first and third states of the multi-stage valve system; when the multi-stage valve system is in its first state, the opening prevents fluid communication between the interior of the ingestible device and the exterior of the ingestible device; when the multi-stage valve system is in its second state, the opening allows fluid communication between the interior of the ingestible device and the exterior of the ingestible device; and when the multi-stage valve system is in its third state, the opening prevents fluid communication between the interior of the ingestible device and the exterior of the ingestible device.

In some embodiments, the ingestible device has an opening between an interior of the ingestible device and an exterior of the ingestible device, and the ingestible device comprises: a chamber; and a multi-stage valve system in the interior of the ingestible device, wherein: the multi-stage valve system comprises: an actuator system comprising a first member; a trigger comprising a first peg and a first lip; a gate comprising a protrusion, and a gate leg having an opening; and a biasing system comprising first and second biasing members; when the multi-stage valve system is in a first stage: the first biasing member applies a force to the trigger so that the first peg contacts the first member; the first member opposes the force applied to the trigger by the first biasing member; the second biasing member applies a force to the gate so that the protrusion contacts the first lip; the first lip opposes the force applied to the gate by the second biasing member; and the opening in the gate leg is not aligned with the opening in the ingestible device.

In some embodiments, the ingestible device has an opening between an interior of the ingestible device and an exterior of the ingestible device, and the ingestible device comprises: a chamber; and a sampling system in the interior of the ingestible device, wherein: the sampling system comprises: a first absorbent member; and a second absorbent member different from the first absorbent member; and the sampling system is configured so that fluid that flows from the exterior of the ingestible device to the interior of the ingestible device enters the first absorbent member; and the sampling system is configured to allow fluid to flow from the first absorbent member to the second absorbent member.

In some embodiments, the device has an opening between an interior of the ingestible device and an exterior of the ingestible device, and the ingestible device comprises: a chamber; and a sampling system in the interior of the ingestible device configured to absorb a fluid that enters the interior of the ingestible device via the opening, the sampling system comprising an absorbent member and at least one preservative at least partially absorbed in the absorbent member.

In some embodiments, the ingestible device comprises: a housing defined by a first end, a second end substantially opposite from the first end, and a wall extending longitudinally from the first end to the second end; a first opening in the wall of the housing; a second opening in the first end of the housing, the second opening being oriented substantially perpendicular to the first opening; and a curved chamber connecting the first opening and the second opening, wherein at least a portion of the curved chamber forms a sampling chamber within the ingestible device.

In some embodiments, the ingestible device comprises: a housing defined by a first end, a second end substantially opposite from the first end, a wall extending longitudinally from the first end to the second end, and an opening; a sampling chamber within the housing, wherein the sampling chamber contains an absorptive material; an inlet port connecting the opening in the housing to the sampling chamber; a single use sealing device positioned within the inlet port that seals the inlet port; and a heating element proximate to the single use sealing device, wherein: the heating element is configured to apply heat to the single use sealing device to unseal the inlet port and open the sampling chamber, and at least a portion of the absorptive material proximate to the inlet port is configured to expand when in contact with a sample and reseal the inlet port.

In some embodiments, the ingestible device comprises: a housing defined by a first end, a second end substantially opposite from the first end, a wall extending longitudinally from the first end to the second end, and an opening; a sampling chamber within the housing having an entry port and an exit port on an opposite end of the sampling chamber from the entry port, wherein the exit port is configured to allow gas to exit the chamber and prevent at least a portion of a sample from exiting the chamber; an inlet region connecting the opening in the housing to the entry port of the sampling chamber; and a moveable valve positioned to open and close the inlet region, wherein: the moveable valve in an open position allows the sample to enter the sampling chamber; and the moveable valve in a closed position prevents the sample from entering the sampling chamber.

In some embodiments, the device comprises one or more processing devices; and one more machine readable hardware storage devices storing instructions that are executable by the one or more processing devices to determine a location of the ingestible device in a portion of a GI tract of a subject to an accuracy of at least 85%. In some embodiments, the device comprises one or more processing devices; and one more machine readable hardware storage devices storing instructions that are executable by the one or more processing devices to determine that the ingestible device is in the cecum of a subject to an accuracy of at least 70%.

In some embodiments, the device comprises one or more processing devices; and one more machine readable hardware storage devices storing instructions that are executable by the one or more processing devices to transmit data to a device capable of implementing the data to determine a location of the medical device in a portion of a GI tract of a subject to an accuracy of at least 85%. In some embodiments, the device comprises one or more processing devices; and one more machine readable hardware storage devices storing instructions that are executable by the one or more processing devices to transmit data to an external device capable of implementing the data to determine that the ingestible device is in the cecum of a subject to an accuracy of at least 70%.

In some embodiments, the device comprises first and second light sources, wherein the first light source is configured to emit light at a first wavelength, and the second light source is configured to emit light at a second wavelength different from the first wavelength. In some embodiments, the device comprises first and second detectors, wherein the first detector is configured to detect light at the first wavelength, and the second detector is configured to detect light at the second wavelength.

In one aspect, provided herein is a kit, comprising a device described herein. In another aspect, provided herein is a system, comprising: an ingestible device, wherein the ingestible device comprises a spectrometer configured to acquire spectral data of gastrointestinal (GI) tract tissue of a subject in vivo; and a processing unit configured to generate a GI tract tissue health profile for the subject based on the spectral data.

In some embodiments, the system comprises a communications unit. In some embodiments, the system comprises memory configured to store the spectral data, the GI tract tissue health profile for the subject, or a combination thereof. In some embodiments, the system is configured to generate a display to a user.

In some embodiments, the system comprises an interface configured to allow a user to configure the processing unit to generate the GI tract tissue health profile for the subject based on one or more inputs. In some embodiments, the one or more inputs comprise information relating to the subject.

In some embodiments, the information relating to the subject comprises at least one member selected from the group consisting of weight, height, sex, diet, physical activity level, a medical condition, a medication, a genetic profile, a phenotypic profile, an immune profile, body mass index (BMI), race, age, tobacco use, alcohol use, heart rate, pulse, place of residence, blood glucose level, adiposity, and a microbiome profile. In some embodiments, the information relating to the subject comprises at least one medical condition selected from the group consisting of cancer, a metabolic disease, diabetes, irritable bowel syndrome, an inflammatory bowel disease, short bowel syndrome, a malabsorption syndrome, a bile metabolism disorder, obesity, a pancreatic insufficiency, chronic pancreatitis, epilepsy, a protein malnutrition, an allergy, and Celiac disease.

In some embodiments, the one or more inputs comprise one or more criteria selected by the user.

In some embodiments, the processing unit is configured to compare the spectral data to one or more spectral standards to generate the GI tract tissue health profile.

In some embodiments, at least one member selected from the group consisting of the processing unit, memory, display and interface is within a base station. In some embodiments, the base station is a computer or a personal electronic device. In some embodiments, the personal electronic device is selected from the group consisting of a watch, a phone, a tablet, a fitness monitor, and a physical activity tracker.

In some embodiments, the processing unit is configured to transmit the spectral data to a server and to receive the GI tract tissue health profile from the server.

In some embodiments, the system comprises an ingestible device comprising a device described herein.

In one aspect, provided herein is a method of generating a gastrointestinal tract tissue health profile for a subject, the method comprising administering an ingestible device to a subject, wherein the device comprises a spectrometer configured to acquire spectral data of gastrointestinal (GI) tract tissue of the subject in vivo. In some embodiments, the method comprises orally administering the device to the subject. In some embodiments, the spectrometer comprises a hyperspectral camera configured to acquire spectral data comprising a hyperspectral image of GI tract tissue. In some embodiments, method comprises using the hyperspectral image to produce one or more spectra corresponding to the tissue. In some embodiments, the method comprises producing the GI tract tissue health profile for the GI tract tissue based on the one or more spectra.

In some embodiments, the method comprises: accessing a plurality of reference spectra corresponding to tissue having a specific health condition or a specific oxygenation level; and comparing the one or more spectra produced from the hyperspectral image with the plurality of reference spectra, thereby determining the health condition of the GI tract tissue. In some embodiments, the specific health condition comprises one or more of normal issue, inflamed tissue, scabbed tissue, and necrotic tissue. In some embodiments, the plurality of reference spectra corresponding to tissue having a specific health condition are produced by performing spectroscopy or hyperspectral imaging on either excised GI tract tissue, formalin-fixed GI tract tissue, or live GI tract tissue.

In some embodiments, the determining of the health condition of the GI tract tissue comprises: determining coefficients of a linear combinations of the plurality of reference spectra that match the one or more spectra produced from the hyperspectral image; and identifying the health condition of the GI tract tissue as a combination of health conditions corresponding to the determined coefficients. In some embodiments, the comparing comprises: comparing a magnitude of the one or more spectra with a magnitude of each reference spectrum within the plurality of reference spectra; and identifying the health condition of the GI tract tissue by matching the magnitude of the acquired spectrum to the magnitude of a reference spectrum corresponding to tissue having a specific health condition. In some embodiments, the specific health condition comprises a specific oxygenation level of the GI tract tissue. In some embodiments, the oxygenation level is from about 1% to about 100%. In some embodiments, the oxygenation level is about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In some embodiments, the comparing comprises: comparing a spectral feature of the one or more spectra with a spectral feature of each reference spectrum within the plurality of reference spectra; and identifying the oxygenation level of the GI tract tissue by matching the spectral features of the one or more spectra to the spectral features of a reference spectrum corresponding to tissue having a specific oxygenation level. In some embodiments, the plurality of reference spectra corresponding to GI tract tissue with various oxygenation levels are produced by performing spectroscopy or hyperspectral imaging of blood samples with various oxygenation levels.

In some embodiments, the method comprises acquiring a spectrum corresponding to a GI tract tissue adjacent to the device. In some embodiments, the method comprises: accessing a plurality of reference spectra corresponding to tissue having a specific health condition; comparing a magnitude of the acquired spectrum with a magnitude of each reference spectrum within the plurality of reference spectra; and determining the health condition of the GI tract tissue by matching the magnitude of the acquired spectrum to the magnitude of a reference spectrum corresponding to tissue having a specific health condition. In some embodiments, the method comprises generating the spectral data at a predetermined region within the GI tract of the subject.

In some embodiments, the generating comprises identifying the location of the device within the GI tract of the subject based on the spectral data. In some embodiments, the method comprises obtaining the spectral data by acquiring a spectrum of light reflected off tissue within the GI tract. In some embodiments, the method comprises: accessing a plurality of reference spectra corresponding to tissue from specific regions of the GI tract; comparing a magnitude of the acquired spectrum with a magnitude of each reference spectrum within the plurality of reference spectra; and identifying the location of the device as a specific region of the GI tract by matching the magnitude of the acquired spectrum to the magnitude of a reference spectrum corresponding to tissue from the specific region of the GI tract. In some embodiments, the method comprises: accessing a plurality of reference spectra corresponding to tissue from specific regions of the GI tract; comparing a spectral feature of the acquired spectrum with a spectral feature of each reference spectrum within the plurality of reference spectra; and identifying the location of the device as a specific region of the GI tract by matching the spectral features of the acquired spectrum to the spectral features of a reference spectrum corresponding to tissue from the specific region of the GI tract. In some embodiments, the plurality of reference spectra corresponds to tissue from the mouth, the throat, the esophagus, the stomach, the small intestine, the proximal duodenum, the distal duodenum, the jejunum, the ileum, the descending colon, the ascending colon, transverse colon, the rectum, the sphincter, and the anus.

In some embodiments, the plurality of reference spectra corresponding to tissue from specific regions of the GI tract are produced by performing spectroscopy or hyperspectral imaging of excised GI tract tissue. In some embodiments, the plurality of reference spectra corresponding to stomach tissue, small intestine tissue and large intestine tissue are produced by performing spectroscopy or hyperspectral imaging of excised GI tract tissue.

In another aspect, provided herein is a device, comprising a hyperspectral camera configured to acquire spectral data within the gastrointestinal (GI) of a subject in vivo, wherein the device is an ingestible device. In some embodiments, the spectral data comprise a hyperspectral image. In some embodiments, the spectral data comprise spectra. In some embodiments, each hyperspectral image comprises spectra. In some embodiments, the spectral data comprise a plurality of images and spectra.

In one aspect, provided herein is a method, comprising generating a gastrointestinal (GI) tract tissue health profile for a subject based on in situ spectral data of the GI tract tissue. In some embodiments, the method further comprises using an ingestible device to acquire the spectral data.

In some embodiments, a digestion profile produced based on the spectral data may be used to provide information to a subject and/or facilitate comparisons between individuals or groups of individuals. For example, it may be possible to provide information regarding the level of an analyte in the subject's diet by comparing spectral data from a subject's digestion profile with one or more spectral standards representing the typical spectral data that would be gathered when there is a predetermined level of the analyte in a person's diet.

In some embodiments, a digestion profile includes spectral data from a subject and information associated with the sample used to generate the spectral data. For example, the digestion profile may contain spectral data as well as information about a meal that the subject recently consumed, or the sample being observed, when the spectral data was generated. This information may be stored as part of the digestion profile in a database.

In some embodiments, the digestion profile may contain information associated with the subject, such as the subject's age, height, and weight, information about the subject's diet, known health conditions, and the like. In some embodiments, information in a digestion profile may be inputted by a user. Exemplary inputted information includes, for example, weight, age, medical conditions, or the effect of eating certain foods, immune profile (e.g., based on white blood cell level or count, erythrocyte sedimentation rate, and/or C-reactive protein level), genetic profile, methylation profile, microbiome profile, allergies, blood glucose levels, physical activity, adiposity, tobacco use, and/or alcohol use. Additionally or alternatively, the information in a digestion profile (e.g., exemplary information noted in the preceding sentence) may be generated by comparing the spectral data for the subject to one or more spectral standards. For example, the spectral data gathered from a subject may be compared to one or more spectral standards in order to determine the relative amounts of fat, protein, and carbohydrates that a subject has consumed, or the general nutritional content of a subject's diet. As an example, in some embodiments, blood or urine markers may be measured before, during, and/or after a meal and incorporated into a digestion profile. For example, carbohydrate levels in the GI tract and blood glucose levels or glycemic responses can be measured after ingesting a standard meal with a predetermined amount of carbohydrates. In some embodiments, blood glucose may be used as a positive control. Optionally, correlation data can be generated, collected and analyzed. As an example, a correlation may be developed and/or investigated relating to digestive profile results and other metabolites and results found in blood and/or urine. In some embodiments, a direct relationship between the protein digestion curve and total blood amino acids (amino acid availability) may be observed.

In one aspect of the disclosure, information may also be generated by comparing a digestion profile for a subject to a database of digestion profiles. Similarities or differences between spectral data and/or digestion profiles for different individuals or groups of individuals may be used to infer information regarding the subject such as the effect of eating certain foods or health outcomes in response to diet or lifestyle changes. Optionally, this information can be presented to a user and/or added to the digestion profile for the subject. For example, in some embodiments, a subject's digestion profile may be submitted to a website, and the website may display information about users with similar digestion profiles. Accordingly, in some embodiments, a digestion profile is indicative of lifestyle and/or diet recommendations, or predictive of the effect of ingesting one or more substances by the subject.

In some embodiments, the digestion profile may be used to identify individuals or groups of individuals with similar characteristics. For example, spectral data generated using the ingestible device may be used to identify individuals or groups of individuals with similar spectral data and/or digestion profiles. Information from these other digestion profiles may be used to infer information about the subject, or may be displayed to the subject. For example, if the spectral data for a given subject is similar to spectral data gathered from subjects with a calorie restricted diet, it may be inferred that that subject also has a calorie restricted diet.

In some embodiments, a digestion profile allows for the contents of a sample from the GI tract to be characterized without necessarily identifying specific analytes. For example, the spectral data may be compared to similar previously gathered spectral data contained in digestion profiles for other individuals. If those other digestion profiles indicate particular types of samples that were present when the previous spectral data was gathered, it may indicate that similar samples were observed in the subject. For instance, the spectral data gathered from the subject may be used to search a database of previously generated digestion profiles, and it may be determined that similar spectral data is indicative of individuals who have recently eaten a carbohydrate rich meal consisting mostly of rice.

In some embodiments, the digestion profile may contain information associated with a medical condition (e.g., a disease or disorder described herein). For example, the digestion profile of a subject having or suspected of having for example diabetes, constipation or kidney disease may be compared with the digestion profiles of other individuals or groups of individuals with the same medical condition. The digestion profiles described herein may also be used for the diagnosis of a medical condition or as a prognostic tool to help guide food or lifestyle choices. For example, if a subject suspects has a similar digestion profile to individuals who are diabetic, it may be inferred that the subject is at a heightened risk for developing diabetes.

In some embodiments, an ingestible standard may be used with the ingestible device in order to generate spectral data that is associated with the ingestible standard. For example, the ingestible standard may be a set meal or a predetermined composition of one or more macronutrients. One advantage of using an ingestible standard is to facilitate the comparison of spectral data and/or digestion profiles from the same individual or from different individuals. In some embodiments, the ingestible standard serves as a control and differences in the spectral data and/or digestion profiles for a subject having ingested the same ingestible standard may be ascribed to changes in the physiology of the GI tract rather than differences in the ingested material. The use of an ingestible standard may also allow for the identification of individuals with similar GI tract characteristics based on similarities in their spectral data. Information on those individuals may then be used to inform or predict the characteristics of a subject.

The ingestible standard may also be a non-absorbed and/or indigestible standard. In some embodiments, the non-absorbed and/or indigestible standard is detected using the spectrometer and provides a reference in order to generate a digestion profile relative to the ingestible standard. For example, if an ingestible standard used to generate spectral data in the GI tract contains a predetermined quantity of indigestible material (e.g., indigestible fiber), this may be used to help determine the relative or absolute amount of other materials or analytes within the same sample. In some embodiments, using a non-absorbed and/or indigestible standard allows for using the standard as a relative marker so that the relative concentrations of other analytes can be compared and/or the relative amounts (e.g., in grams) can be calculated. As an example, in a situation where the initial amount of carbohydrates (or one or more other macronutrients) is known, then the amount of carbohydrates remaining can be calculated based on the amount of remaining non-absorbed and/or indigestible standard. Optionally, the ingestible standard may include or be conjugated to a detectable label such as a fluorescent label, and the ingestible device may be configured to detect the presence of the label within the GI tract. Exemplary labeled analytes are the Stable Isotope Labeled Fatty Acids offered by Sigma-Aldrich for use as metabolic tracers, which may be found, for example, at www.sigmaaldrich.com/technical-documents/articles/stable-isotopes/stable-isotope-labeled-fatty-acids-as-metabolic-tracers.html.

In some embodiments, a test material is used with the ingestible device in order to generate spectral data indicative of the test material in vivo within the GI tract of the subject. For example, the test material may be a natural or prepared food, alcoholic or non-alcoholic beverage, drug, therapeutic agent or nutritional supplement and the spectral data may be used to generate digestion profiles that are indicative of one or more characteristics of the test material within the GI tract of a subject, such as the absorbance and/or metabolism characteristics of the test material. For instance, if the test material is an iron supplement, the ingestible device may be used to generate spectral data indicative of how iron is absorbed and/or metabolized within the GI tract of the subject. This information may be useful for diagnosing any number of medical conditions, such as celiac disease, which may affect the intestine's ability to absorb certain nutrients from digested food.

The ingestible device may also include one or more environmental sensors for measuring environmental data external to the device in the subject. The environmental data may then be used in combination with spectral data to generate a digestion profile for the subject. In some embodiments, the environmental data may also be used to determine the location of the ingestible device within the GI tract of the subject. Environmental sensors may include capacitance sensors, temperature sensors, impedance sensors, pH detectors, heart rate sensors, acoustic sensors, or any other suitable type of sensing device.

In general, a digestion profile for a subject may be generated based on spectral data of the sample within the GI tract and optionally environmental data and/or one or more inputs from a user. The user may be a subject who has ingested the ingestible device, or another individual such as a nutritionist, coach or medical professional.

Examples of inputs that may be used to generate a digestion profile include information on the subject and/or criteria selected by a user. In some embodiments, a digestion profile for a subject is generated based on spectral data and information on the subject such as, weight, height, sex, diet, exercise, medical condition, medication, genotype, phenotype, body mass index (BMI), race, age, exercise routine, tobacco use, and/or alcohol use, heart rate, pulse and/or place of residence. In some embodiments, a digestion profile for a subject is generated based on spectral data and one or more criteria selected by a user, such as, but not limited to, a medical condition, analyte or desired outcome.

For example, in some embodiments, a user may generate a digestion profile based on spectral data generated using an ingestible device as described herein and the criteria of wanting to increase or decrease the absorption of protein in the GI tract. In another embodiment, a user may generate a digestion profile based on spectral data generated using an ingestible device as described herein and the criteria of wanting to lose weight. The digestion profile for the subject may be compared to a database of digestion profiles in order to identify individuals or groups of individuals with similar spectral data and/or digestion profiles and that meet criteria selected by a user, for example individuals who have experienced weight loss or an increase in the absorption of protein.

Differences or similarities between the digestion profile of the subject and the digestion profiles of individuals or groups of individuals in the database of digestion profiles may be presented to the user and/or used to add additional information to the digestion profile of the subject. In some embodiments, the methods and devices described herein may provide lifestyle and/or dietary recommendations to a subject based on a comparison of spectral data and/or digestion profiles for the subject to a database of digestion profiles. The methods and devices described herein may be used to identify and/or quantify the level of one or more analytes in the GI tract of a subject or predict the effect of ingesting certain substances such as foods, analytes (e.g., drugs) and/or nutritional supplements on the GI tract. In some embodiments, the methods and devices described herein may be used to provide dietary or food intake recommendations based on a pre-existing digestion profile for a subject.

Accordingly, in some embodiments, there is provided an ingestible device including a spectrometer for generating spectral data of a sample within the GI tract of a subject. Optionally, the ingestible device includes a communications unit for transmitting data to, and/or receiving operating parameters from, a base station. In some embodiments, the ingestible device includes a processing unit configured to generate a digestion profile for the subject based on the spectral data. In some embodiments, the processing unit is configured to compare the spectral data to one or more spectral standards to generate the digestion profile. Optionally, the processing unit may be within the ingestible device or within a separate base station. In some embodiments, a digestion profile is generated by searching a database of digestion profiles to identify digestion profiles that are similar or dissimilar with respect to spectral data, environmental data, and/or one or more user inputs. In some embodiments, the digestion profile is indicative of, e.g., the presence or absence of one or more analytes in the sample from the subject and/or the ability of the subject to absorb and/or metabolize an analyte (e.g., a therapeutic agent). In some embodiments, the digestion profile is indicative of lifestyle and/or dietary recommendations for the subject. In some embodiments, the digestion profile is predictive of the effect of ingesting one or more substances by the subject.

In one aspect, there is also provided a kit including an ingestible device including a spectrometer as described herein and at least one of an ingestible standard and a detection agent. The ingestible standard may include a predetermined amount of one or more analytes. For example, in some embodiments, the ingestible standard includes a predetermined amount of one or more macronutrients (protein, carbohydrate and/or fats). The kit may include a detection agent that selective binds to one or more analytes. In some embodiments, the detection agent is fluorescently labelled. Optionally, the ingestible standard and/or detection agent may be ingested by a subject in order to generate a standardized digestion profile for the subject that facilitates comparing digestion profiles of the same individual over time or comparing digestion profiles between individuals. In some embodiments, the ingestible standard and/or detection agent is administered prior to the administration of a device, analyte, or substance (e.g., a foodstuff) to the subject. In some embodiments, the ingestible standard and/or detection agent is administered concurrently with the administration of a device, analyte, or substance (e.g., a foodstuff) to the subject. In some embodiments, the ingestible standard and/or detection agent is administered after the administration of a device, analyte, or substance (e.g., a foodstuff) to the subject.

In one aspect, there is also provided a system for generating a digestion profile for a subject including an ingestible device as described herein. In some embodiments, the ingestible device includes a spectrometer for generating spectral data of a sample within the GI tract of a subject. In some embodiments, the system includes a processing unit configured to generate a digestion profile for the subject based on the spectral data. In some embodiments, the processing unit is within a base station, such as a computer or a portable electronic device.

In some embodiments, the system includes a communications unit. The communications unit may be configured for transmitting data from the ingestible device to a base station and/or transmitting operating parameters from the base station to the ingestible device. In some embodiments, the system is configured to transmit one or more of spectral data, environmental data and user input to a server and receive information for a digestion profile for the subject from the server.

In one aspect, there is provided a method for generating a digestion profile for a subject. In some embodiments, the method includes providing an ingestible device including a spectrometer as described herein, operating the spectrometer to obtain spectral data of at least one sample within the GI tract of the subject and generating a digestion profile for the subject based on the spectral data. In some embodiments, the digestion profile may be a data structure written onto computer-readable memory, the data structure including spectral data, information about the subject, environmental data, and/or information about the sample used to generate the spectral data.

In some embodiments, the method includes orally administering the ingestible device to the subject. In some embodiments, the method includes orally administering an ingestible standard to the subject. In some embodiments, the method includes orally administering a detection agent to the subject. The ingestible standard and/or detection agent may be administered to the subject at the same time as the ingestible device or at different times (e.g., before or after the ingestible device is administered to the subject). In some embodiments, the ingestible standard is administered to the subject within 5 minutes, 10 minutes, 30 minutes, 1 hour, 2 hours, 3 hours, 4 hours, 5 hours, 6 hours, 7 hours, 8 hours, 9 hours, or 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours or more relative to the ingestible device. In some embodiments, the ingestible standard is divided into two portions. The first portion of the ingestible standard is administered to the subject, then the ingestible device is administered to the subject, then the second portion of the ingestible standard is administered to the subject. This may ensure that the ingestible device travels through the GI concurrently with the ingestible standard.

In some embodiments, the method includes operating the spectrometer to obtain spectral data at one or more time points as the ingestible device travels through the GI tract of the subject. In some embodiments, spectral data is obtained for a sample in one or more regions in the GI tract selected from the stomach, proximal and distal duodenum, jejunum, ileum, descending colon, ascending colon and transverse colon.

In some embodiments, the method includes generating a digestion profile for the subject by comparing spectral data and optionally environmental data and/or one or more user inputs to a database of digestion profiles. In some embodiments, the database of digestion profiles includes standard spectra representative of typical spectral data gathered when the sample contains a given level of an analyte (e.g., a therapeutic agent). In some embodiments, the database of digestion profiles includes spectral data for a plurality of individuals and information associated with each individual or groups of individuals such as weight, height, sex, diet, exercise, medical condition, allergies, medication, genotype, phenotype, BMI, race, age, exercise routine, tobacco use, and/or alcohol use, heart rate, pulse, and/or place of residence. In some embodiments, the database of digestion profiles may contain information associated with each individual or groups of individuals that is longitudinal data. For example, in some embodiments, a digestion profile for an individual may include spectral data associated with an ingestible standard, a loss in weight for the subject over time, and information on the types of food consumed by the subject over time. This may allow subjects to identify other individuals in a digestion profile database with similar digestion profiles, and to determine whether particular changes in diet have resulted in weight loss for those other individuals.

In some embodiments, the method includes predicting the effect of ingesting a substance, such as a food, based on available nutritional information (such as calories, portion size, ingredients etc.), and an existing digestion profile for a subject. For example, spectral data associated with an ingestible standard for a subject may be used to predict the absorption of calories or macronutrients by the subject for the substance, or whether the substance may be beneficial or detrimental to a criteria selected by a user such as wanting to lose weight, gain weight, manage or treat a medical condition, lose body fat, gain body fat, lose muscle mass, gain muscle mass, increase absorption of a macronutrient, decrease absorption of a macronutrient, absorb carbohydrates (i.e., carb loading for sports performance) or gain lean muscle. For example, a subject's digestion profile may indicate that they are able to only partially digest certain types of vegetables, and this information may be used to infer how many calories and macronutrients the subject will actually absorb and/or metabolize if they consume one of those types of vegetables. In some embodiments, information on the substance is available from a database of nutritional information and/or ingredients for commercially available foods.

Other features and advantages of the disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The above and other objects and advantages of the disclosure will be apparent upon consideration of the following detailed description, taken in conjunction with the accompanying drawings, in which like reference characters refer to like parts throughout, and in which:

FIG. 6 shows an embodiment of a digestion profile for a subject as described herein.

FIGS. 7A-7D show results of a model for predicting concentration of an analyte.

FIGS. 8A and 8D show results of a model for predicting concentration analytes.

FIG. 8B shows a result of a model for predicting concentration of analytes.

FIG. 8C shows a result of a model for predicting concentration of an analyte.

FIGS. 9A-9D show results of a model for predicting caloric content.

FIGS. 41A-41D illustrate results of predictions based on a model.

FIGS. 45A-44D illustrate results of predictions based on a model.

FIGS. 50A-50C show tissue samples including normal, inflamed or necrotic tissue excised from the colon.

FIG. 61 shows raw images of necrotic portions of live colon and their corresponding health-condition images obtained based on the spectra of FIG. 58.

FIGS. 96A-96C illustrate operation of ingestible device.

FIG. 97 illustrates an exploded view of the components of ingestible device.

FIG. 106 is a flowchart of illustrative steps for detecting a transition from a duodenum to a jejunum, which may be used when determining a location of an ingestible device as it transits through a GI tract, in accordance with some embodiments of the disclosure.

FIG. 107 is a plot illustrating data collected during an example operation of an ingestible device, which may be used when detecting a transition from a duodenum to a jejunum, in accordance with some embodiments of the disclosure.

FIG. 108 is a plot illustrating muscle contractions detected by an ingestible device over time, which may be used when determining a location of an ingestible device as it transits through a GI tract, in accordance with some embodiments of the disclosure.

FIG. 109 is a flowchart of illustrative steps for detecting a transition from a jejunum to an ileum, which may be used when determining a location of an ingestible device as it transits through a GI tract, in accordance with some embodiments of the disclosure.

FIG. 110 is a flowchart of illustrative steps for detecting a transition from a jejunum to an ileum, which may be used when determining a location of an ingestible device as it transits through a GI tract, in accordance with some embodiments of the disclosure.

FIG. 111 is a flowchart of illustrative steps for detecting a transition from an ileum to a cecum, which may be used when determining a location of an ingestible device as it transits through a GI tract, in accordance with some embodiments of the disclosure.

FIG. 112 is a flowchart of illustrative steps for detecting a transition from a cecum to a colon, which may be used when determining a location of an ingestible device as it transits through a GI tract, in accordance with some embodiments of the disclosure.

FIG. 113 illustrates an exemplary system for collecting, communicating and/or analyzing data about a subject.

FIG. 114 illustrates an ingestible device for delivering a substance in the GI tract.

FIG. 115 illustrates aspects of a mechanism for an ingestible device with a gas generating cell configured to generate a gas to dispense a substance.

FIG. 116 illustrates an ingestible device having a piston to push for substance delivery.

FIG. 117 illustrates an ingestible device having a bellow structure for a storage reservoir of dispensable substances.

Figure 118:
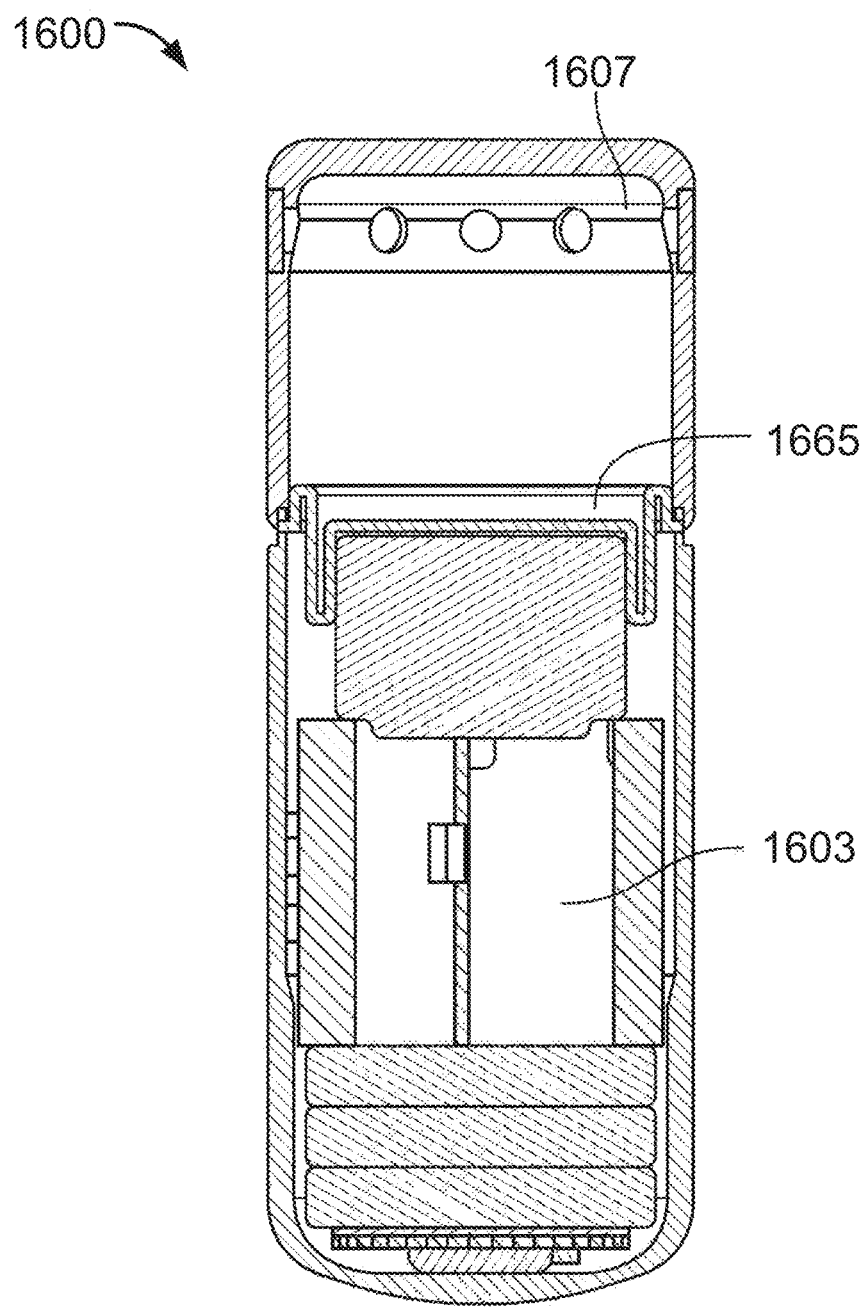

FIG. 118 illustrates an ingestible device having a flexible diaphragm to deform for substance delivery.

Figure 119:
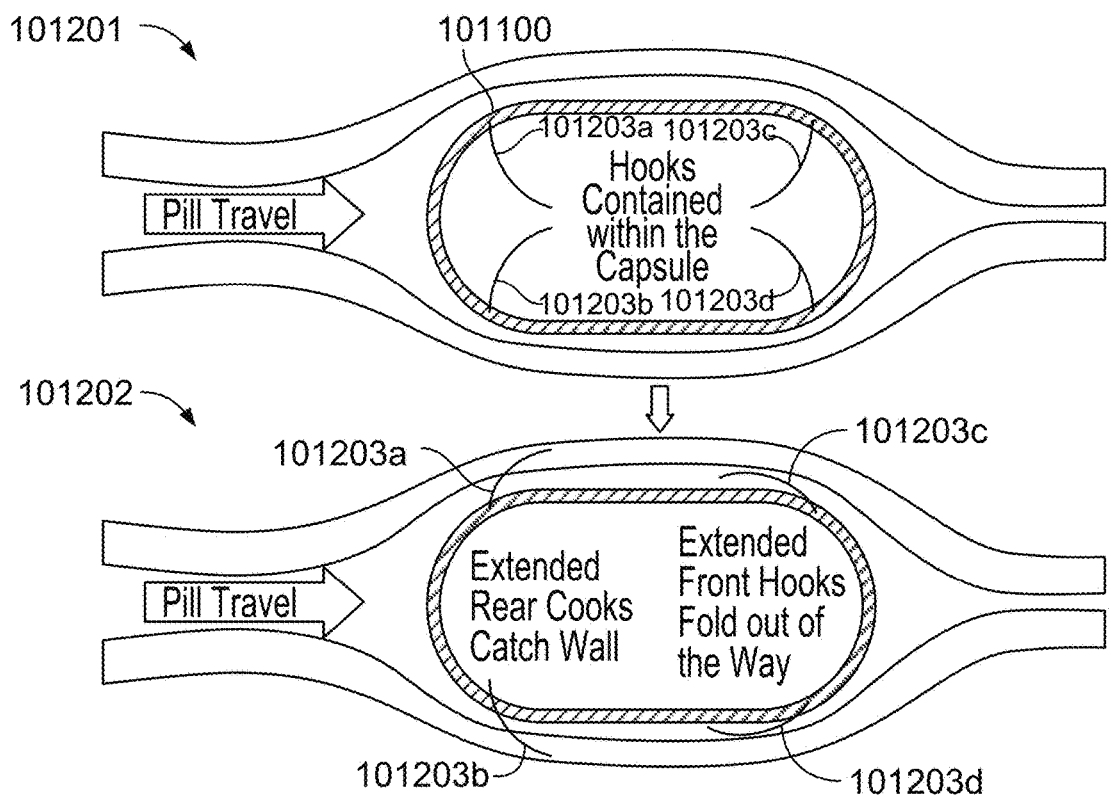
Figure 120:
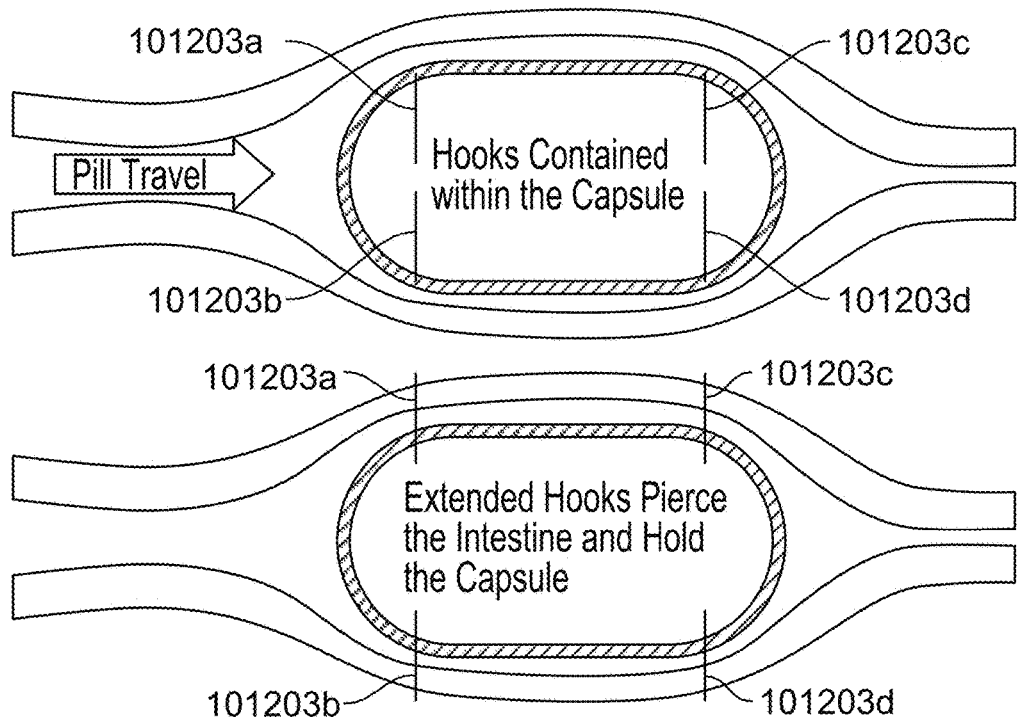
Figure 121:
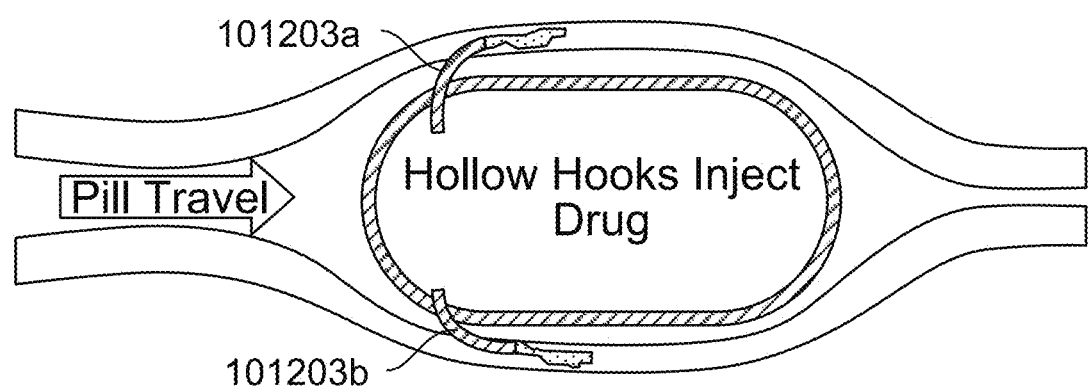

FIGS. 119-121 illustrate exemplary anchoring mechanisms of an ingestible device.

Figure 122:
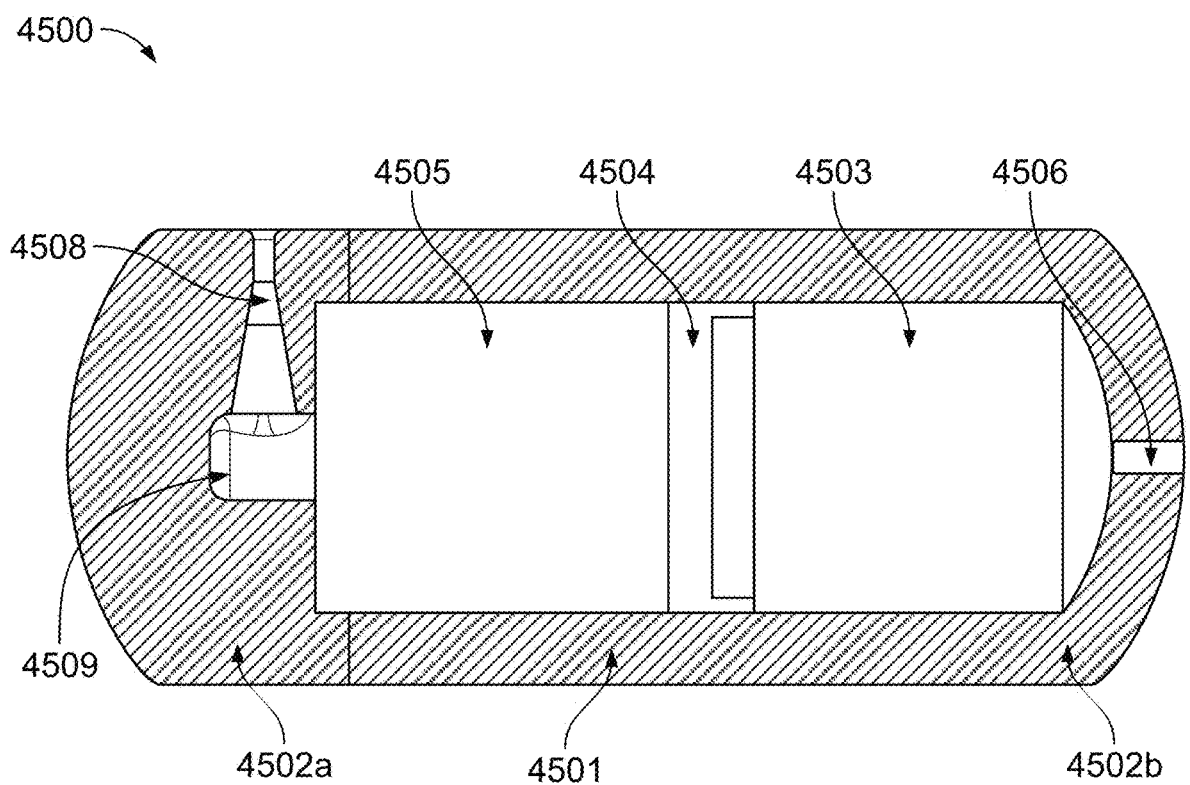

FIG. 122 illustrates an ingestible device including a pre-pressurized actuator chamber and a sliding piston, according to some embodiments described herein.

Figure 123A:
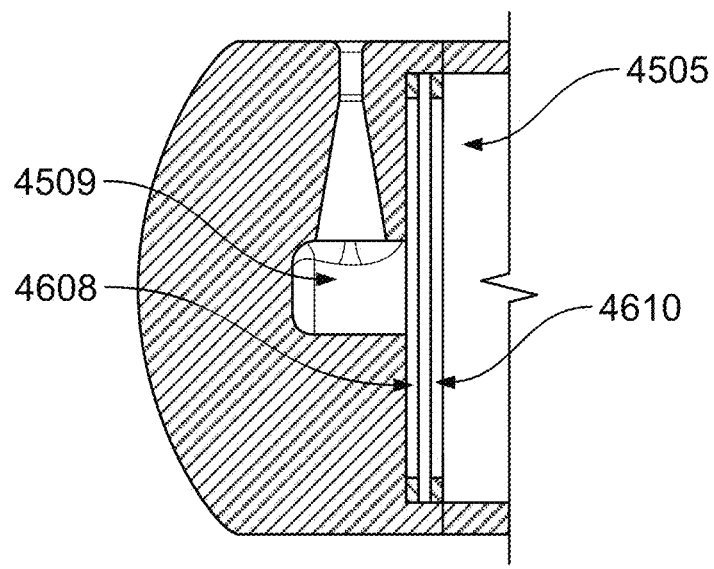

FIG. 123A illustrates a portion of an ingestible device including burst disc in line with a nozzle portion, according to some embodiments described herein.

Figure 123B:
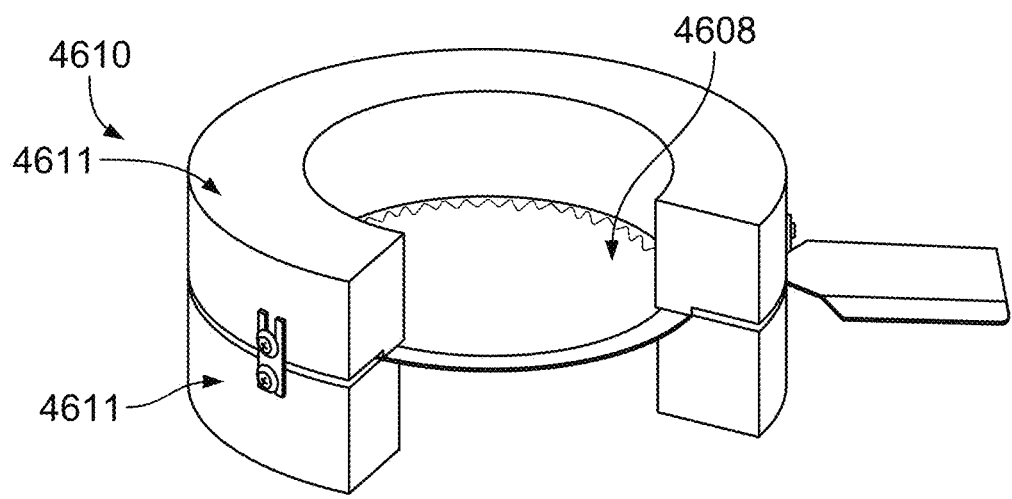

FIG. 123B illustrates a partial sectional view of a burst disc holder, according to some embodiments described herein.

Figure 124:
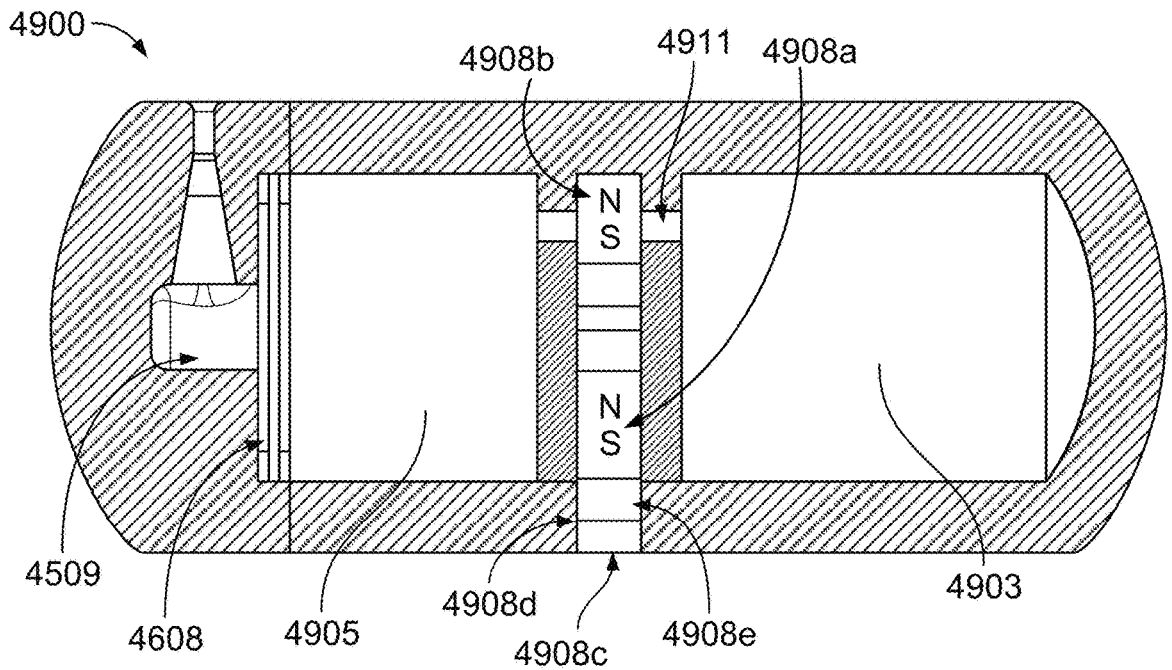

FIG. 124 illustrates an ingestible device including a magnetic occlusion component, a burst disc, and a pre-pressurized actuator chamber, according to some embodiments described herein.

Figure 125:
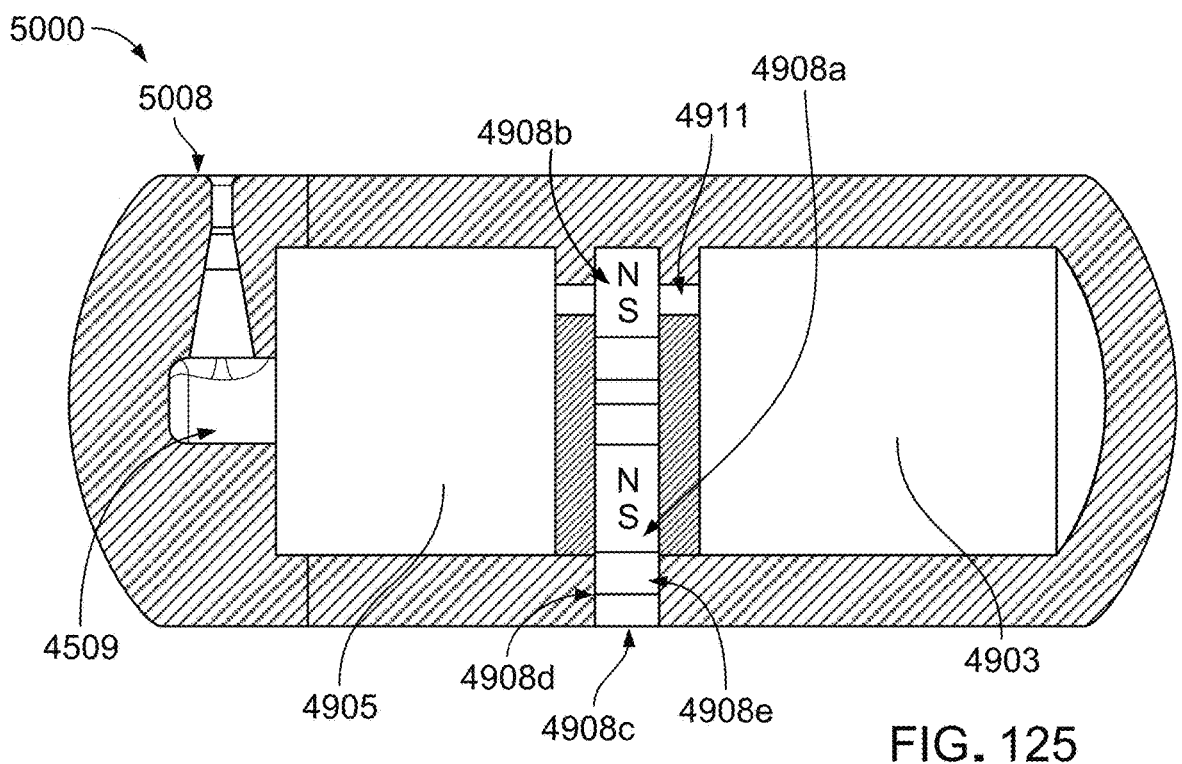

FIG. 125 illustrates an ingestible device including a magnetic occlusion component and pre-pressurized actuator chamber, according to some embodiments described herein.

Figure 126:
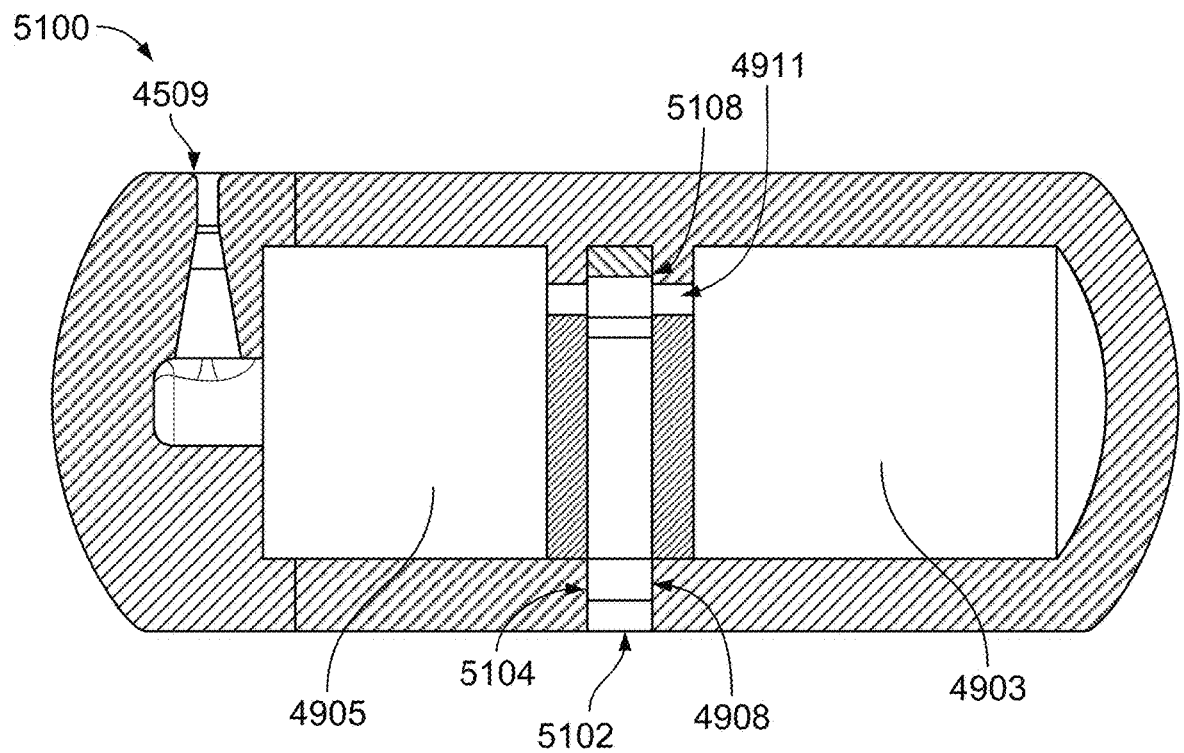

FIG. 126 illustrates an ingestible device including enteric sliding occlusion component and pre-pressurized actuator chamber and a sliding piston, according to some embodiments described herein.

Figure 127:
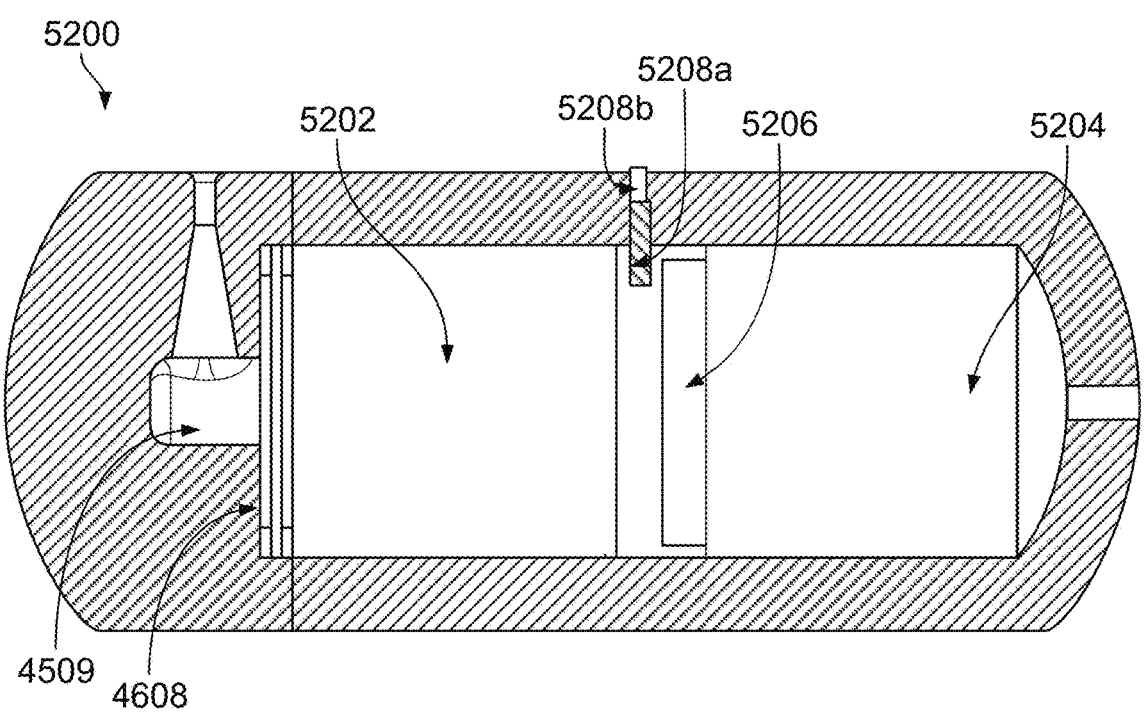
Figure 128:
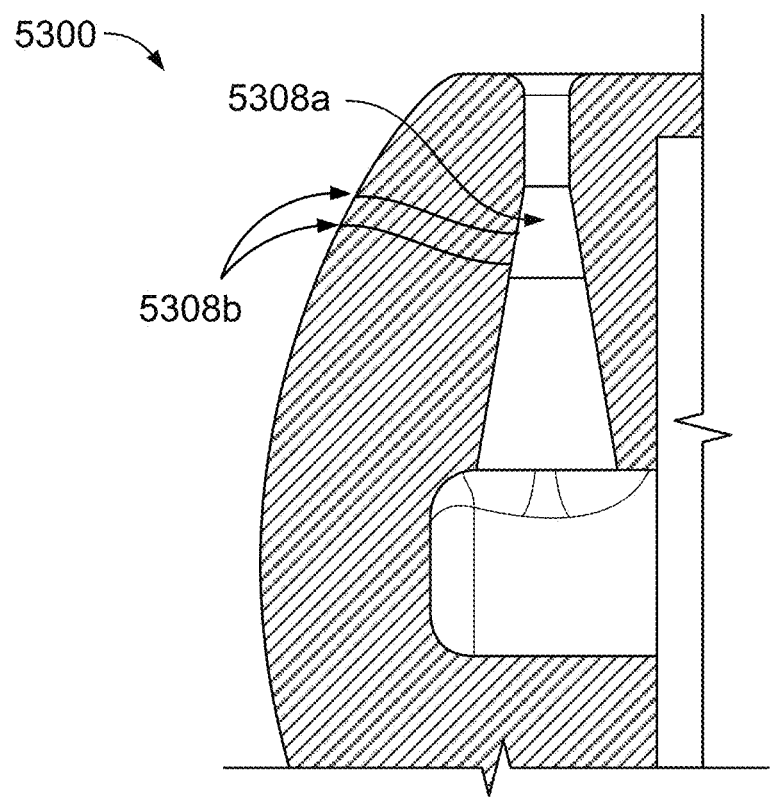
Figure 129:
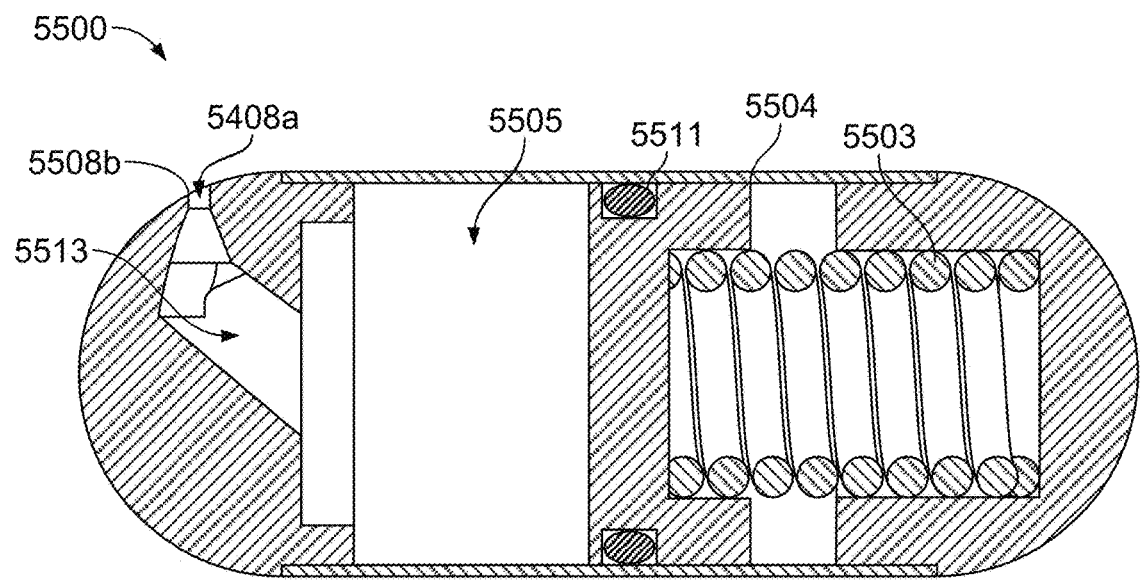
Figure 130:
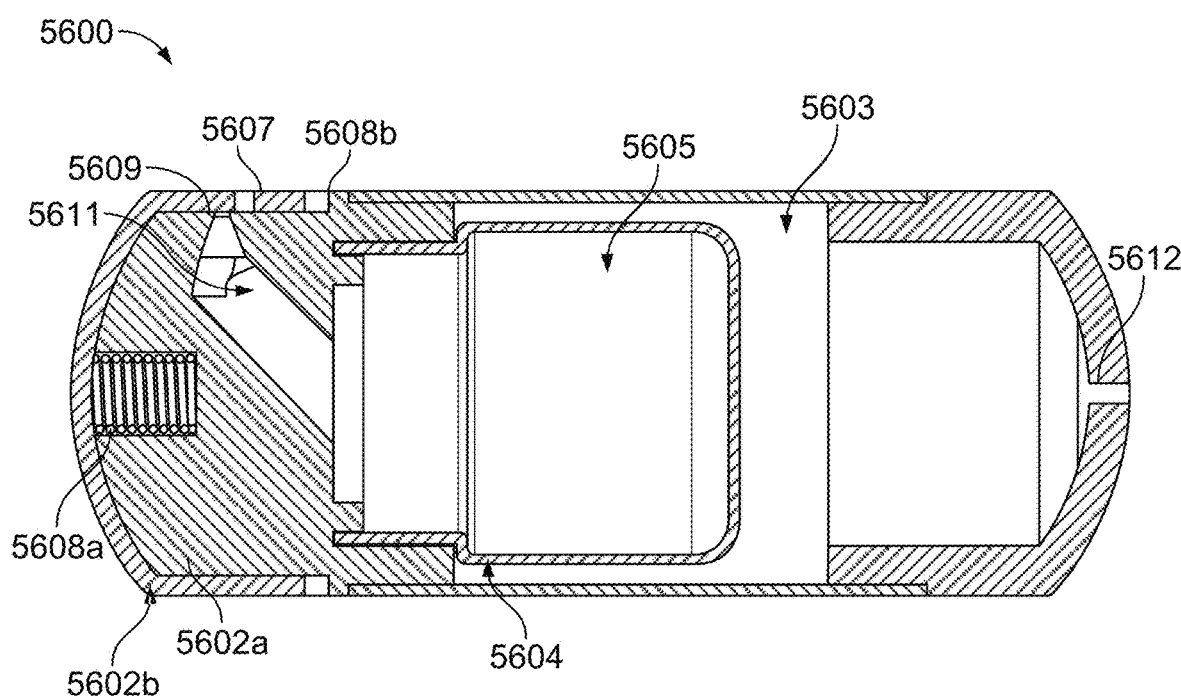
Figure 131:
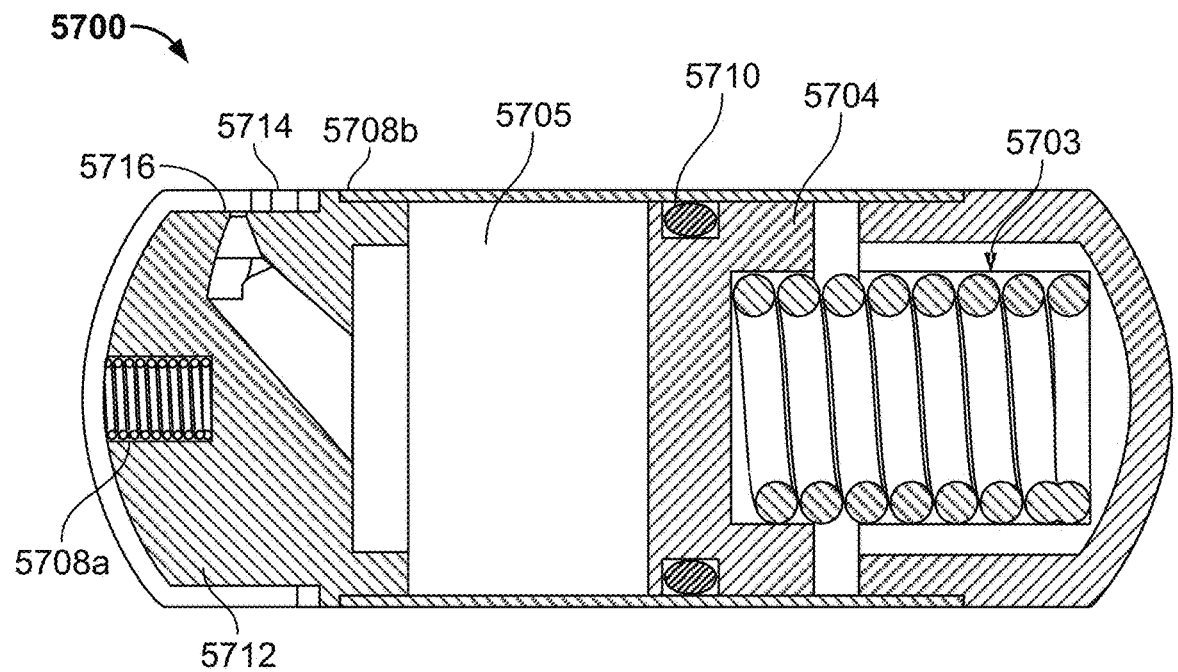
Figure 132:
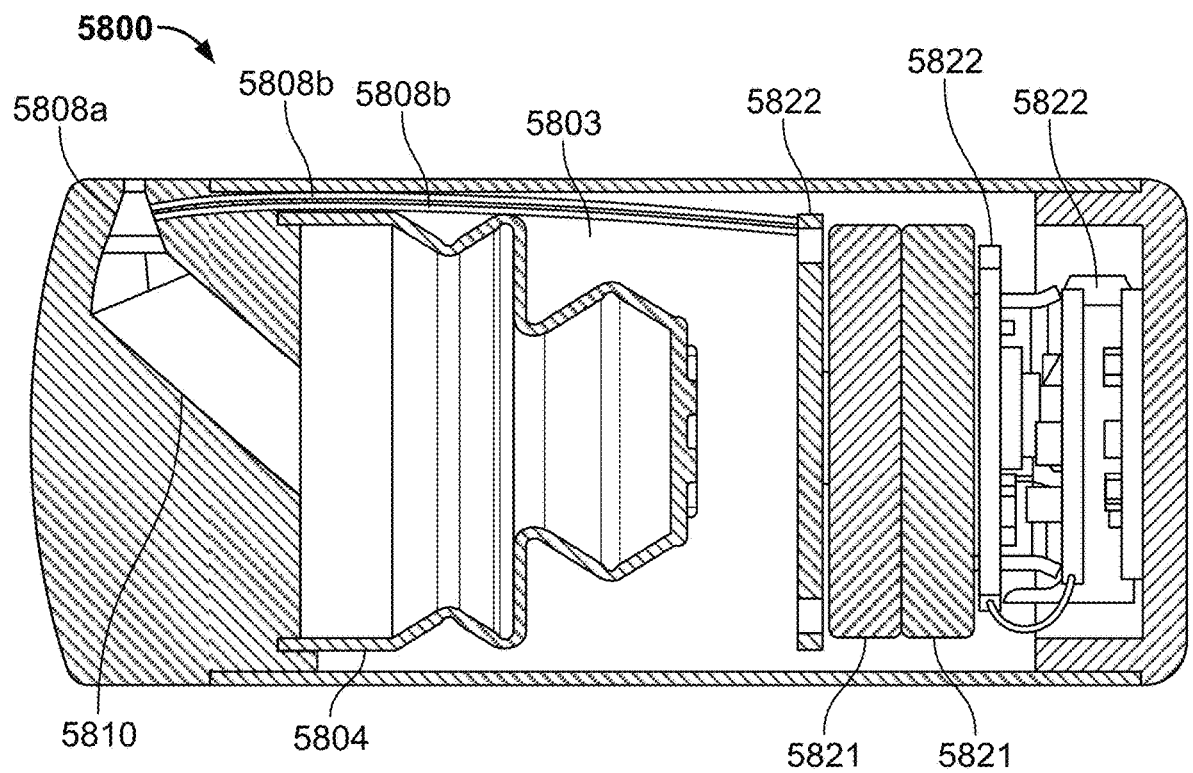
Figure 133:
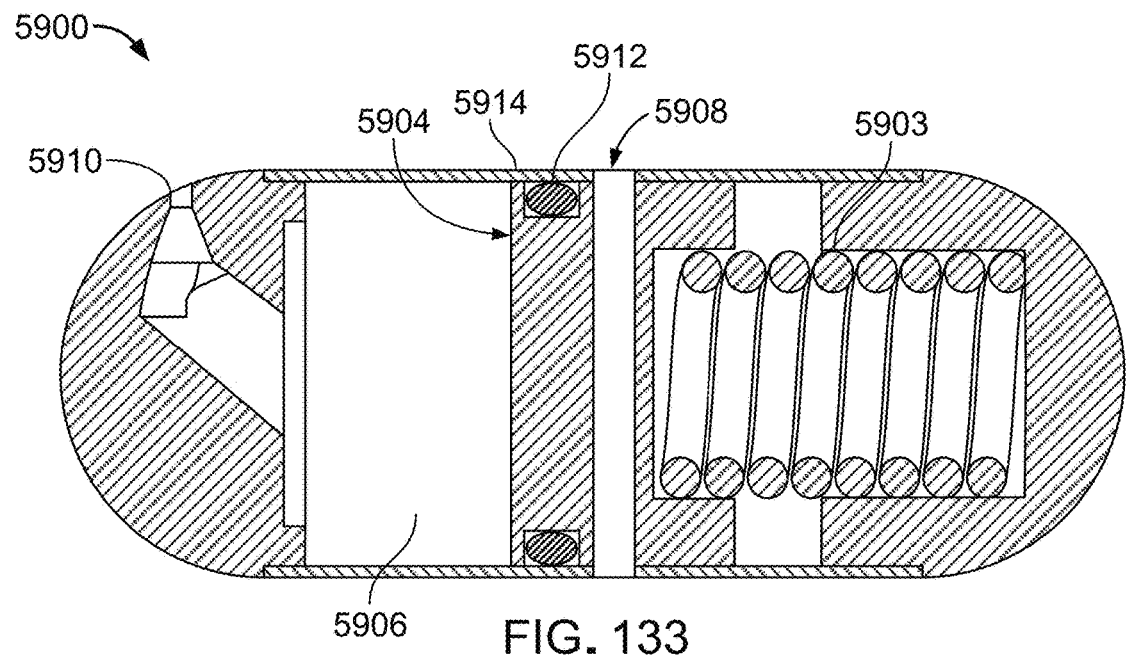
Figure 134:
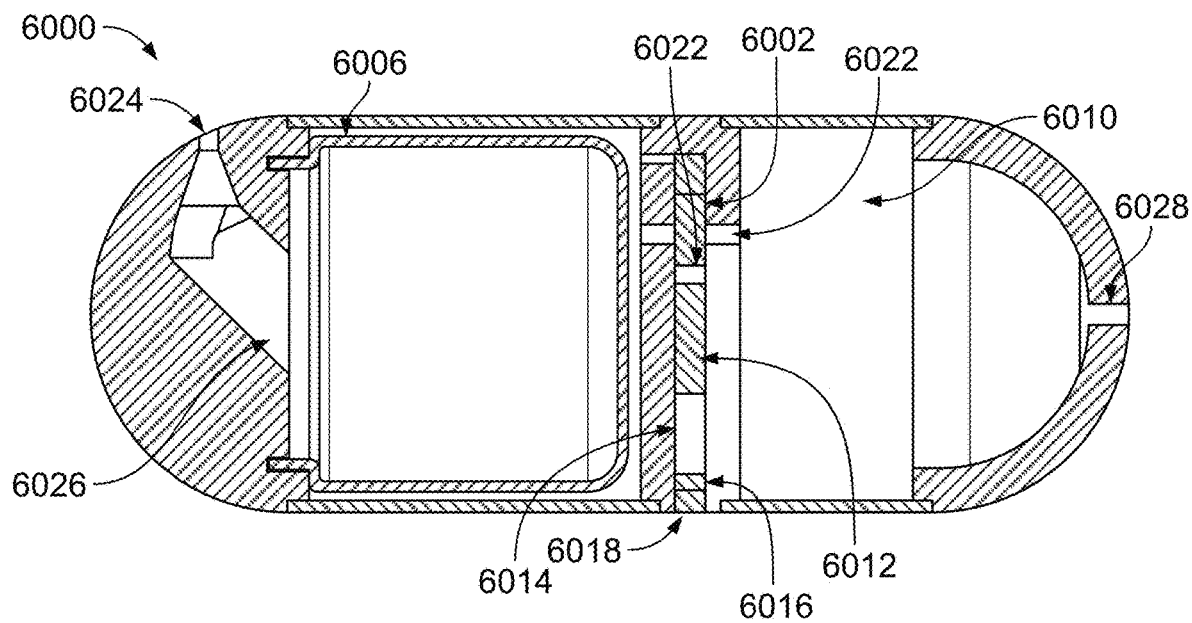

FIG. 127 illustrates an ingestible device.
FIG. 128 illustrates an ingestible device.
FIG. 129 illustrates an ingestible device.
FIG. 130 illustrates an ingestible device.
FIG. 131 illustrates an ingestible device.
FIG. 132 illustrates an ingestible device.
FIG. 133 illustrates an ingestible device.
FIG. 134 illustrates an ingestible device.

Like reference numbers and designations in the various drawings indicate like elements.

DETAILED DESCRIPTION

Various apparatuses or processes will be described below to provide exemplary disclosure. No embodiment described below limits any claimed disclosure and any claimed disclosure may cover processes or apparatuses that differ from those described below. The claimed disclosures are not limited to apparatuses or processes having all of the features of any one apparatus or process described below or to features common to multiple or all of the apparatuses or processes described below. It is possible that an apparatus or process described below is not an embodiment of any claimed disclosure. Any disclosure disclosed in an apparatus or process described below that is not claimed in this document may be the subject matter of another protective instrument, for example, a continuing patent application, and the applicants, inventors or owners do not intend to abandon, disclaim or dedicate to the public any such disclosure in this document.

Furthermore, it will be appreciated that, for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

In general, the disclosure provides ingestible devices, as well as related systems and methods, that can generate spectral data of one or more analytes in the GI tract of a subject and/or that can general spectral data of tissue of one or more regions of the GI tract of a subject. Data relating to the GI tract of a subject can be used to provide information regarding the GI tract (e.g., whether there is a GI disorder associated with the tissue) and/or the location of the ingestible device within the GI tract of a subject (e.g., by comparing the spectral data associated with the GI tract to one or more spectral standards for tissue of the GI tract).

The various embodiments described herein relate generally to an ingestible device for generating spectral data (e.g., hyperspectral data) of a sample within the gastrointestinal tract (GI) tract of a subject, and or for generating spectral data (e.g., hyperspectral data) of tissue associated with one or more regions of the GI tract. Also provided are associated methods, systems and kits that use or include an ingestible device as described herein. In some embodiments, spectral data may be generated at one or more locations as the device travels through the GI tract of the subject. In certain embodiments, spectral data may be generated as the ingestible device is stationary (or at least relatively stationary) in the GI tract and the sample flows by the ingestible device. In some embodiments, spectral data may be time series data, gathered on a continuous basis or at predetermined intervals. In some embodiments, the spectral data is used to generate a digestion profile for the subject. A digestion profile may include spectral data and information associated with the spectral data, associated with the sample, or associated with the subject. For example, a digestion profile may include spectral data and location data identifying where in the GI tract the spectral data was generated. Optionally a digestion profile may include environmental data and one or more user inputs. User inputs may be information on the subject and/or criteria selected by a user such as an analyte, medical condition, a desired outcome, or information about the sample. For example, the digestion profile may include user-inputted information about a meal or ingestible standard that the subject consumed concurrently with the ingestible device, as well as general demographic information about the subject.

A digestion profile may be used to search a database of spectral standards and/or other digestion profiles in order to identify similar digestion profiles and/or generate additional information regarding the sample and/or subject. For example, information indicating that the sample was a particular ingestible standard and general demographic information for the subject may be obtained from the subject's digestion profile. This may be used to search a digestion profile database to identify digestion profiles for individuals with similar demographics, or digestion profiles where the sample was the same ingestible standard as the one consumed by the subject. As another example, spectral data from a digestion profile may be used to search for digestion profiles or spectral standards containing similar spectral data. Any suitable type of signal processing technique may be used to identify similarities between spectral data, and any suitable type of information may be generated based on the digestion profiles or spectral standards identified in the database. For example, this information may include average digestion time for a given sample, average number of macronutrients or calories absorbed from a given sample, level of variation between a subject's spectral data and typical spectral data available in the database, and the like. This additional information may be presented to a user and/or be incorporated into the digestion profile of the subject. For example, information may be stored in the digestion profile for a subject indicating that the subject's ability to absorb nutrients from a particular ingestible standard is superior to 90% of individuals of a similar age and weight. Accordingly, a plurality of different digestion profiles may be generated for a subject, including the same or different spectral data associated with the same or different information associated with the spectral data, information associated with the sample, or information associated with the subject. In some embodiments, the plurality of digestion profiles are obtained from the same subject at different time frames (e.g., prior to treatment with a specific regimen (e.g., a therapeutic regimen or surgical intervention) and may be used to assess the efficacy of a particular regimen.

Definitions

Unless otherwise defined herein, scientific and technical terms used in this disclosure shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification.

Chemistry terms used herein are used according to conventional usage in the art, as exemplified by "The McGraw-Hill Dictionary of Chemical Terms," Parker S., Ed., McGraw-Hill, San Francisco, Calif. (1985).

All of the publications, patents and published patent disclosures referred to in this disclosure are specifically incorporated by reference herein. In case of conflict, the present specification, including its specific definitions, will control.

A "patient," "subject," or "individual" are used interchangeably and refer to either a human or a non-human animal. These terms include mammals, such as humans, primates, livestock animals (including bovine, porcine, etc.), companion animals (e.g., canine, feline, etc.) and rodents (e.g., mice and rats). The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The terms "treating," "treat," or "treatment" embrace both preventative, i.e., prophylactic, and palliative treatment. In some embodiments, the methods described herein include the use of an ingestible device for detecting a GI disorder in a subject who has or is at risk of developing a GI disorder. In some embodiments, the subject has been previously identified as having a GI disorder. Some embodiments of any of the methods provided herein further include, prior to the providing an ingestible device step, determining that the subject has a GI disorder. Some embodiments of any of the methods can further include identifying or diagnosing a subject as having a GI disorder.

As used herein, the term "sample" refers to matter (e.g., one or more analytes) found within, or forming part of, the GI tract of a subject. In some embodiments, the sample is tissue-forming part of the GI tract of the subject. In some embodiments, the sample is matter (e.g., one or more analytes) found within the lumen of the GI tract of a subject. For example, in some embodiments, the sample (e.g., one or more analytes) includes one or more of an ingested matter (e.g., food, e.g., partially or fully digested food), gastric juices and/or chyme, proteins secreted into the lumen of the GI tract, bacteria, and cells or other biological material from the subject. In some embodiments, the sample (e.g., one or more analytes) include one or more of blood, salt, water, minerals, fiber, bile, ketone bodies and mucus. In some embodiments, the sample (e.g., one or more analytes) includes an ingestible standard and/or detection agent. In some embodiments, the sample (e.g., one or more analytes) includes a substance that has been administered to the subject such as a drug or nutritional supplement. In some embodiments, a sample includes one or more body fluids which include, for example, urine, blood, plasma, serum, saliva, semen, stool, sputum, cerebral spinal fluid, tears, mucus, and the like. In some embodiments, the sample is a liquid sample that contains one or more analytes. For example, in some embodiments, the sample includes or consists of a liquid within the lumen of a subject that excludes tissue forming the GI tract of the subject. In some embodiments, the liquid may include dissociated cells or cell debris that previously formed part of the tissue forming the GI tract of the subject. In some embodiments, a single device collects multiple samples, for example, 2, 3, 4, 5, 6, 7, 8, 9, 10, 11, 12, 13, 14, 15, 16, 17, 18, 19, 20, 21, 22, 23, 24, 25, 30, 35, 40, 45, 50, 100 or more samples. In some embodiments, the sample is between 1-2000 µL (e.g., 1-1500 µL, 1-1900 µL, 1-1000 µL, 1-500 µL, 1-250 µL, 1-100 µL, 1-50 µL, 1-10 µL, and 1-5 µL).

As used herein, the term "spectral data" refers to data generated by exposing a sample to electromagnetic radiation. Spectral data may be generated using a spectrometer. In certain embodiments, the spectral data are hyperspectral data. In some embodiments, the spectral data is absorbance spectral data, transmission spectral data, reflectance spectral data, Fourier transform spectral data and/or Raman spectral data. In some embodiments, the spectral data is Near-Infrared (NIR) spectral data. In certain embodiments, spectral can include infrared (IR) spectral data, visible spectral data, and/or ultraviolet (UV) spectral data. Optionally, the methods and devices described herein use or generate two or more different types of spectral data.

As used herein, the term "digestion profile" refers to spectral data from a subject and optionally information associated with the spectral data, associated with the sample, or associated with the subject. For example, in some embodiments, a digestion profile may include spectral data and information on the subject such as, but not limited to, weight, height, sex, diet, activity level, medical condition, medication, genotype, phenotype, BMI, race, age, exercise routine, heart rate, pulse, food ingested by the subject, and/or place of residence.

GI Tract

As used herein, the term "gastrointestinal tract" or "GI tract" refers to all portions of an organ system responsible for consuming and digesting foodstuffs, absorbing nutrients, and expelling waste. This includes orifices and organs such as the mouth, throat, esophagus, stomach, small intestine, large intestine, rectum, anus, and the like, as well as the various passageways and sphincters connecting the aforementioned parts. The device may be used to detect, analyze and/or quantify an analyte, e.g., bacterial cells, in a sample from the GI tract (e.g., in one or more of the mouth, throat, esophagus, stomach, small intestine, large intestine, rectum, anus, sphincter, duodenum, jejunum, ileum, ascending colon, transverse colon, and descending colon) of a subject. The device may also be used to detect or quantify bacterial cells from outside the GI tract, including the female reproductive tract. In some embodiments, the samples from the subject are environmental samples that do not contain eukaryotic cells.

The GI tract is a large organ that extends from the buccal cavity to the anus. The primary function of the GI tract is to digest food, absorb nutrients and eliminated any waste. The GI tract is composed of the esophagus, the stomach, and the intestines. The different segments of the GI tract are generally associated with different characteristics. Chewed food flows through the esophagus, and into the stomach where it is temporarily stored and mixed with gastric acid. Involuntary muscle contractions, termed peristalsis, push the food out of the stomach and into the small intestine. The small intestine can be divided into the duodenum, the jejunum and the ileum. The majority of food digestion and absorption occurs in the ileum. Waste and unwanted products are passed into the colon, or large intestine. Typically, food resides for 10 to 14 seconds in the esophagus, and travels within the small intestine for 2 to 4 hours. Half of the contents of the stomach is emptied within 60 to 90 minutes (Khutoryanskiy (2015) Nature Materials 14: 963-964). While food enters the esophagus at approximately pH 7.0, foods are acidified within the stomach (pH 1-5). The pH in the proximal small intestine is between 6.8 and 7.88; between 5.26 and 6.72 in the distal small intestine, between 5.26-6.72 in the ascending colon, and between 5.20 and 7.02 in the descending colon (Khutoryanskiy (2015) Nature Materials 14: 963-964).

Over 1000 different microbial species have been identified that can live in the human GI tract, e.g., *Actinobacteria, Bifidobacterium* sp., *Coriobacteriales, Eggerthella, Slackia* spp., *Actinomycetales, Bacteroidetes, Firmicutes, Gemella, Clostridia, Lachnospiraceae, Negativicutes, Fusobacteria*, and fungi (e.g., *Eukarya*). See, e.g., Rajilic-Stojanovic and de Vos (2014) FEMS Microbiol. Rev. 38(5): 996-1047; and Carroll et al. (2015) Mamm. Genome 20(7): 395-403. Whereas the small intestine contains very few bacteria, the colon comprises between $10^{13}$ and $10^{14}$ commensal bacteria (Johansson et al. (2013) Nat. Rev. Gastroenterol. Hepatol. 10(6): 352-361).

The intestinal fluid can contain a variety of digestive enzymes (e.g., pepsin, lipase, amylase, enterokinase, sucrose, maltase, lactase, secretin, motilin). See, e.g., Ulleberg et al. (2011) Food Dig. 2(1-3): 52-61.

Diseases or Disorders

The detection and/or analysis of an analyte described herein may be used to determine whether the subject has or is at risk of developing a disease or disorder (e.g., a GI disorder). These diseases and disorders are not limited to diseases and disorders present in the GI tract of the subject, and can include diseases or disorders at sites other than the GI tract of the subject. For example, in some embodiments, analytes present in the GI tract may be indicative of a systemic disease or disorder. In some embodiments, the analytes are associated with a systemic disease or disorder. In some embodiments, analytes present in the GI tract may be indicative of a disease or disorder described herein, including, but not limited to an infectious disease, IBD, Crohn's disease, and cancer.

In some embodiments of any of the methods described herein, the subject has a GI disorder. In some embodiments, the analytes disclosed herein may be indicative of a GI disorder in a subject. Examples of such GI disorders include inflammatory bowel disease (IBD), Crohn's disease (e.g., active Crohn's disease, refractory Crohn's disease, or fistulizing Crohn's disease), ulcerative colitis, indeterminate colitis, infectious colitis, microscopic colitis, drug or chemical-induced colitis, diverticulitis, ischemic colitis, pseudomembranous colitis, hemorrhagic colitis, hemolytic-uremic syndrome colitis, collagenous colitis, colitis associated with disorders of innate immunity as in leukocyte adhesion deficiency-1, diversion colitis, gastritis, peptic ulcers, stress ulcers, bleeding ulcers, gastric hyperacidity, dyspepsia, gastroparesis, Zollinger-Ellison syndrome, gastroesophageal reflux disease, short-bowel (anastomosis) syndrome, mucositis (e.g., oral mucositis, gastrointestinal mucositis, nasal mucositis and proctitis), necrotizing enterocolitis, esophagitis, a hypersecretory state associated with systemic mastocytosis, basophilic leukemia, hyperhistaminemia, Celiac disease (e.g., nontropical Sprue), enteropathy associated with seronegative arthropathies, eosinophilic gastroenteritis, colitis associated with radiotherapy or chemotherapy (such as checkpoint inhibitor chemotherapy), colitis associated with disorders of innate immunity such as leukocyte adhesion deficiency-1, gastritis, chronic granulomatous disease, food allergies, infectious gastritis or enterocolitis (e.g., *Helicobacter pylori*-infected chronic active gastritis), other forms of gastrointestinal inflammation caused by an infectious agent, irritable colon syndrome, small intestinal bacterial overgrowth (SIBO) and pouchitis.

"Inflammatory Bowel Disease" or "IBD" is a chronic inflammatory autoimmune condition of the GI tract. Although the cause of IBD remains unknown, several factors such as genetic, infectious and immunologic susceptibility have been implicated. IBD is much more common in Caucasians, especially those of Jewish descent.

A chronic inflammatory autoimmune condition of the GI tract presents clinically as either ulcerative colitis (UC) or Crohn's disease (CD). Both IBD conditions are associated with an increased risk for malignancy of the GI tract. "Crohn's disease" ("CD") is a chronic transmural inflammatory disease with the potential to affect any part of the entire GI tract, and UC is a mucosal inflammation of the colon. Both conditions are characterized clinically by frequent bowel motions, malnutrition, and dehydration, with disruption in the activities of daily living. CD is frequently complicated by the development of malabsorption, strictures, and fistulae and may require repeated surgery. UC, less frequently, may be complicated by severe bloody diarrhea and toxic megacolon, also requiring surgery. The most prominent feature of Crohn's disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease require surgery at some point, but subsequent relapse is common and continuous medical treatment is usual. Crohn's disease may involve any part of the alimentary tract from the mouth to the anus, although typically it appears in the ileocolic, small-intestinal or colonic-anorectal regions. Histopathologically, the disease manifests by discontinuous granulomatomas, crypt abscesses, fissures and aphthous ulcers. The inflammatory infiltrate is mixed, consisting of lymphocytes (both T and B cells), plasma cells, macrophages, and neutrophils. There is a disproportionate increase in IgM- and IgG-secreting plasma cells, macrophages and neutrophils.

"Ulcerative colitis (UC)" afflicts the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be required for acute, severe or chronic, unremitting ulcerative colitis.

A "symptom" of a disease or disorder (e.g., an inflammatory bowel disease, e.g., ulcerative colitis or Crohn's disease) is any morbid phenomenon or departure from the normal in structure, function, or sensation, experienced by a subject and indicative of disease.

In certain embodiments, the subject has small intestinal bacterial overgrowth (SIBO). The small intestine houses less than $10^3$ bacteria/mL under healthy conditions. When the homeostasis of the gut microbiome is disrupted or aberrant, various functions of the gut microbiota are uncontrolled. See, e.g., Shreiner et al. (2016) Curr. Opin. Gastroenterol. 31(1): 69-75; Bures et al. (2010) World J. Gastroenterol. 16(24): 2978-2990. Excessive levels of bacteria (over $10^5$ bacteria/mL) and abnormal types of bacteria in the small intestine leads to the development of SIBO. SIBO is associated with chronic diarrhea, abdominal discomfort, bloating, malabsorption, flatulence, and unintentional weight loss. While Gram-positive bacteria are typically found in the small intestine, subjects suffering from SIBO have a variety of bacteria in the small intestine including Gram-negative bacteria, which are normally only present in very small numbers or not at all within the small intestine. For example, bacteria present in SIBO may secrete mucosal damaging toxins or metabolize bile salts, which can lead to malabsorption and bloating. A study comparing the prevalence of SIBO in subjects aged 24 to 50 and in subjects aged 61 or older found that SIBO was more prevalent in older subjects as compared to younger subjects (15.6% and 5.9% respectively) (Parlesak et al. (2003) J. Am. Geriatr. Soc. 51(6): 768-773). SIBO was also seen more frequently in subjects with reduced body weight. Risk factors for developing SIBO include: metabolic disorders (e.g., diabetes, hypochloryhydria), malnutrition, irritable bowel syndrome (IBS), Celiac disease, Crohn's disease, cirrhosis, renal failure, gastroparesis, small bowel dysmotility, structural abnormalities of the GI tract (e.g., jejunal diverticula), gastric resection and immuno-deficiency. Additional risk factors include the use of certain medications (e.g., antibiotics, gastric acid secretion inhibitors). See, e.g., Dukowicz et al. (2007) Gastroenterol. Hepatol. 3(2): 112-122. In some embodiments, subjects having SIBO have delayed intestinal transit times (Cuoco et al. (2002) Hepatogastroenterology 49: 1582-1586). In some embodiments, subjects having SIBO have accelerated intestinal transit times (Van Citters and Lin (2006) Clin. Nutrition in Gastrointestinal Disease. Thorofare: Slack Inc; 2006; 271-280).

As used herein, a subject has or is at risk of having SIBO if the subject has intestinal bacteria levels that are greater than $10^3$ colony forming units (CFU)/mL, e.g., greater than $10^4$ CFU/mL, greater than $10^5$ CFU/mL, greater than $10^6$ CFU/mL, greater than $10^7$ CFU/mL, greater than $10^8$ CFU/mL, greater than $10^9$ CFU/mL, greater than $10^{10}$ CFU/mL. In some embodiments, the bacteria are both Gram-positive and Gram-negative bacteria. In some embodiments, the bacteria are Gram-positive bacteria. In some embodiments, the bacteria are Gram-negative bacteria.

The prevalence of SIBO in healthy individuals varies from about 0-20% (see, e.g., Lombardo et at. (2010) Clin. Gastroenterol. Hepatol. 8: 504-8; Sabaté et al. (2008) Obes. Surg. 18: 371-7; Posserud et al. (2007) Gut 56: 802-8; Teo (2004) J. Gastroenterol. Hepatol. 19: 904-9; Lewis et al. (1999) Age Ageing 28: 181-5; Pimentel et al. (2003) Am. J. Gastroenterol. 98: 412-9; Rana et al. (2011) Diabetes Technol. Ther. 13: 1115-20; Bratten et al. (2008) Am. J. Gastroenterol. 103: 958-63; and Scarpellini et al. (2009) J. Pediatr. 155: 416-20). Several clinical conditions are associated with SIBO and are referred to herein as "SIBO-related conditions." Exemplary SIBO-related conditions include, but are not limited to, coeliac disease (see, e.g., Rana et al. (2007) Trop. Gastroenterol. 28: 159-61; Rubio-Tapia et al. (2009) J. Clin. Gastroenterol. 43: 157-61; and Tursi et al. (2003) Am. J. Gastroenterol. 98: 839-43), connective tissue diseases such as scleroderma (see, e.g., Levesque et al. (2009) Rheumatology 48: 1314-9; and Parodi et al. (2008) Am. J. Gastroenterol. 103: 1257-62), Crohn's disease (see, e.g., Fukushima et al. (1999) Dis. Colon Rectum 42: 1072-7; Klaus et al. (2009) Gastroenterol. 9: 61; and U.S. Publication No. 2002/0039599), diabetes mellitus (see, e.g., Rana et al. (2011) Diabetes Technol Ther 13: 1115-20, and Zaccardi et al. (2009) Eur. Rev. Med. Pharmacol. Sci. 13: 419-23), hypothyroidism (see, e.g., Lauritano et al. (2007) J. Clin. Endocr. Metab. 92: 4180-4), nonspecific dysmotility (see, e.g., Jacobs et al. (2013) Aliment. Pharmacol. Ther. 37:

1103-11), radiation enteropathy (see, e.g., Wedlake et al. (2008) *Eur. J Cancer* 44: 2212-7), ulcerative colitis (see, e.g., Ibanez et al. (2008) *Gastroenterology* 134: A-350), chronic fatigue syndrome (see, e.g., Ojetti et al. (2009) *Eur. Rev. Med. Pharmacol. Sci.* 13: 419-23), chronic pancreatitis (see, e.g., Mancilla et al. (2008) 136: 976-80; and Trespi et al (1999) *Curr. Med. Res. Opin.* 15: 47-52), drug-induced inhibition of acid secretion (see, e.g., Jacobs (2013) *Aliment. Pharmacol. Ther.* 37: 1103-11; Compare et al. (2010) *Eur. J. Clin. Invest.* 41: 380-6; and Lombardo et al. (2010) *Clin. Gastroenterol. Hepatol.* 8: 504-8), end-stage renal failure (see, e.g., Strid et al. (2003) *Digestion* 67: 129-37), fibromyalgia (see, e.g., U.S. Publication No. 2002/0039599), irritable bowel syndrome (Posserud et al. (2007) *Gut* 56: 802-8; Bratten et al. (2008) *Am. J. Gastroenterol.* 103: 958-63; 30. Pimentel et al. (2000) *Am. J. Gastroenterol.* 95: 3503-6; Nucera et al. (2005) *Aliment. Pharmacol. Ther.* 21: 1391-5; Lupascu et al. (2005) *Aliment. Pharmacol. Ther.* 22: 1157-60; and Grover et al. (2008) *Neurogastroenterol. Motil.* 20: 998-1008), immunodeficiency syndromes such as HIV-infection and chronic lymphocytic leukaemia (see, e.g., Chave et al. *Am. J. Gastroenterol.* 89: 2168-71; and Smith et al. (1990) *J. Clin. Pathol.* 43: 57-9), liver cirrhosis (see, e.g., Yang et al. (1998) *Scand. J. Gastroenterol.* 33: 867-71; and Gunnarsdottir (2003) *Am. J. Gastroenterol.* 98: 1362-70), obesity (see, e.g., Sabaté et al. (2008) *Obes. Surg.* 18: 371-7; and Madrid et al. (2011) *Dig. Dis. Sci.* 56: 155-60), parenteral nutrition (see, e.g., Gutierrez et al. (2012) *J. Pediatr. Surg.* 47: 1150-4), rosacea (Parodi et al. *Clin. Gastroenterol. Hepatol.* 6: 759-64), muscular dystrophy (see, e.g., Tarnopolsky et al. (2010) *Muscle Nerve* 42: 853-5), and Parkinson's disease (see, e.g., Gabrielli (2011) *Movement Disord.* 26: 889-92). Thus, in some embodiments of any of the methods described herein, the subject has a SIBO-related condition selected from the group consisting of coeliac disease, a connective tissue disease (e.g., scleroderma), Crohn's disease, diabetes mellitus, hypothyroidism, nonspecific dysmotility, radiation enteropathy, ulcerative colitis, chronic fatigue syndrome, chronic pancreatitis, drug-induced inhibition of acid secretion, end-stage renal failure, fibromyalgia, irritable bowel syndrome, an immunodeficiency syndrome (e.g., HIV-infection and chronic lymphocytic leukaemia), obesity, parenteral nutrition, rosacea, muscular dystrophy, and Parkinson's disease. For example, the methods described herein may be used to detect SIBO in a subject having a SIBO-related condition.

In some embodiment of any of the methods described herein, the subject is suspected of having SIBO or a SIBO-related condition. In some embodiments of any of the methods described herein, the subject has one or more symptoms selected from the group consisting of bloating, diarrhea, flatulence, abdominal pain, constipation, weight loss, fever, abdominal tenderness, nausea, gastric stasis, and steatorrhea.

In some embodiments of any of the methods described herein, the subject has been subjected to a surgical intervention. For example, SIBO is prevalent in subjects that have undergone abdominal surgery, bilateral vagotomy, gastrectomy, ileocaecal valve resection, and roux-en-Y reconstruction (see, e.g., Grace et al. (2013) *Aliment. Pharmacol. Ther.* 38(7):674-88, the entire contents of which are expressly incorporated herein by reference). In some embodiment of any of the methods described herein, the subject has been subjected to a surgical intervention selected from the group consisting of abdominal surgery, bilateral vagotomy, gastrectomy, ileocaecal valve resection, and roux-en-Y reconstruction.

In some embodiments, detection of analytes disclosed herein are indicative of disorders of the gastrointestinal tract associated with anomalous bacterial populations. The bacteria may include, but are not limited to, the types of bacteria present in the fluid sample or the concentration of bacteria in specific regions of the GI tract. Data obtained using the methods described herein may be used to determine whether a subject has an infection, such as Small Intestinal Bacterial Overgrowth (SIBO), or to characterize bacterial populations within the GI tract for diagnostic or other purposes. In some embodiments, detection of an analyte disclosed herein in a subject may be indicative of a disease or condition originating from the endoderm in a subject. In some embodiments of any of the methods described herein, the subject has a disease or condition originating from the endoderm selected from the group of: gastritis, Celiac disease, hepatitis, alcoholic lever disease, fatty liver disease (hepatic steatosis), non-alcoholic fatty liver disease (NASH), cirrhosis, primary schlerosing cholangitis, pancreatitis, insterstitial cystitits, asthma, chronic obstructic pulmonary disease, pulmonary fibrosis, pharyngitis, thyroiditis, hyperthyroidism, parathyroiditis, nephritis, Hashimoto's disease, Addison's disease, Graves' disease, Sjögren syndrome, type 1 diabetes, pelvic inflammatory disease, auditory canal inflammation, tinnitus, vestibular neuritis, otitis media, auditory canal inflammation, tracheitis, cholestatic liver disease, primary biliary schlerosis, liver parenchyma, an inherited metabolic disorder of the liver, Byler syndrome, cerebrotendinous, xanthomatosis, Zellweger's syndrome, neonatal hepatitis, cystic fibrosis, ALGS (Alagilles syndrome), PFIC (progressive familial intrahepatic cholestasis), autoimmune hepatitis, primary biliary cirrhosis (PBC), liver fibrosis, NAFLD, portal hypertension, general cholestasis, such as in jaundice due to drugs or during pregnancy, intra- and extrahepatic cholestasis, such as hereditary forms of cholestasis, such as PFIC1, gall stones and choledocholithiasis, malignancy causing obstruction of the biliary tree, symptoms (scratching, pruritus) due to cholestasis/jaundice, chronic autoimmune liver disease leading to progressive cholestasis, and pruritus of cholestatic liver disease, duodenal ulcers, enteritis (radiation-, chemotherapy-, or infection-induced enteritis), diverticulitis, pouchitis, cholecystitis, and cholangitis. In some embodiments of any of the methods described herein, the inflammatory disease or condition that arises in a tissue originating from the endoderm is inflammation of the liver.

In some embodiments, the detection of analytes disclosed herein is indicative of diseases or disorders of the liver. In some embodiments, detection of an analyte disclosed herein in a subject may be indicative of a liver disease or disorder in a subject. For example, the methods, devices, and compositions described herein may be used to determine whether a subject has or is at risk of developing a liver disease or disorder, and/or to determine or monitor a course of treatment for a liver disease or disorder. A non-exhaustive list of liver diseases and disorders, include, but are not limited to fibrosis, cirrhosis, alcoholic lever disease, fatty liver disease (hepatic steatosis), non-alcoholic fatty liver disease (NASH), cholestatic liver disease, liver parenchyma, an inherited metabolic disorder of the liver, PFIC (progressive familial intrahepatic cholestasis), autoimmune hepatitis, primary biliary cirrhosis (PBC), liver fibrosis, NAFLD, chronic autoimmune liver disease leading to progressive cholestasis, pruritus of cholestatic liver disease, inflammation of the liver, and liver fibrosis.

Methods of Selecting and Optimizing Treatment

In some embodiments, the methods described herein include the administration of one or more treatments, e.g., antibiotics, to a subject identified as having or being at risk of developing a GI disorder (e.g., SIBO). The methods can also include selecting a treatment for a subject who has a GI disorder or is determined to be at risk for developing a GI disorder, based upon the presence or absence of an analyte, or based upon the amount of an analyte. The methods can also include administering a treatment selected by a method described hereinto a subject who has or is at risk of developing a GI disorder to treat, delay disease progression, or reduce the risk of developing of the disease. For example, in some embodiments, the methods described herein can include the administration of an antibiotic (e.g., rifaximin) to a subject identified as having or being at risk of developing SIBO. In some embodiments, the methods can also include selecting a subject having SIBO or who is at risk of developing SIBO (e.g., a subject having a SIBO-related condition), and treating the subject with an antibiotic (e.g., rifaximin) to treat, delay disease progression, or reduce the risk of developing SIBO. In some embodiments of any of the methods described herein, the method can further include the step of monitoring a subject, e.g., for an increase or decrease in one or more analytes, or any other parameter associated with clinical outcome. In some embodiments, the step of monitoring includes providing the subject with an ingestible device to determining the presence or absence of an analyte and/or the levels or amount of an analyte. In some embodiments, the step of monitoring occurs prior to administering a treatment, during the course of a treatment, or after treatment. In some embodiments, the step of monitoring includes an additional step of ingesting an ingestible device that was previously provided to the subject to determine the presence or absence of an analyte and/or the levels or amounts of an analyte.

Also provided herein are methods of determining the efficacy of a GI disorder treatment. In some embodiments, providing an ingestible device can determine successful treatment of a GI disorder in a subject (e.g., the presence or absence of an analyte is determined; the levels of an analyte is decreased as compared to the levels of the analyte determined in the subject at an early period of time; the levels of an analyte is decreased as compared to the levels of the analyte determined in a control subject (e.g., a subject that does not have a GI disorder, or is not at risk of developing a GI disorder); the levels of an analyte is increased as compared to the levels of the analyte determined in the subject at an early period of time). In some embodiments, prior to the providing an ingestible device step, the subject received treatment for a GI disorder (e.g., any of the treatment described herein). For example, in some embodiments, the level of an analyte (e.g., any of the analytes described herein) is decreased as compared to the level of the analyte described herein prior to treatment for a GI disorder, and further treatment is discontinued. For example, in some embodiments, the level of an analyte (e.g., any of the analytes described herein) is increased as compared to the level of the analyte described herein prior to treatment for a GI disorder, and a different treatment is administered.

Non-limiting examples of such agents for treating or preventing a gastrointestinal disorder (e.g., Crohn's disease, ulcerative colitis) include substances that suppress cytokine production, downregulate or suppress self-antigen expression, or mask MHC antigens. Examples of such agents include 2-amino-6-aryl-5-substituted pyrimidines (see U.S. Pat. No. 4,665,077); non-steroidal anti-inflammatory drugs (NSAIDs), ganciclovir; tacrolimus; glucocorticoids such as Cortisol or aldosterone; anti-inflammatory agents such as a cyclooxygenase inhibitor; a 5-lipoxygenase inhibitor; or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporine; 6-mercaptopurine; steroids such as corticosteroids or glucocorticosteroids or glucocorticoid analogs, e.g., prednisone, methylprednisolone, including SOLU-MEDROL®, methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, antiinterleukin-2 (IL-2) antibodies and anti-IL-2 receptor antibodies, and anti-interleukin-6 (IL-6) receptor antibodies and antagonists; anti-LFA-1 antibodies, including anti-CD 1 la and anti-CD 18 antibodies; anti-L3T4 antibodies; heterologous anti-lymphocyte globulin; pan-T antibodies, anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodomase; RNA or DNA from the host; FK506; RS-61443; chlorambucil; deoxyspergualin; rapamycin; T-cell receptor (Cohen et al, U.S. Pat. No. 5,114,721); T-cell receptor fragments (Offner et al. Science, 251: 430-432 (1991); WO90/11294; Janeway, Nature, 341: 482 (1989); and WO 91/01133); BAFF antagonists such as BAFF or BR3 antibodies or immunoadhesins and zTNF4 antagonists (for review, see Mackay and Mackay, Trends Immunol. 23: 113-5 (2002); biologic agents that interfere with T cell helper signals, such as anti-CD40 receptor or anti-CD40 ligand (CD 154), including blocking antibodies to CD40-CD40 ligand. (e.g., Durie et al, Science, 261: 1328-30 (1993); Mohan et al, J. Immunol, 154: 1470-80 (1995)) and CTLA4-Ig (Finck et al, Science, 265: 1225-7 (1994)); and T-cell receptor antibodies (EP340,109) such as T10B9. Non-limiting examples of adjunct agents also include the following: budenoside; epidermal growth factor; aminosalicylates; metronidazole; mesalamine; olsalazine; balsalazide; antioxidants; thromboxane inhibitors; IL-1 receptor antagonists; anti-IL-1 monoclonal antibodies; growth factors; elastase inhibitors; pyridinylimidazole compounds; TNF antagonists; IL-4, IL-10, IL-13 and/or TGFβ cytokines or agonists thereof (e.g., agonist antibodies); IL-11, glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TPIO; T Cell Sciences, Inc.); slow-release mesalazine; antagonists of platelet activating factor (PAF); ciprofloxacin; and lignocaine. In some embodiments, the agents for treating or preventing a gastrointestinal disorder (e.g., SIBO) include any antibiotic described herein (e.g., rifaximin). Examples of agents for UC are sulfasalazine and related salicylate-containing drugs for mild cases and corticosteroid drugs in severe cases. Topical administration of either salicylates or corticosteroids is sometimes effective, particularly when the disease is limited to the distal bowel, and is associated with decreased side effects compared with systemic use. Supportive measures such as administration of iron and antidiarrheal agents are sometimes indicated. Azathioprine, 6-mercaptopurine and methotrexate are sometimes also prescribed for use in refractory corticosteroid-dependent cases. In some embodiments, the antibiotic selected for treatment is selected from the group consisting of: beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroids, sulfonamides, tetracycline, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds. Beta-lactam antibiotics include, but are not limited to, 2-(3-alanyl)clavam, 2-hydroxymethylclavam, 8-epi-thienamycin, acetyl-thienamycin, amoxicillin, amoxicillin sodium, amoxicillin trihydrate, amoxicillin-potassium clavulanate combination, ampicillin, ampicillin sodium, ampicillin trihydrate, ampicillin-sulbactam, apalcillin, aspoxicillin, azidocillin, azlocillin, aztreonam, bacampicillin, biapenem, carbenicillin, carbenicillin disodium, carfecillin, carindacillin, carpetimycin, cefacetril, cefaclor, cefadroxil, cefalexin, cefaloridine, cefalotin, cefamandole, cefamandole, cefapirin, cefatrizine, cefatrizine propylene glycol, cefazedone, cefazolin, cefbuperazone, cefcapene, cefcapene pivoxil hydrochloride, cefdinir, cefditoren, cefditoren pivoxil, cefepime, cefetamet, cefetamet pivoxil, cefixime, cefinenoxime, cefinetazole, cefminox, cefminox, cefmolexin, cefodizime, cefonicid, cefoperazone, ceforanide, cefoselis, cefotaxime, cefotetan, cefotiam, cefoxitin, cefozopran, cefpiramide, cefpirome, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftriaxone, cefuroxime, cefuroxime axetil, cephalosporin, cephamycin, chitinovorin, ciclacillin, clavulanic acid, clometocillin, cloxacillin, cycloserine, deoxy pluracidomycin, dicloxacillin, dihydro pluracidomycin, epicillin, epithienamycin, ertapenem, faropenem, flomoxef, flucloxacillin, hetacillin, imipenem, lenampicillin, loracarbef, mecillinam, meropenem, metampicillin, meticillin, mezlocillin, moxalactam, nafcillin, northienamycin, oxacillin, panipenem, penamecillin, penicillin, phenethicillin, piperacillin, tazobactam, pivampicillin, pivcefalexin, pivmecillinam, pivmecillinam hydrochloride, pluracidomycin, propicillin, sarmoxicillin, sulbactam, sulbenicillin, talampicillin, temocillin, terconazole, thienamycin, ticarcillin and analogs, salts and derivatives thereof.

Aminoglycosides include, but are not limited to, 1,2'-N-DL-isoseryl-3',4'dideoxykanamycin B, 1,2'-N-DL-isoserylkanamycin B, I,2'-N-[(S)-4-amino-2-hydroxybutyryl]-3',4'-dideoxykanamycin B, I,2'-N-[(S)-4-amino-2-hydroxybutyryl]kanamycin B, I-N-(2-Aminobutanesulfonyl) kanamycin A, I-N-(2-aminoethanesulfonyl)3',4'-dideoxyribostamycin, I-N-(2-aminoethanesulfonyl)3'deoxyribostamycin, I-N-(2-aminoethanesulfonyl)3'4'-dideoxykanamycin B, I-N-(2-aminoethanesulfonyl) kanamycin A, I-N-(2 aminoethanesulfonyl)kanamycin B, I-N-(2-aminoethanesulfony 1)ribostamycin, 1-N-(2-aminopropanesulfony 1)3'-deoxykanamycin B, I-N-(2-aminopropanesulfony 1)3'4'-dideoxy kanamycin B, I—N-(2-aminopropanesulfony 1) kanamycin A, I-N-(2-aminopropanesulfony 1) kanamycin B, I—N-(L-4-amino-2-hy droxy-butyryl)2,'3'-dideoxy-2'-fluorokanamy cin A, I-N-(L-4-amino-2-hydroxy-propionyl) 2,'3'-dideoxy-2'-fluorokanamycin A, I-N-DL-3',4'-dideoxy-isoserylkanamycin B,1-N-DL-isoserylkanamycin, 1-N-DL-isoserylkanamycin B, I-N-[L-(−)-(alpha-hydroxygamma-aminobutyryl)]-XK-62-2,2,'3'-dideoxy-2'-fluorokanamycin A,2-hydroxygentamycin A 3,2-hydroxygentamycin B, 2-hydroxygentamycin BI, 2-hydroxygentamycin JI-20A, 2-hydroxygentamycin JI-20B, 3"-N-methyl-4"-C-methyl-3',4'-dodeoxy kanamycin A, 3"-N-methyl-4"-C-methyl-3',4'-dodeoxy kanamycin B, 3"-N-methyl-4"-C-methyl-3',4'-dodeoxy-6'methyl kanamycin B, 3',4'-Dideoxy-3'-eno-ribostamycin,3',4'-dideoxyneamine,3', 4'dideoxyribostamycin, 3'-deoxy-6'-N-methyl-kanamycin B,3'-deoxyneamine,3'deoxyribostamycin, 3'-oxysaccharocin,3,3'-nepotrehalosadiamine, 3-demethoxy-2"-Nformimidoylistamycin B disulfate tetrahydrate, 3-demethoxyistamycin B,3-0-demethyl-2-N-formimidoylistamycin B, 3-0-demethylistamycin B,3-trehalosamine,411,611-dideoxydibekacin, 4-N-glycyl-KA-6606VI, 5"-Amino-3',4', 5"-trideoxy-butirosin A, 611-deoxydibekacin,61-epifortimicin A, 6-deoxy-neomycin (structure 6-deoxy-neomycin B),6-deoxy-neomycin B, 6-deoxy-neomycin C, 6-deoxy-paromomycin, acmimycin, AHB-3',4'-dideoxyribostamycin, AHB-3'-deoxykanamycin B, AHB-3'-deoxyneamine, AHB-3'-deoxyribostamycin, AHB-411-611-dideoxydibekacin, AHB-611-deoxydibekacin, AHB-dideoxyneamine, AHB-kanamycin B, AHB-methyl-3'-deoxykanamycin B, amikacin, amikacin sulfate, apramycin, arbekacin, astromicin, astromicin sulfate, bekanamycin, bluensomycin, boholmycin, butirosin, butirosin B, catenulin, coumamidine gammal, coumamidine gamma2,D,L-I-N-(alpha-hydroxy-betaaminopropionyl)-XK-62-2, dactimicin, de-O-methyl-4-N-glycyl-KA-6606V1, de-0-methyl-KA-66061, de-O-methyl-KA-70381, destomycin A, destomycin B, di-N6',03-demethylistamycin A, dibekacin, dibekacin sulfate, dihydrostreptomycin, dihydrostreptomycin sulfate, epi-formamidoylglycidylfortimicin B, epihygromycin, formimidoyl-istamycin A, formimidoyl-istamycin B, fortimicin B, fortimicin C, fortimicin D, fortimicin KE, fortimicin KF, fortimicin KG, fortimicin KGI (stereoisomer KG1/KG2), fortimicin KG2 (stereoisomer KG1/KG2), fortimicin KG3, framycetin, framycetin sulphate, gentamicin, gentamycin sulfate, globeomycin, hybrimycin AI, hybrimycin A2, hybrimycin BI, hybrimycin B2, hybrimycin C1, hybrimycin C2, hydroxystreptomycin, hygromycin, hygromycin B, isepamicin, isepamicin sulfate, istamycin, kanamycin, kanamycin sulphate, kasugamycin, lividomycin, marcomycin, micronomicin, micronomicin sulfate, mutamicin, myomycin, N-demethy 1-7-0-demethylcelesticetin, demethylcelesticetin, methanesulfonic acid derivative of istamycin, nebramycin, nebramycin, neomycin, netilmicin, oligostatin, paromomycin, quintomycin, ribostamycin, saccharocin, seldomycin, sisomicin, sorbistin, spectinomycin, streptomycin, tobramycin, trehalosmaine, trestatin, validamycin, verdamycin, xylostasin, zygomycin and analogs, salts and derivatives thereof.

Antibiotic anthraquinones include, but are not limited to, auramycin, cinerubin, ditrisarubicin, ditrisarubicin C, figaroic acid fragilomycin, minomycin, rabelomycin, rudolfomycin, sulfurmycin and analogs, salts and derivatives thereof.

Antibiotic azoles include, but are not limited to, azanidazole, bifonazole, butoconazol, chlormidazole, chlormidazole hydrochloride, cloconazole, cloconazole monohydrochloride, clotrimazol, dimetridazole, econazole, econazole nitrate, enilconazole, fenticonazole, fenticonazole nitrate, fezatione, fluconazole, flutrimazole, isoconazole, isoconazole nitrate, itraconazole, ketoconazole, lanoconazole, metronidazole, metronidazole benzoate, miconazole, miconazole nitrate, neticonazole, nimorazole, niridazole, omoconazol, omidazole, oxiconazole, oxiconazole nitrate, propenidazole, secnidazol, sertaconazole, sertaconazole nitrate, sulconazole, sulconazole nitrate, tinidazole, tioconazole, voriconazol and analogs, salts and derivatives thereof.

Antibiotic glycopeptides include, but are not limited to, acanthomycin, actaplanin, avoparcin, balhimycin, bleomycin B (copper bleomycin), chloroorienticin, chloropolysporin, demethylvancomycin, enduracidin, galacardin, guanidylfungin, hachimycin, demethylvancomycin, N-nonanoyl-teicoplanin, phleomycin, platomycin, ristocetin, staphylocidin, talisomycin, teicoplanin, vancomycin, victomycin, xylocandin, zorbamycin and analogs, salts and derivatives thereof.

Macrolides include, but are not limited to, acetylleucomycin, acetylkitasamycin, angolamycin, azithromycin, bafilomycin, brefeldin, carbomycin, chalcomycin, cirramycin, clarithromycin, concanamycin, deisovaleryl-niddamycin, demycinosyl-mycinamycin, Di-0-methyltiacumicidin, dirithromycin, erythromycin, erythromycin estolate, erythromycin ethyl succinate, erythromycin lactobionate, erythromycin stearate, flurithromycin, focusin, foromacidin, haterumalide, haterumalide, josamycin, josamycin ropionate, juvenimycin, juvenimycin, kitasamycin, ketotiacumicin, lankavacidin, lankavamycin, leucomycin, machecin, maridomycin, megalomicin, methylleucomycin, methymycin, midecamycin, miocamycin, mycaminosyltylactone, mycinomycin, neutramycin, niddamycin, nonactin, oleandomycin, phenylacetyideltamycin, pamamycin, picromycin, rokitamycin, rosaramicin, roxithromycin, sedecamycin, shincomycin, spiramycin, swalpamycin, tacrolimus, telithromycin, tiacumicin, tilmicosin, treponemycin, troleandomycin, tylosin, venturicidin and analogs, salts and derivatives thereof.

Antibiotic nucleosides include, but are not limited to, amicetin, angustmycin, azathymidine, blasticidin S, epiroprim, flucytosine, gougerotin, mildiomycin, nikkomycin, nucleocidin, oxanosine, oxanosine, puromycin, pyrazomycin, showdomycin, sinefungin, sparsogenin, spicamycin, tunicamycin, uracil polyoxin, vengicide and analogs, salts and derivatives thereof.

Antibiotic peptides include, but are not limited to, actinomycin, aculeacin, alazopeptin, arnfomycin, amythiamycin, antifungal from *Zalerion arboricola*, antrimycin, apid, apidaecin, aspartocin, auromomycin, bacileucin, bacillomycin, bacillopeptin, bacitracin, bagacidin, beminamycin, beta-alanyl-L-tyrosine, bottromycin, capreomycin, caspofungine, cepacidine, cerexin, cilofungin, circulin, colistin, cyclodepsipeptide, cytophagin, dactinomycin, daptomycin, decapeptide, desoxymulundocandin, echanomycin, echinocandin B, echinomycin, ecomycin, enniatin, etamycin, fabatin, ferrimycin, ferrimycin, ficellomycin, fluoronocathiacin, fusaricidin, gardimycin, gatavalin, globopeptin, glyphomycin, gramicidin, herbicolin, iomycin, iturin, iyomycin, izupeptin, janiemycin, janthinocin, jolipeptin, katanosin, killertoxin, lipopeptide antibiotic, lipopeptide from *Zalerion* sp., lysobactin, lysozyme, macromomycin, magainin, melittin, mersacidin, mikamycin, mureidomycin, mycoplanecin, mycosubtilin, neopeptifl uorin, neoviri dogrisein, netropsin, nisin, nocathiacin, nocathiacin 6-deoxyglycoside, nosiheptide, octapeptin, pacidamycin, pentadecapeptide, peptifluorin, permetin, phytoactin, phytostreptin, planothiocin, plusbacin, polcillin, polymyxin antibiotic complex, polymyxin B, polymyxin BI, polymyxin F, preneocarzinostatin, quinomycin, quinupristin-dalfopristin, safracin, salmycin, salmycin, salmycin, sandramycin, saramycetin, siomycin, sperabillin, sporamycin, a *Streptomyces* compound, subtilin, teicoplanin aglycone, telomycin, thermothiocin, thiopeptin, thiostrepton, tridecaptin, tsushimycin, tuberactinomycin, tuberactinomycin, tyrothricin, valinomycin, viomycin, virginiamycin, zervacin and analogs, salts and derivatives thereof.

In some embodiments, the antibiotic peptide is a naturally-occurring peptide that possesses an antibacterial and/or an antifungal activity. Such peptide can be obtained from an herbal or a vertebrate source.

Polyenes include, but are not limited to, amphotericin, amphotericin, aureofungin, ayfactin, azalomycin, blasticidin, candicidin, candicidin methyl ester, candimycin, candimycin methyl ester, chinopricin, filipin, flavofungin, fradicin, hamycin, hydropricin, levorin, lucensomycin, lucknomycin, mediocidin, mediocidin methyl ester, mepartricin, methylamphotericin, natamycin, niphimycin, nystatin, nystatin methyl ester, oxypricin, partricin, pentamycin, perimycin, pimaricin, primycin, proticin, rimocidin, sistomycosin, sorangicin, trichomycin and analogs, salts and derivatives thereof.

Polyethers include, but are not limited to, 20-deoxy-epinarasin, 20-deoxysalinomycin, carriomycin, dianemycin, dihydrolonomycin, etheromycin, ionomycin, iso-lasalocid, lasalocid, lenoremycin, lonomycin, lysocellin, monensin, narasin, oxolonomycin, a polycyclic ether antibiotic, salinomycin and analogs, salts and derivatives thereof.

Quinolones include, but are not limited to, an alkyl-methylendioxy-4(1H)-2 5 oxocinnoline-3-carboxylic acid, alatrofloxacin, cinoxacin, ciprofloxacin, ciprofloxacin hydrochloride, danofloxacin, dermofongin A, enoxacin, enrofloxacin, fleroxacin, flumequine, gatifloxacin, gemifloxacin, grepafloxacin, levofloxacin, lomefloxacin, lomefloxacin, hydrochloride, miloxacin, moxifloxacin, nadifloxacin, nalidixic acid, nifuroquine, norfloxacin, ofloxacin, orbifloxacin, oxolinic acid, pazufloxacine, pefloxacin, pefloxacin mesylate, pipemidic acid, piromidic acid, premafloxacin, rosoxacin, rufloxacin, sparfloxacin, temafloxacin, tosufloxacin, trovafloxacin and analogs, salts and derivatives thereof.

Antibiotic steroids include, but are not limited to, aminosterol, ascosteroside, cladosporide A, dihydrofusidic acid, dehydro-dihydrofusidic acid, dehydrofusidic acid, fusidic acid, squalamine and analogs, salts and derivatives thereof.

Sulfonamides include, but are not limited to, chloramine, dapsone, mafenide, phthalylsulfathiazole, succinylsulfathiazole, sulfabenzamide, sulfacetamide, sulfachlorpyridazine, sulfadiazine, sulfadiazine silver, sulfadicramide, sulfadimethoxine, sulfadoxine, sulfaguanidine, sulfalene, sulfamazone, sulfamerazine, sulfamethazine, sulfamethizole, sulfamethoxazole, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfisomidine, sulfisoxazole, sulfisoxazole acetyl, sulfacarbamide and analogs, salts and derivatives thereof.

Tetracyclines include, but are not limited to, dihydrosteffimycin, demethyltetracycline, aclacinomycin, akrobomycin, baumycin, bromotetracycline, cetocyclin, chlortetracycline, clomocycline, daunorubicin, demeclocycline, doxorubicin, doxorubicin hydrochloride, doxycycline, lymecyclin, marcellomycin, meclocycline, meclocycline sulfosalicylate, methacycline, minocycline, minocycline hydrochloride, musettamycin, oxytetracycline, rhodirubin, rolitetracycline, rubomycin, serirubicin, steffimycin, tetracycline and analogs, salts and derivatives thereof.

Analytes

The compositions and methods described herein can be used to detect, analyze, and/or quantitate a variety of analytes in a human subject. "Analyte" as used in the present application refers to a compound or composition to be detected in a sample. Exemplary analytes suitable for use in the present application include those described in U.S. Pat. No. 6,251,581, which is incorporated by reference herein in its entirety. Broadly speaking, an analyte can be any substance (e.g., a protein, an amino acid, a carbohydrate, a fat, a bacteria, or a therapeutic agent) capable of being detected. An exemplary and non-limiting list of analytes includes proteins and fragments thereof, blood clotting factors, hormones, cytokines, polysaccharides, nucleic acids, carbohydrates, mucopolysaccharides, lipids, fatty acids, microorganisms (e.g., bacteria), microbial antigens, and therapeutic agents (including fragments and metabolites thereof).

For instance, the analyte may be a substance that binds to a detection agent described herein. In some embodiments, the analyte (e.g., a biomolecule) and forms a complex with the detection agent. In some embodiments, the analyte may be monovalent (monoepitopic) or polyvalent (polyepitopic), usually antigenic or haptenic. In some embodiments, the analyte is a single compound or plurality of compounds. In some embodiments, the analyte is a plurality of compounds which share at least one common epitopic or determinant site. The analyte can be a part of a cell such as bacteria or a cell bearing a blood group antigen such as A, B, D, etc., a human leukocyte antigen (HLA), or other cell surface antigen. The analyte can also be a microorganism (e.g., bacterium (e.g. a pathogenic bacterium), a fungus, protozoan, or a virus), a protein, a nucleic acid, a lipid, or a hormone. In some embodiments, the analyte can be an exosome or a part of an exosome (e.g., a bacterial exosome). In some embodiments, the analyte is derived from a subject (e.g., a human subject). In some embodiments, the analyte is derived from a microorganism present in the subject. In some embodiments, the analyte is a nucleic acid (e.g., a DNA molecule or a RNA molecule), a protein (e.g., a soluble protein, a cell surface protein), or a fragment thereof, that can be detected using any of the devices and methods provided herein.

The polyvalent ligand analytes will normally be poly (amino acids), i.e., a polypeptide (i.e., protein) or a peptide, polysaccharides, nucleic acids (e.g., DNA or RNA), and combinations thereof. Such combinations include components of bacteria, viruses, chromosomes, genes, mitochondria, nuclei, cell membranes, and the like.

In some embodiments, the polyepitopic ligand analytes have a molecular weight of at least about 5,000 Da, more usually at least about 10,000 Da. In the poly(amino acid) category, the poly(amino acids) of interest may generally have a molecular weight from about 5,000 Da to about 5,000,000 Da, more usually from about 20,000 Da to 1,000,000 Da; among the hormones of interest, the molecular weights will usually range from about 5,000 Da to 60,000 Da.

In some embodiments, the monoepitopic ligand analytes generally have a molecular weight of from about 100 to 2,000 Da, more usually from 125 to 1,000 Da.

In some embodiments, the analyte has a molecular weight of about 500 Da to about 1,000,000 Da (e.g., about 500 to about 500,000 Da, about 1,000 to about 100,000 Da).

In some embodiments, one or more of the above-noted analytes can be used do develop a digestion profile of a subject. In general, a digestion profile includes longitudinal data for the subject over time, such as a subject's daily caloric intake and fluctuations in weight. In some embodiments, a digestion profile may include spectral data and information indicative of one or more analytes in the sample. In some embodiments, a digestion profile may include spectral data and information indicative of the characteristics of the sample without necessarily identifying any analytes. In some embodiments, the information associated with the spectral data or associated with the subject includes criteria selected by a user, such as the identity of one or more analytes, medical conditions, or a desired outcome. Information associated with the spectral data may include the location within the GI tract where the spectral data was generated, environmental data from the GI tract, or the identity of an ingestible standard ingested by the subject. In some embodiments, a digestion profile may further include one or more desired outcomes or goals for the subject. In some embodiments, all or part of a digestion profile for a subject may be used to search a database of digestion profiles and identify subjects or groups of subjects with similar digestion profiles. Optionally, information obtained from identifying subjects or groups of subjects with similar digestion profiles may then be added to the digestion profile for the subject. A digestion profile may also include lifestyle and/or diet recommendations for the subject. In some embodiments, a digestion profile may include diet recommendations regarding food choices, time of day to eat and/or frequency of eating. In some embodiments, a digestion profile is predictive of the effect of ingesting one or more substances by the subject.

Proteins, Fragments Thereof, and Amino Acids

In some embodiments, the analyte is a protein. As referred to herein, a "protein" refers to nitrogenous organic compounds that are formed of chains of amino acids, with neighboring amino acids being linked via a covalent peptide bond. A protein can be a polypeptide. A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

Examples of proteins include fibrous proteins, globular proteins and membrane proteins. Illustrative examples of proteins include actin, arp2/3, collagen, coronin, dystrophin, elastin, F-spondin, fibronectin, keratin, myosin, nebulin, pikachurin, spectrin, tau, titin, tropomyosin, tubulin, albumins, alpha globulin, beta globulin, C1-inhibitor, C3-convertase, cadherin, carboxypeptidase, C-reactive protein, ependymin, Factor VIII, Factor XIII, fibrin, fibrinogen, gamma globulin, hemoglobin, IgA, IgD, IgE, IgG, IgM, integrin, myoglobin, NCAM, Protein C, Protein S, Protein Z, Protein Z-related protease inhibitor, selectin, serum albumin, serum Amyloid P Component, thrombin, Von Willebrand Factor, CFTR, C-myc, estrogen receptor, FOXP2, FOXP3, glucose transporter, glycophorin D, histones, hydrolases, muscarinic acetylcholine receptor, MyoD, nicotinic acetylcholine receptor, oxidoreductases, P53, potassium channel, rhodopsin, scramblase and transferases.

In some embodiments, the protein is an enzyme (e.g., a hemolysin, a protease, a phospholipase), a soluble protein, a membrane-bound protein, an endotoxin, or an exotoxin. Exemplary classes of protein analytes include, but are not limited to: protamines, histones, albumins, globulins, scleroproteins, phosphoproteins, antibodies, affimers, mucoproteins, chromoproteins, lipoproteins, nucleoproteins, glycoproteins, T-cell receptors, proteoglycans, cell surface receptors, membrane-anchored proteins, transmembrane proteins, secreted proteins, HLA, and unclassified proteins. In some embodiments, the analyte is an affimer (see, e.g., Tiede et al. (2017) *eLife* 6: e24903, which is expressly incorporated herein by reference).

Additional exemplary protein analytes include: Prealbumin, Albumin, Lipoprotein, $\alpha_1$-Antitrypsin, $\alpha_1$-Glycoprotein, Transcortin, 4.6S-Postalbumin, $\alpha_1$-glycoprotein, $\alpha_{1X}$-Glycoprotein, Thyroxin-binding globulin, Inter-$\alpha$-trypsin-inhibitor, Gc-globulin (Gc 1-1, Gc 2-1, Gc 2-2), Haptoglobin (Hp 1-1, Hp 2-1, Hp 2-2), Ceruloplasmin, Cholinesterase, $\alpha_2$-Lipoprotein(s), Myoglobin, C-Reactive Protein, $\alpha_2$-Macroglobulin, $\alpha_2$-HS-glycoprotein, Zn-$\alpha_2$-glycoprotein, $\alpha_2$-Neuramino-glycoprotein, Erythropoietin, $\beta$-lipoprotein, Transferrin, Hemopexin, Fibrinogen, Plasminogen, $\beta_2$-glycoprotein I, $\beta_2$-glycoprotein II, Immunoglobulin G (IgG) or $\gamma$G-globulin, Immunoglobulin A (IgA) or $\gamma$A-globulin, Immunoglobulin M (IgM) or $\gamma$M-globulin, Immunoglobulin D (IgD) or $\gamma$D-Globulin ($\gamma$D), Immunoglobulin E (IgE) or $\gamma$E-Globulin ($\gamma$E), Free $\kappa$ and $\lambda$ light chains, and Complement factors: C'1, (C'1q, C'1 r, C'2, C'3 ($\beta_1$A, $\alpha_2$D), C'4, C'5, C'6, C'7, C'8, C'9, tumor necrosis factor-$\alpha$ (TNF$\alpha$), interleukin-12 (IL-12), IL-23, IL-6, $\alpha 2\beta 1$ integrin, $\alpha 1\beta 1$ integrin, $\alpha 4\beta 7$ integrin, integrin $\alpha 4\beta 1$ (VLA-4), E-selectin, ICAM-1, $\alpha 5\beta 1$ integrin, $\alpha 4\beta 1$ integrin, VLA-4, $\alpha 2\beta 1$ integrin, $\alpha 5\beta 3$ integrin, $\alpha 5\beta 5$ integrin, $\alpha$IIb$\beta 3$ integrin, MAdCAM-1, SMAD7, JAK1, JAK2, JAK3, TYK-2, CHST15, IL-1, IL-1$\alpha$, IL-1$\beta$, IL-18, IL-36$\alpha$, IL-36$\beta$, IL-36$\gamma$, IL-38, IL-33, IL-13, CD40L, CD40, CD3$\gamma$, CD3$\delta$, CD3$\epsilon$, CD3$\zeta$, TCR, TCR$\alpha$, TCR$\beta$, TCR$\delta$, TCR$\gamma$, CD14, CD20, CD25, IL-2, IL-2$\beta$ chain, IL-2$\gamma$ chain, CD28, CD80, CD86, CD49, MMP1, CD89, IgA, CXCL10, CCL11, an ELR chemokine, CCR2, CCR9, CXCR3, CCR3, CCR5, CCL2, CCL8, CCL16, CCL25, CXCR1m CXCR2m CXCL1, CXCL2, CXCL3, CXCL4, CXCL5, CXCL6, CXCL7, and CXCL8, and a nucleic acid (e.g., mRNA) encoding any of the same.

In some embodiments, the analyte is a blood clotting factor. Exemplary blood clotting factors include, but are not limited to:

| International designation | Name |
|---|---|
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

In some embodiments, the analyte is a hormone. Exemplary hormones include, but are not limited to: Peptide and Protein Hormones, Parathyroid hormone, (parathromone), Thyrocalcitonin, Insulin, Glucagon, Relaxin, Erythropoietin, Melanotropin (melancyte-stimulating hormone; intermedin), Somatotropin (growth hormone), Corticotropin (adrenocorticotropic hormone), Thyrotropin, Follicle-stimulating hormone, Luteinizing hormone (interstitial cell-stimulating hormone), Luteomammotropic hormone (luteotropin, prolactin), Gonadotropin (chorionic gonadotropin), Secretin, Gastrin, Angiotensin I and II, Bradykinin, and Human placental lactogen, thyroxine, cortisol, triiodothyronine, testosterone, estradiol, estrone, progestrone, luteinizing hormone-releasing hormone (LHRH), and immunosuppressants such as cyclosporin, FK506, mycophenolic acid, and so forth.

In some embodiments, the analyte is a peptide hormone (e.g., a peptide hormone from the neurohypophysis). Exemplary peptide hormones from the neurohypophysis include, but are not limited to: Oxytocin, Vasopressin, and releasing factors (RF) (e.g., corticotropin releasing factor (CRF), luteinizing hormone releasing factor (LRF), thyrotropin releasing factor (TRF), Somatotropin-RF, growth hormone releasing factor (GRF), follicle stimulating hormone-releasing factor (FSH-RF), prolactin inhibiting factor (PIF), and melanocyte stimulating hormone inhibiting factor (MIF)).

In some embodiments, the analyte is a cytokine or a chemokine. Exemplary cytokines include, but are not limited to: interleukin-1 (IL-1), interleukin-2 (IL-2), interleukin-6 (IL-6), epidermal growth factor (EGF), tumor necrosis factor (TNF, e.g., TNF-$\alpha$ or TNF-$\beta$), and nerve growth factor (NGF).

In some embodiments, the analyte is a cancer antigen. Exemplary cancer antigens include, but are not limited to: prostate-specific antigen (PSA), carcinoembryonic antigen (CEA), $\alpha$-fetoprotein, Acid phosphatase, CA19.9, CA125, CD19, WT-1, CD22, L1-CAM, ROR-1, CD30, CD125, AFP, CEA, ETA, MAGE, and MUC16.

In some embodiments, the analyte is a tissue-specific antigen. Exemplary tissue specific antigens include, but are not limited to: alkaline phosphatase, myoglobin, CPK-MB, calcitonin, and myelin basic protein.

In some embodiments, the analyte is a component of an outer membrane vesicle (OMV) (e.g., an OmpU protein, Elluri et al. (2014) PloS One 9: e106731). See, e.g., Kulp and Kuehn (2010) Annual Review of microbiology 64: 163-184; Berleman and Auer (2013) Environmental microbiology 15: 347-354; Wai et al. (1995) Microbiology and immunology 39: 451-456; Lindmark et al. (2009) BMC microbiology 9: 220; Sjostrom et al. (2015) Scientific Reports 5: 15329.

In some embodiments, the analyte is G-CSF, which can stimulate the bone marrow to produce granulocytes and stem cells and release them into the bloodstream.

In some embodiments, the analyte is an enzyme such as glutathione S-transferase. For example, the ingestible device can include P28GST, a 28 kDa helminth protein from *Schistosoma* with potent immunogenic and antioxidant properties. P28GST prevents intestinal inflammation in experimental colitis through a Th2-type response with mucosal eosinophils and can be recombinantly produced (e.g., in *S. cerevisiae*). See, for example, U.S. Pat. No. 9,593,313, Driss et al., *Mucosal Immunology,* 2016 9, 322-335; and Capron et al., *Gastroenterology,* 146(5):S-638.

In certain embodiments, an analyte is an amino acid or a protein fragment formed from a protein (e.g., via one or more processes in the GI tract). In some embodiments, the analyte is a peptide of at least 5 amino acids (e.g., at least 6, at least 7, at least 8, at least 9, at least 10, at least 25, at least, 50, or at least 100 amino acids). Exemplary lengths include 6, 7, 8, 9, 10, 11, 12, 13, 14, 15, 16, 17, 18, 19, 20, 21, 22, 23, 24, 25, 26, 27, 28, 29, 30, 50, 75, or 100 amino acids. In general, an amino acid is a relatively simple organic molecule that includes both a carboxyl group and an amino group. Illustrative examples of amino acids include histidine, isoleucine, leucine, lysine, methionine, phenylalanine, threonine, tryptophan, valine, arginine, cysteine, glutamine, glycine, proline, serine, tyrosine, alanine, asparagine, aspartic acid, glutamic acid and selenocysteine. Detection and quantification of lysine based on spectral data are described in detail in Example 10.

Microorganisms

In some embodiments, the analyte is a microorganism, or a molecule derived from or produced by a microorganism (e.g., a bacteria, a virus, prion, or a protozoan). For example, in some embodiments, the analyte is a molecule (e.g., a protein or a nucleic acid) that is specific for a particular microbial genus, species, or strain (e.g., a specific bacterial genus, species, or strain). In some embodiments, the microorganism is pathogenic (i.e., causes disease). In some embodiments, the microorganism is non-pathogenic (e.g., a commensal microorganism). Exemplary microorganisms include, but are not limited to:

Corynebacteria
Corynebacterium diphtheria
Pneumococci
Diplococcus pneumoniae
Streptococci
Streptococcus pyrogenes
Streptococcus salivarus
Staphylococci
Staphylococcus aureus
Staphylococcus albus
Neisseria
Neisseria meningitidis
Neisseria gonorrhea
Enterobacteriaciae
Escherichia coli
Aerobacter aerogenes				The coliform
Klebsiella pneumoniae				bacteria
Salmonella typhosa
Salmonella choleraesuis				The Salmonellae
Salmonella typhimurium
Shigella dysenteria				The Shigellae
Shigella schmitzii
Shigella arabinotarda
Shigella flexneri
Shigella boydii
Shigella sonnei
Other enteric bacilli
Proteus vulgaris				Proteus species
Proteus mirabilis
Proteus morgani
Pseudomonas aeruginosa
Alcaligenes faecalis
Vibrio cholerae
Hemophilus-Bordetella group
Hemophilus influenza, H. ducryi			Rhizopus oryzae
						Rhizopus arrhizua
						Phycomycetes
Hemophilus hemophilus				Rhizopus nigricans
Hemophilus aegypticus				Sporotrichum schenkii
Hemophilus parainfluenza			Flonsecaea pedrosoi
Bordetella pertussis				Fonsecacea compact
Pasteurellae					Fonsecacea dermatidis
Pasteurella pestis				Cladosporium carrionii
Pasteurella tulareusis				Phialophora verrucosa
Brucellae					Aspergillus nidulans
Brucella melltensis				Madurella mycetomi
Brucella abortus				Madurella grisea
Brucella suis					Allescheria boydii
Aerobic Spore-forming Bacilli			Phialophora jeanselmei
Bacillus anthracis				Microsporum gypseum
Bacillus subtilis				Trichophyton mentagrophytes
Bacillus megaterium				Keratinomyces ajelloi
Bacillus cereus					Microsporum canis
Anaerobic Spore-forming Bacilli			Trichophyton rubrum
Clostridium botulinum				Microsporum adouini
Clostridium tetani				Viruses
Clostridium perfringens				Adenoviruses
Clostridium novyi				Herpes Viruses -continued Clostridium septicum				Herpes simplex
Clostridium histoyticum				Varicella (Chicken pox)
Clostridium tertium				Herpes Zoster (Shingles)
Clostridium bifermentans			Virus B
Clostridium sporogenes				Cytomegalovirus
Mycobacteria					Pox Viruses
Mycobacterium tuberculosis hominis		Variola (smallpox)
Mycobacterium bovis				Vaccinia
Mycobacterium avium				Poxvirus bovis
Mycobacterium leprae				Paravaccinia
Mycobacterium paratuberculosis			Molluscum contagiosum
Actinomycetes (fungus-ike bacteria)		Picornaviruses
Actinomyces Isaeli				Poliovirus
Actinomyces bovis				Coxsackievirus
Actinomyces naeslundii				Echoviruses
Nocardia asteroides				Rhinoviruses
Nocardia brasiliensis				Myxoviruses
The Spirochetes					Influenza(A, B, and C)
Treponema pallidum				Parainfluenza (14)
Treponema pertenue				Mumps Virus
Spirillum minus
Streptobacillus monoiliformis			Newcastle Disease Virus
Treponema carateum				Measles Virus
Borrelia recurrentis				Rinderpest Virus
Leptospira icterohemorrhagiae			Canine Distemper Virus
Leptospira canicola				Respiratory Syncytial Virus
Trypanasomes					Rubella Virus
Mycoplasmas					Arboviruses
Mycoplasma pneumoniae
Other pathogens					Eastern Equine Encephalitis
						Virus
Listeria monocytogenes				Western Equine Encephalitis
						Virus
Erysipeothrix rhusiopathiae			Sindbis Virus
Streptobacillus moniliformis			Chikugunya Virus
Donvania granulomatis				Semliki Forest Virus
Entamoeba histolytica				Mayora Virus
Plasmodium falciparum				St Louis Encephalitis
Plasmodium japonicum				California Encephalitis Virus
Bartonella bacilliformis			Colorado Tick Fever Virus
Rickettsia (bacteria-like parasites)		Yellow Fever Virus
Rickettsia prowazekii				Dengue Virus
Rickettsia mooseri				Reoviruses
Rickettsia rickettsia				Reovirus Types 14
Rickettsia conori				Retroviruses
Rickettsia australis				Human Immunodeficiency
Rickettsia sibiricus				Viruses I and H (HTLV)
Rickettsia akari				Human T-cell Lymphotrophic
Rickettsia tsutsugamushi			Virus I & II (HIV)
Rickettsia burnetti				Hepatitis
Rickettsia quintana				Hepatitis A Virus
Chlamydia (unclassifiable parasites		Hepatitis B Virus
bacterial/viral)				Hepatitis C Virus
Chlamydia agents (naming uncertain)		Tumor Viruses
Chlamydia trachomatis
Fungi						Rauscher Leukemia Virus
Cryptococcus neoformans				Gross Virus
Blastomyces dermatidis				Maloney Leukemia Virus
Histoplasma capsulatum
Coccidioides immitis				Human Papilloma Virus
Paracoccidioides brasliensis
Candida albicans
Aspergillus fumigatus
Mucor corymbifer (Absidia corymbifera)

In some embodiments, the analyte is a bacterium. Exemplary bacteria include, but are not limited to: *Escherichia coli* (or *E. coli*), *Bacillus anthracis*, *Bacillus cereus*, *Clostridium botulinum*, *Clostridium difficile*, *Yersinia pestis*, *Yersinia enterocolitica*, *Francisella tularensis*, *Brucella* species, *Clostridium perfringens*, *Burkholderia mallei*, *Burkholderia pseudomallei*, *Staphylococcus species*, *Mycobacterium* species, Group A *Streptococcus*, Group B *Streptococcus*, *Streptococcus pneumoniae*, *Helicobacter pylori*, *Salmonella enteritidis*, *Mycoplasma hominis*, *Mycoplasma orale*, *Mycoplasma salivarium*, *Mycoplasma fermentans*, *Mycoplasma pneumoniae*, *Mycobacterium bovis*,

*Mycobacterium tuberculosis, Mycobacterium avium, Mycobacterium leprae, Rickettsia rickettsii, Rickettsia akari, Rickettsia prowazekii, Rickettsia canada, Bacillus subtilis, Bacillus subtilis niger, Bacillus thuringiensis, Coxiella burnetti, Faecalibacterium prausnitzii* (also known as *Bacteroides prausnitzii*), *Roseburia hominis, Eubacterium rectale, Dialister invisus, Ruminococcus albus, Ruminococcus callidus*, and *Ruminococcus bromii*. Additional exemplary bacteria include bacteria of the phyla Firmicutes (e.g., *Clostridium* clusters XIVa and IV), bacteria of the phyla Bacteroidetes (e.g., *Bacteroides fragilis* or *Bacteroides vulgatus*), and bacteria of the phyla *Actinobacteria* (e.g., Coriobacteriaceae spp. or *Bifidobacterium adolescentis*). Bacteria of the *Clostridium* cluster XIVa includes species belonging to, for example, the *Clostridium, Ruminococcus, Lachnospira, Roseburia, Eubacterium, Coprococcus, Dorea*, and *Butyrivibrio* genera. Bacteria of the *Clostridium* cluster IV includes species belonging to, for example, the *Clostridium, Ruminococcus, Eubacterium* and *Anaerofilum* genera. In some embodiments, the analyte is *Candida*, e.g., *Candida albicans*. In some embodiments, the analyte is a byproduct from a bacterium or other microorganism, e.g., helminth ova, enterotoxin (*Clostridium difficile* toxin A; TcdA) or cytotoxin (*Clostridium difficile* toxin B; TcdB).

In some embodiments, the bacterium is a pathogenic bacterium. Non-limiting examples of pathogenic bacteria belong to the genera *Bacillus, Bordetella, Borrelia, Brucella, Campylobacter, Chlamydia, Chlamydophila, Clostridium, Corynebacterium, Enterobacter, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, and *Yersinia*. Non-limiting examples of specific pathogenic bacterial species include a strain of *Bacillus anthracis*, a strain of a strain of *Bordetella pertussis*, a strain of a strain of *Borrelia burgdorferi*, a strain of a strain of *Brucella abortus*, a strain of a strain of *Brucella canis*, a strain of a strain of *Brucella melitensis*, a strain of a strain of *Brucella suis*, a strain of a strain of *Campylobacter jejuni*, a strain of *Chlamydia pneumoniae*, a strain of *Chlamydia trachomatis*, a strain of *Chlamydophila psittaci*, a strain of *Clostridium botulinum*, a strain of *Clostridium difficile*, a strain of *Clostridium perfringens*, a strain of *Clostridium tetani*, a strain of *Corynebacterium diphtheria*, a strain of *Enterobacter sakazakii*, a strain of *Enterococcus faecalis*, a strain of *Enterococcus faecium*, a strain of *Escherichia coli* (e.g., *E. coli* O157 H7), a strain of *Francisella tularensis*, a strain of *Haemophilus influenza*, a strain of *Helicobacter pylori*, a strain of *Legionella pneumophila*, a strain of *Leptospira interrogans*, a strain of *Listeria monocytogenes*, a strain of *Mycobacterium leprae*, a strain of *Mycobacterium tuberculosis*, a strain of *Mycobacterium ulcerans*, a strain of *Mycoplasma* pneumonia, a strain of *Neisseria gonorrhoeae*, a strain of *Neisseria meningitides*, a strain of *Pseudomonas aeruginosa*, a strain of *Rickettsia rickettsia*, a strain of *Salmonella typhi* and *Salmonella typhimurium*, a strain of *Shigella sonnei*, a strain of *Staphylococcus aureus*, a strain of *Staphylococcus epidermidis*, a strain of *Staphylococcus saprophyticus*, a strain of *Streptococcus agalactiae*, a strain of *Streptococcus pneumonia*, a strain of *Streptococcus pyogenes*, a strain of *Treponema pallidum*, a strain of *Vibrio cholera*, a strain of *Yersinia enterocolitica*, and, a strain of *Yersinia pestis*.

In some embodiments, the bacterium is a commensal bacterium (e.g., a probiotic). In some embodiments, the bacterium has been previously administered to a subject, e.g., as a live biotherapeutic agent. Exemplary commensal bacteria include, but are not limited to, *Faecalibacterium prausnitzii* (also referred to as *Bacteroides praussnitzii*), *Roseburia hominis, Eubacterium rectale, Dialister invisus, Ruminococcus albus, Ruminococcus gnavus, Ruminococcus torques, Ruminococcus callidus*, and *Ruminococcus bromii*.

In some embodiments, the analyte is a virus. In some embodiments, the virus is a pathogenic virus. Non-limiting examples of pathogenic viruses belong to the families Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae.

In some embodiments, the analyte is a fungus. In some embodiments, the fungi is a pathogenic fungus. Non-limiting examples of pathogenic fungi belong to the genera *Asperfillus, Candida, Cryptococcus, Histoplasma, Pneumocystis*, and *Stachybotrys*. Non-limiting examples of specific pathogenic fungi species include a strain of *Aspergillus clavatus, Aspergillus fumigatus, Aspergillus flavus, Candida albicans, Cryptococcus albidus, Cryptococcus gattii, Cryptococcus laurentii, Cryptococcus neoformans, Histoplasma capsulatum, Pneumocystis jirovecii, Pneumocystis carinii*, and *Stachybotrys chartarum*.

In some embodiments, the analyte is a protozoan. In some embodiments, the analyte is a pathogenic protozoan. Non-limiting examples of pathogenic protozoa belong to the genera *Acanthamoeba, Balamuthia, Cryptosporidium, Dientamoeba, Endolimax, Entamoeba, Giardia, Iodamoeba, Leishmania, Naegleria, Plasmodium, Sappinia, Toxoplasma, Trichomonas*, and *Trypanosoma*. Non-limiting examples of specific pathogenic protozoa species include a strain of *Acanthamoeba* spp., *Balamuthia mandrillaris, Cryptosporidium canis, Cryptosporidium fells, Cryptosporidium hominis, Cryptosporidium meleagridis, Cryptosporidium muris, Cryptosporidium parvum, Dientamoeba fragilis, Endolimax nana, Entamoeba dispar, Entamoeba hartmanni, Entamoeba histolytica, Entamoeba coli, Entamoeba moshkovskii, Giardia lamblia, Iodamoeba butschlii, Leishmania aethiopica, Leishmania braziliensis, Leishmania chagasi, Leishmania donovani, Leishmania infantum, Leishmania major, Leishmania mexicana, Leishmania tropica, Naegleria fowleri, Plasmodium falciparum, Plasmodium knowlesi, Plasmodium malariae, Plasmodium ovale, Plasmodium vivax, Sappinia diploidea, Toxoplasma Trichomonas vaginalis, Trypanosoma brucei*, and *Trypanosoma cruzi*.

In some embodiments, the analyte is secreted by or expressed on the cell surface of a microorganism (e.g., a bacterium, a colonic bacterium, a viable bacterium, a dead bacterium, a parasite (e.g., *Giardia lamblia, Cryptosporidium, Cystoisosporiasis belli*, and *Balantidium coli*), a virus (e.g., a herpes virus, a cytomegalovirus, a herpes simplex virus, an Epstein-Barr virus, a human papilloma virus, a rotavirus, a human herpesvirus-8; Goodgame (1999) Curr. Gastroenterol. Rep. 1(4): 292-300). In some embodiments, the analyte is secreted by or expressed on the cell surface of a Gram-negative bacterium (e.g., *E. coli, Helicobacter pylori*). In some embodiments, the analyte is secreted by or expressed on the cell surface (e.g., a bacterial surface epitope) of a Gram-positive bacterium (e.g., *Staphylococcus aureus, Clostridium botulinum, Clostridium difficile*).

In some embodiments, the analyte is a molecule expressed on the surface of a bacterial cell (e.g., a bacterial cell surface protein). In some embodiments, the analyte is a bacterial toxin (e.g., TcdA and/or TcdB from *Clostridium difficile*). In some embodiments, the analyte is CFA/I fimbriae, flagella, lipopolysaccharide (LPS), lipoteichoic acid, or a peptidoglycan. Non-limiting examples of bacterium that may express an analyte that can be detected using any of the devices and methods described herein include: *Bacillus anthracis, Bacillus cereus, Clostridium botulinum, Clostridium difficile, Escherichia coli, Yersinia pestis, Yersinia enterocolitica, Francisella tularensis, Brucella species, Clostridium perfringens, Burkholderia mallei, Burkholderia pseudomallei, Helicobacter pylori, Staphylococcus species, Mycobacterium species,* Group A *Streptococcus,* Group B *Streptococcus, Streptococcus pneumoniae, Francisella tularensis, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsii, Rickettsia akari, Rickettsia prowazekii, Rickettsia canada, Bacillus subtilis, Bacillus subtilis niger, Bacillus thuringiensis, Coxiella bumetti, Candida albicans, Bacteroides fragilis, Leptospira interrogans, Listeria monocytogenes, Pasteurella multocida, Salmonella typhi, Salmonella typhimurium, Shigella dysenteriae, Shigella flexneria, Shigella sonnei, Vibrio cholera,* and *Vibrio parahaemolyticus.*

In some embodiments, the analyte is a byproduct from a bacterium or another microorganism, e.g., helminth ova, enterotoxin (*Clostridium difficile* toxin A; TcdA), cytotoxin (*Clostridium difficile* toxin B; TcdB), and ammonia. In some embodiments, the analyte is an antigen from a microorganism (e.g., a bacteria, virus, prion, fungus, protozoan or a parasite).

Bile Acids, Bile Salts, and Related Analytes

In some embodiments, the analyte is a bile acid, a bile salt (also known as a conjugated bile acid), or a related analyte. Bile acids are products of cholesterol synthesis that are synthesized in the liver, conjugated to taurine or glycine, and stored in the gallbladder until released into the small intestine. The primary bile acids are cholic acid, and chenodeoxycholic acid, which are deconjugated and dehydroxylated by instestinal bacteria to form the secondary bile acids deoxycholic acid and lithocholic acid, respectively. The majority of bile acids (about 95%) are reabsorbed in the distal ileum and returned to the liver (see, e.g., U.S. Publication No. 2017/0343535, incorporated herein by reference). Impaired absorption of bile acids in the ileum can lead to excess bile acids in the colon which can cause symptoms of bile acid malabsorption (BAM; also known as bile acid diarrhea), including watery stool and fecal incontinence. Interestingly, up to 50% of patients with irritable bowel syndrome with diarrhea (IBS-D) also have BAM (see, e.g., Camilleri et al. (2009) *Neurogastroeterol. Motil.* 21(7): 734-43). In some embodiments, the presence, absence, and/or a specific level of one or more bile acids or bile salts in the GI tract of a subject is indicative of a condition or disease state (e.g., a GI disorder and/or a non-GI disorder (e.g., a systemic disorder or a liver disease)). In some embodiments, the compositions, devices, and methods described herein may be used to detect, analyze and/or quantify at least one bile acid or bile salt in the GI tract of the subject to diagnose a GI disorder such as BAM or IBS (e.g., IBS-D). In some embodiments, the devices, methods and compositions described herein can be used to detect, quantitate, and/or analyze a bile acid or a bile salt in the GI tract of a subject. For instance, the presence and/or absence, and/or the concentration of a bile acid, a bile salt, or a combination thereof, may be determined at a specific region of the GI tract of a subject (e.g., one or more of the duodenum, jejunum, ileum, ascending colon, transverse colon or descending colon) to determine whether the subject has or is at risk of developing a GI disorder, such as BAM or IBS-D. In some embodiments, the devices, methods and compositions described herein can be used to determine the ratio of two or more bile acids or bile acid salts in the GI tract of a subject (e.g., a specific region of the GI tract of a subject including one or more of the duodenum, jejunum, ileum, ascending colon, transverse colon or descending colon). In some embodiments, the presence and/or absence, and/or the concentration of a bile acid, a bile salt, or a combination thereof, is determined in the ileum of a subject. In some embodiments, the presence and/or absence, and/or the concentration of a bile acid, a bile salt, or a combination thereof, is determined in the colon of a subject. In some embodiments, the concentration of a bile acid, a bile salt, or a combination thereof, is determined in specific regions of the GI tract of the subject, and for example, compared to determine where along the GI tract the compounds are accumulating. In some embodiments, the detection of a concentration of a bile acid, bile salt, or a combination thereof, in a specific region of the GI tract of the subject (e.g., the colon or the ileum) that is above a reference level of a bile acid, bile salt, or a combination thereof (e.g., the average level of a bile acid in healthy subjects) may be indicative of BAM and/or IBS-D in a subject. In some embodiments, the bile acid is selected from the group consisting of chenodeoxycholic acid, cholic acid, deoxycholate, lithocholate, and ursodeoxycholic acid. In some embodiments, the bile acid comprises cholesten-3-one or a structural variant thereof. In some embodiments, the bile acid is cholesten-3-one or a structural variant thereof. In some embodiments, the bile acid is cholesten-3-one. In some embodiments, the bile acid is a structural variant of cholesten-3-one. In some embodiments, the bile salt is selected from the group consisting of glycocholic acid, taurocholic acid, glycodeoxycholic acid, glycochenodeoxycholic acid, taurodeoxycholic acid, taurochenodeoxycholic acid, glycolithocholic acid, and taurolithocholic acid.

In some embodiments, the analyte is 7α-hydroxy-4-cholesten-3-one (7αC4). The measurement of 7αC4 allows for the monitoring of the enzymatic activity of hepatic cholesterol 7α-hydroxylase, the rate limiting enzyme in the synthesis of bile acids and can be used as a surrogate to detect BAM (see, e.g., Galman et al. (2003) *J. Lipid. Res.* 44: 859-66; and Camilleri et al. (2009) Neurogastroeterol. Motil. 21(7): 734-43, incorporated herein by reference in their entirety).

In some embodiments, the analyte comprises cholesterol, a lipid, a fat soluble vitamin (e.g., ascorbic acid, cholecalciferol, ergocalciferol, a tocopherol, a tocotrienol, phylloquinone, and a menaquinone), bilirubin, fibroblast growth factor 19 (FGF19), TGR5 (also known as GP-BAR1 or M-BAR), glycine, taurine, or cholecystokinin (CCK or CCK-PZ). In some embodiments, the analyte comprises cholecystokinin. Cholecystokinin is a peptide hormone that contributes to control intestinal motility (see Rehfeld (2017) *Front. Endocrinol.* (*Lausanne*) 8: 47). In some embodiments, the analyte comprises secretin. Secretin is a peptide hormone that regulates the pH of the duodenal content by controlling gastric acid secretion, regulates bile acid and bicarbonate secretion in the duodenum, and regulates water homeostasis (see, e.g., Afroze et al. (2013) *Ann. Transl. Med.* 1(3): 29). In some embodiments, a subject has been administered cholecystokinin or secretin to induce the release of an analyte (e.g., from the liver and/or gall bladder into the GI tract).

Metabolites in the Serotonin, Tryptophan and/or Kynurenine Pathways

In some embodiments, the analyte is a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof. 5-HT is a molecule that plays a role in the regulation of gastrointestinal motility, secretion, and sensation. Imbalances in the levels of 5-HT are associated with several diseases including inflammatory bowel syndrome (IBS), autism, gastric ulcer formation, non-cardiac chest pain, and functional dyspepsia (see, e.g., Faure et al. (2010) *Gastroenterology* 139(1): 249-58 and Muller et al. (2016) *Neuroscience* 321: 24-41, and International Publication No. WO 2014/188377, each of which are incorporated herein by reference). Conversion of metabolites within the serotonin, tryptophan and/or kynurenine pathways affects the levels of 5-HT in a subject. Therefore, measuring the levels of one or more of the metabolites in this pathway may be used for the diagnosis, management and treatment of a disease or disorder associated with 5-HT imbalance including but not limited to IBS, autism, carcinoid syndrome, depression, hypertension, Alzheimer's disease, constipation, migraine, and serotonin syndrome. One or more analytes in the serotonin, tryptophan and/or kynurenine pathways can be detected and/or quantitated using, for example, methods and detection agents that bind to these metabolites including, e.g., antibodies, known in the art (see, e.g., International Publication No. WO2014/188377, the entire contents of which are expressly incorporated herein by reference).

In some embodiments, the analyte is a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof.

Nucleic Acids

In some embodiments, the analyte is a nucleic acid (e.g., a bacterial DNA molecule or a bacterial RNA molecule (e.g., a bacterial tRNA, a transfer-messenger RNA (tmRNA)). See, e.g., Sjostrom et al. (2015) Scientific Reports 5: 15329; Ghosal (2017) Microbial Pathogenesis 104: 161-163; Shen et al. (2012) Cell Host Microbe. 12(4): 509-520.

In some embodiments, the term "analyte" further includes polynucleotide analytes such as those polynucleotides defined below. These include m-RNA, r-RNA, t-RNA, DNA, DNA-DNA duplexes, DNA-RNA duplexes, nucleic acid molecules comprising modified bases, locked nucleic acid molecules (LNA molecules), antagomirs, peptide nucleic acid molecules (PNA molecules), antisense RNA or DNA molecules (e.g., antisense molecules including modifications to the sugars, bases, backbone linkages that allow for specific detection), chimeric antisense oligonucleotides, antisense oligonucleotides comprising modified linkages, interference RNA (RNAi), short interfering RNA (siRNA); a micro, interfering RNA (miRNA), a small, temporal RNA (stRNA); or a short, hairpin RNA (shRNA); small RNA-induced gene activation (RNAa), small activating RNAs (saRNAs), etc. The term analyte also includes polynucleotide-binding agents, such as, for example, restriction enzymes, transcription factors, transcription activators, transcription repressors, nucleases, polymerases, histones, DNA repair enzymes, intercalating agents, chemotherapeutic agents, and the like.

Carbohydrates

In some embodiments, an analyte is a carbohydrate. As used herein, a "carbohydrate" refers to a biological molecule formed of carbon atoms, hydrogen atoms, and oxygen atoms, typically with a hydrogen atom to oxygen atom ratio of 2:1 (e.g., as in water). Put another way, a carbohydrate typically has the empirical formula $C_m(H_2O)_n$, where m is the same as n, or m is different from n." Illustrative examples of types of carbohydrates include simple carbohydrates (e.g., sugars, such as simple sugars) and complex carbohydrates (e.g., starches and fibers). In some embodiments, a carbohydrate is a monosaccharide, a disaccharide or a polysaccharide. In certain embodiments, a carbohydrate is a soluble fiber or an insoluble fiber. An illustrative list of exemplary carbohydrates includes glucose, fructose, galactose, xylose, sucrose, lactose, maltose, trehalose, sorbitol, mannitol, altodextrin, maltotriose, raffinose, stachyose, fructo-oligosaccharides, amylose, amylopectins, modified starches, celluloses, hemicelluloses, pectins, gums, mucilages, and hydrocolloids. In some embodiments, the analyte is a mucopolysaccharide. Detection and quantification of glucose based on spectral data are described in detail in Example 10.

Fats

In certain embodiments, an analyte is a fat. As used herein, the term "fat" refers to fats, fatty acids, lipids and oils. In some embodiments, a fat, also referred to as a triglyceride, is formed of an ester of three fatty acid chains and an alcohol glycerol. In some embodiments, a fat is an unsaturated fat or a saturated fat (e.g., a monounsaturated fat or a polyunsaturated fat). In certain embodiments, an analyte is trans fat (a partially hydrogenated fat, conjugated linoleic acid, trans vaccenic acid, trans elaidic acid) or a cis fat. In some embodiments, an analyte is an omega-3 fatty acid (e.g., eicosapentaenoic acid, docosahexaenoic acid, α-linolenic acid), an omega-6 fatty acid (e.g., γ-linolenic acid, conjugated linoleic acid), or an omega-9 fatty acid (e.g., oleic acid). In some embodiments, an analyte is an omega-6 polyunsaturated fat. In certain embodiments, an analyte is an omega-3 polyunsaturated fat. An illustrative list of exemplary fats includes oleic acid, linoleic acid, α-linolenic acid, myristic acid, myristoleic acid, palmitic acid, palmitoleic acid, oleic acid, gadoleic acid, erucic acid, nervonic acid, α-linolenic acid, docosahexaenoic acid, eicosapentaenoic acid, elaidic acid, erucic acid, linoleic acid, linoelaidic acid, sapienic acid, stearic acid, vaccenic acid, lauric acid, eicosapentaenoic acid, docosahexaenoic acid, γ-linolenic acid, stearidonic acid, paullinic acid, gondoic acid, eruic acid, nervonic acid, docosohexanoic acid, docosatetraenoic acid, and conjugated linoleic acid.

Exemplary Analytes

In some embodiments, analytes are therapeutic agents, fragments thereof, and metabolites thereof. In some embodiments, analytes are biomarkers. In some embodiments, the analytes are antibodies. In some embodiments, the analytes are antibiotics.

In some embodiments, an analyte is an alcohol, such as, for example, ethanol. In some embodiments, the analyte is a liver product (e.g., acetoacetate, beta-hydroxybutyrate, and acetone). In some embodiments, the analyte is a ketone.

In some embodiments, the analytes is a pesticide, a pollutant, and the like. In some embodiments, the analyte is a pesticide. Among pesticides of interest are polyhalogenated biphenyls, phosphate esters, thiophosphates, carbamates, polyhalogenated sulfenamides, their metabolites and derivatives.

Exemplary analytes (e.g., therapeutic agents (e.g., drugs), antibodies, antibiotics and biomarkers) are provided herein.

A. Antibodies

In some embodiments, the analyte or the detection agent is an antibody. An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv) and domain antibodies), and fusion proteins including an antibody portion, and any other modified configuration of the immunoglobulin molecule that includes an antigen recognition site. The term antibody includes antibody fragments (e.g., antigen-binding fragments) such as an Fv fragment, a Fab fragment, a F(ab')2 fragment, and a Fab' fragment. Additional examples of antigen-binding fragments include an antigen-binding fragment of an IgG (e.g., an antigen-binding fragment of IgG1, IgG2, IgG3, or IgG4) (e.g., an antigen-binding fragment of a human or humanized IgG, e.g., a human or humanized IgG1, IgG2, IgG3, or IgG4), an antigen-binding fragment of an IgA (e.g., an antigen-binding fragment of IgA1 or IgA2) (e.g., an antigen-binding fragment of a human or humanized IgA, e.g., a human or humanized IgA1 or IgA2), an antigen-binding fragment of an IgD (e.g., an antigen-binding fragment of a human or humanized IgD), an antigen-binding fragment of an IgE (e.g., an antigen-binding fragment of a human or humanized IgE); or an antigen-binding fragment of an IgM (e.g., an antigen-binding fragment of a human or humanized IgM). An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies including the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) that contain hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-Lazikani et al, 1997, J. Molec. Biol. 273:927-948). As used herein, a CDR may refer to CDRs defined by either approach or by a combination of both approaches.

As known in the art, a "constant region" of an antibody refers to the constant region of the antibody light chain or the constant region of the antibody heavy chain, either alone or in combination.

A "derivative" refers to any polypeptide (e.g., an antibody) having a substantially identical amino acid sequence to the naturally occurring polypeptide, in which one or more amino acids have been modified at side groups of the amino acids (e.g., a biotinylated protein or antibody). The term "derivative" shall also include any polypeptide (e.g., an antibody) which has one or more amino acids deleted from, added to, or substituted from the natural polypeptide sequence, but which retains a substantial amino acid sequence homology to the natural sequence. A substantial sequence homology is any homology greater than 50 percent.

In some embodiments, the antibody can be a humanized antibody, a chimeric antibody, a multivalent antibody, or a fragment thereof. In some embodiments, an antibody can be a scFv-Fc (Sokolowska-Wedzina et al., *Mol. Cancer Res.* 15(8):1040-1050, 2017), a VHH domain (Li et al., *Immunol. Lett.* 188:89-95, 2017), a VNAR domain (Hasler et al., *Mol. Immunol.* 75:28-37, 2016), a (scFv)$_2$, a minibody (Kim et al., *PLoS One* 10(1):e113442, 2014), or a BiTE. In some embodiments, an antibody can be a DVD-Ig (Wu et al., *Nat. Biotechnol.* 25(11):1290-1297, 2007; WO 08/024188; WO 07/024715), and a dual-affinity re-targeting antibody (DART) (Tsai et al., *Mol. Ther. Oncolytics* 3:15024, 2016), a triomab (Chelius et al., *MAbs* 2(3):309-319, 2010), kih IgG with a common LC (Kontermann et al., *Drug Discovery Today* 20(7):838-847, 2015), a crossmab (Regula et al., *EMBO Mol. Med.* 9(7):985, 2017), an ortho-Fab IgG (Kontermann et al., *Drug Discovery Today* 20(7):838-847, 2015), a 2-in-1-IgG (Kontermann et al., *Drug Discovery Today* 20(7):838-847, 2015), IgG-scFv (Cheal et al., *Mol. Cancer Ther.* 13(7):1803-1812, 2014), scFv2-Fc (Natsume et al., *J. Biochem.* 140(3):359-368, 2006), a bi-nanobody (Kontermann et al., *Drug Discovery Today* 20(7):838-847, 2015), tanden antibody (Kontermann et al., *Drug Discovery Today* 20(7):838-847, 2015), a DART-Fc (Kontermann et al., *Drug Discovery Today* 20(7):838-847, 2015), a scFv-HSA-scFv (Kontermann et al., *Drug Discovery Today* 20(7):838-847, 2015), DNL-Fab3 (Kontermann et al., *Drug Discovery Today* 20(7):838-847, 2015), DAF (two-in-one or four-inone), DutaMab, DT-IgG, knobs-in-holes common LC, knobs-in-holes assembly, charge pair antibody, Fab-arm exchange antibody, SEEDbody, Triomab, LUZ-Y, Fcab, kλ-body, orthogonal Fab, DVD-IgG, IgG(H)-scFv, scFv-(H) IgG, IgG(L)-scFv, scFv-(L)-IgG, IgG (L,H)-Fc, IgG(H)-V, V(H)-IgG, IgG(L)-V, V(L)-IgG, KIH IgG-scFab, 2scFv-IgG, IgG-2scFv, scFv4-Ig, Zybody, DVI-IgG, nanobody (e.g., antibodies derived from *Camelus bactriamus, Calelus dromaderius*, or *Lama paccos*) (U.S. Pat. No. 5,759,808; Stijlemans et al., *J. Biol. Chem.* 279:1256-1261, 2004; Dumoulin et al., *Nature* 424:783-788, 2003; and Pleschberger et al., *Bioconjugate Chem.* 14:440-448, 2003), nanobody-HSA, a diabody (e.g., Poljak, *Structure* 2(12): 1121-1123, 1994; Hudson et al., *J. Immunol. Methods* 23(1-2):177-189, 1999), a TandAb (Reusch et al., *mAbs* 6(3):727-738, 2014), scDiabody (Cuesta et al., *Trends in Biotechnol.* 28(7):355-362, 2010), scDiabody-CH3 (Sanz et al., *Trends in Immunol.* 25(2):85-91, 2004), Diabody-CH3 (Guo et al.), Triple Body, miniantibody, minibody, TriBi minibody, scFv-CH3 KIH, Fab-scFv, scFv-CH-CL-scFv, F(ab')2-scFV2, scFv-KIH, Fab-scFv-Fc, tetravalent HCAb, scDiabody-Fc, diabody-Fc, tandem scFv-Fc, intrabody (Huston et al., *Human Antibodies* 10(3-4):127-142, 2001; Wheeler et al., *Mol. Ther.* 8(3):355-366, 2003; Stocks, *Drug Discov. Today* 9(22):960-966, 2004), dock and lock bispecific antibody, ImmTAC, HSAbody, scDiabody-HSA, tandem scFv, IgG-IgG, Cov-X-Body, and scFv1-PEG-scFv2.

In some embodiments, an antibody can be an IgNAR, a bispecific antibody (Milstein and Cuello, *Nature* 305:537-539, 1983; Suresh et al., *Methods in Enzymology* 121:210, 1986; WO 96/27011; Brennan et al., *Science* 229:81, 1985; Shalaby et al., *J. Exp. Med.* 175:217-225, 1992; Kolstelny et al., *J. Immunol.* 148(5):1547-1553, 1992; Hollinger et al., *Proc. Natl. Acad. Sci. U.S.A.* 90:6444-6448, 1993; Gruber et al., *J. Immunol.* 152:5368, 1994; Tutt et al., *J. Immunol.* 147:60, 1991), a bispecific diabody, a triabody (Schoonooghe et al., *BMC Biotechnol.* 9:70, 2009), a tetrabody, scFv-Fc knobs-into-holes, a scFv-Fc-scFv, a (Fab'scFv)$_2$, a V-IgG, a IvG-V, a dual V domain IgG, a heavy chain immunoglobulin or a camelid (Holt et al., *Trends Biotechnol.* 21(11):484-490, 2003), an intrabody, a monoclonal antibody (e.g., a human or humanized monoclonal antibody), a heteroconjugate antibody (e.g., U.S. Pat. No. 4,676, 980), a linear antibody (Zapata et al., *Protein Eng.* 8(10): 1057-1062, 1995), a trispecific antibody (Tutt et al., *J. Immunol.* 147:60, 1991), a Fabs-in-Tandem immunoglobulin (WO 15/103072), or a humanized camelid antibody.

In some embodiments, the antibody binds specifically to a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid. Exemplary antibodies that bind to metabolites in these pathways are disclosed, for example, in International Publication No. WO2014/188377, the entire contents of which are incorporated herein by reference.

In some embodiments, the antibody is specific for a particular genus, species, or strain of a microorganism, and may therefore be used for the detection, analysis and/or quantitation of the microorganism using the detection methods described below. In some embodiments, the antibody specifically binds to a surface-specific biomolecule (e.g., a pilus subunit or a flagella protein) present in a particular genus, species or strain of microorganism, and does not cross-react with other microorganisms. In some embodiments, these antibodies may be used in the methods described herein to diagnose a subject with a particular infection or disease, or to monitor an infection (e.g., during or after treatment). In some embodiments, the antibody specifically binds to an antigen present in a particular genera, species or strain of a microorganism. Exemplary antigens, the corresponding microorganism that can be detected, and the disease caused by the microorganism (in parentheticals) include: outer membrane protein A OmpA (*Acinetobacter baumannii, Acinetobacter* infections)); HIV p24 antigen, HIV Eenvelope proteins (Gp120, Gp41, Gp160) (HIV (Human immunodeficiency virus), AIDS (Acquired immunodeficiency syndrome)); galactose-inhibitable adherence protein GIAP, 29 kDa antigen Eh29, GaVGaINAc lectin, protein CRT, 125 kDa immunodominant antigen, protein M17, adhesin ADH112, protein STIRP (*Entamoeba histolytica*, Amoebiasis); protective Antigen PA, edema factor EF, lethal facotor LF, the S-layer homology proteins SLH (*Bacillus anthracis*, Anthrax); nucleocapsid protein NP, glycoprotein precursor GPC, glycoprotein GP1, glycoprotein GP2 (Junin virus, Argentine hemorrhagic fever); 41 kDa allergen Asp v13, allergen Asp f3, major conidial surface protein rodlet A, protease Pep1p, GPI-anchored protein Gel1p, GPI-anchored protein Crf1p (*Aspergillus* genus, Aspergillosis); outer surface protein A OspA, outer surface protein OspB, outer surface protein OspC, decorin binding protein A DbpA, flagellar filament 41 kDa core protein Fla, basic membrane protein A precursor BmpA (Immunodominant antigen P39), outer surface 22 kDa lipoprotein precursor (antigen IPLA7), variable surface lipoprotein vlsE (*Borrelia* genus, *Borrelia* infection); OmpA-like transmembrane domain-containing protein Omp31, immunogenic 39-kDa protein M5 P39, 25 kDa outer-membrane immunogenic protein precursor Omp25, outer membrane protein MotY Omp16, conserved outer membrane protein D15, malate dehydrogenase Mdh, component of the Type-IV secretion system (T4SS) VirJ, lipoprotein of unknown function BAB1_0187 (*Brucella* genus, Brucellosis); major outer membrane protein PorA, flagellin FlaA, surface antigen CjaA, fibronectin binding protein CadF, aspartate/glutamate-binding ABC transporter protein Peb1A, protein FspA1, protein FspA2 (*Campylobacter* genus, Campylobacteriosis); glycolytic enzyme enolase, secreted aspartyl proteinases SAP1-10, glycophosphatidylinositol (GPI)-linked cell wall protein, adhesin Als3p, cell surface hydrophobicity protein CSH (usually *Candida albicans* and other *Candida* species, Candidiasis); envelope glycoproteins (gB, gC, gE, gH, gI, gK, gL) (Varicella zoster virus (VZV), Chickenpox); major outer membrane protein MOMP, probable outer membrane protein PMPC, outer membrane complex protein B OmcB (*Chlamydia trachomatis, Chlamydia*); major outer membrane protein MOMP, outer membrane protein 2 Omp2, (*Chlamydophila pneumoniae, Chlamydophila pneumoniae* infection); outer membrane protein U Porin ompU, (*Vibrio cholerae*, Cholera); surface layer proteins SLPs, Cell Wall Protein CwpV, flagellar protein FliC, flagellar protein FliD (*Clostridium difficile, Clostridium difficile* infection); acidic ribosomal protein P2 CpP2, mucin antigens Muc1, Muc2, Muc3 Muc4, Muc5, Muc6, Muc7, surface adherence protein CP20, surface adherence protein CP23, surface protein CP12, surface protein CP21, surface protein CP40, surface protein CP60, surface protein CP15, surface-associated glycopeptides gp40, surface-associated glycopeptides gp15, oocyst wall protein AB, profilin PRF, apyrase (*Cryptosporidium* genus, Cryptosporidiosis); membrane protein pp15, capsid-proximal tegument protein pp150 (Cytomegalovirus, Cytomegalovirus infection); prion protein (vCJD prion, Variant Creutzfeldt-Jakob disease (vCJD, nvCJD)); cyst wall proteins CWP1, CWP2, CWP3, variant surface protein VSP, VSP1, VSP2, VSP3, VSP4, VSP5, VSP6, 56 kDa antigen (*Giardia* intestinalis, Giardiasis); minor pilin-associated subunit pilC, major pilin subunit and variants pilE, pilS (*Neisseria gonorrhoeae*, Gonorrhea); outer membrane protein A OmpA, outer membrane protein C OmpC, outer membrane protein K17 OmpK17 (*Klebsiella granulomatis, Granuloma inguinale* (Donovanosis)); fibronectin-binding protein Sfb (*Streptococcus pyogenes*, Group A streptococcal infection); outer membrane protein P6 (*Haemophilus influenzae, Haemophilus influenzae* infection); integral membrane proteins, aggregation-prone proteins, O-antigen, toxin-antigens Stx2B, toxin-antigen Stx1B, adhesion-antigen fragment Int28, protein EspA, protein EspB, Intimin, protein Tir, protein IntC300, protein Eae (*Escherichia coli* O157:H7, O111 and O104:H4, Hemolytic-uremic syndrome (HUS)); hepatitis A surface antigen HBAg (Hepatitis A Virus, Hepatitis A); hepatitis B surface antigen HBsAg (Hepatitis B Virus, Hepatitis B); envelope glycoprotein E1 gp32 gp35, envelope glycoprotein E2 NS1 gp68 gp70, capsid protein C, (Hepatitis C Virus, Hepatitis C); type IV pilin PilE, outer membrane protein MIP, major outer membrane protein MompS (*Legionella pneumophila*, Legionellosis (Legionnaires' disease, Pontiac fever)); minor pilin-associated subunit pilC, major pilin subunit and variants pilE, pilS (*Neisseria meningitidis*, Meningococcal disease); adhesin P1, adhesion P30 (*Mycoplasma pneumoniae, Mycoplasma* pneumonia); F1 capsule antigen, outer membrane protease Pla, (*Yersinia pestis*, Plague); surface adhesin PsaA, cell wall surface anchored protein psrP (*Streptococcus pneumoniae*, Pneumococcal infection); flagellin FliC, invasion protein SipC, glycoprotein gp43, outer membrane protein LamB, outer membrane protein PagC, outer membrane protein TolC, outer membrane protein NmpC, outer membrane protein FadL, transport protein SadA (*Salmonella* genus, *Salmonellosis*); collagen adhesin Cna, fibronectin-binding protein A FnbA, secretory antigen SssA (*Staphylococcus* genus, *Staphylococcal* food poisoning); collagen adhesin Can (*Staphylococcus* genus, *Staphylococcal* infection); fibronectin-binding protein A FbpA (Ag85A), fibronectin-binding protein D FbpD, fibronectin-binding protein C FbpC1, heat-shock protein HSP65, protein PST-S (*Mycobacterium tuberculosis*, Tuberculosis); and outer membrane protein FobA, outer membrane protein FobB, type IV pili glycosylation protein, outer membrane protein tolC, protein TolQ (*Francisella tularensis*, Tularemia). Additional exemplary microorganisms and corresponding antigens are disclosed, e.g., in U.S. Publication No. 2015/0118264, the entire contents of which are expressly incorporated herein by reference.

In some embodiments, a plurality of antibodies (e.g., 2, 3, 4, 5, 6, 7, 8, 9, 10, 15, 20, 25, 30, or more antibodies) are used as detection agents in any of the methods described herein (e.g., to detect the presence of one or more analytes in a sample). In some embodiments, the plurality of antibodies bind to the same analyte (e.g., an antigen). In some embodiments, the plurality of antibodies bind to the same epitope present on the analyte (e.g., an antigen). In some embodiments, the plurality of antibodies bind to different epitopes present on the same analyte. In some embodiments, the plurality of antibodies bind to overlapping epitopes present on the same analyte. In some embodiments, the plurality of antibodies bind to non-overlapping epitopes present on the same analyte.

B. Antibiotics

In some embodiments, the analyte or detection agent is an antibiotic. An "antibiotic" or "antibiotic agent" refers to a substance that has the capacity to inhibit or slow down the growth of, or to destroy bacteria and/or other microorganisms. In some embodiments, the antibiotic agent is a bacteriostatic antibiotic agent. In some embodiments, the antibiotic is a bacteriolytic antibiotic agent. Exemplary antibiotic agents are set forth in the U.S. Patent Publication US 2006/0269485, which is hereby incorporated by reference herein in its entirety.

In some embodiments, the antibiotic agent is selected from the classes consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroids, sulfonamides, tetracycline, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds. In some embodiments, the antibiotic is rifaximin.

Beta-lactam antibiotics include, but are not limited to, 2-(3-alanyl)clavam, 2-hydroxymethylclavam, 8-epi-thienamycin, acetyl-thienamycin, amoxicillin, amoxicillin sodium, amoxicillin trihydrate, amoxicillin-potassium clavulanate combination, ampicillin, ampicillin sodium, ampicillin trihydrate, ampicillin-sulbactam, apalcillin, aspoxicillin, azidocillin, azlocillin, aztreonam, bacampicillin, biapenem, carbenicillin, carbenicillin disodium, carfecillin, carindacillin, carpetimycin, cefacetril, cefaclor, cefadroxil, cefalexin, cefaloridine, cefalotin, cefamandole, cefamandole, cefapirin, cefatrizine, cefatrizine propylene glycol, cefazedone, cefazolin, cefbuperazone, cefcapene, cefcapene pivoxil hydrochloride, cefdinir, cefditoren, cefditoren pivoxil, cefepime, cefetamet, cefetamet pivoxil, cefixime, cefinenoxime, cefinetazole, cefminox, cefminox, cefmolexin, cefodizime, cefonicid, cefoperazone, cefoxanide, cefoselis, cefotaxime, cefotetan, cefotiam, cefoxitin, cefozopran, cefpiramide, cefpirome, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftriaxone, cefuroxime, cefuroxime axetil, cephalosporin, cephamycin, chitinovorin, ciclacillin, clavulanic acid, clometocillin, cloxacillin, cycloserine, deoxy pluracidomycin, dicloxacillin, dihydro pluracidomycin, epicillin, epithienamycin, ertapenem, faropenem, flomoxef, flucloxacillin, hetacillin, imipenem, lenampicillin, loracarbef, mecillinam, meropenem, metampicillin, meticillin, mezlocillin, moxalactam, nafcillin, northienamycin, oxacillin, panipenem, penamecillin, penicillin, phenethicillin, piperacillin, tazobactam, pivampicillin, pivcefalexin, pivmecillinam, pivmecillinam hydrochloride, pluracidomycin, propicillin, sarmoxicillin, sulbactam, sulbenicillin, talampicillin, temocillin, terconazole, thienamycin, ticarcillin and analogs, salts and derivatives thereof.

Aminoglycosides include, but are not limited to, 1,2'-N-DL-isoseryl-3',4'-dideoxykanamycin B, 1,2'-N-DL-isoseryl-kanamycin B, 1,2'-N-[(S)-4-amino-2-hydroxybutyryl]-3',4'-dideoxykanamycin B, 1,2'-N-[(S)-4-amino-2-hydroxybutyryl]-kanamycin B, 1-N-(2-Aminobutanesulfonyl) kanamycin A, 1-N-(2-aminoethanesulfonyl)3',4'-dideoxyribostamycin, 1-N-(2-Aminoethanesulfonyl)3'-deoxyribostamycin, 1-N-(2-aminoethanesulfonyl)3'4'-dideoxykanamycin B, 1-N-(2- aminoethanesulfonyl)kanamycin A, 1-N-(2-aminoethanesulfonyl)kanamycin B, 1-N-(2-aminoethanesulfonyl)ribostamycin, 1-N-(2-aminopropanesulfonyl)3'-deoxykanamycin B, 1-N-(2-aminopropanesulfonyl)3'4'-dideoxykanamycin B, 1-N-(2-aminopropanesulfonyl) kanamycin A, 1-N-(2-aminopropanesulfonyl)kanamycin B, 1-N-(L-4-amino-2-hydroxy-butyryl)2,'3'-dideoxy-2'-fluoro-kanamycin A, 1-N-(L-4-amino-2-hydroxy-propionyl)2,'3'-dideoxy-2'-fluorokanamycin A, 1-N-DL-3',4'-dideoxy-isoserylkanamycin B, 1-N-DL-isoserylkanamycin, 1-N-DL-isoserylkanamycin B, 1-N-[L-(−)-(alpha-hydroxy-gamma-aminobutyryl)]-XK-62-2,2',3'-dideoxy-2'-fluorokanamycin A,2-hydroxygentamycin A3,2-hydroxygentamycin B, 2-hydroxygentamycin B1, 2-hydroxygentamycin JI-20A, 2-hydroxygentamycin JI-20B, 3"-N-methyl-4"-C-methyl-3',4'-dodeoxy kanamycin A, 3"-N-methyl-4"-C-methyl-3',4'-dodeoxy kanamycin B, 3"-N-methyl-4"-C-methyl-3',4'-dodeoxy-6'-methyl kanamycin B, 3',4'-Dideoxy-3'-enoribostamycin,3',4'-dideoxyneamine,3',4'-dideoxyribostamycin, 3'-deoxy-6'-N-methyl-kanamycin B,3'-deoxyneamine,3'-deoxyribostamycin, 3'-oxysaccharocin,3,3'-nepotrehalosadiamine, 3-demethoxy-2"-N-formimidoylistamycin B disulfate tetrahydrate, 3-demethoxyistamycin B,3-O-demethyl-2-N-formimidoylistamycin B, 3-O-demethylistamycin B,3-trehalosamine,4",6"-dideoxydibekacin, 4-N-glycyl-KA-6606VI, 5"'-Amino-3',4',5"-trideoxy-butirosin A, 6"-deoxydibekacin,6'-epifortimicin A, 6-deoxy-neomycin (structure 6-deoxy-neomycin B),6-deoxy-neomycin B, 6-deoxy-neomycin C, 6-deoxy-paromomycin, acmimycin, AHB-3',4'-dideoxyribostamycin, AHB-3'-deoxykanamycin B, AHB-3'-deoxyneamine, AHB-3'-deoxyribostamycin, AHB-4"-6"-dideoxydibekacin, AHB-6"-deoxydibekacin, AHB-dideoxyneamine, AHB-kanamycin B, AHB-methyl-3'-deoxykanamycin B, amikacin, amikacin sulfate, apramycin, arbekacin, astromicin, astromicin sulfate, bekanamycin, bluensomycin, boholmycin, butirosin, butirosin B, catenulin, coumamidine gamma1, coumamidine gamma2,D,L-1-N-(alpha-hydroxy-beta-aminopropionyl)-XK-62-2, dactimicin, de-O-methyl-4-N-glycyl-KA-6606V1, de-O-methyl-KA-66061, de-O-methyl-KA-70381, destomycin A, destomycin B, di-N6', O3-demethylistamycin A, dibekacin, dibekacin sulfate, dihydrostreptomycin, dihydrostreptomycin sulfate, epi-formamidoylglycidylfortimicin B, epihygromycin, formimidoyl-istamycin A, formimidoyl-istamycin B, fortimicin B, fortimicin C, fortimicin D, fortimicin KE, fortimicin KF, fortimicin KG, fortimicin KG1 (stereoisomer KG1/KG2), fortimicin KG2 (stereoisomer KG1/KG2), fortimicin KG3, framycetin, framycetin sulphate, gentamicin, gentamycin sulfate, globeomycin, hybrimycin A1, hybrimycin A2, hybrimycin B1, hybrimycin B2, hybrimycin C1, hybrimycin C2, hydroxystreptomycin, hygromycin, hygromycin B, isepamicin, isepamicin sulfate, istamycin, kanamycin, kanamycin sulphate, kasugamycin, lividomycin, marcomycin, micronomicin, micronomicin sulfate, mutamicin, myomycin, N-demethyl-7-O-demethylcelesticetin, demethylcelesticetin, methanesulfonic acid derivative of istamycin, nebramycin, nebramycin, neomycin, netilmicin, oligostatin, paromomycin, quintomycin, ribostamycin, saccharocin, seldomycin, sisomicin, sorbistin, spectinomycin, streptomycin, tobramycin, trehalosmaine, trestatin, validamycin, verdamycin, xylostasin, zygomycin and analogs, salts and derivatives thereof.

Ansa-type antibiotics include, but are not limited to, 21-hydroxy-25-demethyl-25-methylth ioprotostreptovaricin, 3-methylth iorifamycin, ansamitocin, atropisostreptovaricin, awamycin, halomicin, maytansine, naphthomycin, rifabutin, rifamide, rifampicin, rifamycin, rifapentine, rifaximin (e.g., Xifaxan®), rubradirin, streptovaricin, tolypomycin and analogs, salts and derivatives thereof.

Antibiotic anthraquinones include, but are not limited to, auramycin, cinerubin, ditrisarubicin, ditrisarubicin C, figaroic acid fragilomycin, minomycin, rabelomycin, rudolfomycin, sulfurmycin and analogs, salts and derivatives thereof.

Antibiotic azoles include, but are not limited to, azanidazole, bifonazole, butoconazol, chlormidazole, chlormidazole hydrochloride, cloconazole, cloconazole monohydrochloride, clotrimazol, dimetridazole, econazole, econazole nitrate, enilconazole, fenticonazole, fenticonazole nitrate, fezatione, fluconazole, flutrimazole, isoconazole, isoconazole nitrate, itraconazole, ketoconazole, lanoconazole, metronidazole, metronidazole benzoate, miconazole, miconazole nitrate, neticonazole, nimorazole, niridazole, omoconazol, ornidazole, oxiconazole, oxiconazole nitrate, propenidazole, secnidazol, sertaconazole, sertaconazole nitrate, sulconazole, sulconazole nitrate, tinidazole, tioconazole, voriconazol and analogs, salts and derivatives thereof.

Antibiotic glycopeptides include, but are not limited to, acanthomycin, actaplanin, avoparcin, balhimycin, bleomycin B (copper bleomycin), chloroorienticin, chloropolysporin, demethylvancomycin, enduracidin, galacardin, guanidylfungin, hachimycin, demethylvancomycin, N-nonanoyl-teicoplanin, phleomycin, platomycin, ristocetin, staphylocidin, talisomycin, teicoplanin, vancomycin, victomycin, xylocandin, zorbamycin and analogs, salts and derivatives thereof.

Macrolides include, but are not limited to, acetylleucomycin, acetylkitasamycin, angolamycin, azithromycin, bafilomycin, brefeldin, carbomycin, chalcomycin, cirramycin, clarithromycin, concanamycin, deisovaleryl-niddamycin, demycinosyl-mycinamycin, Di-O-methyltiacumicidin, dirithromycin, erythromycin, erythromycin estolate, erythromycin ethyl succinate, erythromycin lactobionate, erythromycin stearate, flurithromycin, focusin, foromacidin, haterumalide, haterumalide, josamycin, josamycin ropionate, juvenimycin, juvenimycin, kitasamycin, ketotiacumicin, lankavacidin, lankavamycin, leucomycin, machecin, maridomycin, megalomicin, methylleucomycin, methymycin, midecamycin, miocamycin, mycaminosyltylactone, mycinomycin, neutramycin, niddamycin, nonactin, oleandomycin, phenylacetyideltamycin, pamamycin, picromycin, rokitamycin, rosaramicin, roxithromycin, sedecamycin, shincomycin, spiramycin, swalpamycin, tacrolimus, telithromycin, tiacumicin, tilmicosin, treponemycin, troleandomycin, tylosin, venturicidin and analogs, salts and derivatives thereof.

Antibiotic nucleosides include, but are not limited to, amicetin, angustmycin, azathymidine, blasticidin S, epiroprim, flucytosine, gougerotin, mildiomycin, nikkomycin, nucleocidin, oxanosine, oxanosine, puromycin, pyrazomycin, showdomycin, sinefungin, sparsogenin, spicamycin, tunicamycin, uracil polyoxin, vengicide and analogs, salts and derivatives thereof.

Antibiotic peptides include, but are not limited to, actinomycin, aculeacin, alazopeptin, amfomycin, amythiamycin, antifungal from *Zalerion arboricola*, antrimycin, apid, apidaecin, aspartocin, auromomycin, bacileucin, bacillomycin, bacillopeptin, bacitracin, bagacidin, beminamycin, beta-alanyl-L-tyrosine, bottromycin, capreomycin, caspofungine, cepacidine, cerexin, cilofungin, circulin, colistin, cyclodepsipeptide, cytophagin, dactinomycin, daptomycin, decapeptide, desoxymulundocandin, echanomycin, echinocandin B, echinomycin, ecomycin, enniatin, etamycin, fabatin, ferrimycin, ferrimycin, ficellomycin, fluoronocathiacin, fusaricidin, gardimycin, gatavalin, globopeptin, glyphomycin, gramicidin, herbicolin, iomycin, iturin, iyomycin, izupeptin, janiemycin, janthinocin, jolipeptin, katanosin, killertoxin, lipopeptide antibiotic, lipopeptide from *Zalerion* sp., lysobactin, lysozyme, macromomycin, magainin, melittin, mersacidin, mikamycin, mureidomycin, mycoplanecin, mycosubtilin, neopeptifluorin, neoviridogrisein, netropsin, nisin, nocathiacin, nocathiacin 6-deoxyglycoside, nosiheptide, octapeptin, pacidamycin, pentadecapeptide, peptifluorin, permetin, phytoactin, phytostreptin, planothiocin, plusbacin, polcillin, polymyxin antibiotic complex, polymyxin B, polymyxin B1, polymyxin F, preneocarzinostatin, quinomycin, quinupristin-dalfopristin, safracin, salmycin, salmycin, salmycin, sandramycin, saramycetin, siomycin, sperabillin, sporamycin, a *Streptomyces* compound, subtilin, teicoplanin aglycone, telomycin, thermothiocin, thiopeptin, thiostrepton, tridecaptin, tsushimycin, tuberactinomycin, tuberactinomycin, tyrothricin, valinomycin, viomycin, virginiamycin, zervacin and analogs, salts and derivatives thereof.

In some embodiments, the antibiotic peptide is a naturally-occurring peptide that possesses an antibacterial and/or an antifungal activity. Such peptide can be obtained from an herbal or a vertebrate source.

Polyenes include, but are not limited to, amphotericin, amphotericin, aureofungin, ayfactin, azalomycin, blasticidin, candicidin, candicidin methyl ester, candimycin, candimycin methyl ester, chinopricin, filipin, flavofungin, fradicin, hamycin, hydropricin, levorin, lucensomycin, lucknomycin, mediocidin, mediocidin methyl ester, mepartricin, methylamphotericin, natamycin, niphimycin, nystatin, nystatin methyl ester, oxypricin, partricin, pentamycin, perimycin, pimaricin, primycin, proticin, rimocidin, sistomycosin, sorangicin, trichomycin and analogs, salts and derivatives thereof.

Polyethers include, but are not limited to, 20-deoxy-epinarasin, 20-deoxysalinomycin, carriomycin, dianemycin, dihydrolonomycin, etheromycin, ionomycin, iso-lasalocid, lasalocid, lenoremycin, lonomycin, lysocellin, monensin, narasin, oxolonomycin, a polycyclic ether antibiotic, salinomycin and analogs, salts and derivatives thereof.

Quinolones include, but are not limited to, an alkylmethylendioxy-4(1H)-oxocinnoline-3-carboxylic acid, alatrofloxacin, cinoxacin, ciprofloxacin, ciprofloxacin hydrochloride, danofloxacin, dermofongin A, enoxacin, enrofloxacin, fleroxacin, flumequine, gatifloxacin, gemifloxacin, grepafloxacin, levofloxacin, lomefloxacin, lomefloxacin, hydrochloride, miloxacin, moxifloxacin, nadifloxacin, nalidixic acid, nifuroquine, norfloxacin, ofloxacin, orbifloxacin, oxolinic acid, pazufloxacine, pefloxacin, pefloxacin mesylate, pipemidic acid, piromidic acid, premafloxacin, rosoxacin, rufloxacin, sparfloxacin, temafloxacin, tosufloxacin, trovafloxacin and analogs, salts and derivatives thereof.

Antibiotic steroids include, but are not limited to, aminosterol, ascosteroside, cladosporide A, dihydrofusidic acid, dehydro-dihydrofusidic acid, dehydrofusidic acid, fusidic acid, squalamine and analogs, salts and derivatives thereof.

Sulfonamides include, but are not limited to, chloramine, dapsone, mafenide, phthalylsulfathiazole, succinylsulfathiazole, sulfabenzamide, sulfacetamide, sulfachlorpyridazine, sulfadiazine, sulfadiazine silver, sulfadicramide, sulfadimethoxine, sulfadoxine, sulfaguanidine, sulfalene, sulfamazone, sulfamerazine, sulfamethazine, sulfamethizole, sulfamethoxazole, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfisomidine, sulfisoxazole, sulfisoxazole acetyl, sulfacarbamide and analogs, salts and derivatives thereof.

Tetracyclines include, but are not limited to, dihydrosteffimycin, demethyltetracycline, aclacinomycin, akrobomycin, baumycin, bromotetracycline, cetocyclin, chlortetracycline, clomocycline, daunorubicin, demeclocycline, doxorubicin, doxorubicin hydrochloride, doxycycline, lymecyclin, marcellomycin, meclocycline, meclocycline sulfosalicylate, methacycline, minocycline, minocycline hydrochloride, musettamycin, oxytetracycline, rhodirubin, rolitetracycline, rubomycin, serirubicin, steffimycin, tetracycline and analogs, salts and derivatives thereof.

Dicarboxylic acids, having between about 6 and about 14 carbon atoms in their carbon atom skeleton are particularly useful in the treatment of disorders of the skin and mucosal membranes that involve microbial. Suitable dicarboxylic acid moieties include, but are not limited to, adipic acid, pimelic acid, suberic acid, azelaic acid, sebacic acid, 1,11-undecanedioic acid, 1,12-dodecanedioic acid, 1,13-tridecanedioic acid and 1,14-tetradecanedioic acid. Thus, in one or more embodiments of the present disclosure, dicarboxylic acids, having between about 6 and about 14 carbon atoms in their carbon atom skeleton, as well as their salts and derivatives (e.g., esters, amides, mercapto-derivatives, anhydraides), are useful immunomodulators in the treatment of disorders of the skin and mucosal membranes that involve inflammation. Azelaic acid and its salts and derivatives are preferred. It has antibacterial effects on both aerobic and anaerobic organisms, particularly *Propionibacterium acnes* and *Staphylococcus epidermidis*, normalizes keratinization, and has a cytotoxic effect on malignant or hyperactive melanocytes. In a preferred embodiment, the dicarboxylic acid is azelaic acid in a concentration greater than 10%. Preferably, the concentration of azelaic acid is between about 10% and about 25%. In such concentrates, azelaic acid is suitable for the treatment of a variety of skin disorders, such as acne, rosacea and hyperpigmentation.

In some embodiments, the antibiotic agent is an antibiotic metal. A number of metals ions have been shown to possess antibiotic activity, including silver, copper, zinc, mercury, tin, lead, bismutin, cadmium, chromium and ions thereof. It has been theorized that these antibiotic metal ions exert their effects by disrupting respiration and electron transport systems upon absorption into bacterial or fungal cells. Antimicrobial metal ions of silver, copper, zinc, and gold, in particular, are considered safe for in vivo use. Anti-microbial silver and silver ions are particularly useful due to the fact that they are not substantially absorbed into the body. Thus, in one or more embodiment, the antibiotic metal consists of an elemental metal, selected from the group consisting of silver, copper, zinc, mercury, tin, lead, bismutin, cadmium, chromium and gold, which is suspended in the composition as particles, microparticles, nanoparticles or colloidal particles. The antibiotic metal can further be intercalated in a chelating substrate.

In further embodiments, the antibiotic metal is ionic. The ionic antibiotic metal can be presented as an inorganic or organic salt (coupled with a counterion), an organometallic complex or an intercalate. Non-binding examples of counter inorganic and organic ions are sulfadiazine, acetate, benzoate, carbonate, iodate, iodide, lactate, laurate, nitrate, oxide, and palmitate, a negatively charged protein. In preferred embodiments, the antibiotic metal salt is a silver salt, such as silver acetate, silver benzoate, silver carbonate, silver iodate, silver iodide, silver lactate, silver laurate, silver nitrate, silver oxide, silver palmitate, silver protein, and silver sulfadiazine.

In one or more embodiments, the antibiotic metal or metal ion is embedded into a substrate, such as a polymer, or a mineral (such as zeolite, clay and silica).

In one or more embodiments, the antibiotic agent includes strong oxidants and free radical liberating compounds, such as oxygen, hydrogen peroxide, benzoyl peroxide, elemental halogen species, as well as oxygenated halogen species, bleaching agents (e.g., sodium, calcium or magnesium hypochloride and the like), perchlorite species, iodine, iodate, and benzoyl peroxide. Organic oxidizing agents, such as quinones, are also included. Such agents possess a potent broad-spectrum activity.

In one or more embodiments, the antibiotic agent is a cationic antimicrobial agent. The outermost surface of bacterial cells universally carries a net negative charge, making them sensitive to cationic substances. Examples of cationic antibiotic agents include: quaternary ammonium compounds (QAC's)—QAC's are surfactants, generally containing one quaternary nitrogen associated with at least one major hydrophobic moiety; alkyltrimethyl ammonium bromides are mixtures of where the alkyl group is between 8 and 18 carbons long, such as cetrimide (tetradecyltrimethylammonium bromide); benzalkonium chloride, which is a mixture of n-alkyldimethylbenzyl ammonium chloride where the alkyl groups (the hydrophobic moiety) can be of variable length; dialkylmethyl ammonium halides; dialkylbenzyl ammonium halides; and QAC dimmers, which bear bi-polar positive charges in conjunction with interstitial hydrophobic regions.

In one or more embodiments, the cationic antimicrobial agent is a polymer. Cationic antimicrobial polymers include, for example, guanide polymers, biguanide polymers, or polymers having side chains containing biguanide moieties or other cationic functional groups, such as benzalkonium groups or quarternium groups (e.g., quaternary amine groups). It is understood that the term "polymer" as used herein includes any organic material including three or more repeating units, and includes oligomers, polymers, copolymers, block copolymers, terpolymers, etc. The polymer backbone may be, for example a polyethylene, polypropylene or polysilane polymer.

In one or more embodiments, the cationic antimicrobial polymer is a polymeric biguanide compound. When applied to a substrate, such a polymer is known to form a barrier film that can engage and disrupt a microorganism. An exemplary polymeric biguanide compound is polyhexamethylene biguanide (PHMB) salts. Other exemplary biguanide polymers include, but are not limited to poly(hexamethylenebiguanide), poly(hexamethylenebiguanide) hydrochloride, poly(hexamethylenebiguanide) gluconate, poly(hexamethylenebiguanide) stearate, or a derivative thereof. In one or more embodiments, the antimicrobial material is substantially water-insoluble.

In some embodiments, the antibiotic agent is selected from the group of biguanides, triguanides, bisbiguanides and analogs thereof.

Guanides, biguanides, biguanidines and triguanides are unsaturated nitrogen containing molecules that readily obtain one or more positive charges, which make them effective antimicrobial agents. The basic structures a guanide, a biguanide, a biguanidine and a triguanide are provided below.

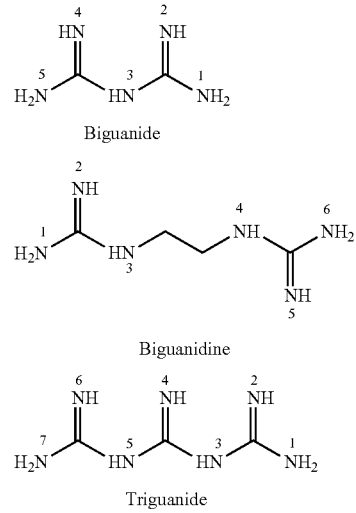

In some embodiments, the guanide, biguanide, biguanidine or triguanide, provide bi-polar configurations of cationic and hydrophobic domains within a single molecule.

Examples of guanides, biguanides, biguanidines and triguanides that are currently been used as antibacterial agents include chlorhexidine and chlorohexidine salts, analogs and derivatives, such as chlorhexidine acetate, chlorhexidine gluconate and chlorhexidine hydrochloride, picloxydine, alexidine and polihexanide. Other examples of guanides, biguanides, biguanidines and triguanides that can conceivably be used according to the present disclosure are chlorproguanil hydrochloride, proguanil hydrochloride (currently used as antimalarial agents), mefformin hydrochloride, phenformin and buformin hydrochloride (currently used as antidiabetic agents).

Yet, in one or more embodiments, the antibiotic is a non-classified antibiotic agent, including, without limitation, aabomycin, acetomycin, acetoxycycloheximide, acetylnanaomycin, an *Actinoplanes* sp. compound, actinopyrone, aflastatin, albacarcin, albacarcin, albofungin, albofungin, alisamycin, alpha-R,S-methoxycarbonylbenzylmonate, altromycin, amicetin, amycin, amycin demanoyl compound, amycine, amycomycin, anandimycin, anisomycin, anthramycin, anti-syphilis immune substance, anti-tuberculosis immune substance, an antibiotic from *Escherichia coli*, an antibiotic from *Streptomyces refuineus*, anticapsin, antimycin, aplasmomycin, aranorosin, aranorosinol, arugomycin, ascofuranone, ascomycin, ascosin, *Aspergillus flavus* antibiotic, asukamycin, aurantinin, an Aureolic acid antibiotic substance, aurodox, avilamycin, azidamfenicol, azidimycin, bacillaene, a *Bacillus larvae* antibiotic, bactobolin, benanomycin, benzanthrin, benzylmonate, bicozamycin, bravomicin, brodimoprim, butalactin, calcimycin, calvatic acid, candiplanecin, carumonam, carzinophilin, celesticetin, cepacin, cerulenin, cervinomycin, chartreusin, chloramphenicol, chloramphenicol palmitate, chloramphenicol succinate sodium, chlorflavonin, chlorobiocin, chlorocarcin, chromomycin, ciclopirox, ciclopirox olamine, citreamicin, cladosporin, clazamycin, clecarmycin, clindamycin, coliformin, collinomycin, copiamycin, corallopyronin, corynecandin, coumermycin, culpin, cuprimyxin, cyclamidomycin, cycloheximide, dactylomycin, danomycin, danubomycin, delaminomycin, demethoxyrapamycin, demethylscytophycin, dermadin, desdamethine, dexylosylbenanomycin, pseudoaglycone, dihydromocimycin, dihydronancimycin, diumycin, dnacin, dorrigocin, dynemycin, dynemycin triacetate, ecteinascidin, efrotomycin, endomycin, ensanchomycin, equisetin, ericamycin, esperamicin, ethylmonate, everninomicin, feldamycin, flambamycin, flavensomycin, florfenicol, fluvomycin, fosfomycin, fosfonochlorin, fredericamycin, frenolicin, fumagillin, fumifungin, funginon, fusacandin, fusafungin, gelbecidine, glidobactin, grahamimycin, granaticin, griseofulvin, griseoviridin, grisonomycin, hayumicin, hayumicin, hazymicin, hedamycin, heneicomycin, heptelicid acid, holomycin, humidin, isohematinic acid, karnatakin, kazusamycin, kristenin, L-dihydrophenylalanine, a L-isoleucyl-L-2-amino-4-(4'-amino-2',5'-cyclohexadienyl) derivative, lanomycin, leinamycin, leptomycin, libanomycin, lincomycin, lomofungin, lysolipin, magnesidin, manumycin, melanomycin, methoxycarbonylmethylmonate, methoxycarbonylethylmonate, methoxycarbonylphenylmonate, methyl pseudomonate, methylmonate, microcin, mitomalcin, mocimycin, moenomycin, monoacetyl cladosporin, monomethyl cladosporin, mupirocin, mupirocin calcium, mycobacidin, myriocin, myxopyronin, pseudoaglycone, nanaomycin, nancimycin, nargenicin, neocarcinostatin, neoenactin, neothramycin, nifurtoinol, nocardicin, nogalamycin, novobiocin, octylmonate, olivomycin, orthosomycin, oudemansin, oxirapentyn, oxoglaucine methiodide, pactacin, pactamycin, papulacandin, paulomycin, phaeoramularia fungicide, phenelfamycin, phenyl, cerulenin, phenylmonate, pholipomycin, pirlimycin, pleuromutilin, a polylactone derivative, polynitroxin, polyoxin, porfiromycin, pradimicin, prenomycin, prop-2-enylmonate, protomycin, Pseudomonas antibiotic, pseudomonic acid, purpuromycin, pyrinodemin, pyrrolnitrin, pyrrolomycin, amino, chloro pentenedioic acid, rapamycin, rebeccamycin, resistomycin, reuterin, reveromycin, rhizocticin, roridin, rubiflavin, naphthyridinomycin, saframycin, saphenamycin, sarkomycin, sarkomycin, sclopularin, selenomycin, siccanin, spartanamicin, spectinomycin, spongistatin, stravidin, streptolydigin, *Streptomyces arenae* antibiotic complex, streptonigrin, streptothricins, streptovitacin, streptozotocine, a strobilurin derivative, stubomycin, sulfamethoxazol-trimethoprim, sakamycin, tejeramycin, terpentecin, tetrocarcin, thermorubin, thermozymocidin, thiamphenicol, thioaurin, thiolutin, thiomarinol, thiomarinol, tirandamycin, tolytoxin, trichodermin, trienomycin, trimethoprim, trioxacarcin, tyrissamycin, umbrinomycin, unphenelfamycin, urauchimycin, usnic acid, uredolysin, variotin, vermisporin, verrucarin and analogs, salts and derivatives thereof.

In one or more embodiments, the antibiotic agent is a naturally occurring antibiotic compound. As used herein, the term "naturally-occurring antibiotic agent" includes all antibiotics that are obtained, derived or extracted from plant or vertebrate sources. Non-limiting examples of families of naturally-occurring antibiotic agents include phenol, resorcinol, antibiotic aminoglycosides, anamycin, quinines, anthraquinones, antibiotic glycopeptides, azoles, macrolides, avilamycin, agropyrene, cnicin, aucubin antibioticsaponin fractions, berberine (isoquinoline alkaloid), arctiopicrin (sesquiterpene lactone), lupulone, humulone (bitter acids), allicin, hyperforin, echinacoside, coniosetin, tetramic acid, imanine and novoimanine.

Ciclopirox and ciclopiroxolamine possess fungicidal, fungistatic and sporicidal activity. They are active against a broad spectrum of dermatophytes, yeasts, moulds and other fungi, such as *Trichophytons* species, *Microsporum* species, *Epidermophyton* species and yeasts (*Candida albicans, Candida glabrata*, other *Candida* species and *Cryptococcus neoformans*). Some *Aspergillus* species are sensitive to ciclopirox as are some *Penicillium*. Likewise, ciclopirox is effective against many Gram-positive and Gram-negative bacteria (e.g., *Escherichia coli, Proteus mirabilis, Pseudomonas aeruginosa, Staphylococcus* and *Streptococcus* species), as well as *Mycoplasma* species, *Trichomonas vaginalis* and *Actinomyces*.

Plant oils and extracts which contain antibiotic agents are also useful. Non-limiting examples of plants that contain agents include thyme, *Perilla*, lavender, tea tree, *Terfezia clayeryi, Micromonospora, Putterlickia verrucosa, Putterlickia pyracantha, Putterlickia retrospinosa, Maytenus ilicifolia, Maytenus evonymoides, Maytenus aquifolia, Faenia interjecta, Cordyceps sinensis, couchgrass*, holy thistle, plantain, burdock, hops, *echinacea*, buchu, chaparral, myrrh, red clover and yellow dock, garlic, and St. John's wort. Mixtures of the antibiotic agents as described herein may also be employed.

C. Biomarkers

In some embodiments, the analyte or detection agent is a biomarker. In general, biomarkers of diseases and disorders may be detected, analyzed and/or quantitated using the devices, compositions and methods described herein. The detection, analysis and quantification of a biomarker using the devices, methods and compositions described herein is particular useful in determining and monitoring the course of treatment that could be used to treat a condition in a subject (e.g., a human subject). Biomarkers can be detected and analyzed locally in the GI tract of a subject to determine whether the subject has or is at risk of developing a disease or disorder. In addition, biomarkers can be monitored using the compositions and methods described herein to determine whether a particular course of treatment in a subject diagnosed with a disease or disorder is effective or should be altered. For example, in some embodiments, inflammatory biomarker(s) is/are detected and analyzed in a subject using the ingestible devices described herein to determine whether a subject has or is at risk of developing IBD. As necessary, the subject can then be administered one or more courses of treatment (e.g., an anti-TNFα antibody) and the level of such inflammatory biomarker(s) can be monitored to assess efficacy of treatment. In some embodiments, the analyte(s) include one or more biomarkers whose presence is indicative of a phenomenon such as disease, infection, or environmental exposure.

In some embodiments, biomarkers are detected and analyzed in a subject to determine whether the subject has or is at risk of developing a disease or disorder. These diseases and disorders may occur in the GI tract of the subject or at a non-GI tract site in the subject. For example, biomarkers present in the GI tract may be indicative of a systemic disease or disorder. In some embodiments, the biomarkers are associated with a systemic disease or disorder. In some embodiments, the biomarkers are associated with one or more of a GI disorder, inflammation (e.g., cytokines), cancer, an infectious disease, a liver disease, and an inflammatory disease. Exemplary clases of biomarkers include antibodies (e.g., therapeutic antibodies), antigens (e.g., bacterial antigens), and cytokines. In some embodiments, the analyte or the detection agent is a biomarker, e.g., a biomarker of a GI disorder. An illustrative list of examples of biomarkers for detection, diagnosis or monitoring of treatment efficacy for GI disorders includes interferon-γ, IL-1β, IL-6, IL-22, IL-17A, TNFα, IL-2, memory cells ($CD44^+CD45RB^-CD4^+$ cells); a4β7, VEGF; ICAM VCAM; SAA; Calprotectin; lactoferrin; FGF2; TGFb; ANG-1; ANG-2; PLGF; a biologic (e.g., infliximab (REMICADE); adalimumab (HUMIRA);

ustekinumab (STELARA); vedolizumab (ENTYVIO); golimumab (SIMPONI); Jak inhibitors; and others); EGF; IL12/23p40, GMCSF; A4 B7; AeB7; CRP; SAA; CAM; VCAM; AREG; EREG; HB-EGF; HRG; BTC; TGFα; SCF; TWEAK; MMP-9; MMP-6; Ceacam CD66, IL10; ADA; Madcam-1; CD166 (AL CAM); FGF2; FGF7; FGF9; FGF19; Anti-neutrophil cytoplasmic antibody (ANCA); Anti-*Saccharomyces cerevisiae* Antibody IgA (ASCAA); Anti-*Saccharomyces cerevisiae* Antibody IgG (ASCAG); Anti-*Clostridium* cluster XIVa flagellin CBir1 antibody (CBir1); Anti-*Clostridium* cluster XIVa flagellin 2 antibody (A4-Fla2), Anti-*Clostridium* cluster XIVa flagellin X antibody (FlaX), Anti-*Escherichia coli* Outer Membrane Protein C (OmpC); Perinuclear AntiNeutrophil Cytoplasmic Antibody (ANCA); Amphiregulin Protein (AREG); Betacellulin Protein (BTC); Epidermal Growth Factor (EGF); Epiregulin Protein (EREG); Heparin Binding Epidermal Growth Factors (HBEGF); Hepatocyte Growth Factor (HGF); Neuregulin-1 (HRG); Transforming Growth Factor alpha (TGFA); C-Reactive Protein (CRP); Serum Amyloid A (SAA); Intercellular Adhesion Molecule 1 (ICAM-1), Vascular Cell Adhesion Molecule 1 (VCAM-1); and fibroblasts underlying the intestinal epithelium.

In some embodiments, a biomarker is an IBD biomarker, such as, for example: anti-glycan; anti-*Saccharomyces cerevisiae* (ASCA); anti-laminaribioside (ALCA); anti-chitobioside (ACCA); anti-mannobioside (AMCA); anti-laminarin (anti-L); anti-chitin (anti-C) antibodies: anti-outer membrane porin C (anti-OmpC), anti-Cbir1 flagellin; anti-I2 antibody; autoantibodies targeting the exocrine pancreas (PAB); and perinuclear anti-neutrophil antibody (pANCA); and calprotectin.

In some embodiments, a biomarker is associated with membrane repair, fibrosis, angiogenesis. In certain embodiments, a biomarker is an inflammatory biomarker, an anti-inflammatory biomarker, an MMP biomarker, an immune marker, or a TNF pathway biomarker. In some embodiments, a biomarker is gut-specific.

For tissue samples, HER2 can be used as a biomarker relating to cytotoxic T cells. Additionally, other cytokine levels can be used as biomarkers in tissue (e.g., phospho STAT 1, STAT 3 and STAT 5), in plasma (e.g., VEGF, VCAM, ICAM, IL-6), or both.

In some embodiments, the biomarker includes one or more immunoglobulins, such as, for example, immunoglobulin M (IgM), immunoglobulin D (IgD), immunoglobulin G (IgG), immunoglobulin E (IgE) and/or immunoglobulin A (IgA). In some embodiments, IgM is a biomarker of infection and/or inflammation. In some embodiments, IgD is a biomarker of autoimmune disease. In some embodiments, IgG is a biomarker of Alzheimer's disease and/or for cancer. In some embodiments, IgE is a biomarker of asthma and/or allergen immunotherapy. In some embodiments, IgA is a biomarker of kidney disease.

In some embodiments, the biomarker is High Sensitivity C-reactive Protein (hsCRP); 7α-hydroxy-4-cholesten-3-one (7αC4); Anti-Endomysial IgA (EMA IgA); Anti-Human Tissue Transglutaminase IgA (tTG IgA); Total Serum IgA by Nephelometry; Fecal Calprotectin; or Fecal Gastrointestinal Pathogens.

In some embodiments, the biomarker is:
a) an anti-gliadin IgA antibody, an anti-gliadin IgG antibody, an anti-tissue transglutaminase (tTG) antibody, an anti-endomysial antibody;
b)i) a serological biomarker that is ASCA-A, ASCA-G, ANCA, pANCA, anti-OmpC antibody, anti-CBir1 antibody, anti-FlaX antibody, or anti-A4-Fla2 antibody;
b)ii) an inflammation biomarker that is VEGF, ICAM, VCAM, SAA, or CRP;
b)iii) the genotype of the genetic biomarkers ATG16L1, ECM1, NKX2-3, or STAT3;
c) a bacterial antigen antibody biomarker;
d) a mast cell biomarker;
e) an inflammatory cell biomarker;
f) a bile acid malabsorption (BAM) biomarker;
g) a kynurenine biomarker;
or
h) a serotonin biomarker.

In some embodiments, the biomarker is a bacterial antigen antibody biomarker selected from the group consisting of an anti-Fla1 antibody, anti-Fla2 antibody, anti-FlaA antibody, anti-FliC antibody, anti-FliC2 antibody, anti-FliC3 antibody, anti-YBaN1 antibody, anti-ECFliC antibody, anti-Ec0FliC antibody, anti-SeFljB antibody, anti-CjFlaA antibody, anti-CjFlaB antibody, anti-SfFliC antibody, anti-CjCgtA antibody, anti-Cjdmh antibody, anti-CjGT-A antibody, anti-EcYidX antibody, anti-EcEra antibody, anti-EcFrvX antibody, anti-EcGabT antibody, anti-EcYedK antibody, anti-EcYbaN antibody, anti-EcYhgN antibody, anti-RtMaga antibody, anti-RbCpaF antibody, anti-RgPilD antibody, anti-LaFrc antibody, anti-LaEno antibody, anti-LjEFTu antibody, anti-BfOmpa antibody, anti-PrOmpA antibody, anti-Cp10bA antibody, anti-CpSpA antibody, anti-EfSant antibody, anti-LmOsp antibody, anti-SfET-2 antibody, anti-Cpatox antibody, anti-Cpbtox antibody, anti-EcSta2 antibody, anti-EcOStx2A antibody, anti-CjcdtB/C antibody, anti-CdTcdA/B antibody, and combinations thereof.

In some embodiments, the biomarker is a mast cell biomarker selected from the group consisting of beta-tryptase, histamine, prostaglandin E2 (PGE2), and combinations thereof.

In some embodiments, the biomarker is an inflammatory biomarker is selected from the group consisting of CRP, ICAM, VCAM, SAA, GROα, and combinations thereof.

In some embodiments, the biomarker is a bile acid malabsorption biomarker selected from the group consisting of 7α-hydroxy-4-cholesten-3-one, FGF19, and a combination thereof.

In some embodiments, the biomarker is a kynurenine biomarker selected from the group consisting of kynurenine (K), kynurenic acid (KyA), anthranilic acid (AA), 3-hydroxykynurenine (3-HK), 3-hydroxyanthranilic acid (3-HAA), xanthurenic acid (XA), quinolinic acid (QA), tryptophan, 5-hydroxytryptophan (5-HTP), and combinations thereof.

In some embodiments, the biomarker is a serotonin biomarker selected from the group consisting of serotonin (5-HT), 5-hydroxyindoleacetic acid (5-HIAA), serotonin-O-sulfate, serotonin-O-phosphate, and combinations thereof.

Additional biomarkers are disclosed, e.g., at U.S. Pat. No. 9,739,786, the entire contents of which are incorporated herein by reference.

In some embodiments, the biomarker is associated with a liver disease or disorder. In some embodiments, the analyte or detection agent is a biomarker of a liver disease or liver disorder. In some embodiments, the devices, compositions and methods disclosed herein may be used to detect, analyze and/or quantitate a biomarker associated with a liver disease or disorder, e.g., to determine whether a subject has or is at risk of developing a liver disease or disorder. In some embodiments, the devices, compositions, and methods described herein can be used to detect an analyte (e.g., a biomarker) in a sample from the gastrointestinal tract of the subject to determine whether the subject has or is at risk of developing a liver disease or disorder (e.g., NASH). In some embodiments, the detection, analysis and quantification of a liver disease biomarker using the devices, methods and compositions described herein may be used in determining and monitoring the course of treatment that could be used to treat a liver disease or disorder in a subject (e.g., a human subject). An illustrative list of examples of biomarkers that may be used for the detection, diagnosis, or monitoring of treatment efficacy for a liver disease or disorder includes bilirubin, gamma-glutamyl transferase (GGT), haptoglobin, apolipoprotein A1, alpha2-macroglobulin, cholesterol, triglycerides, alanine aminotransferase (ALT), aspartate aminotransferase (AST), glucose, cytokeratin-18 (CK18) fragment, hyaluronic acid, TGF-β, fatty acid binding protein, hydroxysteroid 17-beta dehydrogenase 13 (17β-HSD13), glutamyl dipeptides, glutamyl valine, glutamyl leucine, glutamyl phenylalanine, glutamyl tyrosine, carnitine, butylcarnitine, lysine, tyrosine, isoleucine, glycerophosphatidylcholine, glycerylphsphorylethanolamine, taurine, glycine conjugates, taurocholic acid, taurodeoxycholic acid, lactate, glutamate, cysteine-gluthatione disulfide, caprate, 10-undecenoate, oleoyl-lysophosphatidylcholine, oxidized and reduced gluthatione, glutamate, andenosine triphosphate, creatine, cholic acid, and glycodeoxycholic acid. Additional biomarkers, as well as therapeutic agents, for liver diseases and disorders are known in the art (see, e.g., Hirsova and Gores (2015) *Cell. Mol. Gastroenterol. Hepatol.* 1(1): 17-27; Willebrords et al. (2015) *Progress in Lipid Research* 59: 106-125; Alkhouri et al. (2011) *Expert Rev. Gastroenterol. Hepatol.* 5(2): 201-12; Wang (2014) *Cell Death and Disease* 5: e996; and Alonso et al. (2017) *Gastroenterology* 152: 1449-61, incorporated herein by reference).

Any of the foregoing biomarkers can be used as a biomarker for one or more of other conditions as appropriate.

D. Therapeutic Agents

In some embodiments, the disclosure provides methods in which the analyte(s) include one or more therapeutic agents (e.g., drugs).

In certain embodiments, the methods include determining based on spectral data whether one or more therapeutic agents (e.g., drugs) are present at a location within the GI tract of a subject. In some embodiments, the methods include measuring via spectral data the amount (relative or absolute) of one or more therapeutic agents at a location within the GI tract of a subject. The location of the GI tract can be, for example, the upper GI tract, the small intestine or the large intestine. Exemplary locations include the esophagus, the stomach, duodenum, the jejunum, the ileum, the cecum or the colon. Optionally, the ingestible device may be attached to a surface at a location in the GI tract, as described elsewhere herein, and the sample containing the one or more analytes (e.g., therapeutic agents) may flow past the ingestible device. Information about the presence and/or amount of one or more therapeutic agents at the location of the GI tract of the subject can be generated, for example, as a function of time. Such information can be used, for example, to develop a therapeutic agent (e.g., drug) absorbance profile for the subject for one or more drugs.

In certain embodiments, the methods include determining based on spectral data whether one or more therapeutic agents (e.g. drugs) are present at multiple different locations of the GI tract of a subject. In some embodiments, the methods include measuring via spectral data the amount (relative or absolute) of one or more therapeutic agents present at multiple different locations of the GI tract of a subject. The locations of the GI tract can include, for example, the upper GI tract, the small intestine or the large intestine. Exemplary locations include the esophagus, the stomach, duodenum, the jejunum, the ileum, the cecum or the colon. Typically, the ingestible device is used to collect spectral data at different locations in the GI tract of a subject as the ingestible device passes through the GI tract of the subject. Information about the presence and/or amount of one or more drugs at multiple different locations in the GI tract of a subject can be generated, for example, as a function of time. Such information can be used, for example, to develop a drug absorbance profile for the subject for one or more drugs.

The disclosure is not limited in terms of the therapeutic agent that may be used as an analyte or a detection agent using the devices, compositions and methods described herein. For example, the therapeutic agent can be a small molecule or a biologic (e.g., an antibody). The disclosure also is not limited in terms of the condition sought to be treated by the drug. For example, the condition may be a GI tract disorder or a non-GI tract disorder (e.g., a systemic disorder). The disclosure is not limited by the manner in which the drug is administered. For example, the drug can be administered orally, sublingually, rectally, topically, intravenously, intramuscularly and/or subcutaneously.

In some embodiments, the goal of administering the therapeutic agent (e.g., drug) is to treat a condition of the GI tract. In such embodiments, information relating to the presence and/or concentration at one or more locations of the GI tract can be useful in assessing the safety and/or effectiveness of the therapeutic agent (e.g., drug) and its form of administration toward treating the condition of the GI tract. In certain embodiments, the therapeutic agent (e.g., drug) may not be administered for the purpose of treating a condition of the GI tract. In such embodiments, information about the presence and/or concentration of the therapeutic agent in the GI tract can still be useful in determining what is a safe and/or effective dosage for the subject.

In some embodiments, the analyte or detection agent is a therapeutic agent, a fragment of a therapeutic agent and/or a metabolite of a therapeutic agent. In some embodiments, the compositions, devices and methods provided below may be used to detect, analyze and/or quantitate a therapeutic agent, a fragment of a therapeutic agent, and/or a metabolite of a therapeutic agent. Exemplary therapeutic agents include antibodies, nucleic acids (e.g., inhibitory nucleic acids), small molecules, and live biotherapeutics such as probiotics. In some embodiments, the analyte or the detection agent used in any of the detection methods described herein is a drug or a therapeutic agent. In some embodiments, the drug or therapeutic agent is used for the treatment of inflammatory bowel disease (IBD), for example, Crohn's Disease or Ulcerative Colitis (UC). Nonlimiting examples of such agents for treating or preventing inflammatory bowel disease include substances that suppress cytokine production, downregulate or suppress self-antigen expression, or mask the MHC antigens. Examples of such agents include CHST15 inhibitors (e.g., STNM01), IL-6 receptor inhibitors (e.g., tocilizumab); IL-12/IL-23 inhibitors (e.g., ustekinumab and brazikumab); integrin inhibitors (e.g., vedolizumab and natalizumab); JAK inhibitors (e.g., tofacitinib); SMAD7 inhibitors (e.g., Mongersen); IL-13 inhibitors; IL-1 receptor inhibitors; TLR agonists (e.g., Kappaproct); stem cells (e.g., Cx601), 2-amino-6-aryl-5-substituted pyrimidines (see U.S. Pat. No. 4,665,077); nonsteroidal anti-inflammatory drugs (NSAIDs), ganciclovir; tacrolimus; glucocorticoids such as Cortisol or aldosterone; anti-inflammatory agents such as a cyclooxygenase inhibitor; a 5-lipoxygenase inhibitor; or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporine; 6-mercaptopurine; steroids such as corticosteroids or glucocorticosteroids or glucocorticoid analogs, e.g., prednisone, methylprednisolone, including SOLU-MEDROL®, methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, antiinterleukin-2 (IL-2) antibodies and anti-IL-2 receptor antibodies, and anti-interleukin-6 (IL-6) receptor antibodies and antagonists; anti-LFA-1 antibodies, including anti-CD 1 la and anti-CD 18 antibodies; anti-L3T4 antibodies; heterologous anti-lymphocyte globulin; pan-T antibodies, anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodomase; RNA or DNA from the host; FK506; RS-61443; chlorambucil; deoxyspergualin; rapamycin; T-cell receptor (Cohen et al, U.S. Pat. No. 5,114,721); T-cell receptor fragments (Offner et al, Science, 251: 430-432 (1991); WO 90/11294; laneway, Nature, 341: 482 (1989); and WO 91/01133); BAFF antagonists such as BAFF or BR3 antibodies or immunoadhesins and zTNF4 antagonists (for review, see Mackay and Mackay, Trends Immunol, 23: 113-5 (2002) and see also definition below); 10 biologic agents that interfere with T cell helper signals, such as anti-CD40 receptor or anti-CD40 ligand (CD 154), including blocking antibodies to CD40-CD40 ligand. (e.g., Durie et al, Science, 261: 1328-30 (1993); Mohan et al, J. Immunol, 154: 1470-80 (1995)) and CTLA4-Ig (Finck et al, Science, 265: 1225-7 (1994)); and T-cell receptor antibodies (EP 340,109) such as T10B9. Non-limiting examples of agents also include the following: budenoside; epidermal growth factor; aminosalicylates; metronidazole; mesalamine; olsalazine; balsalazide; antioxidants; thromboxane inhibitors; IL-1 receptor antagonists; anti-IL-1 monoclonal antibodies; growth factors; elastase inhibitors; pyridinylimidazole compounds; TNF antagonists; IL-4, IL-10, IL-13 and/or TGFβ cytokines or agonists thereof (e.g., agonist antibodies); IL-11, glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TPIO; T Cell Sciences, Inc.); slow-release mesalazine; antagonists of platelet activating factor (PAF); ciprofloxacin; and lignocaine. Examples of agents for UC are sulfasalazine and related salicylate-containing drugs for mild cases and corticosteroid drugs in severe cases. Exemplary therapeutic agents that may be used for the treatment of a liver disease or disorder (e.g., liver fibrosis or NASH) include elafibranor (GFT 505; Genfit Corp.), obeticholic acid (OCA; Intercept Pharmaceuticals, Inc.), cenicriviroc (CVC; Allergan plc), selonsertib (formerly GS-4997; Gilead Sciences, Inc.), an anti-LOXL2 antibody (simtuzumab (formerly GS 6624; Gilead Sciences, Inc.)), GS-9450 (Gilead Sciences, Inc.), GS-9674 (Gilead Sciences, Inc.), GS-0976 (formerly NDI-010976; Gilead Sciences, Inc.), Emricasan (Conatus Pharmaceuticals, Inc.), Arachidyl-amido cholanoic acid (Aramchol™; Galmed Pharmaceuticals Ltd.), AKN-083 (Allergan plc (Akarna Therapeutics Ltd.)), TGFTX4 (Genfit Corp.), TGFTX5 (Genfit Corp.), TGFTX1 (Genfit Corp.), a RoRy agonist (e.g., LYC-55716; Lycera Corp.), an ileal bile acid transporter (iBAT) inhibitor (e.g., elobixibat, Albireo Pharma, Inc.; GSK2330672, GlaxoSmithKline plc; and A4250; Albireo Pharma, Inc.), stem cells, a CCR2 inhibitor, bardoxolone methyl (Reata Pharmaceuticals, Inc.), a bone morphogenetic protein-7 (BMP-7) mimetic (e.g., THR-123 (see, e.g., Sugimoto et al. (2012) Nature Medicine 18: 396-404)), an anti-TGF-β antibody (e.g., fresolimumab; see also U.S. Pat. Nos. 7,527,791 and 8,383,780, incorporated herein by reference), pirfenidone (Esbriet®, Genentech USA Inc.), an anti-integrin αvβ6 antibody, an anti-connective tissue growth factor (CTGF) antibody (e.g., pamrevlumab; FibroGen Inc.), pentoxifylline, vascular endothelial growth factor (VEGF), a renin angiotensin aldosterone system (RAAS) inhibitor (e.g., a rennin inhibitor (e.g. pepstatin, CGP2928, aliskiren), or an ACE inhibitor (e.g., captopril, zofenopril, enalapril, ramipril, quinapril, perindopril, lisinopril, benazepril, imidapril, fosinopril, and trandolapril)), thrombospondin, a statin, bardoxolone, a PDES inhibitor (e.g., sidenafil, vardenafil, and tadalafil), a NADPH oxidase-1 (NOX1) inhibitor (see, e.g., U.S. Publication No. 2011/0178082, incorporated herein by reference), a NADPH oxidase-4 (NOX4) inhibitor (see, e.g., U.S. Publication No. 2014/0323500, incorporated herein by reference), an $ET_A$ antagonist (e.g., sitaxentan, ambrisentan, atrasentan, BQ-123, and zibotentan), nintedanib (Boehringer Ingelheim), INT-767 (Intercept Pharmaceuticals, Inc.), VBY-376 (Virobay Inc.), PF-04634817 (Pfizer), EXC 001 (Pfizer), GM-CT-01 (Galectin Therapeutics), GCS-100 (La Jolla Pharmaceuticals), hepatocyte growth factor mimetic (Refanalin®; Angion Biomedica), SAR156597 (Sanofi), tralokinumab (AstraZeneca), pomalidomide (Celgene), STX-100 (Biogen IDEC), CC-930 (Celgene), anti-miR-21 (Regulus Therapeutics), PRM-151 (Promedior), BOT191 (BiOrion), Palomid 529 (Paloma Pharamaceuticals), IMD1041 (IMMD, Japan), serelaxin (Novartis), PEG-relaxin (Ambrx and Bristol-Myers Squibb), ANG-4011 (Angion Biomedica), FT011 (Fibrotech Therapeutics), pirfenidone (InterMune), F351 (pirfenidone derivative (GNI Pharma), vitamin E (e.g., tocotrienol (alpha, beta, gamma, and delta) and tocopherol (alpha, beta, gamma, and delta)), pentoxifylline, an insulin sensitizer (e.g., rosiglitazone and pioglitazone), cathepsin B inhibitor R-3020, etanercept and biosimilars thereof, peptides that block the activation of Fas (see, e.g., International Publication No. WO 2005/117940, incorporated herein by reference), caspase inhibitor VX-166, caspase inhibitor Z-VAD-fmk, fasudil, belnacasan (VX-765), and pralnacasan (VX-740).

In some embodiments, a drug is a GLP-1 analog.

In certain embodiments, a drug is an opioid.

In some embodiments, a drug is a parathyroid hormone.

In certain embodiments, a drug is human growth hormone.

In some embodiments, a drug is a somatostatin.

In certain embodiments, a drug is a long lasting insulin.

In some embodiments, a drug is a cancer drug that boosts the immune system.

In certain embodiments, a drug provides long-term, HIV Pre-exposure prophylaxis, or PrEP. An example of such a drug is Truvada® (emtricitabine/tenofovir disoproxil fumarate).

In certain embodiments, a drug is Tacrolimus. Tacrolimus (also known as FK-506 or fujimycin, Prograf®, Advagraf®, and Protopic®) is an immunosuppressive drug that is frequently used after allogeneic organ transplant to lower the risk of organ rejection by inhibiting the production of interleukin-2, a molecule that promotes the development and proliferation of T cells. Tacrolimus has been used to suppress the inflammation associated with ulcerative colitis (UC), a form of inflammatory bowel disease.

In some embodiments, a drug is an analgesic drug, an antibiotic drug, an anticoagulant drug, an antidepressant drug, an anticancer drug, an antiepileptic drug, an anti-inflammatory drug (nonsteroidal anti-inflammatory drug, steroidal anti-inflammatory drug), an antipsychotic drug, an antiviral drug, a sedative drug, and/or an antidiabetic drug. In certain embodiments, a drug is a cyclooxygenase inhibitor, a 5-lipoxygenase inhibitor, or a leukotriene receptor antagonist. In some embodiments, a drug is Ibuprofen. In certain embodiments, a drug is Acetominophen. Detection and quantification of the latter two drugs based on spectral data are described in detail in Example 11 and Example 12.

In certain embodiments, a drug is a diuretic drug, a cholinergic drug, a dopaminergic drug, a GABAergic drug, and/or a serotonergic drug.

In some embodiments a drug is a 5-Alpha-reductase inhibitor, an angiotensin II receptor antagonist, an ACE inhibitor (e.g., Lisinopril), an alpha-adrenergic agonist, a beta blocker, a dopamine agonist, a dopamine antagonist, an incretin mimetic, a nonsteroidal anti-inflammatory drug—cyclooxygenase inhibitor, a proton-pump inhibitor, a renin inhibitor, a selective glucocorticoid receptor modulator, a selective serotonin reuptake inhibitor, and/or a statin—HMG-CoA reductase inhibitor. Detection and quantification of Lisinopril based on spectral data are described in detail in Example 11.

In certain embodiments, a drug is a β-lectam antibiotic, a benzodiazepine, a cardiac glycoside, a fibrate or a thiazide diuretic.

In some embodiments, the analyte is an alkaloid. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

In some embodiments, the analyte is a steroid selected from the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

In some embodiments, the analyte is a lactam having from 5 to 6 annular members selected from barbituates, e.g., phenobarbital and secobarbital, diphenylhydantonin, primidone, ethosuximide, and metabolites thereof.

In some embodiments, the analyte is an aminoalkylbenzene, with alkyl of from 2 to 3 carbon atoms, selected from the amphetamines; catecholamines, which includes ephedrine, L-dopa, epinephrine; narceine; papaverine; and metabolites thereof.

In some embodiments, the analyte is a benzheterocyclic selected from oxazepam, chlorpromazine, tegretol, their derivatives and metabolites, the heterocyclic rings being azepines, diazepines and phenothiazines.

In some embodiments, the analyte is a purine selected from theophylline, caffeine, their metabolites and derivatives.

In some embodiments, the analyte is marijuana, cannabinol or tetrahydrocannabinol.

In some embodiments, the analyte is a vitamin such as vitamin A, vitamin B, e.g. vitamin $B_{12}$, vitamin C, vitamin D, vitamin E and vitamin K, folic acid, thiamine.

In some embodiments, the analyte is selected from prostaglandins, which differ by the degree and sites of hydroxylation and unsaturation.

In some embodiments, the analyte is a tricyclic antidepressant selected from imipramine, dismethylimipramine, amitriptyline, nortriptyline, protriptyline, trimipramine, chlomipramine, doxepine, and desmethyldoxepin.

In some embodiments, the analyte is selected from antineoplastics, including methotrexate.

In some embodiments, the analyte is an antibiotic as described herein, including, but not limited to, penicillin, chloromycetin, actinomycetin, tetracycline, terramycin, and metabolites and derivatives.

In some embodiments, the analyte is a nucleoside or nucleotide selected from ATP, NAD, FMN, adenosine, guanosine, thymidine, and cytidine with their appropriate sugar and phosphate substituents.

In some embodiments, the analyte is selected from methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

In some embodiments, the analyte is a metabolite related to a diseased state. Such metabolites include, but are not limited to spermine, galactose, phenylpyruvic acid, and porphyrin Type 1.

In some embodiments, the analyte is an aminoglycoside, such as gentamycin, kanamycin, tobramycin, or amikacin.

Exemplary additional therapeutic agents are provided below and include exemplary drug classes, and exemplary embodiments for each, that may be detected and analyzed using the methods herein.

1. TNF Inhibitors

The term "TNFα inhibitor" refers to an agent which directly or indirectly inhibits, impairs, reduces, down-regulates, or blocks TNFα activity and/or expression. In some embodiments, a TNFα inhibitor is an inhibitory nucleic acid, an antibody or an antigen-binding fragment thereof, a fusion protein, a soluble TNFα receptor (a soluble TNFR1 or a soluble TNFR2), or a small molecule TNFα antagonist. In some embodiments, the inhibitory nucleic acid is a ribozyme, small hairpin RNA, a small interfering RNA, an antisense nucleic acid, or an aptamer.

Exemplary TNFα inhibitors that directly inhibit, impair, reduce, down-regulate, or block TNFα activity and/or expression can, e.g., inhibit or reduce binding of TNFα to its receptor (TNFR1 and/or TNFR2) and/or inhibit or decrease the expression level of TNFα or a receptor of TNFα (TNFR1 or TNFR2) in a cell (e.g., a mammalian cell). Non-limiting examples of TNFα inhibitors that directly inhibit, impair, reduce, down-regulate, or block TNFα activity and/or expression include inhibitory nucleic acids (e.g., any of the examples of inhibitory nucleic acids described herein), an antibody or fragment thereof, a fusion protein, a soluble TNFα receptor (e.g., a soluble TNFR1 or soluble TNFR2), and a small molecule TNFα antagonist.

Exemplary TNFα inhibitors that can indirectly inhibit, impair, reduce, down-regulate, or block TNFα activity and/ or expression can, e.g., inhibit or decrease the level of downstream signaling of a TNFα receptor (e.g., TNFR1 or TNFR2) in a mammalian cell (e.g., decrease the level and/or activity of one or more of the following signaling proteins: TRADD, TRAF2, MEKK1/4, MEKK4/7, JNK, AP-1, ASK1, RIP, MEKK 3/6, MAPK, NIK, IKK, and NF-κB in a mammalian cell), and/or decrease the level of TNFα-induced gene expression in a mammalian cell (e.g., decrease the transcription of genes regulated by, e.g., one or more transcription factors selected from the group of NF-κB, c-Jun, and ATF2). A description of downstream signaling of a TNFα receptor is provided in Wajant et al., *Cell Death Differentiation* 10:45-65, 2003 (incorporated herein by reference). For example, such indirect TNFα inhibitors can be an inhibitory nucleic acid that targets (decreases the expression) a signaling component downstream of a TNFα receptor (e.g., any one or more of the signaling components downstream of a TNFα receptor described herein or known in the art), a TNFα-induced gene (e.g., any TNFα-induced gene known in the art), or a transcription factor selected from the group of NF-κB, c-Jun, and ATF2.

In other examples, such indirect TNFα inhibitors can be a small molecule inhibitor of a signaling component downstream of a TNFα receptor (e.g., any of the signaling components downstream of a TNFα receptor described herein or known in the art), a small molecule inhibitor of a protein encoded by a TNFα-induced gene (e.g., any protein encoded by a TNFα-induced gene known in the art), and a small molecule inhibitor of a transcription factor selected from the group of NF-κB, c-Jun, and ATF2.

In other embodiments, TNFα inhibitors that can indirectly inhibit, impair, reduce, down-regulate, or block one or more components in a mammalian cell (e.g., a macrophage, a CD4+ lymphocyte, a NK cell, a neutrophil, a mast cell, a eosinophil, or a neuron) that are involved in the signaling pathway that results in TNFα mRNA transcription, TNFα mRNA stabilization, and TNFα mRNA translation (e.g., one or more components selected from the group of CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, and MK2). For example, such indirect TNFα inhibitors can be an inhibitory nucleic acid that targets (decreases the expression) of a component in a mammalian cell that is involved in the signaling pathway that results in TNFα mRNA transcription, TNFα mRNA stabilization, and TNFα mRNA translation (e.g., a component selected from the group of CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, and MK2). In other examples, an indirect TNFα inhibitors is a small molecule inhibitor of a component in a mammalian cell that is involved in the signaling pathway that results in TNFα mRNA transcription, TNFα mRNA stabilization, and TNFα mRNA translation (e.g., a component selected from the group of CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, and MK2).

Inhibitory Nucleic Acids

Inhibitory nucleic acids that can decrease the expression of TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, MEK3/6, p38, PKR, TTP, or MK2 mRNA expression in a mammalian cell include antisense nucleic acid molecules, i.e., nucleic acid molecules whose nucleotide sequence is complementary to all or part of a TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2 mRNA.

An antisense nucleic acid molecule can be complementary to all or part of a non-coding region of the coding strand of a nucleotide sequence encoding a TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2 protein. Non-coding regions (5' and 3' untranslated regions) are the 5' and 3' sequences that flank the coding region in a gene and are not translated into amino acids.

Another example of an inhibitory nucleic acid is a ribozyme that has specificity for a nucleic acid encoding a TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2 protein (e.g., specificity for a TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2 mRNA.

An inhibitory nucleic acid can also be a nucleic acid molecule that forms triple helical structures. For example, expression of a TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2 polypeptide can be inhibited by targeting nucleotide sequences complementary to the regulatory region of the gene encoding the TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

In some embodiments, a TNFα inhibitor can be a siRNA molecule used to decrease expression of a TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2 mRNA.

Exemplary TNFα inhibitors that are inhibitory nucleic acids targeting TNFα include, e.g., antisense DNA (e.g., Myers et al., *J Pharmacol Exp Ther.* 304(1):411-424, 2003; Wasmuth et al., Invest. Opthalmol. Vis. Sci, 2003; Dong et al., *J. Orthop. Res.* 26(8):1114-1120, 2008; U.S. Patent Application Serial Nos. 2003/0083275, 2003/0022848, and 2004/0770970; ISIS 104838; U.S. Pat. Nos. 6,180,403, 6,080,580, and 6,228,642; Kobzik et al., Inhibition of TNF Synthesis by Antisense Oligonucleotides, in Manual of Antisense Methodology, Kluwer Academic Publishers, Vol. 4, pp. 107-123, 1999; Taylor et al., *Antisense Nucleic Acid Drug Develop.* 8(3):199-205, 1998; Mayne et al., Stroke 32:240-248, 2001; Mochizuki et al., *J. Controlled Release* 151(2):155-161, 2011; Dong et al., *J. Orthopaedic Res.* 26(8):1114-1120, 2008; Dong et al., *Pharm. Res.* 28(6): 1349-1356, 2011; and Pampfer et al., *Biol. Reproduction* 52(6):1316-1326, 1995), antisense RNA, short interfering RNA (siRNA) (e.g., Taishi et al., *Brain Research* 1156:125-132, 2007; Presumey et al., *Eur. J. Pharm. Biopharm.* 82(3):457-467, 2012; Laroui et al., *J. Controlled Release* 186:41-53, 2014; D'Amore et al., *Int. J. Immunopathology Pharmacol.* 21:1045-1047, 2008; Choi et al., *J. Dermatol. Sci.* 52:87-97, 2008; Qin et al., *Artificial Organs* 35:706-714, 2011; McCarthy et al., *J. Controlled Release* 168: 28-34, 2013; Khoury et al., *Current Opin. Mol. Therapeutics* 9(5):483-489, 2007; Lu et al., *RNA Interference Technology From Basic Science to Drug Development* 303, 2005; Xie et al., *PharmaGenomics* 4(6):28-34, 2004; Aldawsari et al., *Current Pharmaceutical Design* 21(31):4594-4605, 2015; Zheng et al., *Arch. Med. Sci.* 11:1296-1302, 2015; Peng et al., *Chinese J. Surgery* 47(5):377-380, 2009; Aldayel et al., *Molecular Therapy. Nucleic Acids* 5(7):e340, 2016; Bai et al., *Current Drug Targets* 16:1531-1539, 2015; U.S. Patent Application Publications Nos. 2008/0097091, 2009/0306356, and 2005/0227935; and WO 14/168264), short hairpin RNA (shRNA) (e.g., Jakobsen et al., *Mol. Ther.* 17(10): 1743-1753, 2009; Ogawa et al., *PLoS One* 9(3): e92073, 2014; Ding et al., *Bone Joint* 94-6(Suppl. 11):44, 2014; and Hernandez-Alejandro et al., *J. Surgical Res.* 176(2):614-620, 2012), and microRNAs (see, e.g., WO 15/26249). In some embodiments, the inhibitory nucleic acid blocks pre-mRNA splicing of TNFα (e.g., Chiu et al., *Mol. Pharmacol.* 71(6): 1640-1645, 2007).

In some embodiments, the inhibitory nucleic acid, e.g., an aptamer (e.g., Orava et al., *ACS Chem Biol.* 2013; 8(1): 170-178, 2013), can block the binding of a TNFα protein with its receptor (TNFR1 and/or TNFR2).

In some embodiments, the inhibitory nucleic acid can down-regulate the expression of a TNFα-induced downstream mediator (e.g., TRADD, TRAF2, MEKK1/4, MEKK4/7, JNK, AP-1, ASK1, RIP, MEKK 3/6, MAPK, NIK, IKK, NF-κB, p38, JNK, IκB-α, or CCL2). Further teachings of downstream TNFα-induced mediators can be found in, e.g., Schwamborn et al., *BMC Genomics* 4:46, 2003; and Zhou et al., *Oncogene* 22: 2034-2044, 2003, incorporated by reference herein. Additional aspects of inhibitory nucleic acids are described in Aagaard et al., *Adv. Drug Delivery Rev.* 59(2):75-86, 2007, and Burnett et al., *Biotechnol. J.* 6(9):1130-1146, 2011.

In certain embodiments, the inhibitory nucleic acid targets a nucleic acid encoding a TNFα, TNFR1, TNFR2, TRADD, TRAF2, MEKK1/4, MEKK4/7, JNK, AP-1, ASK1, RIP, MEKK 3/6, MAPK, NIK, IKK, NF-κB, CD14, MyD88, IRAK, lipopolysaccharide binding protein (LBP), TRAF6, ras, raf, MEK1/2, ERK1/2, NIK, IKK, IκB, NF-κB, rac, MEK4/7, JNK, c-jun, MEK3/6, p38, PKR, TTP, or MK2.

Antibodies

In some embodiments, the TNFα inhibitor is an antibody or an antigen-binding fragment thereof (e.g., a Fab or a scFv). In some embodiments, an antibody or antigen-binding fragment described herein binds specifically to any one of TNFα, TNFR1, or TNFR2. In some embodiments, an antibody or antigen-binding fragment of an antibody described herein can bind specifically to TNFα. In some embodiments, an antibody or antigen-binding fragment of an antibody described herein can bind specifically to a TNFα receptor (TNFR1 or TNFR2).

Non-limiting examples of TNF inhibitors that are antibodies that specifically bind to TNFα are described in Elliott et al., *Lancet* 1994; 344: 1125-1127, 1994; Rankin et al., *Br. J. Rheumatol.* 2:334-342, 1995; Butler et al., *Eur. Cytokine Network* 6(4):225-230, 1994; Lorenz et al., *J. Immunol.* 156(4):1646-1653, 1996; Hinshaw et al., *Circulatory Shock* 30(3):279-292, 1990; Wanner et al., *Shock* 11(6):391-395, 1999; Bongartz et al., *JAMA* 295(19):2275-2285, 2006; Knight et al., *Molecular Immunol.* 30(16):1443-1453, 1993; Feldman, *Nature Reviews Immunol.* 2(5):364-371, 2002; Taylor et al., *Nature Reviews Rheumatol.* 5(10):578-582, 2009; Garces et al., *Annals Rheumatic Dis.* 72(12):1947-1955, 2013; Palladino et al., *Nature Rev. Drug Discovery* 2(9):736-746, 2003; Sandborn et al., *Inflammatory Bowel Diseases* 5(2):119-133, 1999; Atzeni et al., *Autoimmunity Reviews* 12(7):703-708, 2013; Maini et al., *Immunol. Rev.* 144(1):195-223, 1995; Ordas et al., *Clin. Pharmacol. Therapeutics* 91(4):635-646, 2012; Cohen et al., *Canadian J. Gastroenterol. Hepatol.* 15(6):376-384, 2001; Feldmann et al., *Ann. Rev. Immunol.* 19(1):163-196, 2001; Ben-Horin et al., *Autoimmunity Rev.* 13(1):24-30, 2014; and U.S. Pat. Nos. 6,090,382; 6,258,562; and 6,509,015).

In certain embodiments, the TNFα inhibitor can include or is infliximab (Remicade™), CDP571, CDP 870, golimumab (Golimumab™), adalimumab (Humira™), or certolizumab pegol (Cimzia™). In certain embodiments, the TNFα inhibitor can be a TNFα inhibitor biosimilar. Examples of approved and late-phase TNFα inhibitor biosimilars include, but are not limited to, infliximab biosimilars such as Remsima™ and Inflectra® (CT-P13) from Celltrion/Pfizer, GS071 from Aprogen, Flixabi™ (SB2) from Samsung Bioepis, PF-06438179 from Pfizer/Sandoz, NI-071 from Nichi-Iko Pharmaceutical Co., and ABP 710 from Amgen; adalimumab biosimilars such as Exemptia™ (ZRC3197) from Zydus Cadila, India, Solymbic® and Amgevita® (ABP 501) from Amgen, Imraldi (SB5) from Samsung Bioepis, GP-2017 from Sandoz, Switzerland, ONS-3010 from Oncobiologics, M923/Viropro, U.S.A., from Momenta Pharmaceuticals/Baxalta (Baxter spinoff USA), PF-06410293 from Pfizer, BMO-2 or MYL-1401-A from Biocon/Mylan, CHS-1420 from Coherus, FKB327 from Fujifilm/Kyowa Hakko Kirin (Fujifilm Kyowa Kirin Biologics), and Cyltezo (BI 695501) from Boehringer Ingelheim, CT-P17 from Celltrion, BAX 923 from Baxalta (now a part of Shire), MSB11022 from Fresenius Kabi (bought from Merck kGaA (Merck Group) in 2017), LBAL from LG Life Sciences/Mochida Pharmaceutical, South Korea/Japan, PBP1502 from Prestige Biopharma, Adfrar from Torrent Pharmaceuticals, India, a biosimilar of adalimumab in development by Adello Biologics, a biosimilar of adalimumab in development by AET Biotech/BioXpress Therapeutics, Germany/Switzerland, a biosimilar of adalimumab from mAbxience, Spain, a biosimilar of adalimumab in development by PlantForm, Canada; and etanercept biosimilars such as Erelzi™ from Sandoz/Novartis, Brenzys™ (SB4) from Samsung Bioepis, GP2015 from Sandoz, TuNEX® from Mycenax, LBEC0101 from LG Life, and CHS-0214 from Coherus.

In some embodiments, a biosimilar is an antibody or antigen-binding fragment thereof that has a light chain that has the same primary amino acid sequence as compared to a reference antibody (e.g., adalimumab) and a heavy chain that has the same primary amino acid sequence as compared to the reference antibody. In some examples, a biosimilar is an antibody or antigen-binding fragment thereof that has a light chain that includes the same light chain variable domain sequence as a reference antibody (e.g., adalimumab) and a heavy chain that includes the same heavy chain variable domain sequence as a reference antibody. In some embodiments, a biosimilar can have a similar glycosylation pattern as compared to the reference antibody (e.g., adalimumab). In other embodiments, a biosimilar can have a different glycosylation pattern as compared to the reference antibody (e.g., adalimumab).

Changes in the N-linked glycosylation profile of a biosimilar as compared to a reference antibody (e.g., adalimumab) can be detected using 2-anthranilic acid (AA)-derivatization and normal phase liquid chromatography with fluorescence detection, as generally described in Kamoda et al., *J. Chromatography J.* 1133:332-339, 2006. For example, a biosimilar can have changes in one or more (e.g., two, three, four, five, six, seven, eight, nine, ten, or eleven) of the following types of N-glycosylation as compared to the reference antibody (e.g., adalimumab): neutrally-charged oligosaccharides; monosialylated fucose-containing oligosaccharides; monosialylated oligosaccharides; bisialylated fucose-containing oligosaccharide; bisialylated oligosaccharides; triantennary, trisiaylated oligosaccharides of form 1; triantennary, trisialylated oligosaccharides of form 2; mannose-6-phosphate oligosaccharides; monophosphorylated oligosaccharides; tetrasialylated oligosaccharides; monosialylated and monophosphorylated oligosaccharides; and bis-mannose-6-phosphate oligosaccharides.

In some embodiments, the biosimilar can have a change in one, two, or three of: the percentage of species having one C-terminal lysine, the percentage of species having two C-terminal lysines, and the percentage of species having three C-terminal lysines as compared to the reference antibody (e.g., adalimumab).

In some embodiments, the biosimilar can have a change in the level of one, two, or three of acidic species, neutral species, and basic species in the composition as compared to the reference antibody (e.g., adalimumab).

In some embodiments, the biosimilar can have a change in the level of sulfation as compared to the reference antibody.

In some embodiments, the TNFα inhibitor can be SAR252067 (e.g., a monoclonal antibody that specifically binds to TNFSF14, described in U.S. Patent Application Publication No. 2013/0315913) or MDGN-002 (described in U.S. Patent Application Publication No. 2015/0337046). In some embodiments, the TNFα inhibitor can be PF-06480605, which binds specifically to TNFSF15 (e.g., described in U.S. Patent Application Publication No. 2015/0132311). Additional examples of TNFα inhibitors include DLCX105 (described in Tsianakas et al., Exp. Dermatol. 25:428-433, 2016) and PF-06480605, which binds specifically to TNFSF15 (described in U.S. Patent Application Publication No. 2015/0132311).

Fusion Proteins

In some embodiments, the TNFα inhibitory agent is a fusion protein (e.g., an extracellular domain of a TNFR fused to a partner peptide, e.g., an Fc region of an immunoglobulin, e.g., human IgG) (see, e.g., Peppel et al., *J. Exp. Med.* 174(6):1483-1489, 1991; Deeg et al., *Leukemia* 16(2): 162, 2002) or a soluble TNFR (e.g., TNFR1 or TNFR2) that binds specifically to TNFα. In some embodiments, the TNFα inhibitor includes or is etanercept (Enbrel™) (see, e.g., WO 91/03553 and WO 09/406,476, incorporated by reference herein). In some embodiments, the TNFα inhibitor includes or is r-TBP-I (e.g., Gradstein et al., *J. Acquir. Immune Defic. Syndr.* 26(2): 111-117, 2001). In some embodiments, the TNFα inhibitor includes or is a soluble TNFα receptor (e.g., Watt et al., *J Leukoc Biol.* 66(6):1005-1013, 1999; Tsao et al., *Eur Respir J.* 14(3):490-495, 1999; Kozak et al., *Am. J. Physiol. Reg. Integrative Comparative Physiol.* 269(1):R23-R29, 1995; Mohler et al., *J. Immunol.* 151(3):1548-1561, 1993; Nophar et al., *EMBO J.* 9(10): 3269, 1990; Bjornberg et al., *Lymphokine Cytokine Res.* 13(3):203-211, 1994; Piguet et al., *Eur. Respiratory J.* 7(3):515-518, 1994; and Gray et al., *Proc. Natl. Acad. Sci. U.S.A.* 87(19):7380-7384, 1990).

Small Molecules

In some embodiments, the TNFα inhibitor is a small molecule. In some embodiments, the TNFα inhibitor is C87 (Ma et al., *J. Biol. Chem.* 289(18):12457-66, 2014). In some embodiments, the small molecule is LMP-420 (e.g., Haraguchi et al., *AIDS Res. Ther.* 3:8, 2006). In some embodiments, the small molecule is a tumor necrosis factor-converting enzyme (TACE) inhibitor (e.g., Moss et al., *Nature Clinical Practice Rheumatology* 4: 300-309, 2008). In some embodiments, the TACE inhibitor is TMI-005 and BMS-561392. Additional examples of small molecule inhibitors are described in, e.g., He et al., *Science* 310(5750):1022-1025, 2005.

In some examples, the TNFα inhibitor is a small molecule that inhibits the activity of one of TRADD, TRAF2, MEKK1/4, MEKK4/7, JNK, AP-1, ASK1, RIP, MEKK 3/6, MAPK, NIK, IKK, and NF-κB, in a mammalian cell.

In some examples, the TNFα inhibitor is a small molecule that inhibits the activity of one of CD14, MyD88 (see, e.g., Olson et al., *Scientific Reports* 5:14246, 2015), IRAK (Chaudhary et al., *J. Med. Chem.* 58(1):96-110, 2015), lipopolysaccharide binding protein (LBP) (see, e.g., U.S. Pat. No. 5,705,398), TRAF6 (e.g., 3-[(2,5-Dimethylphenyl) amino]-1-phenyl-2-propen-1-one), ras (e.g., Baker et al., *Nature* 497:577-578, 2013), raf (e.g., vemurafenib (PLX4032, RG7204), sorafenib tosylate, PLX-4720, dabrafenib (GSK2118436), GDC-0879, RAF265 (CHIR-265), AZ 628, NVP-BHG712, SB590885, ZM 336372, sorafenib, GW5074, TAK-632, CEP-32496, encorafenib (LGX818), CCT196969, LY3009120, RO5126766 (CH5126766), PLX7904, and MLN2480), MEK1/2 (e.g., Facciorusso et al., *Expert Review Gastroenterol. Hepatol.* 9:993-1003, 2015), ERK1/2 (e.g., Mandal et al., *Oncogene* 35:2547-2561, 2016), NIK (e.g., Mortier et al., *Bioorg. Med. Chem. Lett.* 20:4515-4520, 2010), IKK (e.g., Reilly et al., *Nature Med.* 19:313-321, 2013), IκB (e.g., Suzuki et al., *Expert. Opin. Invest. Drugs* 20:395-405, 2011), NF-κB (e.g., Gupta et al., *Biochim. Biophys. Acta* 1799(10-12):775-787, 2010), rac (e.g., U.S. Pat. No. 9,278,956), MEK4/7, JNK (e.g., AEG 3482, BI 78D3, CEP 1347, c-JUN peptide, IQ 1S, JIP-1 (153-163), SP600125, SU 3327, and TCS JNK6o), c-jun (e.g., AEG 3482, BI 78D3, CEP 1347, c-JUN peptide, IQ 1S, JIP-1 (153-163), SP600125, SU 3327, and TCS JNK6o), MEK3/6 (e.g., Akinleye et al., *J. Hematol. Oncol.* 6:27, 2013), p38 (e.g., AL 8697, AMG 548, BIRB 796, CMPD-1, DBM 1285 dihydrochloride, EO 1428, JX 401, ML 3403, Org 48762-0, PH 797804, RWJ 67657, SB 202190, SB 203580, SB 239063, SB 706504, SCIO 469, SKF 86002, SX 011, TA 01, TA 02, TAK 715, VX 702, and VX 745), PKR (e.g., 2-aminopurine or CAS 608512-97-6), TTP (e.g., CAS 329907-28-0), and MK2 (PF 3644022 and PHA 767491).

2. IL-12/IL-23 Inhibitors

The term "IL-12/IL-23 inhibitors" refers to an agent which decreases IL-12 or IL-23 expression and/or the ability of IL-12 to bind to an IL-12 receptor or the ability of IL-23 to bind to an IL-23 receptor. IL-12 is a heterodimeric cytokine that includes both IL-12A (p35) and IL-12B (p40) polypeptides. IL-23 is a heterodimeric cytokine that includes both IL-23 (p19) and IL-12B (p40) polypeptides. The receptor for IL-12 is a heterodimeric receptor includes IL-12R β1 and IL-12R β2. The receptor for IL-23 receptor is a heterodimeric receptor that includes both IL-12R β1 and IL-23R.

In some embodiments, the IL-12/IL-23 inhibitor can decrease the binding of IL-12 to the receptor for IL-12. In some embodiments, the IL-12/IL-23 inhibitor can decrease the binding of IL-23 to the receptor for IL-23. In some embodiments, the IL-12/IL-23 inhibitor decreases the expression of IL-12 or IL-23. In some embodiments, the IL-12/IL-23 inhibitor decreases the expression of a receptor for IL-12. In some embodiments, the IL-12/IL-23 inhibitor decreases the expression of a receptor for IL-23.

In some embodiments, the IL-12/IL-23 inhibitory agent targets IL-12B (p40) subunit. In some embodiments, the IL-12/IL-23 inhibitory agent targets IL-12A (p35). In some embodiments, the IL-12/IL-23 inhibitory agent targets IL-23 (p19). In some embodiments, the IL-12/IL-23 inhibitory agent targets the receptor for IL-12 (one or both of IL-12R β1 or IL-12R β2). In some embodiments, the IL-12/IL-23 inhibitory agent targets the receptor for IL-23 (one or both of IL-12R β1 and IL-23R).

In some embodiments, an IL-12/IL-23 inhibitor can be an inhibitory nucleic acid. In some embodiments, the inhibitory nucleic acid can be an antisense nucleic acid, a ribozyme, and a small interfering RNA (siRNA).

Inhibitory nucleic acids that can decrease the expression of IL-12A (p35), IL-12B (p40), IL-23 (p19), IL-12R β1, IL-12R β2, or IL-23R mRNA expression in a mammalian cell include antisense nucleic acid molecules, i.e., nucleic acid molecules whose nucleotide sequence is complementary to all or part of an IL-12A (p35), IL-12B (p40), IL-23 (p19), IL-12R β1, IL-12R β2, or IL-23R mRNA. An antisense nucleic acid molecule can be complementary to all or part of a non-coding region of the coding strand of a nucleotide sequence encoding an IL-12A (p35), IL-12B (p40), IL-23 (p19), IL-12R β1, IL-12R β2, or IL-23R protein. Non-coding regions (5' and 3' untranslated regions) are the 5' and 3' sequences that flank the coding region in a gene and are not translated into amino acids.

Another example of an inhibitory nucleic acid is a ribozyme that has specificity for a nucleic acid encoding an IL-12A (p35), IL-12B (p40), IL-23 (p19), IL-12R β1, IL-12R β2, or IL-23R protein (e.g., specificity for an IL-12A (p35), IL-12B (p40), IL-23 (p19), IL-12R β1, IL-12R β2, or IL-23R mRNA).

An inhibitor nucleic acid can also be a nucleic acid molecule that forms triple helical structures. For example, expression of an IL-12A (p35), IL-12B (p40), IL-23 (p19), IL-12R β1, IL-12R β2, or IL-23R protein can be inhibited by targeting nucleotide sequences complementary to the regulatory region of the gene encoding the IL-12A (p35), IL-12B (p40), IL-23 (p19), IL-12R β1, IL-12R β2, or IL-23R protein (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

Other examples of a IL-12/IL-23 inhibitor include siRNA that decrease the level of IL-12A (p35), IL-12B (p40), IL-23 (p19), IL-12R β1, IL-12R β2, or IL-23R mRNA.

Non-limiting examples of siRNAs targeting IL-12A (p35), IL-12B (p40), IL-23 (p19), IL-12R β1, IL-12R β2, or IL-23R are described in Tan et al., *J. Alzheimers Dis.* 38(3): 633-646, 2014; Niimi et al., *J. Neuroimmunol.* 254(1-2):39-45, 2013. Non-limiting examples of short hairpin RNA (shRNA) targeting IL-12A (p35), IL-12B (p40), IL-23 (p19), IL-12R β1, IL-12R β2, or IL-23R are described in Bak et al., *BMC Dermatol.* 11:5, 2011.

Non-limiting examples of inhibitory nucleic acids are microRNAs (e.g., microRNA-29 (Brain et al., *Immunity* 39(3):521-536, 2013), miR-10a (Xue et al., *J. Immunol.* 187(11):5879-5886, 2011), microRNA-155 (Podsiad et al., *Am. J. Physiol. Lung Cell Mol. Physiol.* 310(5):L465-75, 2016).

Antibodies

In some embodiments, the IL-12/IL-23 inhibitor is an antibody or an antigen-binding fragment thereof (e.g., a Fab or a scFv). In some embodiments, an antibody or antigen-binding fragment described herein binds specifically to any one of IL-12A (p35), IL-12B (p40), IL-23 (p19), IL-12R β1, IL-12R β2, or IL-23R, or a combination thereof.

In some embodiments, the antibody is ustekinumab (ONTO 1275, Stelara®) or a variant thereof (Krueger et al., *N. Engl. J. Med.* 356(6):580-592, 2007; Kauffman et al., *J. Invest. Dermatol.* 123(6):1037-1044, 2004; Gottlieb et al., *Curr. Med. Res. Opin.* 23(5):1081-1092, 2007; Leonardi et al., *Lancet* 371(9625):1665-1674, 2008; Papp et al., *Lancet* 371(9625):1675-1684, 2008). In some embodiments, the antibody is briakinumab (ABT-874, J-695) or a variant thereof (Gordon et al., *J. Invest. Dermatol.* 132(2):304-314, 2012; Kimball et al., *Arch Dermatol.* 144(2): 200-207, 2008).

In some embodiments, the antibody is guselkumab (ONTO-1959) (Callis-Duffin et al., *J. Am. Acad. Dermatol.* 70(5 Suppl 1), 2014); AB162 (Sofen et al., *J. Allergy Clin. Immunol.* 133: 1032-40, 2014); tildrakizumab (MK-3222, SCH900222) (Papp et al. (2015) *Br. J. Dermatol.* 2015); Langley et al., Oral Presentation at: American Academy of Dermatology, March 21-25, Denver Colo., 2014); AMG 139 (MEDI2070, brazikumab) (Gomollon, *Gastroenterol. Hepatol.* 38(Suppl. 1):13-19, 2015; Kock et al., *Br. J. Pharmacol.* 172(1):159-172, 2015); FM-202 (Tang et al., *Immunology* 135(2):112-124, 2012); FM-303 (Tang et al., *Immunology* 135(2):112-124, 2012); ADC-1012 (Tang et al., *Immunology* 135(2):112-124, 2012); LY-2525623 (Gaffen et al., *Nat. Rev. Immunol.* 14:585-600, 2014; Sands, *Gastroenterol. Hepatol.* 12(12):784-786, 2016), LY-3074828 (Coskun et al., *Trends Pharmacol.* 38(2):127-142, 2017), BI-655066 (risankizumab) (Singh et al., *MAbs* 7(4):778-791, 2015; Krueger et al., *J. Allergy Clin. Immunol.* 136(1):116-124, 2015) or a variant thereof.

See e.g., Tang et al., *Immunology* 135(2):112-124, 2012. Further teachings of IL-12/IL-23 antibodies and antigen-binding fragments thereof are described in U.S. Pat. Nos. 6,902,734; 7,247,711; 7,252,971; and 7,491,391; US 2012/0288494; and US 2013/0302343, each of which is incorporated by reference in its entirety.

In some embodiments, the IL-12/IL-23 inhibitor is PTG-200, an IL-23R inhibitor currently in preclinical development by Protagonist Therapeutics.

In some embodiments, the IL-12/IL-23 inhibitor is Mirikizumab (LY 3074828), an IL-23R inhibitor currently in clinical development (Phase II) by Eli Lilly.

Fusion Proteins

In some embodiments, the IL-12/IL-23 inhibitor is a fusion protein, a soluble antagonist, or an antimicrobial peptide. In some embodiments, the fusion protein comprises a soluble fragment of a receptor of IL-12 or a soluble fragment of a receptor of IL-23. In some embodiments, the fusion protein comprises an extracellular domain of a receptor of IL-12 or an extracellular domain of a receptor of IL-23.

In some embodiments, the fusion protein is adnectin or a variant thereof (Tang et al., *Immunology* 135(2):112-124, 2012). In some embodiments, the soluble antagonist is a human IL-23Ra-chain mRNA transcript (Raymond et al., *J. Immunol.* 185(12):7302-7308, 2010). In some embodiments, the IL-12/IL-23 is an antimicrobial peptide (e.g., MP-196 (Wenzel et al., *PNAS* 111(14):E1409-E1418, 2014)).

Small Molecules

In some embodiments, the IL-12/IL-23 inhibitor is a small molecule. In some embodiments, the small molecule is STA-5326 (apilimod) or a variant thereof (Keino et al., *Arthritis Res. Ther.* 10: R122, 2008; Wada et al., *Blood* 109(3):1156-1164, 2007; Sands et al., *Inflamm. Bowel Dis.* 16(7):1209-1218, 2010).

3. IL-6 Receptor Inhibitors

The term "IL-6 receptor inhibitor" refers to an agent which decreases IL-6 receptor expression and/or the ability of IL-6 to bind to an IL-6 receptor. In some embodiments, the IL-6 receptor inhibitor targets the IL-6 receptor β-subunit, glycoprotein 130 (sIL6gp130). In other embodiments, the IL-6 receptor inhibitor targets the IL-6 receptor subunit (IL6R). In other embodiments, the IL-6 receptor inhibitor targets the complex consisting of both the IL-6 receptor subunit (IL6R) and the IL-6 receptor β-subunit, glycoprotein 130 (sIL6gp130). In some embodiments, the IL-6 receptor inhibitor targets IL-6.

In some embodiments, an IL-6 receptor inhibitor is an inhibitory nucleic acid, an antibody or an antigen-binding fragment thereof, a fusion protein, a IL-6 receptor antagonist, or a small molecule. In some embodiments, the inhibitory nucleic acid is a small interfering RNA, an antisense nucleic acid, an aptamer, or a microRNA. Exemplary IL-6 receptor inhibitors are described herein. Additional examples of IL-6 receptor inhibitors are known in the art.

Exemplary aspects of different inhibitory nucleic acids are described below. Any of the examples of inhibitory nucleic acids that can decrease expression of an IL6R, sIL6gp130, or IL-6 mRNA. Inhibitory nucleic acids that can decrease the expression of IL6R, sIL6gp130, or IL-6 mRNA in a mammalian cell include antisense nucleic acid molecules, i.e., nucleic acid molecules whose nucleotide sequence is complementary to all or part of an IL6R, sIL6gp130, or IL-6 mRNA.

Inhibitory Nucleic Acids

An antisense nucleic acid molecule can be complementary to all or part of a non-coding region of the coding strand of a nucleotide sequence encoding an IL6R, sIL6gp130, or IL-6 protein. Non-coding regions (5' and 3' untranslated regions) are the 5' and 3' sequences that flank the coding region in a gene and are not translated into amino acids. Exemplary antisense nucleic acids that are IL-6 receptor inhibitors are described in Keller et al., *J. Immunol.* 154(8): 4091-4098, 1995; and Jiang et al., *Anticancer Res.* 31(9): 2899-2906, 2011.

Another example of an inhibitory nucleic acid is a ribozyme that has specificity for a nucleic acid encoding an IL6R, sIL6gp130, or IL-6 protein (e.g., specificity for an IL6R, sIL6gp130, or IL-6 mRNA).

An inhibitory nucleic acid can also be a nucleic acid molecule that forms triple helical structures. For example, expression of an IL6R, sIL6gp130, or IL-6 polypeptide can be inhibited by targeting nucleotide sequences complementary to the regulatory region of the gene encoding the IL6R, sIL6gp130, or IL-6 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

Additional examples of IL-6 receptor inhibitors include siRNA that decrease the level of IL6R, sIL6gp130, or IL-6 mRNA. Non-limiting examples of short interfering RNA (siRNA) that are IL-6 receptor inhibitors are described in Yi et al., *Int. J. Oncol.* 41(1):310-316, 2012; and Shinriki et al., *Clin. Can. Res.* 15(17):5426-5434, 2009). Non-limiting examples of microRNAs that are IL-6 receptor inhibitors are described in miR34a (Li et al., *Int. J. Clin. Exp. Pathol.* 8(2):1364-1373, 2015) and miR-451 (Liu et al., *Cancer Epidemiol.* 38(1):85-92, 2014).

Non-limiting examples of aptamers that are IL-6 receptor inhibitors are described in Meyer et al., *RNA Biol.* 11(1): 57-65, 2014; Meyer et al., *RNA Biol.* 9(1):67-80, 2012; and Mittelberger et al., *RNA Biol.* 12(9):1043-1053, 2015. Additional examples of inhibitory nucleic acids that are IL-6 receptor inhibitors are described in, e.g., WO 96/040157.

Antibodies

In some embodiments, the IL-6 receptor inhibitor is an antibody or an antigen-binding fragment thereof (e.g., a Fab or a scFv). In some embodiments, an antibody or antigen-binding fragment described herein binds specifically to IL-6. In some embodiments, an antibody or antigen-binding fragment described herein binds specifically to IL-6 receptor (e.g., one or both of IL6R and sIL6gp130).

In certain embodiments, the antibody comprises or consists of an antigen-binding fragment or portion of tocilizumab (artlizumab, Actemra®; Sebba, Am. J. *Health Syst. Pharm.* 65(15):1413-1418, 2008; Tanaka et al., *FEBS Letters* 585(23):3699-3709, 2011; Nishimoto et al., *Arthritis Rheum.* 50:1761-1769, 2004; Yokota et al., *Lancet* 371 (9617):998-1006, 2008; Emery et al., *Ann. Rheum. Dis.* 67(11):1516-1523, 2008; Roll et al., *Arthritis Rheum.* 63(5): 1255-1264, 2011); clazakizumab (BMS945429; ALD518, a humanized monoclonal antibody that binds circulating IL-6 cytokine rather than the IL-6 receptor, blocking both classic signaling and trans-signaling (Weinblatt, Michael E., et al. "The Efficacy and Safety of Subcutaneous Clazakizumab in Patients With Moderate-to-Severe Rheumatoid Arthritis and an Inadequate Response to Methotrexate: Results From a Multinational, Phase IIb, Randomized, Double-Blind, Placebo/Active-Controlled, Dose-Ranging Study." Arthritis & Rheumatology 67.10 (2015): 2591-2600)); sarilumab (REGN88 or SAR153191, Huizinga et al., *Ann. Rheum. Dis.* 73(9):1626-1634, 2014; Sieper et al., *Ann. Rheum. Dis.* 74(6):1051-1057, 2014; Cooper, *Immunotherapy* 8(3): 249-250, 2016); MR-16 (Hartman et al., *PLosOne* 11(12): e0167195, 2016; Fujita et al., *Biochim. Biophys. Acta.* 10:3170-80, 2014; Okazaki et al., *Immunol. Lett.* 84(3):231-40, 2002; Noguchi-Sasaki et al., *BMC Cancer* 16:270, 2016; Ueda et al., *Sci. Rep.* 3:1196, 2013); rhPM-1 (MRA; Nishimoto et al., *Blood* 95: 56-61, 2000; Nishimoto et al., *Blood* 106: 2627-2632, 2005; Nakahara et al., *Arthritis Rheum.* 48(6): 1521-1529, 2003); NI-1201 (Lacroix et al., *J. Biol. Chem.* 290(45):26943-26953, 2015); EBI-029 (Schmidt et al., *Eleven Biotherapeutics Poster* #B0200, 2014). In some embodiments, the antibody is a nanobody (e.g., ALX-0061 (Van Roy et al., *Arthritis Res. Ther.* 17: 135, 2015; Kim et al., *Arch. Pharm. Res.* 38(5):575-584, 2015)). In some embodiments, the antibody is NRI or a variant thereof (Adachi et al., *Mol. Ther.* 11(1):5262-263, 2005; Hoshino et al., *Can. Res.* 67(3): 871-875, 2007). In some embodiments, the antibody is PF-04236921 (Pfizer) (Wallace et al., *Ann. Rheum. Dis.* 76(3):534-542, 2017).

In some embodiments, the antibody is siltuximab (Sylvant®), also known as ONTO 328, a chimeric, human-murine, immunoglobulin (Ig) GK mAb that binds and neutralizes human IL-6 with high affinity and specificity. The variable region of siltuximab is derived from a murine anti-IL-6 antibody, CLB8, and the constant region is derived from a human IgG1κ molecule. Sylvant® is approved for the treatment of patients with multicentric Castleman's disease (MCD).

In some embodiments, the IL-6R inhibitor is AMG220, also known as 0326, an avimer that displays bi-specificity to its interleukin target, as well as binding to the Fc domain of IgG (resulting in reduced renal clearance and FcRn recycling). The compound has subpicomolar affinity for IL-6 and displays a moderate serum half-life (~30 h). Phase I clinical trials of AMG220 in Crohn's disease revealed dose-dependent reduction in serum C-reactive protein, an inflammation biomarker synthesized by hepatocytes in response to IL-6. Despite its apparent efficacy, Amgen has suspended the clinical development of the compound.

Fusion Proteins

In some embodiments, the IL-6 receptor inhibitor is a fusion protein, a soluble receptor, or a peptide (see e.g., U.S. Pat. No. 5,591,827). In some embodiments, the IL-6 receptor fusion protein comprises or consists of soluble gp130 (Jostock et al., *Eur. J. Biochem.* 268(1):160-167, 2001; Richards et al., *Arthritis Rheum.* 54(5):1662-1672, 2006; Rose-John et al., *Exp. Opin. Ther. Targets* 11(5):613-624, 2007).

In some embodiments, the IL-6 receptor fusion protein comprises or consists of FE999301 (Jostock et al., *Eur. J. Biochem.* 268(1):160-167, 2001) or sgp130Fc protein (Jones et al., *J. Clin. Invest.* 121(9):3375-3383, 2011). In some embodiments, the IL-6 receptor inhibitor is a peptide (e.g., S7 (Su et al., *Cancer Res.* 65(11):4827-4835, 2005). In some embodiments, the IL-6 receptor inhibitor is a triterpenoid saponin (e.g., chikusetsuaponin IVa butyl ester (CS-Iva-Be) (Yang et al., *Mol. Cancer. Ther.* 15(6):1190-200, 2016).

Small Molecules

In some embodiments, the IL-6 receptor inhibitor is a small molecule (see, e.g., U.S. Pat. No. 9,409,990). In some embodiments, the small molecule is LMT-28 (Hong et al., *J. Immunol.* 195(1): 237-245, 2015); ERBA (Enomoto et al., *Biochem. Biophys. Res. Commun.* 323:1096-1102, 2004; Boos et al., *J. Nat. Prod.* 75(4):661-668, 2012), ERBF (TB-2-081) (Hayashi et al., *J. Pharmacol. Exp. Ther.* 303: 104-109, 2002; Vardanyan et al., *Pain* 151(2):257-265, 2010; Kino et al., *J. Allergy Clin. Immunol.* 120(2):437-444, 2007), or a variant thereof.

4. Integrin Inhibitors

The term "integrin inhibitor" refers to an agent which decreases the expression of one or more integrins and/or decreases the binding of an integrin ligand to one or more integrins that play a role in the recruitment, extravasation, and/or activation of a leukocyte. In some embodiments, the integrin inhibitor specifically binds to at least a portion of a ligand binding site on a target integrin. In some embodiments, the integrin inhibitor specifically binds to a target integrin at the same site as an endogenous ligand. In some embodiments, the integrin inhibitor decreases the level of expression of the target integrin in a mammalian cell. In some embodiments, the integrin inhibitor specifically binds to an integrin ligand.

Non-limiting examples of integrins that can be targeted by any of the integrin inhibitors described herein include: α2β1 integrin, α1β1 integrin, α4β7 integrin, integrin α4β1 (VLA-4), E-selectin, ICAM-1, α5β1 integrin, α4β1 integrin, VLA-4, α2β1 integrin, α5≈3 integrin, α5β5 integrin, αIIbβ3 integrin, and MAdCAM-1. A non-limiting example of integrin inhibitor that can decrease the expression and/or activity of α4≈7 integrin is FTY720. A non-limiting example of an integrin inhibitor that specifically targets MAdCAM is PF-547659 (Pfizer). Non-limiting examples of an integrin inhibitor that specifically targets α4β7 is AJM300 (Ajinomoto), etrolizumab (Genentech), and vedolizumab (Millennium/Takeda).

In some embodiments, the integrin inhibitor is an αIIb≈3 integrin inhibitor. In some embodiments, the αIIbβ3 integrin inhibitor is abciximab (ReoPro®, c7E3; Kononczuk et al., *Curr. Drug Targets* 16(13):1429-1437, 2015; Jiang et al., *Appl. Microbiol. Biotechnol.* 98(1):105-114, 2014), eptifibatide (Integrilin®; Scarborough et al., *J. Biol. Chem.* 268: 1066-1073, 1993; Tcheng et al., *Circulation* 91:2151-2157, 1995) or tirofiban (Aggrastat®; Hartman et al., *J. Med. Chem.* 35:4640-4642, 1992; Pierro et al., *Eur. J. Ophthalmol.* 26(4):e74-76, 2016; Guan et al., *Eur. J. Pharmacol* 761:144-152, 2015). In some embodiments, the integrin inhibitor is an αL-selective integrin inhibitor. In some embodiments, the integrin inhibitor is a β2 integrin inhibitor.

In some embodiments, the integrin inhibitor is an α4 integrin (e.g., an α4β1 integrin (e.g., Very Late Antigen-4 (VLA-4), CD49d, or CD29)) inhibitor, an α4β7 integrin inhibitor. In some embodiments, the integrin inhibitor targets endothelial VCAM1, fibronectin, mucosal addressin cellular adhesion molecule-1 (MAdCAM-1), vitronectin, tenascin-C, osteopontin (OPN), nephronectin, agiostatin, tissue-type transglutaminase, factor XIII, Von Willebrand factor (VWF), an ADAM protein, an ICAM protein, collagen, e-cadherin, laminin, fibulin-5, or TGFβ. In some embodiments, the α4 integrin inhibitor is natalizumab (Tysabri®; Targan et al., *Gastroenterology* 132(5):1672-1683, 2007; Sandborn et al., *N. Engl. J. Med.* 353(18):1912-1925, 2005; Nakamura et al., *Intern. Med.* 56(2):211-214, 2017; and Singh et al., *J. Pediatr. Gastroenterol. Nutr.* 62(6):863-866, 2016). In some embodiments, the integrin inhibitor is an endogenous integrin inhibitor (e.g., SHARPIN (Rantala et al., *Nat. Cell. Biol.* 13(11):1315-1324, 2011).

In some embodiments, the integrin inhibitor is an αv integrin (e.g., an α5β1 integrin, an α5β3 integrin, an α5β5 integrin inhibitor, and/or an α5β6 integrin) inhibitor.

In some embodiments, the integrin inhibitor is an α5β1 integrin inhibitor.

In some embodiments, an integrin inhibitor is an inhibitory nucleic acid, an antibody or antigen-binding fragment thereof, a fusion protein, an integrin antagonist, a cyclic peptide, a disintegrin, a peptidomimetic, or a small molecule. In some embodiments, the inhibitory nucleic acid is a small hairpin RNA, a small interfering RNA, an antisense, an aptamer, or a microRNA.

Inhibitory Nucleic Acids

In some embodiments, the inhibitory nucleic acid can be an antisense nucleic acid, a ribozyme, a small interfering RNA, a small hairpin RNA, or a microRNA. Inhibitory nucleic acids that can decrease the expression of target integrin mRNA or a target integrin ligand mRNA (e.g., any of the exemplary integrins described herein or any of the exemplary integrin ligands described herein) in a mammalian cell include antisense nucleic acid molecules, i.e., nucleic acid molecules whose nucleotide sequence is complementary to all or part of target integrin mRNA or a target integrin ligand mRNA. An antisense nucleic acid molecule can be complementary to all or part of a non-coding region of the coding strand of a nucleotide sequence encoding a target integrin or a target integrin ligand (e.g., any of the exemplary target integrins or any of the exemplary integrin ligands described herein). Non-coding regions (5' and 3' untranslated regions) are the 5' and 3' sequences that flank the coding region in a gene and are not translated into amino acids. Exemplary integrin inhibitors that are antisense nucleic acids include ATL1102 (e.g., Limmroth et al., *Neurology* 83(20):1780-1788, 2014; Li et al., *Dig. Liver Dis.* 39(6):557-565, 2007; Goto et al., *Inflamm. Bowel Dis.* 12(8):758-765, 2006).

Another example of an inhibitory nucleic acid is a ribozyme that has specificity for a nucleic acid encoding a target integrin (e.g., any of the exemplary target integrins described herein) or an integrin ligand (e.g., any of the exemplary integrin ligands described herein).

An inhibitory nucleic acid can also be a nucleic acid molecule that forms triple helical structures. For example, expression of a target integrin (e.g., any of the exemplary target integrins described herein) or an integrin ligand (e.g., any of the exemplary integrin ligands described herein) can be inhibited by targeting nucleotide sequences complementary to the regulatory region of the gene encoding the target integrin (e.g., any of the exemplary target integrins described herein) or the integrin ligand (e.g., any of the exemplary integrin ligands described herein) (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

In some embodiments, an integrin inhibitor is a siRNA that decreases the level of a target integrin (e.g., any of the exemplary target integrins described herein) mRNA or an integrin ligand (e.g., any of the exemplary integrin ligands described herein) mRNA. Non-limiting examples of integrin inhibitors that are short interfering RNAs (siRNAs) are described in Wang et al., *Cancer Cell Int.* 16:90, 2016). In some embodiments, the integrin inhibitor is a short hairpin RNA (shRNA).

Non-limiting examples of integrin inhibitors that are microRNA include miR-124 (Cai et al., *Sci. Rep.* 7:40733, 2017), miR-134 (Qin et al., *Oncol. Rep.* 37(2):823-830, 2017), miR-92b (Ma et al., *Oncotarget* 8(4):6681-6690, 2007), miR-17 (Gong et al., *Oncol. Rep.* 36(4), 2016), miR-338 (Chen et al., *Oncol. Rep.* 36(3):1467-74, 2016), and miR-30a-5p (Li et al., *Int. J. Oncol.* 48(3):1155-1164, 2016).

Antibodies

In some embodiments, the integrin inhibitor is an antibody or an antigen-binding fragment thereof (e.g., a Fab or a scFv). In some embodiments, the antibody can be a humanized antibody, a chimeric antibody, a multivalent antibody, or a fragment thereof.

In some embodiments, the antibody is a pan-β1 antibody (e.g., OS2966 (Carbonell et al., *Cancer Res.* 73(10):3145-3154, 2013). In some embodiments, the integrin antibody is a monoclonal antibody (e.g., 17E6 (Castel et al., *Eur. J. Cell. Biol.* 79(7):502-512, 2000); Mitjans et al., *Int. J. Cancer* 87(5):716-723, 2000)). In some embodiments, the monoclonal antibody is vedolizumab (e.g., Entyvio®) or a variant thereof (Feagan et al., *N. Engl. J. Med* 369:699-710, 2013; Sandborn et al., *N. Engl. J. Med.* 369:711-721, 2013; Sands et al., *Gastroenterology* 147:618-627, 2014; and Milch et al., *Neuroimmunol.* 264:123-126, 2013; Wyant et al., *J. Crohns Colitis* 10(12):1437-1444, 2016; and Feagan et al., *Gastroenterology* 142(5):S160-S161, 2012).

In some embodiments, the antibody can be a Fab fragment of a monoclonal chimeric mouse-human antibody (e.g., abciximab (ReoPro, c7E3), Kononczuk et al., *Curr. Drug Targets* 16(13):1429-1437, 2015; Jiang et al., *Appl. Microbiol. Biotechnol.* 98(1):105-114, 2014), or a variant thereof. In some embodiments, the integrin antibody is a humanized monoclonal antibody. In some embodiments, the humanized monoclonal antibody is natalizumab (Tysabri®) (Targan et al., *Gastroenterology* 132(5):1672-1683, 2007; Sandborn et al., *N. Engl. J. Med.* 353(18):1912-1925, 2005; Nakamura et al., *Intern Med.* 56(2):211-214, 2017; Singh et al., *J. Pediatr. Gastroenterol. Nutr.* 62(6):863-866, 2016). In some embodiments, the humanized monoclonal antibody is vitaxin (MEDI-523) or a variant thereof (Huveneers et al., *Int. J. Radiat. Biol.* 81(11-12):743-751, 2007; Coleman et al., *Circ. Res.* 84(11):1268-1276, 1999). In some embodiments, the humanized monoclonal antibody is etaracizumab (Abegrin®, MEDI-522, LM609) or a variant thereof (Hersey et al., *Cancer* 116(6):1526-1534, 2010; Delbaldo et al., *Invest New Drugs* 26(1):35-43, 2008). In some embodiments, the humanized monoclonal antibody is CNTO95 (Intetumumab®) or a variant thereof (Jia et al., *Anticancer Drugs* 24(3):237-250, 2013; Heidenreich et al., *Ann. Oncol.* 24(2): 329-336, 2013; Wu et al., *J. Neurooncol.* 110(1):27-36, 2012). In some embodiments, the humanized monoclonal antibody is efalizumab (Raptiva®) or a variant thereof (Krueger et al., *J. Invest. Dermatol.* 128(11):2615-2624, 2008; Li et al., *PNAS* 106(11):4349-4354, 2009; Woolacott et al., *Health Technol. Assess* 10:1-233, 2006). In some embodiments, the humanized monoclonal antibody is STX-100 (Stromedix®) or a variant thereof (van Aarsen et al., *Cancer Res.* 68:561-570, 2008; Lo et al., *Am. J. Transplant.* 13(12):3085-3093, 2013). In some embodiments, the humanized monoclonal antibody is 264RAD or a variant thereof (Eberlein et al., *Oncogene* 32(37):4406-4417, 2013).

In some embodiments, the humanized monoclonal antibody is rovelizumab or a variant thereof (Goodman et al., *Trends Pharmacol. Sci* 33:405-412, 2012). In some embodiments, the humanized monoclonal antibody is Cytolin® or a variant thereof (Rychert et al., *Virology J.* 10:120, 2013). In some embodiments, the humanized monoclonal antibody is etrolizumab or a variant thereof (Vermeire et al., *Lancet* 384:309-318, 2014; Rutgeerts et al., *Gut* 62:1122-1130, 2013; Lin et al., *Gastroenterology* 146:307-309, 2014; Ludviksson et al., *J. Immunol.* 162(8):4975-4982, 1999; Stefanich et al., *Br. J. Pharmacol.* 162(8):1855-1870, 2011). In some embodiments, the humanized monoclonal antibody is abrilumab (AMG 181; MEDI-7183) or a variant thereof (Pan et al., *Br. J. Pharmacol.* 169(1):51-68, 2013; Pan et al., *Br. J. Clin. Pharmacol.* 78(6):1315-1333, 2014). In some embodiments, the humanized monoclonal antibody is PF-00547659 (SHP647) or a variant thereof (Vermeire et al., *Gut* 60(8):1068-1075, 2011; Sandborn et al., *Gastroenterology* 1448(4):S-162, 2015). In some embodiments, the humanized monoclonal antibody is SAN-300 (hAQC2) or a variant thereof (Karpusas et al., *J. Mol. Biol.* 327:1031-1041, 2003). In some embodiments, the humanized monoclonal antibody is D1176E6 (EMD 5257) or a variant thereof (Goodman et al., *Trends Pharmacol. Sci* 33:405-412, 2012; and Sheridan et al., *Nat. Biotech.* 32:205-207, 2014).

In some embodiments, the integrin antibody is a chimeric monoclonal antibody. In some embodiments, the chimeric monoclonal antibody is volociximab or a variant thereof (Kuwada et al., *Curr. Opin. Mol. Ther.* 9(1):92-98, 2007; Ricart et al., *Clin. Cancer Res.* 14(23):7924-7929, 2008; Ramakrishnan et al., *J. Exp. Ther. Oncol.* 5(4):273-86, 2006;

Bell-McGuinn et al., *Gynecol. Oncol.* 121:273-279, 2011; Almokadem et al., *Exp. Opin. Biol. Ther.* 12:251-7, 2012).

In some embodiments, the antibody specifically binds one or more (e.g., 1, 2, 3, 4, or 5) integrin. In some embodiments, the antibody specifically binds an integrin dimer (e.g., MLN-00002, MLN02 (Feagan et al., *Clin. Gastroenterol. Hepatol.* 6(12):1370-1377, 2008; Feagan et al., *N. Engl. J. Med.* 352(24):2499-2507, 2005). In certain embodiments, the antibody comprises or consists of an antigen-binding fragment of abciximab (Reopro™) (Straub et al., *Eur. J. Cardiothorac Surg.* 27(4):617-621, 2005; Kim et al., *Korean J. Intern. Med.* 19(4):220-229, 2004). In some embodiments, the integrin inhibitor is an antibody-drug conjugate (e.g., IMGN388 (Bendell et al., *EJC Suppl* 8(7):152, 2010).

Further examples of antibodies and antigen-binding fragments thereof are described in U.S. Pat. Nos. 5,919,792; 6,214,834; 7,074,408; 6,833,373; 7,655,624; 7,465,449; 9,558,899; 7,659,374; 8,562,986; 8,398,975; and 8,853,149; US 2007/0117849; US 2009/0180951; US 2014/0349944; US 2004/0018192; WO 11/137418; and WO 01/068586; each of which is incorporated by reference in its entirety.
Fusion Proteins In some embodiments, the integrin inhibitor is a fusion protein (e.g., an Fc fusion protein of an extracellular domain of an integrin or an integrin receptor), a soluble receptor (e.g., the extracellular domain of an integrin or an integrin receptor), or a recombinant integrin binding protein (e.g., an integrin ligand). See, e.g., Lode et al., *PNAS* 96(4):1591-1596, 1999; Stephens et al., *Cell Adhesion Comm.* 7:377-390, 2000; and US 2008/0739003; incorporated by reference herein). Non-limiting examples of fusion proteins that are integrin inhibitors include Ag25426 (Proteintech).
Small Molecules Antagonists In some embodiments, the integrin inhibitor is a small molecule. In some embodiments, the small molecule is a non-peptide small molecule. In some embodiments, the non-peptide small molecule is a RGD (ArgGlyAsp)-mimetic antagonist (e.g., tirofiban (Aggrastat®); Pierro et al., *Eur. J. Ophthalmol.* 26(4):e74-76, 2016; Guan et al., *Eur. J. Pharmacol* 761:144-152, 2015. In some embodiments, the small molecule is a4 antagonist (e.g., firategrast (Miller et al., *Lancet Neurol.* 11(2):131-139, 2012) AJM300 (Yoshimura et al., *Gastroenterology* 149(7):1775-1783, 2015; Takazoe et al., *Gastroenterology* 136(5):A-181, 2009; Sugiura et al., *J. Crohns Colitis* 7(11):e533-542, 2013)). In some embodiments, the small molecule is a4β1 antagonist (e.g., IVL745 (Norris et al., *J. Allergy Clin. Immunol.* 116(4):761-767, 2005; Cox et al., *Nat. Rev. Drug Discov.* 9(10):804-820, 2010)), BIO-1211 (Abraham et al., *Am. J. Respir. Crit. Care Med.* 162:603-611, 2000; Ramroodi et al., *Immunol. Invest* 44(7):694-712, 2015; Lin et al., *J. Med. Chem.* 42(5):920-934, 1999), HMR 1031 (Diamant et al., *Clin. Exp. Allergy* 35(8):1080-1087, 2005); valategrast (R411) (Cox et al., *Nat. Rev. Drug Discov.* 9(10):804-820, 2010), GW559090X (Ravensberg et al., *Allergy* 61(9):1097-1103, 2006), TR14035 (Sircar et al., *Bioorg. Med. Chem.* 10(6):2051-2066, 2002; Cortijo et al., *Br. J. Pharmacol.* 147(6):661-670, 2006)). In some embodiments, the small molecule is αvβ3 antagonist (e.g., L0000845704, SB273005). In some embodiments, the small molecule is α5β1 antagonist (e.g., JSM6427). In some embodiments, the small molecule is GLPG0974 (Vermeire et al., *J. Crohns Colitis* Suppl. 1:S39, 2015). In some embodiments, the small molecule is MK-0429 (Pickarksi et al., *Oncol. Rep.* 33(6):2737-45, 2015; Rosenthal et al., *Asia Pac J. Clin. Oncol.* 6:42-8, 2010). In some embodiments, the small molecule is JSM-6427 or a variant thereof (Zahn et al., *Arch. Ophthalmol.* 127(10):1329-1335, 2009; Stragies et al., *J. Med. Chem.* 50:3786-94, 2007).

In some embodiments, the small molecule targets a β2 integrin. In some embodiments, the small molecule is SAR-118 (SAR1118) or a variant thereof (Zhong et al., *ACS Med. Chem. Lett.* 3(3):203-206, 2012; Suchard et al., *J. Immunol.* 184:3917-3926, 2010; Yandrapu et al., *J. Ocul. Pharmacol. Ther.* 29(2):236-248, 2013; Semba et al., *Am. J. Ophthalmol.* 153:1050-60, 2012). In some embodiments, the small molecule is BMS-587101 or a variant thereof (Suchard et al., *J. Immunol.* 184(7):3917-3926, 2010; Potin et al., *J. Med. Chem.* 49:6946-6949, 2006). See e.g., Shimaoka et al., *Immunity* 19(3):391-402, 2003; U.S. Pat. Nos. 7,138,417; 7,928,113; 7,943,660; and 9,216,174; US 2008/0242710; and US 2008/0300237.

In some embodiments, the small molecule integrin inhibitor can be PTG-100, which is described in, e.g., Shames et al., "Pharmakokinetics and Pharmacodynamics of the Novel Oral Peptide Therapeutic PTG-100 (α4β7 Integrin Antagonist) in Normal Healthy Volunteers," 24th United European Gastroentrology Week, October 15-19, Vienna, Austria, 2016.
Cyclic Peptides In some embodiments, the integrin inhibitor is a cyclic peptide. In some embodiments, the cyclic peptide comprises or consists of an amino acid sequence as set forth in the amino acid sequence of a ligand recognition sequence of an endogenous integrin ligand. In some embodiments, the cyclic peptide competes for a target integrin ligand binding site with an endogenous integrin ligand. In some embodiments, the cyclic peptide includes one or more (e.g., 1, 2, 3, 4, 5, 6, 7, 8) D-amino acids. In some embodiments, the cyclic peptide is a synthetic cyclic peptide. In some embodiments, the synthetic cyclic peptide is a heptapeptide. In some embodiments, the synthetic cyclic peptide is eptifabitide (Integrilin™), or a variant thereof. In some embodiments, the cyclic peptide comprises a heterocyclic nucleic (e.g., a benzodiazepinone, a piperazine, a benzoazepinone, a nitroaryl, an isoxazoline, an indazole, or a phenol; Spalluto et al., *Curr. Med. Chem.* 12:51-70, 2005). In some embodiments, the cyclic peptide is a macrocycle (see, e.g., Halland et al., *ACS Med. Chem. Lett.* 5(2):193-198, 2014). In some embodiments, the peptide is ALG-1001 or a variant thereof (Mathis et al., *Retin. Phys.* 9:70, 2012). In some embodiments, the cyclic peptide is an imidazolone-phenylalanine derivative, a heteroaryl, hetrocyclic, and aryl derivative, a bicyclic-aromatic amino acid derivative, a cyclohexane-carboxylic acid derivative, a di-aryl substituted urea derivative, a multimeric L-alanine derivative, a L-alanine derivative, or a pyrimidyl-sulfonamide derivative (see, e.g., U.S. Pat. Nos. 6,630,492; 6,794,506; 7,049,306; 7,371,854; 7,759,387; 8,030,328; 8,129,366; 7,820,687; 8,350,010; and 9,345,793).
Peptidomimetics In some embodiments, the integrin inhibitor is a peptidomimetic. In some embodiments, the peptidomimetic has an integrin-ligand recognition motif (e.g., RGD, KTS, or MLD). See, e.g., Carron et al., *Cancer Research* 58:1930-1935, 1998; Fanelli et al., *Vascular Cell* 6:11, 2014; and De Marco et al., *Curr. Top. Med. Chem.* 16(3):343-359, 2016.

In some embodiments, the peptidomimetic is an RGD (ArgGlyAsp)-based peptide (U.S. Pat. No. 8,809,338, incorporated by reference in its entirety herein). In some embodiments, the RGD-based peptide can be cilengitide or a variant thereof (EMD 12974) (Mas-Moruno et al., *Anticancer Agents Med. Chem.* 10:753-768, 2010; Reardon et al., *Future Oncol.* 7(3):339-354, 2011; Beekman et al., *Clin.*

*Genitourin Cancer* 4(4):299-302, 2006; SC56631 (e.g., Engleman et al., *Am Soc. Clin. Invest.* 99(9):2284-2292, 1997; Peng et al., *Nature Chem Biol.* 2:381-389, 2006). In some embodiments, the peptidomimetic can be a Lys-Gly-Asp (KGD)-based peptide. In some embodiments, the peptidomimetic can be vipegitide or a variant thereof (Momic et al., *Drug Design Devel. Therapy* 9:291-304, 2015). In some embodiments, the peptidomimetic can be a peptide conjugated with an antimicrobial synthetic peptide. (e.g., ACDCRGDCFC conjugated with (KLAKLAK)$_2$ (Ellerby et al., *Nat. Med.* 5(9):1032-1038, 1999). See, e.g., U.S. Pat. No. 8,636,977.

Disintegrins

In some embodiments, the integrin inhibitor can be a disintegrin. The term "disintegrin" as used herein refers to a low molecular weight peptide integrin inhibitor derived from a snake venom (e.g., pit viper venom). In some embodiments, the disintegrin is a RGD(ArgGlyAsp)-, a KTS- or an MLD-based disintegrin.

Non-limiting examples of disintegrins include accutin, accurhagin-C, albolabrin, alternagin-c, barbourin, basilicin, bitisgabonin-1, bitisgabonin-2, bitistatin, cerastin, cereberin, cumanastatin 1, contortrostatin, cotiarin, crotatroxin, dendroaspin, disba-01, durissin, echistatin, EC3, elegantin, eristicophin, eristostatin, EMS11, EO4, EO5, flavoridin, flavostatin, insularin, jarastatin, jerdonin, jerdostatin, lachesin, lebein (e.g., lebein-1, lebein-2), leberagin-C, lebestatin, lutosin, molossin, obtustatin, ocellatusin, rhodocetin, rhodostomin, R-mojastin 1, salmosin, saxatilin, schistatin, tablysin-15, tergeminin, triflavin, trigramin, trimestatin, VA6, vicrostatin, viridin, viperstatin, VB7, VLO4, and VLO5, or a variant thereof. See, e.g., Arruda Macedo et al., *Curr. Protein. Pept. Sci.* 16(6):532-548, 2015; Hsu et al., *Sci. Rep.* 6:23387, 2016; Kele et al. *Curr. Protein Pept. Sci.* 6:532-548, 2015; Koh et al., *Toxicon* 59(4):497-506, 2012; Scarborough et al., *J. Biol. Chem.* 268:1058-1065, 1993; Kisiel et al., *FEBS Lett.* 577:478-482, 2004; Souza et al., *Arch. Biochem. Biophys.* 384:341-350, 2000; Eble et al., *J. Biol. Chem.* 278:26488-26496, 2003; Marcinkiewicz et al., *J. Biol. Chem.* 274:12468-12473, 1999; Calvete et al., *J. Proteome Res.* 6:326-336, 2007; Scibelli et al., *FEMS Microbiol. Lett.* 247:51-57, 2005; Oliva et al., *Toxicon* 50:1053-1063, 2007; Minea et al., *Toxicon* 59:472-486, 2012; Smith et al., *FEBS Lett.* 512:111-115, 2002; Tselepis et al., *J. Biol. Chem.* 272:21341-21348, 1997; Da Silva et al., *Tromb. Res.* 123:731-739, 2009; Thibault et al., *Mol. Pharmacol.* 58:1137-1145, 2000; Lu et al., *Biochem. J.* 304:818-825, 1994; Yeh et al., *Biochim. Biophys. Acta.* 1425:493-504, 1998; Huang et al., *Exp. Hematol.* 36:1704-1713, 2008; Shih et al., *Matrix Biol.* 32:152-159, 2013; Wang et al., *Br. J. Pharmacol.* 160:1338-1351, 2010; Della-Casa et al., *Toxicon* 57:125-133, 2011; Sheu et al., *Biochim. Biophys. Acta.* 1336:445-454, 1997; Fujii et al., *J. Mol. Biol.* 332:115-122, 2003; Bilgrami et al., *J. Mol. Biol.* 341:829-837, 2004; Zhou et al., *Toxicon* 43:69-75, 2004; Scarborough et al., *J. Biol. Chem.* 268:1066-1073, 1993; Shebuski et al., *J. Biol. Chem.* 264:21550-21556, 1989; Lu et al., *Biochem. J.* 304:929-936, 1994; McLane et al., *Biochem. J.* 301:429-436, 1994; Juarez et al., *Toxicon* 56:1052-1058, 2010; Olfa et al., *Lab. Invest.* 85:1507-1516, 2005; Elbe et al., *Matrix Biol.* 21:547-558, 2002; Bazan-Socha et al., *Biochemistry* 43:1639-1647, 2004; Danen et al., *Exp. Cell. Res.* 238:188-196, 1998; Marcinkiewicz et al., *Biochemistry* 38(40): 13302-13309, 1999; Calvete et al., *Biochem. J.* 372:725-734, 2003; Swenson et al., *Pathophysiol. Haemost. Thromb.* 34:169-176, 2005; Kwon et al., *PLoS One* 8; e81165, 2013; Yang et al., *Toxicon* 45:661-669, 2005; Limam et al., *Matrix Biol.* 29:117-126, 2010; Gan et al., *J. Biol. Chem.* 263: 19827-19832, 1988; Ma et al., *Thromb. Haemost.* 105(6): 1032-1045, 2011; and U.S. Pat. No. 7,074,408, incorporated in their entirety herein.

5. TLR Agonists/Antagonists

The term "TLR agonist" is an agent that binds to and activates a toll-like receptor (TLR) expressed in a mammalian cell (e.g., a human cell). In some embodiments, the TLR agonist binds to and activates TLR1. In some embodiments, the TLR agonist binds to and activates TLR2. In some embodiments, the TLR agonist binds to and activates TLR3. In some embodiments, the TLR agonist binds to and activates TLR4. In some embodiments, the TLR agonist binds to and activates TLR5. In some embodiments, the TLR agonist binds to and activates TLR6. In some embodiments, the TLR agonist binds to and activates TLR7. In some embodiments, the TLR agonist binds to and activates TLR8. In some embodiments, the TLR agonist binds to and activates TLR9. In some embodiments, the TLR agonist binds to and activates TLR10. In some embodiments, the TLR agonist binds to and activates TLR11. In some embodiments, the TLR agonist binds to and activates two or more (e.g., three, four, five, six, seven, eight, nine, ten, or eleven) TLRs (e.g., two or more of any of TLR1, TLR2, TLR3, TLR4, TLR5, TLR6, TLR7, TLR8, TLR9, TLR10, and TLR11 (in any combination)).

In some embodiments, the TLR agonist is a synthetic TLR agonist, a TLR mimic, or a small molecule. Non-limiting examples of TLR agonists are described in Bhardwaj et al., *Cancer J.* 16(4):382-391, 2010; Meyer et al., *Exp. Opin. Investig. Drugs* 17(7):1051-1065, 2008; Adams, *Immunotherapy* 1(6):949-964, 2009; Hennessy et al., *Nat. Rev. Drug Discov.* 9:293-307, 2010; and U.S. Pat. Nos. 7,498,409; 9,421,254; 8,409,813; 8,361,986; 8,795,678; 8,728,486; 8,636,979; 8,999,946; 9,359,360; 9,050,376; and 9,556,167; US 2014/0322271; US 2016/0206690; US 2009/0253622; US 2011/0135669; US 2011/0250175; US 2014/0220074; and US 2012/0219615; each incorporated in its entirety herein. In some embodiments, the TLR agonist is a peptide or a fusion protein (Huleatt et al., *Vaccine* 25: 763-775, 2007).

In some embodiments, a TLR agonist specifically binds to and activates a single TLR (e.g., TLR4, TLR7, TLR8, or TLR9, Zhu et al., *J. Clin. Invest.* 120:607-616, 2010; Zhu et al., *PNAS* 105:16260-16265, 2008; Wang et al., *J. Virol.* 79(22):14355-14370, 2005). In some embodiments, the TLR agonist binds to and activates more than one TLR (e.g., Bacillus of Calmette-Guerin, Myobacterium bovis (BOG); Morton et al., *Ann. Surg.* 180(4):635-643, 1974; Mortoon et al., *J. Clin. Oncol. ASCO Ann. Meeting Proceedings Part I* 25(18 Suppl), 2007). In some embodiments, the TLR agonist is a TLR2/TLR6 agonist (e.g., Pam2CSK4 or MALP-2 (Agnihotri et al., *J. Med. Chem.* 54: 8148-8160, 2011; Wu et al., *J. Med. Chem.* 53: 3198-3213, 2010)).

In some embodiments, the TLR agonist is an endogenous molecule released from dead cells (e.g., a heat shock protein (HSP) and mobility group box 1 (HMGB1); Asea et al., *J. Biol. Chem.* 277:15028-15034, 2002; Kepp et al., *Cancer Metastasis* 30: 61-69, 2011).

TLR3 Agonists

In some embodiments, the TLR agonist specifically binds and activates TLR3 (e.g., a synthetic agonist). Non-limiting examples of TLR agonists that bind and activate TLR3 are described in Nicodemus et al., *Immunotherapy* 2:137-140, 2010. In some embodiments, the TLR3 agonist is a synthetic double-stranded RNA (dsRNA) complex (e.g., polyribosinic: polyribocytidic acid (polyI:C); Sivori et al., *PNAS*

101:10116-10121, 2004; Sloat et al., *Pharmaceutical Res.* 23:1217-1226, 2006; Ichinohe et al., *Microbes and infection/ Institut Pasteur* 9:1333-1340, 2007; Robinson et al., *J. Natl. Cancer Inst.* 57(3):599-602, 1976). In some embodiments, the TLR3 agonist is a TLR3 mimic (e.g., polyadenosine-polyuridylic acid (poly A:U) (Veyrat et al., *Oncotarget* 7(50):82580-82593, 2016; Alizadeh et al., *Iran J. Allergy Asthma Immunol.* 12(2):161-167, 2013); rintatolimod (polyI: polyCU, Ampligen®) (Steinman et al., *Nature* 449: 419-426, 2007; Jasani et al., *Vaccine* 27(25-26):3401-3404, 2009; Strayer et al., *PLoS One* 7(3): e31334, 2012). In some embodiments, the TLR3 mimic is polyionisinic-polycytidylic acid stabilized with poly-L-lysine and carboxymethylcellulose (Poly-ICLC, Hiltonol®; Hawkins et al., *J. Biol. Resp. Mod.* 4:664-668, 1985; Butowski et al., *J. Neurooncol.* 91:175-182, 2009; Jeong et al., *J. Neurochem.* doi.10.1111, 2015). In some embodiments, the TLR3 agonist is RGC100 (Naumann et al., *Clin. Dev. Immunol.* 283649, 2013), IPH-3102 (Basith et al., *Exp. Opin. Ther. Pat.* 21: 927-944, 2011), or a variant thereof. In some embodiments, the TLR3 agonist is CQ-07001 (Clinquest). In some embodiments, the TLR3 agonist is Ampligen poly(I):poly(C12U) (Hemispherx Biopharma). In some embodiments, the TLR3 agonist is IPH-31XX (Innate Pharma). In some embodiments, the TLR3 agonist is MCT-465-dsRNA (MultiCell Technologies).

TLR4 Agonists

In some embodiments, the TLR agonist specifically binds to and activates TLR4 (Pen et al., *J. Med. Chem.* 57(9): 3612-3622, 2014). In some embodiments, the TLR4 agonist is bacterial lipopolysaccharide (LPS) or a variant thereof. In some embodiments, the TLR4 agonist is monophosphoryl lipid A (MPL, MPLA, GLA, GLA-SE) (Ribi et al., *J. Immunol.* 6:567-572, 1984; Okemoto et al., *J. Immunol.* 176:1203-1208, 2006; Metzner et al., *Int. J. Cancer* 138: 1754-1764, 2016; Cauwelaert et al., *PLoS One* 11(1): e0146372, 2016). In some embodiments, the TLR agonist is AS15 or AS02b (Brichard et al., *Vaccine* 25(Suppl. 2):B61-B71, 2007; Kruit et al., *J. Clin. Oncol.* 26(Suppl): Abstract 9065, 2008). In some embodiments, the TLR agonist is an aminoalkyl glucosaminide 4-phosphate (e.g., RC-529, Ribi.529, E6020) or a variant thereof (Baldridge et al., *J. Endotoxin Res.* 8:453-458, 2002; Morefield et al., *Clin. Vaccine Immunol.* 14: 1499-1504, 2007). In some embodiments, the TLR agonist is picibanil (OK-432) (Hazim et al., *Med. J. Malaysia* 71(6):328-330, 2016; Tian et al., *Asian Pac J. Cancer Prev.* 16(11):4537-4542, 2015; Rebuffini et al., *Dent Rese. J.* 9(Suppl. 2):S192-S196, 2012). In some embodiments, the TLR4 agonist is *Spirulina* complex polysaccharide (Kwanishi et al., *Microbiol. Immunol.* 57:63-73, 2013). In some embodiments, the TLR4 agonist is chitohexaose or a variant thereof (Panda et al., 8:e1002717, 2012; Barman et al., *Cell Death Dis.* 7:e2224, 2016). In some embodiments, the TLR4 agonist is E5564 (Eritoran) (Eisai). In some embodiments, the TLR4 agonist is CRX-675 or CRX-527 (GSK).

TLR5 Agonists

In some embodiments, the TLR agonist binds and activates TLR5. In some embodiments, the TLR5 agonist is flagellin or a variant thereof (e.g., entolimod (CBLB502)) (Yoon et al., *Science* 335: 859-864, 2012; Fukuzawa et al., *J. Immunol.* 187:3831-3839, 2011; Brackett et al., *PNAS* 113(7):E874-E883, 2015; Leigh et al., *PLoS One* 9(1): e85587, 2014; Hossain et al., *Blood* 120:255, 2012). In some embodiments, the TLR5 agonist is flagellin HuHa (Vaxinate) or flagellin HuM2e (Vaxinate).

TLR7/8 Agonists

In some embodiments, the TLR agonist binds and activates TLR7/8 (e.g., TLR7 agonist, TLR8 agonist, or a TLR7 and TLR8 agonist). In some embodiments, the TLR7/8 agonist is ANA975 (isotorabine) (Anadys/Novartis), ANA773 (Anadys/Novartis), In some embodiments, the TLR7/8 agonist is an imidazoquinoline or a variant thereof (e.g., imiquimod (Aldara™ Kaspari et al., *British J. Dermatology* 147: 757-759, 2002; Smorlesi et al., *Gene Therapy* 12: 1324-133, 2005; Prins et al., *J. Immunol.* 176: 157-164, 2006; Shackleton et al., *Cancer Immun.* 4:9, 2004; Green et al., *Br. J. Dermatol.* 156(2):337-345, 2007; Geisse et al., *Am. Acad. Dermatol.* 50(5):722-733, 2004; Wolf et al., *Arch. Dermatol.* 139(3): 273-276, 2003), resiquimod (R848; Hemmi et al., *Nat. Immunol.* 3:196-200, 2002; Jurk et al., *Nat. Immunol.* 3:49, 2002; Rook et al., *Blood* 126(12):1452-1461, 2015; Dovedi et al., *Blood* 121: 251-259, 2013). In some embodiments, the TLR agonist is a synthetic imiadzoquinoline mimicking viral single stranded RNA (ssRNA) (852A) or a variant thereof (Dudek et al., *Clin. Cancer Res.* 13(23):7119-7125, 2007; Dummer et al., *Clin. Cancer Res.* 14(3):856-864, 2008; Weigel et al., *Am. J. Hematol.* 87(10):953-956, 2012; Geller et al., *Cancer Immunol. lmmunother.* 59(12):1877-1884, 2010; Inglefield et al., *J. Interferon Cytokine Res.* 28(4):253-263, 2008). In some embodiments, the TLR agonist is a small molecule. In some embodiments, the small molecule mimics viral ssRNA (e.g., motolimod (VTX-2337)) or a variant thereof (Dietsch et al., *Clin. Cancer Res.* 21(24):5445-5452, 2015; Northfelt et al., *Clin. Cancer Res.* 20(14):3683-3691, 2014; Lu et al., *Clin. Cancer Res.* 18(2): 499-509, 2012). In some embodiments, the small molecule is GS-9620 or a variant thereof (Bam et al., *Antimicrob Agents Chemother.* 61(1):e01369, 2016; Rebbapragada et al., *PLoS One* 11(1):e0146835, 2016; Gane et al., *J. Hepatol.* 63(2): 320-328, 2015; Fosdick et al., *J. Med. Chem.* 56(18): 7324-7333, 2013). In some embodiments, the small molecule is SC1 (Wiedemann et al., *Oncoimmunology* 5(7): e1189051, 2016; Hamm et al., *J. Immunol.* 6(4):257-265, 2009). In some embodiments, the small molecule is gardiquimod (Ma et al., *Cell. Mol. Immunol.* 7:381-388, 2010; Hjelm et al., *Hum. Vaccin. lmmunother.* 10(2): 410-416, 2014; Buitendijk et al., *AIDS Res. Hum. Retroviruses* 29(6):907-918, 2013), CL075 (Philbin et al., *J. Allergy Clin. Immunol.* 130:195-204, 2012; Dowling et al., *PLoS One* 8(3): e58164, 2013), CL097 (Gorden et al., *J. Immunol.* 174:1259-1268, 2005; Gorski et al., *Int. Immunol.* 18:1115, 2006; Levy et al., *Blood* 108:1284-1289, 2006; Wille-Reece et al., *J. Exp. Med.* 203: 1249-1258, 2006), loxoribine (Pope et al., *Cell Immunol.* 162:333, 1995; Heil et al., *Eur. J. Immunol.* 33:2987-2997, 2003; Lee et al., *PNAS* 100:6646-6651, 2003), or VTX-294 (Dowling et al., *PLoS One* 8(3): e58164, 2013). In some embodiments, the TLR7/8 agonist is IMO-9200. In some embodiments, the TLR7 agaonist is IPH-32XX (Innate Pharma).

TLR9 Agonists

In some embodiments, the TLR agonist binds and activates TLR9. In some embodiments, the TLR9 agonist is a synthetic oligonucleotide. In some embodiments, the synthetic oligonucleotide contains unmethylated CpG dinucleotide (CpG-ODN) (Krieg, *J. Clin. Invest* 117:1184-1194, 2007; Carpentier et al., *Neuro-oncol.* 8(1):60-66, 2006; Link et al., *J. Immunother.* 29(5): 558-568, 2006; Pashenkov et al., *J. Clin. Oncol.* 24(36): 5716-5724, 2006; Meng et al., *BMC Biotechnol.* 11:88, 2011). In some embodiments, the TLR9 agonist is PF-3512676 or a variant thereof (Hofmann et al., *J. Immunother.* 31(5):520-527, 2008; Molenkamp et al., *Clin. Caner. Res.* 14(14):4532-4542, 2008). In some embodiments, the TLR9 agonist is IMO-2055 (EMD1201801) or a variant thereof (Machiels et al., *Investig. New Drugs* 31:1207-1216, 2013). In some embodiments, the TLR9 agonist is DIMS0150 (Atreya et al., *J. Crohns Colitis* 10(11):1294-1302, 2016). In some embodiments, the TLR9 agonist is CpG7909 (Vaximmune) (Coley, GSK, Novartis, DARPA). In some embodiments, the TLR9 agonist is IMO-9200. In some embodiments, the TLR9 agonist is AVE0675 (Coley, Sanofi Aventis). In some embodiments, the TLR9 agonist is Amplivax (Idere).

Microbial Products as TLR Agonists

In some embodiments, the TLR agonist is a bacterial or viral component. In some embodiments, the TLR agonist is derived from the cell wall *Mycobacterium bovis* (BCG). In some embodiments, the *Mycobacterium bovis* cell wall component is a TLR2 and/or TLR4 agonist (e.g., SMP105 (Murata et al., *Cancer Sci.* 99:1435-1440, 2008; Miyauchi et al., *Drug Discov. Ther.* 6: 218-225, 2013; Tsuji et al., *Infect Immun.* 68: 6883-6890, 2000; Smith et al., *Cancer Immunol. Immunother.* 63(8):787-796, 2014). Additional examples of TLR agonists are known in the art.

TLR Antagonists

By the term "TLR antagonist" means an agent that decreases the binding of a TLR agonist to TLR4 or TLR9 expressed in a mammalian cell (e.g., a human cell). For example, a TLR antagonist can be a TLR4 antagonist. In other examples, a TLR antagonist is a TLR9 antagonist. Non-limiting examples of TLR antagonists are described in Fukata et al., *Mucosal Immunity* 6:451-463, 2013.

A non-limiting example of a TLR4 antagonist is 1A6 (Ungaro et al., *Am. J. Physiol. Gastrointest. Liver Physiol.* 296:G1167-G1179, 2009) or CRX-526 (Fort et al., *J. Immunol.* 174:6416-6423, 2005). Additional examples of TLR4 antagonists include eritoran tetrasodium (E5564) (Sun et al., *Investigative Ophthalmol. Visual Sci.* 50(3):1247-1254, 2009), small heat shock protein B8 (HSP22) (Roelofs et al., *J. Immunol.* 176(11):7021-7027, 2006), CRX-527 (Bazin et al., *Bioorganic Med. Chem. Letters* 18(2):5350-5354, 2008), E5564 (Kitazawa et al., *J. Gastroentrol. Hepatol.* 25(5): 1009-1012, 2010), IAXO-102 (Huggins et al., *Atherosclerosis* 242(2):563-570, 2015), AG-411 (Kondo et al., *Trends Immunol.* 33(9):449-458, 2012), CRX-52624 (Alderson et al., *J. Endotoxin Res.* 12(5):313-319, 2006), E5531 (Becker et al., *Toxicol. Appl. Pharmacol.* 207(2):269-275, 2005).

A non-limiting example of a TLR9 antagonist is adenoviral oligodeoxynucleotides (AV-ODN) (Obermeier et al., *Gastroenterology* 129:913-927, 2005). Additional examples of TLR9 antagonists include ODN 2088, ODN 4084-F, ODN INH-1, ODN INH-18, ODN TTAGGG (A151), and G-ODN (each commercially available from InvivoGen). In some embodiments, the TLR9 antagonist is CpG-ODN c41 (Li et al., *Vaccine* 29:2193-2198, 2011). In some embodiments, the TLR9 antagonist is COV08-0064 (Shaker et al., *Biochemical Pharmacol.* 112:90-101, 2016; Hoque et al., *J. Immunol.* 190(8):4297-4304, 2013); ODN 1585, ODN 1826, ODN 2395, and ODN 2088 (Boivin et al., *Antiviral Res.* 96(3):414-421, 2012); IMO-8400 (Zhu et al., *J. Immunol.* 188(1):119, 2012); IRS869 (Mandl et al., *Nature Med.* 14(10:1077-1087, 2008); IMO-3100 (Hennessy et al., *Nature Rev. Drug Discov.* 9(4):293-307, 2010); TTAGGG (Carvalho et al., *PLoS One* 6(11):e28256, 2011); and CpG ODN 2088 (David et al., *J. Neurotrauma* 31(21):1800-1806, 2014).

6. SMAD7 Inhibitors

The term "SMAD7 inhibitor" refers to an agent which decreases SMAD7 expression, decreases SMAD7's ability to decrease formation of Smad2/Smad4 complexes, and/or decreases the ability of SMAD7 to bind to TGF-β type I receptor. In some embodiments, the SMAD7 inhibitor decreases SMAD7 expression in a mammalian cell. In some embodiments, the SMAD7 inhibitor decreases SMAD7's ability to decrease formation of Smad2/Smad4 complexes in a mammalian cell. In some embodiments, the SMAD7 inhibitor decreases the ability of SMAD7 to bind to a TGF-β type I receptor in a mammalian cell. In some embodiments, the SMAD7 inhibitor decreases SMAD7 expression in a mammalian cell.

In some embodiments, a SMAD7 inhibitory agent is an inhibitory nucleic acid. In some embodiments, the inhibitory nucleic acid is an antisense nucleic acid, a small interfering RNA, or a microRNA. Examples of aspects of these different inhibitory nucleic acids are described below.

Inhibitory nucleic acids that can decrease the expression of SMAD7 expression in a mammalian cell include antisense nucleic acid molecules, i.e., nucleic acid molecules whose nucleotide sequence is complementary to all or part of SMAD7 mRNA. An antisense nucleic acid molecule can be complementary to all or part of a non-coding region of the coding strand of a nucleotide sequence encoding a SMAD7 protein. Non-coding regions (5' and 3' untranslated regions) are the 5' and 3' sequences that flank the coding region in a gene and are not translated into amino acids. Non-limiting examples of SMAD7 inhibitors that are antisense nucleic acids include mongersen (GED0301) (Monteleon et al., *N. Engl. J. Med.* 372:1104-1113, 2015) and Smad7-as (Kleiter et al., *J. Neuroimmunol.* 187(1-2):61-73, 2007; and Boirivant et al., *Gastroenterology* 131(6):1786-1798, 2006).

Another example of an inhibitory nucleic acid is a ribozyme that has specificity for a nucleic acid encoding a SMAD7 protein (e.g., specificity for a SMAD7 mRNA).

An inhibitory nucleic acid can also be a nucleic acid molecule that forms triple helical structures. For example, expression of a SMAD7 polypeptide can be inhibited by targeting nucleotide sequences complementary to the regulatory region of the gene encoding the SMAD7 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

An inhibitory nucleic acid can be a siRNA that decreases the level of a SMAD7 mRNA. Non-limiting examples of short interfering RNA (siRNA) that target nucleic acid that encodes SMAD7 are described in, e.g., Su et al., *Mol. Vis.* 18:1881-1884, 2012.

Inhibitory nucleic acids targeting SMAD7 also include microRNAs (e.g., miR-497 (Hu et al., *Am. J. Transl. Res.* 8(7): 3023-3031, 2016; Liu et al., *DNA Cell Biol.* 35(9): 521-529, 2016), miR-21 (Lin et al., *Cell Physiol. Biochem.* 38(6): 2152-2162, 2016; He et al., *Heart Vessels* 31(10): 1696-1708, 2016).

7. Inhibitory Agents of Janus Kinase (JAK) Activity and/or Expression

The term "JAK inhibitor" refers to an agent which decreases the expression of Janus kinase 1 (JAK1), JAK2, JAK3, or non-receptor protein tyrosine kinase 2 (TYK-2) and/or the kinase activity of at least one of JAK1, JAK2, JAK3, and TYK-2. In some embodiments, the JAK inhibitor decreases the expression of JAK1. In some embodiments, the JAK inhibitor decreases the expression of JAK2. In some embodiments, the JAK inhibitor decreases the expression of JAK3. In some embodiments, the JAK inhibitor decreases the expression of TYK-2.

In some embodiments, the JAK inhibitor decreases the kinase activity of JAK1. In some embodiments, the JAK inhibitor decreases the kinase activity of JAK2. In some embodiments, the JAK inhibitor decreases the kinase activity of JAK3. In some embodiments, the JAK inhibitor decreases the kinase activity of TYK-2. In some embodiments, the JAK inhibitor is a decreases the kinase activity of JAK1, JAK2, JAK3, and TYK2. In some embodiments, the JAK inhibitor decreases the kinase activity of two or more (e.g., 3 or 4) of: JAK1, JAK2, JAK3 and TYK2. In some embodiments, the JAK inhibitor decreases the kinase activity of a single JAK isoform (e.g., JAK1, JAK2, JAK3, or TYK2).

In some embodiments, the JAK inhibitor decreases the kinase activity of JAK1 and JAK2. In some embodiments, the JAK inhibitor decreases the kinase activity of JAK1 and JAK3. In some embodiments, the JAK inhibitor decreases the kinase activity of JAK2 and JAK3. In some embodiments, the JAK inhibitor decreases the kinase activity of JAK1, JAK2 and JAK3.

In some embodiments, a JAK inhibitory agent is an inhibitory nucleic acid or a small molecule. In some embodiments, the inhibitory nucleic acid is an antisense nucleic acid, a ribozyme, a small interfering RNA, a small hairpin RNA, or a microRNA. Examples of aspects of these different inhibitory nucleic acids are described below.

Inhibitory nucleic acids that can decrease the expression of JAK1, JAK2, JAK3, or TYK2 mRNA expression in a mammalian cell include antisense nucleic acid molecules, i.e., nucleic acid molecules whose nucleotide sequence is complementary to all or part of a JAK1, JAK2, JAK3, or TYK2 mRNA.

Inhibitory Nucleic Acids

An antisense nucleic acid molecule can be complementary to all or part of a non-coding region of the coding strand of a nucleotide sequence encoding a JAK1, JAK2, JAK3, or TYK2 protein. Non-coding regions (5' and 3' untranslated regions) are the 5' and 3' sequences that flank the coding region in a gene and are not translated into amino acids.

Another example of an inhibitory nucleic acid is a ribozyme that has specificity for a nucleic acid encoding a JAK1, JAK2, JAK3, or TYK2 protein (e.g., specificity for a JAK1, JAK2, JAK3, or TYK2 mRNA).

An inhibitory nucleic acid can also be a nucleic acid molecule that forms triple helical structures. For example, expression of a JAK1, JAK2, JAK3, or JAK4 polypeptide can be inhibited by targeting nucleotide sequences complementary to the regulatory region of the gene encoding the JAK1, JAK2, JAK3, or TYK2 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

An inhibitory nucleic acid can also be a siRNA that decreases the level of a JAK1, JAK2, JAK3, or TYK2 mRNA. Non-limiting examples of JAK inhibitors that are short interfering RNAs (siRNAs) are described in Cook et al., *Blood* 123:2826-2837, 2014. Non-limiting examples of JAK inhibitors that are short hairpin RNAs (shRNAs) are described in Koppikar et al., *Nature* 489(7414):155-159, 2012).

Small Molecules

In some embodiments, the JAK inhibitor is a small molecule. In some embodiments, the JAK inhibitory agent is a pan-JAK inhibitor (e.g., 3-O-methylthespesilactam (Li et al., *Biochem. Pharmacol.* 86(10):1411-8, 2013)).

In some embodiments, the JAK inhibitor is a JAK1 and JAK2 inhibitor. In some embodiments, the JAK1 and JAK2 inhibitor is ruxolitinib (Jakafi®, Jakavi®, INCB018424) (Harrison et al., *N. Engl. J. Med.* 366:787-798, 2012; Pieri et al., *Am. J. Hematol.* 92(2):187-195, 2017; Mackay-Wiggan et al., *JCI Insight* 1(15):e89790, 2016; Rudolph et al., *Leukemia* 30(10):2119-2123, 2016; Fuman et al., *Biomark Res.* 1(1):5, 2013), baricitinib (INCB028050, LY3009104) (Gras, *Drugs Today (Barc)* 52(10):543-550, 2016; Smolen et al., *Ann. Rheum. Dis.* 76(4):694-700, 2016; Kubo et al., *Expert. Rev. Clin. Immunol.* 12(9):911-919, 2016; Fridman et al., *J. Immunol.* 84(9):5298-5307, 2010), AZD1480 (Guschin et al., *EMBO J.* 14:1421-1429, 1995; Ioannidis et al., *J. Med. Chem.* 54: 262-276, 2011; Moisan et al., *Nat. Cell Biol.* 17(1):57-67, 2015; Qin et al., *J. Neurosci.* 36(18):5144059, 2016; Jiang et al., *Biochem. Biophys. Res. Commun.* 458(4): 908-912, 2015; Verstovsek et al., *Leuk. Res.* 39(2):157-163, 2015; Plimack et al., *Oncologist* 18(7): 819-820, 2013; Yan et al., *Oncotarget* 4(3):433-445, 2013), filgotinib (GLPG0634, G146034) (Vermeire et al., *Lancet* 389 (10066):266-275, 2017; Menet et al., *J. Med. Chem.* 57(22): 9323-9342, 2014; Van Rompaey et al., *J. Immunol.* 191(7): 3568-3577, 2013; Namour et al., *Clin. Pharmacokinet.* 54(8):859-874, 2015), momelotinib (GS-0387, CYT387) (Pardanani et al., *Leukemia* 23: 1441-1445, 2009; Gupta et al., *Haematologica* 102(1):94-102, 2017; Hu et al., *Mol. Pharm.* 13(2):689-697, 2016; Abubaker et al., *BMC Cancer* 14: 317, 2014; Durmus et al., *Pharmacol. Res.* 76:9-16, 2013; Pardanani et al., *Leukemia* 27(6): 1322-1327, 2013; Monaghan et al., *Leukemia* 25(12):1891-1899, 2011; Tyner et al., *Blood* 115(25):5232-5240, 2010).

In some embodiments, the JAK inhibitory agent is a JAK1 inhibitor (e.g., GSK2586184 (Kahl et al., *Lupus* 25(13): 1420-1430, 2016; Ludbrook et al., *Br. J. Dermatol.* 174(5): 985-995, 2016; van Vollenhoven et al., *Lupus* 24(6): 648-649, 2015), oclacitinib (PF03394197, Apoquel®) (Gonzales et al., *J. Vet. Pharmacol. Ther.* 37(4):317-324, 2014; Collard et al., *J. Vet. Pharmacol. Ther.* 37(3):279-285, 2014; Cosgrove et al., *Vet. Dermatol.* 24(6):587-597, 2013), upadacitinib (ABT494) (Kremer et al., *Arthritis Rheumatol.* 68(12): 2867-2877, 2016; Mohamed et al., *Clin. Pharmaco.* 55(12): 1547-1558, 2016), GLG0778 (O'Shea et al., *Ann. Rev. Med.* 66(1):311-28, 2015; Schwartz et al., *Nat. Rev. Rheum.* 12: 25-36, 2016), INCB039110 (Mascarenhas et al., *Haematologica* 102(2):327-335, 2017; Bissonnette et al., *J. Dermatolog. Treat.* 27(4):332-338, 2016; Rosenthal et al., *Exp. Opin. Pharmacother.* 15(9):1265-1276, 2014), PF04965842 (Gadina et al., *Curr. Opin. Rheumatol.* 26(2):237-243, 2014; Degryset et al., *J. Hematol. Oncol.* 8:91, 2015); SAR-20347 (Works et al., *J. Immunol.* 193(7):3278-3287, 2014)).

In some embodiments, the JAK inhibitory agent is a JAK2 inhibitor (e.g., CEP-33779 (Dugan et al., *J. Med. Chem.* 55(11):5243-5254, 2012; Seavey et al., *Mol. Cancer Ther.* 11(4):984-993, 2012; Stump et al., *Arthritis Res. Ther.* 13(2):R68, 2011), fedratinib (TG101348, SAR302503) (Pardanani et al., *J. Clin. Oncol.* 29:789-796, 2011; Jamieson et al., *J. Transl. Med.* 13:294, 2015; Zhang et al., *Oncotarget* 6(16):14329-14343, 2015; Wernig et al., *Blood* 105:4508-4515, 2008); lestaurtinib (CEP-701) (Hexnet et al., *Blood* 111:5663-5671, 2008; Santos et al., *Blood* 115: 1131-1136, 2010; Smith et al., *Blood* 103: 3669-3676, 2004; Hexner et al., *Leuk. Lymphoma.* 56(9):2543, 2015; Geyer et al., *Hematology* 17(Suppl1):5129-132, 2012; Diaz et al., *PLoS One* 6(4):e18856, 2011; Minturn et al., *Cancer Chemother. Pharmacol.* 68(4):1057-1065, 2011), AC-430 (O'Shea et al., *Immunity* 36(4):542-550, 2012; Patterson et al., *Clin. Exp. Immunol.* 176:1-10, 2014), pacritinib (SB1518) (Deeg et al., J. Clin. Oncol. 29: Abstract 6515, 2011; Verstovsek et al., J. Hematol. Oncol. 9(1):137, 2016; Chow et al., Onco Targets. Ther. 9:2655-2665, 2016; Komrokji et al., Blood 125(17): 2649-2655, 2015; Jayaraman et al., Drug Metab. Lett. 9(1): 28-47, 2015), BMS-911543 (Mace et al., Oncotarget 6(42): 44509-44522, 2015; Wan et al., ACS Med. Chem. Lett. 6(8):850-855, 2015; Purandare et al., Leukemia 26(2):280-288, 2012), XL019 (Verstovsek et al., Leuk. Res. 38(3):316-322, 2014; Forsyth et al., Bioorg. Med. Chem. Lett. 22(24): 7653-7658, 2012), INCB039110 (Mascarenhas et al., Haematologica 102(2):327-335, 2017; Bissonnette et al., J. Dermatol. Treat. 27(4):332-338, 2016), Gandotinib® (LY-2784544) (Ma et al., Blood Cancer J. 3:e109, 2013; Verstovsek et al., Blood 122: 665, 2013; Mitchell et al., Org. Process Res. Dev. 16(1):70-81. 2012); R723 (Shide et al., Blood 117(25): 6866-6875, 2011)); Z3 (Sayyah et al., Mol. Cancer. Ther. 7(8):2308-2318, 2008)) or a variant thereof.

In some embodiments, the JAK inhibitory agent is a JAK3 inhibitor (e.g., decernotinib (VX-509) (Elwood et al., J. Pharmacol. Exp. Ther. 2017; Genovese et al., Ann Rheum Dis. 75(11):1979-1983, 2016; Gadina et al., Arthritis Rheumatol. 68(1):31-34, 2016; Farmer et al., J. Med. Chem. 58(18):7195-7216, 2015; Fleischmann et al., Arthritis Rheumatol. 67(2):334-343, 2015; Mahajan et al., J. Pharmacol. 353(2):405-414, 2015), R348 or a variant thereof (Velotta et al., Transplantation 87(5):653-659, 2009; Deuse et al., Transplantation 85(6):885-892, 2008)). In some embodiments, the small molecule is R256 or a variant thereof (Ashino et al., J. Allergy Clin. Immunol. 133(4):1162-1174, 2014). In some embodiments, the small molecule is R333 or a variant thereof. In some embodiments, the small molecule is INCB047986 or a variant thereof (Norman, Exp. Opin. Investig. Drugs 23(8):1067-1077, 2014). In some embodiments, the small molecule is INCB16562 or a variant thereof (Koppikar et al., Blood 115(4):2919-2927, 2010; Li et al., Neoplasia 12(1):28-38, 2010). In some embodiments, the small molecule is NVP-BSK805 or a variant thereof (Ringel et al., Acta Haematol. 132(1):75-86, 2014; Baffert et al., Mol. Cancer. Ther. 9(7):1945-1955, 2010). In some embodiments, the small molecule is peficitinib (ASP015K, JNJ-54781532) or a variant thereof (Genovese et al., Arthritis Rheumatol., 2017; Ito et al., J. Pharmacol. Sci. 133(1):25-33, 2017; Cao et al. (2016) Clin. Pharmacol. Drug Dev. 5(6):435-449, 2016; Takeuchi et al., Ann. Rheum. Dis. 75(6):1057-1064, 2016). In some embodiments, the small molecule is tofacitinib (Xeljanz®, Jakvinus®, CP-690, 500) or a variant thereof (Ghoreschi et al., J. Immunol. 186(7): 4234-4243, 2011; Yoshida et al., Biochem. Biophys. Res. Commun 418(2):234-240, 2012; Calama et al., Pulm. Pharmacol. Ther. S1094-5539(16):30060-30068, 2017; Cutolo et al., J. Inflamm. Res. 6:129-137, 2013). In some embodiments, the small molecule is cucurbitacin I (JSI-124) or a variant thereof (Oi et al., Int. J. Oncol. 49(6):2275-2284, 2016; Qi et al., Am. J. Chin. Med. 43(2):337-347, 2015; Seo et al., Food Chem. Toxicol. 64:217-224, 2014). In some embodiments, the small molecule is CHZ868 or a variant thereof (Wu et al., Cancer Cell 28(1):29-41, 2015; Meyer et al., Cancer Cell 28(1):15-28, 2015).

In some embodiments, the small molecule is a TYK2 inhibitor (e.g., Masse et al., J. Immunol. 194(1):67, 2015; Menet, Pharm. Pat. Anal. 3(4):449-466, 2014; Liang et al., Euro. J. Med. Chem. 67: 175-187, 2013; Jang et al., Bioorg. Med. Chem. Lett. 25(18):3947-3952, 2015); U.S. Pat. Nos. 9,296,725 and 9,309,240; US 2013/0231340; and US 2016/0251376). In some embodiments, the TYK2 inhibitor is Ndi-031301 (Akahane et al., Blood 128:1596, 2016); BMS-986165 (Gillooly et al., 2016 ACR/ARHP Annual Meeting, Abstract 11L, 2016); SAR-20347 (Works et al., J. Immunol. 193(7):3278-3287, 2014); tyrphostin A1 (Ishizaki et al., Int. Immunol. 26(5):257-267, 2014); a triazolopyridine (US 2013/0143915); or a variant thereof.

Additional examples of JAK inhibitors that are small molecules are described in, e.g., Furomoto et al., BioDrugs 27(5):431-438, 2013; O'Shea et al., Ann. Rheum. Dis. 72(2): ii111-ii-115, 2013; Sonbol et al., Ther. Adv. Hematol. 4(1): 15-35, 2013; and Tanaka et al. (2015) J. Biochem. 158(3): 173-179, 2015.

In some embodiments, the JAK inhibitor is a pan-JAK inhibitor. As used herein, the term "pan-JAK inhibitor" is an agent that has an $IC_{50}$ of about 500 nM to 4 µM (e.g., about 500 nM to about 2 µM) for each of human JAK1, human JAK2, and human JAK3 isoforms, when the $IC_{50}$ is determined for each of wildtype human JAK1, wildtype human JAK2, and wildtype human JAK3 using similar assay conditions (e.g., the same assay conditions). In some embodiments, a pan-JAK inhibitor can be an agent that has an $IC_{50}$ for wildtype human JAK1, wildtype human JAK2, and wildtype human JAK3 that are within ±10% of each other, when each of the $IC_{50}$ values is assays under similar assay conditions (e.g., the same assay, e.g., the human wildtype JAK1, wildtype human JAK2, and wildtype human JAK3 assay described in Kim et al., J. Med. Chem. 58(18):7596-5602, 2015).

In some embodiments, the pan-JAK inhibitor is tofacitinib (Xeljanz®, Jakvinus®, tasocitinib, CP-690550; Yokoyama et al., J. Clin. Immunol. 33(3):586-594, 2013; and Thoma et al., J. Med. Chem. 54(1):284-288, 2011); cerdulatinib (PRT2070, Coffey et al. (2014) J. Pharmacol. Exp. Ther. 351(3):538-548, 2014; and Ma et al., Oncotarget 6(41):43881-43896, 2015); Pyridone 6 (P6; Nakagawa et al., J. Immunol. 187(9): 4611-4620, 2011; and Pedranzini et al., Cancer Res. 66(19):9714-9721, 2006); PF-06263276 (Jones et al. "Design and Synthesis of a Pan-Janus Kinase Inhibitor Clinical Candidate (PF-06263276) Suitable for Inhaled and Topical Delivery for the Treatment of Inflammatory Diseases of the Lungs and Skin", J. Med. Chem., 2017, 60 (2), pp 767-786); JAK inhibitor 1 (CAS 457081-03-07; JAKi; Wang et al., Antimicrob. Agents Chemother. 60(5):2834-48, 2016; Bordonaro et al., PLoS One 9:e115068, 2014; and Osorio et al., PLoS Pathogens 10(6):e1004165, 2014); or baricitinib (Olumiant; LY3009104; INCB-28050; and Hsu and Armstrong, J. Immunol. Res. Article ID 283617, 2014).

In some embodiments, the JAK inhibitor is a selective JAK1/JAK3 inhibitor. As used herein, the term "selective JAK1/JAK3 inhibitor" means an agent that has an $IC_{50}$ for wildtype human JAK1 and wildtype human JAK3, that are each at least 5-fold (e.g., at least 10-fold or at least 20-fold) lower than the $IC_{50}$ for wildtype human JAK2, when the $IC_{50}$ is determined for each of wildtype human JAK1, wildtype human JAK2, and wildtype human JAK3 using similar assay conditions (e.g., the same assay, e.g., the human wildtype JAK1, wildtype human JAK2, and wildtype human JAK3 assay described in Kim et al., J. Med. Chem. 58(18): 7596-5602, 2015).

In some embodiments, the JAK inhibitor is a selective JAK1 inhibitor. As used herein, the term "selective JAK1 inhibitor" means an agent that has an $IC_{50}$ for wildtype human JAK1 that is at least 10-fold (e.g., at least 20-fold) lower than each of the $IC_{50}$ for wildtype human JAK2 and the $IC_{50}$ for wildtype human JAK3 when measured using similar assay conditions (e.g., the same assay, e.g., the human wildtype JAK1, wildtype human JAK2, and wildtype human JAK3 assay described in Kim et al., J. Med. Chem. 58(18):7596-5602, 2015). In some embodiments, the JAK1 inhibitor is (31S,4R)-3-ethyl-4-(3H-imidazo[1,2-a]pyrrolo[2,3-e]pyrazin-8-yl)-N-(2,2,2-trifluoroethyl)pyrrolidine-1-carboxamide as disclosed in international patent application PCT/US2014/062145, incorporated by reference herein in its entirety.

In some embodiments, the JAK inhibitor is a selective JAK3 inhibitor. As used herein, the term "selective JAK3 inhibitor" means an agent that has an $IC_{50}$ for wildtype human JAK3 that is at least 10-fold (e.g., at least 20-fold) lower than each of the $IC_{50}$ for wildtype human JAK2 and the $IC_{50}$ for wildtype human JAK1 when measured using similar assay conditions (e.g., the same assay, e.g., the human wildtype JAK1, wildtype human JAK2, and wildtype human JAK3 assay described in Kim et al., *J. Med. Chem.* 58(18):7596-5602, 2015).

In some embodiments, the JAK inhibitor is a JAK1 and JAK3 inhibitor (e.g., a selective JAK1/JAK3 inhibitor). In some embodiments, the selective JAK1/JAK3 inhibitor is ZM 39923 (Brown et al., *Bioorg. Med. Chem. Lett.* 10(6):575-579, 2000; and Lai et al., *Chem. Biol.* 15(9):969-978, 2008); or peficitinib (ASP015K, JNJ-54781532; Ito et al., *J. Pharmacol. Sci.* 133(1):25-33, 2017; Cao et al., *Clin. Pharmacol. Drug Dev.* 5(6):435-449, 2016; Takeuchi et al., *Ann. Rheum. Dis.* 75(6):1057-1064, 2016); and Papp et al., *Br. J. Dermatol.* 173(3):767-776, 2015).

In some embodiments, the kinase inhibitor is TOP-1288 from TopiVert Pharma Ltd., which is described in "The Pharmacological Profile of TOP1288, a Narrow Spectrum Kinase Inhibitor (NSKI) in Clinical Development as an Anti-Inflammatory Treatment for Ulcerative Colitis" Foster, Martyn et al. *Gastroenterology*, Volume 152, Issue 5, S766.

8. Immunosuppressants

An "immunosuppressant" as disclosed is a low molecular weight immunosuppressants, with low molecular weight defined as <1500 Da, such as <1000 Da. The term "immunosuppressant" refers to a corticosteroid, a direct calcineurin inhibitor, a cytostatic, or a direct mTOR inhibitor that can suppress, restrict, or reduce the response of the immune system of a subject (e.g., one or both of the innate and adaptive immune system). In some examples, an immunosuppressant drug can decrease the level of activation and/or migration of a leukocyte (e.g., a T lymphocyte or a B lymphocyte, a macrophage, a mononcyte, a natural killer cell, a neutrophil, an eosinophil, or a basophil).

In some embodiments, the immunosuppressant is methotrexate, sulfasalazine, minocycline, or leflunomide) (Zink et al., *Annals of the Rheumatic Diseases* 64: 1274-1279, 2005).

Non-limiting examples of FDA-approved immunosuppressant drugs include: CellCept®, Rapamune®, Velcade®, Protopic®, Afinitor®, Arava®, Zenapax®, Sandimmune®, Advagraf®, Protopic®, Prograf®, Astagraf XL®, Elidel®, Myfortic®, Imuran®, and Azasan®.

Non-limiting examples of immunosuppressants are described in: Bakr et al., *Exp. Clin. Transplant* 15(Suppl. 1):16-23, 2017; Palmer et al., *Am. J. Kidney Dis.* S0272-6386(17):30036-7, 2017; Moran et al., *Semin Hematol* 49(3):270-276, 2012; Kamel et al., *World J. Transplant* 6(4):697-702, 2016; Shrestha et al., *Exp. Clin. Trasnplant.* 15(1):1-9, 2017; Liu et al., *PLoS One* 12(1):e0170246, 2017; Chon and Josephson, *Expert Rev. Clin. Immunol.* 7(3):273-281, 2011; Sollinger et al., *Transplantation* 60: 225-232, 1995; Salvardori et al., *Am. J. Transplant* 4: 231-236, 2004; Webster et al., *Cochrane Database Syst. Rev.* 19(2):CD004290, 2006; Nashan et al., *Transplantation* 78: 1332-1340, 2004; and Hardinger et al., *Am. J. Transplant* 2: 867-871, 2002.

Exemplary corticosteroids, cytostatics, calcineurin inhibitors, and mTOR inhibitors, are described below.

Corticosteroids

In some embodiments, the immunosuppressant drug is a corticosteroid. In some embodiments, the immunosuppressant drug can be a glucocorticosteroid (Coutinho et al., *Mol. Cell. Endocrinol.* 335(1): 2-13, 2011; van Staa et al., QJM 93: 105-111, 2000; Wust et al., *J. Immunol.* 180: 8434-8443, 2008) or glucocorticoid. Non-limiting examples of corticosteroids include: 11-dehydrocorticosterone (also called 11-oxocorticosterone and 17-deoxycortisone); 11-deoxycorticosterone (also called deoxycortone, desoxycortone, and 21-hydroxyprogesterone); 11-deoxycortisol (also called cortodoxone and cortexolone); 11-ketoprogesterone (also called 11-oxoprogesterone and ketogestin); 11β-hydroxypregnenolone, 11β-hydroxyprogesterone (also known as 21-deoxycorticosterone); 11β,17α,21-trihydroxypregnenolone, 17α,21-dihydroxypregnenolone; 17α-hydroxypregnenolone; 17α-hydroxyprogesterone; 18-hydroxy-11-deoxycorticosterone, 18-hydroxycorticosterone, 18-hydroxyprogesterone; 21-deoxycortisol; 21-doxycortisone; 21-hydroxypregnenolone (also known as prebediolone); aldosterone; corticosterone (also known as 17-deoxycortisol); cortisol (also known as hydrocortisone); cortisone; pregnenolone; progesterone; flugestone (also known as flurogestone); fluorometholone; medrysone (also known as hydroxymethylprogesterone); prebediolone acetate (also known as 21-acetoxypregnenolone); chlormadinone acetate; cyproterone acetate; medrogestone, medroxyprogesterone acetate; megastrol acetate; segesterone acetate; chloropredisone; cloprednol; difluprednate; fludrocortisone; fluocinolone; fluperolone; fluprednisolone; loteprednol; methylprednisolone; prednicarbate; prednisolone; prednisone; tixocortol; triamcinolone; methasone; alclometasone; beclomethasone; betamethasone; clobetasol; clobetasone; clocortolone; desoximetasone; dexamethasone; diflorasone; difluocortolone; fluclorolone; flumetasone; fluocortin; fluocortolone; fluprednidene; fluticasone; fluticasone furoate; halometasone; meprednisone; mometasone; mometasone furoate; paramethasone; prednylidene; rimexolone; ulobetasol (also known as halobetasol); amcinonide; budesonide; ciclesonide; deflazacort; desonide; formocortal (also known as fluoroformylone); fluclorolone acetonide (also known as flucloronide); fludroxycortide (also known as flurandrenolone and flurandrenolide); flunisolide; fluocinolone acetonide; fluocinonide; halcinonide; triamcinolone acetonide; cortivazol; and RU-28362. In some embodiments, the corticosteroid can be budesonide (e.g., Entocort®), dexamethasone, hydrocortisone (e.g., Cortef®, Cortenema®, and Proctofoam®), methylprednisolone, prednisolone (e.g., Orapred®), and prednisone. Additional examples of corticosteroids are known in the art.

Cytostatics

In some embodiments, the immunosuppressant drug is a cytostatic (e.g., an alkylating agent or an antimetabolite) (Mor et al., *BioDrugs* 8(6): 469-88, 1997). In some embodiments, the cytostatic is an antimetabolite drug (e.g., a folic acid analogue, (e.g., methotrexate), a purine analogue (e.g., azathioprine or mercaptopurine), a pyrimidine analogue (e.g., fluorouracil), a protein synthesis inhibitor, and cytotoxic antibiotics (e.g., dactinomycin, an anthracycline, mitomycin C, bleomycin, and mithramycin).

In some embodiments, the cytostatic can be an inhibitor of de novo purine synthesis (e.g., azathioprine (AZA, Imuran®, or Azasan®), mycophenolate mofetil (MMF, CellCept®), mycophenolate acid (MPA, Myfortic®), mizoribin, or methotrexate). In some embodiments, the cytostatic is an inhibitor of de novo pyrimidine synthesis (e.g., leflunomide, brequinar, or methotrexate).

In some embodiments, the cytostatic is an alkylating agent. In some embodiments, the alkylating agent is cyclophosphamide (Luznik et al., *Blood* 115(16): 3224-330, 2010). In some embodiments, the cytostatic is chlorambucil (Chen et al., *Clin. J. Am. Soc. Nephrol.* 8(5):787-796, 2013). In some embodiments, the cytostatic is mycophenolate mofetil (MMF, CellCept®) (Mor et al., *BioDrugs* 8(6):469-88, 1997). In some embodiments, the cytostatic is mycophenolate sodium (Albano et al., *Ann Transplant* 21: 250-261, 2016). In some embodiments, the cytostatic is azathioprine (Imuran®) (Maley et al., *J. Am. Acad Dermatol* 73(3): 439-43, 2015). In some embodiments, the immunosuppressant drug is 6-mercaptopurine (e.g., Purinethol®) (Kombluth et al., *Gastroenterologist* 2(3): 239-46, 1994). In some embodiments, the cytostatic is an inhibitor of inosine monophosphate dehydrogenase (e.g., VX-148; Jain et al., *J. Pharmacol Exper Ther* 302(2): 1272-1277, 2002).

In some embodiments, the cytostatic is a vitamin D analog (e.g., MC1288). See, e.g., Binderup et al., *Biochem. Pharmacol.* 42:1569-1575, 1991; and Johnsson et al., *Transplant Int.* 7:392-397, 1994).

In some embodiments, the cytostatic is brequinar (Cramer et al., *Transplantation* 53:303-308, 1992; Xu et al., *J. Immunol.* 160(2):846-53, 1998). In some embodiments, the cytostatic is mizoribine (Bredinin) (Aikawa et al., *Transplant. Proc.* 37(7):2947-50, 2005). In some embodiments, the cytostatic is gusperimus (Perenyei et al., *Rheumatology* (Oxford) 53(10):1732-1741, 2014).

Calcineurin Inhibitors

In some embodiments, the immunosuppressant is a calcineurin inhibitor. See, e.g., Beland et al., *Transpl. Int.* doi: 10.1111/tri 12934, 2017. In some embodiments, the calcineurin inhibitor is voclosporin (Luveniq®) (Busque et al., *Am. J. Transplant* 11(12):2675-2684, 2011). Voclosporin is a structural analog of cyclosporine A, with an additional single carbon extension that has a double-bond on one side chain. The binding affinities of voclosporin and cyclosporine A for cyclophilin are comparable; however, upon binding, the ethynyl side chain of voclosporin induces structural changes in calcineurin that may result in increased immunosuppressive activity relative to cyclosporine A. In some embodiments, the calcineurin inhibitor is cyclosporin A (e.g., gengraf, Neural®, or Sandimmune®) (Canafax and Ascher, *Clin. Pharm.* 2(6):515-524, 1983; Goring et al., *Curr. Med. Res. Opin.* 30(8): 1473-87, 2014), a cyclosporin analogue (see, e.g., Wenger et al., *Transplant Proc.* 18:213-218, 1986; Jeffery, *Clin. Biochem.* 24:15-21, 1991; Wenger, *Angewandte Chem.* 24:77-85, 1985; Lazarova et al., *Expert Opin. Ther. Patents* 13(9):1327-1332, 2003; Thomson, *Lancet* 338:195, 1991; U.S. Pat. Nos. 4,885,276, 7,511,013, 8,367,053, 8,481,483, 9,175,042, 9,200,038, and 9,226,927; US 2011/0092669, US 2006/0069016, US 2010/0708671, US 2012/0088734, WO 12/051193, WO 15/31381, WO 12/51194, and WO 12/051193), or a cyclosporin analogue (see, e.g., Rothbard et al., *Nature* 6(11):1253-1257, 2000; Cho et al., *Arch. Pharm. Res.* 27:662, 2004; US 2012/0157385; and U.S. Pat. No. 6,316,405). In some embodiments, the calcineurin inhibitor is tacrolimus, also called FK-506 or fujimycin (e.g., Hecoria®, Prograf®, Astagraf XL®, or Protopic®) (Helmschrott et al., *Drug Des. Devel. Ther.* 9:1217-1224, 2015; Bloom et al., *Clin. Transplant* 27(6):E685-93, 2013; Riva et al., *Fam. Hosp.* 41(2):150-168, 2017; McCormack, *Drugs* 74917, 2014); Cryan et al., *Biochem. Biophys. Res. Commun.* 180(2): 846-852, 1991; and Graf et al., *J. Clin. Rheumatol.* 9(5):310-315, 2003). In some embodiments, the calcineurin inhibitor is pimecrolimus (Enderl®) (Malachowski et al., *Pediatr. Dermatol.* 33(6): e360-e361, 2016; Eichenfiled and Eichenfield, *J. Pediatr.* 167(5):1171-1172, 2015). In some embodiments, the calcineurin inhibitor is Sanglifehrin A (SFA) (see, e.g., Hartel et al., *Scand. J. Immunol.* 63(1):26-34, 2006; Zhang et al., *J. Immunol.* 166(9):5611-5618, 2001; and Woltman et al., *J. Immunol.* 172(10): 6482-6489, 2004). Additional examples of calcineurin inhibitors are described in U.S. Pat. No. 7,041,283.

mTOR Inhibitors

In some embodiments, an mTOR inhibitor can be rapamycin (mTOR) inhibitor (e.g., sirolimus (Rapamune®), everolimus) (Forster et al., *Transplantation* 100(11):2461-2470, 2016; Opelz et al., *Nephrol. Dial. Transplant.* 31(8): 1360-1367, 2016; and Baroja-Mazo et al., *World J. Transplant.* 6(1): 183-92, 2016. Another example of an mTOR inhibitor is everolimus (e.g., Afinitor® or Zortress®). Another example of an mTOR inhibitor is dactolisib (also called BEZ235 or NVP-BEZ235). Another example of an mTOR inhibitor is temsirolimus (also called CCI-779) (e.g., Torisel®).

In some embodiments, the low molecular weight immunosuppressant is selected from (molecular weights are shown in parenthesis):

a. Cyclosporine (1202 Da);
b. Tacrolimus (804 Da);
c. Methotrexate (454 Da);
d. Sirolimus (914 Da);
e. Everolimus (958 Da);
f. Corticosteroids (360-430 Da);
g. Voclosporin (1214 Da);
h. Azathioprine (277 Da); and
i. Purinethol or 6-MP (6-mercaptopurine) (152 Da).

9. Live Biotherapeutics

In some embodiments, a live biotherapeutic (also can be referred to as a live cell therapy) can be detected and analyzed by the methods herein.

In some embodiments, the live biotherapeutic includes populations of live bacteria and/or yeast, optionally in combination with a prebiotic such as a non-digestible carbohydrate, oligosaccharide, or short polysaccharide (e.g., one or more of inulin, oligofructose, galactofructose, a galacto-oligosaccharides, or a xylo-oligosaccharide) and/or an antibiotic or antifungal agent, or both an antibiotic and antifungal agent. The bacteria or the yeast can be recombinant. The populations of live bacteria and/or yeast can be used to selectively alter beneficial species within the GI tract and/or to reduce detrimental species within the GI tract of the subject. See, for example, U.S. Patent Publication No. 20070258953; U.S. Patent Publication No. 20080003207; WO2007076534; WO2007136719; and WO2010099824.

In some embodiments, the live biotherapeutic includes one or more species of bacteria (e.g., two or more, three or more, four or more, five or more, six or more, or seven or more species) that are underrepresented in patients with IBD. The microbiotas of Crohn's disease (CD) and ulcerative colitis (UC) patients have statistically significant differences from those of non-inflammatory bowel disease controls, including a reduction in beneficial commensal bacteria in IBD patients relative to non-inflammatory bowel disease patients. For example, members of the phyla Firmicutes (e.g., *Clostridium* clusters XIVa and IV), Bacteroidetes (e.g., *Bacteroides fragilis* or *Bacteroides vulgatus*), and Actinobacteria (e.g., Coriobacteriaceae spp. or *Bifidobacterium adolescentis*) are reduced in CD and UC patients. See, e.g., Frank, et al., *Proc Nati Acad Sci USA*, 2007, 104: 13780-13785; Forbes, et al., *Front Microbiol.*, 2016; 7: 1081, and Nagao-Kitamoto and Kamada, *Immune Netw.* 2017 17(1): 1-12. *Clostridium* cluster XIVa includes species belonging to, for example, the *Clostridium, Ruminococcus, Lachnospira, Roseburia, Eubacterium, Coprococcus, Dorea*, and *Butyrivibrio* genera. *Clostridium* cluster IV includes species belonging to, for example, the *Clostridium, Ruminococcus, Eubacterium* and *Anaerofilum* genera. For example, *Faecalibacterium prausnitzii* (also referred to as *Bacteroides praussnitzii*), *Roseburia hominis, Eubacterium rectale, Dialister invisus, Ruminococcus albus, Ruminococcus callidus*, and *Ruminococcus bromii* are less abundant in CD or UC patients. See, e.g., Nagao-Kitamoto and Kamada, 2017, supra.

In some embodiments, the live biotherapeutic includes one or more species of bacteria (e.g., two or more, three or more, four or more, five or more, six or more, or seven or more species) that produce a desired product such as a short chain fatty acid (SOFA) (e.g., butyrate, acetate, or propionate) or induce production (e.g., *Clostridium butyricum* or *F. prausnitzii*) of an anti-inflammatory agent such as interleukin-10 in host cells. See, e.g., Hayashi, et al., *Cell Host Microbe* (2013) 13:711-722.

In some embodiments, the live biotherapeutic includes one or more species of bacteria (e.g., two or more, three or more, four or more, five or more, six or more, or seven or more species) that are underrepresented in patients with IBD and one or more probiotics (e.g., two or more, three or more, four or more, five or more, six or more, seven or more, or eight or more probiotics).

In some embodiments, the live biotherapeutic is FIN-524 (Finch Therapeutics, Somerville, Mass.), a cocktail of cultured microbial strains that are linked to positive outcomes among IBD patients.

In some embodiments, the live biotherapeutic includes one or more species of bacteria from a healthy donor (e.g., as collected from a stool sample). See, e.g., Vermeire, *J Crohns Colitis*, 2016, 10(4): 387-394. For example, the live biotherapeutic can be FIN-403 (Finch Therapeutics, Somerville, Mass.), a candidate for *Clostridium difficile* treatment.

In some embodiments, the live biotherapeutic includes one or more agents for inhibiting the growth of a fungus (e.g., a yeast such as a species of *Candida*). In some subjects with Crohn's disease, the bacterial species of *E. coli* and *Serratia marcescens* and the yeast species *Candida tropicalis* are found at higher concentrations versus that of healthy relatives, indicating that the bacteria and fungus may interact in the intestines. In some embodiments, the agent inhibiting the growth of a fungus (i.e., an anti-fungal agent) is amphotericin B, an echinocandin such as Caspofungin, Micafungin, or Anidulafungin, or an extended-spectrum triazole. In some embodiments, the therapeutic includes about 2.5 mg/L of Amphotericin B.

In some embodiments, the live biotherapeutic is a bacteriophage or prophage (i.e., the genetic material of a bacteriophage incorporated into the genome of a bacterium or existing as an extrachromosomal plasmid of the bacterium, and able to produce phages if specifically activated). The bacteriophage can be lytic or lysogenic. In some embodiments, the bacteriophage can infect bacteria commonly found in the GI tract. For example, the bacteriophage can infect one or more, two or more, three or more, four or more, five or more, six or more, seven or more, eight or more, nine or more, or ten or more species of bacteria within the GI tract. See, for example, Wang, et al., *Inflamm Bowel Dis.*, 2015; 21(6): 1419-1427. In some embodiments, the bacteriophage can be lytic bacteriophage and infect one or more detrimental bacterial species in the GI tract to reduce the detrimental species in the GI tract. For example, the bacteriophage can infect two or more, three or more, four or more, five or more, six or more, or seven or more detrimental bacterial species. In some embodiments, bacteriophage can be a member of the families from the order Caudovirales such as Siphoviridae, Myroviridae, Podoviridae, or Microviridae. See, e.g., Babickova and Gardlik, *World J. Gastroentrol.* 2015; 21(40):11321-11330. In some embodiments, the bacteriophage can include one or more of bacteriophage K (such as ATCC strain 19685-B I), bacteriophage 17 (such as ATCC strain 23361-B I), and Stab8. See, e.g., WO2016172380A1. In some embodiments, the live biotherapeutic includes one or more bacteriophages, and one or more probiotics or prebiotics, optionally in combination with an antibiotic.

In some embodiments, the live biotherapeutic can include bacteriophage or prophage that are genetically modified to produce one or more products that are anti-inflammatory and/or that can enhance intestinal barrier function.

In some embodiments, the live biotherapeutic includes regulatory T cells (Treg cells). Autologous Treg cells can be prepared by isolating peripheral blood mononuclear cells (PBMCs) from the subject's blood and then expanding ova-specific T cells by culturing the PBMCs in the presence of ovalbumin using *Drosophila* derived artificial antigen presenting cells transfected with specific stimulatory molecules. See, e.g., Brun, et al., *Int Immunopharmacol.*, 2009, 9(5):609-13. T cells can be cloned and Ova-Treg clones can be selected based on an ovalbumin-specific IL-10 production. A phase 1/2a study in 20 patients showed that a single injection of antigen-specific (ovalbumin) Treg cells was safe in CD and about 40% of the patients show a clinical response after treatment. See, e.g., Neurath, 2014, supra; and Desreumaux, et al., *Gastroenterology*, 2012, 143:1207-1217.

In some embodiments, the live biotherapeutic can be bacteriophage or bacteria carrying plasmids that encode a targeted antimicrobial. A targeted antimicrobial can include RNA-guided nucleases (RGNs) targeting specific DNA sequences within a target bacteria. For example, a targeted antimicrobial can couple a phage vector with the CRISPR (clustered regularly interspaced short palindromic repeats)/Cas system (e.g., the biological nanobots from Eligo Bioscience (Eligobiotics)). The biological nanobots can be composed of a capsid from a bacteriophage virus (modified to not multiply) that infect targeted bacteria and deliver the CRISPR/Cas9 system into the targeted bacteria, resulting in the targeted bacteria being killed by cleavage of the bacterial genome by Cas9 enzyme within a predetermined pathogenic sequence. See, for example, WO2017/009399A1 and Citorik, et al., *Nat Biotechnol.*, 2014, 32(11): 1141-1145.

In some embodiments, the live biotherapeutic can comprise stem cells. The term "stem cell" is used herein to refer to a cell that is capable of differentiating into a two or more different cell types. As used herein, the term "a stem cell" may refer to one or more stem cells.

In some embodiments, the stem cells can be hematopoietic stem cells (HSC) capable of differentiating into different types of blood cells, including myeloid and lymphoid lineages of blood cells. HSC can be obtained from bone marrow, cord blood, or peripheral blood, and are commonly used for bone marrow transfusions in combination with chemotherapy to restart the immune system. HSC are $CD34^+$ cells. Cell-surface markers can be identified by any suitable conventional technique, including, for example, positive selection using monoclonal antibodies against cell-surface markers.

In some embodiments, the stem cells are capable of differentiating into two or more different cell types other than blood cells. In some embodiments, the stem cells are capable of differentiating into cells of each of the three embryonic germ layers (i.e., endoderm, ectoderm, and mesoderm). As used herein, "capable of differentiating" means that a given cell, or its progeny, can proceed to a differentiated phenotype under the appropriate culture conditions. The capacity of the cells to differentiate into at least two cell types can be assayed by methods known in the art.

Non-limiting examples of stem cells include embryonic stem cells or adult stem cells such as mesenchymal stem cells (MSC) (also can be referred to as mesenchymal stromal cells) or other multipotent stem cells; endothelial progenitor cells; stem cells from a particular tissue or organ such as intestinal stem cells, adipose stem cells, or testes stem cells; or induced pluripotent stem cells (iPSC). In some embodiments, stem cells from a particular tissue also can be classified as MSC.

In some embodiments, the stem cells are MSC, which can differentiate into bone, muscle, cartilage, or adipose type cells. MSC can down-regulate inflammation and have a strong immunoregulatory potential. MSC can be obtained from various tissues, including from, for example, bone marrow, placenta, amniotic fluid, Wharton's jelly, amniotic membrane, chorionic villi, umbilical cord, umbilical cord blood, adipose tissue, dental pulp, synovial membrane, or peripheral blood. Depending on the source of MSC and the stemness (i.e., multipotency), the MSC can express a variety of different markers, including, for example, one or more of CD105, CD73, CD90, CD13, CD29, CD44, CD10, Stro-1, CD271, SSEA-4, CD146, CD49f, CD349, GD2, 3G5, SSEA-3, SISD2, Stro-4, MSCA-1, CD56, CD200, PODXI, Sox11, or TM4SF1 (e.g., 2 or more, 3 or more, 4 or more, 5 or more, 6 or more, 7 or more, 8 or more, 9 or more, or 10 or more of such markers), and lack expression of one or more of CD45, CD34, CD14, CD19, and HLA-DR (e.g., lack expression of two or more, three or more, four or more, or five or more such markers). In some embodiments, MSC can express CD105, CD73, and CD90. In some embodiments, MSC can express CD105, CD73, CD90, CD13, CD29, CD44, and CD10. In some embodiments, MSC can express CD105, CD73, and CD90 and one or more stemness markers such as Stro-1, CD271, SSEA-4, CD146, CD49f, CD349, GD2, 3G5, SSEA-3. SISD2, Stro-4, MSCA-1, CD56, CD200, PODXI, Sox11, or TM4SF1. In some embodiments, MSC can express CD105, CD73, CD90, CD13, CD29, CD44, and CD10 and one or more stemness markers such as Stro-1, CD271, SSEA-4, CD146, CD49f, CD349, GD2, 3G5, SSEA-3. SISD2, Stro-4, MSCA-1, CD56, CD200, PODXI, Sox11, or TM4SF1. See, e.g., Lv, et al., Stem Cells, 2014, 32:1408-1419.

Intestinal stem cells (ISC) can be positive for one or more biomarkers such as Musashi-1 (Msi-1), Ascl2, Bmi-1, Doublecortin and Ca2+/calmodulin-dependent kinase-like 1 (DCAMKL1), and Leucin-rich repeat-containing G-protein-coupled receptor 5 (Lgr5). See, e.g., Mohamed, et al., Cytotechnology, 2015 67(2): 177-189.

In some embodiments, MSCs are commercially available. See, e.g. Prochymal® from Osiris Therapeutics.

In some embodiments, the stem cells can be PF-05285401 cells (Multistem® cells), which are human stem cells obtained from adult bone marrow or other nonembryonic tissue sources. Multistem® cells are commercially available from Athersys Inc.

In some embodiments, the stem cells can be autologous adipose derived stem cells such as Cx401 cells.

In some embodiments, the stem cells can be human iPSCs, which can be generated from adult somatic cells (e.g., fibroblasts, keratinocytes, dental pulp cells, cord blood, or peripheral blood mononuclear cells) or MSC. iPSCs can be generated using retroviral or non-retroviral methods. See, for example, Loh, et al., Blood 2009, 113: 5476-5479, Okita, et al., Nat Methods. 2011, 8(5):409-12, or Okita, et al., Stem Cells, 2013, 31(3): 458-466. In some embodiments, p53 suppression and nontransforming L-Myc can be used to generate human induced pluripotent stem cells (iPSCs) with episomal plasmid vectors encoding OCT3/4, SOX2, KLF4, and LIN28. In some embodiments, adult somatic cells can be transduced with retroviruses encoding four pluripotency factors (SOX2, KLF4, c-MYC, and OCT4). Fully reprogrammed iPSCs have similar properties to embryonic stem cells (ESCs). Patient's cells can be used to derive iPSCs, which can then be induced to undergo differentiation into various types of somatic cells, all with the same genetic information as the patient. See, Azizeh-Mitra, et al., Stem Cells Int. 2016; 6180487. In other embodiments, allogenic cells are used to derive iPSCs.

In some embodiments, the stem cells can be intestinal stem cells (ISC), which can differentiate into intestinal cell subtypes such as goblet cells, Paneth cells, and enterocytes. ISC are located at the crypt base within the intestine and can be positive for one or more markers such as Musashi-1 (Msi-1), Ascl2, Bmi-1, Doublecortin and $Ca^{2+}$/calmodulin-dependent kinase-like 1 (DCAMKL1), and Leucin-rich repeat-containing G-protein-coupled receptor 5 (Lgr5). See, e.g., Mohamed, et al., Cytotechnology, 2015 67(2): 177-189. In addition, ISC or crypts can be used to produce intestinal organoids using a biodegradable scaffold (e.g., poly-glycolic acid), growth factors such as epidermal growth factor (EGF), R-spondin, Jagged-1 peptide, or Noggin, and extracellular matrix. In some embodiments, mesenchymal cells are included in the culture to support the growth. The intestinal organoid can include a central lumen lined by a villus-like epithelium. See, e.g., US20160287670A1 and WO2015183920A2. Pre-clinical studies have demonstrated the intestinal organoid efficacy in differentiating into all GI cell lineages and regrowing parts of the intestine, muscle layer included. See, Agopian, et al., J Gastrointest Surg., 2009, 13(5):971-82; Kuratnik and Giardina, Biochem Pharmacol., 2013, 85:1721-1726; and Belchior et al., Semin Pediatr Surg., 2014, 23:141-149.

In some embodiments, the stem cells can be allogeneic adipose-derived stem cells (ASC) such as ALLO-ASC cells or expanded ASC (eASC) (e.g., Cx601 cells). See, for example, Panes et al., Lancet; 2016, 388: 1281-90; and U.S. Patent Publication No. 20120020930. Cx601 cells are commercially available from TiGenix. Cx601 cells have been used for treating complex perianal fistulas in Crohn's disease patients. ALLO-ASC cells are commercially available from Anterogen Co., Ltd., and have been used for treating Crohn's disease.

In some embodiments, the stem cells can be human placental derived stem cells such as PDA-001 cells from Celgene. PDA-001 cells are a culture-expanded, plastic adherent, undifferentiated in vitro cell population that express the nominal phenotype CD34−, CD10+, CD105+ and CD200+. PDA-001 cells constitutively express moderate levels of HLA Class I and undetectable levels of HLA Class II, and they do not express the co-stimulatory molecules CD80 and CD86. PDA-001 is genetically stable, displaying a normal diploid chromosome count, normal karyotype and exhibit normal senescence after prolonged in vitro culture. See, e.g., U.S. Pat. No. 8,916,146.

10. Carbohydrate Sulfotransferase 15 (CHST15) Inhibitor

The term "CHST15 inhibitor" refers to an agent which decreases CHST15 activity and/or expression. A non-limiting example of CHST15 activity is the transfer of sulfate from 3'-phosphoadenosine 5'-phosphosulfate (PAPS) to the C-6 hydroxyl group of the GalNAc 4-sulfate residue of chondroitin sulfate A.

In some embodiments, a CHST15 inhibitor can be an inhibitory nucleic acid. In some embodiments, the inhibitory nucleic acid can be an antisense nucleic acid, a ribozyme, and a small interfering RNA (siRNA). Examples of aspects of these different oligonucleotides are described below. Any of the examples of inhibitory nucleic acids that can decrease expression of CHST15 mRNA in a mammalian cell can be synthesized in vitro.

Inhibitory nucleic acids that can decrease the expression of CHST15 mRNA expression in a mammalian cell include antisense nucleic acid molecules, i.e., nucleic acid molecules whose nucleotide sequence is complementary to all or part of an CHST15 mRNA.

An antisense nucleic acid molecule can be complementary to all or part of a non-coding region of the coding strand of a nucleotide sequence encoding a CHST15 protein. Non-coding regions (5' and 3' untranslated regions) are the 5' and 3' sequences that flank the coding region in a gene and are not translated into amino acids.

Another example of an inhibitory nucleic acid is a ribozyme that has specificity for a nucleic acid encoding a CHST15 protein (e.g., specificity for a CHST15 mRNA).

An inhibitory nucleic acid can also be a nucleic acid molecule that forms triple helical structures. For example, expression of a CHST15 polypeptide can be inhibited by targeting nucleotide sequences complementary to the regulatory region of the gene encoding the CHST15 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

An inhibitory nucleic acid is a siRNA molecule that decreases the level of a CHST15 mRNA. Non-limiting examples of siRNAs targeting CHST15 are described in Takakura et al., *PLosOne* 10(12):e0142981, 2015; Watanabe et al., *Cell Signal.* 27(7):1517-1524, 2015; Suzuki et al., *PLos One* 11(7):e0158967, 2016; Kai et al., *Mol. Ther. Nucl. Acids* 6: 163-172, 2017). In some embodiments, the siRNA targeting CHST15 is STNM01 or a variant thereof (Suzuki et al., *J. Crohns Colitis* 11(2):221-228, 2017; Atreya et al., *Eur. Crohn's Colitis Organisation*, Congress Abstract DOP073, 2017; US 2016/0355818; US 2017/0067058; US 2016/0348118). Additional examples of CHST15 inhibitory nucleic acids are described in US 2015/0337313 and US 2016/0348118, which are incorporated by reference in its entirety.

11. IL-1 Inhibitors

The term "IL-1 inhibitor" refers to an agent that decreases the expression of an IL-1 cytokine or an IL-1 receptor and/or decreases the ability of an IL-1 cytokine to bind specifically to an IL-1 receptor. Non-limiting examples of IL-1 cytokines include IL1α, IL1β, IL-18, IL-36α, IL-36β, IL-36γ, IL-38, and IL-33. In some examples, an IL-1 cytokine is IL1α. In some examples, an IL-1 cytokine is IL-1β.

As is known in the art, IL-1α and IL-1β each binds to a complex of IL-1R1 and IL1RAP proteins; IL-18 binds to IL-18Rα, IL-36α, IL-36β, and IL-36γ each binds to a complex of IL-1RL2 and IL-1 RAP proteins; and IL-33 binds to a complex of IL1RL1 and IL1RAP proteins. IL-1Rα is an endogenous soluble protein that decreases the ability of IL-1α and IL-1β to bind to their receptor (e.g., a complex of IL-1R1 and IL1RAP proteins). IL-36Rα is an endogenous soluble protein that decreases the ability of IL-36α, IL-36β, and IL-36γ to bind to their receptor (e.g., a complex of IL-1RL2 and IL-1RAP proteins).

In some embodiments, the IL-1 inhibitor mimics native human interleukin 1 receptor antagonist (IL1-Ra).

In some embodiments, the IL-1 inhibitor targets IL-1α. In some embodiments, the IL-1 inhibitor targets IL-1β. In some embodiments, the IL-1 inhibitor targets one or both of IL-1R1 and IL1RAP. For example, an IL-1 inhibitor can decrease the expression of IL-1α and/or decrease the ability of IL-1α to bind to its receptor (e.g., a complex of IL-1R1 and IL1RAP proteins). In another example, an IL-1 inhibitor can decrease the expression of IL-1β and/or decrease the ability of IL-1β to binds to its receptor (e.g., a complex of IL-1R1 and IL1RAP proteins). In some embodiments, an IL-1 inhibitor can decrease the expression of one or both of IL-1R1 and IL1RAP.

In some embodiments, the IL-1 inhibitor targets IL-18. In some embodiments, the IL-1 inhibitor targets IL-18Rα. In some embodiments, the IL-1 inhibitor decreases the ability of IL-18 to bind to its receptor (e.g., IL-18Rα). In some embodiments, the IL-1 inhibitor decreases the expression of IL-18. In some embodiments, the IL-1 inhibitor decreases the expression of IL-18Rα.

In some embodiments, the IL-1 inhibitor targets one or more (e.g., two or three) of IL-36α, IL-36β, and IL-36γ. In some embodiments, the IL-1 inhibitor targets one or both of IL-1RL2 and IL-1 RAP. In some embodiments, the IL-1 inhibitor decreases the expression of one or more (e.g., two or three) of IL-36α, IL-36β, and IL-36γ. In some embodiments, the IL-1 inhibitor decreases the expression of one or both of IL-1RL2 and IL-1RAP proteins. In some embodiments, the IL-1 inhibitor decreases the ability of IL-36α to bind to its receptor (e.g., a complex including IL-1RL2 and IL-1RAP). In some examples, the IL-1 inhibitor decreases the ability of IL-36β to bind to its receptor (e.g., a complex including IL-1RL2 and IL-1RAP). In some examples, the IL-1 inhibitor decreases the ability of IL-36γ to bind to its receptor (e.g., a complex including IL-1RL2 and IL-1RAP).

In some embodiments, the IL-1 inhibitor targets IL-33. In some embodiments, the IL-1 inhibitor targets one or both of IL1RL1 and IL1RAP. In some embodiments, the IL-1 inhibitor decreases the expression of IL-33. In some embodiments, the IL-1 inhibitor decreases the expression of one or both of IL1RL1 and IL1RAP. In some embodiments, the IL-1 inhibitor decreases the ability of IL-33 to bind to its receptor (e.g., a complex of IL1RL1 and IL1RAP proteins).

In some embodiments, an IL-1 inhibitory agent is an inhibitory nucleic acid, an antibody or fragment thereof, or a fusion protein. In some embodiments, the inhibitory nucleic acid is an antisense nucleic acid, a ribozyme, or a small interfering RNA.

Inhibitory Nucleic Acids

Inhibitory nucleic acids that can decrease the expression of IL-1α, IL-1β, IL-18, IL-36α, IL-36β, IL-36γ, IL-38, IL-33, IL-1R1, IL1RAP, IL-18Rα, IL-1RL2, or IL1RL1 mRNA in a mammalian cell include antisense nucleic acid molecules, i.e., nucleic acid molecules whose nucleotide sequence is complementary to all or part of an IL-1α, IL-16, IL-18, IL-36α, IL-36β, IL-36γ, IL-38, IL-33, IL-1R1, IL1RAP, IL-18Rα, IL-1RL2, or IL1RL1 mRNA.

An antisense nucleic acid molecule can be complementary to all or part of a non-coding region of the coding strand of a nucleotide sequence encoding an IL-1α, IL-1β, IL-18, IL-36α, IL-36β, IL-36γ, IL-38, IL-33, IL-1R1, IL1RAP, IL-18Rα, IL-1RL2, or IL1RL1 protein. Non-coding regions (5' and 3' untranslated regions) are the 5' and 3' sequences that flank the coding region in a gene and are not translated into amino acids.

Another example of an inhibitory nucleic acid is a ribozyme that has specificity for a nucleic acid encoding an IL-1α, IL-1β, IL-18, IL-36α, IL-366, IL-36γ, IL-38, IL-33, IL-1R1, IL1RAP, IL-18Rα, IL-1RL2, or IL1RL1 protein (e.g., specificity for an IL-1α, IL-1β, IL-18, IL-36α, IL-36β, IL-36γ, IL-38, IL-33, IL-1R1, IL1RAP, IL-18Rα, IL-1RL2, or IL1RL1 mRNA).

An inhibitory nucleic acid can also be a nucleic acid molecule that forms triple helical structures. For example, expression of an IL-1α, IL-1β, IL-18, IL-36α, IL-36β, IL-36γ, IL-38, IL-33, IL-1R1, IL1RAP, IL-18Rα, IL-1RL2, or IL1RL1 polypeptide can be inhibited by targeting nucleotide sequences complementary to the regulatory region of the gene encoding the IL-1α, IL-1β, IL-18, IL-36α, IL-36β, IL-36γ, IL-38, IL-33, IL-1R1, IL1RAP, IL-18Rα, IL-1RL2, or IL1RL1 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

An inhibitory nucleic acid can be a siRNA that decreases the expression of an IL-1α, IL-1β, IL-18, IL-36α, IL-36β, IL-36γ, IL-38, IL-33, IL-1R1, IL1RAP, IL-18Rα, IL-1RL2, or IL1RL1 mRNA.

As described herein, inhibitory nucleic acids preferentially bind (e.g., hybridize) to a nucleic acid encoding IL-1α, IL-1β, IL-18, IL-36α, IL-36β, IL-36γ, IL-38, IL-33, IL-1R1, IL1RAP, IL-18Rα, IL-1RL2, or IL1RL1 protein to treat allergic diseases (e.g., asthma (Corren et al., *N. Engl. J. Med.* 365: 1088-1098, 2011)), radiation lung injury (Chung et al., *Sci. Rep.* 6: 39714, 2016), ulcerative colitis (Hua et al., *Br. J. Clin. Pharmacol.* 80:101-109, 2015), dermatitis (Guttman-Yassky et al., *Exp. Opin. Biol. Ther.* 13(4):1517, 2013), and chronic obstructive pulmonary disease (COPD) (Walsh et al. (2010) *Curr. Opin. Investig Drugs* 11(11):1305-1312, 2010).

Exemplary IL-1 inhibitors that are antisense nucleic acids are described in Yilmaz-Elis et al., *Mol. Ther. Nucleic Acids* 2(1): e66, 2013; Lu et al., *J. Immunol.* 190(12): 6570-6578, 2013), small interfering RNA (siRNA) (e.g., Ma et al., *Ann. Hepatol.* 15(2): 260-270, 2016), or combinations thereof.

Antibodies

In some embodiments, the IL-1 inhibitor is an antibody or an antigen-binding fragment thereof (e.g., a Fab or a scFv). In some embodiments, an antibody or antigen-binding fragment described herein binds specifically to any one of IL-1α, IL-1β, IL-18, IL-36α, IL-36β, IL-36γ, IL-38, and IL-33. In some embodiments, an antibody or antigen-binding fragment of an antibody described herein can bind specifically to one or both of IL-1R1 and IL1RAP. In some embodiments, an antibody or antigen-binding fragment of an antibody described herein can bind specifically to IL-18Rα. In some embodiments, an antibody or antigen-binding fragment of an antibody described herein can bind specifically to one or both of IL1RL1 and IL1RAP. In some embodiments, an antibody or antigen-binding fragment of an antibody described herein can bind to one or both of IL-1RL2 and IL-1RAP.

In some embodiments, the IL-1 inhibitor is canakinumab (ACZ885, Ilaris®) (Dhimolea, *MAbs* 2(1): 3-13, 2010; Yokota et al., *Clin. Exp. Rheumatol.* 2016; Torene et al., *Ann. Rheum. Dis.* 76(1):303-309, 2017; Gram, *Curr. Opin. Chem. Biol.* 32:1-9, 2016; Kontzias et al., *Semin. Arthritis Rheum* 42(2):201-205, 2012). In some embodiments, the IL-1 inhibitor is anakinra (Kineret®; Beynon et al., *J. Clin. Rheumatol.* 23(3):181-183, 2017; Stanam et al., *Oncotarget* 7(46):76087-76100, 2016; Nayki et al., *J. Obstet Gynaecol. Res.* 42(11):1525-1533, 2016; Greenhalgh et al., *Dis. Model Mech.* 5(6):823-833, 2012), or a variant thereof. In some embodiments, the IL-1 inhibitor is gevokizumab (XOMA 052; Knicklebein et al., *Am. J. Ophthalmol.* 172:104-110, 2016; Roubille et al., *Atherosclerosis* 236(2):277-285, 2014; Issafras et al., *J. Pharmacol. Exp. Ther.* 348(1):202-215, 2014; Handa et al., *Obesity* 21(2):306-309, 2013; Geiler et al., *Curr. Opin. Mol. Ther.* 12(6):755-769, 2010), LY2189102 (Bihorel et al., *AAPS J.* 16(5):1009-1117, 2014; Sloan-Lancaster et al., *Diabetes Care* 36(8):2239-2246, 2013), MABp1 (Hickish et al., *Lancey Oncol.* 18(2):192-201, 2017; Timper et al., *J. Diabetes Complications* 29(7): 955-960, 2015), CDP-484 (Braddock et al., *Drug Discov.* 3:330-339, 2004), or a variant thereof (Dinarello et al., *Nat. Rev. Drug Discov.* 11(8): 633-652, 2012).

Further teachings of IL-1 inhibitors that are antibodies or antigen-binding fragments thereof are described in U.S. Pat. Nos. 5,075,222; 7,446,175; 7,531,166; 7,744,865; 7,829,093; and 8,273,350; US 2016/0326243; US 2016/0194392, and US 2009/0191187, each of which is incorporated by reference in its entirety.

Fusion Proteins or Soluble Receptors

In some embodiments, the IL-1 inhibitor is a fusion protein or a soluble receptor. For example, a fusion can include an extracellular domain of any one of IL-1R1, IL1RAP, IL-18Rα, IL-1RL2, and IL1RL1 fused to a partner amino acid sequence (e.g., a stabilizing domain, e.g., an IgG Fc region, e.g., a human IgG Fc region). In some embodiments, the IL-1 inhibitor is a soluble version of one or both of IL-1RL1 and IL1RAP. In some embodiments, the IL-1 inhibitor is a soluble version of IL-18Rα. In some embodiments, the IL-1 inhibitor is a soluble version of one or both of IL-1RL2 and IL-1RAP.

In some embodiments, the IL-1 inhibitor is a fusion protein comprising or consisting of rilonacept (IL-1 Trap, Arcalyst®) (see, e.g., Kapur & Bonk, P. T. 34(3):138-141, 2009; Church et al., *Biologics* 2(4):733-742, 2008; McDermott, *Drugs Today (Barc)* 45(6):423-430, 2009). In some embodiments, the IL-1 inhibitor is a fusion protein that is chimeric (e.g., EBI-005 (Isunakinra®) (Furfine et al., *Invest. Ophthalmol. Vis. Sci.* 53(14):2340-2340, 2012; Goldstein et al., *Eye Contact Lens* 41(3):145-155, 2015; Goldstein et al., *Eye Contact Lens*, 2016)).

In some embodiments, the IL-1 inhibitor is a soluble receptor that comprises or consists of sIL-1RI and/or sIL-1RII (Svenson et al., *Eur. J. Immunol.* 25(10): 2842-2850, 1995).

Endogenous IL-I Inhibitor Peptides

In some embodiments, the IL-1 inhibitor can be an endogenous ligand or an active fragment thereof, e.g., IL-1Ra or IL-36Ra. IL-1Rα is an endogenous soluble protein that decreases the ability of IL-1α and IL-1β to bind to their receptor (e.g., a complex of IL-1R1 and IL1RAP proteins). IL-36Rα is an endogenous soluble protein that decreases the ability of IL-36α, IL-36β, and IL-36γ to bind to their receptor (e.g., a complex of IL-1RL2 and IL-1RAP proteins).

12. IL-13 Inhibitors

The term "IL-13 inhibitor" refers to an agent which decreases IL-13 expression and/or decreases the binding of IL-13 to an IL-13 receptor. In some embodiments, the IL-13 inhibitor decreases the ability of IL-13 to bind an IL-13 receptor (e.g., a complex including IL-4Rα and IL-13Rα1, or a complex including IL-13Rα1 and IL-13Rα2).

In some embodiments, the IL-13 inhibitor targets the IL-4Rα subunit. In some embodiments, the IL-13 inhibitor targets the IL-13Rα1. In some embodiments, the IL-13 inhibitor targets IL-13Rα2. In some embodiments, the IL-13 inhibitor targets an IL-13 receptor including IL-4Rα and IL-13Rα1. In some embodiments, the IL-13 inhibitor targets an IL-13 receptor including IL-13Rα1 and IL-13Rα2. In some embodiments, the IL-13 inhibitor targets IL-13.

In some embodiments, an IL-13 inhibitor is an inhibitory nucleic acid, an antibody or an antigen-binding fragment thereof, or a fusion protein. In some embodiments, the inhibitory nucleic acid can be an antisense nucleic acid, a ribozyme, a small interfering RNA, a small hairpin RNA, or a microRNA. Examples of aspects of these different inhibitory nucleic acids are described below.

Inhibitory nucleic acids that can decrease the expression of IL-13, IL-13Rα1, IL-13Rα2, or IL-4Rα mRNA expression in a mammalian cell include antisense nucleic acid molecules, i.e., nucleic acid molecules whose nucleotide sequence is complementary to all or part of an IL-13, IL-13Rα1, IL-13Rα2, or IL-Ra mRNA.

An antisense nucleic acid molecule can be complementary to all or part of a non-coding region of the coding strand of a nucleotide sequence encoding an IL-13, IL-13Rα1, IL-13Rα2, or IL-4Rα protein. Non-coding regions (5' and 3' untranslated regions) are the 5' and the 3' sequences that flank the coding region in a gene and are not translated into amino acids. Non-limiting examples of an inhibitors that are antisense nucleic acids are described in Kim et al., *J. Gene Med.* 11(1):26-37, 2009; and Mousavi et al., *Iran J. Allergy Asthma Immunol.* 2(3):131-137, 2003.

Another example of an inhibitory nucleic acid is a ribozyme that has specificity for a nucleic acid encoding an IL-13, IL-13Rα1, IL-13Rα2, or IL-4Rα (e.g., specificity for an IL-13, IL-13Rα1, IL-13Rα2, or IL-4Rα mRNA).

An inhibitory nucleic acid can also be a nucleic acid molecule that forms triple helical structures. For example, expression of an IL-13, IL-13Rα1, IL-13Rα2, or IL-4Rα polypeptide can be inhibiting by targeting nucleotide sequences complementary to the regulatory region of the gene encoding the IL-13, IL-13Rα1, IL-13Rα2, or IL-4Rα polypeptide (e.g., the promoter and/or enhancer, e.g., a sequence that is at least 1 kb, 2 kb, 3 kb, 4 kb, or 5 kb upstream of the transcription initiation start site) to form triple helical structures that prevent transcription of the gene in target cells.

As described herein, inhibitory nucleic acid preferentially bind (e.g., hybridize) to a nucleic acid encoding IL-13, IL-13Rα1, IL-13Rα2, or IL-4Rα protein to treat allergic diseases (e.g., asthma (Corren et al., *N. Engl. J. Med.* 365:1088-1098, 2011), radiation lung injury (Chung et al., *Sci. Rep.* 6:39714, 2016), ulcerative colitis (Hua et al., *Br. J. Clin. Pharmacol.* 80:101-109, 2015), dermatitis (Guttman-Yassky et al., *Exp. Opin. Biol. Ther.* 13(4):1517, 2013), and chronic obstructive pulmonary disease (COPD) (Walsh et al., *Curr. Opin. Investig. Drugs* 11(11):1305-1312, 2010)).

An inhibitory nucleic acid can be a siRNA molecule that decreases the level of an IL-13, IL-13Rα1, IL-13Rα2, or IL-4Rα mRNA. Non-limiting examples of siRNAs that are IL-13 inhibitors are described in Lively et al., *J. Allergy Clin. Immunol.* 121(1):88-94, 2008. Non-limiting examples of short hairpin RNA (shRNA) that are IL-13 inhibitors are described in Lee et al., *Hum. Gene Ther.* 22(5):577-586, 2011, and Shilovskiy et al., *Eur. Resp. J.* 42:P523, 2013.

In some embodiments, an inhibitory nucleic acid can be a microRNA. Non-limiting examples of microRNAs that are IL-13 inhibitors are let-7 (Kumar et al., *J. Allergy Clin. Immunol.* 128(5):1077-1085, 2011).

Antibodies

In some embodiments, the IL-13 inhibitor is an antibody or an antigen-binding fragment thereof (e.g., a Fab or a scFv). In some embodiments, an antibody or antigen-binding fragment described herein binds specifically to any one of IL-13, IL-13Rα1, IL-13Rα2, or IL-4Rα, or a combination thereof. In some embodiments, an antibody or antigen-binding fragment of an antibody described herein can bind specifically to IL-13. In some embodiments, an antibody or antigen-binding fragment of an antibody described herein can bind specifically to an IL-13 receptor (e.g., a complex including IL-4Rα and IL-13Rα1, or a complex including IL-13Rα1 and IL-13Rα2).

In some embodiments, the IL-13 inhibitor is a monoclonal antibody (Bagnasco et al., *Int. Arch. Allergy Immunol.* 170:122-131, 2016). In some embodiments, the IL-13 inhibitor is QAX576 (Novartis) or an antigen-binding fragment thereof (see, e.g., Kariyawasam et al., 892 *New Treatment Approaches for Asthma and Allergy* San Diego, 2009; Rothenberg et al., *J. Allergy Clin. Immunol.* 135:500-507, 2015). In some embodiments, the IL-13 inhibitor is ABT-308 (Abbott) or an antigen-binding fragment thereof (see, e.g., Ying et al., American Thoracic Society 2010 International Conference, May 14-19, 2010, New Orleans; Abstract A6644). In some embodiments, the IL-13 inhibitor is CNTO-5825 (Centocore) or an antigen-binding fragment thereof (see, e.g., van Hartingsveldt et al., *British J. Clin. Pharmacol.* 75:1289-1298, 2013). In some embodiments, the IL-13 inhibitor is dupilumab (REGN668/SAR231893) or an antigen-binding fragment thereof (see, e.g., Simpson et al., *N. Eng. J. Med.* 375:2335-2348, 2016; Thaci et al., *Lancet* 387:40-52, 2016). In some embodiments, the IL-13 inhibitor is AMG317 (Amgen) or an antigen-binding fragment thereof (Polosa et al., *Drug Discovery Today* 17:591-599, 2012; Holgate, *British J. Clinical Pharmacol.* 76:277-291, 2013). In some embodiments, the IL-13 inhibitor is an antibody that specifically binds to IL-13Rα1 (see, e.g., U.S. Pat. No. 7,807,158; WO 96/29417; WO 97/15663; and WO 03/080675).

In some embodiments, the IL-13 inhibitor is a humanized monoclonal antibody (e.g., lebrikizumab (TNX-650) (Thomson et al., *Biologics* 6:329-335, 2012; and Hanania et al., *Thorax* 70(8):748-756, 2015). In some embodiments, the IL-13 inhibitor is an anti-IL-13 antibody, e.g., GSK679586 or a variant thereof (Hodsman et al., *Br. J. Clin. Pharmacol.* 75(1):118-128, 2013; and De Boever et al., *J. Allergy Clin. Immunol.* 133(4):989-996, 2014). In some embodiments, the IL-13 inhibitor is tralokinumab (CAT-354) or a variant thereof (Brightling et al., *Lancet* 3(9): 692-701, 2015; Walsh et al. (2010) *Curr. Opin. Investig. Drugs* 11(11):1305-1312, 2010; Piper et al., *Euro. Resp. J.* 41:330-338, 2013; May et al., *Br. J. Pharmacol.* 166(1): 177-193, 2012; Singh et al., *BMC Pulm Med.* 10:3, 2010; Blanchard et al., *Clin. Exp. Allergy* 35(8): 1096-1103, 2005). In some embodiments, the 11-13 inhibitor is anrukinzumab (IMA-638) (Hua et al., *Br.*

J. Clin. Pharmacol. 80: 101-109, 2015; Reinisch et al., Gut 64(6): 894-900, 2015; Gauvreau et al., Am. J. Respir. Crit. Care Med. 183(8):1007-1014, 2011; Bree et al., J. Allergy Clin. Immunol. 119(5):1251-1257, 2007). Further teachings of IL-13 inhibitors that are antibodies or antigen-binding fragments thereof are described in U.S. Pat. Nos. 8,067,199; 7,910,708; 8,221,752; 8,388,965; 8,399,630; and 8,734,801; US 2014/0341913; US 2015/0259411; US 2016/0075777; US 2016/0130339, US 2011/0243928, and US 2014/0105897 each of which is incorporated by reference in its entirety.

Fusion Proteins

In some embodiments, the IL-13 inhibitor is a fusion protein or a soluble antagonist. In some embodiments, the fusion protein comprises a soluble fragment of a receptor of IL-13 (e.g., a soluble fragment of a complex including IL-13Rα1 and IL-4Rα, a soluble fragment of a complex including IL-13Rα1 and IL-13Rα2, a soluble fragment of IL-13Rα1, a soluble fragment of IL-13Rα2, or soluble fragment of IL-4Rα). In some embodiments, the fusion protein comprises an extracellular domain of a receptor of IL-13 (e.g., a fusion protein including an extracellular domain of both IL-13Rα1 and IL-4Rα, a fusion protein including an extracellular domain of both IL-13Rα1 and IL-13Rα2, a fusion protein including an extracellular domain of IL-13Rα1, a fusion protein including an extracellular domain of IL-13Rα2, or a fusion protein including an extracellular domain of IL-4Rα).

In some embodiments, the fusion protein comprises or consists of sIL-13Rα2-Fc (see, e.g., Chiaramonte et al., J. Clin. Invest. 104(6):777-785, 1999; Kasaian et al., Am. J. Respir. Cell. Mol. Biol. 36(3):368-376, 2007; Miyahara et al., J. Allergy Clin. Immunol. 118(5):1110-1116, 2006; Rahaman et al., Cancer Res. 62(4):1103-1109, 2002; incorporated by reference herein). In some embodiments, the fusion protein comprises or consists of an IL-13 fusion cytotoxin (e.g., IL-13/diphtheria toxin fusion protein (Li et al., Protein Eng. 15(5):419-427, 2002), IL-13-PE38QQR (IL-13-PE) (Blease et al. (2001) J. Immunol. 167(11):6583-6592, 2001; and Husain et al., J. Neuro-Oncol. 65(1):37-48, 2003)).

13. IL-10 and IL-10 Receptor Agonists

The term "IL-10 receptor agonist" is any molecule that binds to and activates a receptor for IL-10 expressed on a mammalian cell or a nucleic acid that encodes any such molecule. A receptor for IL-10 can include, e.g., a complex of two IL-10 receptor-1 (IL-10R1) proteins and two IL-10 receptor 2 (IL-10R2) proteins. In some examples, an IL-10 receptor agonist is an antibody or an antigen-binding antibody fragment that specifically binds to and activates a receptor for IL-10 (e.g., a human receptor for IL-10). In some examples, an IL-10 receptor agonist is a recombinant IL-10 (e.g., human recombinant IL-10). In some examples, an IL-10 receptor agonist is a pegylated recombinant IL-10 (e.g., pegylated recombinant human IL-10). In some examples, an IL-10 receptor agonist is a fusion protein. In some examples, an IL-10 receptor agonist is an IL-10 peptide mimetic.

Further teachings of IL-1 inhibitors that are antibodies or antigen-binding fragments thereof are described in U.S. Pat. Nos. 5,075,222; 7,446,175; 7,531,166; 7,744,865; 7,829,093; and 8,273,350; US 2016/0326243; US 2016/0194392, and US 2009/0191187, each of which is incorporated by reference in its entirety.

Recombinant IL-10

In some examples, an IL-10 receptor agonist is a recombinant IL-10 protein. In some examples, a recombinant IL-10 protein has an amino acid sequence that is identical to a human IL-10 protein. Non-limiting commercial sources of recombinant human IL-10 protein are available from Peprotech (Rocky Hill, N.J.), Novus Biologicals (Littleton, Colo.), Stemcell™ Technologies (Cambridge, Mass.), Millipore Sigma (Billerica, Mass.), and R&D Systems (Minneapolis, Minn.). In some examples, a recombinant human IL-10 protein can be Tenovil™ (Schering Corporation).

In some examples, a recombinant IL-10 protein is a functional fragment of human IL-10 protein. In some examples, a functional fragment of human IL-10 is a fragment of a human IL-10 protein that is able to specifically bind to and activate a human receptor of IL-10. A functional fragment of a human IL-10 protein can have one, two, three, four, five, six, seven, eight, nine, ten, eleven, twelve, thirteen, fourteen, fifteen, sixteen, seventeen, eighteen, nineteen, or twenty amino acids removed from the N- and/or C-terminus of the wildtype mature human IL-10 protein. In some embodiments, the recombinant human IL-10 can include a sequence that is at least 80% identical (e.g., at least 82% identical, at least 84% identical, at least 86% identical, at least 88% identical, at least 90% identical, at least 92% identical, at least 94% identical, at least 95% identical, at least 96% identical, at least 98% identical, or at least 99% identical) to the sequence of wildtype, mature human IL-10, and is able to specifically bind to and activate a human receptor of IL-10. Mutation of amino acids that are not conserved between different mammalian species is less likely to have a negative effect on the activity of a recombinant IL-10 protein.

In some embodiments, the IL-10 receptor agonist is rhuIL-10 (Tenovil) or a variant thereof. See, e.g., McHutchison et al., J. Interferon Cytokine Res. 1:1265-1270, 1999; Rosenblum et al., Regul. Toxicol. Pharmacol. 35:56-71, 2002; Schreiber et al., Gastroenterology 119(6):1461-1472, 2000; Maini et al., Arthritis Rheum. 40(Suppl):224, 1997.

Exemplary methods of making a recombinant human IL-10 are described in Pajkrt et al., J. Immunol. 158: 3971-3977, 1997). Additional exemplary methods of making recombinant IL-10 are described herein and are known in the art.

In some embodiments, a recombinant IL-10 is a pegylated recombinant IL-10 (e.g., pegylated recombinant human IL-10) (e.g., a 5 kDa N-terminally PEGylated form of IL-10, AM0010) (Infante et al., ASCO Meeting Abstracts 33(15_suppl):3017, 2015; Chan et al., PLoS One 11(6): e0156229, 2016; Mumm et al., Cancer Cell 20(6):781-796, 2011; Teng et al., Cancer Cell 20(6):691-693, 2011; U.S. Pat. Nos. 8,691,205; 8,865,652; 9,259,478; and 9,364,517; and U.S. Patent Application Publication Nos. 2008/0081031; 2009/0214471; 2011/0250163; 2011/0091419; 2014/0227223; 2015/0079031; 2015/0086505; 2016/0193352; 2016/0367689; 2016/0375101; and 2016/0166647).

In some embodiments, a recombinant IL-10 is a stabilized isoform of a recombinant IL-10. In some embodiments, the stabilized isoform of a recombinant IL-10 is a viral IL-10 protein (e.g., a human cytomegalovirus IL10 (e.g., cmv-IL10, LA-cmv-IL-10 (e.g., Lin et al., Virus Res. 131(2):213-223, 2008; Jenkins et al., J. Virol. 78(3):1440-1447, 2004; Kotenko et al., Proc. Natl. Acad. Sci. U.S.A. 97(4):1695-1700, 2000; Jones et al., Proc. Natl. Acad. Sci. U.S.A. 99(14):9404-9409, 2002) or a latency-associated viral IL-10 protein (e.g., Poole et al., J. Virol. 88(24):13947-13955, 2014).

In some embodiments, the recombinant IL-10 is a mammalian IL-10 homolog (see, e.g., WO 00/073457). In some embodiments, a mammalian IL-10 homolog is BCRF1, an EBV homolog of human IL-10, also known as viral IL-10, or a variant thereof (Liu et al., *J. Immunol.* 158(2):604-613, 1997).

Fusion Proteins

In some embodiments, the IL-10 receptor agonist is a fusion protein. In some embodiments, the fusion protein comprises the amino acid sequence of an IL-10 protein (or a functional fragment thereof) and a fusion partner (e.g., an Fc region (e.g., human IgG Fc) or human serum albumin). In some embodiments the fusion partner can be an antibody or an antigen-binding antibody fragment (e.g., an scFv) that targets IL-10 receptor agonist to an inflamed tissue. In some embodiments, the antibody or antigen-binding fragment that is a fusion partner can bind specifically, or preferentially, to inflamed gastrointestinal cells by, e.g., CD69. In some embodiments, an IL-10 receptor agonist that is a fusion protein can be, e.g., F8-IL-10, such as Dekavil (Philogen).

In some embodiments, the fusion protein is a L19-IL-10 fusion protein, a HyHEL10-IL-10 fusion protein, or a variant thereof. See, e.g., Trachsel et al., *Arthritis Res. Ther.* 9(1):R9, 2007, and Walmsley et al., *Arthritis Rheum.* 39: 495-503, 1996.

IL-10 Peptide Mimetic

In some embodiments, the IL-10 receptor agonist is an IL-10 peptide mimetic. A non-limiting example of an IL-10 peptide mimetic is IT 9302 or a variant thereof (Osman et al., *Surgery* 124(3):584-92, 1998; Lopez et al., *Immunobiology* 216(10):1117-1126, 2011). Additional examples of IL-10 peptide mimetics are described in DeWitt, *Nature Biotech.* 17:214, 1999, and Reineke et al., *Nature Biotech.* 17:271-275, 1999.

Antibodies

In some embodiments, the IL-10 receptor agonist is an antibody or an antigen-binding antibody fragment that binds to and activates an IL-10 receptor (e.g., a human IL-10 receptor). In some embodiments, the antibody or antigen-binding antibody fragment that specifically binds to an epitope on IL-10R-1 protein (e.g., human IL-10R-1 protein). In some embodiments, the antibody or antigen-binding antibody fragment that specifically binds to an epitope on IL-10R-2 protein (e.g., a human IL-10R-2 protein). In some embodiments, the antibody or the antigen-binding antibody fragment that specifically binds to an epitope on IL-10R-1 and IL-10R-2 proteins (e.g., human IL-10R-1 and human IL-10R-2 proteins).

In some embodiments, the IL-10 receptor agonist is an antibody (e.g., F8-IL10 (also known as DEKAVIL) or a variant thereof (see, e.g., Schwager et al., *Arthritis Res. Ther.* 11(5):R142, 2009; Franz et al., *Int. J. Cardiol.* 195:311-322, 2015; Galeazzi et al., *Isr. Med. Assoc. J.* 16(10):666, 2014).

Cells Producing a Recombinant IL-10

In some embodiments, a recombinant cell (e.g., a recombinant mammalian cell) secretes a recombinant IL-10 (e.g., any of the recombinant IL-10 proteins described herein). In some embodiments, a cell (e.g., a mammalian cell) secretes IL-10 (e.g., human IL-10). In some embodiments, the mammalian cell can be a mammalian cell obtained from the subject, after the introduction of a nucleic acid encoding the recombinant IL-10 (e.g., any of the recombinant IL-10 proteins described herein) into the cell obtained from the subject.

In some examples, the recombinant mammalian cell can be a Chinese Hamster Ovary (CHO) cell, a B cell, a CD8$^+$ T cell, a dendritic cell, a keratinocyte or an epithelial cell. See, e.g., Mosser et al., *Immunol. Rev.* 226:205-218, 2009; Fillatreau et al., *Nat. Rev. Immunol.* 8:391-397, 2008; Ryan et al., *Crit. Rev. Immunol.* 27:15-32, 2007; Moore et al., *Annu. Rev. Immunol.* 19:683-765, 2001. In some embodiments, the recombinant mammalian cell can be a mesenchymal stem cell (e.g., Gupte et al., *Biomed. J.* 40(1):49-54, 2017).

Nucleic Acids and Vectors the Encode an IL-10 Receptor Agonist

In some examples, an IL-10 receptor agonist can be a nucleic acid (e.g., a vector) that includes a sequence encoding an IL-10 receptor agonist (e.g., any of the IL-10 proteins described herein). In some embodiments, the nucleic acid includes a sequence encoding IL-10 (e.g., human IL-10). In some embodiments, the nucleic acid includes a sequence encoding a recombinant IL-10 (e.g., a recombinant human IL-10).

The nucleic acid can be, e.g., a vector. In some embodiments, a vector can be a viral vector (e.g., an adenovirus vector, a herpes virus vector, a baculovirus vector, or a retrovirus vector). A vector can also be, e.g., a plasmid or a cosmid. Additional examples of vectors are known in the art. A vector can include a promoter sequence operably linked to the sequence encoding an IL-10 receptor agonist (e.g., any of the recombinant IL-10 proteins described herein).

A non-limiting example of a composition including a nucleic acid that encodes an IL-10 receptor agonist is XT-150 (Xalud Therapeutics).

Additional Examples of IL-10 Receptor Agonists

In some embodiments, the recombinant cell is a recombinant Gram-positive bacterial cell (e.g., a genetically modified *Lactococcus lactis* (LL-Thy12) (see, e.g., Steidler et al., *Science* 289:1352-1355, 2000; Braat et al., *Clin. Gastroenterol. Heptal.* 4:754-759, 2006). In some embodiments, the recombinant cell is a recombinant Gram-negative bacterial cell (e.g., a *Shigella flexneri* cell) that secretes an IL-10 receptor agonist (e.g., a recombinant IL-10 protein) (Chamekh et al., *J. Immunol.* 180(6): 4292-4298, 2008).

In some embodiments, the IL-10 receptor agonist is a cell (e.g., a *Clostridium butyricum* cell) that induces IL-10 production and secretion by a different cell (e.g., a macrophage) (e.g., Hayashi et al., *Cell Host Microbe* 13:711-722, 2013). In some embodiments, the IL-10 receptor agonist is a recombinant bacterial cell (e.g., a *Lactobacillus acidophilus* cell) that is deficient in lipoteichoic acid and induces IL-10 production and secretion by a different cell (e.g., a dendritic cell) (e.g., Mohamadzadeh et al., *Proc. Natl. Acad. Sci. U.S.A.* 108(Suppl. 1):4623-4630, 2011; Konstantinov et al., *Proc. Natl. Acad. Sci. U.S.A.* 105(49):19474-9, 2008). In some embodiments, the IL-10 receptor agonist is a bacterial cell or a fragment of a bacterial cell that is maintained in the supernatant that induces IL-10 secretion in a different cell (e.g., an immune cell) (e.g., a *Faecalibacterium prausnitzii* cell or a *Faecalibacterium prausnitzii* supernatant) (see, e.g., Sokol et al., *Proc. Natl. Acad. Sci. U.S.A.* 105(43):16731-16736, 2008).

Additional examples of other IL-10 receptor agonists are described in, e.g., U.S. Pat. No. 6,936,586; WO 96/01318; WO 91/00349; WO 13/130913; each incorporated in its entirety herein.

14. Glatiramer Acetate

Glatiramer acetate, formerly known as copolymer-1, consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecule weight of glatiramer acetate is 4,700-11,000 daltons.

Chemically, glatiramer acetate is designated L-glutamic acid polymer with L-alanine, L-lysine and L-tyrosine, acetate (salt). The CAS number for glatiramer acetate is CAS-147245-92-9. The IUPAC name for glatiramer acetate is acetic acid; (2S)-2-amino-3-(4-hydroxyphenyl)propanoic acid; (2S)-2-aminopentanedioic acid; (2S)-2-aminopropanoic acid; (2S)-2,6-diaminohexanoic acid.

Glatiramer acetate is marketed as the active ingredient of Copaxone® by Teva Pharmaceuticals Ltd., Israel. Copaxone® is a clear, colorless to slightly yellow, sterile, nonpyrogenic solution. Each 1 mL of Copaxone® solution contains 20 mg or 40 mg of glatiramer acetate and 40 mg of mannitol. The pH of Copaxone® solution is approximately 5.5 to 7.0. Copaxone® 20 mg/mL is an FDA-approved product. Copaxone® 40 mg/mL in a prefilled syringe was developed as a newer formulation of the active ingredient glatiramer acetate.

Glatiramer acetate is known as being useful for the treatment of inflammatory and autoimmune diseases, in addition to its uses for treating multiple sclerosis, see, e.g., U.S. Pat. Nos. 7,033,582, 7,053,043, 7,074,580, 7,279,172, and 7,425,332, hereby incorporated by reference in their entirety. Glatiramer acetate has been shown to therapeutically reduce inflammation and ameliorate the pathological manifestations of inflammatory bowel disease (IBD) in numerous murine models (see, e.g., Aharoni et al., *J. of Pharmacology and Experimental Therapeutics* 318:68-78, 2006; Yao et al., *Eur. J. Immunol.* 43:125-136, 2013; and Yablecovitch et al., *J. of Pharmacology and Experimental Therapeutics* 337:391-399, 2011, each of which is hereby incorporated by reference in its entirety).

Various glatiramer acetate formulations and methods of preparing glatiramer acetate and glatiramer acetate formulations have been described in, for example, U.S. Pat. Nos. 8,399,413, 8,859,489, 8,920,373, 8,921,116, 8,969,302, 8,993,722, 9,018,170, 9,029,507, 9,155,775, and 9,402,874, which are hereby incorporated by reference in their entirety.

15. CD40/CD40L Inhibitors

The term "CD40/CD40L inhibitors" refers to an agent which decreases CD40 or CD40L (CD154) expression and/or the ability of CD40 to bind to CD40L (CD154). CD40 is a costimulatory receptor that binds to its ligand, CD40L (CD154).

In some embodiments, the CD40/CD40L inhibitor can decrease the binding between CD40 and CD40L by blocking the ability of CD40 to interact with CD40L. In some embodiments, the CD40/CD40L inhibitor can decrease the binding between CD40 and CD40L by blocking the ability of CD40L to interact with CD40. In some embodiments, the CD40/CD40L inhibitor decreases the expression of CD40 or CD40L. In some embodiments, the CD40/CD40L inhibitor decreases the expression of CD40. In some embodiments, the CD40/CD40L inhibitor decreases the expression of CD40L.

In some embodiments, the CD40/CD40L inhibitor is an inhibitory nucleic acid, an antibody or an antigen-binding fragment thereof, a fusion protein, or a small molecule. In some embodiments, the inhibitory nucleic acid is a small interfering RNA, an antisense nucleic acid, an aptamer, or a microRNA. Exemplary CD40/CD40L inhibitors are described herein. Additional examples of CD40/CD40L inhibitors are known in the art.

Exemplary aspects of different inhibitory nucleic acids are described below. Any of the examples of inhibitory nucleic acids that can decrease expression of CD40 or CD40L mRNA in a mammalian cell can be synthesized in vitro. Inhibitory nucleic acids that can decrease the expression of CD40 or CD40L mRNA in a mammalian cell include antisense nucleic acid molecules, i.e., nucleic acid molecules whose nucleotide sequence is complementary to all or part of a CD40 or CD40L mRNA.

Inhibitory Nucleic Acids

An antisense nucleic acid molecule can be complementary to all or part of a non-coding region of the coding strand of a nucleotide sequence encoding a CD40 or CD40L protein. Non-coding regions (5' and 3' untranslated regions) are the 5' and 3' sequences that flank the coding region in a gene and are not translated into amino acids.

Some exemplary antisense nucleic acids that are CD40 or CD40L inhibitors are described, e.g., in U.S. Pat. Nos. 6,197,584 and 7,745,609; Gao et al., *Gut* 54(1):70-77, 2005; Arranz et al., *J. Control Release* 165(3):163-172, 2012; Donner et al., *Mol. Ther. Nucleic Acids* 4:e265, 2015.

Another example of an inhibitory nucleic acid is a ribozyme that has specificity for a nucleic acid encoding a CD40 or CD40L protein (e.g., specificity for a CD40 or CD40L mRNA).

An inhibitory nucleic acid can also be a nucleic acid molecule that forms triple helical structures. For example, expression of a CD40 or CD40L polypeptide can be inhibited by targeting nucleotide sequences complementary to the regulatory region of the gene encoding the CD40 or CD40L polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells.

An inhibitory nucleic acid can be a siRNA molecule that decreases the level of a CD40 or CD40L mRNA. Non-limiting examples of short interfering RNA (siRNA) that are CD40/CD40L inhibitors are described in, e.g., Pluvinet et al., *Blood* 104:3642-3646, 2004; Karimi et al., *Cell Immunol.* 259(1):74-81, 2009; and Zheng et al., *Arthritis Res. Ther.* 12(1):R13, 2010. Non-limiting examples of short hairpin RNA (shRNA) targeting CD40/CD40L are described in Zhang et al., *Gene Therapy* 21:709-714, 2014. Non-limiting examples of microRNAs that are CD40/CD40L inhibitors include, for example, miR146a (Chen et al., *FEBS Letters* 585(3):567-573, 2011), miR-424, and miR-503 (Lee et al., *Sci. Rep.* 7:2528, 2017).

Non-limiting examples of aptamers that are CD40/CD40L inhibitors are described in Soldevilla et al., *Biomaterials* 67:274-285, 2015.

Antibodies

In some embodiments, the CD40/CD40L inhibitor is an antibody or an antigen-binding fragment thereof (e.g., a Fab or a scFv). In some embodiments, an antibody or antigen-binding fragment described herein binds specifically to CD40 or CD40L, or to both CD40 and CD40L.

In certain embodiments, the antibody comprises or consists of an antigen-binding fragment or portion of PG102 (Pangenetics) (Bankert et al., *J. Immunol.* 194(9):4319-4327, 2015); 2C10 (Lowe et al., *Am. J. Transplant* 12(8): 2079-2087, 2012); ASKP1240 (Bleselumab) (Watanabe et al., *Am. J. Transplant* 13(8):1976-1988, 2013); 4D11 (Imai et al., *Transplantation* 84(8):1020-1028, 2007); BI 655064 (Boehringer Ingelheim) (Visvanathan et al., 2016 American College of Rheumatology Annual Meeting, Abstract 1588, Sep. 28, 2016); 5D12 (Kasran et al., *Aliment. Pharmacol. Ther.,* 22(2):111-122, 2005; Boon et al., *Toxicology* 174(1): 53-65, 2002); ruplizumab (hu5c8) (Kirk et al., *Nat. Med.* 5(6):686-693, 1999); CHIR12.12 (HCD122) (Weng et al., *Blood* 104(11):3279, 2004; Tai et al., *Cancer Res.* 65(13): 5898-5906, 2005); CDP7657 (Shock et al., *Arthritis Res. Ther.* 17(1):234, 2015); BMS-986004 domain antibody (dAb) (Kim et al., *Am. J. Transplant.* 17(5):1182-1192, 2017); 5c8 (Xie et al., *J. Immunol.* 192(9):4083-4092, 2014); dacetuzumab (SGN-40) (Lewis et al., *Leukemia* 25(6):1007-1016, 2011; and Khubchandani et al., *Curr. Opin. Investig. Drugs* 10(6):579-587, 2009); lucatumumab (HCD122) (Bensinger et al., *Br. J. Haematol.* 159: 58-66, 2012; and Byrd et al., *Leuk. Lymphoma* 53(11): 10.3109/10428194.2012.681655, 2012); PG102 (FFP104) (Bankert et al., *J. Immunol.* 194(9):4319-4327, 2015); Chi Lob 7/4 (Johnson et al., *J. Clin. Oncol.* 28:2507, 2019); and ASKP1240 (Okimura et al., *Am. J. Transplant.* 14(6): 1290-1299, 2014; and Ma et al., *Transplantation* 97(4): 397-404, 2014).

Further teachings of CD40/CD40L antibodies and antigen-binding fragments thereof are described in, for example, U.S. Pat. Nos. 5,874,082; 7,169,389; 7,271,152; 7,288,252; 7,445,780; 7,537,763; 8,277,810; 8,293,237, 8,551,485; 8,591,900; 8,647,625; 8,784,823; 8,852,597; 8,961,976; 9,023,360, 9,028,826; 9,090,696, 9,221,913; US2014/0093497, and US2015/0017155, each of which is incorporated by reference in its entirety.

Fusion and Truncated Proteins and Peptides

In some embodiments, the CD40/CD40L inhibitor is a fusion protein, a truncated protein (e.g., a soluble receptor) or a peptide. In some embodiments, the CD40/CD40L inhibitor is a truncated protein as disclosed in, for example, WO 01/096397. In some embodiments, the CD40/CD40L inhibitor is a peptide, such as a cyclic peptide (see, e.g., U.S. Pat. No. 8,802,634; Bianco et al., *Org. Biomol. Chem.* 4:1461-1463, 2006; Deambrosis et al., *J. Mol. Med.* 87(2): 181-197, 2009; Vaitaitis et al., *Diabetologia* 57(11):2366-2373, 2014). In some embodiments, the CD40/CD40L inhibitor is a CD40 ligand binder, for example, a Tumor Necrosis Factor Receptor-associated Factor (TRAF): TRAF2, TRAF3, TRAF6, TRAF5 and TTRAP, or E3 ubiquitin-protein ligase RNF128.

Small Molecules

In some embodiments, the CD40/CD40L inhibitor is a small molecule (see, e.g., U.S. Pat. No. 7,173,046, U.S. Patent Application No. 2011/0065675). In some embodiments, the small molecule is Bio8898 (Silvian et al., *ACS Chem. Biol.* 6(6):636-647, 2011); Suramin (Margolles-Clark et al., *Biochem. Pharmacol.* 77(7):1236-1245, 2009); a small-molecule organic dye (Margolles-Clark et al., *J. Mol. Med.* 87(11):1133-1143, 2009; Buchwald et al., *J. Mol. Recognit.* 23(1):65-73, 2010), a naphthalenesulphonic acid derivative (Margolles-Clark et al., *Chem. Biol. Drug Des.* 76(4):305-313, 2010), or a variant thereof.

16. CD3 Inhibitors

The term "CD3 inhibitor" refers to an agent which decreases the ability of one or more of CD3γ, CD3δ, CD3ε, and CD3ζ to associate with one or more of TCR-α, TCR-β, TCR-δ, and TCR-γ. In some embodiments, the CD3 inhibitor can decrease the association between one or more of CD3γ, CD3δ, CD3ε, and CD3 and one or more of TCR-α, TCR-β, TCR-δ, and TCR-γ by blocking the ability of one or more of CD3γ, CD3δ, CD3ε, and CD3ζ to interact with one or more of TCR-α, TCR-β, TCR-δ, and TCR-γ.

In some embodiments, the CD3 inhibitor is an antibody or an antigen-binding fragment thereof, a fusion protein, or a small molecule. Exemplary CD3 inhibitors are described herein. Additional examples of CD3 inhibitors are known in the art.

Antibodies

In some embodiments, the CD3 inhibitor is an antibody or an antigen-binding fragment thereof (e.g., a Fab or a scFv). In some embodiments, the CD3 inhibitor is an antibody or antigen-binding fragment that binds specifically to CD3γ. In some embodiments, the CD3 inhibitor is an antibody or antigen-binding fragment that binds specifically to CD3δ. In some embodiments, the CD3 inhibitor is an antibody or antigen-binding fragment that binds specifically to CD3ε. In some embodiments, the CD3 inhibitor is an antibody or antigen-binding fragment that binds specifically to CD3ζ. In some embodiments, the CD3 inhibitor is an antibody or an antigen-binding fragment that can bind to two or more (e.g., two, three, or four) of CD3γ, CD35, CD3ε, and CD3ζ.

In certain embodiments, the antibody comprises or consists of an antigen-binding fragment or portion of visiluzumab (Nuvion; HuM-291; M291; SMART anti-CD3 antibody) (Carpenter et al., *Biol. Blood Marrow Transplant* 11(6): 465-471, 2005; Trajkovic *Curr. Opin. Investig. Drugs* 3(3): 411-414, 2002; Malviya et al., *J. Nucl. Med.* 50(10): 1683-1691, 2009); muromonab-CD3 (orthoclone OKT3) (Hori et al., *Surg. Today* 41(4): 585-590, 2011; Norman *Ther. Drug Monit.* 17(6): 615-620, 1995; and Gramatzki et al., *Leukemia* 9(3): 382-390, 19); otelixizumab (TRX4) (Vossenkamper et al., *Gastroenterology* 147(1): 172-183, 2014; and Wiczling et al., *J. Clin. Pharmacol.* 50(5): 494-506, 2010); foralumab (NI-0401) (Ogura et al., *Clin. Immunol.* 183: 240-246; and van der Woude et al., *Inflamm. Bowel Dis.* 16: 1708-1716, 2010); ChAgly CD3; teplizumab (MGA031) (Waldron-Lynch et al., *Sci. Transl. Med.* 4(118): 118ra12, 2012; and Skelley et al., *Ann. Pharmacother.* 46(10): 1405-1412, 2012); or catumaxomab (Removab®) (Linke et al., *Mabs* 2(2): 129-136, 2010; and Bokemeyer et al., *Gastric Cancer* 18(4): 833-842, 2015).

Additional examples of CD3 inhibitors that are antibodies or antibody fragments are described in, e.g., U.S. Patent Application Publication Nos. 2017/0204194, 2017/0137519, 2016/0368988, 2016/0333095, 2016/0194399, 2016/0168247, 2015/0166661, 2015/0118252, 2014/0193399, 2014/0099318, 2014/0088295, 2014/0080147, 2013/0115213, 2013/0078238, 2012/0269826, 2011/0217790, 2010/0209437, 2010/0183554, 2008/0025975, 2007/0190045, 2007/0190052, 2007/0154477, 2007/0134241, 2007/0065437, 2006/0275292, 2006/0269547, 2006/0233787, 2006/0177896, 2006/0165693, 2006/0088526, 2004/0253237, 2004/0202657, 2004/0052783, 2003/0216551, and 2002/0142000, each of which is herein incorporated by reference in its entirety (e.g., the sections describing the CD3 inhibitors). Additional CD3 inhibitors that are antibodies or antigen-binding antibody fragments are described in, e.g., Smith et al., *J. Exp. Med.* 185(8):1413-1422, 1997; Chatenaud et al., *Nature* 7:622-632, 2007.

In some embodiments, the CD3 inhibitor comprises or consists of a bispecific antibody (e.g., JNJ-63709178) (Gaudet et al., *Blood* 128(22): 2824, 2016); JNJ-64007957 (Girgis et al., *Blood* 128: 5668, 2016); MGD009 (Tolcher et al., *J. Clin.* Oncol. 34:15, 2016); ERY974 (Ishiguro et al., *Sci. Transl. Med.* 9(410): pii.eaa14291, 2017); AMV564 (Hoseini and Cheung *Blood Cancer J.* 7:e522, 2017); AFM11 (Reusch et al., *MAbs* 7(3): 584-604, 2015); duvortuxizumab (JNJ 64052781); RO6958688; blinatumomab (Blincyto®; AMG103) (Ribera *Expert Rev. Hematol.* 1:1-11, 2017; and Mon et al., *N Engl. J. Med.* 376(23):e49, 2017); XmAb13676; or REGN1979 (Bannerji et al., *Blood* 128: 621, 2016; and Smith et al., *Sci. Rep.* 5:17943, 2015)).

In some embodiments, the CD3 inhibitor comprises or consists of a trispecific antibody (e.g., ertumaxomab (Kiewe and Thiel, *Expert Opin. Investig. Drugs* 17(10): 1553-1558, 2008; and Haense et al., *BMC Cancer* 16:420, 2016); or FBTA05 (Bi20; Lymphomun) (Buhmann et al., *J. Transl. Med.* 11:160, 2013; and Schuster et al., *Br. J. Haematol.* 169(1): 90-102, 2015)).

Fusion and Truncated Proteins and Peptides

In some embodiments, the CD3 inhibitor is a fusion protein, a truncated protein (e.g., a soluble receptor), or a peptide. In some embodiments, the CD3 inhibitor can be a fusion protein (see, e.g., Lee et al., *Oncol. Rep.* 15(5): 1211-1216, 2006).

Small Molecules

In some embodiments, the CD3 inhibitor comprises or consists of a bispecific small molecule-antibody conjugate (see, e.g., Kim et al., *PNAS* 110(44): 17796-17801, 2013; Viola et al., *Eur. J. Immunol.* 27(11):3080-3083, 1997).

17. CD14 Inhibitors

The term "CD14 inhibitors" refers to an agent which decreases the ability of CD14 to bind to lipopolysaccharide (LPS). CD14 acts as a co-receptor with Toll-like receptor 4 (TLR4) that binds LPS in the presence of lipopolysaccharide-binding protein (LBP).

In some embodiments, the CD14 inhibitor can decrease the binding between CD14 and LPS by blocking the ability of CD14 to interact with LPS.

In some embodiments, the CD14 inhibitor is an antibody or an antigen-binding fragment thereof. In some embodiments, the CD14 inhibitor is a small molecule. Exemplary CD14 inhibitors are described herein. Additional examples of CD14 inhibitors are known in the art.

Antibodies

In some embodiments, the CD14 inhibitor is an antibody or an antigen-binding fragment thereof (e.g., a Fab or a scFv). In some embodiments, the CD14 inhibitor is an antibody or antigen-binding fragment that binds specifically to CD14.

In certain embodiments, the antibody comprises or consists of an antigen-binding fragment or portion of 1C14 (Axtelle and Pribble, *J. Endotoxin Res.* 7(4): 310-314, 2001; Reinhart et al., *Crit. Care Med.* 32(5): 1100-1108, 2004; Spek et al., *J. Clin. Immunol.* 23(2): 132-140, 2003). Additional examples of anti-CD14 antibodies and CD14 inhibitors can be found, e.g., in WO 2015/140591 and WO 2014/122660, incorporated in its entirety herein.

Additional examples of CD14 inhibitors that are antibodies or antibody fragments are described in, e.g., U.S. Patent Application Serial No. 2017/0107294, 2014/0050727, 2012/0227412, 2009/0203052, 2009/0029396, 2008/0286290, 2007/0106067, 2006/0257411, 2006/0073145, 2006/0068445, 2004/0092712, 2004/0091478, and 2002/0150882, each of which is herein incorporated by reference (e.g., the sections that describe CD14 inhibitors).

Small Molecules

In some embodiments, the CD14 inhibitor is a small molecule. Non-limiting examples of CD14 inhibitors that are small molecules are described in, e.g., methyl 6-deoxy-6-N-dimethyl-N-cyclopentylammonium-2, 3-di-O-tetradecyl-α-D-glucopyranoside iodide (IAXO-101), methyl 6-Deoxy-6-amino-2,3-di-O-tetradecyl-α-D-glucopyranoside (IAXO-102); N-(3,4-bis-tetradecyloxy-benzyl)-N-cyclopentyl-N,N-dimethylammonium iodide (IAXO-103); and IMO-9200.

Additional examples of CD14 inhibitors that are small molecules are known in the art.

18. CD20 Inhibitors

The term "CD20 inhibitors" refers to an agent that binds specifically to CD20 expressed on the surface of a mammalian cell.

In some embodiments, the CD20 inhibitor is an antibody or an antigen-binding fragment thereof, or a fusion protein or peptide. Exemplary CD20 inhibitors are described herein.

Additional examples of CD20 inhibitors are known in the art.

Antibodies

In some embodiments, the CD20 inhibitor is an antibody or an antigen-binding fragment thereof (e.g., a Fab or a scFv).

In certain embodiments, the antibody comprises or consists of an antigen-binding fragment or portion of rituximab (Rituxan®, MabThera®, MK-8808) (Ji et al., *Indian J. Hematol. Blood Transfus.* 33(4): 525-533, 2017; and Calderon-Gomez and Panes *Gastroenterology* 142(1): 1741-76, 2012); -PF-05280586; ocrelizumab (Ocrevus™) (Sharp N. *Engl. J. Med.* 376(17): 1692, 2017); ofatumumab (Arzerra®; HuMax-CD20) (AlDallal *Ther. Clin. Risk Manag.* 13:905-907, 2017; and Furman et al., *Lancet Haematol.* 4(1): e24-e34, 2017); PF-05280586 (Williams et al., *Br. J. Clin. Pharmacol.* 82(6): 1568-1579, 2016; and Cohen et al., *Br. J. Clin. Pharmacol.* 82(1): 129-138, 2016); obinutuzumab (Gazyva®) (Reddy et al., *Rheumatology* 56(7): 1227-1237, 2017; and Marcus et al., *N. Engl. J. Med.* 377(14): 1331-1344, 2017); ocaratuzumab (AME-133v; LY2469298) (Cheney et al., *Mabs* 6(3): 749-755, 2014; and Tobinai et al., *Cancer Sci.* 102(2): 432-8, 2011); GP2013 (Jurczak et al., *Lancet Haenatol.* 4(8): e350-e361, 2017); IBI301; HLX01, veltuzumab (hA20) (Kalaycio et al., *Leuk. Lymphoma* 57(4): 803-811, 2016; and Ellebrecht et al., *JAMA Dermatol.* 150(12): 1331-1335, 2014); SCT400 (Gui et al., *Chin. J. Cancer Res.* 28(2): 197-208); ibritumomab tiuxetan (Zevalin®) (Philippe et al., *Bone Marrow Transplant* 51(8): 1140-1142, 2016; and Lossos et al., *Leuk. Lymphoma* 56(6): 1750-1755, 2015); ublituximab (TG1101) (Sharman et al., *Blood* 124: 4679, 2014; and Sawas et al., *Br. J. Haematol.* 177(2): 243-253, 2017); LFB-R603 (Esteves et al., *Blood* 118: 1660, 2011; and Baritaki et al., *Int. J. Oncol.* 38(6): 1683-1694, 2011); or tositumomab (Bexxar) (Buchegger et al., *J. Nucl. Med.* 52(6): 896-900, 2011; and William and Bierman *Expert Opin. Biol. Ther.* 10(8): 1271-1278, 2010). Additional examples of CD20 antibodies are known in the art (see, e.g., WO 2008/156713).

In certain embodiments, the antibody comprises or consists of an antigen-binding fragment or portion of a bispecific antibody (e.g., XmAb13676, REGN1979 (Bannerji et al., *Blood* 128: 621, 2016; and Smith et al., *Sci. Rep.* 5: 17943, 2015); PRO131921 (Casulo et al., *Clin. Immnol.* 154(1): 37-46, 2014; and Robak and Robak BioDrugs 25(1): 13-25, 2011); or Acellbia).

In some embodiments, the CD20 inhibitor comprises or consists of a trispecific antibody (e.g., FBTA05 (Bi20; Lymphomun) (Buhmann et al., *J. Transl. Med.* 11:160, 2013; and Schuster et al., *Br. J. Haematol.* 169(1): 90-102, 2015)).

Additional examples of CD20 inhibitors that are antibodies or antigen-binding fragments are described in, e.g., U.S. Patent Application Publication Nos. 2017/0304441, 2017/0128587, 2017/0088625, 2017/0037139, 2017/0002084, 2016/0362472, 2016/0347852, 2016/0333106, 2016/0271249, 2016/0243226, 2016/0115238, 2016/0108126, 2016/0017050, 2016/0017047, 2016/0000912, 2016/0000911, 2015/0344585, 2015/0290317, 2015/0274834, 2015/0265703, 2015/0259428, 2015/0218280, 2015/0125446, 2015/0093376, 2015/0079073, 2015/0071911, 2015/0056186, 2015/0010540, 2014/0363424, 2014/0356352, 2014/0328843, 2014/0322200, 2014/0294807, 2014/0248262, 2014/0234298, 2014/0093454, 2014/0065134, 2014/0044705, 2014/0004104, 2014/0004037, 2013/0280243, 2013/0273041, 2013/0251706, 2013/0195846, 2013/0183290, 2013/0089540, 2013/0004480, 2012/0315268, 2012/0301459, 2012/0276085, 2012/

0263713, 2012/0258102, 2012/0258101, 2012/0251534, 2012/0219549, 2012/0183545, 2012/0100133, 2012/0034185, 2011/0287006, 2011/0263825, 2011/0243931, 2011/0217298, 2011/0200598, 2011/0195022, 2011/0195021, 2011/0177067, 2011/0165159, 2011/0165152, 2011/0165151, 2011/0129412, 2011/0086025, 2011/0081681, 2011/0020322, 2010/0330089, 2010/0310581, 2010/0303808, 2010/0183601, 2010/0080769, 2009/0285795, 2009/0203886, 2009/0197330, 2009/0196879, 2009/0191195, 2009/0175854, 2009/0155253, 2009/0136516, 2009/0130089, 2009/0110688, 2009/0098118, 2009/0074760, 2009/0060913, 2009/0035322, 2008/0260641, 2008/0213273, 2008/0089885, 2008/0044421, 2008/0038261, 2007/0280882, 2007/0231324, 2007/0224189, 2007/0059306, 2007/0020259, 2007/0014785, 2007/0014720, 2006/0121032, 2005/0180972, 2005/0112060, 2005/0069545, 2005/0025764, 2004/0213784, 2004/0167319, 2004/0093621, 2003/0219433, 2003/0206903, 2003/0180292, 2003/0026804, 2002/0039557, 2002/0012665, and 2001/0018041, each herein incorporated by reference in their entirety (e.g., sections describing CD20 inhibitors).

Peptides and Fusion Proteins

In some embodiments, the CD20 inhibitor is an immunotoxin (e.g., MT-3724 (Hamlin *Blood* 128: 4200, 2016).

In some embodiments, the CD20 inhibitor is a fusion protein (e.g., TRU-015 (Rubbert-Roth *Curr. Opin. Mol. Ther.* 12(1): 115-123, 2010). Additional examples of CD20 inhibitors that are fusion proteins are described in, e.g., U.S. Patent Application Publication Nos. 2012/0195895, 2012/0034185, 2009/0155253, 2007/0020259, and 2003/0219433, each of which are herein incorporated by reference in their entirety (e.g., sections describing CD20 inhibitors).

19. CD25 Inhibitors

The term "CD25 inhibitors" refers to an agent which decreases the ability of CD25 (also called interleukin-2 receptor alpha chain) to bind to interleukin-2. CD25 forms a complex with interleukin-2 receptor beta chain and interleukin-2 common gamma chain.

In some embodiments, the CD25 inhibitor is an antibody or an antigen-binding fragment thereof, or a fusion protein. Exemplary CD25 inhibitors are described herein. Additional examples of CD25 inhibitors are known in the art.

Antibodies

In some embodiments, the CD25 inhibitor is an antibody or an antigen-binding fragment thereof (e.g., a Fab or a scFv). In some embodiments, a CD25 inhibitor is an antibody or an antigen-binding fragment thereof that specifically binds to CD25. In some embodiments, a CD25 inhibitor is an antibody that specifically binds to IL-2.

In certain embodiments, the antibody comprises or consists of an antigen-binding fragment or portion of basiliximab (Simulect™) (Wang et al., *Clin. Exp. Immunol.* 155(3): 496-503, 2009; and Kircher et al., *Clin. Exp. Immunol.* 134(3): 426-430, 2003); daclizumab (Zenapax; Zinbryta®) (Berkowitz et al., *Clin. Immunol.* 155(2): 176-187, 2014; and Bielekova et al., *Arch Neurol.* 66(4): 483-489, 2009); or IMTOX-25.

In some embodiments, the CD25 inhibitor is an antibody-drug-conjugate (e.g., ADCT-301 (Flynn et al., *Blood* 124: 4491, 2014)).

Additional examples of CD25 inhibitors that are antibodies are known in the art (see, e.g., WO 2004/045512). Additional examples of CD25 inhibitors that are antibodies or antigen-binding fragments are described in, e.g., U.S. Patent Application Publication Nos. 2017/0240640, 2017/0233481, 2015/0259424, 2015/0010539, 2015/0010538, 2012/0244069, 2009/0081219, 2009/0041775, 2008/0286281, 2008/0171017, 2004/0170626, 2001/0041179, and 2010/0055098, each of which is incorporated herein by reference (e.g., sections that describe CD25 inhibitors).

Fusion Proteins

In some embodiments, the CD25 inhibitor is a fusion protein. See, e.g., Zhang et al., *PNAS* 100(4): 1891-1895, 2003.

20. CD28 Inhibitors

The term "CD28 inhibitors" refers to an agent which decreases the ability of CD28 to bind to one or both of CD80 and CD86. CD28 is a receptor that binds to its ligands, CD80 (also called B7.1) and CD86 (called B7.2).

In some embodiments, the CD28 inhibitor can decrease the binding between CD28 and CD80 by blocking the ability of CD28 to interact with CD80. In some embodiments, the CD28 inhibitor can decrease the binding between CD28 and CD86 by blocking the ability of CD28 to interact with CD86. In some embodiments, the CD28 inhibitor can decrease the binding of CD28 to each of CD80 and CD86.

In some embodiments, the CD28 inhibitor is an antibody or an antigen-binding fragment thereof, a fusion protein, or peptide. Exemplary CD28 inhibitors are described herein. Additional examples of CD28 inhibitors are known in the art.

Antibodies

In some embodiments, the CD28 inhibitor is an antibody or an antigen-binding fragment thereof (e.g., a Fab or a scFv).

In some embodiments, the CD28 inhibitor is a monovalent Fab' antibody (e.g., CFR104) (Poirier et al., *Am. J. Transplant* 15(1): 88-100, 2015).

Additional examples of CD28 inhibitors that are antibodies or antigen-binding fragments are described in, e.g., U.S. Patent Application Publication Nos. 2017/0240636, 2017/0114136, 2016/0017039, 2015/0376278, 2015/0299321, 2015/0232558, 2015/0150968, 2015/0071916, 2013/0266577, 2013/0230540, 2013/0109846, 2013/0078257, 2013/0078236, 2013/0058933, 2012/0201814, 2011/0097339, 2011/0059071, 2011/0009602, 2010/0266605, 2010/0028354, 2009/0246204, 2009/0117135, 2009/0117108, 2008/0095774, 2008/0038273, 2007/0154468, 2007/0134240, 2007/0122410, 2006/0188493, 2006/0165690, 2006/0039909, 2006/0009382, 2006/0008457, 2004/0116675, 2004/0092718, 2003/0170232, 2003/0086932, 2002/0006403, 2013/0197202, 2007/0065436, 2003/0180290, 2017/0015747, 2012/0100139, and 2007/0148162, each of which is incorporated by reference in its entirety (e.g., sections that described CD28 inhibitors).

Fusion Proteins and Peptides

In some embodiments, the CD28 inhibitor is a fusion protein (see, e.g., U.S. Pat. No. 5,521,288; and US 2002/0018783). In some embodiments, the CD28 inhibitor is abatacept (Orencia®) (Herrero-Beaumont et al., *Rheumatol. Clin.* 8: 78-83, 2012; and Korhonen and Moilanen *Basic Clin. Pharmacol. Toxicol.* 104(4): 276-284, 2009).

In some embodiments, the CD28 inhibitor is a peptide mimetic (e.g., AB103) (see, e.g., Bulger et al., *JAMA Surg.* 149(6): 528-536, 2014), or a synthetical peptoid (see, e.g., Li et al., *Cell Mol. Immunol.* 7(2): 133-142, 2010).

21. CD49 Inhibitors

The term "CD49 inhibitors" refers to an agent which decreases the ability of CD49 to bind to one of its ligands (e.g., MMP1). In some embodiments, the CD49 inhibitor is an antibody or an antigen-binding fragment thereof. Exemplary CD49 inhibitors are described herein. Additional examples of CD49 inhibitors are known in the art.

Antibodies

In some embodiments, the CD49 inhibitor is an antibody or an antigen-binding fragment thereof (e.g., a Fab or a scFv).

In certain embodiments, the antibody comprises or consists of an antigen-binding fragment or portion of natalizumab (Tysabri®; Antegren®) (see, e.g., Pagnini et al., *Expert Opin. Biol. Ther.* 17(11): 1433-1438, 2017; and Chataway and Miller Neurotherapeutics 10(1): 19-28, 2013; or vatelizumab (ELND-004)).

22. CD89 Inhibitors

The term "CD89 inhibitors" refers to an agent which decreases the ability of CD89 to bind to IgA. CD89 is a transmembrane glycoprotein that binds to the heavy-chain constant region of IgA. In some embodiments, the CD89 inhibitor can decrease the binding between CD89 and IgA by blocking the ability of CD89 to interact with IgA. In some embodiments, the CD89 inhibitor is an antibody or an antigen-binding fragment thereof. Exemplary CD89 inhibitors are described herein. Additional examples of CD89 inhibitors are known in the art.

Antibodies

In some embodiments, the CD89 inhibitor is an antibody or an antigen-binding fragment thereof (e.g., a Fab or a scFv).

In certain embodiments, the antibody comprises or consists of an antigen-binding fragment or portion of HF-1020. Additional examples of CD89 antibodies are known in the art (see, e.g., WO 2002/064634).

23. Chemokine/Chemokine Receptor Inhibitors

The term "chemokine/chemokine receptor inhibitors" refers to an agent which decreases the ability of a chemokine to bind to its receptor, where the chemokine is one of CXCL10 (IL-10), CCL11, or an ELR chemokine, or the chemokine receptor is CCR2 or CCR9.

CXCL10 (IP-10) Inhibitors

As used herein "CXCL10", "interferon gamma-induced protein 10" and "IP-10" can be used interchangeably. CXCL10 binds to the CXCR3 receptor (e.g., CXCR3-A or CXCR3-B).

The term "CXCL10 inhibitor" refers to an agent which decreases the ability of CXCL10 to bind to a CXCR3 receptor (e.g., CXCR3-A and/or CXCR3-B).

In some embodiments, the CXCL10 inhibitor can decrease the binding between CXCL10 and CXCR3-A by blocking the ability of CXCL10 to interact with CXCR3-A. In some embodiments, the CXCL10 inhibitor can decrease the binding between CXCL10 and CXCR3-B by blocking the ability of CXCL10 to interact with CXCR3-B.

In some instances, the CXCL10 inhibitor that decreases the binding between CXCL10 and a CXCR3 (e.g., CXCR3-A and/or CXCR3-B) is a small molecule. In some instances, the CXCL10 inhibitor that decreases the binding between CXCL10 and a CXCR3 (e.g., CXCR3-A and/or CXCR3-B) is an antibody or an antigen-binding antibody fragment. In some instances, the CXCL10 inhibitor that decreases the binding between CXCL10 and a CXCR3 (e.g., CXCR3-A and/or CXCR3-B) is a peptide (e.g., a peptide antagonist of a CXCR3 receptor, e.g., one or both of CXCR-A and/or CXCR-B).

CXCL10 Inhibitors—Antibodies

In some embodiments, the CXCL10 inhibitor is an antibody or an antigen-binding fragment thereof (e.g., a Fab or a scFv). In some embodiments, an antibody or antigen-binding fragment described herein binds specifically to CXCL10 or a CXCR3 receptor (e.g., CXCR3-A and/or CXCR3-B), or both a CXCL10 and a CXCR3 receptor (e.g., CXCR3-A and/or CXCR3-B). In some embodiments, a CXCL10 inhibitor can bind to both CXCR3-A and CXCR3-B.

In other instances, the CXCL10 inhibitor is a monoclonal antibody (mAb) (see, e.g., WO 05/58815). For example, the CXCL10 inhibitor can be Eldelumab® (MDX-1100 or BMS-936557), BMS-986184 (Bristol-Meyers Squibb), or NI-0801 (NovImmune). See, e.g., Kuhne et al., *J. Immunol.* 178(1):5241, 2007; Sandborn et al., *J. Crohns Colitis* 11(7): 811-819, 2017; and Danese et al., *Gastroenterology* 147(5): 981-989, 2014. Additional examples of CXCL10 inhibitors that are antibodies are described in U.S. Patent Application Publication Nos. 2017/0158757, 2017/0081413, 2016/0009808, 2015/0266951, 2015/0104866, 2014/0127229, 2014/0065164, 2013/0216549, 2010/0330094, 2010/0322941, 2010/0077497, 2010/0021463, 2009/0285835, 2009/0169561, 2008/0063646, 2005/0191293, 2005/0112119, 2003/0158392, 2003/0031645, and 2002/0018776; and WO 98/11218, each of which is incorporated by reference in its entirety (e.g., the description of CXCL10 inhibitors).

CCL11 Inhibitors

The term "CCL11 inhibitor" refers to an agent which decreases the ability of CCL11 to bind to one or more of CCR2, CCR3, and CCR5.

In some embodiments, the CCL11 inhibitor can decrease the binding between CCL11 and CCR2 by blocking the ability of CCL11 to interact with CCR2. In some embodiments, the CCL11 inhibitor can decrease the binding between CCL11 and CCR3 by blocking the ability of CCL11 to interact with CCR3. In some embodiments, the CCL11 inhibitor can decrease the binding between CCL11 and CCR5 by blocking the ability of CCL11 to interact with CCR5.

In some embodiments, a CCL11 inhibitor is an antibody or an antigen-binding fragment thereof.

CCL11 Inhibitors—Antibodies

In some embodiments, the CCL11 inhibitor is an antibody or an antigen-binding fragment thereof (e.g., a Fab or a scFv). In some embodiments, an antibody or antigen-binding fragment described herein binds specifically to CCL11, CCR2, CCR3, or CCR5, or can specifically bind to two or more of CCL11, CCR2, CCR3, and CCR5. In some embodiments, a CCL11 inhibitor can bind to two or more of CCR2, CCR3, and CCR5.

In some examples the chemokine/chemokine receptor inhibitor is bertilimumab (Immune Pharmaceuticals), an anti-eotaxin-1 monoclonal antibody that targets CCL11, and is currently in a Phase II clinical study for ulcerative colitis. Additional examples of CCL11 inhibitors are described in U.S. Patent Application Publication Nos. 2016/0289329, 2015/0086546, 2014/0342450, 2014/0178367, 2013/0344070, 2013/0071381, 2011/0274696, 2011/0038871, 2010/0074886, 2009/0297502, 2009/0191192, 2009/0169541, 2009/0142339, 2008/0268536, 2008/0241923, 2008/0241136, 2005/0260139, 2005/0048052, 2004/0265303, 2004/0132980, 2004/0126851, 2003/0165494, 2002/0150576, 2002/0150570, 2002/0051782, 2002/0051781, 2002/0037285, 2002/0028436, 2002/0015700, 2002/0012664, 2017/0131282, 2016/0368979, 2016/0208011, 2011/0268723, 2009/0123375, 2007/0190055, 2017/0049884, 2011/0165182, 2009/0226434, 2009/0110686, 2009/0047735, 2009/0028881, 2008/0107647, 2008/0107595, 2008/0015348, 2007/0274986, 2007/0231327, 2007/0036796, 2007/0031408, 2006/0229336, 2003/0228306, 2003/0166870, 2003/0003440, 2002/

0019345, and 2001/0000241, each of which is incorporated by reference in its entirety (e.g., the description of CCL11 inhibitors).

CXCL10 Inhibitors—Small Molecules and Peptides

In some instances, the CXCL10 inhibitor is a small molecule. For example, the CXCL10 inhibitor can be ganodermycin (see, e.g., Jung et al., *J. Antiobiotics* 64:683-686, 2011). Additional exemplary small molecule CXCL10 inhibitors are described in: U.S. Patent Application Publication No. 2005/0075333; U.S. Patent Application Publication No. 2004/0242498; U.S. Patent Application Publication No. 2003/0069234; U.S. Patent Application Publication No. 2003/0055054; U.S. Patent Application Publication No. 2002/0169159; WO 97/24325; WO 98/38167; WO 97/44329; WO 98/04554; WO 98/27815; WO 98/25604; WO 98/25605; WO 98/25617; WO 98/31364; Hesselgesser et al., *J. Biol. Chem.* 273(25):15687-15692 (1998); and Howard et al., *J. Med. Chem.* 41(13):2184-2193 (1998).

In some examples, the CXCL10 inhibitor is a peptide antagonist of a CXCR3 receptor (e.g., as described in U.S. Patent Application Publication No. 2007/0116669, 2006/0204498, and WO 98/09642). In some examples, the CXCL10 inhibitor is a chemokine mutant or analogue, e.g., those described in U.S. Pat. No. 5,739,103, WO 96/38559, and WO 98/06751. Additional examples of CXCL10 inhibitors that are small molecules or peptides are known in the art.

CCR2 Inhibitors

As used herein "CCR2," "CC chemokine receptor 2," or "MCP-1" can be used interchangeably. CCL2, CCL8, and CCL16 each individually bind to CCR2.

The term "CCR2 inhibitor" refers to an agent which decreases the ability of CCR2 to bind to one or more (e.g., two, or three) of CCL2, CCL8, and CCL16.

In some embodiments, the CCR2 inhibitor can decrease the binding between CCL2 and CCR2 by blocking the ability of CCL2 to interact with CCR2. In some embodiments, the CCR2 inhibitor can decrease the binding between CCL8 and CCR2 by blocking the ability of CCL8 to interact with CCR2. In some embodiments, the CCR2 inhibitor can decrease the binding between CCL16 and CCR2 by blocking the ability of CCL16 to interact with CCR2.

In some embodiments, the CCR2 inhibitor decreases the ability of CCR2 to bind to each of CCL2 and CCL8. In some embodiments, the CCR2 inhibitor decreases the ability of CCR2 to bind to each of CCL2 and CCL16. In some embodiments, the CCR2 inhibitor decreases the ability of CCR2 to bind to each of CCL8 and CCL16. In some embodiments, the CCRS inhibitor decreases the ability of CCR2 to bind to each of CCL2, CCL8, and CCL16.

In some instances, the CCR2 inhibitor is a small molecule. In some instances, the CCR2 inhibitor is an antibody or an antigen-binding antibody fragment. In some instances, the CCR2 inhibitor is a peptide.

CCR2 Inhibitors—Antibodies

In some embodiments, the CCR2 inhibitor is an antibody or an antigen-binding fragment thereof (e.g., a Fab or a scFv). In some embodiments, an antibody or antigen-binding fragment described herein binds specifically to CCR2. In some embodiments, an antibody or antigen-binding fragment described herein binds specifically to CCL2. In some embodiments, an antibody or antigen-binding fragment described herein binds specifically to CCL8. In some embodiments, an antibody or antigen-binding fragment described herein binds specifically to CCL16. In some embodiments, an antibody or antigen-binding fragment described herein binds specifically to CCR2 and one or more of (e.g., one, two, or three) of CCL2, CCL8, and CCL16.

In some embodiments, the CCR2 inhibitor is a monoclonal antibody. For example, the CCR2 inhibitor can be MLN1202 (Millennium Pharmaceuticals), C775, STI-B0201, STI-B0211, STI-B0221, STI-B0232, carlumab (ONTO 888; Centocor, Inc.), or STI-B0234, or an antigen-binding fragment thereof. See also, e.g., Vergunst et al., *Arthritis Rheum.* 58(7):1931-1939, 2008. Additional examples of CCR2 inhibitors that are antibodies or antigen-binding antibody fragments are described in, e.g., U.S. Patent Application Publication Nos. 2015/0086546, 2016/0272702, 2016/0289329, 2016/0083482, 2015/0361167; 2014/0342450, 2014/0178367, 2013/0344070, 2013/0071381, 2011/0274696, 2011/0059107, 2011/0038871, 2009/0068109, 2009/0297502, 2009/0142339, 2008/0268536, 2008/0241923, 2008/0241136, 2007/0128112, 2007/0116708, 2007/0111259, 2006/0246069, 2006/0039913, 2005/0232923, 2005/0260139, 2005/0058639, 2004/0265303, 2004/0132980, 2004/0126851, 2004/0219644, 2004/0047860, 2003/0165494, 2003/0211105, 2002/0150576, 2002/0051782, 2002/0042370, and 2002/0015700; and U.S. Pat. Nos. 6,312,689, 6,084,075, 6,406,694, 6,406,865, 6,696,550, 6,727,349, 7,442,775, 7,858,318, 5,859,205, 5,693,762, and 6,075,181, each of which is incorporated by reference (e.g., the description of the CCR2 inhibitors). Additional examples of CCR2 inhibitors are described in, e.g., WO 00/05265. Additional examples of CCR2 inhibitors that are antibodies or antigen-binding antibodies fragments are described in, e.g., Loberg et al., *Cancer Res.* 67(19):9417, 2007.

CCR2 Inhibitors—Small Molecules and Peptides

In some examples, the CCR2 inhibitor is a small molecule. For example, the CCR2 inhibitor can be elubrixin, PF-04634817, BMS-741672, or CCX872. See, e.g., U.S. Pat. No. 9,434,766; U.S. Patent Application Publication No. 20070021466; Deerberg et al., *Org. Process Rev. Dev.* 20(11):1949-1966, 2016; and Morganti et al., *J. Neurosci.* 35(2):748-760, 2015.

Additional non-limiting examples of CCR2 inhibitors that are small molecules include, e.g., the phenylamino substituted quaternary salt compounds described in U.S. Patent Application Publication No. 2009/0112004; the biaryl derivatives described in U.S. Patent Application Publication No. 2009/0048238; the pyrazol derivatives described in U.S. Patent Application Publication No. 2009/0029963; the heterocyclic compounds described in U.S. Patent Application Publication No. 2009/0023713; the imidazole derivatives described in U.S. Patent Application Publication No. 2009/0012063; the aminopyrrolidines described in U.S. Patent Application Publication No. 2008/0176883; the heterocyclic cyclopentyl tetrahydroisoquinolones and tetrahydropyridopyridines described in U.S. Patent Application Publication No. 2008/0081803; the heteroaryl sulfonamides described in U.S. Patent Application Publication No. 2010/0056509; the triazolyl pyridyl benzenesulfonamides described in U.S. Patent Application Publication No. 2010/0152186; the bicyclic and bridged nitrogen heterocycles described in U.S. Patent Application Publication No. 2006/0074121; the fused heteroaryl pyridyl and phenyl benzenesulfonamides described in WO 09/009740; and the 3-aminopyrrolidene derivatives described in WO 04/050024.

Additional non-limiting examples of CCR2 inhibitors include: N-((1R,3S)-3-isopropyl-3-{[3-(trifluoromethyl)-7,8-dihydro-1,6-naph-thyri-din-6(5H)-yl]carbonyl}cyclopentyl)-N-[(3S,4S)-3-methoxytetrahydro-2H-pyran- -4-yl]amine; 3[(3S,4R)-1-((1R,3S)-3-isopropyl- 2-oxo-3-{[6-(trifluoromethyl)-2H-1,3-ben-z-oxazin-3(4H)-yl]methyl}cyclopentyl)-3-methylpiperidin-4-yl]benzoic acid; (3S,48)-N-((1R,3S)-3-isopropyl-3-{[7-(trifluoromethyl)-3,4-dihydroisoquin-olin-2(1B)-yl]carbonyl}cyclopentyl)-3-methyltetrahydro-2H-p-yran-4-aminium; 3-[(3S,4R or 3R,4S)-1-((1R,3S)-3-Isopropyl-3-{[6-(trifluoromethyl)-2H-1,3-benzoxazin-3-(4H)-yl]carbonyl}cyclopentyl)-3-methylpiperidin-4-yl]benzoic acid; INCB3284, Eotaxin-3; PF-04178903 (Pfizer), and pharmaceutically acceptable salts thereof.

Additional non-limiting examples of CCR2 inhibitors include: bindarit (2-((1-benzyl-1H-indazol-3-yl)methoxy)-2-methylpropionic acid); AZD2423 (AstraZeneca); the indole describes described in U.S. Pat. Nos. 7,297,696, 6,962,926, 6,737,435, and 6,569,888; the bicyclic pyrrole derivatives described in U.S. Pat. Nos. 6,441,004 and 6,479,527; the CCR2 inhibitors described in U.S. Patent Application Publications Nos. 2005/0054668, 2005/0026975, 2004/0198719, and 2004/0047860, and Howard et al., *Expert Opin. Ther. Patents* 11(7):1147-1151 (2001).

Additional non-limiting examples of CCR2 inhibitors that are small molecules are described in, e.g., WO 97/24325; WO 98/38167; WO 97/44329; WO 98/04554; WO 98/27815; WO 98/25604; WO 98/25605; WO 98/25617; WO 98/31364; Hesselgesser et al., *J. Biol. Chem.* 273(25): 15687-15692, 1998; and Howard et al., *J. Med. Chem.* 41(13):2184-2193, 1998.

In some embodiments, the CCR2 inhibitor is a small nucleic acid, e.g., NOX-E36 (a 40-nucleotide L-RNA oligonucleotide that is linked to a 40-kDa PEG; NOXXON Pharma AG).

In some embodiments, the CCR2 inhibitor is a peptide, e.g., a dominant negative peptide described in, e.g., Kiyota et al., *Mol. Ther.* 17(5):803-809, 2009, and U.S. Patent Application Publication No. 20070004906, or an antagonistic peptide, e.g., the antagonistic peptides described in WO 05/037305 and Jiang-Hong Gong, et al., *J. Exp. Med.* 186:131, 1997. Additional examples of CCR2 inhibitors that are peptides are described in, e.g., U.S. Pat. No. 5,739,103; WO 96/38559; WO 98/06751; and WO 98/09642. In some embodiments, a CCR2 inhibitor is a CCR2 mutein (e.g., U.S. Patent Application Publication No. 2004/0185450).

Additional examples of CCR2 inhibitors that are small molecules and peptides are known in the art.

CCR9 Inhibitors

As used herein "CCR9" or "CC chemokine receptor 9" can be used interchangeably. CCR9 specifically binds to CCL25.

The term "CCR9 inhibitor" refers to an agent which decreases the ability of CCR9 to bind to CCL25.

In some embodiments, the CCR9 inhibitor can decrease the binding between CCL25 and CCR9 by blocking the ability of CCL25 to interact with CCR9. In some instances, the CCR9 inhibitor is a small molecule. In some instances, the CCR9 inhibitor is an antibody or an antigen-binding antibody fragment.

CCR9 Inhibitors—Antibodies

In some embodiments, the CCR9 inhibitor is an antibody or an antigen-binding fragment thereof (e.g., a Fab or a scFv). In some embodiments, an antibody or antigen-binding fragment described herein binds specifically to CCR9. In some embodiments, an antibody or antigen-binding fragment described herein binds specifically to CCL25. In some embodiments, an antibody or antigen-binding fragment described herein binds specifically to both CCR9 and CCL25.

In other instances, the CCR9 inhibitor is a monoclonal antibody. For example, the CCR9 antibody can be 91R, see, e.g., Chamorro et al., *MAbs* 6(4): 1000-1012, 2014. Additional non-limiting examples of CCR9 inhibitors are described in, e.g., U.S. Patent Application Publication Nos. 2012/0100554, 2012/0100154, 2011/0123603, 2009/0028866, and 2005/0181501.

CCR9 Inhibitors—Small Molecules

In some instances, the CCR9 inhibitor is a small molecule. For example, the CCR9 inhibitor can be Traficet-EN® (also called Vercirnon, CCX282, and GSK1605786) or Tu1652 CCX507. See, e.g., Eksteen et al., *IDrugs* 13(7): 472-481, 2010; and Walters et al., *Gastroenterology* 144(5): S-815, 2013.

Additional examples of CCR9 inhibitors that are small molecules are known in the art.

ELR Chemokine Inhibitors

ELR chemokines are CXC chemokines that have a glutamic acid-leucine-arginine (ELR) motif. See, e.g., Strieter et al., *J. Biol. Chem.* 270:27348-27357, 1995.

The term "ELR chemokine inhibitor" refers to an agent which decreases the ability of CXCR1 and/or CXCR2 to bind to one or more (e.g., two, three, four, five, six, seven, or eight) of CXCL1, CXCL2, CXCL3, CXCL4, CXCL5, CXCL6, CXCL7, and CXCL8.

In some embodiments, the ELR chemokine inhibitor can decrease the binding between CXCR1 and CXCL8 by blocking the ability of CXCR1 to interact with CXCL8. In some embodiments, the ELR chemokine inhibitor can decrease the binding between CXCR1 and CXCL6 by blocking the ability of CXCR1 to interact with CXCL6. In some embodiments, the ELR chemokine inhibitor can decrease the binding between CXCR1 and each of CXCL8 and CXCL6.

In some embodiments, the ELR chemokine inhibitor can decrease the binding between CXCR2 and CXCL1 by blocking the ability of CXCR2 to interact with CXCL1. In some embodiments, the ELR chemokine inhibitor can decrease the binding between CXCR2 and CXCL2 by blocking the ability of CXCR2 to interact with CXCL2. In some embodiments, the ELR chemokine inhibitor can decrease the binding between CXCR2 and CXCL3 by blocking the ability of CXCR2 to interact with CXCL3. In some embodiments, the ELR chemokine inhibitor can decrease the binding between CXCR2 and CXCL4 by blocking the ability of CXCR2 to interact with CXCL4. In some embodiments, the ELR chemokine inhibitor can decrease the binding between CXCR2 and CXCL5 by blocking the ability of CXCR2 to interact with CXCL5. In some embodiments, the ELR chemokine inhibitor can decrease the binding between CXCR2 and CXCL6 by blocking the ability of CXCR2 to interact with CXCL6. In some embodiments, the ELR chemokine inhibitor can decrease the binding between CXCR2 and CXCL7 by blocking the ability of CXCR2 to interact with CXCL7. In some embodiments, the ELR chemokine inhibitor can decrease the binding between CXCR2 and one or more (e.g., two, three, four, five, six, or seven) of CXCL1, CXCL2, CXCL3, CXCL4, CXCL5, CXCL6, and CXCL7.

In some embodiments, the ELR chemokine inhibitor can decrease the binding of CXCR1 to one or both of CXCL6 and CXCL8, and can decrease the binding to CXCR2 to one or more (e.g., two, three, four, five, six, or seven) of CXCL1, CXCL2, CXCL3, CXCL4, CXCL5, CXCL6, and CXCL7.

In some instances, the ELR chemokine inhibitor is a small molecule. In some instances, the ELR chemokine inhibitor is an antibody or an antigen-binding antibody fragment.

ELR Chemokine Inhibitors—Antibodies

In some embodiments, the ELR chemokine inhibitor is an antibody or an antigen-binding fragment thereof (e.g., a Fab or a scFv). In some embodiments, an antibody or antigen-binding fragment described herein binds specifically to CXCR1 and/or CXCR2. In some embodiments, an antibody or antigen-binding fragment described herein binds specifically to one or more (e.g., two, three, four, five, six, seven, or eight) of: CXCL1, CXCL2, CXCL3, CXCL4, CXCL5, CXCL6, CXCL7, and CXCL8 (IL-8).

An ELR chemokine inhibitor can be, e.g., a monoclonal antibody. A non-limiting example of an ELR inhibitor is TAB-099MZ. Additional examples of ELR chemokine inhibitors that are antibodies or antigen-binding antibody fragments are described in, e.g., U.S. Pat. No. 9,290,570; and U.S. Patent Application Publication Nos. 2004/0170628, 2010/0136031, 2015/0160227, 2015/0224190, 2016/0060347, 2016/0152699, 2016/0108117, 2017/0131282, 2016/0060347, 2014/0271647, 2014/0170156, 2012/0164143, 2010/0254941, 2009/0130110, 2008/0118517, 2004/0208873, 2003/0021790, 2002/0082396, and 2001/0006637, each of which is herein incorporated by reference (e.g., the portions describing ELR chemokine inhibitors).

ELR Chemokine Inhibitors—Small Molecules

In some instances, the ELR chemokine inhibitor is, e.g., a small molecule. For example, the ELR chemokine inhibitor can be, e.g., LY-3041658 or repertaxin (Reparixin; DF 1681Y). Additional non-limiting examples of ELR chemokine inhibitors that are small molecules are described in, e.g., U.S. Patent Application Publication Nos. 2007/0248594, 2006/0014794, 2004/0063709, 2004/0034229, 2003/0204085, 2003/0097004, 2004/0186142, 2004/0235908, 2006/0025453, 2017/0224679, 2017/0190681, 2017/0144996, and 2017/0128474, each of which are incorporated by reference (e.g., the portions describing the ELR chemokine inhibitors).

In some embodiments, the ELR chemokine inhibitor is a peptide, e.g., any of the peptides described in U.S. Patent Application Publication Nos. 2009/0270318, 2009/0118469, and 2007/0160574, 2007/0021593, 2003/0077705, and 2007/0181987, each of which is incorporated by reference (e.g., the portions describing the ELR chemokine inhibitors).

E. Blood Constituents

Bleedings in the GI tract may occur due to different health disturbances of the digestive tract, such as, for example, esophageal varices or gastric or duodenal ulcers. Even after an endoscopic treatment of such disturbances of health, there often occur recurrent bleedings that constitute a severe complication. Bleeding in the GI tract may occur in various locations along the GI tract which may indicate different pathologies present at those locations. For example, bleeding in the esophagus may be due to esophagitis or due to ruptures in varices in the esophagus. An ulcer in the stomach, as well as an ulcer in the duodenum, may cause bleeding. And in the lower digestive tract, colorectal cancer may cause occult bleeding. Recurrent bleedings may occur several hours or days after a treatment, which renders their detection difficult. Bleedings in the digestive tract may lead to an acute-emergency situation, since they may entail a large loss of blood if they go unnoticed. Therefore, it is desirable to provide reliable and early detection of such bleedings.

Accordingly, in some embodiments, the analyte(s) can include one or more constituents of blood, such as for example, hemoglobin. In some embodiments, a constituent of blood is detected, quantitated and/or analyzed in the GI tract and/or tissue associated with one or more regions of the GI tract of a subject (e.g., in one or more of the mouth, throat, esophagus, stomach, small intestine, large intestine, rectum, anus, sphincter, duodenum, jejunum, ileum, ascending colon, transverse colon, and descending colon). In some embodiments, a detection agent is administered to the subject in order to detect, quantitate and/or analyze a blood constituent in the GI tract of the subject. For example, in some embodiments, an detection agent (e.g., an antibody) comprising a fluorescent probe that is specific for one or more blood constituents is administered to the subject prior to or concurrently with the administration of a device described herein to a subject. Detection and quantification of hemoglobin based on spectral data are described in detail in Example 13. In some embodiments, the blood constituent is a blood cell (e.g., a leukocyte (e.g., a neutrophil, a granulocyte, a basophil, an eosinophil, a lymphocyte, a monocyte, or a phagocyte), an erythrocyte, a thrombocyte. In some embodiments, detecting, and optionally quantifying, a constituent of blood in the GI tract can be used to determine whether the subject has a GI bleed (e.g., gastrointestinal hemorrhage). In some embodiments, the detection, quantitation and/or analysis of a blood constituent in the GI tract of the subject may be used to determine whether the subject has acute GI bleeding or occult (chronic) GI bleeding. In some embodiments, the detection, quantitation and/or analysis of a blood constituent in the GI tract of a subject may be used to determine whether the subject has or is at risk of developing a disease associated with GI bleeding including, but not limited to, peptic ulcer disease (e.g. from use of aspirin or other non-steroidal anti-inflammatory drugs (NSAIDs), variceal hemorrhage, Mallory-Weiss tear, a neoplasm (e.g., a gastrointestinal cancer (e.g., gastric cancer or colorectal cancer)), esophagitis, erosive gastritis/duodenitis, vascular ectasias, Dieulafoy's lesions, non-alcholohic cirrhosis, a *Helicobacter pylori* infection, esophageal varices, diverticular disease, angiodysplasia, angioectasia, colitis (e.g., amoebic colitis), Crohn's disease, ulcerative colitis, benign anorectal lesions (e.g., hemorrhoids, anal fissures, and rectal ulcers), abdominal aortic aneurysm, an aortic graft, aortoenteric fistula, gastric ulcers, duodenal ulcers, Celiac disease, diverticula, portal hypertensive gastropathy, hemoptysis, oropharyngeal bleeding, a bleed of unknown origin, duodenal ulcers, and/or a post-surgery bleed (see, e.g., Kim et al. (2014) *World J. Gastrointest. Pathophysiol.* 5(4): 467-78).

Combination Detection

Optionally, spectral data can be generated for more than one analyte (e.g., two different analytes). In some embodiments, spectral data are generated for one or more proteins, one or more amino acids, one or more carbohydrates, one or more fats, one or more microbes, one or more therapeutic agents, and/or one or more blood constituents. The technology disclosed herein is capable of distinguishing different analytes from each other. For example, in some embodiments, spectral data can be collected for a given analyte in a sample in which one or more other analytes are present, and the spectral data generated for the given analyte can be used to detect and/or quantify the given analyte.

Any combination of the analytes can be detected using any of the methods described herein. For example, the methods and devices disclosed herein can be used to detect combinations of analytes such as a biomarker indicative of a GI disorder and a drug used to treat the GI disorder. The methods and devices can be used to detect a drug disclosed above and another drug, e.g., another drug used in combination with the first drug. Examples of such drugs include 2-amino-6-aryl-5-substituted pyrimidines (see U.S. Pat. No. 4,665,077); non-steroidal antiinflammatory drugs (NSAIDs); ganciclovir; tacrolimus; lucocorticoids such as Cortisol or aldosterone; anti-inflammatory agents such as a cyclooxygenase inhibitor; a 5-lipoxygenase inhibitor; or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporine; 6-mercaptopurine; steroids such as corticosteroids or glucocorticosteroids or glucocorticoid analogs, e.g., prednisone, methylprednisolone, including SOLU-MEDROL®, methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists; anti-LFA-1 antibodies, including anti-CD 1 la and anti-CD 18 antibodies; anti-L3T4 antibodies; heterologous anti-lymphocyte globulin; pan-T antibodies, anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodomase; RNA or DNA from the host; FK506; RS-61443; chlorambucil; deoxyspergualin; rapamycin; T-cell receptor (Cohen et al, U.S. Pat. No. 5,114,721); T-cell receptor fragments (Offner et al, Science, 251: 430-432 (1991); WO 90/11294; laneway, Nature, 341: 482 (1989); and WO 91/01133); BAFF antagonists such as BAFF or BR3 antibodies or immunoadhesins and zTNF4 antagonists (for review, see Mackay and Mackay, Trends Immunol, 23: 113-5 (2002) and see also definition below); biologic agents that interfere with T cell helper signals, such as anti-CD40 receptor or anti-CD40 ligand (CD 154), including blocking antibodies to CD40-CD40 ligand. (e.g., Duriee et al, Science, 261: 1328-30 (1993); Mohan et al, J. Immunol, 154: 1470-80 (1995)) and CTLA4-Ig (Finck et al, Science, 265: 1225-7 (1994)); and T-cell receptor antibodies (EP 340,109) such as T10B9. Non-limiting examples of drugs that may be detected using any of the methods described herein also include: budenoside; epidermal growth factor; aminosalicylates; metronidazole; mesalamine; olsalazine; balsalazide; antioxidants; thromboxane inhibitors; IL-1 receptor antagonists; anti-IL-1 monoclonal antibodies; growth factors; elastase inhibitors; pyridinyl-imidazole compounds; TNF antagonists; IL-4, IL-10, IL-13 and/or TGFβ cytokines or agonists thereof (e.g., agonist antibodies); IL-11, glucuronide- or dextran-conjugated prodrugs of prednisolone, dexamethasone or budesonide; ICAM-I antisense phosphorothioate oligodeoxynucleotides (ISIS 2302; Isis Pharmaceuticals, Inc.); soluble complement receptor 1 (TPIO; T Cell Sciences, Inc.); slow-release mesalazine; antagonists of platelet activating factor (PAF); ciprofloxacin; and lignocaine. Examples of drugs that can be detected using the presently claimed methods include sulfasalazine, related salicylate-containing drugs, and corticosteroids. In some embodiments, the methods described herein can be used to detect iron, antidiarrheal agents, azathioprine, 6-mercaptopurine, and/or methotrexate.

In other embodiments, the methods described herein can provide for detection of a TNF inhibitor as described herein and one or more of: a CHST15 inhibitor, a IL-6 receptor inhibitor, an IL-12/IL-23 inhibitor, an integrin inhibitor, a JAK inhibitor, a SMAD7 inhibitor, a IL-13 inhibitor, an IL-1 receptor inhibitor, a TLR agonist, an immunosuppressant, a live biotherapeutic (e.g., bacteria of the species *Roseburia hominis, Eubacterium rectale, Dialister invisus, Ruminococcus albus, Ruminococcus callidus*, and *Ruminococcus bromii*), or a stem cell.

Detection Agents

Certain detection methods described herein can utilize at least one detection agent in order to detect an analyte in a sample. A "detection agent" is a molecule that binds to a specific analyte. Some detection agents may comprise analytes (e.g., the analytes described above) in accordance with the ability of the analyte to bind to another molecule to be detected using the methods described below. For example, in some embodiments, the detection agent comprises an antibody when used as a reagent to detect and/or quantify an antigen that the antibody specifically binds to. However, in some embodiments, the antibody is an analyte (e.g., an antibody which is a drug, such as a TNFα antibody) and the detection agent comprises an antigen to which the antibody specifically binds, thereby allowing for its use as a reagent to detect and/or quantify the antibody. In some embodiments, the detection agent binds to analyte that is specific to a particular genus, species, or strain of a microorganism (e.g., a pathogenic bacteria). In some embodiments, a detection agent comprises an area on the surface or in a cavity which specifically binds to and is thereby defined as complementary with a particular spatial and polar organization of the analyte. In some embodiments, the detection agent and the corresponding analyte form a binding pair, such as, but not limited to, an immunological pair (such as antigen-antibody), a biotin-avidin pair, a hormone-hormone receptor pair, a nucleic acid duplex, IgG-protein A pair, a polynucleotide pair such as DNA-DNA, DNA-RNA, and the like. In some embodiments, the detection agent comprises an antibody (e.g., a monoclonal antibody), an affimer, an aptamer, an antigen, a receptor, a small molecule, and a nucleic acid (e.g., a DNA molecule or an RNA molecule). In some embodiments, either member of the binding pair (e.g., the detection agent and/or the analyte) can be detectably labeled as described herein.

In some embodiments, the detection agent comprises a portion of a nucleic acid that is complementary to a nucleic acid sequence of an analyte. As used herein, "complementary" refers to the capacity for pairing through hydrogen binding between two nucleic acid sequences. For example, if a nucleic acid base at one position of an analyte is capable of hydrogen bonding with a nucleic acid base at a corresponding position of a detection agent, then the bases are considered to be complementary to each other at that position. In some embodiments, 100% complementarity is not required. In some embodiments, 100% complementarity is required. Routine methods can be used to design a detection agent that binds to a nucleic acid sequence of an analyte. In some embodiments, the detection agent comprises a nucleic acid sequence that is complementary to at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65 or more contiguous nucleotides or nucleosides present in the nucleic acid sequence of an analyte (e.g., a DNA molecule or an RNA molecule). In general, the detection agents useful in the devices, compositions and methods described herein have at least 80% sequence complementarity to a nucleic acid sequence of a analyte, e.g., at least 85%, at least 90%, at last 92%, at least 94%, at least 95%, at least 96%, at least 97%, at least 98%, at least 99%, or are 100% complementary to a nucleic acid sequence of an analyte).

In some embodiments, the detection agent comprises a detectable moiety such as a fluorescent compound. In some embodiments, the detection agent includes or is conjugated to a label that facilitates the detection of the detection agent using a spectrometer. For example, in some embodiments, the detection agent includes a fluorescent label.

Ingestible Devices Including Spectrometers

Figure 1:
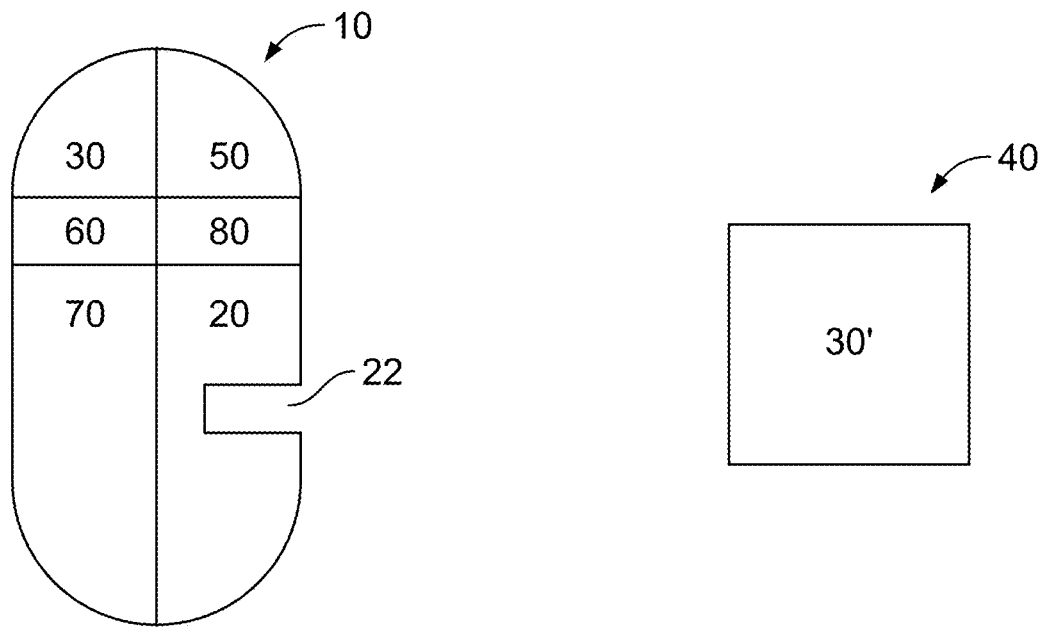
FIG. 1 shows an embodiment of an exemplary ingestible device including a spectrometer and a separate base station (not to scale).

Referring to FIG. 1, there is shown an ingestible device 10 including spectrometer 20 operable to generate spectral data of a sample within the GI tract of a subject in vivo. Alternatively or additionally, in some embodiments, the ingestible device may be used to obtain spectral data relating to the tissue lining of the GI tract of a subject. Optionally, ingestible device 10 may include communications unit 30, processing unit 50, memory 60, one or more environmental sensors 70, and/or microcontroller 80. Optionally, ingestible device 10 may include a detection chamber 22 for containing a sample from the GI tract of the subject. In general, detection chamber 22 may be exposed to the exterior of the device or contained within the device. In some embodiments, one or more ports, valves, pumps and/or conduits provide fluid communication between a detection chamber 22 contained within the ingestible device 10 and the exterior of ingestible device 10. In general, a sample (e.g., a sample from the GI tract of the subject) is collected in the detection chamber 22, and the spectrometer 20 is used to generate spectral data for the sample.

Optionally, the spectrometer 20 can be designed to generate spectral data of one or more samples external to the ingestible device 10. As an example, the spectromter 20 can be designed to generate spectral data of one or more regions of the GI tract of the subject (e.g., one or more regions of tissue of the GI tract of the subject). In embodiments in which the spectrometer 20 is designed to generate spectral data of one or more samples external to the ingestible device 10, the ingestible device 10 may or may not include the detection chamber 22.

Base station 40 contains a communications unit 30' for communicating with the ingestible device 20. In general, communications units 30 and 30' may exchange data through any suitable wired or wireless communication scheme, including radio communications (RF), WiFi communications, Bluetooth™ communications, universal serial bus (USB) communications, infrared or near infrared communications, acoustic signaling, and the like. In some embodiments, the ingestible device 20 may be recovered after travelling though the GI tract of the subject, and the ingestible device 20 exchanges data with the base station 40 via the communications units 30 and 30' after the ingestible device 20 has been recovered. In some embodiments, the ingestible device 20 communicates with the base station 40 while transiting the GI tract of the subject, and the base station 40 received data either continuously or at predetermined intervals. For example, the ingestible device 20 may be configured to transmit information to the base station 40 every minute, or after reaching certain predetermined locations within the GI tract of the subject.

The ingestible device 10 may generally be in the shape of a capsule, like a conventional pill, or alternatively in the shape of a sphere. Accordingly, the shape of the ingestible device provides for easier ingestion, and is also familiar to healthcare practitioners and patients.

Unlike a conventional pill, ingestible device 10 is designed to withstand the chemical and mechanical environment of the GI tract (e.g., effects of muscle contractile forces and concentrated hydrochloric acid in the stomach). However, unlike other devices that are intended to stay inside a patient's body (e.g., medical implants), in some embodiments, ingestible device 10 is designed to only temporarily travel or remain within the body. Accordingly, the regulatory rules governing the materials and manufacture of the ingestible device may be less strict than for the devices that are intended to stay inside the body. Nevertheless, since the ingestible device still enters the body, the material(s) used to manufacture the ingestible device are generally selected to at least comply with the standards for biocompatibility (e.g., ISO 10993). Furthermore, components inside the ingestible device are free of any restricted and/or toxic metals and are lead-free pursuant to the Directive 2002/95/EC, which is also known as the Restriction of Hazardous Substances (RoHS).

There is a broad range of materials that may be used for manufacturing the ingestible device. Different materials may be used for each of the different components of the ingestible device. Examples of these materials include, but are not limited to, thermoplastics, fluoropolymers, elastomers, stainless steel and glass complying with ISO 10993 and USP Class VI specifications for biocompatibility. In certain embodiments, these materials may further include liquid silicone rubber material with a hardness level of 10 to 90 as determined using a durometer (e.g., MED-4942™ manufactured by NuSil™), a soft biocompatible polymer material such as, but not limited to, polyvinyl chloride (PVC), polyethersulfone (PES), polyethylene (PE), polyurethane (PU) or polytetrafluoroethylene (PTFE), and a rigid polymer material coated with a biocompatible material that is soft or pliable (e.g., a poly(methyl methacrylate) (PMMA) material coated with silicone polymer). Teflon® may be used as a material in the ingestible device for any movable components in order to reduce friction between these components. Other example materials may include other materials commonly used in micro-fabrication, such as polydimethylsiloxane (PDMS), borosilicate glass, and/or silicon.

Generally, an enclosure of ingestible device 10 may be manufactured from a type of plastic, such as a photosensitive acrylic polymer material. The enclosure may be formed by coupling two enclosure ends together. The enclosure, in effect, protects the interior of the ingestible device from its external environment and also protects the external environment (e.g., the GI tract) from components inside the ingestible device. In some embodiments, when the ingestible device 10 includes a detection chamber 22 exposed to the exterior of the ingestible device 10, the enclosure of the ingestible device 10 forms a portion of the detection chamber 22. In some embodiments, the spectrometer 20 of the ingestible device 10 is located behind the enclosure, and a portion of the enclosure is manufactured from materials that are transparent to one or more spectra of light (e.g., near-infrared or visible light) used by the spectrometer 20.

Furthermore, ingestible device 10 may include one or more additional layers of protection. The additional protection may protect the patient against any adverse effects arising from any structural problems associated with the enclosure (e.g., the two enclosure ends falling apart or a fracture developing in the enclosure). For example, a power supply inside the ingestible device may be coated with an inert and pliable material (e.g., a thin layer of silicone polymer) so that only electrical contacts on the power supply are exposed. This additional protection to the power supply may prevent chemicals inside the ingestible device from seeping into the patient's body.

Also, a surface of the ingestible device 10 and surfaces of the different components in the ingestible device may receive different treatments that vary according to their intended use. For example, the surface of the ingestible device 10 may receive plasma activation for increasing hydrophilic behavior. Detection chamber 22 or ports, valves, pumps and/or conduits that are intended to come into contact with a fluid such as fluid sample from the GI tract during normal operation of the device may also receive hydrophilic treatment while certain other components may receive hydrophobic treatments.

In some embodiments, ingestible device 10 includes communications unit 30 for transmitting data to, and/or receiving operating parameters from, base station 40. For example, communications unit 30 may transmit spectral data and/or environmental data to base station 40 located ex vivo that contains a corresponding communications unit 30'. Base station 40 may be any electronic device configured to communicate with ingestible device 10 such as, but not limited to, a computer, or a personal electronic device such as a watch, physical activity tracker, fitness monitor, personal digital assistant (PDA), phone or tablet. Other examples of electronic devices that may be configured to communicate with ingestible device 10 and serve as base station 40 include a "smart" home appliance that is able to connect to a network such as the internet. In some embodiments, base station 40 may be a home appliance connected to a network such as home speakers, a fridge or other kitchen appliance, a toilet and/or a scale, such as a bathroom scale. In some embodiments, the base station and/or ingestible device are connected to a network such as the internet. For example, base station 40 may include network circuitry for communicating over an internet connection with a database of digestion profiles and/or spectral standards stored on a remote server. In some embodiments, base station 40 may include a display unit for presenting information to a user. For example, base station 40 may include a display for presenting information about the subject's digestion profile. In some embodiments, base station 40 may include a user input interface for receiving user inputs. For example, base station 40 may include a keyboard, mouse, touch-screen screen enabled display, or other suitable user interface.

Ingestible device 10 and/or base station 40 may include memory 60 for storing the spectral data, environmental data and/or digestion profiles. For example, base station 40 may store multiple sets of spectral data gathered from multiple ingestible devices (e.g., multiple instances of ingestible device 10) in memory 60, which may or may not be shared as part of public database of digestion profiles. In some embodiments, memory 60 may also include operational parameters for controlling ingestible device 10. In general, memory 60 may be any form of computer-readable memory suitable for storing and retrieving data such as semiconductor memory or a secondary storage device such as a hard disk drive or solid state drive. In some embodiments, ingestible device 10 and/or base station 40 are connected to networked storage suitable for storing the spectral data, environmental data and/or digestion profiles for a subject. In general, this networked storage may include a searchable database of digestion profiles. For example, spectral data may be transmitted from the ingestible device 10 to the base station 40, the base station 40 may use the spectral data to generate a digestion profile for the subject, and the base station 40 may communicate the digestion profile to a remote server to be added to a digestion profile database.

Spectrometers of Ingestible Devices

In some embodiments, spectrometer 20 is operable to generate spectral data for a sample within the GI tract of a subject. The spectral data may be intensity spectral data, absorbance spectral data, transmission spectral data, reflectance spectral data, fluorescence spectral data, Fourier transform spectral data and/or Raman spectral data. Optionally, ingestible device 10 may include a plurality of spectrometers for generating different types of spectral data. In some embodiments, the spectrometer 20 may be configured to gather spectral data from a portion of the sample within the GI tract of the subject surrounding the enclosure of the ingestible device. In some embodiments, where the ingestible device 10 includes a detection chamber 22, the spectrometer 20 may be configured to gather spectral data for a sample contained with the detection chamber 22. In certain embodiments, spectrometer 20 is operable to generate spectral data of a sample (e.g., tissue of the GI tract of the subject) external to ingestible device 10 (e.g., via a hyperspectral camera as the spectrometer). In such embodiments, ingestible device 10 may or may not include detection chamber 22.

Different types of spectrometers known in the art may be used to generate the spectral data. In some embodiments, spectrometer 20 includes a light source and a photodetector. For example, the spectrometer 20 may include a source for generating light in the near-infrared spectrum, and an accompanying photodetector sensitive to the near-infrared spectrum. In some embodiments, spectrometer 20 further includes one or more of a dispersive element, lens and/or filter. In some embodiments, spectrometer 20 includes one or more lenses, fisheye lenses, filters, color filters, polarization filters, optical filters, beam splitters, interferometers, tunable filters or spectral reformers.

In some embodiments, the spectrometer 20 includes elements that are suitable for miniaturization and/or use on an ingestible device. In some embodiments, the spectrometer 20 includes a tuneable interferometer such as a Fabry-Perot interferometer (FPI). In some embodiments, the spectrometer 20 includes a micro-electro-mechanical system (MEMS). Elements suitable for use in the ingestible device 10 include FPI interferometers and other elements available from Hamamatsu Photonics K.K. and FPI tunable wavelength filters available from VTT Technical Research Centre of Finland Ltd.

In some embodiments, the light source is a lamp, such as a tungsten or xenon lamp, light emitting diode (LED), tunable LED or laser. In some embodiments, the light source produces light at one or more wavelengths in the Ultraviolet, Visible, Near-infrared and/or Mid-infrared. In some embodiments, the light source produces a continuous output and/or a pulsed output.

In some embodiments, the photodetector includes one or more photodiodes. Photodiodes may be made out of materials known in the art such as, but not limited to, silicon, germanium, indium gallium arsenide, lead (II) sulfide and/or mercury cadmium telluride. In some embodiments, the photodetector detects light at one or more wavelengths in the Ultraviolet, Visible, Near-infrared and/or Mid-infrared.

In some embodiments, the spectrometer 20 includes two or more photodetectors configured to detect spectral data at different wavelengths and/or for detecting different analytes. For example, in some embodiments, the spectrometer 20 may include a plurality of photodetectors configured to detect light or spectra at different wavelengths associated with the detection of different analytes, such as proteins, fats and/or carbohydrates. Optionally, the spectrometer 20 includes an array of photodetectors.

In some embodiments, the photodetector is a 2-dimensional array, optionally a two-dimensional array of photodiodes. For example, in some embodiments, the photodetector is a 40×40 array with 1600 pixels. Larger or smaller arrays may also be used depending on the resolution desired for hyperspectral data. Examples of two-dimensional arrays that may be used in an ingestible device as described herein include smaller arrays with low power consumption and a spectral range suitable for detection of light across wavelengths in one or more of UV, VIS, NIR and/or MIR. Accordingly, in some embodiments the spectral data generated using an ingestible device described herein (e.g., the ingestible device 10) is hyperspectral data. NIR hyperspectral imaging of biological materials is described in greater detail in Manley, Near-infrared spectroscopy and hyperspectral imaging: non-destructive analysis of biological materials *Chem. Soc. Rev.,* 2014, 43, 8200, hereby incorporated by reference in its entirety.

Hyperspectral imaging may be advantageously used in the methods and devices described herein as the additional spatial dimensions may allow for images to be analyzed in order to identify non-homogeneous samples and/or obtain spectra from different areas of the image such as to focus on liquid sample or particular matter such as food particles, etc. The results of this analysis may be included in the digestion profile for a subject, or may be used in conjunction with a digestion profile to infer information about the subject or provide recommendations for the subject. For example, spectral data may be used to detect the presence of a particular chemical or macronutrient present within the sample over time, which may indicate the subject's ability to absorb the chemical or macronutrient from the sample as it transits through the GI tract of the subject.

Further, hyperspectral imaging may be advantageously used in the methods and devices described herein as the additional spatial dimensions may allow for images to be analyzed in order to detect and/or measure either "hot spots" or a particular spatial pattern of tissue that lines the GI tract. Such a hot spot is region of GI tract tissue where the material property, and thus spectral information, is very different in the spot relative to a global average over an entire portion of GI tract tissue that includes the region. For example, results obtained based on hyperspectral imaging can be advantageously used for understanding the existence and nature of such localized differences, when it is important to assess the health condition of tissue lining the GI tract, for instance. For example, analysis of images acquired with the spectrometer 20, which includes a hyperspectral camera, can be used for detecting lesions/diseased portions of GI tract tissue by detecting, in the acquired images, spectroscopic patterns corresponding to diseased states of the GI tract tissue, as described in detail in Example 15 and Example 17. As another example, images acquired with a hyperspectral camera-equipped spectrometer 20 can be analyzed to advantageously localize bleeds on the intestinal wall. In contrast, a spectrometer 20 can be used to detect such bleeds, without being able to determine the location(s) of the bleed(s) on the intestinal wall. Further description relating to the latter capability of the disclosed technologies is described in Example 18.

Moreover, spectral data produced by the spectrometer 20 of the ingestible device 10 can be used to determine, in vivo, locations of the ingestible device 10 as it travels through the GI tract. As described in detail in Example 14, spectral data corresponding to tissue lining the GI tract was found to be unique to predetermined locations along the GI tract. In this manner, a processor associated with the ingestible device 10 can compare spectra corresponding to GI tract tissue obtained in vivo, by the spectrometer 20 (either directly, or produced based on hyperspectral images), with reference spectra corresponding to tissue from predetermined locations along the GI tract. In the case of a spectrometer 20 equipped with a hyperspectral camera, the spatial information, which is included along with the spectral information in a hyperspectral image, can indicate, e.g., a large density of villi, which is characteristic to the small intestine and is not characteristic to other portions of the GI tract. Such additional spatial information, available in an image acquired with the hyperspectral camera of the spectrometer 20, complements the available spectral information and, thus, can improve determination of the location(s) of the ingestible device 10 along the GI tract.

Furthermore, spectral data produced by the spectrometer 20 of the ingestible device 10 can be used to determine, in vivo, a level of oxygenation of tissue lining the GI tract. As noted in Example 18, spectral data allows for the differentiation of GI tract tissue having different oxygenation levels. In this manner, a processor associated with the ingestible device 10 can compare spectra corresponding to GI tract tissue obtained in vivo, that has been produced directly or based on hyperspectral images by the spectrometer 20, with reference spectra corresponding to GI tract tissue having different predetermined oxygenation levels e.g., 15%, 20%, 25%, 30%, 35%, 40%, 45%, 50%, 55%, 60%, 65%, 70%, 75%, 80%, 85%, 90%, 95%, or 100%. As the GI tract tissue is very rich in blood vessels, a large contribution to a spectrum obtained in vivo by the spectrometer 20 of the ingestible device 10 can be attributed to the oxygenation level of the blood in the GI tract tissue. For this reason, in some implementations, the obtained spectrum can be compared with reference spectra corresponding to blood samples having different oxygenation levels, e.g., 3%, 5%, 10%, 15%, 20%, 25%, 30%, 35%, 40%, 45%, 50%, 55%, 60%, 65%, 70%, 75%, 80%, 85%, 90%, 95%, or 100%.

In some embodiments, spectrometer 20 generates spectral data in the Ultraviolet (UV) spectrum. For example, in some embodiments, the spectral data includes intensity, absorbance, reflectance, transmission or fluorescence at one or more wavelengths between about 10 nm and 400 nm.

In some embodiments, spectrometer 20 generates spectral data in the Visible (Vis) spectrum. For example, in some embodiments, the spectral data includes intensity, absorbance, reflectance, transmission or fluorescence at one or more wavelengths between about 400 nm and 700 nm.

In some embodiments, spectrometer 20 generates spectral data in the Near Infrared (NIR) spectrum. For example, in some embodiments, the spectral data includes intensity, absorbance, reflectance, transmission or fluorescence at one or more wavelengths between about 600 nm and 2600 nm, between about 600 nm and 1500 nm or between about 800 and 2000 nm.

In some embodiments, spectrometer 20 generates spectral data in the Mid-Infrared (MIR) spectrum. For example, in some embodiments, the spectral data includes intensity, absorbance, reflectance, transmission or fluorescence at one or more wavelengths between about 1500 nm and 5600 nm, between about 2000 nm and 4000 nm, or between about 2500 and 5000 nm.

The spectrometer may also generate spectral data that overlaps two or more areas of the electromagnetic spectrum. For example, in some embodiments, the spectral data may include wavelengths from the NIR and MIR, such as wavelengths between about 1000 nm and 2500 nm. In some embodiments, the spectral data may include wavelengths from the VIS and NIR, such as between about 500 nm and 1500 nm.

In one aspect of the disclosure, generating spectral data at one or more pre-determined wavelengths allows for the detection of particular analytes within the sample. For example, spectral data in the low NIR such as 700-1100 nm may be suitable for detecting for food and macronutrients, and spectral data in the high NIR such as 1000-2500 nm is suitable for detecting features of human anatomy, physiology, pathophysiology and biology (e.g., analytes relating to human digestion, microbiome analytes (e.g., a commensal or pathogenic bacterium), a ketone, an inflammatory marker (e.g., a cytokine), a therapeutic agent (e.g., a drug), and analytes produced by the liver (e.g., acetoacetate, beta-hydroxybutyrate, and acetone)). Spectral data at longer wavelengths such as 2500-16000 may be suitable for detecting chemical compounds and dissolved gases. Spectral data may also be used for detecting the presence of liquid water as well. For example, in the NIR range liquid water has absorption bands around 1950 nm, 1450 nm, 1200 nm and 970 nm. In some embodiments, generating spectral data at one or more pre-determined wavelengths allows for information to be obtained regarding the sample and/or subject without necessarily identifying specific analytes. For example, the spectral data gathered by an ingestible device 10 may be used to search a database of spectral standards or digestion profiles (e.g., via an Internet connected base station 40), and it may be determined that similar spectral data is indicative of individuals with a vegetarian diet who have recently eaten a particular type of ingestible standard.

Spectral data generated using an ingestible device as described herein may be analyzed in order to extract information from complex biological samples in the GI tract of a subject. For example, the analysis of spectral data of biological samples to determine various characteristics such as the relative level of macronutrients, gross energy content and/or utilizable energy content are disclosed in Fusch et al., "Rapid measurement of macronutrients in breast milk: How reliable are infrared milk analyzers?" *Clinical Nutrition* 34 (2015) 465-476; Manley, "Near-infrared spectroscopy and hyperspectral imaging: non-destructive analysis of biological materials" *Chem. Soc. Rev.*, 2014, 43, 8200; Szigedi et al., "Fourier Transform Near-Infrared Spectroscopy to Predict the Gross Energy Content of Food Grade Legumes" *Food Anal. Methods* (2013) 6:1205-1211; Kays and Barton, "Rapid Prediction of Gross Energy and Utilizable Energy in Cereal Food Products Using Near-Infrared Reflectance Spectroscopy" *J. Agric. Food Chem.* 2002, 50, 1284-1289 all of which are hereby incorporated by reference in their entirety.

Spectrometer 20 may optionally include detection chamber 22. In some embodiments, spectrometer 20 includes a light source and a photodetector defining a light path through detection chamber 22. For example, a light source and a photodetector may be positioned on either side of the detection chamber 22 such that light emitted from the light source passes through the detection chamber 22 before being detected by the protodetector. In general, detection chamber 22 may be used to contain a sample from the GI tract of the subject in order to generate spectral data of the sample in vivo.

In some embodiments, detection chamber 22 is exposed to the exterior of device 10. In operation, fluid from the GI tract may enter into the detection chamber of ingestible device 10 in vivo through surface tension, movement of the subject and/or peristaltic effects. In some embodiments, the detection chamber may be coated with a hydrophilic coating to encourage fluid to flow into the detection chamber. In some embodiments, detection chamber 22 is formed by a depression along the exterior surface of the enclosure of ingestible device 10. In some embodiments, ingestible device 10 may include a cover (not shown) movable to expose detection chamber 22 to the exterior of the device.

In some embodiments, detection chamber 22 may be located within device 10. A fluid sample from the GI tract of the subject may be actively or passively brought into the detection chamber in order to generate spectral data of the sample. For example, in some embodiments, device 10 includes one or more ports, valves, pumps and/or conduits for controlling the transfer of the fluid sample from the GI tract into the detection chamber.

In some embodiments, spectrometer 20 includes a light source and a photodetector positioned on the exterior of ingestible device 10, or positioned behind the enclosure of ingestible device 10 and directed towards the exterior of ingestible device 10 (e.g., spectrometer 20 includes a hyperspectral camera). In some embodiments, the light source is configured to transmit light radially towards the environment external to the device and the photodetector is configured to detect a reflectance from the environment external to the device. In some embodiments, the light source is adjacent to the photodetector on the exterior of device 10. In some embodiments, spectrometer 20 is configured to generate reflectance spectral data. In some embodiments, the spectrometer 20 is positioned either fully or partially behind a material that is transparent to one or more spectra of light, such as optically transparent plastic. For example, the spectrometer 20 may include a light source and photodetector that operate in the Ultraviolet, Visible, Near-infrared and/or Mid-infrared, and the light source and/or the photodetector may be placed behind a portion of the device enclosure that is formed from a material that is transparent to light in the Ultraviolet, Visible, Near-infrared and/or Mid-infrared spectra. In some embodiments, the spectrometer 20 may be positioned either fully or partially behind one or more lenses. For example, the photodetector of spectrometer 20 may be positioned behind a lens configured to focus light onto the surface of the photodetector. In some embodiments, the spectrometer 20 may include a light source positioned behind a lens configured to collimate the light into a beam. The collimated beam of light may be directed into a detection chamber 20, and oriented in the direction of one or more photodetectors positioned on the other side of the detection chamber. In some embodiments, the collimated beam of light may be configured to travel along a pre-defined light path through the detection chamber. In embodiments described in this paragraph, ingestible device 10 may or may not include detection chamber 22.

Additional Sensors of Ingestible Devices

Ingestible device 10 may also include one or more environmental sensors 70. Environmental sensor 70 may be used to generate environmental data for the environment external to device 10 in the GI tract of the subject. Environmental data may be used to further characterize the GI tract of the subject either alone or in combination with the spectral data. In some embodiments, environmental data is generated at the same time as spectral data such that data are generated from the same location within the GI tract of the subject. Optionally, environmental data may be information associated with spectral data or associated with the subject and form part of a digestion profile. In some embodiments, processing unit 50 is configured to generate a digestion profile based on spectral data and environmental data.

Examples of environmental sensor 70 include, but are not limited to a capacitance sensor, a temperature sensor, an impedance sensor, a pH level sensor, a heart rate sensor, an acoustic sensor such as a microphone, image sensor, and/or a movement sensor. In some embodiments, the ingestible device 10 includes a plurality of different environmental sensors for generating different kinds of environmental data. In some embodiments, the movement sensor is a step sensor. In some embodiments, the movement sensor is used to generate data for determining calories burned by a subject. In some embodiments, the image sensor is a video camera suitable for obtaining images in vivo of the tissues forming the GI tract of the subject. In some embodiments, the environmental data is used to help determine one or more characteristics of the GI tract of the subject such as for the diagnosis of a medical condition. Additionally or alternatively, the data is used to determine the location of the ingestible device within the GI tract (e.g., by comparing spectral data associated with the GI tract with one or more spectral standards for GI tract tissue).

In some embodiments, the one or more environmental sensors measure pH, temperature, transit times, or combinations thereof. Examples of devices useful to detect pH changes include Medimetrics' IntelliCap® technology (see Becker, Dieter, et al. "Novel orally swallowable IntelliCap® device to quantify regional drug absorption in human GI tract using diltiazem as model drug." *AAPS PharmSciTech* 15.6 (2014): 1490-1497) and Rani Therapeutics' AutoPill™ technology (see U.S. Pat. No. 9,149,617), hereby incorporated by reference in its entirety.

In some embodiments, the spectral data and/or environmental data generated by the ingestible device 10 is used to determine the location of the device within the GI tract of the subject. For example, it may be possible for the ingestible device 10 to use various combinations of light-emitting diodes and sensors to determine whether the device is in the stomach, small intestine, or large intestine. This may be done by emitting light at different wavelengths, measuring the level of light reflected at each wavelength by the environment surrounding the ingestible device 10, and using this information to determine an approximate location of the ingestible device 10 based on the different reflectance properties of the various different portions of the GI tract. Once the ingestible device 10 determines that it is in a particular predetermined region of the GI tract (e.g., the small intestine, or a specific part of the small intestine such as the jejunum), the ingestible device 10 may be configured to generate spectral data and/or environmental data from that region of the GI tract. Additional examples of systems and methods for determining the location of an ingestible device within a GI tract are discussed in greater detail in U.S. Ser. Nos. 15/514,413; 62/480,187; and 62/540,873. Exemplary related disclosure is provided below in Example 19 and with respect to FIGS. 64-134.

In some embodiments, the ingestible device described herein may be localized using a gamma scintigraphy technique or other radio-tracker technology as employed by Phaeton Research's Enterion™ capsule (see Teng, Renli, and Juan Maya. "Absolute bioavailability and regional absorption of ticagrelor in healthy volunteers." *Journal of Drug Assessment* 3.1 (2014): 43-50), or monitoring the magnetic field strength of permanent magnet in the ingestible device (see T. D. Than, et al., "A review of localization systems for robotic endoscopic capsules," *IEEE Trans. Biomed. Eng.*, vol. 59, no. 9, pp. 2387-2399, September 2012).

In some embodiments, the ingestible device 10 may include a camera for generating video imaging data of the GI tract, which can be used to determine, among other things, the location of the device. Examples of video imaging capsules include Medtronic's PillCam™ Olympus' Endocapsule®, and IntroMedic's MicroCam™ (see Basar et al. "Ingestible Wireless Capsule Technology: A Review of Development and Future Indication" *International Journal of Antennas and Propagation* (2012); 1-14). Other imaging technologies include thermal imaging cameras, and those that employ ultrasound or Doppler principles to generate different images (see Chinese patent application CN104473611: "Capsule endoscope system having ultrasonic positioning function").

In some embodiments, the ingestible device 10 is operable to generate spectral data and/or environmental data at one or more predetermined locations within the GI tract. For example, in some embodiments, the ingestible device 10 is operable to generate data in one or more of the stomach, proximal and distal duodenum, jejunum, ileum, descending colon, ascending colon and transverse colon.

Connectors for Attaching Ingestible Devices

In some embodiments, ingestible device 10 may be attached to the interior surface of tissues forming the GI tract of a subject. In some embodiments, attaching the ingestible device 10 to the GI tract allows the device to generate data associated with a specific location within the GI tract. For example, in some embodiments, the ingestible device 10 may be attached to a particular location in the GI tract of an subject (e.g., an obese subject) to help monitor the presence and/or amount of one or more analytes. Such information can be used as described herein. As an example, the information can be used to assess calorie and/or food intake. The ingestible device 10 may periodically transmit data to a base station (e.g., base station 40) with spectral data or other data indicative of the samples detected by the ingestible device 10. This may be used to generate data as described herein. For example, a log of all of the food consumed by the subject over a given period of time may be generated. In some embodiments, this information may be combined with other information (e.g., contained in the subject's digestion profile, such as, for example, information regarding the subject's ability to absorb calories from particular types of macronutrients) in order to create desired information (e.g., a detailed profile of the subject's food consumption and the actual number of calories absorbed by the subject over time). This information may be presented to the subject or other users through any convenient mechanism, such as a display located on base station 40.

In some embodiments, ingestible device 10 includes a connector for attaching the device to the interior surface of the GI tract. The connector may be operable to attach ingestible device 10 to the interior surface of the GI tract using an adhesive, negative pressure and/or fastener. For example, in some embodiments, the device may be attached to the interior surface of the GI tract with a dissolvable or permanent stitch or staple, suction cup, pins, hooks, loops, clips, surgical clip, chemical adhesive, magnets, barbs or any combination thereof. In some embodiments, the ingestible device 10 may be positioned and surgically attached to the GI tract of a subject by a surgeon. In some embodiments, the ingestible device 10 that has been surgically attached to the interior surface of the GI tract may also be operable to detach from the interior surface of the GI tract of the subject, such as in response to instructions received from a base station, or in response to determining that energy reserves remaining within the ingestible device (e.g., the percentage of the remaining charge on a battery powering the ingestible device) have reached a minimum threshold level. In some embodiments, the device is released from the interior surface of the GI tract over time as, e.g., stitches and/or adhesive is dissolved.

In some embodiments, the ingestible device described herein may be attached to the interior surface of the GI tract using a plurality of fasteners (e.g. microneedles), optionally by drawing tissue towards the plurality of fasteners as described in U.S. patent application Ser. No. 15/113,521, "Gastrointestinal Sensor Implantation System", published as U.S. Publication No. 2017/0027520, hereby incorporated by reference in its entirety.

In some embodiments, operation of the connector is controlled by microcontroller 80, optionally in response to information regarding the location of the device and/or in response to operating parameters from base station 40. Ingestible device 10 may be attached to a particular location in the GI tract of the subject in order to generate spectral data and/or environmental data at a fixed location. Ingestible device 10 may then be released and will continue to flow through the GI tract.

Operation of Ingestible Devices

In operation, after ingestible device 10 is ingested by a subject, the ingestible device 10 will travel through the GI tract before eventually being expelled. Movement of the ingestible device 10 through the GI tract will generally be aided by gravity, peristaltic effects and the natural movement of ingested fluids and/or food through the GI tract. Accordingly, by operating spectrometer 20 at different time points it is possible to obtain spectral data for samples at different locations of the GI tract. In some embodiments, the ingestible device 10 is operable to generate spectral data at a plurality of time points as the ingestible device travels through the GI tract of the subject. In some embodiments, device 10 and/or processing unit 50 is operable to generate a plurality of digestion profiles at a plurality of time points as the ingestible device travels through the GI tract of the subject. In some embodiments, certain actions within the ingestible device 10 or base station 40, such as generating spectral data and/or environmental data, are triggered based on its location in the GI tract. For example, the ingestible device 10 may be configured to begin gathering spectral data at five-minute intervals after entering the small intestine. Every time the spectral data is gathered, it may be transmitted to base station 40, where it may be incorporated along with user input or any suitable type of information into a digestion profile for the subject.

In some embodiments, ingestible device 10 includes processing unit 50 configured to generate a digestion profile for the subject based on the spectral data and optionally environmental data and/or one or more inputs. Alternatively, processing unit 50 may be located within base station 40 located ex vivo. In some embodiments, ingestible device 10 and/or base station 40 are configured to transmit spectral data, and optionally environmental data and one or more inputs, to a server and receive information such as a digestion profile from the server. For example, spectral data and unit inputs may be transmitted to the server by the base station 40, and the server may generate base station 40, which may be a computer or a personal electronic device such as a watch, phone, tablet or physical activity tracker or fitness monitor. In some embodiments, base station 40 may be a stand-alone chip or set of circuitry that may be incorporated into a computer, or other personal electronic device.

Production and Use of Spectral Standards

In general, spectral data generated as describe herein is compared to a spectral standard to determine, for example, the presence and/or amount of an analyte, the condition of a region of GI tissue, the location of the ingestible device within the GI tract, and/or to generate a digestion profile.

In embodiments in which it is desirable to use the spectral data to determine the presence and/or amount of an analyte, the spectral standard may be for that analyte (e.g., a known spectral standard for the analyte, a spectral determined on an ad hoc basis, such as in a custom made simulated GI tract liquid).

In embodiments in which it is desirable to use the spectral data to analyze tissue of the GI tract, the spectral standard(s) may be for healthy tissue of the GI tract. Such information may be used, for example, to determine information regarding to a GI disorder associated with the GI tissue and/or the location of the ingestible device within the GI tract.

In embodiments in which it is desirable to use the spectral data to a digestion profile for a subject, the digestion profile for the subject may be generated by comparing spectral data for a sample from the GI tract of the subject to one or more spectral standards and/or spectra contained in other digestion profiles. For example, information associated with a sample may be obtained by comparing the spectral data gathered by the ingestible device 10 with one or more spectral standards representative of typical spectral data gathered under known conditions. For example, a particular spectral standard may represent the typical spectral data that would be observed in a healthy individual from a partially digested ingestible standard with half of the nutrients remaining. If the spectral data gathered by the ingestible device is similar to a particular spectral standard, information about the spectral standard may then be incorporated into the digestion profile for the subject. For example, if the spectral data is similar to spectral standards gathered from individuals who are diabetic, the digestion profile for the subject may indicate that the subject has produced similar spectral data to diabetic individuals, and therefore may aid in determining whether the subject is at risk of developing or has diabetes.

In general, in embodiments in which it is desirable to us the generated spectral to determine the presence and/or amount of an analyte, a spectral standard may represent typical spectral data gathered from a sample comprising an analyte or from a subject having an analyte in the subject's GI tract. In some embodiments, the spectral standard may represent typical spectral data gathered from a subject having an analyte bound to a detection agent in the subject's GI tract and/or spectral data gathered from a sample comprising an analyte bound to a detection agent (e.g., a detection agent comprising a fluorescent probe). In some embodiments, the spectral standard may represent typical spectral data gathered from individuals having a particular condition (e.g., a disease or disorder described herein). In some embodiments, spectral standards may represent typical spectral data gathered from a sample having a predetermined level of an analyte and/or a predetermined level of an analyte bound to a detection agent. These standards may be used in the methods described herein to compare spectral data gathered by ingestible device 10 with the spectral data of the spectral standards in order to detect, quantify and/or analyze a sample obtained from the GI tract of a subject or the GI tract of the subject. For example, in some embodiments, the methods described herein comprise comparing the spectral data gathered by the ingestible device with the spectral data of a spectral standard to determine whether a particular analyte or a combination of analytes is present in the GI tract of a subject and/or a sample from the GI tract of the subject. In some embodiments, the methods described herein comprise comparing the spectral data gathered by the ingestible device with the spectral data of a spectral standard to determine a level of analyte present in the GI tract of a subject and/or GI tract of the subject. In some embodiments, the methods described herein comprising comparing the spectral data gathered by the ingestible device with the spectral data of a spectral standard to determine whether the subject has or is at risk of developing a disease or disorder. In some embodiments, the methods described herein comprise comparing the spectral data gathered by the ingestible device with the spectral data of a spectral standard to determine whether the subject has or is at risk of developing an abnormality (e.g., inflammation or necrotic tissue) in the tissue lining of the GI tract. In some embodiments, the methods described herein comprise comparing the spectral data gathered by the ingestible device with one or more spectral standards to determine the location of the ingestible device within the GI tract of the subject (e.g., by comparing spectral data associated with tissue of the GI tract with one or more spectral standards for tissue of the GI tract). Spectral standards may be stored in a database accessible to either the ingestible device 10 or the base station 40, and the ingestible device 10 or the base station 40 may use any suitable criteria for identifying spectral standards in the spectral standards database or selecting one or more spectral standards in the spectral standards database to compare against the spectral data gathered by the ingestible device 10.

In some embodiments, spectral standards and/or spectra contained in other digestion profiles are selected for comparison in order to match the sample type used to generate the spectral data. For example, if the spectral data gathered by the ingestible device 10 was obtained from a particular type of sample (e.g., a particular pre-determined ingestible standard), the spectral data may be compared to spectral standards that represent typical spectral data gathered for that same type of sample. This may control for any differences or similarities between the spectral data and the spectral standards, which may be due to differences between the different samples used to generate the respective data, and may be used to generate a more accurate digestion profile indicative of information associated with the spectral data or the subject.

In some embodiments, spectral standards and/or spectra contained in other digestion profiles are selected for comparison in order to match the region in the GI tract where the spectral data was generated for the subject with spectral standards that are representative of spectral data for samples gathered from the same region in the GI tract (e.g., one or more of the stomach, proximal and distal duodenum, jejunum, ileum, descending colon, ascending colon and transverse colon). In some embodiments, a digestion profile is generated by comparing the spectral data to spectral standards that are gender-matched, age-matched, and/or matched for the presence or absence of a particular condition.

In some embodiments, the spectral standards and/or spectra contained in other digestion profiles are selected for comparison in order to match the subject used to generate the spectral data. For example, the gathered spectral data may be compared to spectra obtained from the subject at an earlier time point. Accordingly, the methods and devices described herein may be used for monitoring the GI tract of a subject over time. For example, in some embodiments, this comparative data may be used to detect changes in how the subject absorbs nutrients or digests particular ingestible standards over time. In some embodiments, the comparative data may be used to analyze the progression of a disease or disorder (e.g., a GI disease or disorder). In some embodiments, the comparative data may be used to determine the effectiveness of a particular course of treatment.

In some embodiments, the spectral standards are spectra associated with digestion profiles for individuals or groups of individuals in a database of digestion profiles. For example, the spectral standards may be a set of spectra in a database of digestion profiles associated with a particular ingestible standard, analyte, desired outcome, or medical condition (e.g., a disease or disorder described herein). In one aspect, digestion profiles of subjects generated using the ingestible device described herein are saved in a database of digestion profiles. The database of digestion profiles containing spectral data and information regarding other individuals or groups of individuals, such as, but not limited to, medical conditions, analytes, food sensitivities, desired outcomes, or the effect of ingesting a substance, and can then be used to inform the digestion profile of a subject by comparing the digestion profile of the subject to the digestion profiles contained in the database.

Spectral standards may also be generated that are associated with a particular condition such as the level of one or more analytes or a desired outcome using the methods described herein and in Example 1. For example, spectral standards representative of the level of a particular analyte may be generated using a benchtop spectrometer and a GI tract model such as the TNO Gastro-Intestinal Model (TIM) described in Mans Minekus, *Chapter 5: The TNO Gastro-Intestinal Model (TIM)* in K. Verhoeckx et al. (eds.), *The Impact of Food Bio-Actives on Gut Health*, Springer International Publishing (2015), hereby incorporated by reference in its entirety.

Spectral standards may also be produced that are associated with a particular health condition of tissue lining the GI tract, e.g., normal tissue, inflamed tissue, necrotic tissue, necroptotic tissue, etc. Such spectral standards can be produced as described in Example 15, Example 16, and Example 17. They are compared with spectral data obtained, in vivo, and may be used to determine the health condition of GI tract tissue of a subject, who has ingested a spectrometer-equipped, or hyperspectral camera-equipped, ingestible device. These spectral standards may be compared to the spectra obtained using the devices described herein to determine whether there is an abnormality in the tissue lining the GI tract of a subject. The presence of an abnormality in the tissue lining of the GI tract of the subject may be indicative of a disease or disorder, including, but not limited to a bacterial, viral or protozoal infection (e.g., an *Entamoeba histolytica* infection), an inflammatory bowel disease (e.g., Crohn's disease or ulcerative colitis), and cancer (e.g., colorectal cancer). In some embodiments, spectral data obtained from a subject may be compared to spectral standards obtained from subjects having a healthy GI tract and/or spectral standards from subjects having a medical condition that affects health (e.g., the integrity) of the GI tract in order to determine whether a subject is at risk of or has a disease or disorder. For example, in some embodiments, the spectral data obtained from a subject may be compared to spectral standards of subjects having an inflammatory bowel disease (e.g., Crohn's disease or ulcerative colitis) to determine whether the subject has or is at risk of developing an inflammatory bowel disease. In some embodiments, the devices and methods described herein may be used to determine whether the tissue lining of the GI tract of a subject has an abnormality (e.g., the tissue lining may be inflamed and/or comprise necrotic tissue). In some embodiments, information relating to the condition of the tissue lining of the GI tract may be used to assess the effectiveness of an analyte (e.g., a therapeutic agent (e.g., an anti-inflammatory drug)) to determine the course of treatment to pursue in the subject. For example, in some embodiments, the devices and methods described herein may be used to monitor inflammation in the GI tract of a subject having an inflammatory bowel disease (e.g., Crohn's disease or ulcerative colitis). In some embodiments, the devices and methods described herein may be used to monitor the effectiveness of a treatment for an inflammatory bowel disease (e.g., treatment with an anti-TNFα antibody (e.g., adalimumab or with an anti-integrin antibody (e.g., vedolizumab)).

Spectral standards may also be produced that are associated with tissue lining the GI tract (e.g., at predetermined regions of the GI tract). In such embodiments, the result can yield information regarding the location of the ingestible device within the GI tract. Such spectral standards can be produced as described in Example 14. They are compared with spectral data obtained, in vivo, for determining locations within the GI tract of a spectrometer-equipped, or hyperspectral camera-equipped, ingestible device.

Spectral standards may also be generated by preparing samples in vitro that simulate samples of digested or partially digested food and spectra for each sample may be generated ex vivo. Base samples may include, for example, a predetermined amount of macronutrients or an ingestible standard. Various components such as saliva, gastric acid, pancreatic enzymes, bile and/or bacteria may be added to the base samples in order to generate samples that reflect various regions of the GI tract.

Spectral standards may be generated in human subjects without the use of an ingestible device as described herein. For example, spectral standards may be generated in subjects that have been intubated by collecting samples from various regions of the GI tract. An endoscope connected via a fiber optic cable may be used to generate spectral data of samples in situ within the GI tract of a subject. Spectral standards may also be generated by working with subjects who have had an ileostomy or are fed using an enteral nutrition tube. Samples from the GI tract of these subjects may be obtained and spectral data generated using a spectrometer ex vivo. The spectral data so obtained may then be associated with personal data and/or data regarding the consumption of particular foods or ingestible standards by the subject when the samples were obtained in order to generate spectral standards.

Spectral data may be compared to spectral standards or other spectral data using various techniques known in the art. For example, the intensity and/or location of peaks or troughs in the spectra may be compared. In some embodiments, spectral data may be compared using algorithms or statistical methodologies for quantifying the difference or similarity between two or more spectra. Optionally, the spectra data may be pre-processed prior to comparing the spectra or sets of spectra. For example, in some embodiments, machine-learning, genetic algorithms, multivariate data analysis, chemometric methods, pattern recognition methods and/or or principle component analysis (PCA) may be used for comparing spectra or a set of spectra. In some embodiments, an unsupervised classification method is used to compare spectra or set of spectra such as PCA. In another embodiment, a supervised classification method is used such as soft independent modelling of class analogy (SIMCA), linear discriminant analysis (LDA), multiple discriminant analysis (MDA), factorial discriminant analysis (FDA), PLS discriminant analysis (PLS-DA), canonical variate analysis (CVA), artificial neural networks (ANNs) and/or k-nearest neighbor (k-NN) analysis. Hyperspectral data may be compared using Multivariate Image Analysis (MIA) techniques. Various mathematical techniques and methods for comparing and analyzing spectral data including hyperspectral data are described in Manley, "Near-infrared spectroscopy and hyperspectral imaging: non-destructive analysis of biological materials" *Chem. Soc. Rev.,* 2014, 43, 8200, hereby incorporated by reference in its entirety.

User Information and User Criteria

In some embodiments, processing unit 50 is configured to generate desired data (e.g., a digestion profile) based on the spectral data and one or more inputs. The inputs may provide additional information regarding the sample and/or the subject, or allow the digestion profile to provide information that is indicative of a particular characteristic such as, but not limited to, a medical condition, analyte, food or drug sensitivity, effectiveness of a treatment regimen (e.g., with a therapeutic agent), desired outcome, or the effect of ingesting a substance. For example, spectral data gathered by the ingestible device 10 may be transmitted to base station 40, where a processing unit 50 located within the base station 40 combines the spectral data with input from the user in order to generate the desired data (e.g., a full digestion profile). While certain examples of spectral data and spectral standards are discussed in this paragraph, the disclosure is not limited in this sense. Any spectral data, or combination of spectral data, as well as corresponding spectral standards, can likewise be implemented.

The one or more inputs may include information on the subject or criteria selected by a user. In some embodiments, the one or more inputs are entered or selected by a subject using a computer interface, which then configures processing unit 50 to generate desired data (e.g., a digestion profile) based on the one or more inputs. For example, a user may select criteria using a computer interface and/or display located on base station 40. While certain examples of spectral data and spectral standards are discussed in this paragraph, the disclosure is not limited in this sense. Any spectral data, or combination of spectral data, as well as corresponding spectral standards, can likewise be implemented.

In some embodiments, the information on the subject includes at least one of weight, height, sex, diet, exercise, medical condition (e.g., a disease or disorder described herein), medication, genotype, phenotype, BMI, race, age, exercise routine, tobacco use, and/or alcohol use, heart rate, pulse and place of residence. Examples of medical conditions include, cancer (e.g., gastric cancer or colorectal cancer), metabolic disease, prediabetes, diabetes, irritable bowel syndrome (IBS), inflammatory bowel disease, short bowel syndrome, malabsorption syndromes such as carbohydrate malabsorption or bile acid malabsorption and/or other bile acid diseases, pancreatic insufficiency/chronic pancreatitis (i.e., inability to digest fat in small intestine), nutritional insufficiencies linked to old age, an allergy (e.g., a food allergy), kidney disease, epilepsy, protein malnutrition such as from lysinuric protein intolerance or low gastric acid in stomach (hypochlorhydria), gastroparesis (slow gastric emptying) and chronic constipation. For example, the methods and devices described herein may be useful for monitoring a ketogenic diet to help control seizures in subjects with epilepsy. In some embodiments, the methods and devices described herein are useful for detecting blood and/or bile in the GI tract of a subject. In some embodiments, a bile acid metabolism profile may be generated. Bile acid metabolism profiles may be indicative of the presence or absence of *C. difficile*. A bile acid metabolism profile of a subject may be generated to determine the presence or absence of *C. difficile*, for example, after a fecal microbiota transplant or treatment with an antibiotic. In certain embodiments, one or more intra-colonic bile acid profiles may be used to predict the success of fecal microbiota transplantation (FMT).

In some embodiments, the methods and devices described herein are useful for monitoring subjects following a "Fermentable, Oligo-, Di-, Mono-saccharides And Polyols" (FODMAP) diet for managing Irritable Bowel Syndrome (IBS). For example, the ingestible device and methods described herein may be used to determine the absorption of short-chain carbohydrates such as fructose, lactose, polyols, fructans, and galacto-oligosaccharides within the GI tract of a subject with IBS. Diets low in FODMAP have been shown to be effective at managing symptoms in subjects with IBS (see, for example, Halmos et al. *Gastroenterology* 2014; 146:67-75, Gibson and Shepherd, *Journal of Gastroenterology and Hepatology* 25 (2010) 252-258) hereby incorporated by reference.

For example, in some embodiments, a user may specify that the subject is a female subject 35 years of age with type II diabetes by providing user input to the base station 40. Processing unit 50 may then be configured to generate a digestion profile based on spectral data gathered by the ingestible device 10 using a given ingestible standard and the information that the subject is a 35-year-old female with type II diabetes. This digestion profile may then be stored in a digestion profile database, may be used to search for similar digestion profiles, may be used to provide dietary or lifestyle recommendations for the subject, or may be used for any other suitable purpose.

In some embodiments, a digestion profile may be generated based on one or more criteria selected by a user. For example, a user may select criteria indicative of a particular medical condition, analyte, food sensitivity, desired outcome, or the effect of ingesting a substance. In some embodiments, the desired outcome is to lose weight, gain weight, lose body fat, gain body fat, lose muscle mass, manage a medical condition (e.g., a disease or disorder), treat a medical condition, or increase or decrease the absorption of a macronutrient. Processing unit 50 may then be configured to generate a digestion profile based on spectral data and the criteria selected by the user. For example, a user may input criteria identifying a subset of medical conditions of the subject, different types on ingestible standards that will be consumed concurrently with the ingestible device 10, or personal subject goals for the subject. These criteria may be used along with the spectral data to generate a digestion profile, and may be used to identify a subset of individuals or groups of individuals in a database of digestion profiles. The spectral data for a subject may then be compared to the spectral data for the selected subset of individuals or groups of individuals.

For example, in some embodiments, the methods and devices described herein involve searching a database of digestion profiles to identify individuals or groups of individuals with similar digestion profiles. For example, if the user input indicates that the subject is a 35-year-old female with type II diabetes, processing unit 50 may be configured to search a database of digestion profiles to identify individuals or groups of individuals that have similar spectral data obtained using an ingestible standard and are females 30-40 years old with type II diabetes. Information from the digestion profiles for those individuals or groups of individuals may then be presented to a user and/or be incorporated into the digestion profile for the subject. For instance, if the spectral data indicated that subject absorbs a particular type of macronutrient less efficiently than 90% of the identified individuals (e.g., as indicated by high levels of the macronutrient being detected in sample throughout its transit through the subject's GI tract), this information may be displayed to the subject and incorporated into the subject's digestion profile. In some embodiments, a user is able to view or access the digestion profiles for those individuals or groups of individuals so identified, including additional information such as, but not limited to, weight, height, sex, diet, exercise, medical condition, food ingested, medication, genotype, phenotype, BMI, race, age, exercise routine, tobacco use, and/or alcohol use, heart rate, pulse, and/or place of residence.

In some embodiments, processing unit 50 is configured to generate for display information regarding the individuals or groups of individuals with similar digestion profiles to a user. For example, processing unit 50 may search and identify digestion profiles of individuals or groups of individuals in a database of digestion profiles based on a first set of criteria, and then generate a display presenting the user with additional information contained in the digestion profiles for those individuals or groups of individuals that were not necessarily used to search the database. For example, a database of digestion profiles may be searched to identify individuals that are females, 30-40 years old with type II diabetes who have lost weight. Additional information contained in the digestion profiles of those individuals (that was not necessarily used to search the database) may then be displayed to the user (e.g., using a display screen connected with base station 40), optionally in response to the user selecting one or more criteria. For example, a user may select to view information such as food intake or exercise routines of those individuals identified as females, 30-40 years old with type II diabetes who have lost weight.

In some embodiments, information regarding the individuals or groups of individuals with similar digestion profiles is added to the digestion profile for the subject. For example, this information may be used to recommend foods that the subject should avoid or foods that the subject should consume in order to obtain a desired outcome. For example, if the subject desires to lose weight, the digestion profile database may be searched for profiles of subjects of the same sex, age, and/or having the same medical condition who have lost weight. The identified digestion profiles may contain information about typical foods consumed by subjects falling within the searched demographic group who have lost weight, and this information may be presented to the user (e.g., using a display located on base station 40) in order to recommend foods that the subject should consume in order for the subject to achieve weight loss. In some embodiments, processing unit 50 is configured to transmit the spectral data to a server and receive the digestion profile from the server. For example, the server may also store previously stored user input, and combine the user input with the spectral data to create the digestion profile. Optionally, processing unit 50 is configured to transmit the spectral data, environmental data and/or one or more inputs to a server and receive the digestion profile from the server.

While the discussion in this section of the disclosure has provided examples of data, as well as the utilization and manipulation thereof, this section of the disclosure is not limited in this sense. Any spectral data, or combination of spectral data, as well as corresponding spectral standards, can likewise be implemented.

Macronutrient Detection and Quantification

In some embodiments, the devices and methods described herein may be used to generate information indicative of one or more analytes in a sample from the GI tract of the subject, wherein the information may be used to generate a digestion profile of the subject. For example, the spectrometer 20 may be configured to detect spectral components that are indicative of the presence of particular analytes within the sample. In some embodiments, processing unit 50 is configured to generate a digestion profile indicative of one or more analytes in the sample.

The digestion profile may be indicative of the relative or total amount of one or more analytes in one or more samples. For example, in some embodiments, the digestion profile may indicate to a user the relative concentration of one or more macronutrients in a region of the GI tract of the subject (e.g., the stomach). In some embodiments, the digestion profile may indicate to a user the total amount in grams of fat in the intestine of the subject. Additional details of macronutrient detection and/or quantification are described in Example 2, Example 3, Example 4, and Example 6, for instance. In some embodiments, data indicative of the presence of one or more analytes may be gathered by the ingestible device 10 at several points in time, and be used to determine how effectively the subject digests, absorbs, and/or metabolizes particular analytes, e.g., as described in Example 5. For instance, if the level of a particular macronutrient detected in the sample is reduced over time or as a food containing the macronutrient transits through the GI tract, it may indicate that the subject has absorbed and/or metabolized the macronutrient. This information may then be optionally incorporated into a digestion profile.

The analyte may be any substance detectable using a spectrometer in vivo as described herein. In some embodiments, the analyte may be detected by detecting a detection agent, such as a fluorescent molecule, that selectively binds to an analyte. For example, the subject may be administered a detection agent prior to obtaining a digestion profile using the methods described herein. Examples of analytes include, but are not limited to, macronutrients, blood components, water, fiber, bile acids or bile salts, ketone bodies, mucus, bacteria, gastric juices, therapeutic agents (e.g., drugs), nutritional supplements, or ingestible standards. For instance, detection and quantification of blood and bile, in meals, based on spectral data are described in detail in Example 7 and Example 8. In some embodiments, the analyte is a macronutrient such as alcohol, a carbohydrate, a protein and/or a fat. In some embodiments, the analyte may be a metabolite and/or digestion product of a substance ingested or administered to the subject. In some embodiments, the analyte is an ingestible standard that has been administered to the subject. The ingestible standard may be a non-absorbed and/or indigestible standard. For example, in some embodiments, the ingestible standard is an indigestible carbohydrate or fiber that is not broken down or appreciably absorbed and/or metabolized in the GI tract of a subject. In some embodiments, detecting a level of a non-absorbed and/or indigestible standard is used to determine the relative or absolute level of another analyte, such as the relative of absolute levels of macronutrients. In some embodiments, using a non-absorbed and/or indigestible standard allows for using the standard as a relative marker so that the relative concentration of other analytes can be compared and/or the relative amounts (e.g., in grams) of other analytes can be calculated. As an example, in a situation where the initial amount of carbohydrates (or one or more other macronutrients) is known, then the amount of carbohydrates remaining can be calculated based on the amount of remaining non-absorbed and/or indigestible standard. Examples of indigestible and/or non-absorbed materials that may be used as standards include cellulose, sterculia, methylcellulose and chlorophyll. Other examples of indigestible and/or non-absorbed materials that may be used to determine the relative or absolute level of another analyte, such as the relative of absolute levels of macronutrients, include fluorescent molecules like the ones described below in Example 9.

In some embodiments, a digestion profile generated using the methods and/or devices described herein is indicative of calories intake and/or absorbed by the subject. In another embodiment, a digestion profile is indicative of the weight or mass in grams of one or more analytes ingested and/or absorbed by the subject. In some embodiments, the methods and devices described herein are useful for tracking whether the substances ingested by a subject fall within the parameters of a specific diet, such as the total number of calories consumed, metabolized and/or absorbed by a subject, or the relative amount of calories from different macronutrients such as proteins, carbohydrates and fats consumed, metabolized and/or absorbed by the subject.

In some embodiments, the methods and/or devices described herein may provide a user information such as lifestyle and/or dietary recommendations for a subject. For example, if the spectral data gathered by the ingestible device 10 for a given subject indicates that the subject is unable to digest a particular macronutrient efficiently, a digestion profile may be generated that recommends that the subject supplement their diet with foods that have higher concentrations of that macronutrient. In some embodiments, processing unit 50 is configured to generate a digestion profile that is indicative of lifestyle and/or diet recommendations for a subject based on outcomes associated with certain lifestyles (such as an exercise routine) and/or diets in the database of digestion profiles. For example, if the subject desires to gain weight and/or increase muscle mass, the user may search a digestion profile database for profiles of subjects with similar demographics to obtain spectral data of subjects who have successfully gained weight and/or increased muscle mass. Information from the identified digestion profiles, such as common foods consumed by individuals who have successfully gained weight and/or increased muscle mass, may then be incorporated into the digestion profile for the subject as a dietary recommendation. It will be understood that any other suitable type of information contained in the identified digestion profiles, such as typical caloric intake and/or typical exercise regimens for individuals associated with the identified digestion profiles, may be presented to the subject as well.

Kits Including Ingestible Devices

In another aspect, provided herein are kits including an ingestible device as described herein. In some embodiments, the kits include an ingestible device and at least one of an ingestible standard and a detection agent. In some embodiments, the kit includes instructions for use of the ingestible device, optionally with instructions for use of the ingestible device either alone or in combination with the ingestible standard and/or detection agent. In some embodiments, the ingestible device, ingestible standard and/or detection agent are provided in separate packaging. The ingestible standards and/or detection agents herein may also be administered to a subject in the methods described herein.

In some embodiments, the ingestible standard includes a predetermined quantity of one or more analytes. For example, the ingestible standard may include a predetermined quantity of macronutrients, either alone or in combination with other substances such as flavoring agents, and/or preservatives. In some embodiments, the ingestible standard is a hydratable formulation, optionally a powder or concentrate.

In some embodiments, the ingestible standard is a set meal. For example, in some embodiments, the ingestible standard includes a predetermined meal including set amounts of particular foods, such as eggs, toast, and fruit, and/or chicken, potatoes and vegetables in a specific total amount or a set amount based on a demographic of the subject (e.g., sex, age, and weight). In some embodiments, the set meal is a commercially available meal replacement such as Boost™, Ensure™ Met-RX™, Slim Fast™, Soylent™, or the like.

In some embodiments, the kit includes a non-absorbed and/or indigestible marker. For example, the non-absorbed and/or indigestible marker may comprise one or more carbohydrates such as cellulose that are not broken down into constituent sugars within the GI tract of the subject. In some embodiments, the non-absorbed and/or indigestible marker includes or is conjugated to a detectable label. In some embodiments, the detectable label is detectable using a spectrometer as described herein, such as fluorescent label. In this manner, some food dyes can be used to quantify absorption of macronutrients and/or water in the small intestine, as described below in Example 9.

The kit may also include a detection agent that facilitates the detection of one or more analytes within the GI tract of the subject. In some embodiments, the detection agent selectively binds to one or more analytes. Examples of detection agents include, but are not limited to, an antibody or aptamer that selectively binds an analyte. In some embodiments, the detection agent includes or is conjugated to a label that facilitates the detection of the detection agent using a spectrometer. For example, in some embodiments, the detection agent includes a fluorescent label.

Systems Including Ingestible Devices

Figure 2:
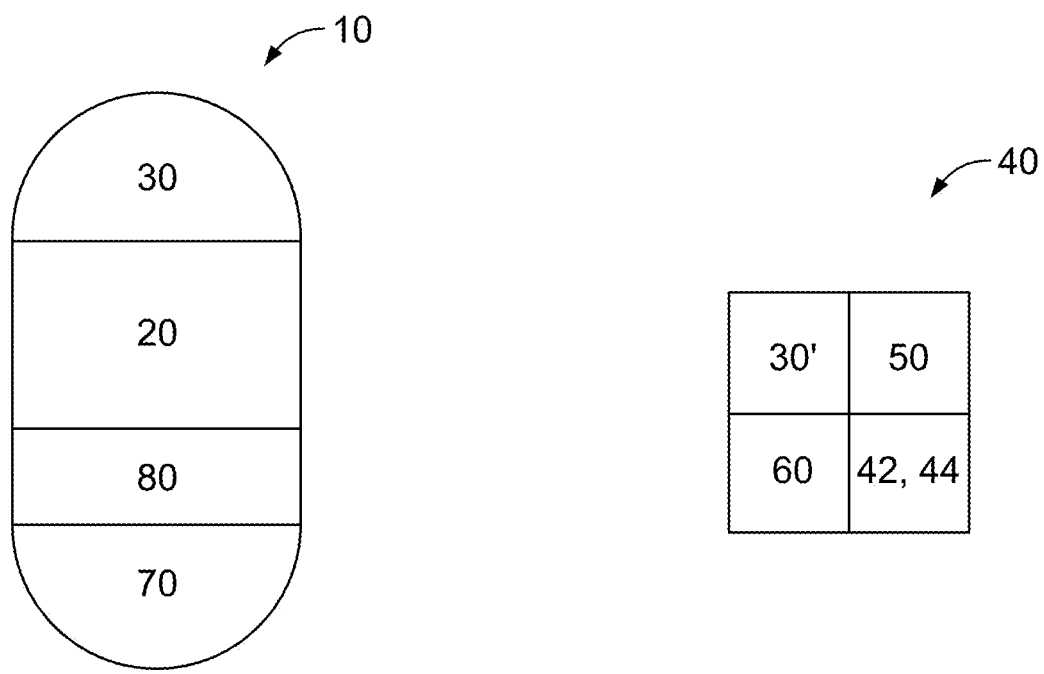
FIG. 2 shows an embodiment of another exemplary system including an ingestible device and a separate base station (not to scale).

In one aspect, there is provided a system that includes an ingestible device having a spectrometer. Referring to FIG. 2, there is shown some embodiments, of a system for generating a digestion profile including an ingestible device 10 and base station 40. In some embodiments, the system includes an ingestible device 10 including a spectrometer 20 for generating spectral data of a sample within the gastrointestinal (GI) tract of a subject in vivo as described herein. In some embodiments, the system includes an ex vivo base station 40. In general, base station 40 may be any electronic device configured to communicate with ingestible device 10 such as, but not limited to, a computer, or a personal electronic device such as a watch, physical activity tracker, fitness monitor, personal digital assistant (PDA), phone or tablet.

In some embodiments, base station 40 includes a communications unit 30' for receiving data from, and/or transmitting operating parameters to, ingestible device 10. Base station 40 may also include memory 60 for storing spectral data, environmental data and/or digestion profiles and processing unit 50 configured to generate a digestion profile for the subject.

In some embodiments, the base station 40 includes or is operably connected to display 42 for displaying information to a user. Display 42 may be a monitor, projector and/or screen. In some embodiments, the system is configured to present information on display 42 to a user, such as operating characteristics of the device, spectral data, environmental data and/or information obtained by comparing spectral data and/or digestion profiles with one or more spectral standards.

In some embodiments, base station 40 includes or is operably connected to interface 44 allowing a user to configure processing unit 50. In some embodiments, interface 44 allows a user to configure processing unit 50 to generate a digestion profile based on one or more inputs. In some embodiments, interface 44 allows a user to input operating parameters for ingestible device 10, information on the subject and/or criteria selected by the user. For example, in some embodiments, interface 44 allows a user to input information on the subject such as weight, height, sex, diet, exercise, medical condition, medication, genotype, phenotype, BMI, race, age, exercise routine, tobacco use, and/or alcohol use, heart rate, pulse and place of residence. In some embodiments, interface 44 allows a user to input one or more criteria selected by the user, optionally criteria for analyzing the spectral data, e.g., generating one or more digestion profiles for the subject. The criteria may be the identity of an analyte and/or a desired outcome and/or information relating to GI tissue (e.g., a condition associated with GI tissue), and/or the location of the ingestible device within the GI tract (e.g., by identifying GI tissue associated with one or more regions of the GI tract). For example, in some embodiments, the desired outcome may be for the subject to lose weight, gain weight, manage and/or treat a medical condition, or increase or decrease the absorption and/or metabolism of an analyte such as a macronutrient. Optionally, interface 44 is operably connected to display 42, or may be integrated within display 42.

In some embodiments, processing unit 50 is configured to generate information based on spectral data generated via spectrometer 20 (e.g., one or more digestion profiles) by comparing the spectral data to one or more spectral standards as described herein. For example, if the gathered spectral data is similar to spectral standards indicative of individuals with a particular type of medical condition who have consumed a given ingestible standard, this may be noted a part of the digestion profile. In some embodiments, the spectral standards are selected by a user through interface 44. For example, if the sample that the spectral data is being gathered from is a particular type of ingestible standard, this may be indicated by the user through the interface 44, and the system may identify spectral standards for that particular ingestible standard to compare the spectral data to the identified spectral standards. While certain examples of spectral data are discussed in this paragraph, the disclosure is not limited in this sense. Any spectral data, or combination of spectral data, as well as corresponding spectral standards, can likewise be implemented.

In some embodiments, processing unit 50 is configured to search a database of relevant data as appropriate (e.g., a database digestion profiles and identify individuals or groups of individuals with similar digestion profiles relative to the digestion profile for the subject as described herein). For example, if the subject is a 35-year-old woman with a given medical condition, processing unit 50 may be configured to identify digestion profiles for women of a similar age and with the same medical condition. In some embodiments, processing unit 50 is configured to present information on display 42 regarding the individuals or groups of individuals identified as having similar digestion profiles. For example, in some embodiments, processing unit 50 is configured to present on display 42 information based on all or part of the digestion profiles for individuals in the database of digestion profiles. In some embodiments, information regarding the individuals or groups of individuals with similar digestion profiles is added to the digestion profile for the subject. For example, if it is found that the identified individuals share certain types of dietary restrictions, that information may be incorporated into the digestion profile for the subject. Optionally, information can be presented to a user on display 42 and the user can choose to add information to the digestion profile for a subject using interface 44. In some embodiments, processing unit 50 is configured to display on display 42 lifestyle and/or dietary recommendations for the subject based on the digestion profile. While certain examples of spectral data spectral standards are discussed in this paragraph, the disclosure is not limited in this sense. Any spectral data, or combination of spectral data, as well as corresponding spectral standards, can likewise be implemented.

In some embodiments, processing unit 50 is configured to generate data (e.g., a digestion profile) by comparing the spectral data to one or more spectral standards saved in memory 60. For example, the spectral data gathered by an ingestible device 10 may be used to search a database of spectral standards in order to determine that the subject is absorbing and/or metabolizing the nutrients in a given ingestible standard normally. This information may then be incorporated into a digestion profile for the user. Alternatively or in addition, processing unit 50 may be connected to a server that stores a database of spectral standards and/or digestion profiles. Accordingly, processing unit 50 may be configured to transmit spectral data to a server and receive the digestion profile from the server. Similarly, processing unit 50 may be configured to transmit one or more of spectral data, environmental data and user inputs to a server and receive information based on the digestion profile for the subject from the server. While certain examples of spectral data and spectral standards are discussed in this paragraph, the disclosure is not limited in this sense. Any spectral data, or combination of spectral data, as well as corresponding spectral standards, can likewise be implemented.

Figure 3:
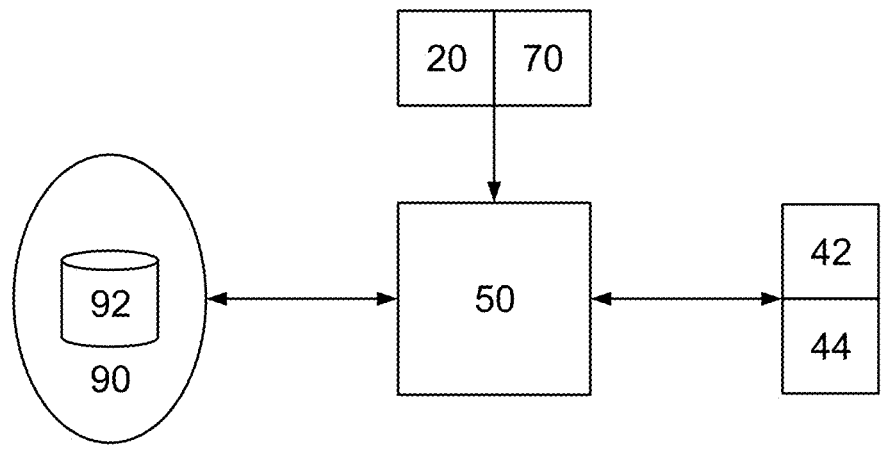
FIG. 3 shows an embodiment of a system for generating a digestion profile as described herein.

FIG. 3 shows an embodiment of a system for generating a digestion profile as described herein. Spectral data obtained using spectrometer 20 is transmitted to processing unit 50. Optionally, environmental data obtained from environmental sensor 70 is transmitted to processing unit 50. Processing unit 50 is configured by a user using interface 44 and/or display 42 by inputting information on the subject and/or selecting criteria for generating a digestion profile that is, e.g., indicative of a particular analyte or predictive of the effect of ingesting a particular substance or food. Processing unit 50 generates a digestion profile by transmitting spectral data and information inputted by the user to server 90. Server 90 contains a searchable database of digestion profiles and/or standard spectra 92. Information based on comparing the spectral data to the database of digestion profiles and/or standard spectra 92 is then presented to the user. In some embodiments, the information is displayed to the user on display 42. Optionally, server 90 may provide the information based on the digestion profile to a user in the form of an electronic communication such as email or text. In some embodiments, the digestion profile for the subject may be added to the searchable database of digestion profiles 92 stored on server 90. While certain examples of spectral data spectral standards are discussed in this paragraph, the disclosure is not limited in this sense. Any spectral data, or combination of spectral data, as well as corresponding spectral standards, can likewise be implemented as discussed herein.

Methods of Using Ingestible Devices

In some embodiments, there is provided a method for generating a digestion profile for a subject using an ingestible device, kit and/or system as described herein. In some embodiments, the method includes providing an ingestible device including a spectrometer 20, operating the spectrometer 20 to obtain spectral data of at least one sample within the GI tract of the subject, and generating a digestion profile for the subject based on the spectral data.

In some embodiments, the method includes orally administering the ingestible device to the subject. In some embodiments, ingestible device 10 may be swallowed alone or swallowed along with a liquid such as water. In some embodiments, an ingestible device may be administered to the subject at the same time as an ingestible standard, an analyte (e.g., a therapeutic agent) and/or detection agent, or at separate times (e.g., before and/or after the ingestible standard, analyte, and/or detection agent is administered to the subject). For example, in some embodiments, an ingestible device is administered to the subject within 1 minute, 5 minutes, 10 minutes, 15 minutes, 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours or more of the ingestible standard, analyte (e.g., therapeutic agent) and/or detection agent. In some embodiments, it is preferable that the ingestible device be swallowed at the same time as an ingestible standard, analyte and/or detection agent such that the device and the standard, the analyte (e.g., therapeutic agent) and/or agent travel through at least part (e.g., one or more regions) of the GI tract concurrently. For example, the subject may be instructed to ingest the first half of an ingestible standard, wait a predetermined amount of time (e.g., 5 or more minutes), ingest the ingestible device 10, wait another predetermined amount of time (e.g., 3 or more minutes), and then ingest the second half of the ingestible standard.

In some embodiments, the method includes operating the spectrometer 20 to obtain spectral data and/or environmental data at one or more predetermined locations within the GI tract. For example, the spectrometer 20 may be operated to obtain spectral data and/or environmental data (e.g., spectral and/or environmental data of a sample and/or of GI tract tissue) in one or more of, for example, the stomach, proximal and distal duodenum, jejunum, ileum, descending colon, ascending colon and transverse colon of the subject.

In some embodiments, the method includes operating the spectrometer 20 to obtain spectral data at a plurality of time points as the ingestible device 10 travels through the GI tract of the subject. In some embodiments, the spectrometer 20 may be continuously operated to generate spectral data, or periodically such as every 30 seconds, every minute, every 2 minutes, every 5 minutes, every 10 minutes, every 30 minutes, or every hour.

In some embodiments, the ingestible device 10 may be pre-programmed to generate spectral data and/or environmental data at pre-determined locations or time points prior to administering the device to a subject. For example, the ingestible device 10 may be programmed using the base station 40 prior to being ingested by the subject. Alternatively or in addition, the ingestible device may receive operating parameters to generate spectral data and/or environmental data while the device is in vivo in the GI tract of a subject. For example, the base station 40 may transmit operating parameters to the ingestible device (e.g., via the communication units 30 and 30') while the device is in vivo.

In some embodiments, the method includes identifying the location of the device within the GI tract of the subject. Information regarding the location of the device within the GI tract may be used to generate data (e.g., a digestion profile) for a sample that is associated with a particular location in the GI tract of the subject. In some embodiments, information regarding the location of the device may be used to determine when the spectrometer 20 is to be operated to generate spectral data. For example, the ingestible device may be configured to operate the spectrometer 20 and generate spectral data after determining that the ingestible device is located in a predetermined region of the GI tract, such as the ileum.

In some embodiments, the ingestible device may be attached to tissue forming the interior surface of the GI tract. For example, in some embodiments, the method for generating a digestion profile as described herein includes administering an ingestible device to a subject and attaching the device to a predetermined location within the GI tract of the subject. In some embodiments, ingestible device 10 includes a connector for attaching the device to the interior surface of the GI tract. Operation of the connector may be controlled by microcontroller 80, optionally in response to information regarding the location of the device and/or in response to operating parameters from base station 40.

In some embodiments, the device is attached to tissue forming the interior surface of the stomach, proximal or distal duodenum, jejunum, ileum, descending colon, ascending colon or transverse colon. In some embodiments, the device may be releasably attached to the interior surface of the GI tract. Optionally, the device may be attached to a first location in the GI tract of the subject, released, and then attached to a second location further along the GI tract of the subject.

In some embodiments, the method includes attaching the ingestible device to an interior surface of the GI tract and generating spectral data at a plurality of time points as material flows past the device in the GI tract of the subject. In some embodiments, the method includes releasing the device from the interior surface of the GI tract such that the device proceeds to move through the GI tract before being expelled.

In some embodiments, the method includes generating a digestion profile for the subject based on spectral data and one or more inputs. In some embodiments, the method includes receiving one or more inputs from a user and generating a digestion profile based on the one or more inputs and spectral data. In some embodiments, the method includes receiving information on the subject or criteria selected by a user, and generating a digestion profile based on the information on the subject and/or selected criteria. For example, the digestion profile may be generated by combining user inputted information about the subject, and spectral data gathered by the ingestible device 10. Examples of information on the subject include, but are not limited to weight, height, sex, diet, exercise or activity level, medical condition, medication, genotype, phenotype, body mass index (BMI), race, age, exercise routine, tobacco use, and/or alcohol use, heart rate, pulse or place of residence. Examples of criteria selected by a user include analytes or a desired outcome such as to lose weight, gain weight, manage a medical condition, or increase or decrease the absorption and/or metabolism of an analyte such as a macronutrient. While certain examples of spectral data spectral standards are discussed in this paragraph, the disclosure is not limited in this sense. Any spectral data, or combination of spectral data, as well as corresponding spectral standards, can likewise be implemented as discussed herein.

In some embodiments, the method includes transmitting spectral data to a server, wherein the server generates a digestion profile based on the spectral data and, optionally, environmental data and one or more inputs from a user. For example, the server may use the spectral data and the inputs from the user to select one or more spectral standards to compare the spectral data to, and information determined from, the spectral standards (e.g., the amount of an analyte present in the sample) may be incorporated into a digestion profile. In general, the spectral data and/or digestion profile may optionally be saved on the server. In some embodiments, the spectral data and/or digestion profiles saved on the server form a database of digestion profiles that can be searched by a user. While certain examples of spectral data spectral standards are discussed in this paragraph, the disclosure is not limited in this sense. Any spectral data, or combination of spectral data, as well as corresponding spectral standards, can likewise be implemented as discussed herein.

In some embodiments, there is provided methods and systems for predicting the effect of ingesting a substance (e.g., an analyte) by a subject. In some embodiments, the method includes identifying a substance to be ingested and predicting the effect of ingesting the substance based on a digestion profile for the subject as described herein. For example, a user may identify a given substance (e.g., a particular pre-packaged meal) by providing user input to the base station 40, and the digestion profile for the subject may be used to predict how the subject will digest, absorb and/or metabolize the substance. In some embodiments, the effect of ingesting the substance includes the absorption of calories or macronutrients in the GI tract of the subject. For example, the digestion profile for the subject may be used to predict how efficiently the subject will absorb and/or metabolized an analyte (e.g., the fat, protein, and carbohydrates present in the substance). In some embodiments, the method includes obtaining nutritional data on the substance (e.g., a food stuff) and predicting the effect of ingesting the substance based on the digestion profile for the subject and the nutritional data. For example, nutritional data about the various amounts of fat, protein, and carbohydrates within the substance may be found on a central database or repository, and the subject's digestion profile may be used to estimate how much of the fat, protein, and carbohydrates contained in the substance will actually be absorbed by the subject. Optionally, the method includes predicting the effect of ingesting the substance based on a digestion profile for the subject and database of digestion profiles and/or standard spectra as described herein. For example, the amount of an analyte (e.g., fat, protein, and carbohydrates) absorbed from a given substance may be predicted using empirical data from digestion profiles similar to the subject's digestion profile. For instance, if the other digestion profiles indicate that individuals typically absorb half of the macronutrients in a given substance (e.g., a food stuff), it may be inferred that the subject will absorb approximately half the macronutrients in a given sample on average. The information in the other digestion profiles may also be used to generate a range of possible outcomes to the subject. For example, if the digestion profiles on the database indicate that there is a wide variance in the amount of macronutrients absorbed from a given substance, this information may be used to predict a possible range of outcomes for the subject. While certain examples of spectral data spectral standards are discussed in this paragraph, the disclosure is not limited in this sense. Any spectral data, or combination of spectral data, as well as corresponding spectral standards, can likewise be implemented as discussed herein.

Figure 4:
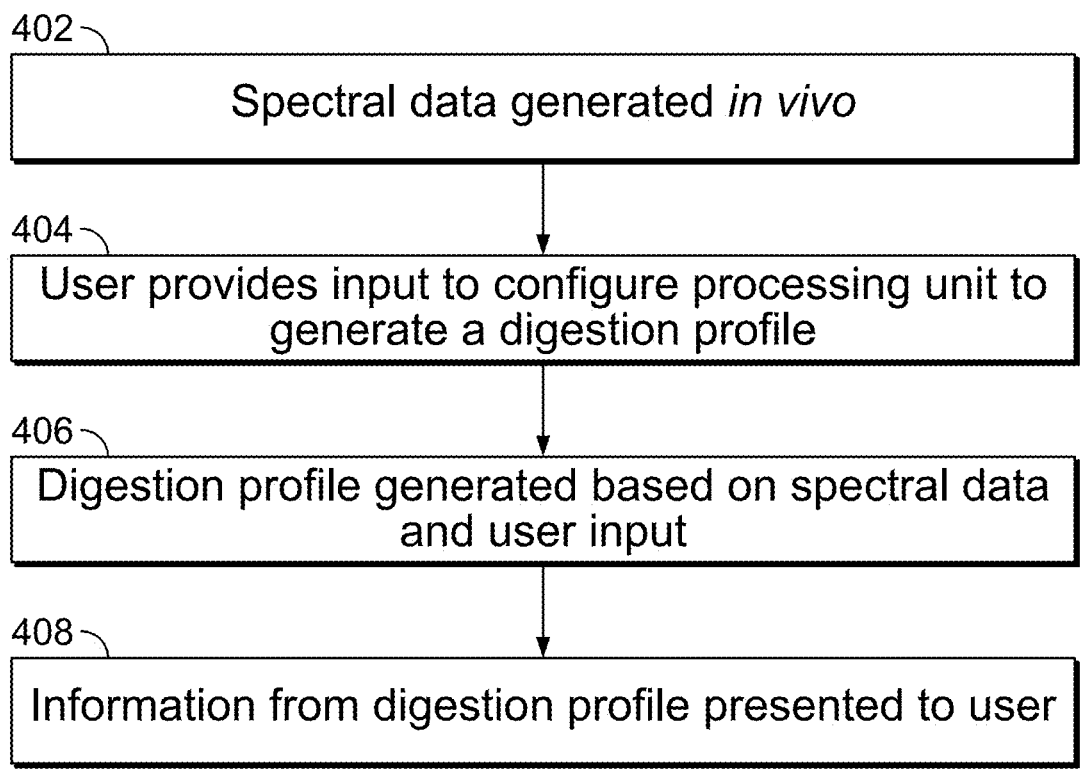
FIG. 4 shows an embodiment of a method for generating a digestion profile as described herein.

FIG. 4 shows an embodiment of a method for generating a digestion profile as described herein. At 402, spectral data is generated in vivo using an ingestible device including a spectrometer. For example, spectral data may be gathered at predetermined locations as an ingestible device (e.g., the ingestible device 10) transits through the GI tract of the subject.

At 402, a user provides one or more inputs to configure a processing unit to generate a digestion profile for the subject based on the spectral data and the one or more inputs. For example, the inputs may be information on the subject, the sample used to generate the spectral data, and/or criteria selected by a user as described herein. In general, the user may provide the input before, during or after the spectral data is generated (e.g., using the interface 44 of the base station 40 (FIG. 2)). While certain examples of spectral data spectral standards are discussed in this paragraph, the disclosure is not limited in this sense. Any spectral data, or combination of spectral data, as well as corresponding spectral standards, can likewise be implemented as discussed herein.

At 406, the digestion profile is generated based on spectral data and the user input. For example, the digestion profile may be generated by comparing the spectral data for the subject to a database of spectral standards and/or digestion profiles. The user input may be used to select a subset of the database of standards and/or digestion profiles in order to generate a digestion profile that is indicative of particular criteria, such as spectral standards indicative of spectral data where a particular analyte is present in the sample. While certain examples of spectral data spectral standards are discussed in this paragraph, the disclosure is not limited in this sense. Any spectral data, or combination of spectral data, as well as corresponding spectral standards, can likewise be implemented as discussed herein.

At 408, information based on the digestion profile generated by comparing the spectral data to the database of spectral standards and/or digestion profiles is presented to a user. For example, the information presented to the user may include food recommendations, be indicative of a particular analyte present in the sample, or be predictive of the effect of ingesting a particular substance by the subject. While certain examples of spectral data spectral standards are discussed in this paragraph, the disclosure is not limited in this sense. Any spectral data, or combination of spectral data, as well as corresponding spectral standards, can likewise be implemented as discussed herein.

Figure 5:
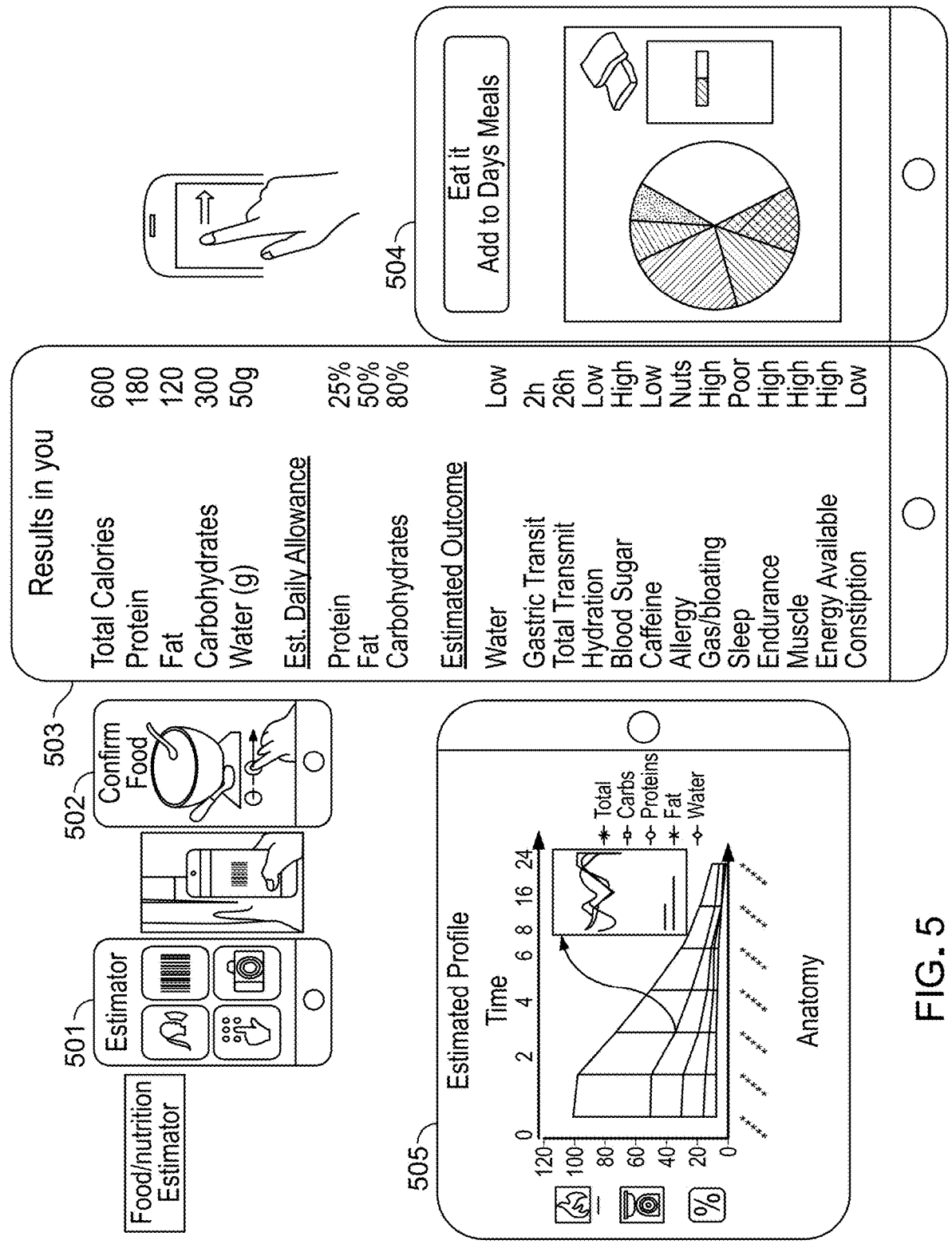
FIG. 5 shows an embodiment of generating a digestion profile based on user input.

FIG. 5 shows an embodiment of generating a digestion profile-based user input. In general, user input may be provided through the use of a user interface (e.g., interface 44 of base station 40). For illustrative purposes, FIG. 5 depicts a user interface similar to one that may be presented on a handheld personal electronic device, although any type of system may be used to receive user input.

At 501, a user selects a food/nutrition estimator from graphical menu, and is presented with the ability to select a food that will potentially be consumed by the subject. The food may be selected any number of ways. For example, it may be selected by performing a text search, using a drop-down menu, or by and scanning a barcode present on the food packaging.

At 502, the identity of the selected food is confirmed by the user. Information is then generated to predict the effect of the selected food in the subject by searching a database of spectral standards and/or digestion profiles for data on individuals or groups of individuals who have ingested the same or a similar food and otherwise exhibit a similar digestion profile to the subject. For example, if the food is a particular type of cereal, digestion profiles will be identified for people who are similar to the subject and who have ingested a similar type of cereal. Individuals with a similar digestion profile may be identified by comparing spectral data generated with the same ingestible standard, and information associated with eating the selected food or a similar food in their digestion profiles may be used to predict the effect of ingesting the food by the user. Information may also be generated to predict the effect of the selected food based on data previously obtained using an ingestible device 10 and ingestible standard as described herein, optionally in combination with data contained in a database of digestion profiles. For example, if it is known that the subject absorbs calories from carbohydrates with a particular level of efficiency (e.g., as a result of spectral data gathered using an ingestible device 10 and a carbohydrate-rich ingestible standard), this may be used to predict the actual amount of macronutrients that will be absorbed from consuming the carbohydrates in the cereal.

At 503, information including general nutritional information and information predicting the effect of ingesting the food is then presented to a user. For example, this may include the standard nutritional information available on the cereal packaging, as well as a more accurate prediction of the total nutrients that the subject would actually absorb from consuming the cereal.

At 504, a user may then elect to ingest the selected food and the cereal will be added to their digestion profile. Optionally, this information may be saved onto a digestion profile database, and other users may be able to look up that the subject has intended to eat the selected cereal. In some embodiments, the subject may be prompted whether or not they intend to eat the cereal concurrently with an ingestible device 10, at which point any spectral data generated by the ingestible device 10 may be stored in a digestion profile with the cereal as a known component of the sample.

At 505, additional information such as the predicted time-dependent absorption of different macronutrients in the selected food at various locations in the GI tract of the subject may be displayed to the user. This may include predictions for how the subject will absorb the carbohydrates, fat, protein, and water content in the cereal. Optionally, if the subject ingests an ingestible device 10 concurrently with the cereal, the display may be updated to include the actual amounts of the different macronutrients absorbed at the various locations in the GI tract of the subject.

The above disclosure generally describes the technology of the present disclosure. Additional information is presented in the following specific examples of certain embodiments of the disclosure. Examples below relate to the use of benchtop spectrometers and hyperspectral imagers which were calibrated and tested in a simulated glassware model of human digestion. The use of simulated models of digestion is accepted by those of skill in the art, for example, as models for salivary, gastric and intestinal digestion, and may be correlated to in vivo processes, methods and procedures (see, e.g., Champ, M., Kozlowski, F. and Lecannu, G. (2000)

In-vivo and In-vitro Methods for Resistant Starch Measurement, in Advanced Dietary Fibre Technology (eds. B. V. McCleary and L. Prosky), Blackwell Science Ltd, Oxford, UK; and Minekus et al. (2014) *Food Funct.* 5: 1113-24, both of which are expressly incorporated herein by reference).

While FIG. 5 is presented in connection with certain data, the disclosure is not limited in this sense. Any spectral data, or combination of spectral data, as well as corresponding spectral standards, can likewise be implemented as discussed herein.

EXAMPLES

Example of a Digestion Profile

FIG. 6 shows an embodiment of a digestion profile for a subject as described herein. The digestion profile includes personal data, desired outcomes or goals, and data corresponding to the use of three ingestible devices taken with a base meal (ingestible standard), a lunch and a high-protein, low-fat dinner. Optionally, an ingestible device can be ingested by a subject at regular and/or irregular intervals as appropriate. For example, an ingestible device can be ingested by a subject daily, weekly, once every month, once every three months, yearly, etc. Such an approach can allow for the generation and collection of longitudinal data for the subject, which can allow for monitoring changes over time, detecting trends, offering recommendations, and/or predicting future profiles. The digestion profile may also include information presented to a user based on criteria selected by the user as described herein, such as wanting to lose weight, manage a medical condition or gain lean muscle. In some embodiments, the information presented to a user includes food or diet recommendations that are based on the digestion profile for the subject. For example, the information may include personalized food or diet recommendations that will allow a subject to absorb fewer calories from a meal. If a subject wants to gain lean muscle, the digestion profile may generate personalized recommendations such as the right level and type of protein, time of day to eat, frequency of eating, and portion size that allow a subject to best digest food and gain lean muscle.

Example 1: Determination of Spectral Standards for Macronutrients Using NIR Spectroscopy A series of ingestible standards including set amounts of water, protein, carbohydrates and fat were generated as set out below. Concentration of macronutrients in each ingestible standard used to determine spectral standards for macronutrients is listed in Table 1.

TABLE 1

| Ingestible Standard | Protein (grams/liter) | Carbohydrates (grams/liter) | Fat (grams/liter) |
|---|---|---|---|
| 1 (Water Blank) | 0 | 0 | 0 |
| 2 (Protein only) | 1 | 0 | 0 |
| 3 (Carbs only) | 0 | 1 | 0 |
| 4 (Fat only) | 0 | 0 | 1 |
| 5 (Standard A) | 1 | 1 | 1 |
| 6 (Standard B) | 5 | 1 | 1 |
| 7 (Standard C) | 1 | 5 | 1 |
| 8 (Standard D) | 1 | 1 | 5 |
| 9 (Standard E) | 5 | 5 | 5 |

Various amounts of whey protein, maltodextrin and/or flax oil were mixed with purified water to form standard solutions as set out in Table 1. Three different gastrointestinal tract models are generated using the TNO Gastro-Intestinal Model (TIM) platform as described in Mans Minekus, *Chapter 5: The TNO Gastro-Intestinal Model (TIM)* in K. Verhoeckx et al. (eds.), *The Impact of Food Bio-Actives on Gut Health*, Springer International Publishing (2015), hereby incorporated by reference in its entirety.

Each of the ingestible standards identified in Table 1 was administered to the three different model GI tracts. Fluid samples were taken from the stomach, small intestine and large intestine of the model GI tracts at 15-minute intervals for a period of 6 hours following the administration of the ingestible standards.

A benchtop spectrometer was used to generate spectra between 1000 nm and 2500 nm and/or 700 nm to 1100 nm for each of the samples. The spectral data was then used to train a machine-learning algorithm to predict the relative amounts of protein, carbohydrates and/or fats in samples taken from the stomach, small intestine or large intestine.

In general, it will be understood that any of the generated spectral standards may then be stored as part of a database, and may be compared against spectral data gathered by an ingestible device as described herein in order to determine the relative amount of macronutrients present in a sample.

Examples 2-9 below were directed to detecting specific macronutrients, e.g., proteins, carbohydrates/sugars, and fats, in the GI tract. Determining concentration of the detected macronutrients allowed for generating at least some of the digestion/absorption profiles described above.

Example 2: Spectroscopy Used for Quantifying Macronutrients

Figure 15A:
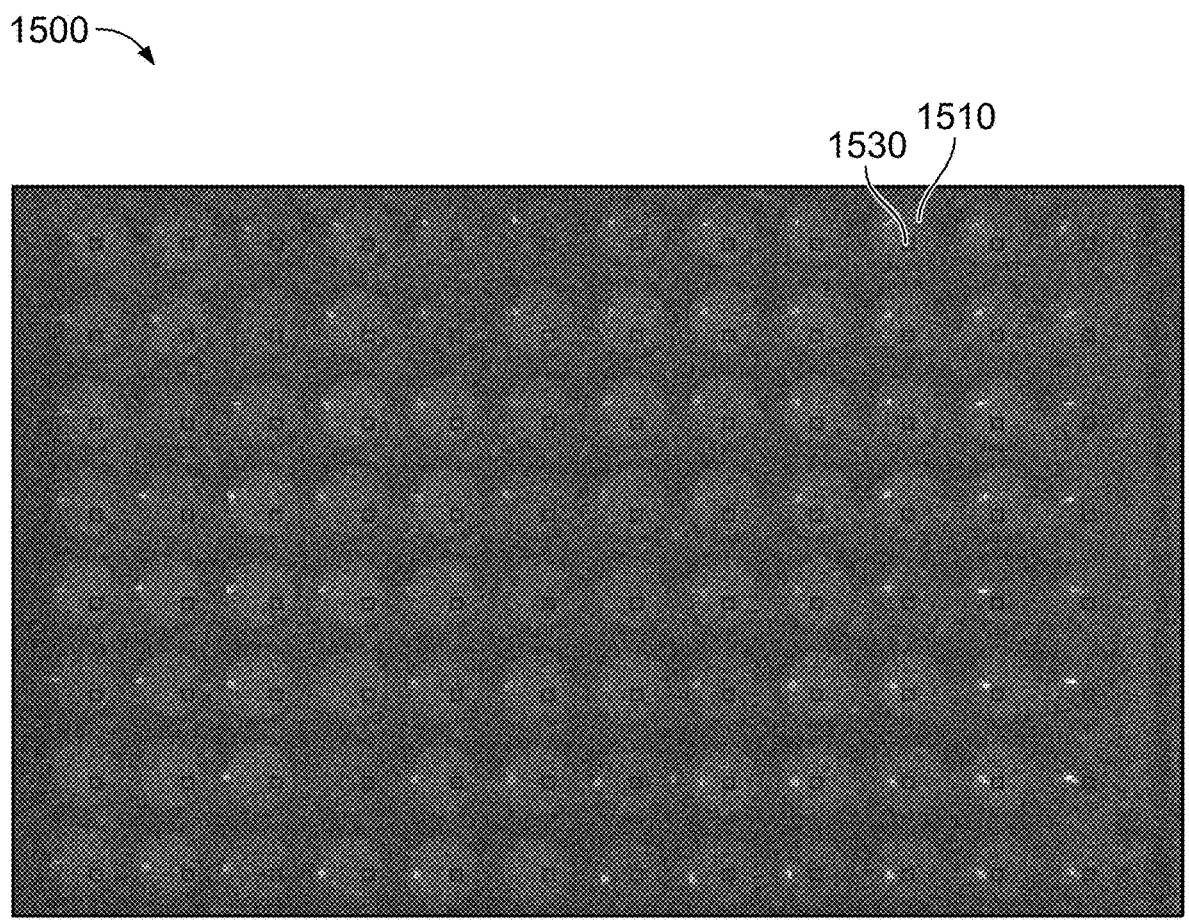
FIG. 15A shows a tray that includes an array of cuvettes.

In a first category of experiments, spectroscopy was performed using either: 1) a low-cost, miniature spectrometer, which, is configured (e.g., in terms of size and/or power budget) so that it can be integrated into, and/or used with, an ingestible device as described herein; or 2) benchtop spectrometers. The test samples included mixtures of Intralipid (which is an emulsified soybean oil), whey (which is a milk protein) and lactose in water, each of the foregoing analytes were varied independently from each other in the range of 0-4% (w/v). Such mixtures replicated various compositions of milk. Well plates like the well plate 1500 shown in FIG. 15A were used to hold the samples, each well 1510 holding a respective sample. The well plate 1500 used in the spectroscopy measurements included a two-dimensional (2D) array of wells, e.g., 4×24 wells. Here, 96 samples having randomized concentrations were placed in respective 96 wells. Three spectra of light reflected from each of the samples was acquired with each of the spectrometers listed in Table 2.

TABLE 2

| Spectrometer | Wavelength range (nm) |
|---|---|
| Miniature; spectrometer size = (6 mm) × (7 mm) | 740-1070 |
| Benchtop #1 | 760-1050 |
| Benchtop #2 | 660-1260 |
| Benchtop #3 | 1010-2170 |

Here, the miniature spectrometer was SCIO fabricated by Analog Devices; Benchtop spectrometer #1 was a first embodiment of USB2000+ fabricated by Ocean Optics; Benchtop spectrometer #2 is Flame-S was fabricated by Ocean Optics; and Benchtop spectrometer #3 was a NIR-Quest512 fabricated by Ocean Optics.

The acquired spectra were preprocessed using either a moving average filter, or a standard normal variate (SNV) transformation. Moreover, a subset of the acquired spectra was used as training inputs for machine learning modeling, e.g., machine learning modeling that uses a partial least squares (PLS) algorithm. Once this PLS-based model was trained in this manner, it was used to predict the concentration of one or more analytes of a mixture to which one of the acquired spectra corresponds. As such, an unknown concentration of an analyte in a mixture having an acquired spectrum was determined by (i) identifying one of a number of spectra corresponding to mixtures having known concentrations of the analyte that best matches the acquired spectrum, and (ii) assigning to the unknown concentration a value of the concentration of the analyte in the mixture to which the identified spectrum corresponds.

FIGS. 7A-7D show results 712, 714, 716, 718 of a PLS-based model for predicting concentration of Intralipid in a mixture, the mixture further including whey and lactose in water. Here, the result 712 represents a correlation between the estimated and known concentrations of Intralipid, where the spectra used to determine this correlation were acquired with the SCIO spectrometer noted in Table 2. Further, the result 714/716/718 represented a correlation between the estimated and known concentrations of Intralipid, where the spectra used to determine this correlation was acquired with the Benchtop #1/#2/#3 spectrometer, respectively, as listed in Table 2.

Performance of models used to generate correlation results like the ones shown in FIGS. 7A-7D was evaluated based on parameters that quantify departure from perfect model prediction. In these examples, in which the known values are represented along the horizontal axis, and the estimated values, i.e., predicted based on a model, are represented along the vertical axis, the line with slope=1 corresponds to perfect model prediction. So, the closer the points are disposed to the line with slope=1, i.e., the smaller the spread of the points relative to the line with slope=1, the better the model performance. A parameter (or standard metric) for evaluating the spread of the points is the root mean square error (RMSE).

$$RMSE = \sqrt{\frac{\sum_{i=1}^{N}(\hat{y}_i - y_i)^2}{N}}. \quad (1)$$

In Equation (1), $\hat{y}_i$ is a predicted value and $y_i$ is an actual value for each data point i of N samples. In some cases, a ratio of the RMSE to the mean of the known values is a metric that can better reveal how well the model performs. Note that, in this specification, RMSE is also referred to as RMSE of cross-validation (RMSECV).

Referring again to the results summarized in FIGS. 7A-7D, respective values of the foregoing metrics are listed in Table 3.

TABLE 3

| | Intralipid | | |
|---|---|---|---|
| Spectrometer | Result | RMSECV (%) | RMSECV/Mean (%) |
| SCIO | 712 | 0.3 | 13.5 |
| Benchtop #1 | 714 | 0.3 | 11.9 |
| Benchtop #2 | 716 | 0.2 | 8.6 |
| Benchtop #3 | 718 | 0.2 | 10 |

Note that result 712 obtained based on the model that uses input spectra acquired with the SCIO spectrometer is comparable to the results 714, 716 or 718 obtained based on the models that use input spectra acquired with benchtop spectrometers. As such, spectra acquired with the SCIO spectrometer, which could be integrated in an ingestible device as described herein, enable modeling that can accurately predict concentrations of Intralipid in mixtures with whey and lactose in water, which may, in turn, be used as a basis for modeling potential behavior in the GI tract of a subject. Also note that the best performance among the models having results summarized in Table 3 belongs to the model that used spectra acquired by the Benchtop spectrometer #2 that has a wavelength range that extends over the high end of the visible spectral range and the low end of the NIR spectral range. This indicates that the Intralipid has spectral features that are sensitive to Intralipid's concentration in the mixture over most of the spectral range of the Benchtop spectrometer #2.

FIGS. 8A and 8D show results 842 and 848 of a model for predicting concentration of whey and lactose in a mixture, the mixture further including Intralipid in water, based on spectra of light that interacted with the mixture, the spectra having been acquired with different spectrometers. Here, the result 842 represents a correlation between the estimated and known combined concentrations of whey and lactose, where the spectra used to determine this combined correlation was acquired with the SCIO spectrometer, implemented as noted in Table 2. Further, the result 848 represents a correlation between the estimated and known combined concentrations of whey and lactose, where the spectra used to determine this correlation were acquired with the Benchtop spectrometer #3, as listed in Table 2.

FIG. 8B shows a result 828 of a model for predicting concentration of lactose in a mixture, the mixture further including whey and Intralipid in water, based on a spectrum of light that interacted with the mixture. Here, the result 828 represents a correlation between the estimated and known concentration of lactose, where the spectra used to determine this correlation were acquired with the Benchtop spectrometer #3. FIG. 8C shows a result 838 of a model for predicting concentration of whey in a mixture, the mixture further including lactose and Intralipid in water, based on a spectrum of light that interacted with the mixture. Here, the result 838 represents a correlation between the estimated and known concentration of whey, where the spectra used to determine this correlation were acquired with the Benchtop spectrometer #3.

Respective values of model performance metrics for the models having results summarized in FIGS. 8A and 8D are listed in Table 4.

TABLE 4

Lactose and Whey

| Spectrometer | Result | RMSECV (%) | RMSECV/Mean (%) |
|---|---|---|---|
| SCIO | 842 | 0.9 | 23 |
| Benchtop 3 | 848 | 1.2 | 30 |

Spectra associated with solutions of lactose and with solutions of whey are too similar to be distinguishable relative each other, so results of models for predicting concentration of lactose and separately concentration of whey are not shown in Table 4. Note that result 842 obtained based on the model that uses input spectra acquired with the SCIO spectrometer have better metric values than corresponding metric values of the result 848 obtained based on the model that uses input spectra acquired with the Benchtop spectrometer #3. As such, spectra acquired over a wavelength range 740-1070 nm with the SCIO spectrometer, which can be integrated in an ingestible device as described herein, enable modeling that can more accurately predict combined concentrations of lactose and whey in mixtures with Intralipid in water compared to corresponding modeling enabled by spectra acquired over a wavelength range 1010-2170 nm with the Benchtop spectrometer #3. A potential reason for obtaining the foregoing results is that the SCIO spectrometer has produced spectra that are less noisy than the spectra that were produced with the Benchtop spectrometer #3.

Moreover, respective values of model performance metrics for the models having results summarized in FIGS. 8B-8C are listed in Table 5.

TABLE 5

Spectrometer Benchtop #3

| Analyte | Result | RMSECV (%) | RMSECV/Mean (%) |
|---|---|---|---|
| Lactose | 828 | 1 | 52 |
| Whey | 838 | 0.9 | 42 |

Note that the results 828, 838, 848 summarized in FIGS. 8B-8D suggest that models that use spectra acquired over the wavelength range 1010-2170 nm with the Benchtop spectrometer #3 can be inaccurate in predicting the concentration of lactose or the concentration of whey in the mixtures noted above. However, the result 842 summarized in FIG. 8A suggests that a model that uses spectra acquired over the wavelength range 740-1070 nm with the SCIO spectrometer can predict the concentration of whey and lactose in the mixtures noted above.

FIGS. 9A-9D show results 952, 954, 956, 958 of a model for predicting caloric content per 100 ml of a mixture including Intralipid, whey and lactose in water, based on spectra of light that interacted with the mixture, the spectra having been acquired with different spectrometers. The caloric content of a mixture was established based on the calorie conversions listed in Table 6.

TABLE 6

Calorie conversion

| Analyte | Mass (g) | Caloric content (calories) | Source |
|---|---|---|---|
| Intralipid | 1 | 8.6 | USDA |
| Whey | 1 | 4 | Naked Whey package label |
| Lactose | 1 | 3.9 | Wikipedia |

The result 952 represents a correlation between the estimated and known caloric contents, where the spectra used to determine this correlation were acquired with the SCIO spectrometer, implemented as noted in Table 2. Further, the result 954/956/958 represents a correlation between the estimated and known caloric contents, where the spectra used to determine this correlation were acquired with the Benchtop spectrometer #1/#2/#3, respectively, as listed in Table 2.

Respective values of model performance metrics for the models having results summarized in FIGS. 9A-9D are listed in Table 7.

TABLE 7

Caloric content

| Spectrometer | Result | RMSECV (%) | RMSECV/Mean (%) |
|---|---|---|---|
| SCIO | 952 | 3.1 | 9.2 |
| Benchtop #1 | 954 | 6.4 | 19 |
| Benchtop #2 | 956 | 6 | 17.8 |
| Benchtop #3 | 958 | 5.1 | 15.2 |

Note that result 952 obtained based on the model that uses input spectra acquired with the SCIO spectrometer is comparable to the results 954, 956 or 958 obtained based on the models that use input spectra acquired with benchtop spectrometers. As such, spectra acquired with the SCIO spectrometer, which can be integrated in an ingestible device as described herein, enable modeling that can accurately predict caloric content of mixtures of Intralipid, whey and lactose in water. In fact, note that the best performance among the models having results summarized in Table 7 belongs to the model that used spectra acquired by the SCIO spectrometer. These results indicate that the SCIO spectrometer, as configured for the foregoing measurements, is capable of performing as well as, if not better than, some benchtop spectrometers for determining caloric content of macronutrients in the GI tract.

Example 3: Hyperspectral Imaging for Quantifying Macronutrients

In a second category of experiments, hyperspectral imaging was performed using a hyperspectral camera (e.g., XIMEA SM5X5-NIR camera) having an imaging sensor with a size of 6×12 mm. This hyperspectral camera, which is used to perform the second category of experiments, is configured (e.g., in terms of its size and/or power budget) so that it can be integrated into, and/or used with, an ingestible device as described herein. Additionally, the imaging sensor of the foregoing hyperspectral camera has 25-wavelength bins distributed over a wavelength range of 600-975 nm, and can produce a 409×217 pixel image. As in Example 2, the test samples in Example 3 also were mixtures of Intralipid, whey and lactose in water, each of the foregoing analytes having been varied independently from each other in respective ranges of 0-2%, 0-4%, and 0-4%, to replicate various compositions of milk. Well plates like the well plate 1500 shown in FIG. 15A were used to hold the samples, each well 1510 holding a respective sample. The well plate 1500 used for hyperspectral imaging includes a two-dimensional (2D) array of wells, e.g., 8×12 wells. Here, 96 samples having random concentrations were placed in respective 96 wells.

An image of the well plate 1500, acquired as it was holding the 96 samples in the respective 96 wells, was processed in the following manner. To correct for non-uniform illumination of the 96 samples held by the well plate 1500, an image of a uniform white calibration surface was used to normalize the image of the well plate holding the 96 samples via pixel-by-pixel division. A respective region of interest (ROI) 1530 of the acquired image, for each well 1510 of the well plate 1500, was defined to have 3×3 pixels, for instance. The spectral signature of light corresponding to each ROI was averaged to obtain a respective spectrum of light that interacted with the respective mixture held by the well associated with the ROI.

Figure 10:
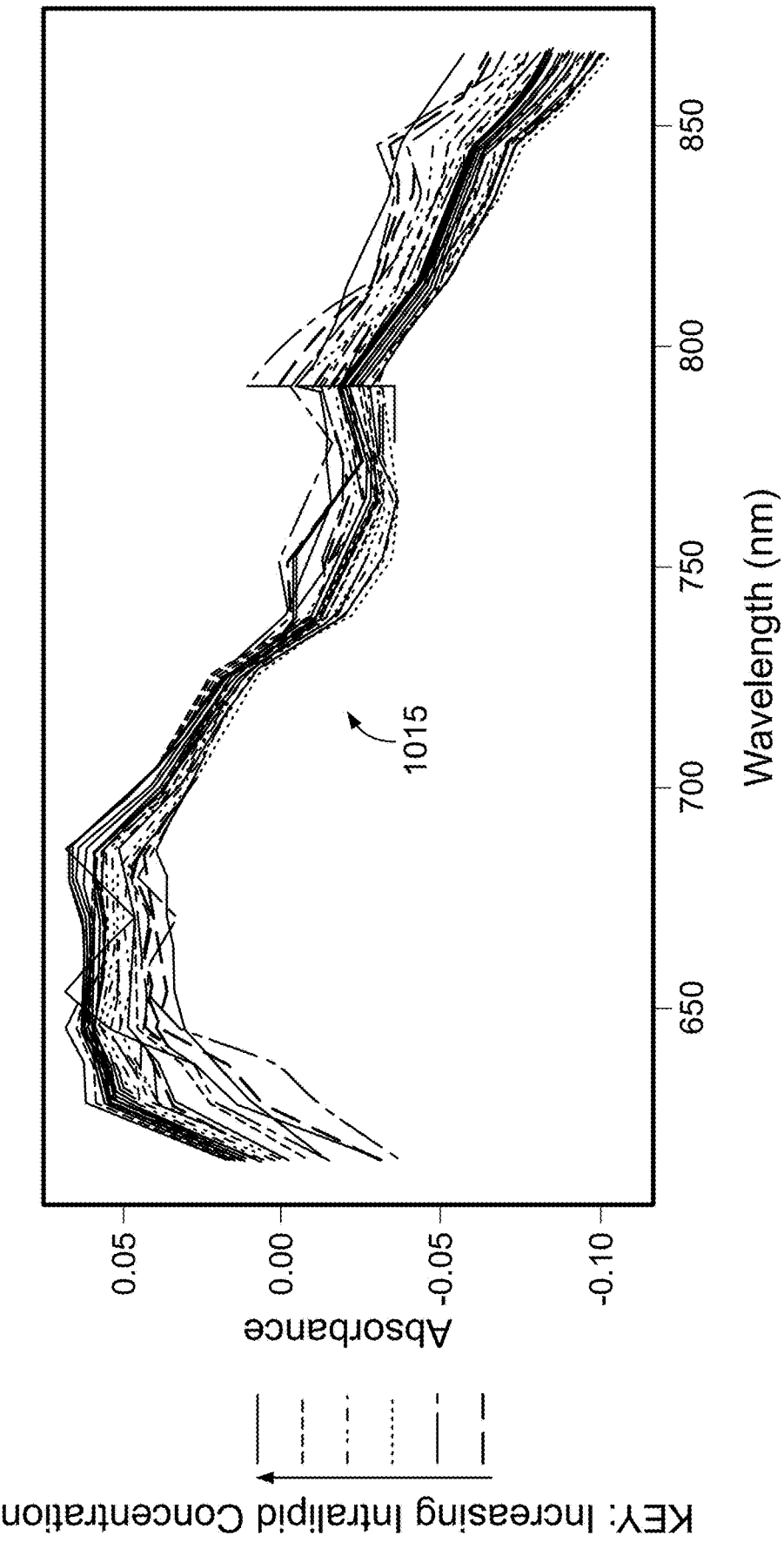
FIG. 10 shows spectra.
Figure 11A:
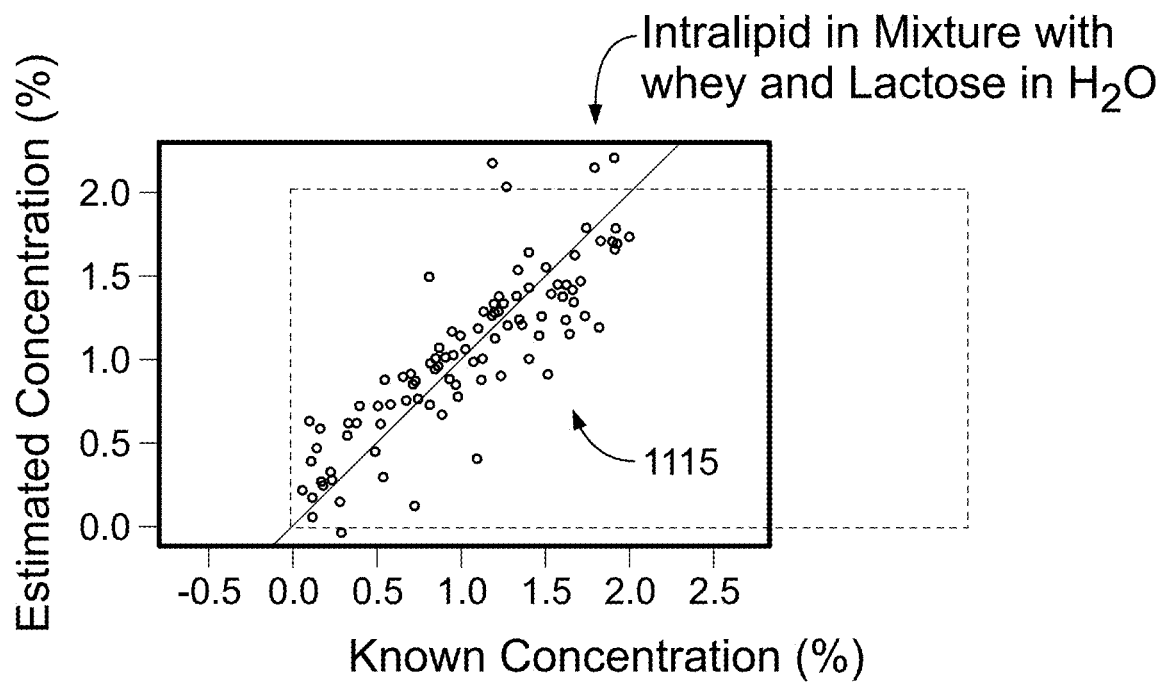
FIGS. 11A-11D illustrate results of predictions based on a model.
Figure 11B:
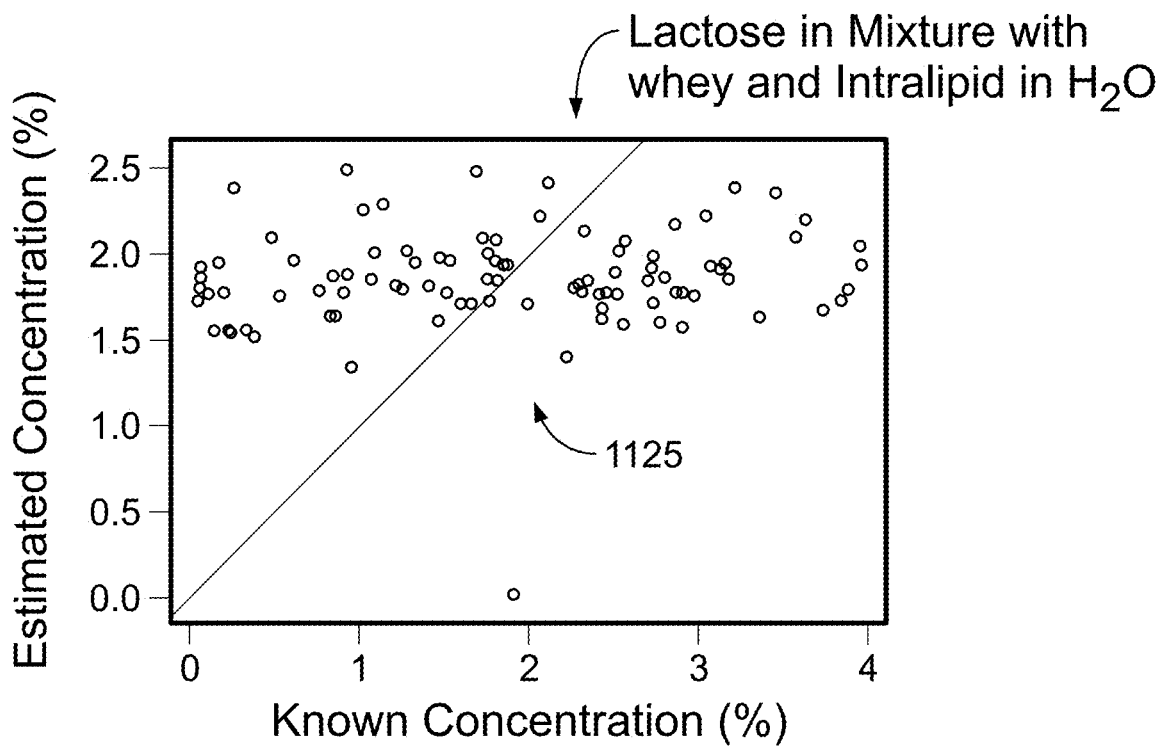
Figure 11C:
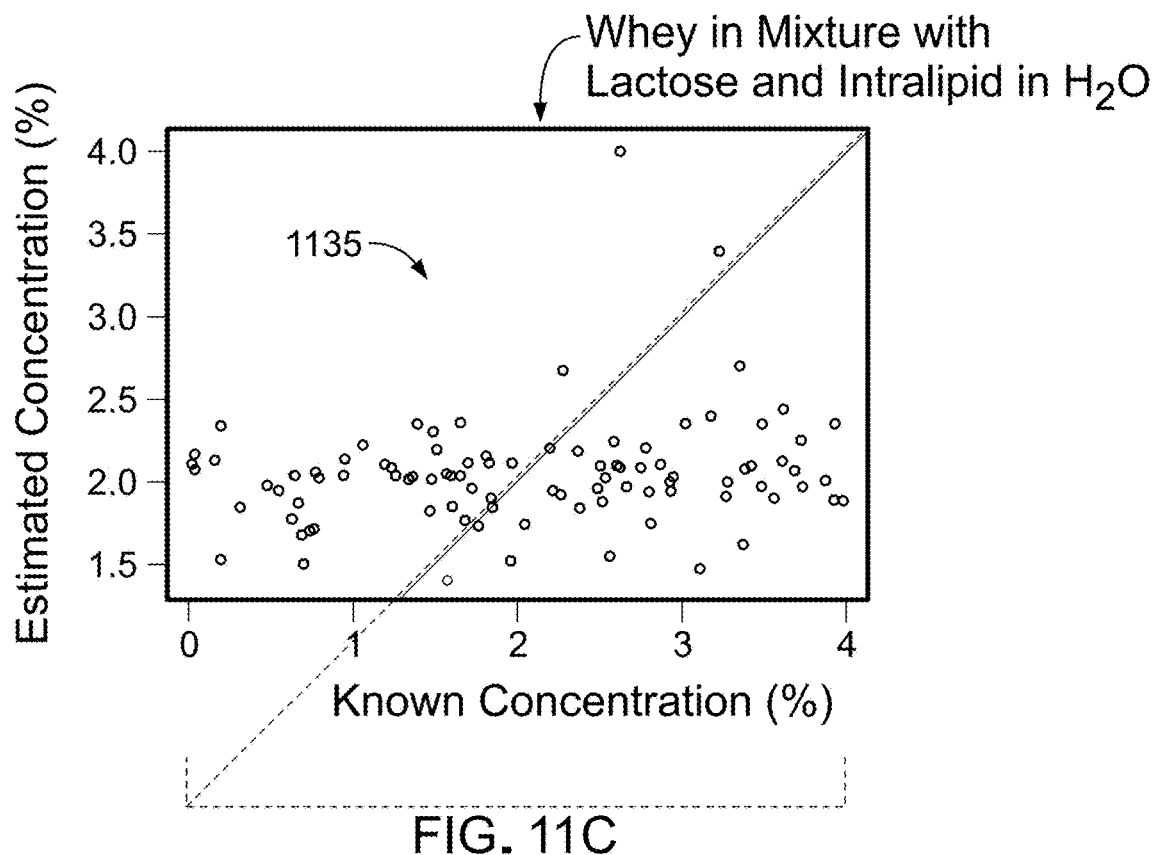
Figure 11D:
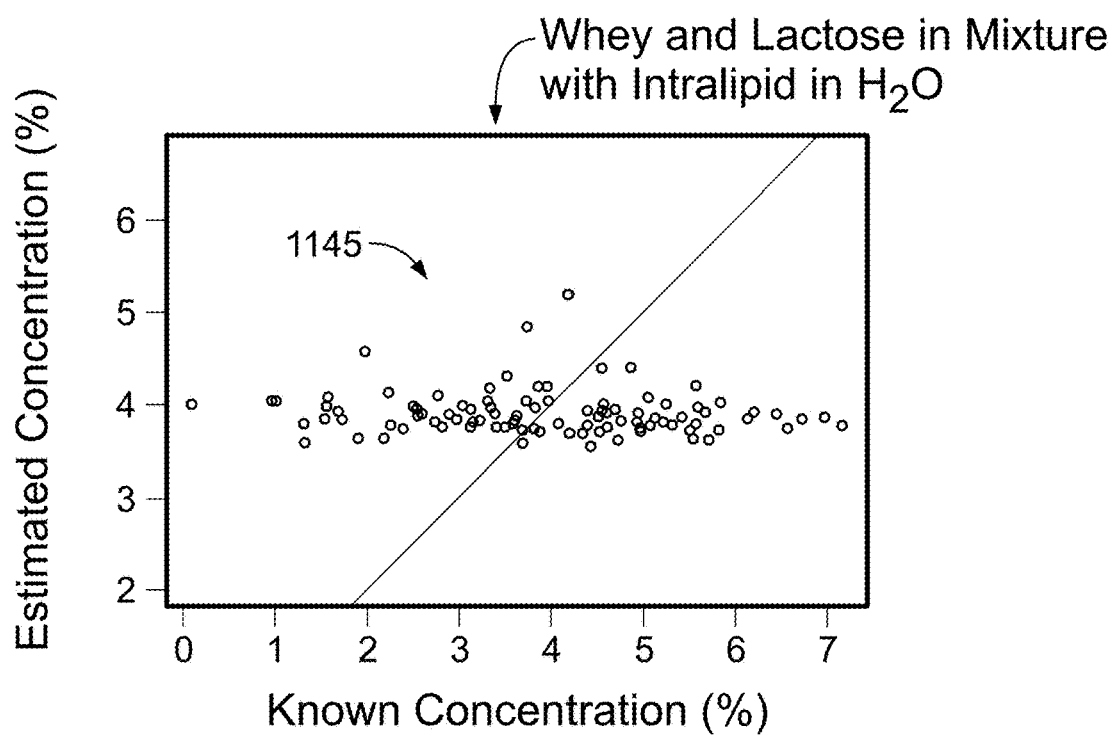

FIG. 10 shows spectra 1015 of light that interacted with mixtures including Intralipid, whey and lactose in water, the spectra were acquired based on images acquired with the hyperspectral camera. The spectra 1015 were preprocessed using a moving average filter and mean correction. Moreover, a subset of the spectra 1015 were used as inputs for machine learning modeling, e.g., based on partial least squares (PLS), to predict the concentration of one or more analytes of a mixture to which one of the spectra 1015 corresponds. Other approaches, such as Standard Normal Variate (SNV), Savitzky-Golay, or multiplicative scatter correction, were used for pre-preprocessing the acquired spectra, and the prediction results were similar to those of the approach that used the mean correction for pre-preprocessing the acquired spectra. In this manner, an unknown concentration of an analyte in a mixture having an acquired spectrum was determined by (i) identifying one of the spectra 1015 corresponding to mixtures having known concentrations of the analyte that best matches the acquired spectrum, and (ii) assigning to the unknown concentration a value of the concentration of the analyte in the mixture to which the identified spectrum corresponds.

FIGS. 11A-11D show results of respective models for predicting concentration of various analytes in the mixtures having the spectra 1015. Here, the result 1115 represents a correlation between the estimated and known concentrations of Intralipid in the mixtures having the spectra 1015. Further, the result 1125 represents a correlation between the estimated and known concentrations of lactose in the mixtures having the spectra 1015. Furthermore, the result 1135 represents a correlation between the estimated and known concentrations of whey in the mixtures having the spectra 1015. Also, the result 1145 represents a correlation between the estimated and known combined concentrations of whey and lactose in the mixtures having the spectra 1015.

Respective values of model performance metrics for the models having results summarized in FIGS. 11A-11D are listed in Table 8.

TABLE 8

| Hyperspectral camera | | | |
|---|---|---|---|
| Analyte | Result | RMSECV (%) | RMSECV/Mean (%) |
| Intralipid | 1115 | 0.3 | 26.9 |
| Lactose | 1125 | 1.1 | 58.6 |

TABLE 8-continued

| Hyperspectral camera | | | |
|---|---|---|---|
| Analyte | Result | RMSECV (%) | RMSECV/Mean (%) |
| Whey | 1135 | 1.1 | 52.9 |
| Whey and Lactose | 1145 | 1.5 | 39 |

Note that the best performance among the models having results summarized in Table 8 belongs to the model used for predicting Intralipid. However, a comparison between the results shown in FIGS. 11A-11D and the results shown in FIGS. 7A-7D and 8A-8D suggests that the prediction models that use the spectra 1015 acquired with the hyperspectral camera are less accurate than prediction models that use spectra acquired with the spectrometers listed in Table 2. A reason for the prediction models described in Example 2 to be more accurate than the prediction models described in Example 3 is the fact that the former models used spectra acquired with spectrometers having a spectral resolution that is about an order of magnitude higher than the spectral resolution of the hyperspectral camera that acquired the spectra 1015 used for the latter models. Additionally, the signal-to-noise and dynamic range performance was also much better for dedicated spectrometers compared to the hyperspectral camera.

Figure 12:
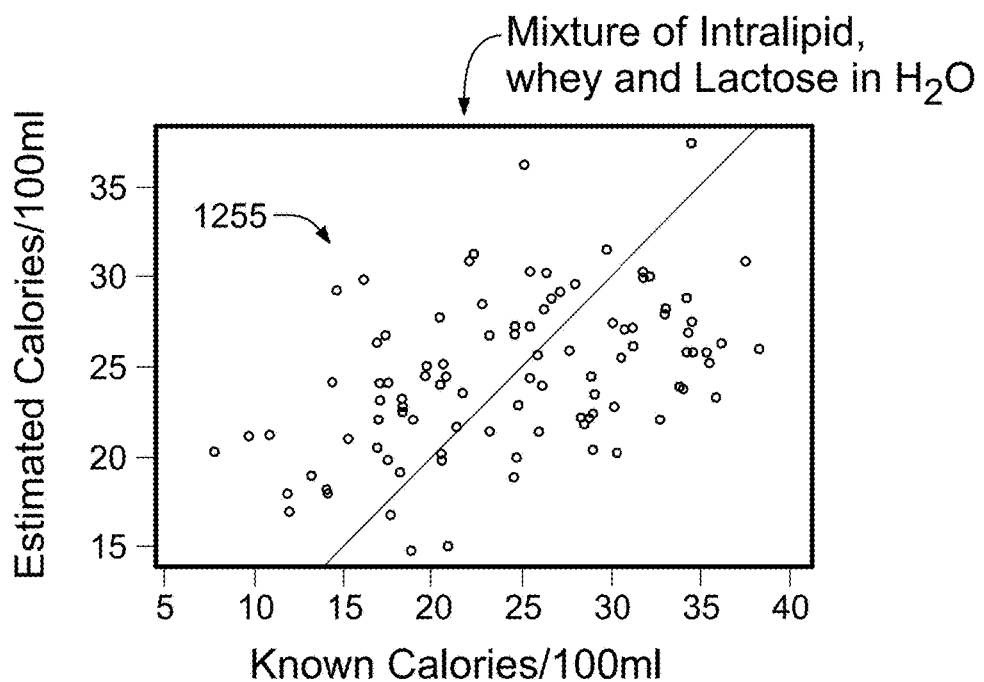
FIG. 12 shows a result of a model for predicting caloric content.

FIG. 12 shows a result 1255 of a model for predicting caloric content per 100 ml of the mixtures having the spectra 1015. Here, the result 1255 represents a correlation between the estimated and known caloric content of the mixtures having the spectra 1015. The caloric content of a mixture was established based on the calorie conversions listed in Table 6. Values of model performance metrics for the model having results summarized in FIG. 12 are listed in Table 9.

TABLE 9

| Hyperspectral camera | | |
|---|---|---|
| Result | RMSECV (%) | RMSECV/Mean (%) |
| 1255 | 6.5 | 26.3 |

A comparison between the result shown in FIG. 12 and the results shown in FIGS. 9A-9D suggests that the prediction models that use the spectra 1015 acquired with the hyperspectral camera are less accurate than a prediction model that use spectra acquired with the spectrometers listed in Table 2. The reason for this finding is the same as the one discussed in the paragraph following Table 8.

Example 4: Hyperspectral Imaging for Quantifying Other Macronutrients

Continuing with the second category of experiments, additional hyperspectral imaging was performed using the same hyperspectral camera used in Example 3. The test samples were solutions of Ensure (a representative commercially available meal replacement) in water, each solution having a respective predetermined concentration. A well plate like the well plate 1500 shown in FIG. 15A (e.g., having 6×4 wells) was used to hold the samples, each well 1510 holding a respective sample.

An image of the well plate 1500, acquired as it was holding the samples in respective wells, was processed in the following manner. A respective region of interest (ROI) 1530 of the acquired image, for each well 1510 of the well plate 1500, was defined as described in Example 3. A spectral signature of light corresponding to each ROI was averaged to obtain a respective spectrum of light that reflected off the respective solution of Ensure held by the well associated with the ROI. Here, a spectral signature of the illumination source was factored out from the spectral signature corresponding to each ROI.

Figure 13A:
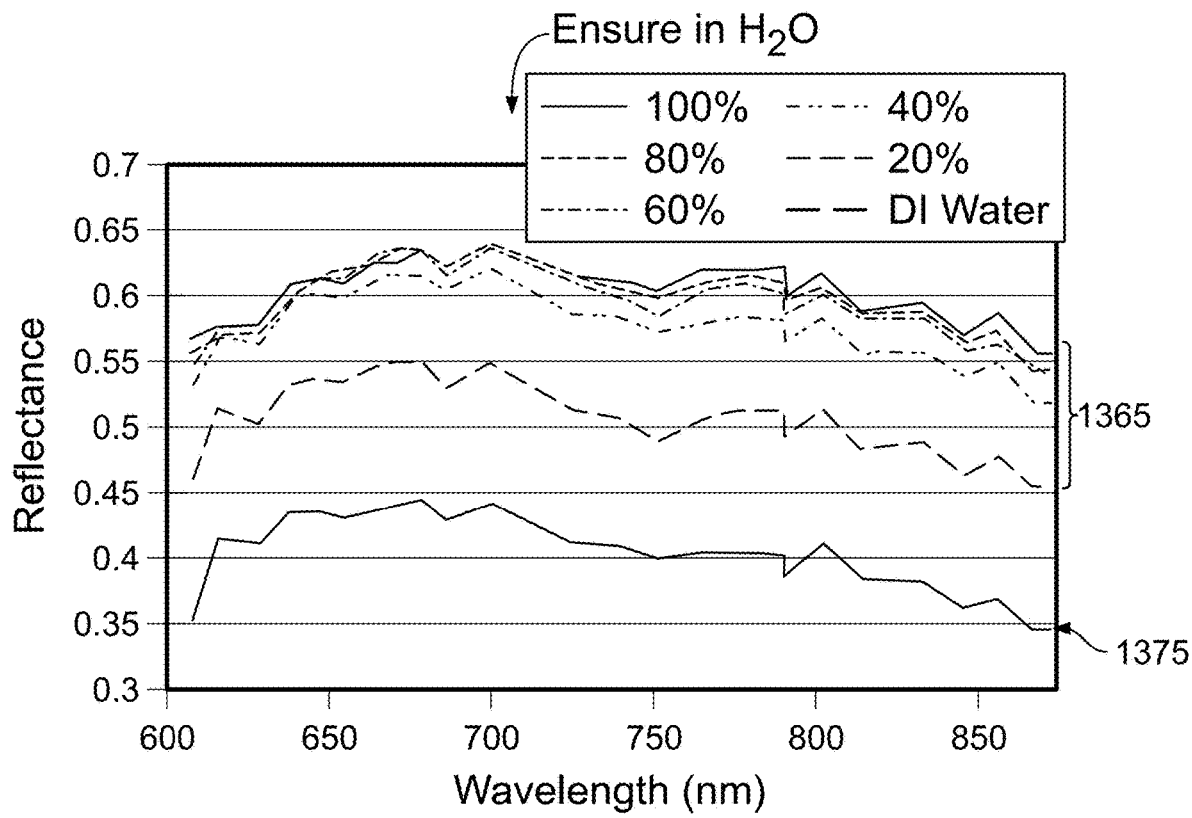
FIG. 13A shows spectra.

FIG. 13A shows spectra 1365 of light that interacted with the solutions of Ensure in water, and a spectrum 1375 of light that interacted with water (or equivalently with a 0% Ensure solution). The spectra 1365, 1375 were produced based on images acquired with the hyperspectral camera. The spectra 1365 shown in FIG. 13A suggest that, although there is not a statistically significant difference between spectral features corresponding to different Ensure concentrations, the overall reflectance of the Ensure solutions varies as a function of the Ensure concentration. This result indicates that it possible to ex-vivo distinguish between Ensure solutions having different concentrations. By extension, the experiments performed as part of Example 4 suggest that, if a hyperspectral camera and light source similar to the ones used in Example 4 were integrated in an ingestible device as described herein, it would possible to determine concentration of Ensure solutions in the GI tract.

The spectroscopy experiments described above as part of Example 2 and the hyperspectral imaging experiments described above as part of Examples 3 and 4 were intended to emulate measurements performed by the miniature spectrometer or the hyperspectral camera when an ingestible device as described herein, that would carry either of these instruments, is at rest relative to the macronutrients present in the GI tract. Such situations can occur when an ingestible device as described herein moves through the GI tract along with the macronutrients (e.g., with the same, non-zero speed), or when an ingestible device as described herein is at rest at a location of the GI tract where the macronutrients also are at rest.

In other situations, an ingestible device as described herein could be at rest at a location of the GI tract while the macronutrients flow by it through the GI tract. Hyperspectral imaging experiments intended to emulate measurements performed by the hyperspectral camera when an ingestible device as described herein, that would carry it, and the macronutrients present in the GI tract are moving relative to each other with a non-zero speed. Examples of the latter hyperspectral imaging experiments are described below.

Figure 15B:
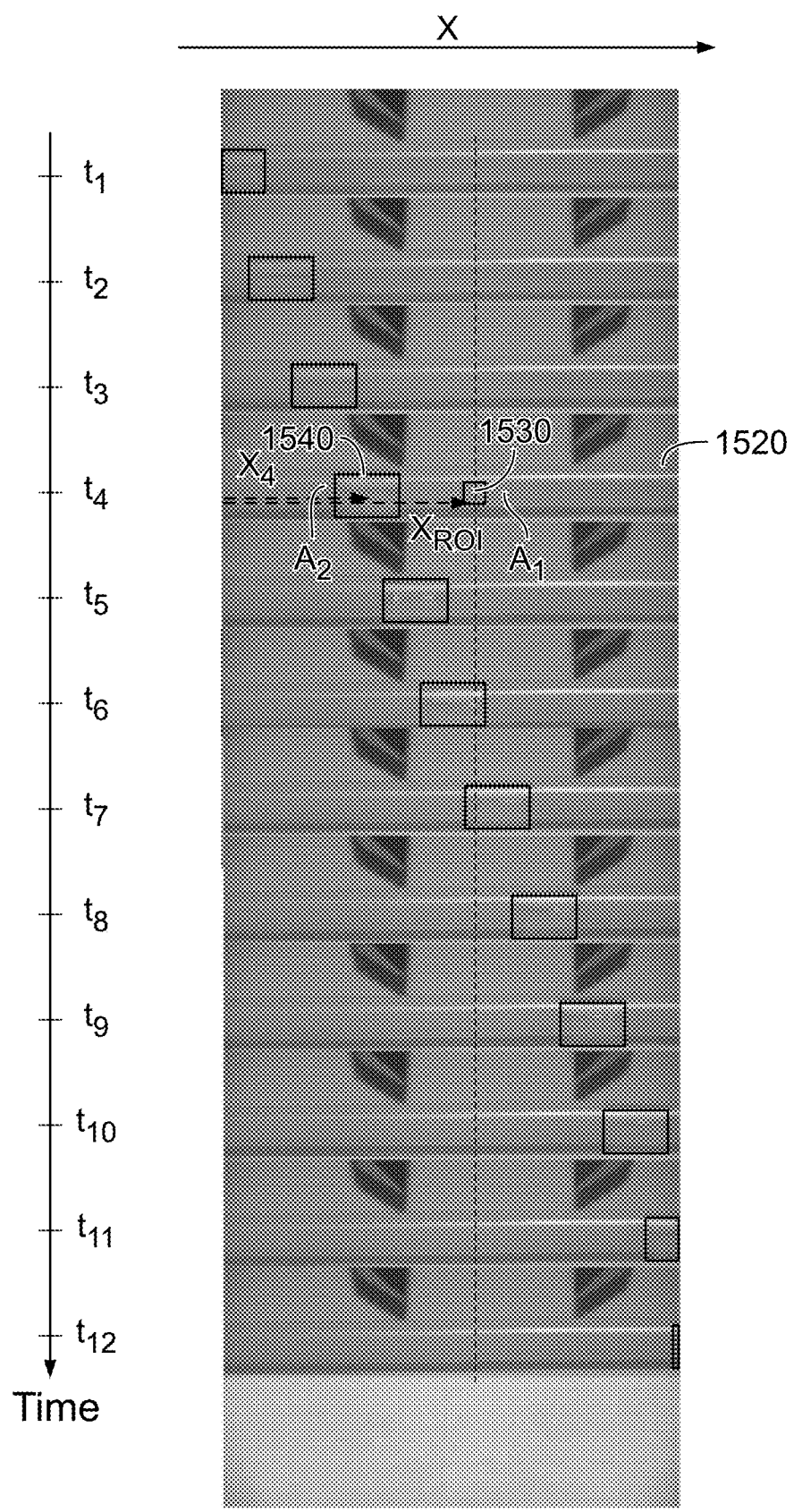
FIG. 15B shows time instances in which different macronutrients flow through a region of interest.

Example 5: Hyperspectral Imaging for Quantifying Macronutrients that are in Motion Relative to the Hyperspectral Camera In a third category of experiments, hyperspectral imaging was performed using the hyperspectral camera, e.g., XIMEA SM5X5-NIR camera, used for the experiments described in Example 3. The test samples in Example 5 were pushed (e.g., using a peristaltic pump) through a tube 1520 (e.g., silicone tubing having a 3 mm inner diameter) that is disposed along the x-axis, as shown in FIG. 15B. Here, the test samples are (i) a plug 1540, (ii) a first solution that includes a first analyte A1, and (iii) a second solution that includes a second analyte A2, where the plug separates the first and second solutions. Moreover, the first and second solutions separated by the plug 1540 were pushed through the tube 1520, e.g., from left to right, while the hyperspectral camera acquires, e.g., at t1, t2, . . . a sequence of images, shown in FIG. 15B, corresponding to a sequence of positions x1, x2, . . . of the plug 1540.

A region of interest (ROI) 1530, located at a fixed position xROI, was used to average the spectral signature of light corresponding to the ROI to obtain, at a time tj, a spectrum of light that interacted with a sample that flowed by xROI at the time tj. As such, for the sequence of images shown in FIG. 15B, the hyperspectral camera obtained spectra associated with the first solution prior to t6, spectra associated with a material of the plug 1540 between t6 and t7, and spectra associated with the second solution after t7. Note that in some cases, the plug 1540 can be implemented as a controlled-size air bubble.

The spectra obtained for different solutions, which flow through the tube 1520, were preprocessed to account for illumination non-uniformities and other sources of noise. The preprocessing included subtracting a dark background spectrum from a raw ("as-measured") spectrum, and then normalizing the difference spectrum by a white reference spectrum. As determined over multiple experiments described below, the obtained spectra (i) changed (outside an experimental error range) when samples with different compositions flow by the ROI 1530, and (ii) remained constant (within the experimental error range) when samples with the same composition flow by the ROI 1530.

The experimental setup described above can be used to simulate operation of an ingestible device as described herein carrying a miniaturized spectrometer, in a scenario when the ingestible device lodges itself at a location of the GI tract and monitors macronutrients as they pass by down the GI tract. In this scenario, the miniaturized spectrometer (e.g., implemented as a hyperspectral camera) can be used to identify the macronutrients that pass by and their concentration. Optionally, an ingestible device as described herein can use the foregoing identifications of (i) the macronutrient and (ii) the identified nutrient's concentration to determine the caloric content that flows by the miniaturized spectrometer.

In a first experiment, the experimental set described above in connection with FIG. 15B was used to characterize solutions of Ensure in water, for various concentrations of Ensure, e.g., in the range of 0 to 25%, when the solutions of Ensure flow by the region of interest 1530 through the tube 1520. Here, the first solution corresponded to a solution of Ensure having a first concentration, and the second solution corresponded to a solution of Ensure having a second concentration, different from the first concentration.

Figure 13B:
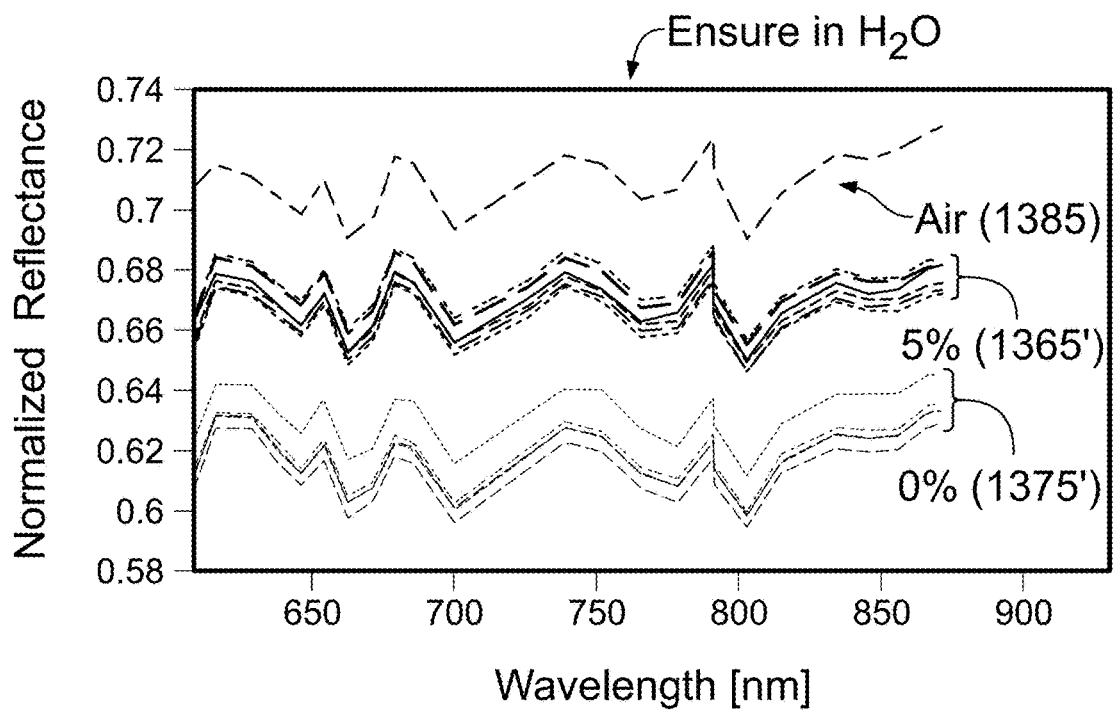
FIGS. 13B-13C show spectra.

FIG. 13B shows spectra 1365' of light that interacted with a 5% Ensure solution, spectra 1375' of light that interacted with water (which is 0% Ensure solution), and a spectrum 1385 of light that interacted with the air, which was included in the plug 1540 that separates the 5% Ensure solution from the water. Each of the spectra shown in FIG. 13B was obtained using a respective image in a sequence of images acquired by the hyperspectral camera as shown in FIG. 15B. Note that there is a statistically significant difference between spectral features of the spectra 1365' and the spectra 1375', which makes it possible to distinguish between a 5% Ensure solution and water flowing by the hyperspectral camera.

Figure 13C:
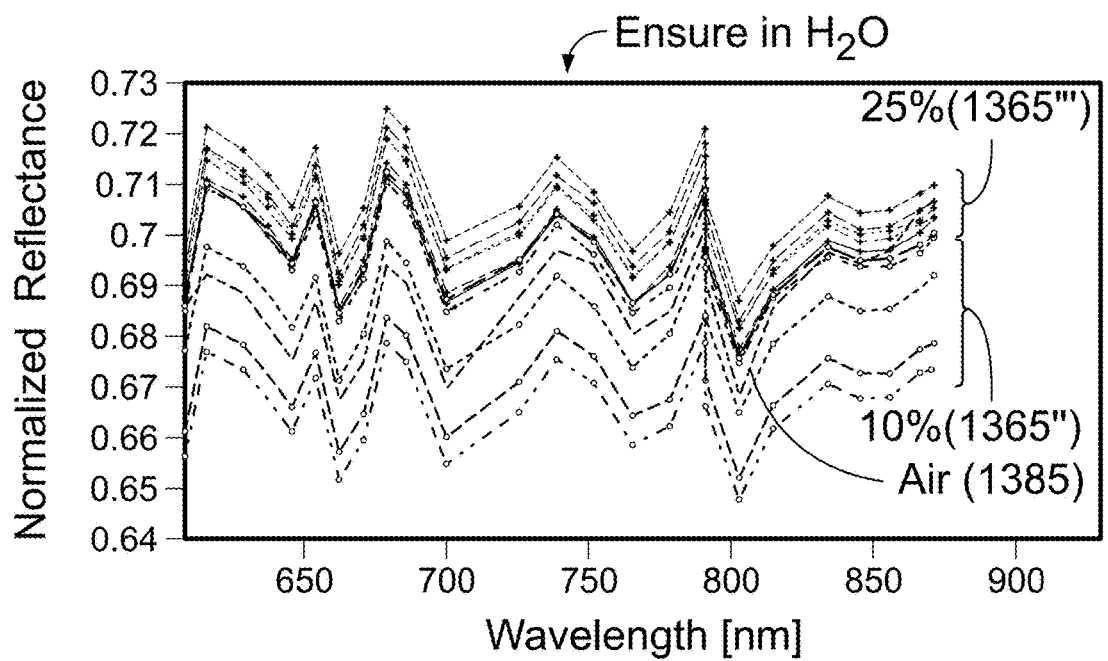

FIG. 13C shows spectra 1365" of light that interacted with a 10% Ensure solution, spectra 1365''' of light that interacted with a 25% Ensure solution, and spectra 1385 of light that interacted with the air, which is included in the plug 1540 that separates the 10% Ensure solution from the 25% Ensure solution. Each of the spectra shown in FIG. 13C was obtained using a respective image in a sequence of images acquired by the hyperspectral camera as shown in FIG. 15B. Although there is not a statistically significant difference between spectral features of the spectra 1365" and the spectra 1365''', the reflection from the 25% Ensure solution is higher on average than that from the 10% Ensure solution, which makes the intensity of the spectra 1365''' larger than the intensity of the spectra 1365". This result makes it possible to distinguish between a 10% Ensure solution and a 25% Ensure solution flowing by the hyperspectral camera.

In a second experiment, the experimental set described above in connection with FIG. 15B was used to characterize mixtures of Intralipid, whey and lactose in water. Here, the first solution corresponded to a mixture in which one of the Intralipid, whey and lactose has a first concentration, and the second solution corresponded to a mixture in which another one of the Intralipid, whey and lactose has a second concentration, different from the first concentration.

Figure 14A:
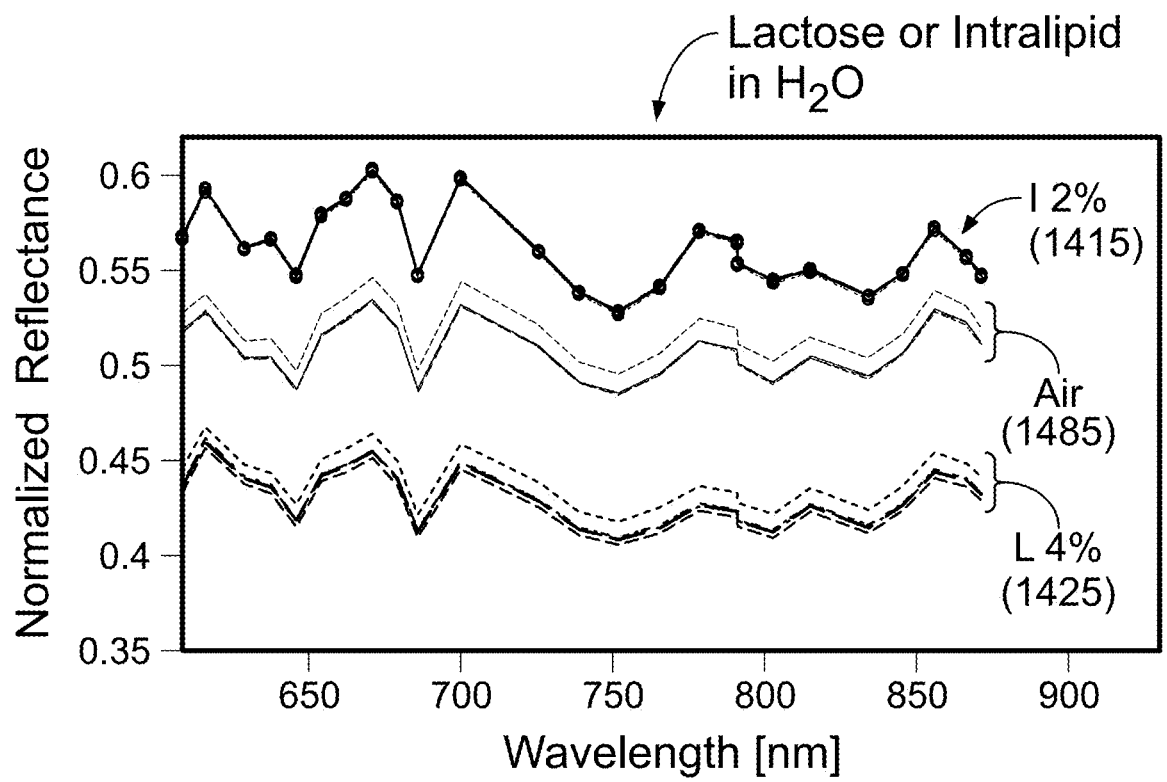
FIG. 14A shows a comparison of spectra.

FIG. 14A shows spectra 1415 of light that interacted with a 2% Intralipid mixture, spectra 1425 of light that interacted with a 4% lactose mixture, and spectra 1485 of light that interacted with the air, which is included in the plug 1540 that separates the 2% Intralipid mixture from the 4% lactose mixture. Each of the spectra shown in FIG. 14A was obtained using a respective image in a sequence of images acquired by the hyperspectral camera as shown in FIG. 15B. Note that the reflection from the 2% Intralipid mixture was higher on average than that from the 4% lactose mixture, which made the intensity of the spectra 1415 larger than the intensity of the spectra 1425. This result suggests that it would be possible to distinguish between a 2% Intralipid mixture and a 4% lactose mixture flowing by the hyperspectral camera.

Figure 14B:
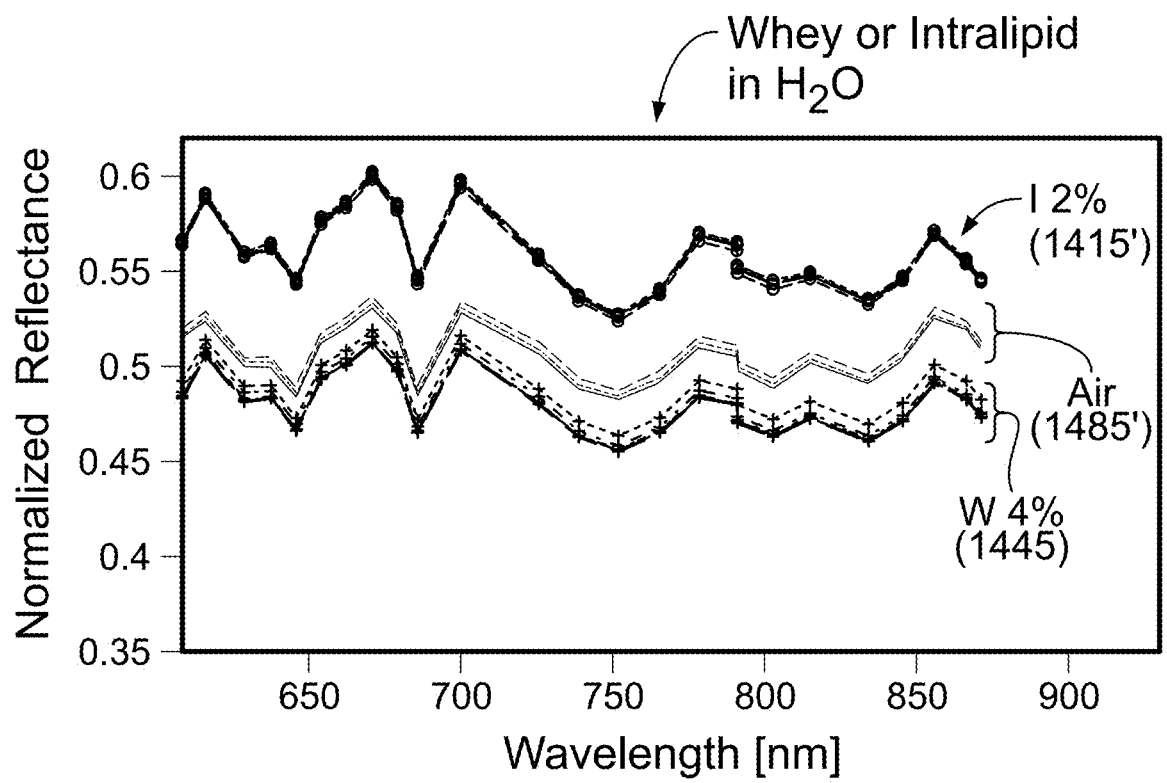
FIG. 14B shows a comparison of spectra.

FIG. 14B shows spectra 1415' of light that interacted with a 2% Intralipid mixture, spectra 1445 of light that interacted with a 4% whey mixture, and spectra 1485' of light that interacted with the air, which is included in the plug 1540 that separates the 2% Intralipid mixture from the 4% whey mixture. Each of the spectra shown in FIG. 14B was obtained using a respective image in a sequence of images acquired by the hyperspectral camera as shown in FIG. 15B. Note that the reflection from the 2% Intralipid mixture was higher on average than that from the 4% whey mixture, which made the intensity of the spectra 1415' larger than the intensity of the spectra 1445. This result suggests that it would be possible to distinguish between a 2% Intralipid mixture and a 4% whey mixture flowing by the hyperspectral camera.

Figure 14C:
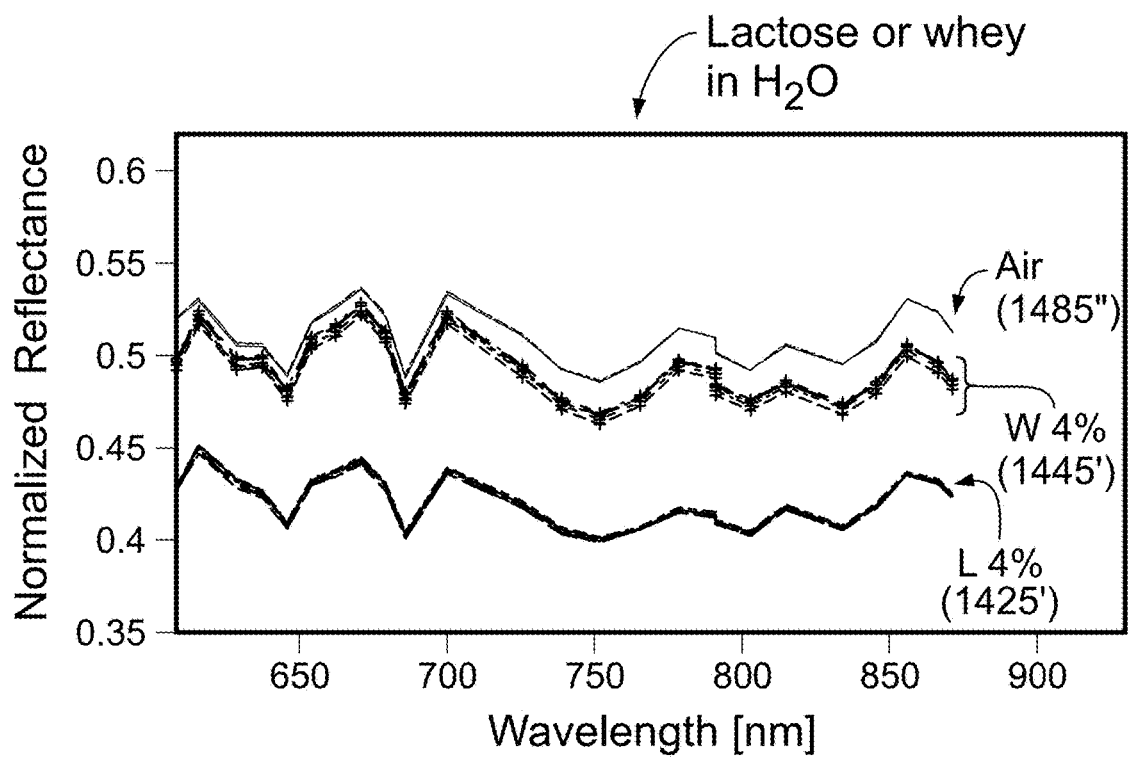
FIG. 14C shows a comparison of spectra.

FIG. 14C shows spectra 1425' of light that interacted with a 4% lactose mixture, spectra 1445' of light that interacted with a 4% whey mixture, and spectra 1485" of light that interacted with the air, which is included in the plug 1540 that separates the 4% lactose mixture from the 4% whey mixture. Each of the spectra shown in FIG. 14C was obtained using a respective image in a sequence of images acquired by the hyperspectral camera as shown in FIG. 15B. Note that the reflection from the 4% lactose mixture was lower on average than that from the 4% whey mixture, which made the intensity of the spectra 1425' lower than the intensity of the spectra 1445'. This result suggests that it would be possible to distinguish between a 4% lactose mixture and a 4% whey mixture flowing by the hyperspectral camera.

Figure 14D:
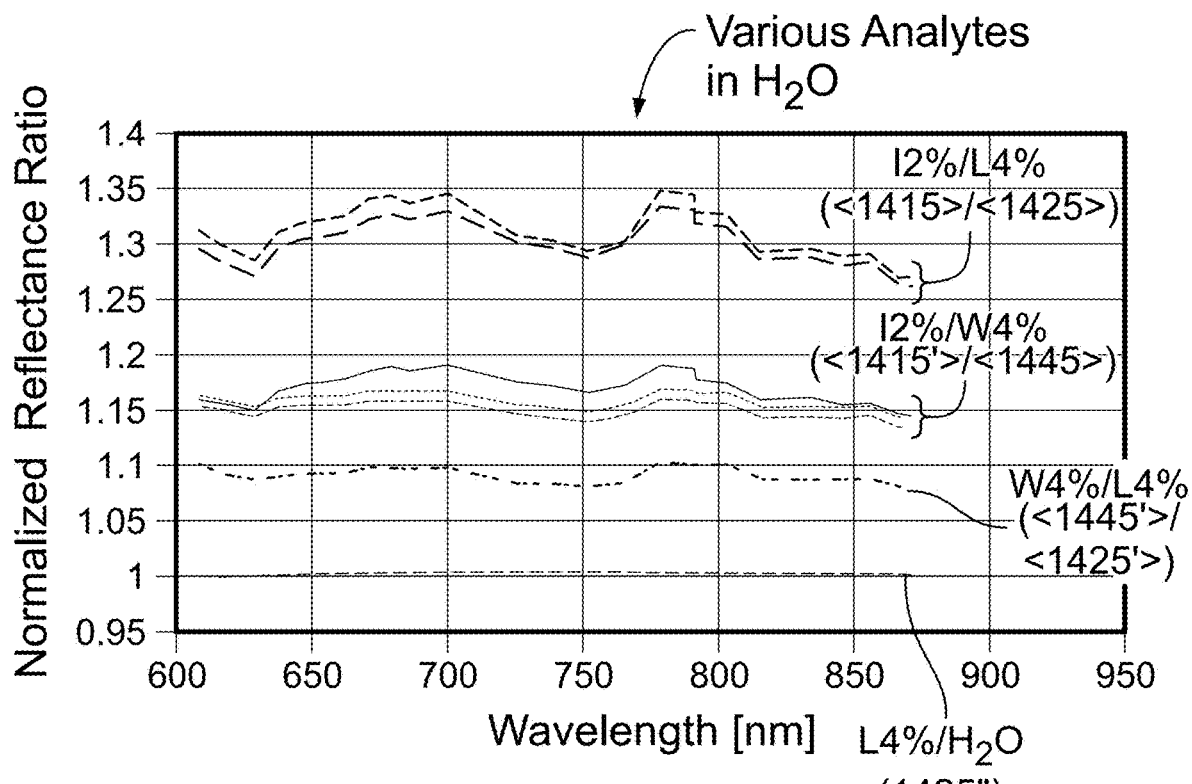
FIG. 14D shows ratios of the spectra shown in FIGS. 14A-14C.

FIG. 14D shows ratios of the spectra shown in FIGS. 14A-14C. For example, with reference to FIG. 14A, the ratio <915>/<925> has been determined in the following manner. First, the spectra 1415 of light that interacted with the 2% Intralipid mixture was averaged together to obtain an average spectrum <915>, and the spectra 1425 of light that interacted with the 4% lactose mixture was averaged together to obtain an average spectrum <925>. Second, the ratio <915>/<925> was obtained by taking the ratio of the average spectra <915>, <925> at each individual wavelength.

As another example, with reference to FIG. 14B, the ratio <915'>/<945> was determined in the following manner. First, the spectra 1415' of light that interacted with the 2% Intralipid mixture was averaged together to obtain an average spectrum <915'>, and the spectra 1445 of light that interacted with the 4% whey mixture was averaged together to obtain an average spectrum <945>. Second, the ratio <915'>/<945> was obtained by taking the ratio of the average spectra <915'>, <945> at each individual wavelength.

As yet another example, with reference to FIG. 14C, the ratio <945'>/<925'> was determined in the following manner. First, the spectra 1445' of light that interacted with the 4% whey mixture as averaged together to obtain an average spectrum <945'>, and the spectra 1425' of light that interacted with the 4% lactose mixture as averaged together to obtain an average spectrum <925'>. Second, the ratio <945'>/<925'> was obtained by taking the ratio of the average spectra <945'>, <925'> at each individual wavelength.

Note that the spectrum ratios <915>/<925>, <915'>/<945> and <945'>/<925'> shown in FIG. 14D have statistically different spectral features relative to each other, which makes it possible to pair-wise distinguish between different macronutrients. In contrast, a ratio 1425" between a spectrum of light that interacted with the 4% lactose mixture and a spectrum of light that interacted with water is completely featureless and has a value close to one. Accordingly, the ratio 1425" indicates that a 4% lactose mixture has substantially the same spectrum as plain water, so such a 4% lactose mixture could not be differentiated from plain water based solely on spectral differences.

It was observed experimentally that sugars (e.g., lactose) had almost no absorbance at UV wavelengths (except, e.g., fructose that has a very small absorption at 260 nm), while proteins (e.g., whey) had strong absorbance peaks at UV wavelengths, fats/oils (e.g., Intralipid) also have strong absorbance at UV wavelengths; however, the spectral profile of the latter was clearly different from the spectral profile of the former. As described in Examples 2-3 and 5, the fats were accurately estimated using other spectral spectroscopy in the VIS-NIR.

The following demonstrates that the contribution of fat can be (i) subtracted off, or (ii) modeled to UV absorbance spectra to estimate protein concentration. Two processes were used to demonstrate this. The first process simply used fat subtraction. The second process used PLS modeling that includes full spectra subtraction and fat subtraction.

Example 6: UV Spectroscopy for Quantifying Proteins

Here, samples included randomized mixtures of lactose, whey and Intralipid. The concentration of each analyte was known. Spectroscopy was performed using a Benchtop spectrometer #4 included in Table 10.

TABLE 10

| Spectrometer | Wavelength range (nm) |
| --- | --- |
| Benchtop #4 | 220-350 |

As indicated in Table 10, the Benchtop spectrometer #4 was configured to acquire spectra in the UV wavelength range. Benchtop spectrometer #4 was a spectrometer fabricated by Ocean Optics and integrated in Thermo-Fisher's Nanodrop product (ND-1000).

These experiments explored whether whey concentration could be estimated when the Intralipid concentration is known. Such an estimate was based on UV absorbance spectra of solutions of whey in water, and UV absorbance spectra of Intralipid in water.

Figure 16A:
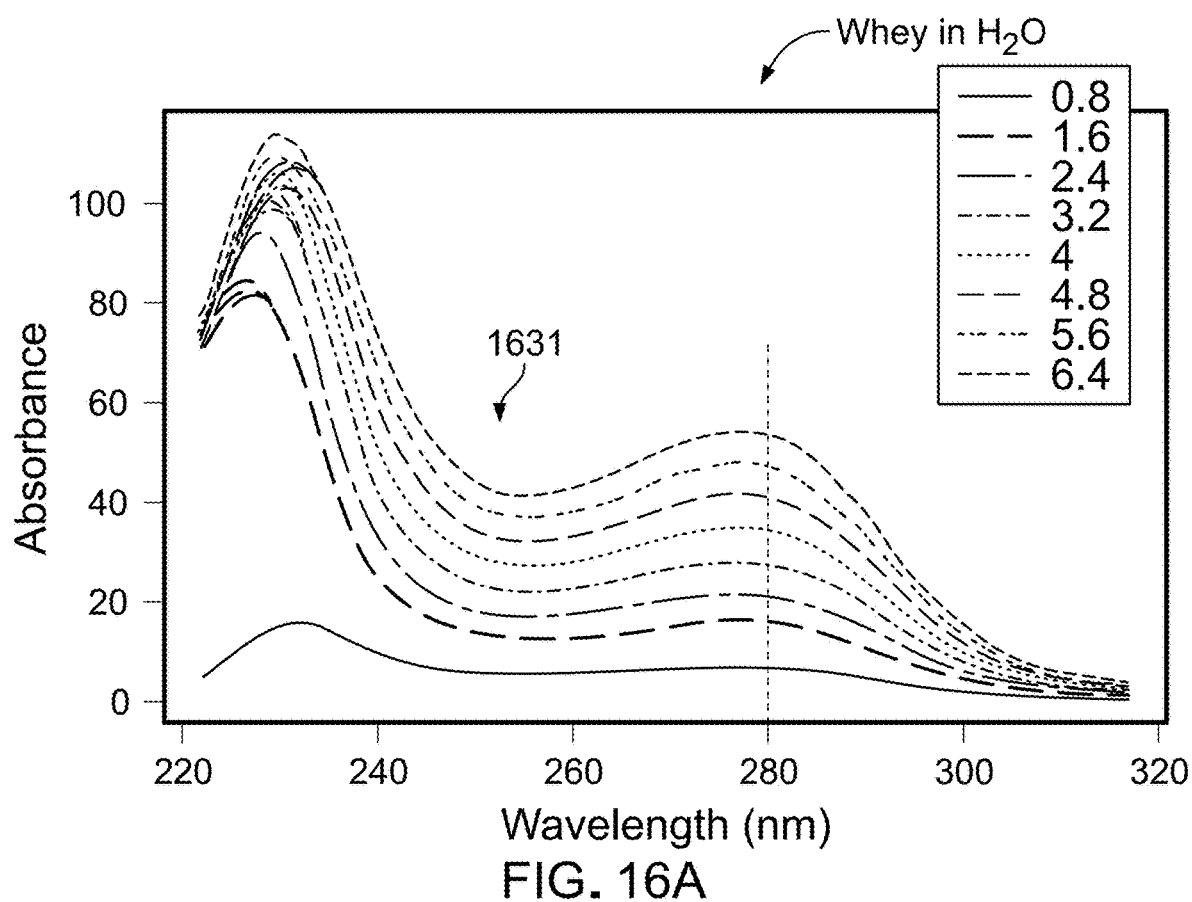
FIG. 16A shows spectra.
Figure 16B:
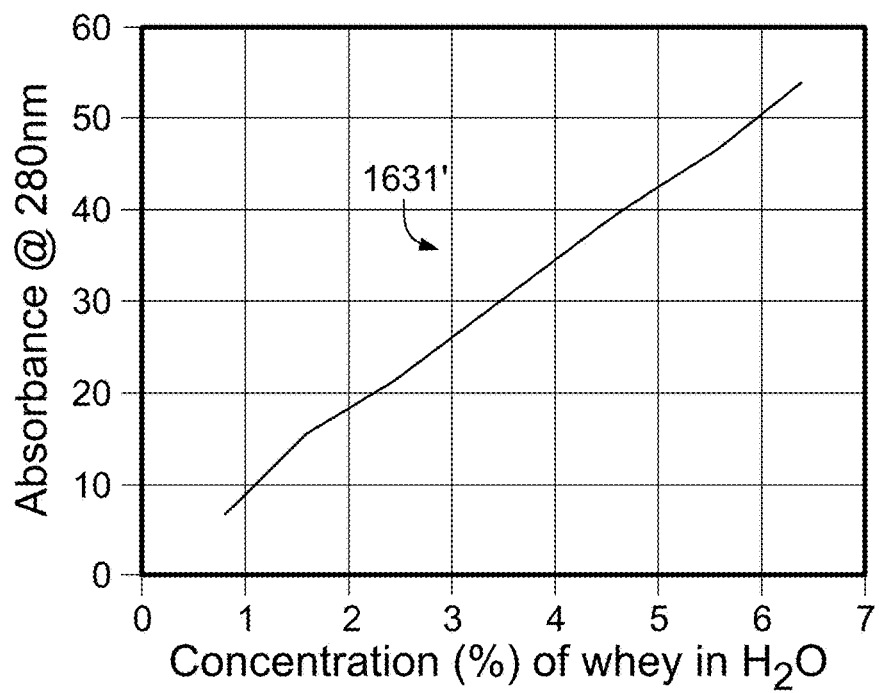
FIG. 16B shows absorbance values.

FIG. 16A shows a set 1631 of spectra corresponding to whey solutions in water, in which the concentration represents grams/100 ml and is expressed in %. The spectra of the set 1631 are acquired using the Benchtop spectrometer #4. FIG. 16B shows a set 1631' of values of the whey absorbance spectra at 280 nm. The set 1631' will also be referred to as a mapping of whey concentration to values of whey absorbance at 280 nm. The result shown in FIG. 16B suggests that the whey had an absorbance at 280 nm that depends linearly on the concentration of whey in water.

Figure 17A:
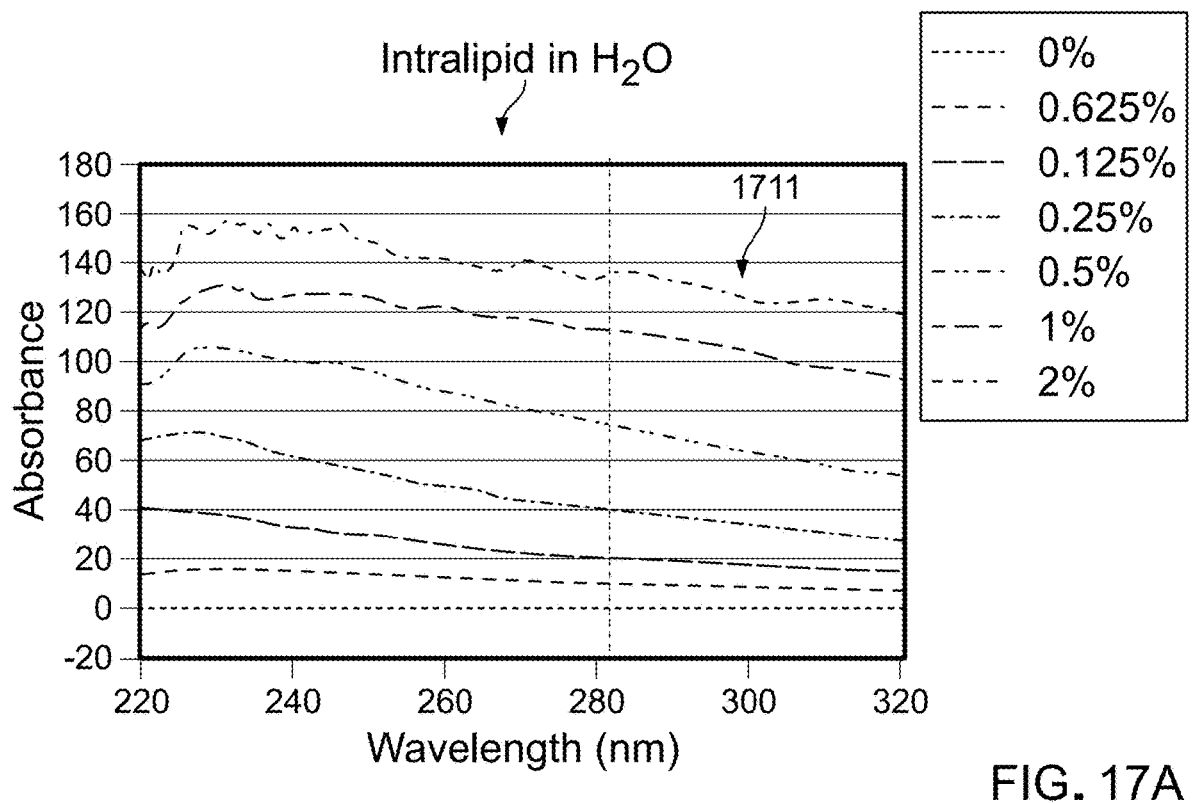
FIG. 17A shows spectra.
Figure 17B:
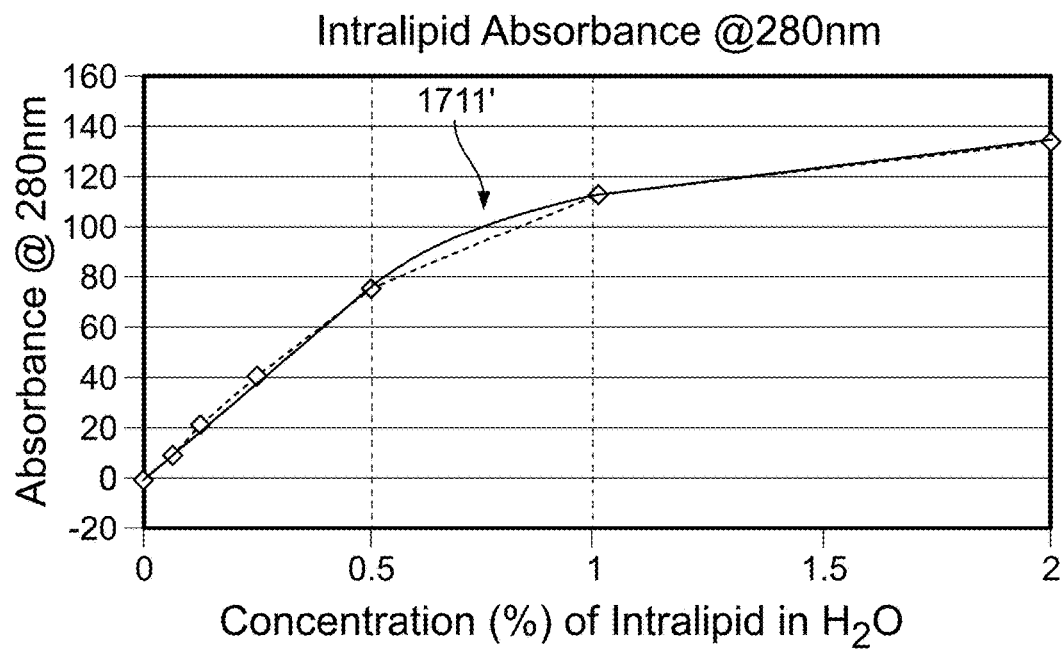
FIG. 17B shows absorbance values.

FIG. 17A shows a set 1711 of spectra corresponding to Intralipid solutions in water, in which the concentration is expressed in %. The spectra of the set 1711 were acquired using the Benchtop spectrometer #4. The spectra indicate that the Intralipid is highly absorbing in this spectral range, at least partially due to Rayleigh scatter. FIG. 17B shows a set 1711' of values of the Intralipid absorbance spectra at 280 nm. The set 1711' will also be referred to as a mapping of Intralipid concentration to values of Intralipid absorbance at 280 nm. The result shown in FIG. 17B suggests that the Intralipid has an absorbance at 280 nm that depends non-linearly on the concentration of Intralipid in water. This may have been because the acquisition of the spectra became non-linear (and unreliable) on the Benchtop spectrometer #4 above 0.5%, for samples having a 1-mm transmission path length.

Figure 18A:
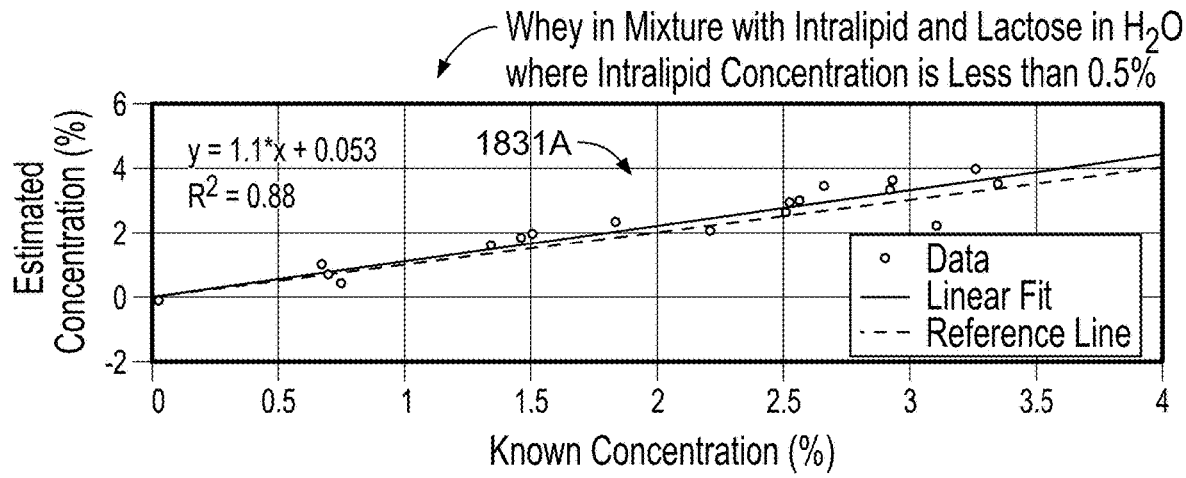
FIG. 18A-18C show results of modelling.

As part of the above noted first process, the following analysis, for which the results are presented in FIGS. 18A-180, is performed to predict concentration of whey based solely on empirical absorbance at 280 nm, as shown in FIGS. 16A-16B and 17A-17B. As part of the analysis, interpolation was applied to the set 1631' of values of the whey absorbance spectra 1631 at 280 nm associated with the solutions of whey in water, and to the set 1711' of values of the Intralipid absorbance spectra 1711 at 280 nm associated with the solutions of Intralipid in water. Here, linear interpolation was applied to the whey set 1631' for the entire whey concentration range, and to the Intralipid set 1711' for Intralipid concentrations up to 0.5%; quadratic interpolation was applied for Intralipid concentrations between 0.5% and 1%; and, once again, linear interpolation was used for Intralipid concentrations higher than 1%. Note that for the latter Intralipid concentrations, quadratic fitting would overestimate Intralipid's absorbance. Moreover, to determine the unknown whey concentration of a mixture, the Intralipid concentration was assumed known from the experimental results 712, 714, 716, 718, or 1115.

The first process for predicting concentration of whey in a mixture with Intralipid and lactose in water was performed in the following manner. As a first stage, a couple of spectra were collected: a first spectrum of light that interacted with the mixture, such that the first spectrum has a UV spectral range (e.g., 220-320 nm), and a second spectrum of light that interacted with the mixture, such that the second spectrum has a vis, NIR, and/or midIR spectral range (e.g., one of the spectral ranges from Table 2). As noted above, a value of the first spectrum at 280 nm was the value of interest for performing the first process. As such, in some implementations, instead of acquiring the entire first spectrum, the absorbance at 280 nm was obtained by using a simple unfiltered silicon detector and a light source (e.g., a UV LED) that emits UV light near 280 nm. Such a detector could be integrated into one of the spectrometers from Table 2, or could be implemented as a separate detector. In some implementations, the UV LED light source is implemented as a separate light source from the broadband NIR LED (e.g., fabricated by OSRAM) used to acquire the second spectrum.

As a second stage, a processor applied a model for predicting the whey concentration in the mixture, such that the modeling includes (i) determining the concentration of Intralipid based on the second spectrum using the experimental results 712, 714, 716, 718, or 1115; (ii) determining, from the Intralipid set 1711', an absorbance @280 nm for the determined concentration of Intralipid; (iii) determining a difference between (a) the absorbance @280 nm of the first spectrum and (b) the Intralipid absorbance @280 nm determined at (ii); and (iv) attributing the absorbance difference determined at (iii) to the whey absorbance @280 nm, and determining, from the whey set 1631', the unknown whey concentration corresponding to the whey absorbance @280 nm determined at (iv).

FIG. 18A shows a result 1831A of the foregoing model for predicting the whey concentration in the mixture, for Intralipid concentrations that are no larger than 0.5%. The result 1831A represents a correlation between the estimated and known concentrations of whey, where the spectra used to determine this correlation correspond to mixtures for which Intralipid concentrations that are no larger than 0.5%. Here, the slope of a linear fit to the result 1831A is larger than the slope of 1 of "a perfect linear fit" by about 10%, and an $R^2$ of the linear fit is $R^2=0.88$.

Figure 18B:
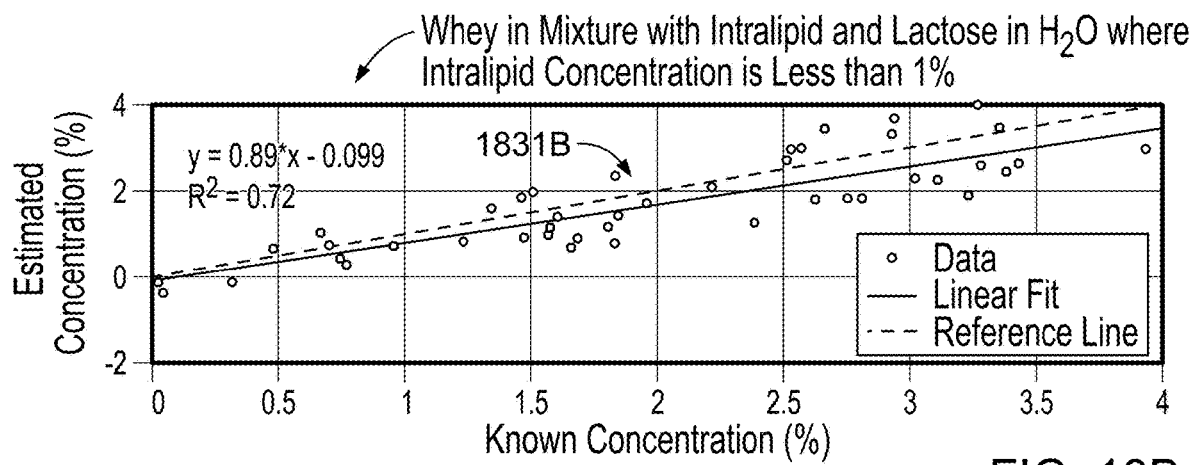

FIG. 18B shows a result 1831B of the foregoing model for predicting the whey concentration in the mixture, for Intralipid concentrations that are no larger than 1%. The result 1831B represents a correlation between the estimated and known concentrations of whey, where the spectra were used to determine this correlation correspond to mixtures for which Intralipid concentrations that are no larger than 1%. Here, the slope of a linear fit to the result 1831B is smaller than the slope of 1 of "a perfect linear fit" by about 11%, and an $R^2$ of the linear fit is $R^2=0.72$. The smaller value of $R^2$ indicates that the result 1831B has a wider distribution than the distribution of result 1831A.

Figure 18C:
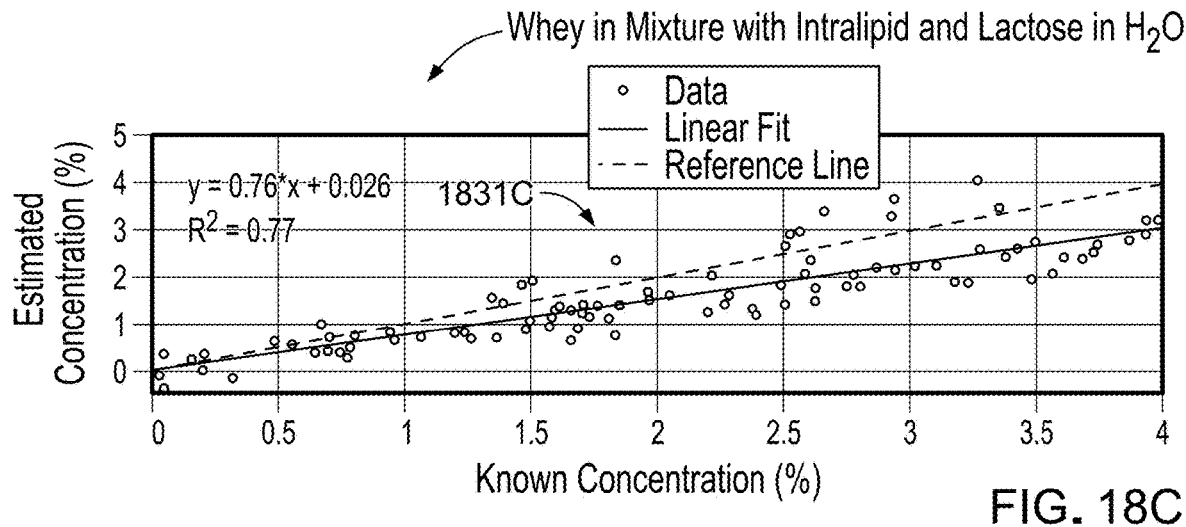

FIG. 18C shows a result 1831C of the foregoing model for predicting the whey concentration in the mixture, for all used concentrations of Intralipid. The result 1831C represents a correlation between the estimated and known concentrations of whey, where all the spectra acquired for the mixture, regardless of Intralipid concentration. Here, the slope of a linear fit to the result 1831C is smaller than the slope of 1 of "a perfect linear fit" by about 24%, and an $R^2$ of the linear fit is $R^2=0.77$. This value of $R^2$ indicates that the result 1831C has a distribution than is larger than the distribution of the result 1831A but slightly narrower than the distribution of the result 1831B. The result 1831C indicates that the predicted whey concentration tends to be smaller than the actual whey concentration. This suggests that the interpolated Intralipid absorbance is higher than actual Intralipid absorbance. Note that additional calibration could correct the inaccuracy of the result 1831C.

In view of the above, the concentration of whey in a mixture of whey, Intralipid and lactose can be determined based (i) on a value at 280 nm of a UV spectrum corresponding to the mixture and (ii) an estimation of the Intralipid concentration obtained from a vis, NIR, and/or midIR spectrum corresponding to the mixture in conjunction with the experimental results 712, 714, 716, 718, or 1115, where the UV spectrum has been separately acquired from the vis, NIR, and/or midIR spectrum.

Referring now to the second process for estimating whey concentration in a mixture of whey, Intralipid and lactose, PLS modeling was applied to the set 1631 of spectra corresponding to whey solutions in water and the set 1711 of spectra corresponding to Intralipid solutions in water. The second process was used to estimate whey concentration in mixtures having Intralipid concentrations that are at most 1%. Mixtures with larger concentrations of Intralipid was removed because such samples may produce saturated spectra. Moreover, the PLS modeling was applied over two wavelength sub-ranges 270-290 nm and 260-300 nm.

As part of the second process, the "known" Intralipid absorbance was subtracted from the measured spectra. This first step included a first sub-step of interpolating the pre-calibrated Intralipid absorbance by quadratic interpolation, one interpolation for each wavelength, and a second sub-step of subtracting the Intralipid absorbance from each measured spectra based on its Intralipid concentration.

The second process for predicting concentration of whey in a mixture with Intralipid and lactose in water was performed in the following manner. As a first stage, a couple of spectra were collected in the following manner: a first spectrum of light that interacted with the mixture, such that the first spectrum has been acquired with a first spectrometer over a UV spectral range (e.g., 220-320 nm), and a second spectrum of light that interacted with the mixture, such that the second spectrum has been acquired with one of the spectrometers from Table 2 over a corresponding vis, NIR, and/or midIR spectral range. The first spectrometer was implemented with a light source (e.g., a UV LED) that emits light near 280 nm, rather than a broadband light source with an emission spectrum from 260-300 nm. Such a UV spectrometer could be integrated into one of the spectrometers from Table 2, or could be implemented as a separate spectrometer. In some implementations, the UV LED light source was implemented as a separate light source from the broadband NIR LED (e.g., fabricated by OSRAM) used to acquire the second spectrum.

Second, a processor applied a model for predicting the whey concentration in the mixture, such that the modeling includes (i) determining the concentration of Intralipid based on the second spectrum using the experimental results 712, 714, 716, 718, or 1115; (ii) determining, over a subrange of the first spectrum's wavelength range, a difference spectrum as the difference between the first spectrum and the spectrum from among the set 1711 of spectra that corresponds to the Intralipid concentration determined at (i); and (iii) identify a spectrum from among the set 1631 of spectra that best matches the difference spectrum determined at (ii); and (iv) attribute to the unknown whey concentration the value of the whey concentration corresponding to the spectrum from the set 1631 identified at (iii).

Note that when the first spectrum's wavelength range is 220-320 nm, the subrange, over which the difference spectrum is determined at (ii), can be a narrow subrange of 270-290 nm, or a broad subrange of 260-300 nm.

Further note that when the set 1631 of spectra is sparse, the steps (iii) and (iv) can be replaced by a PLS modeling step for determining the unknown whey concentration corresponding to the difference spectrum based on the set 1631 of spectra. The PLS modeling step included calculation of leave-one-out-cross-validation RMSE and RMSE/Mean, and optimization of model components. For the available experimental samples, it was found that the PLS modeling step produced the most accurate results when 3 PLS components were used.

Figure 19A:
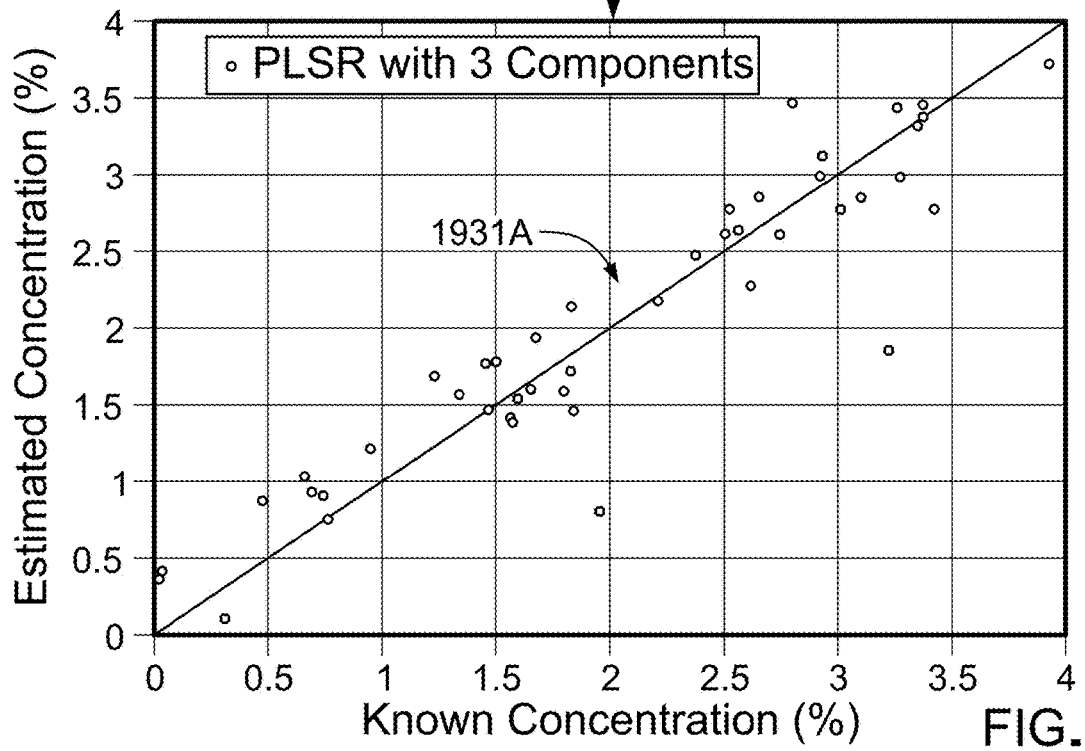
FIGS. 19A-19B show results of modelling.
Figure 19B:
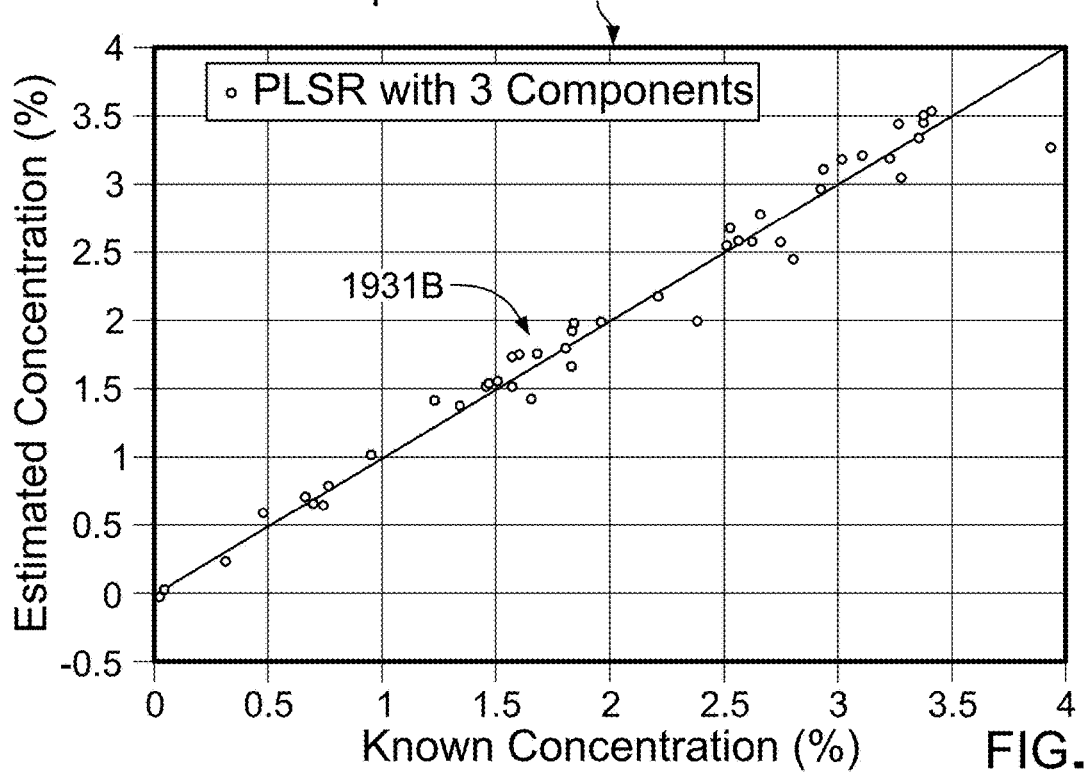

FIGS. 19A-19B show results of respective PLS models, each of which used 3 PLS components, for predicting concentration of whey in the mixtures having Intralipid concentrations no larger than 1% for respective subranges. Here, the result 1931A represents a correlation between the estimated and known whey concentrations, where the estimates were obtained based on 3-PLS component model over a narrow subrange of 270-290 nm. The result 1931B represents a correlation between the estimated and known whey concentrations, where the estimates were obtained based on 3-component PLSR modelling over a broad subrange of 260-300 nm. Respective values of model performance metrics for the models having results summarized in FIGS. 19A-19B are listed in Table 11.

TABLE 11

Whey concentration using PLS modeling with 3 PLS components

| Subrange (nm) | Result | RMSECV (%) | RMSECV/Mean (%) |
|---|---|---|---|
| 270-290 | 1931A | 0.5 | 22.2 |
| 260-300 | 1931B | 0.2 | 10.7 |

The results summarized in Table 11 indicate that the PLS modeling used to identify the unknown whey concentration based on the set 1631 of spectra produces results that have narrower distributions when using broader subranges.

In view of the above, the concentration of whey in a mixture of whey, Intralipid and lactose can be determined based (i) on a UV spectrum corresponding to the mixture and (ii) an estimation of the Intralipid concentration obtained from a vis, NIR, and/or midIR spectrum corresponding to the mixture in conjunction with the experimental results 712, 714, 716, 718, or 1115, where the UV spectrum has been separately acquired from the vis, NIR, and/or midIR spectrum.

Referring now to both the first and second processes described above in Example 6, the estimated whey concentration can be combined with the whey concentration estimated based on results 838 described in Example 2 or results 1135 described in Example 3 to increase estimation accuracy. Alternatively or additionally, the whey concentration estimated as described above in Example 6 can be subtracted from, or modeled along with, the concentration of a combination of whey and lactose, that has been obtained based on results 842, 848 described above in Example 2, to estimate the concentration of lactose in the mixture.

The techniques described above can be used, e.g., for diagnostic purposes, for detecting blood or bile in the GI tract when a meal is present in the GI tract, as described in the following Examples.

Example 7: Spectroscopy for Detecting and Quantifying Blood in Meals

The goal of the experiments described in Example 7 was to demonstrate the ability to detect, and determine the concentration of, blood in a liquid meal formed from Ensure diluted in water. The results of this experiment can provide evidence of the ability to detect blood in the GI tract (e.g., due to bleeds in the GI tract) in the presence of one or more macronutrients. These experiments were performed using spectroscopy of Ensure solutions over different wavelength ranges in reflection mode.

A volumetric flow rate through the small intestine of about 14 mL/min was assumed based on the information listed in Table 12.

TABLE 12

| Small intestine | | |
|---|---|---|
| Parameter | Value | Unit |
| Diameter | 2.5 | cm |
| Length | 670 | cm |
| Cross-sectional area | 4.9 | cm$^2$ |
| Total volume | 3289 | mL |
| Transit time | 240 | min |
| Volumetric flow rate | 13.7 | mL/min |

Note that bleeds with small volumetric flow rates in the range of 0.1-0.5 mL/min can be detected clinically using Tc$^{99m}$-labeled red blood cell detection techniques. In fact, angiography can only detect active bleeds that have a volumetric flow rate larger than 0.5 mL/min. As such, using the above-noted volumetric flow rate through the small intestine of about 14 mL/min, a bleed of 0.1 mL/min (which is comparable to the capability of Tc$^{99}$m-labeled red blood cell detection techniques) corresponds to about 0.7% blood concentration in a liquid meal background in the small intestine.

As such, samples were prepared in the following manner. 60 samples were formed using Ensure solutions with randomized Ensure concentrations in the range of 6-77%. Each sample was held in a respective well 1510 of a well plate 1500. A number of 12 of the Ensure solution samples included no blood. Porcine blood was used to form the remaining samples with blood concentrations in the range of 0.1-3.5%. Note that some of the samples having concentrations of Ensure less than 10% was found to cause reflectance off the bottom of the wells holding such solutions.

Spectra were acquired using the Benchtop spectrometers #s 2-3 included in Table 2 and the Benchtop spectrometer #5 included in Table 13.

TABLE 13

| Spectrometer | Wavelength range (nm) |
|---|---|
| Benchtop #5 | 400-1000 |

Benchtop spectrometer #5 was a second version of USB2000+ fabricated by Ocean Optics. Note that unlike the SCIO spectrometer, which can be integrated in an ingestible device as described herein, or the Benchtop spectrometers #2 and #3, the Benchtop spectrometer #5 had a wavelength range that extended to the lower end of the visible spectral range.

The optical absorbance of blood was tied strongly to the optical absorbance of hemoglobin in the visible spectral range. For example, detection of hemoglobin was based on hemoglobin-specific spectral features below 600 nm. Spectral features in the wavelength range of 600-1000 nm was typically used to differentiate between oxygenated hemoglobin and deoxygenated hemoglobin, for instance. As such, it was determined as part of the experiments of Example 7 that the magnitude of some spectral features below 600 nm depends on the hemoglobin concentration, in this case on the concentration of blood in the various Ensure solutions.

Figure 20:
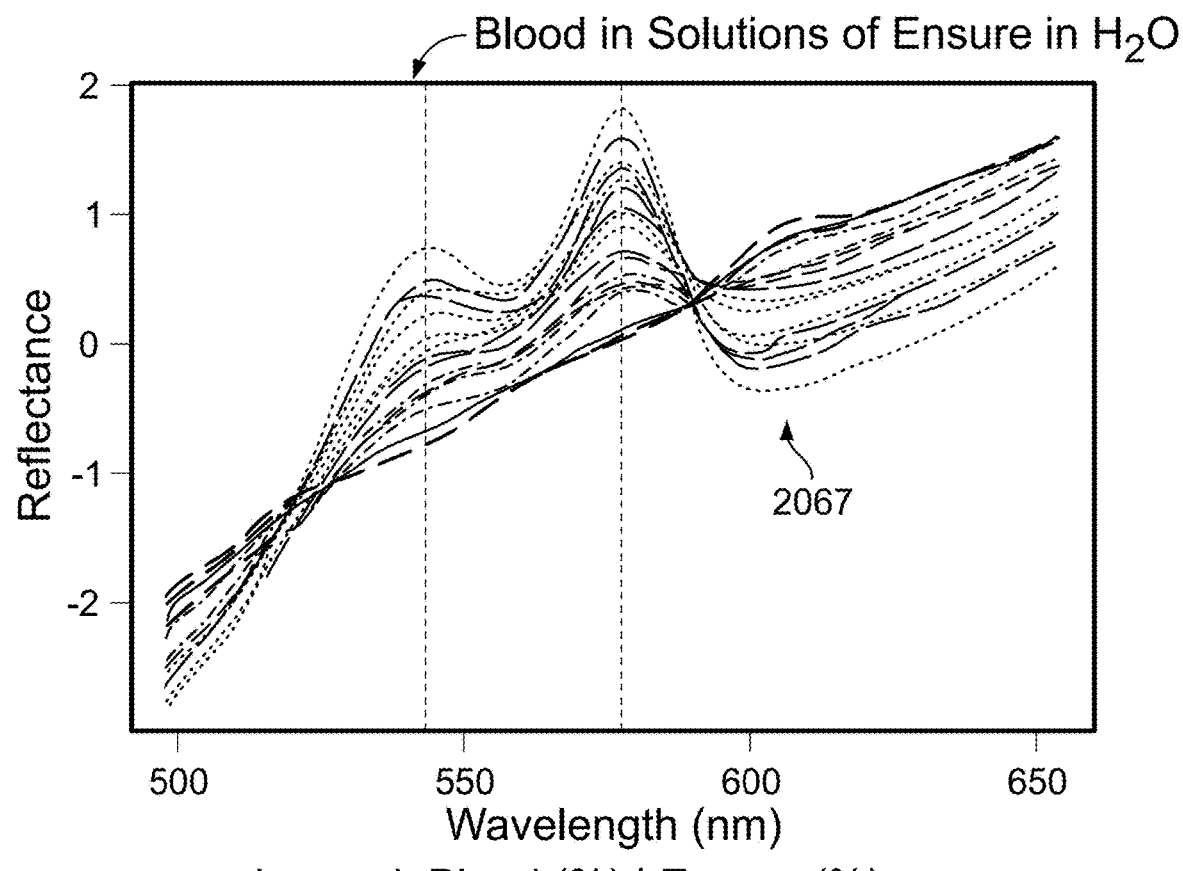
FIG. 20 shows spectra.
Figure 21:
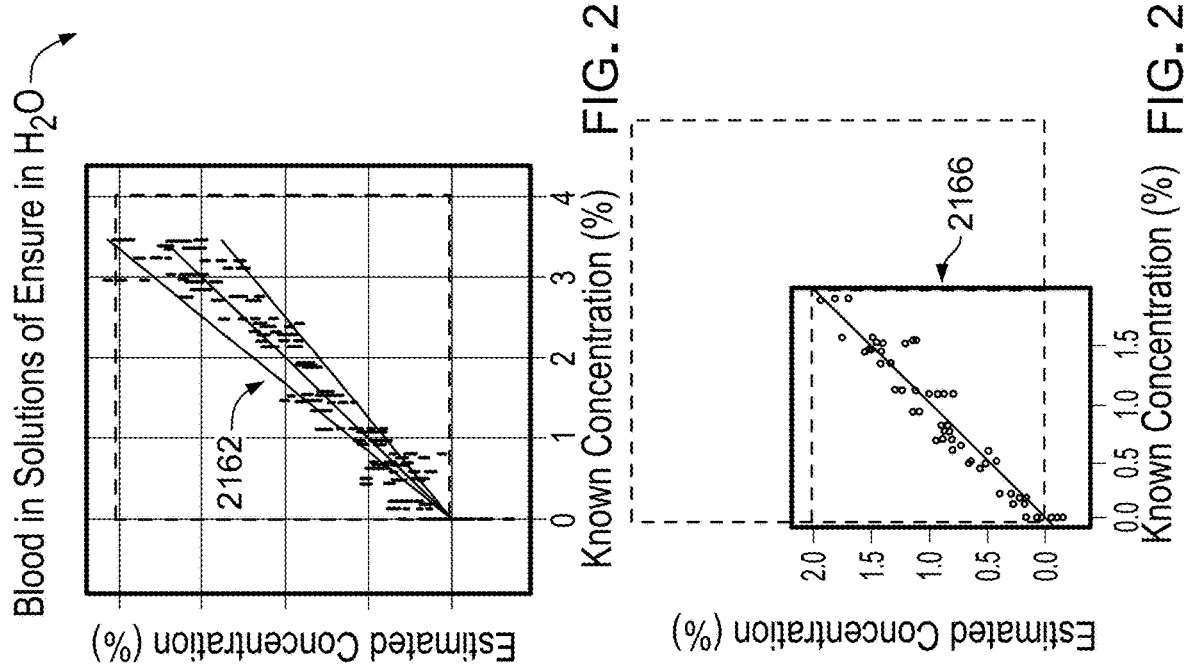
FIGS. 21A-21D show results of modelling spectrometers.

FIG. 20 shows spectra 2067 of light that reflected off samples including Ensure solutions with or without traces of blood, the spectra was acquired with the Benchtop spectrometer #5. Here, the spectra 2067 were displayed over the wavelength range 500-650 nm, which highlights the blood concentration-dependent peaks at 545 nm and 580 nm. Three spectra were acquired for each sample. The spectra were further preprocessed using a moving average filter to reduce acquisition noise and a standard normal variate transform to normalize the spectra and correct for shifting baselines.

A subset of the spectra 2067 were used as inputs for supervised machine learning modeling, e.g., based on partial least squares (PLS), to predict concentrations of blood in the Ensure solutions to which the spectra correspond. In this manner, once a spectrum corresponding to an Ensure solution is produced, an unknown blood concentration of the Ensure solution can be determined by (i) identifying one from among the spectra 2067 corresponding to Ensure solutions with known blood concentrations that best matches the produced spectrum, and (ii) assigning to the unknown blood concentration a value of the blood concentration in the Ensure solution to which the identified spectrum corresponds.

FIGS. 21A-21D show results 2162, 2167, 2166, 2168 of a leave-one-out cross-validation of a model for predicting blood concentration in Ensure solutions. Such validation results were used to determine a threshold concentration for distinguishing between Ensure solutions with blood and without blood. Here, the result 2162 represents a correlation between the estimated and known blood concentrations for a concentration range from 0-3.5%, where spectra used to determine this correlation were acquired with the SCIO spectrometer, implemented as noted in Table 2. Further, the result 2167 represents a correlation between the estimated and known blood concentrations for the concentration range from 0-3.5%, where this correlation was determined based on the spectra 2067 acquired with the Benchtop spectrometer #5, as listed in Table 13. Results 2162 and 2167 indicate that better discrimination between the Ensure solutions with blood and without blood can be achieved if the spectra used for modeling correspond to Ensure solutions having low blood concentrations, e.g., below 2%. Furthermore, the results 2166, 2168 represent correlations between the estimated and known blood concentrations for a concentration range limited to 0-2%, where the spectra used to determine these correlations were acquired with the Benchtop spectrometers #2 and #3, respectively, as listed in Table 2.

Moreover, the results 2162, 2167, 2166, 2168 indicate that spectra, like the spectra 2067, that extend below 600 nm represent better inputs to models for predicting unknown blood concentrations in Ensure solutions compared to spectra that do not extend below 600 nm, even though the latter spectra may extend to much longer wavelengths that the former spectra. By using better inputs, the prediction models can more accurately predict whether blood is present in an Ensure solution, and if so, predict the blood's concentration.

In summary, it was shown in Example 7 that blood can be detected in a random background of a liquid meal (e.g., Ensure) using spectra acquired over a wavelength range 500-650 nm. The spectrometers that were used acquired the spectra were operated in reflectance mode, on a benchtop. The samples included blood in a random background of Ensure diluted in water, where the blood concentration range was 0% to 3.5%, and the Ensure concentration range was 6% to 77%. Note that a number of samples included no blood. Leave-one-out cross-validation of PLS modeling suggests that the modeling was able to accurately predict whether an Ensure solution had blood or did not have blood.

Example 8: Spectroscopy for Detecting and Quantifying Bile in Meals

The goal of the experiments described in Example 8 was to demonstrate the ability to detect, and determine the concentration of, bile in a liquid meal formed from Ensure diluted in water. These experiments were performed using spectroscopy of Ensure solutions over different wavelength ranges in reflection mode.

Here, samples were prepared in the following manner. There are 60 samples formed using Ensure solutions with randomized Ensure concentrations in the range of 15-78%, each of the samples was held in a respective well 1510 of a well plate 1500. A number of 12 of the Ensure solution samples include no bile. Bile was used to form the remaining samples with bile concentrations in the range of 0.4-9.9%.

Figure 22:
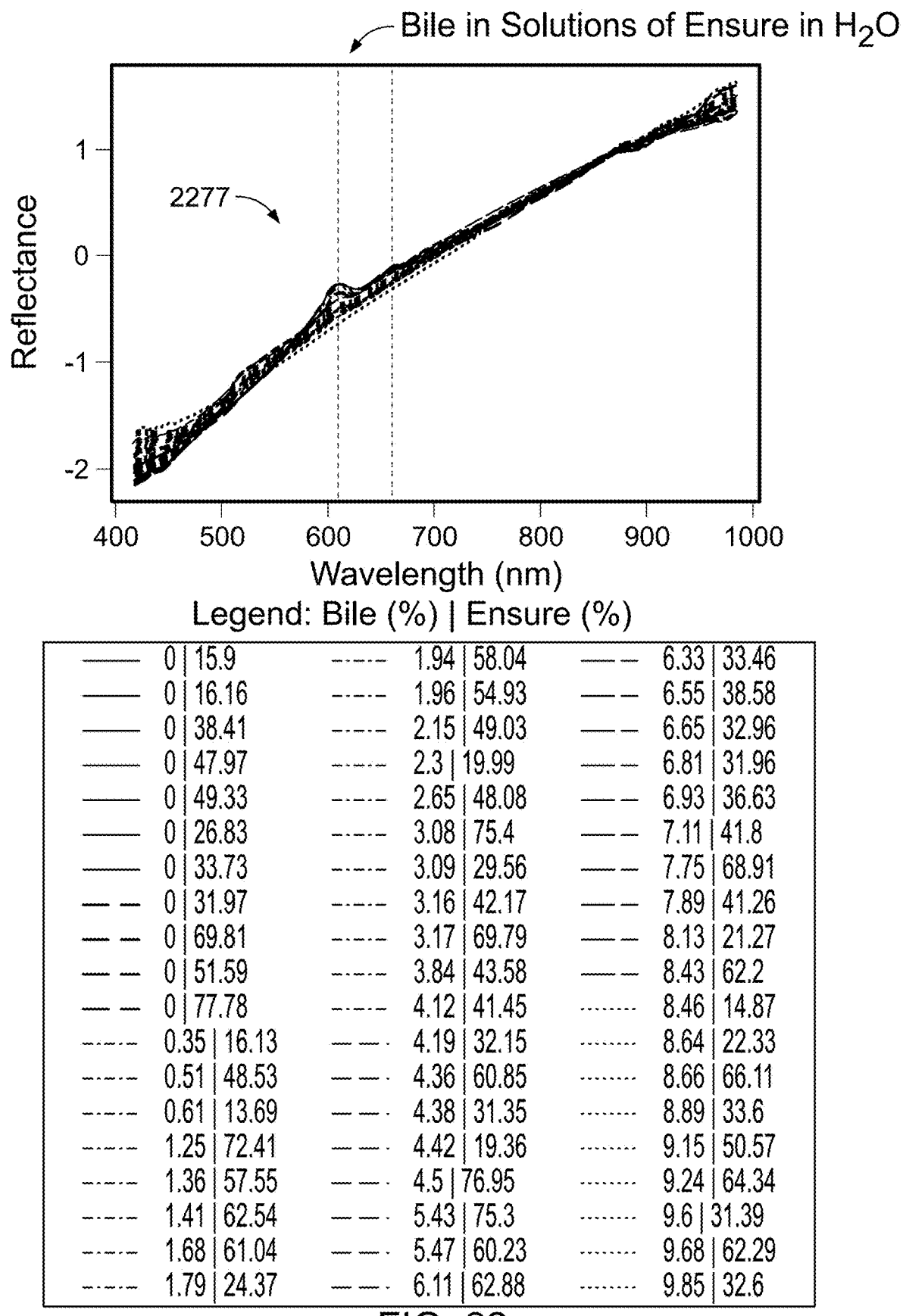
FIG. 22 shows spectra.

Spectra were acquired using the Benchtop spectrometers #2 and #3 included in Table 2 and the Benchtop spectrometer #5 included in Table 13. FIG. 22 shows spectra 2277 of light that reflected off samples including Ensure solutions with or without traces of bile, the spectra were acquired with the Benchtop spectrometer #5. Three spectra were acquired for each sample. The spectra were further preprocessed using a moving average filter to reduce acquisition noise and a standard normal variate transform to normalize the spectra and correct for shifting baselines. Note the presence of at least two bile concentration-dependent spectral features at 610 nm and 670 nm.

A subset of the spectra 2277 were used as inputs for supervised machine learning modeling, e.g., based on partial least squares (PLS), to predict concentrations of bile in the Ensure solutions to which the spectra correspond. In this manner, once a spectrum corresponding to an Ensure solution is produced, an unknown bile concentration of the Ensure solution can be determined by (i) identifying one from among the spectra 2277 corresponding to Ensure solutions with known bile concentrations that best matches the produced spectrum, and (ii) assigning to the unknown bile concentration a value of the bile concentration in the Ensure solution to which the identified spectrum corresponds.

Figure 23B:
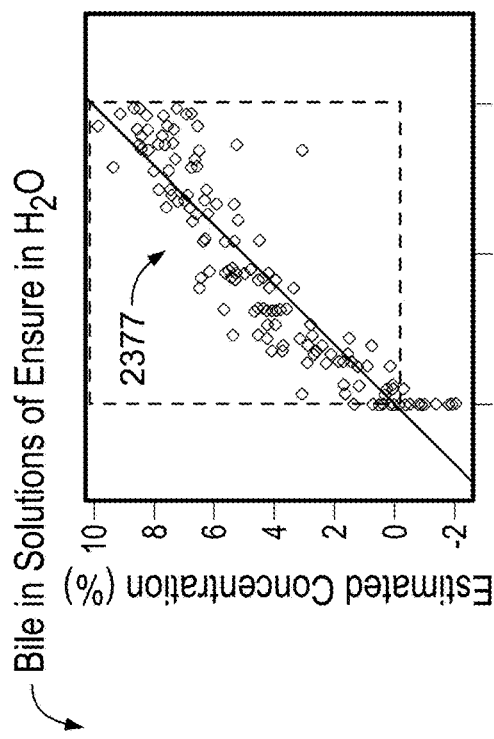
FIGS. 23A-23D show results of modelling.
Figure 23A:
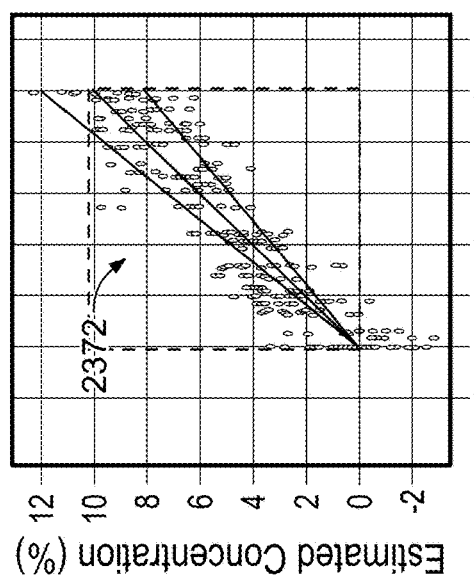
Figure 23D:
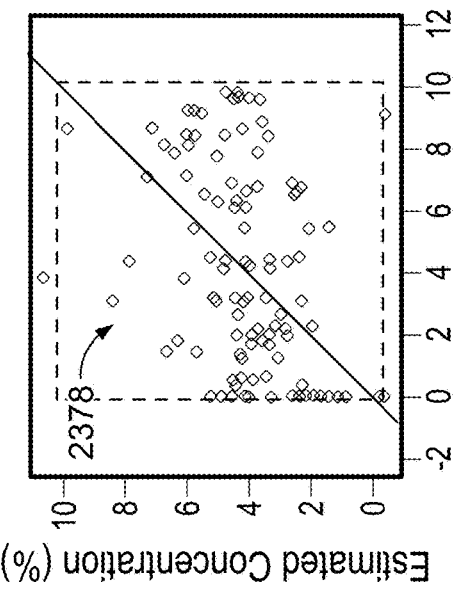
Figure 23C:
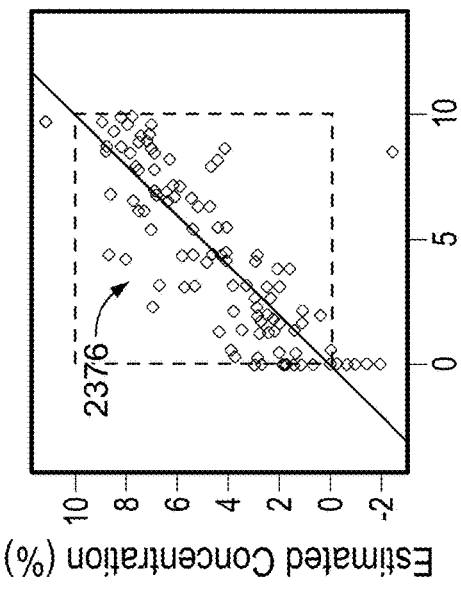

FIGS. 23A-23D show results 2372, 2377, 2376, 2378 of a leave-one-out cross-validation of a model for predicting bile concentration in Ensure solutions. Such validation results were used to determine a threshold concentration for distinguishing between Ensure solutions with bile and without bile. Here, the result 2372 represents a correlation between the estimated and known bile concentrations, where spectra used to determine this correlation were acquired with the miniature spectrometer 20, implemented as noted in Table 2. Further, the result 2377 represents a correlation between the estimated and known bile concentrations, where this correlation has been determined based on the spectra 2277 acquired with the Benchtop spectrometer #5, as listed in Table 13. Values of model performance metrics for the model having results summarized in FIG. 23B are listed in Table 14.

TABLE 14

| Spectra 2277 acquired with Benchtop spectrometer #5 | | |
| --- | --- | --- |
| Result | RMSECV (%) | RMSECV/Mean (%) |
| 2377 | 1.2 | 29 |

Furthermore, the results 2376, 2378 represent correlations between the estimated and known bile concentrations, where the spectra used to determine these correlations were acquired with the Benchtop spectrometers #2 and #3, respectively, as listed in Table 2.

Moreover, the results 2372, 2377, 2376, 2378 indicate that spectra, like the spectra 2277, that extend below 700 nm represent better inputs to models for predicting unknown bile concentrations in Ensure solutions compared to spectra that do not extend below 700 nm, even though the latter spectra may extend to much longer wavelengths that the former spectra. By using better inputs, the prediction models can more accurately predict whether bile is present in an Ensure solution, and if so, predict the bile's concentration.

In summary, it was shown in Example 8 that bile can be detected in a random background of a liquid meal (e.g., Ensure) using spectra acquired over a wavelength range 400-1000 nm. The spectrometers used acquire the spectra were operated in reflectance mode, on a benchtop. The samples included bile in a random background of Ensure diluted in water, where the bile concentration range was 0% to about 10%, and the Ensure concentration range was 6% to 77%. Note that a number of samples included no bile. Leave-one-out cross-validation techniques of PLS modeling suggests that the modeling was able to accurately predict whether an Ensure solution had bile or did not have bile.

Example 9: Spectroscopy Directed to Markers

Fluorescent molecules, e.g., food dyes, were used to determine the relative or absolute level of another analyte, as described in this example. Some food dyes are approved by the FDA for ingestion, because, typically, they have low intestinal absorption. Moreover, such food dyes have distinct spectral absorbance peaks, making them ideal reference standards. Note that to limit any possible intestinal absorption, the dyes can be bound to PolyEthylene Glycol (PEG).

Figure 24:
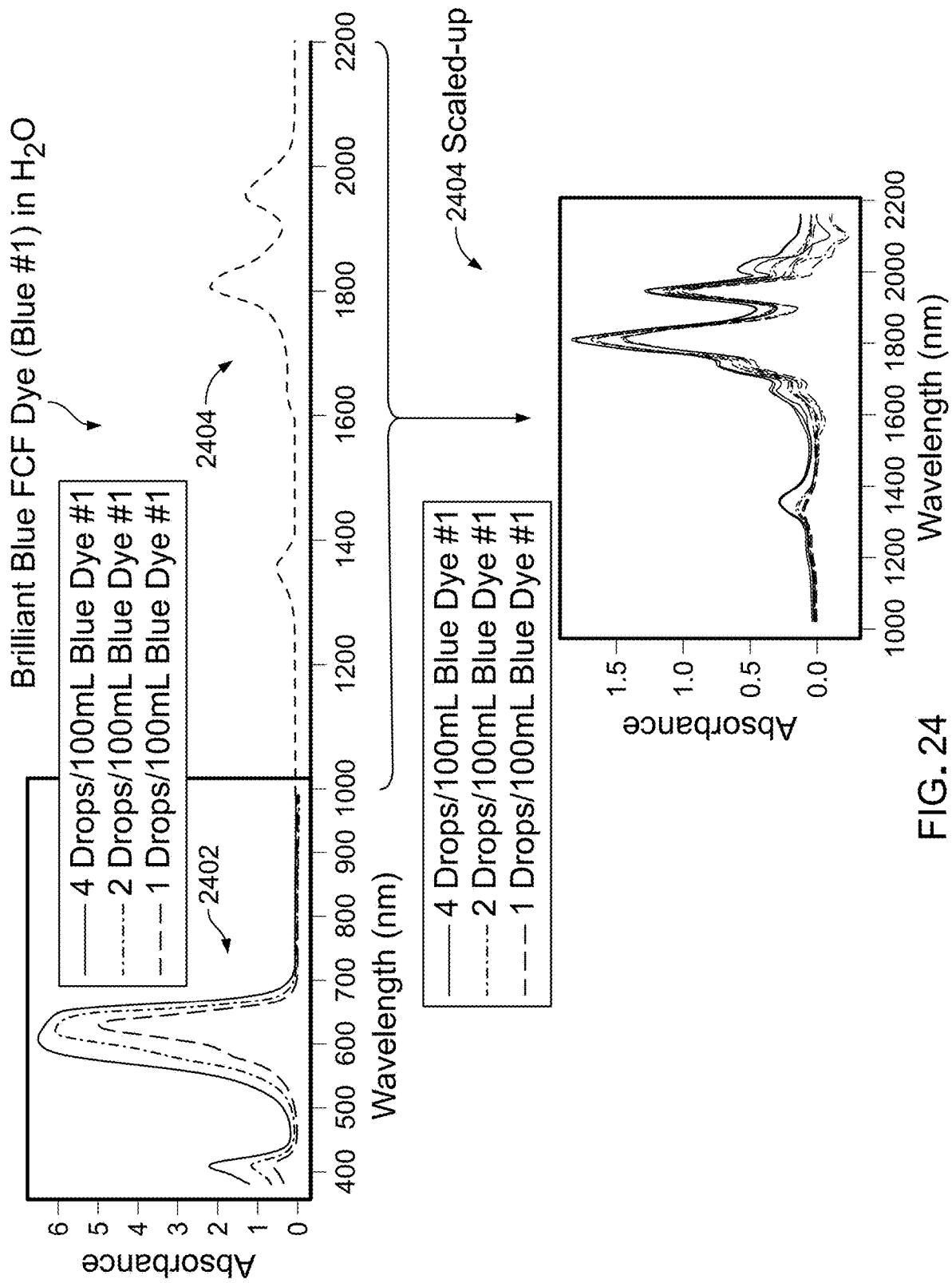
FIG. 24 shows spectra of a first example of food dye.
Figure 25:
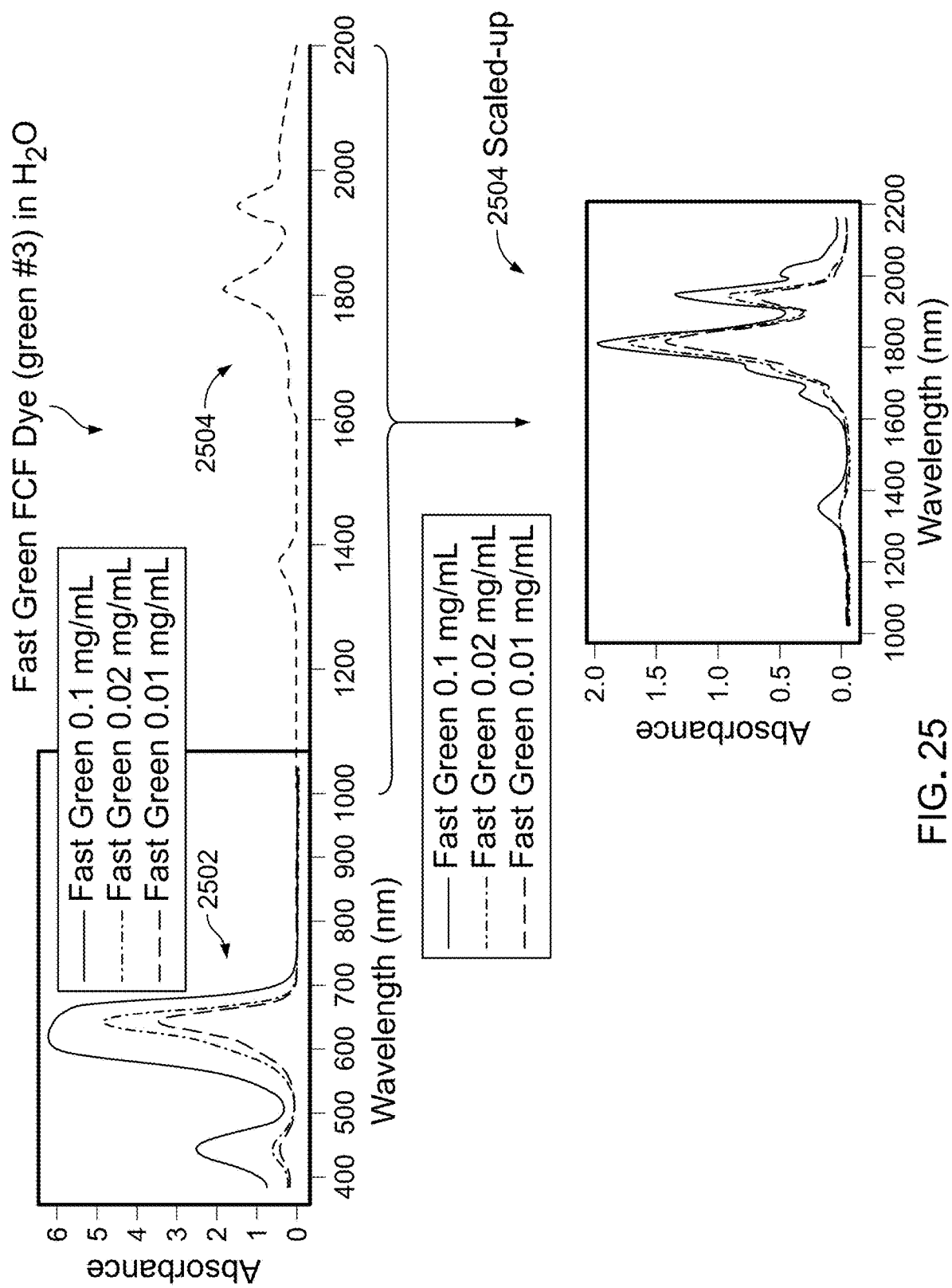
FIG. 25 shows spectra of a second example of food dye.

For example, FIG. 24 shows spectra 2402 over a wavelength range 400-1000 nm and spectra 2404 over a wavelength range 1000-2200 nm for solutions of Brilliant Blue for coloring food (FCF) dye (also known as Blue #1) in water at different dye concentrations. As another example, FIG. 25 shows spectra 2502 over a wavelength range 400-1000 nm and spectra 2504 over a wavelength range 1000-2200 nm for solutions of Fast Green FCF dye (Green #3) in water at different dye concentrations. The spectra 2402/2502 over the wavelength range 400-1000 nm were produced using the Benchtop spectrometer #5 from Table 14. The spectra 2404/2504 over the wavelength range 1000-2200 nm were produced using the Benchtop spectrometer #3 from Table 2.

The Green #3 can be used to quantify absorption of macronutrient, e.g., Ensure, and/or water in the small intestine. As water is absorbed, local concentrations of macronutrients can vary independently of the total quantity of macronutrient in the GI tract. Spectra corresponding to water or solutions of macronutrients were compared against a stable reference standard, e.g., a spectrum of Green #3, to calculate absorption of water and macronutrients in the small intestine.

Figure 26A:
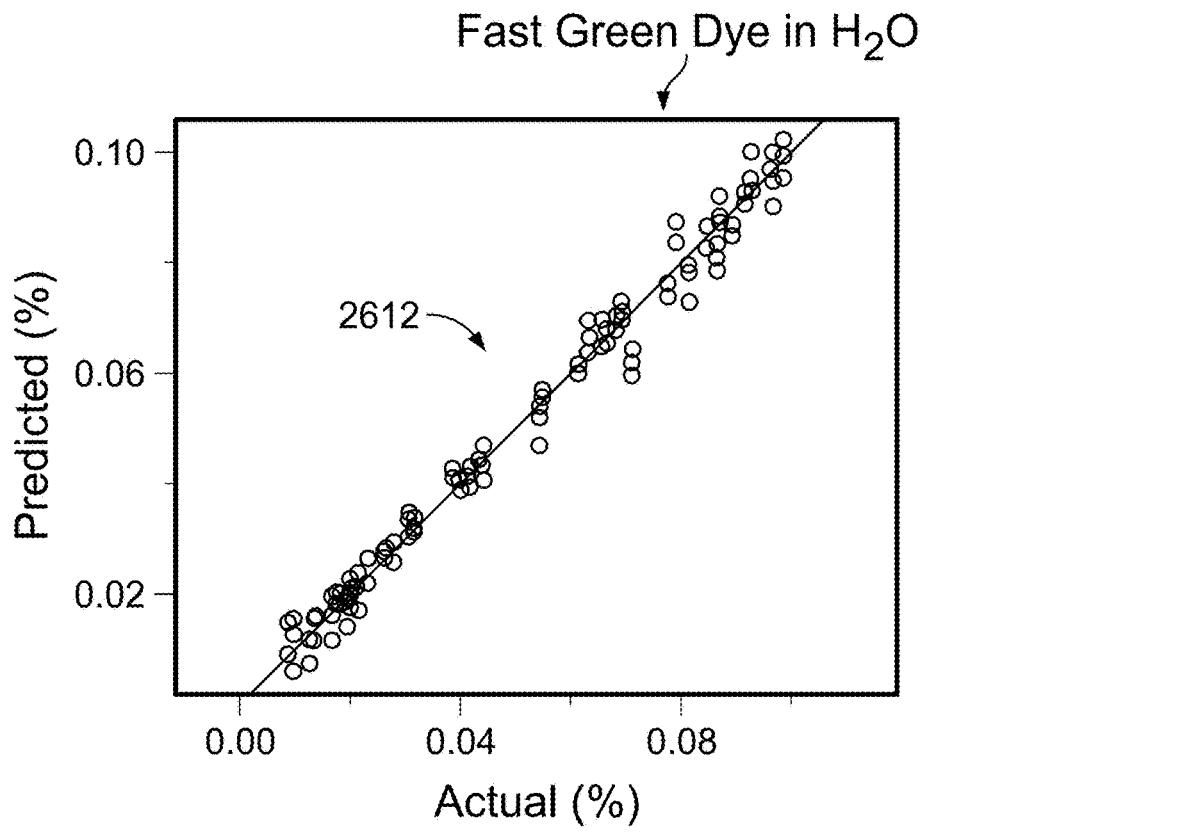
FIGS. 26A-26B show aspects of a model for predicting concentration of an analyte based on a spectrum of light that interacted with a solution of the analyte.

FIG. 26A shows a plot 2612 of predicted concentrations of Green #3 in water versus actual concentrations of the Green #3 in water. Here, the predicted values were obtained in the following manner. N instances of a Green #3 solution in water at different dye concentrations were prepared and a respective spectrum 2502 was produced for each instance. (N−1) of these spectra were used as inputs of a simulation model to predict the value of the Green #3 concentration of the solution having the $N^{th}$ spectrum. And the foregoing modeling process has been iterated for each of the N spectra. The results shown in plot 2612 have an RMSECV/mean=6.3%.

The absorption of water in the GI tract can be calculated, using a reference standard, based on the following equation:

$$AW\ \%(t) = 1 - \frac{RS\ \%(t_0)}{RS\ \%(t)} \quad (2)$$

where AW % (t) is the fraction of water absorbed, RS % ($t_0$) is the starting reference-standard concentration, and RS % (t) is the estimated reference-standard concentration. For example, a spectrum is produced, at time t, for a solution of Green #3 that had an initial concentration RS % ($t_0$). If the Green #3 concentration, estimated based on the produced spectrum, is found to quadruple relative to the initial concentration, i.e., RS % (t)=4RS % ($t_0$), that means 75% of water has been absorbed.

Figure 26B:
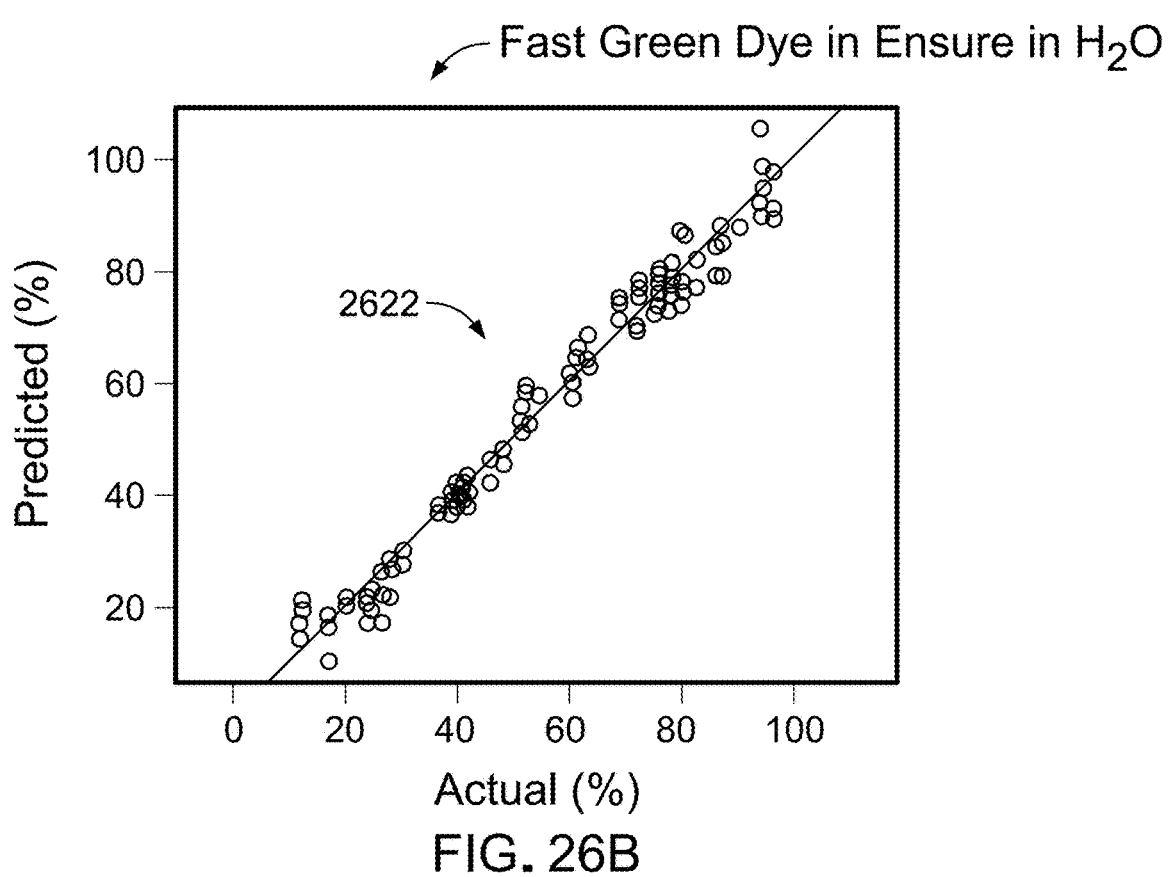

FIG. 26B shows a plot 2622 of predicted concentrations of Ensure in a mixture with Green #3 and water versus actual concentrations of the Ensure in the mixture with Green #3 and water. Here, the predicted values were obtained in the following manner. N instances of a randomized mixture of Green #3 and Ensure and water at different dye concentrations and different Ensure concentrations were prepared and a respective spectrum over the wavelength range 400-1000 nm has been produced for each instance. (N−1) of these spectra were used as inputs of a model to predict the value of the Ensure concentration of the mixture having the $N^{th}$ spectrum. And the foregoing modeling process has been iterated for each of the N spectra. The results shown in plot 2622 have an RMSECV/mean=5.7%.

The absorption of Ensure can be calculated, using a reference standard, based on the following equation:

$$AM\ \%(t) = 1 - \frac{\left(\frac{M\ \%(t)}{RS\ \%(t)}\right)}{\left(\frac{M\ \%(t_0)}{RS\ \%(t_0)}\right)} \quad (3)$$

where AM % (t) is the fraction of macronutrient absorbed, M % ($t_0$) is the starting macronutrient concentration, and M % (t) is the measured macronutrient concentration; RS % ($t_0$) is the starting reference standard concentration, and RS % (t) is the measured reference standard concentration. For example, if in the starting meal base the concentration of Green #3 is RS % ($t_0$)=0.1%, and the concentration of Ensure is M % ($t_0$)=4%, then the ratio in the denominator of EQ. (2) is fixed and known:

$$\frac{M\ \%(t_0)}{RS\ \%(t_0)} = 40.$$

Later, the fraction of remaining macronutrient and the fraction of reference standard are estimated and used to compute the numerator of EQ. (3). For example, if no water is added or subtracted from the system, then the concentration of the Green #3 remains the same at RS % (t)=0.1%. If the amount of Ensure left in the system is estimated, from a spectrum of the mixture that is produced at t, to be M % (t)=2%, then the current ratio is $$\frac{M\ \%(t)}{RS\ \%(t)} = 20.$$

So, in this case, AM % (t)=0.5, which means that half of the soybean oil was absorbed. As another example, if the actual contents were diluted by water by a factor of two, then the estimated fraction of Green #3 and Ensure would be ½ of the fractions in the previous example, with RS % (t)=0.05% green dye and M % (t)=1% soybean oil. However, because the estimated ratio is still $$\frac{M\ \%(t)}{RS\ \%(t)} = 20,$$

the same amount of soybean oil is estimated to be absorbed AM % (t)=0.5.

The estimation of the reference material (e.g., Green #3) concentration is what allows one to account for the dilution or increase in concentration of the Ensure contents, for instance. To do so, it is assumed that the reference material is not absorbed in the GI tract, so any change of the reference concentration is only due to dilution or increase in concentration of water.

Example 10: Spectroscopy Used for Quantifying L-Lysine and Glucose in Mixed Solutions The purpose of this experiment was to use a miniaturized spectrometer in the short-wavelength infrared (SWIR) range to quantify L-lysine and glucose in mixed solutions.

Stock solutions were made by diluting glucose (dextrose, Sigma D9434), L-lysine HCl (Nutraceutical, Nature's Life) and L-lysine (Sigma L5501) with milliQ water in containers (white, plastic 88.7 mL) to provide solutions of 150 mg/mL glucose/water, solutions of 50 mg/ML of L-lysine HCl, and solutions of 50 mg/mL of L-lysine, respectively. 21 samples were prepared as shown in Table 15.

TABLE 15

| Sample | Glucose concentration (mg/mL) | L-lysine or L-lysine HCL concentration (mg/mL) |
|---|---|---|
| 1 | 25 | 8.3 |
| 2 | 150 | 0 |
| 3 | 18.8 | 0 |
| 4 | 12.5 | 4.2 |
| 5 | 50 | 8.3 |
| 6 | 0 | 0 |
| 7 | 9.4 | 0 |
| 8 | 37.5 | 0 |
| 9 | 50 | 4.2 |
| 10 | 0 | 25 |
| 11 | 0 | 6.3 |
| 12 | 37.5 | 18.8 |
| 13 | 12.5 | 8.3 |
| 14 | 25 | 16.7 |
| 15 | 75 | 0 |
| 16 | 25 | 4.2 |
| 17 | 0 | 50 |
| 18 | 50 | 16.7 |
| 19 | 12.5 | 16.7 |
| 20 | 0 | 3.1 |
| 21 | 0 | 12.5 |

Spectra of the samples were taken using the miniature SCIO spectrometer, as listed in Table 2, using one of the following two methods: 1) taking five consecutive scans inside a cup and proceeding through all 21 samples; or 2) taking measurements of all 21 samples five different times (round-robin sampling). Between each sample, the system was dried, cleaned with water, and dried again.

The samples were analyzed using standard chemometric routines from Consumer Physics to develop measurement models and to test the models' capabilities in estimating material concentrations, either alone or in the presence of interference from other materials. The conditions were standard pre-processing (expert mode off) at wavelengths from 759 nm to 1052 nm.

Figure 27:
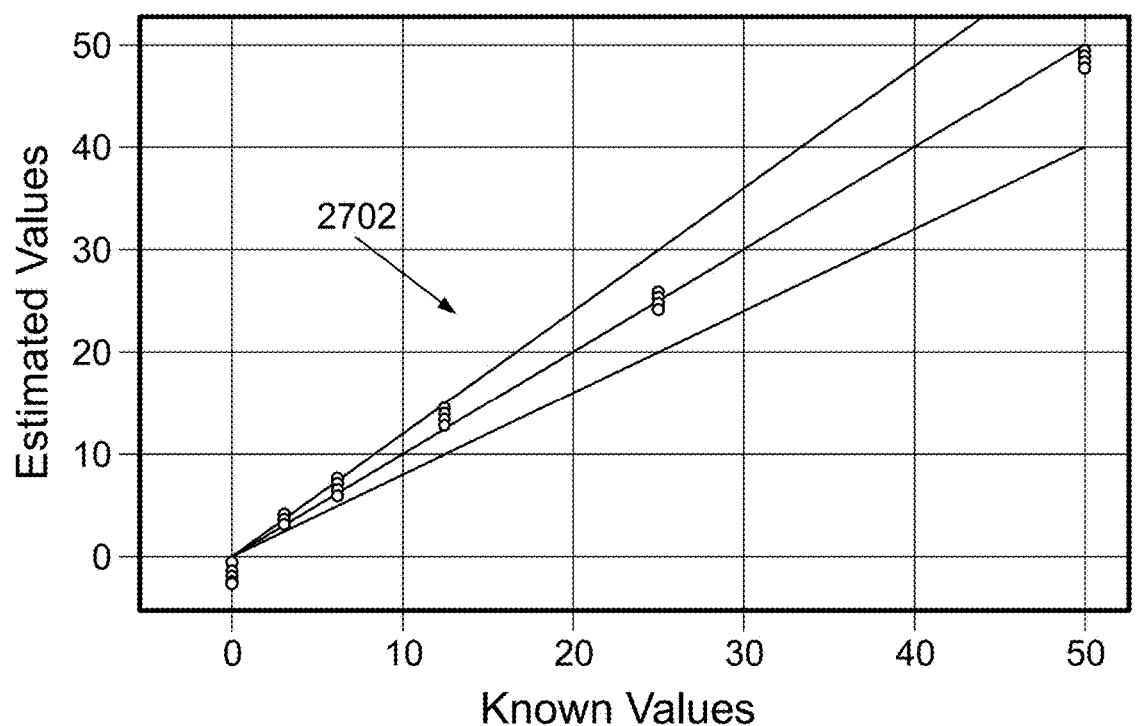
FIG. 27 shows data for estimating L-lysine.

FIG. 27 shows a result 2702 of a model for estimating L-lysine alone (no glucose interference) using single pass with five replicate measurements of the samples. The result 2702 represents a correlation between the estimated and known concentration of L-lysine. Here, RMSE=1.244 with $r^2$=0.995.

Figure 28:
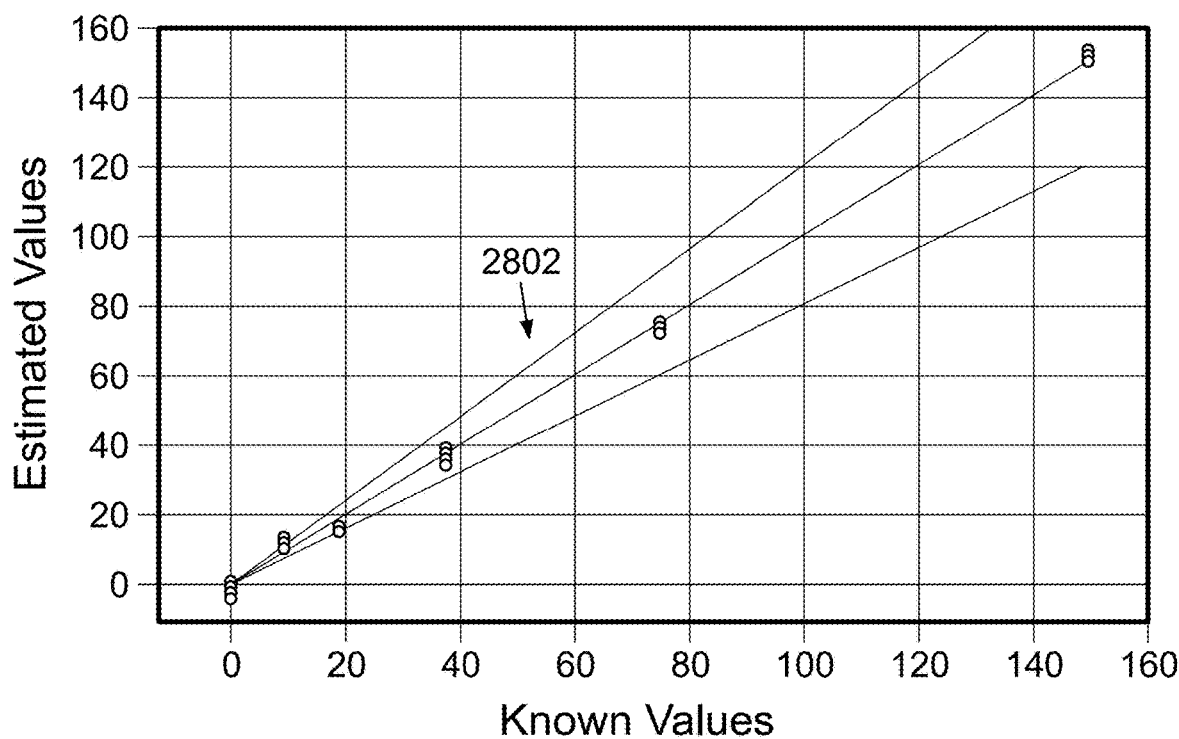
FIG. 28 shows data for estimating glucose.

FIG. 28 shows a result 2802 of a model for estimating glucose alone (no L-lysine interference) using single pass with five replicate measurements of the samples. The result 2802 represents a correlation between the estimated and known concentration of glucose. Here, RMSE=2.239 with $r^2$=0.998.

Figure 29:
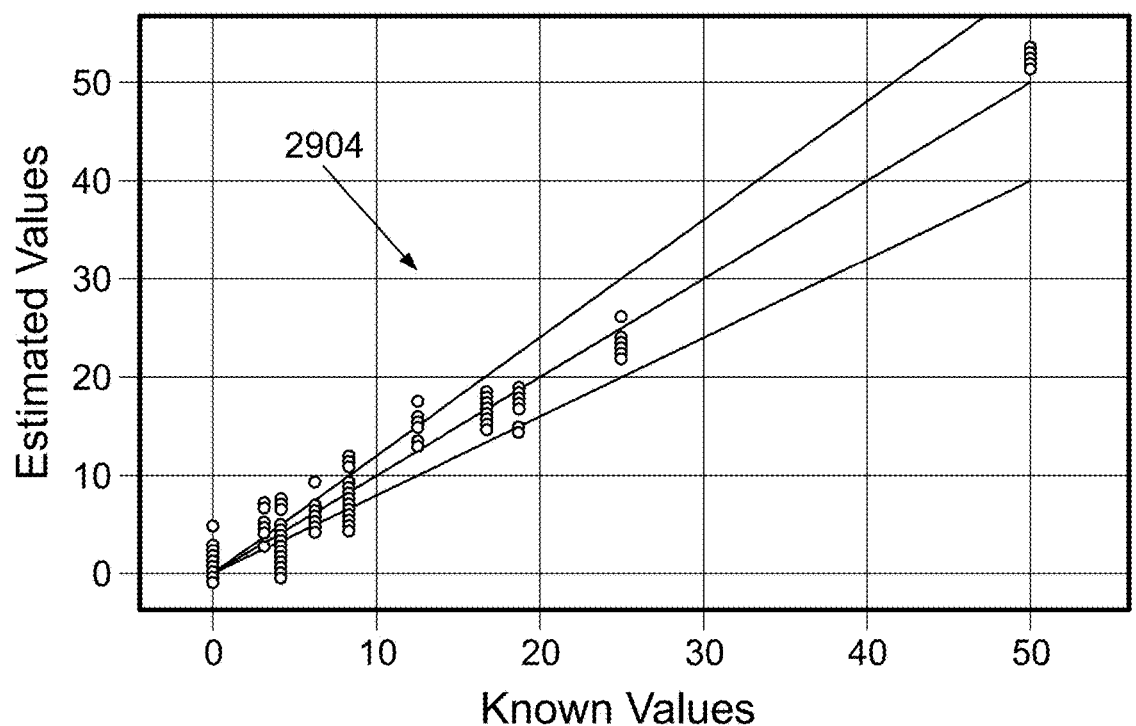
FIG. 29 shows data for estimating L-lysine.

FIG. 29 shows a result 2904 of a model for estimating L-lysine in the presence of variable glucose interference using single pass with five replicate measurements of the samples. The result 2904 represents a correlation between the estimated and known combined concentrations of L-lysine and glucose. Here, RMSE=1.956 with $r^2$=0.971.

Figure 30:
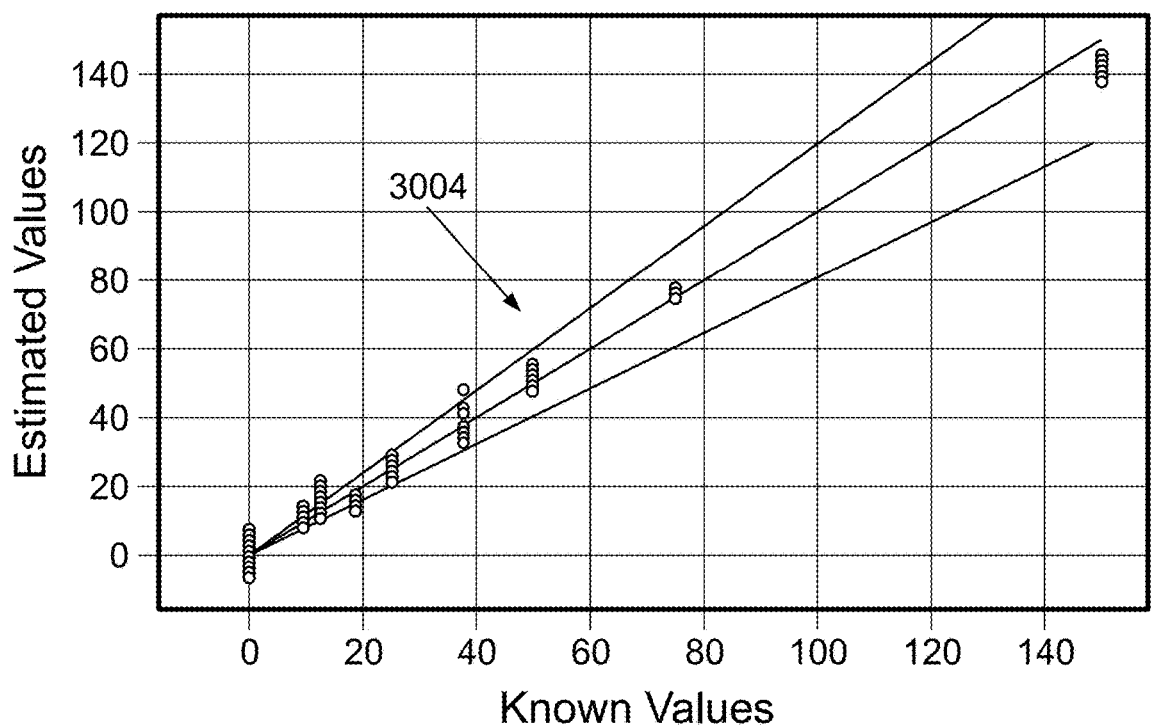
FIG. 30 shows data for estimating glucose.

FIG. 30 shows a result 3004 of a model for estimating glucose in the presence of variable L-lysine interference using single pass with five replicate measurements of the samples. The result 3004 represents a correlation between the estimated and known combined concentrations of glucose and L-lysine. Here, RMSE=3.802 with $r^2$=0.988.

Figure 31:
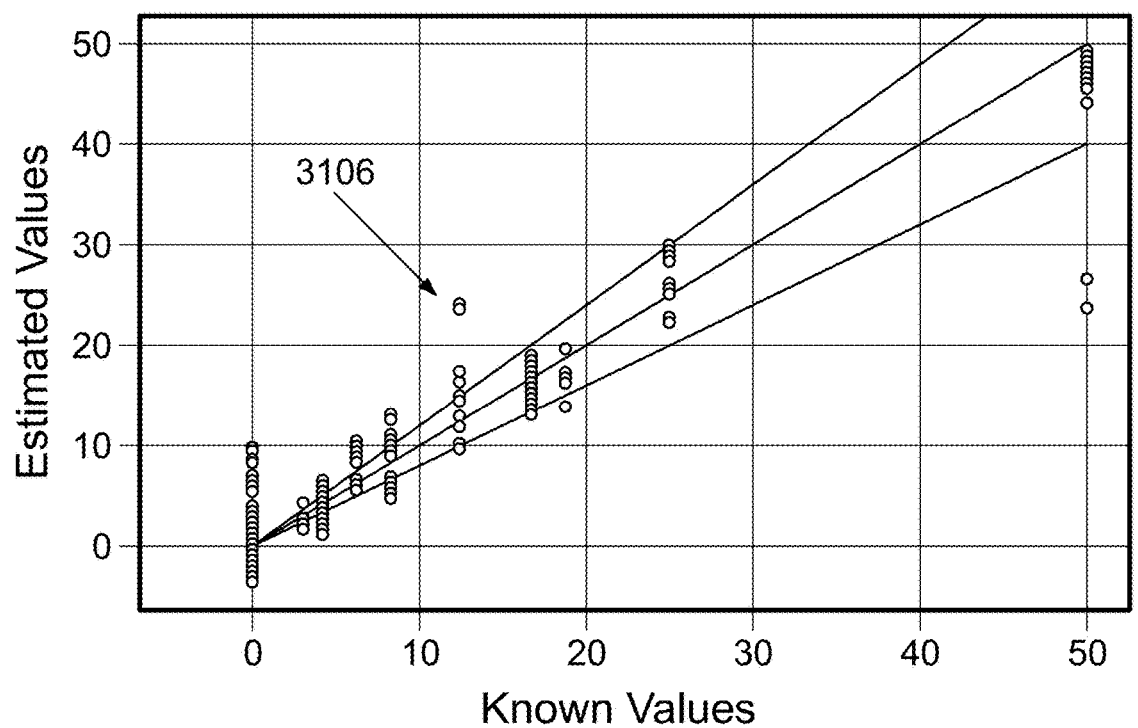
FIG. 31 shows data for estimating L-lysine.

FIG. 31 shows a result 3106 of a model for estimating L-lysine in the presence of variable glucose interference using round robin measurements of the samples. The result 3106 represents a correlation between the estimated and known combined concentrations of L-lysine and glucose. Here, RMSE=3.858 with $r^2$=0.889.

Figure 32:
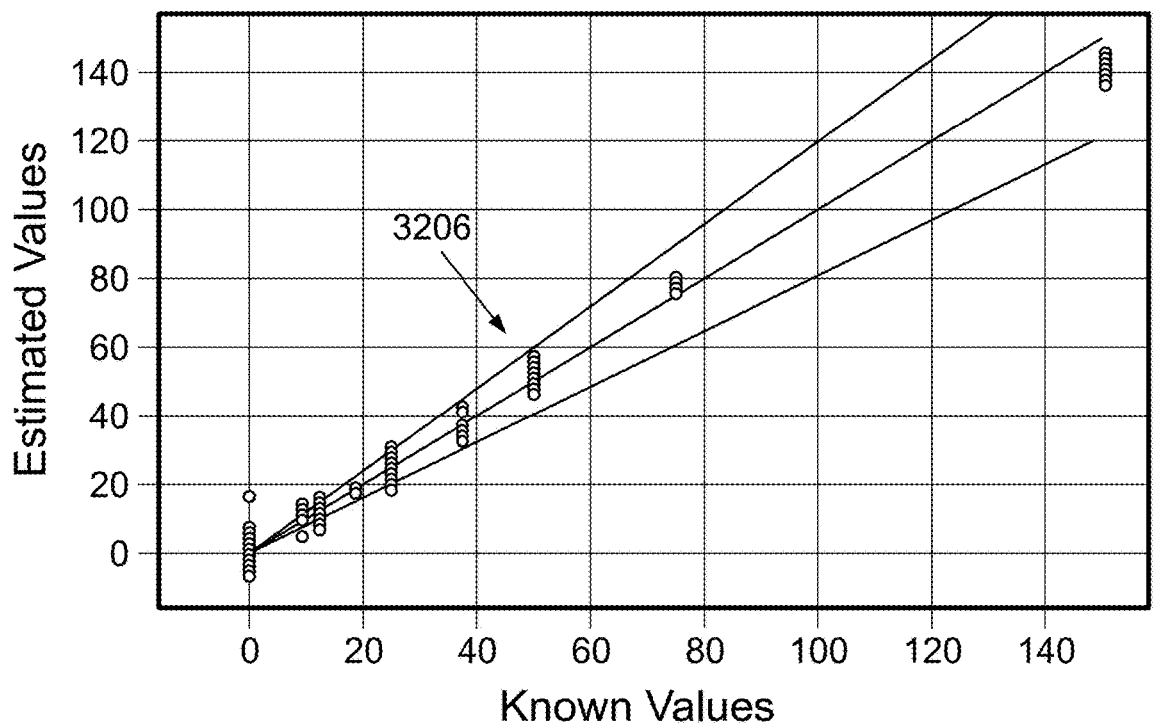
FIG. 32 shows data for estimating glucose.

FIG. 32 shows a result 3206 of a model for estimating glucose in the presence of variable L-lysine interference round robin measurements of the samples. The result 3206 represents a correlation between the estimated and known combined concentrations of glucose and L-lysine. Here, RMSE=3.916 with $r^2$=0.987.

Figure 33:
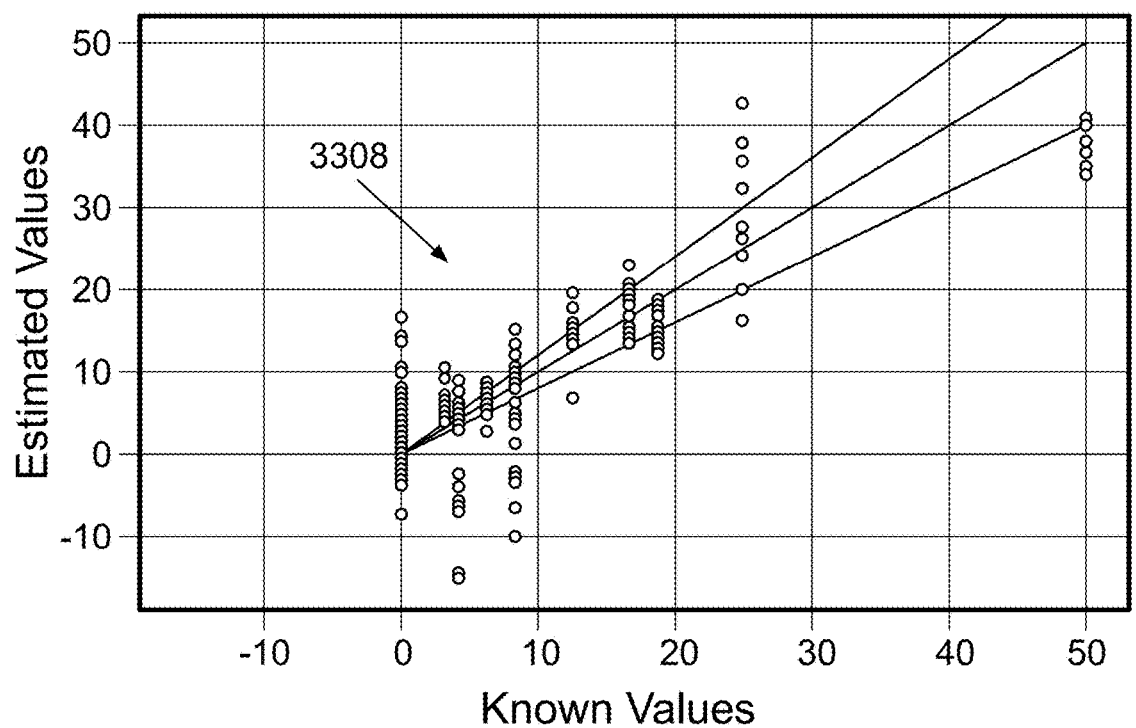
FIG. 33 shows data for estimating L-lysine HCl.

FIG. 33 shows a result 3308 of a model for estimating L-lysine HCl in the presence of variable glucose interference using single pass with five replicate measurements of the samples. The result 3308 represents a correlation between the estimated and known combined concentrations of L-lysine HCl and glucose. Here, RMSE=6.279 with $r^2$=0.703.

Figure 34:
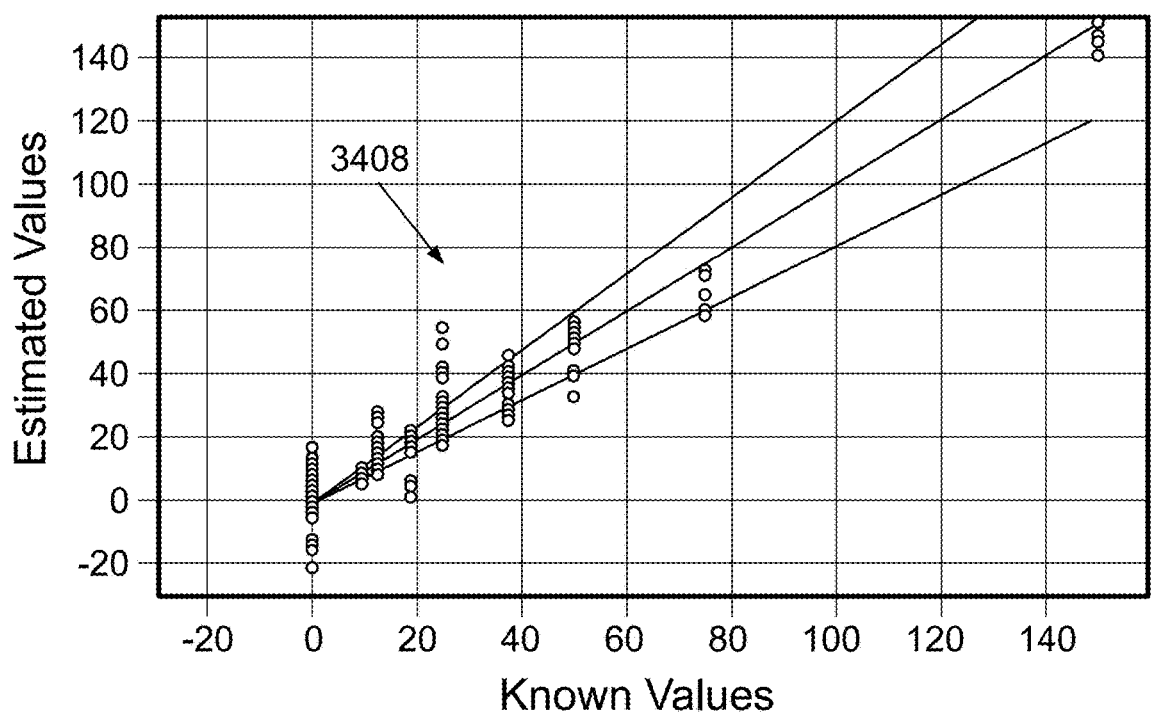
FIG. 34 shows data for estimating glucose.

FIG. 34 shows a result 3408 of a model for estimating glucose in the presence of variable L-lysine HCl interference using single pass with five replicate measurements of the samples. The result 3408 represents a correlation between the estimated and known combined concentrations of glucose and L-lysine HCl. Here, RMSE=7.27 with $r^2$=0.954.

The results of Example 10 demonstrate that L-lysine and glucose can be isolated and measured in the presence of varying amounts of each other using a miniaturized spectrometer (SCiO) and chemometric techniques. The SCIO spectrometer had a design such that it could have been integrated into an ingestible device as described herein.

Example 11: Spectroscopy Used for Detecting and Classifying Drugs

Spectroscopy was performed using spectrometers from among the spectrometers from Tables 2, 10 and 13 in reflectance mode and in transmission mode, for detecting and classifying various drugs dissolved in water.

Figure 35A:
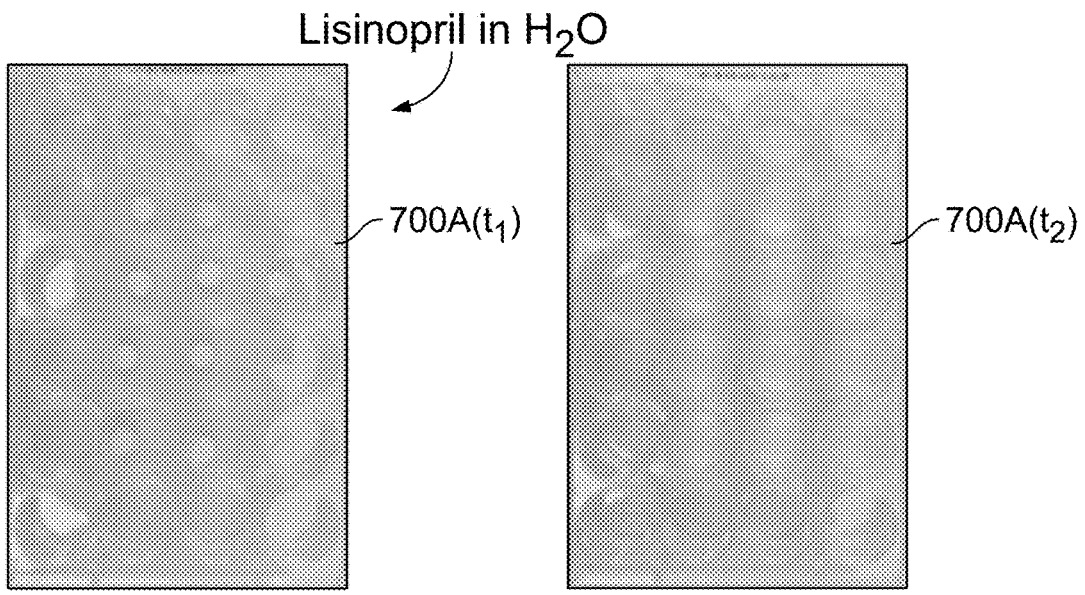
FIG. 35A shows pills in a well plate.

Some test samples included an angiotensin converting enzyme (ACE) inhibitor, e.g., Lisinopril 10 mg, dissolved in water. FIG. 35A shows that 12 pills including 10 mg of Lisinopril were placed, at $t_1$, in water held by respective wells of a 4×6 well plate 700A, and a few minutes later, at $t_2$, the pills were fully dissolved. Here, most of the insoluble materials settled to the bottom of each well. These 12 ACE inhibitor samples held by the well plate 700A were used to perform spectroscopy of the ACE inhibitor in reflectance mode using Benchtop spectrometers #5 and #2. Further, the ACE inhibitor samples were siphoned from the well plate 700A and combined into three cuvettes. The ACE inhibitor solution in each of the cuvettes had an optical path thickness of 10 mm. These three ACE inhibitor samples held by the cuvettes were used to perform spectroscopy of the ACE inhibitor in transmission mode using Benchtop spectrometers #4, #5 and #2.

Figure 35B:
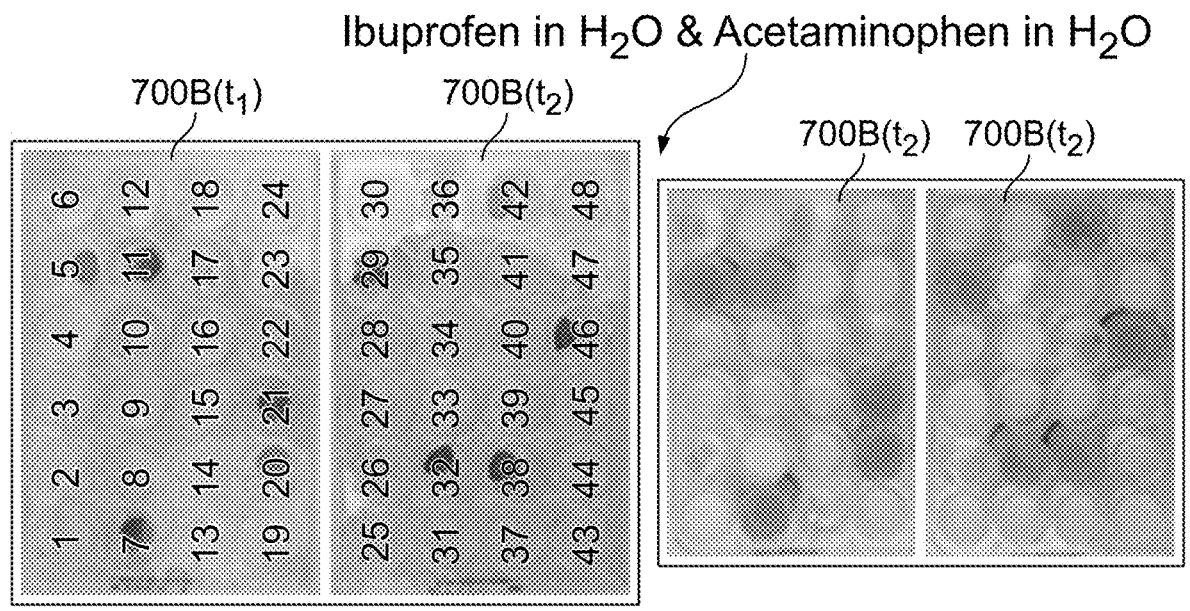
FIG. 35B shows the dissolution of pills in a well plate.

Other test samples included anti-inflammatory drugs, e.g., Ibuprofen and Acetaminophen, dissolved in water. Yet other test samples included microcrystalline cellulose, which can be one primary filler material in anti-inflammatory drugs, dissolved in water. FIG. 35B shows that 12 pills of (i) Ibuprofen, some of which were coated and some uncoated, (ii) Acetaminophen, and (iii) microcrystalline cellulose were placed, at $t_1$, in water held by respective wells of 4×6 well plates 700B, and a few minutes later, at $t_2$, the pills were at least partially dissolved. It is noted that Acetaminophen appears to have limited solubility in water. The Ibuprofen, Acetaminophen and microcrystalline cellulose samples held by the well plate 700B were used to perform spectroscopy of Ibuprofen, Acetaminophen and microcrystalline cellulose in reflectance mode using Benchtop spectrometers #5, #2 and #3. Further, the Ibuprofen and Acetaminophen samples were siphoned from the well plate 700B and combined into a few cuvettes. The Ibuprofen solutions or Acetaminophen solutions in each of the cuvettes had an optical path thickness of 10 mm. These Ibuprofen and Acetaminophen samples held by the cuvettes were used to perform spectroscopy of Ibuprofen and Acetaminophen in transmission mode using Benchtop spectrometers #4, #5, #2 and #3.

Figure 36A:
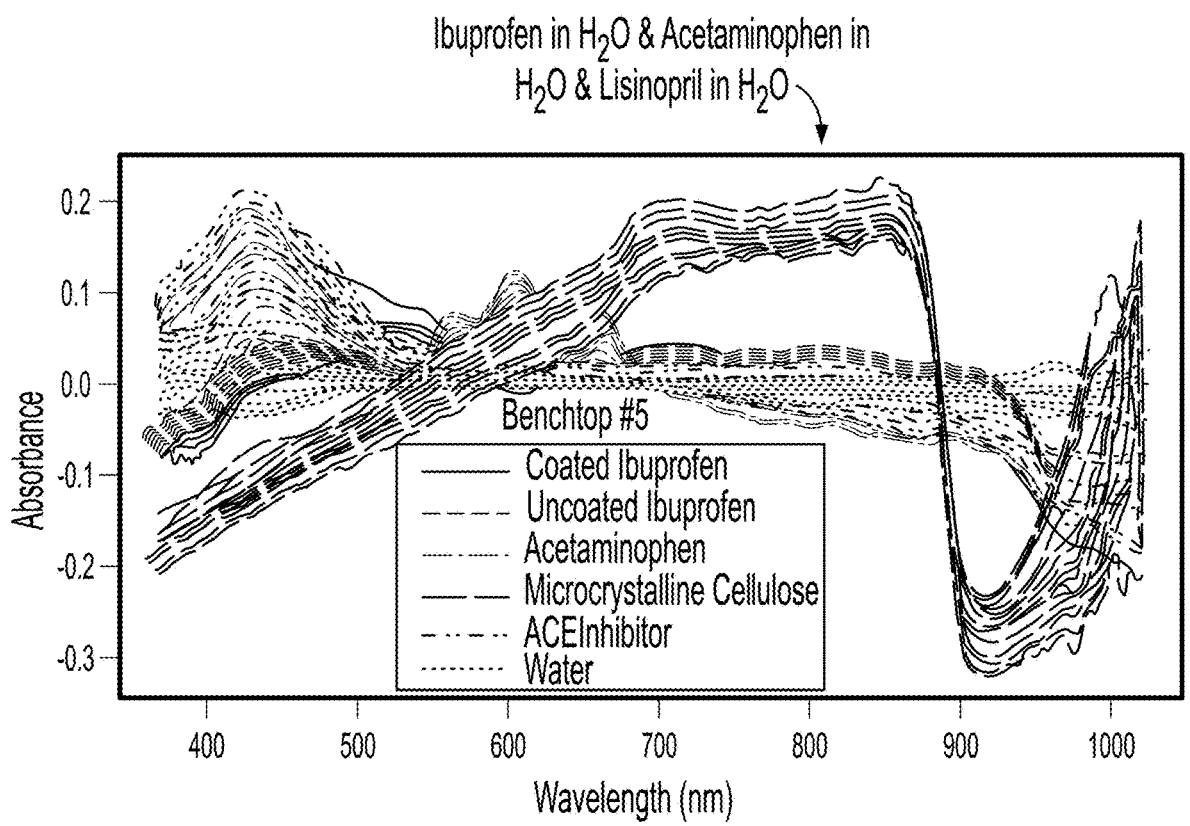
FIGS. 36A-36C show sets of spectra.
Figure 36B:
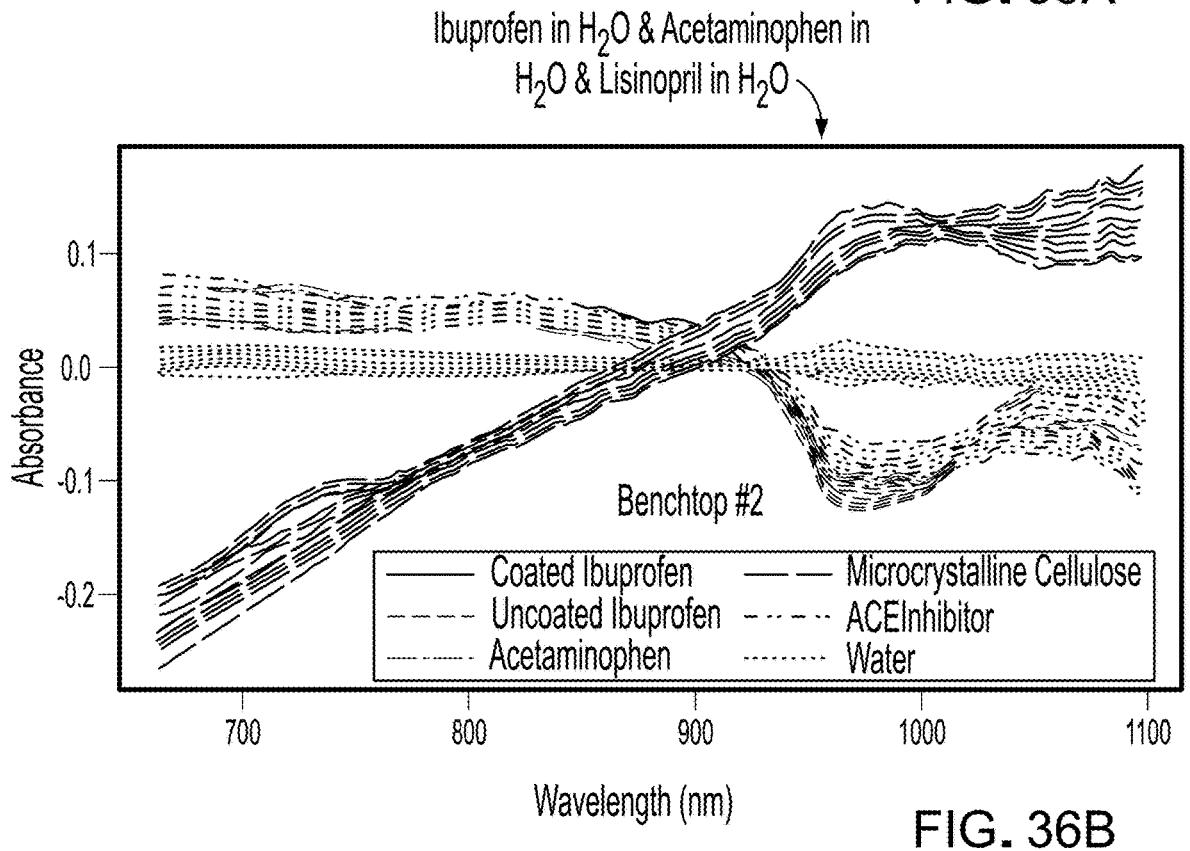
Figure 36C:
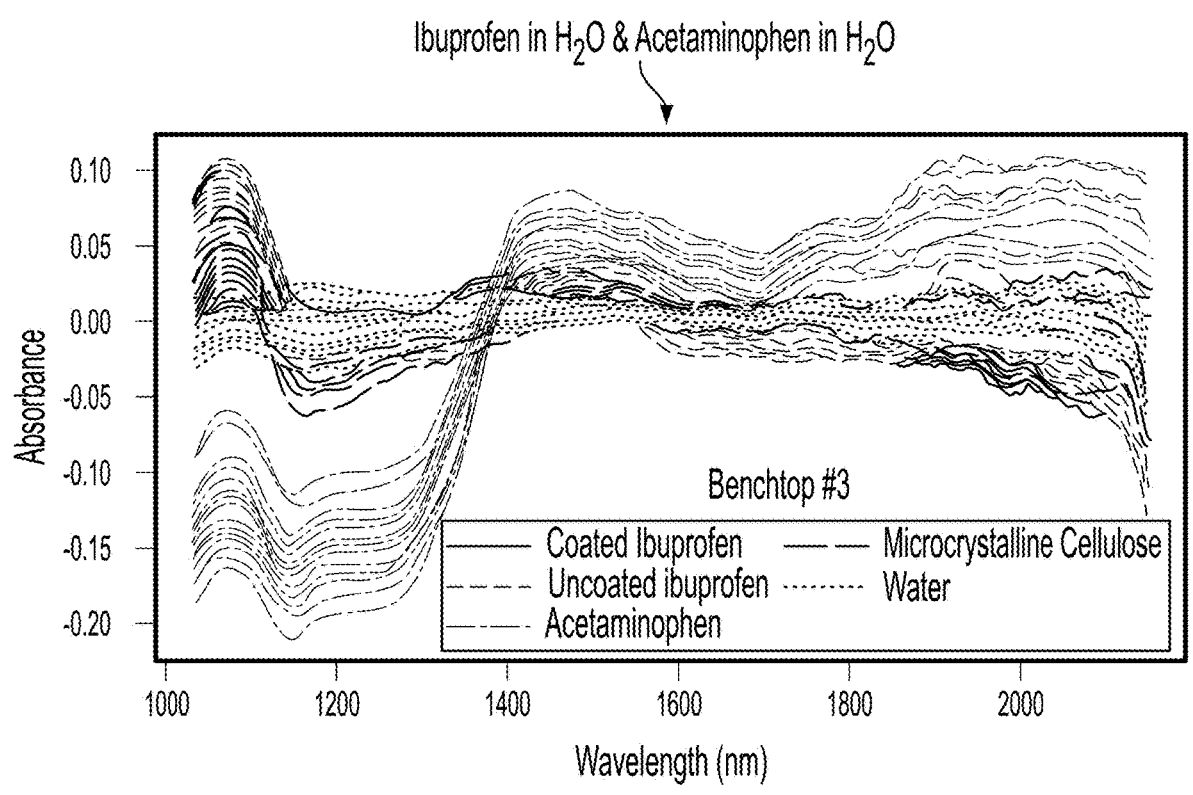

FIGS. 36A-36C show sets of spectra of light reflected off solutions of coated and uncoated Ibuprofen, Acetaminophen, microcrystalline cellulose, and ACE inhibitor in water, where each set of spectra corresponds to a respective drug. FIG. 36C shows sets of spectra of light reflected off solutions of coated and uncoated Ibuprofen, Acetaminophen, and microcrystalline cellulose in water, where each set of reflection spectra corresponds to a respective drug. The reflection spectra shown in FIG. 36A were acquired with Benchtop spectrometer #5. The reflection spectra shown in FIG. 36B were been acquired with Benchtop spectrometer #2. The reflection spectra shown in FIG. 36C were acquired with Benchtop spectrometer #3. Note that in addition to acquiring the reflection spectra corresponding to the above-noted solutions of coated and uncoated Ibuprofen, Acetaminophen, microcrystalline cellulose and ACE inhibitor in water, spectra of light reflected off plain water were also acquired.

The reflection spectra corresponding to the water samples also are shown in FIGS. 36A-36C for reference purposes. The reflection spectra shown in FIGS. 36A-36C correspond to thirty spectra per analyte, in the following manner: three spectra per sample, and ten samples per analyte.

Figure 37A:
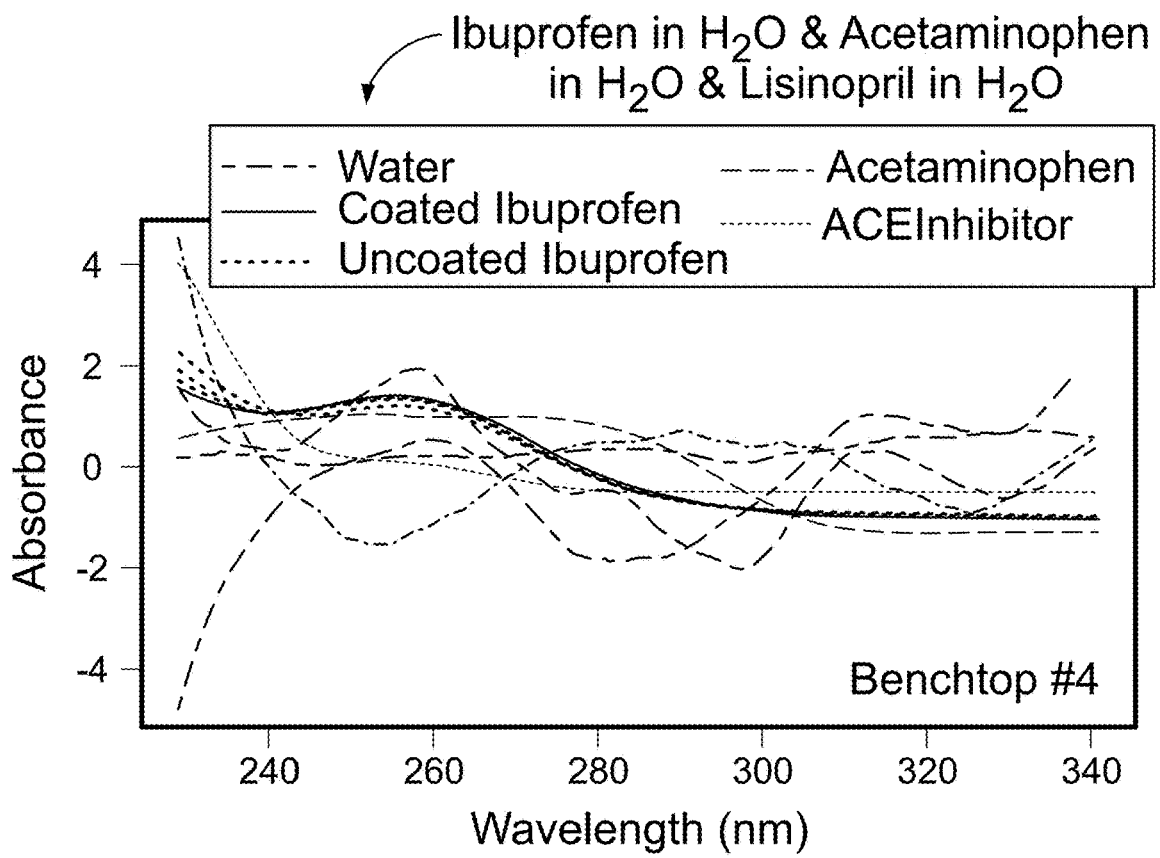
FIGS. 37A-37D show sets of spectra.
Figure 37B:
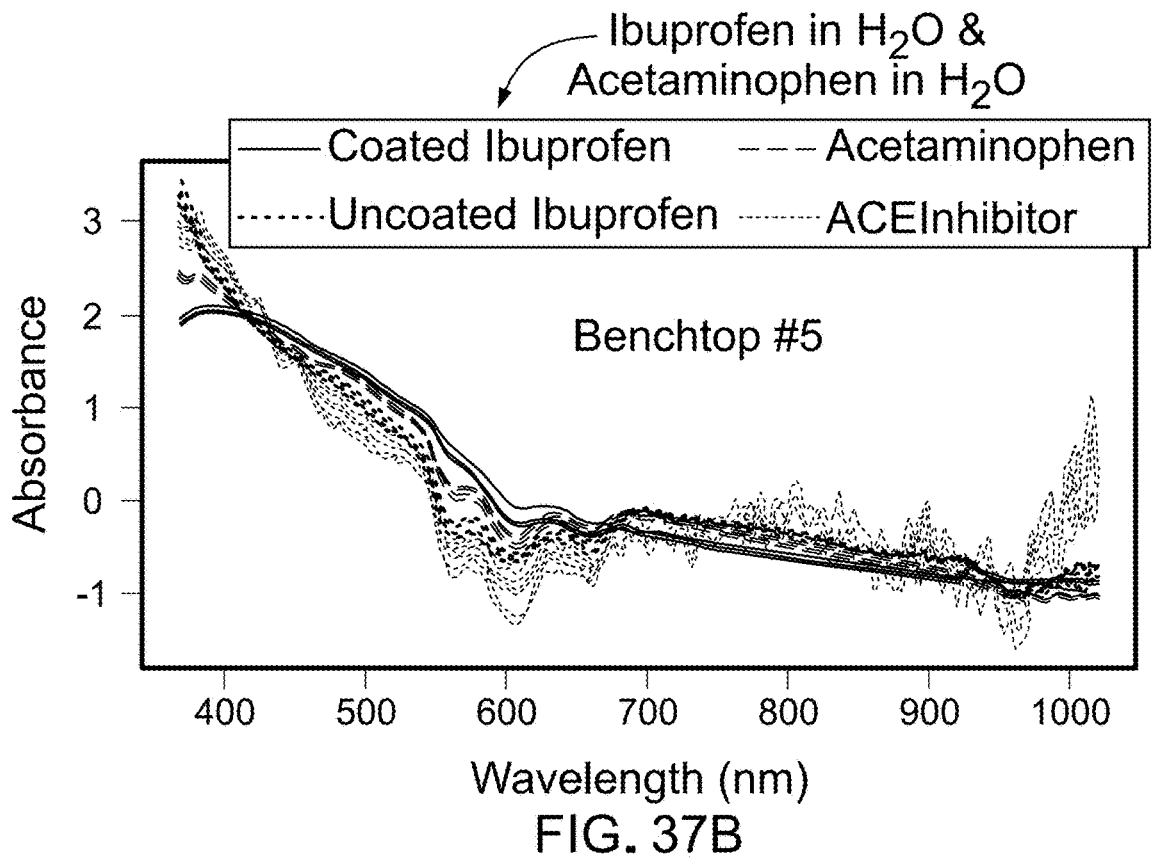
Figure 37C:
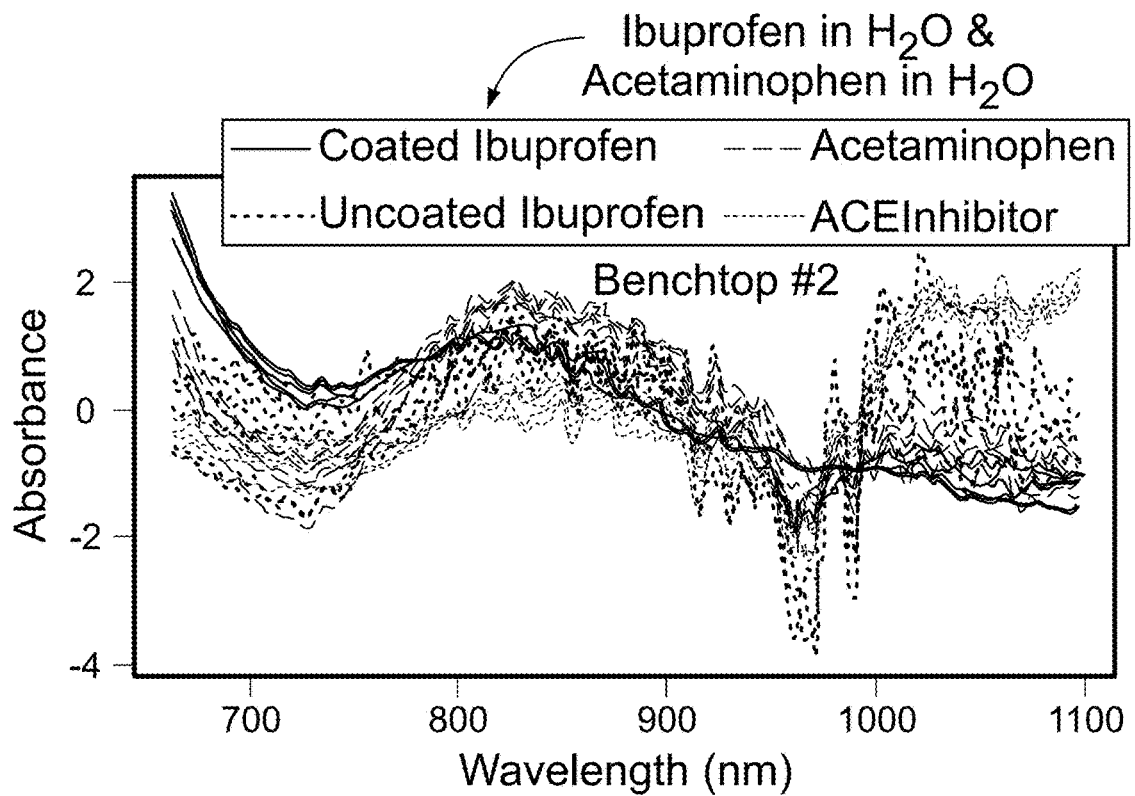
Figure 37D:
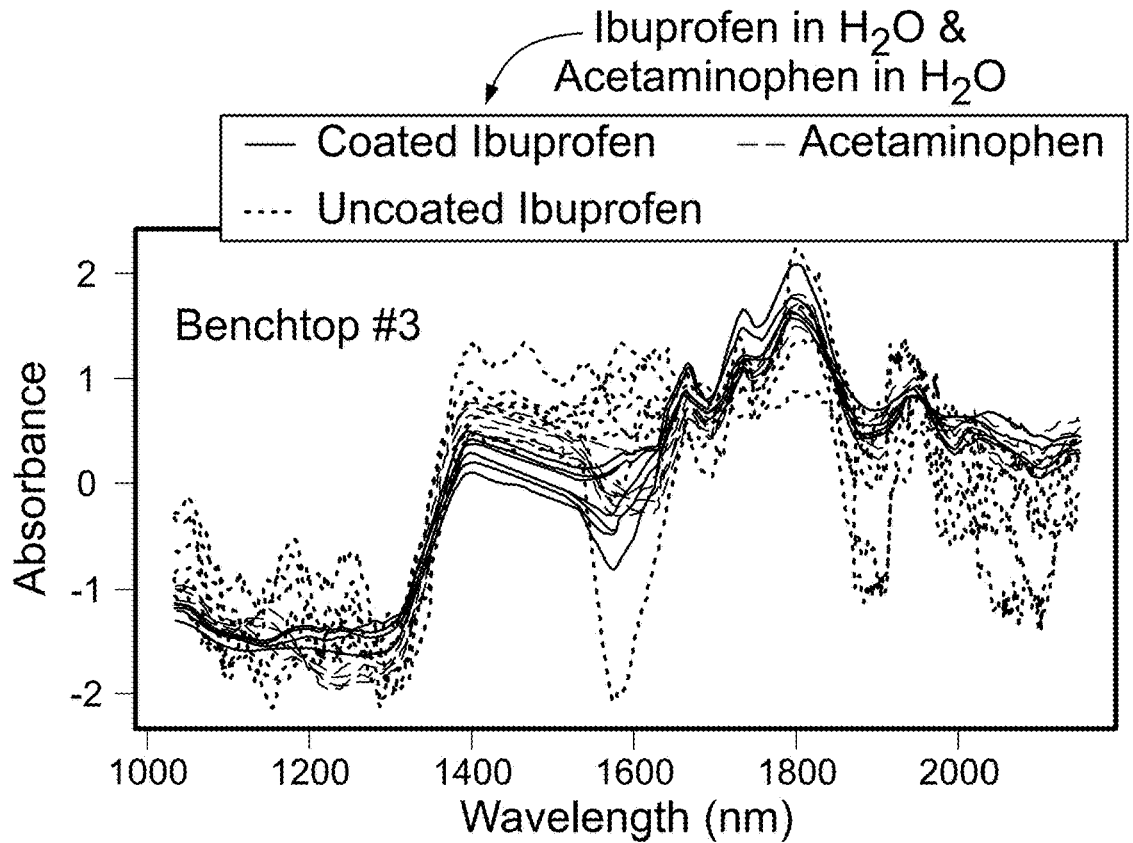
Figure 38A:
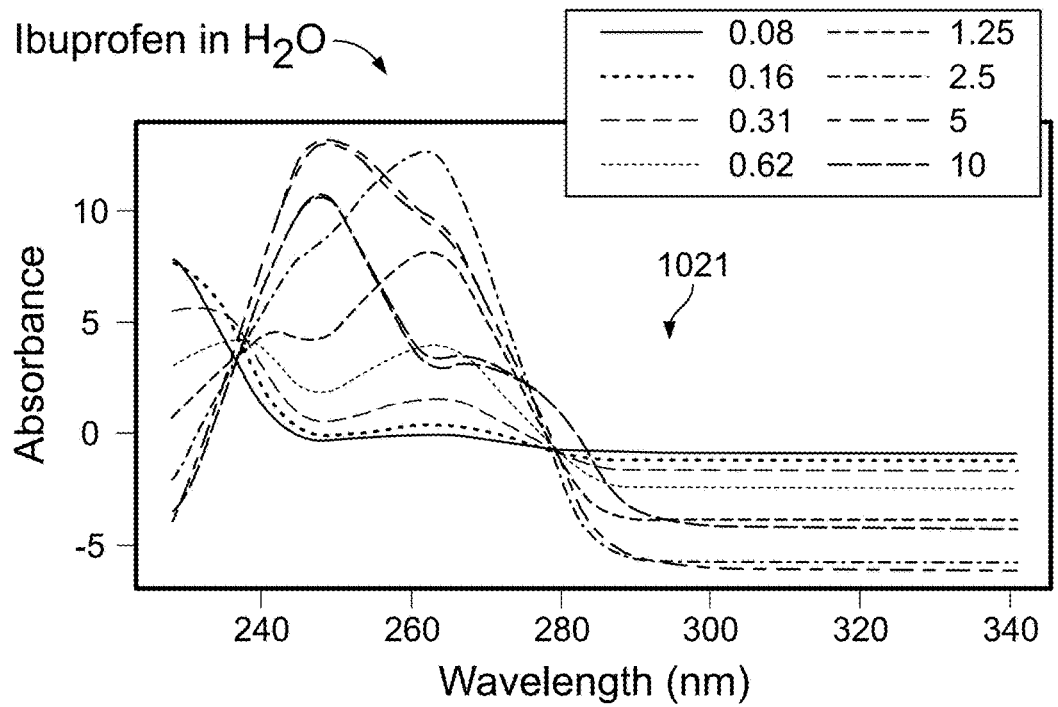
FIGS. 38A-38D show sets of spectra.
Figure 38B:
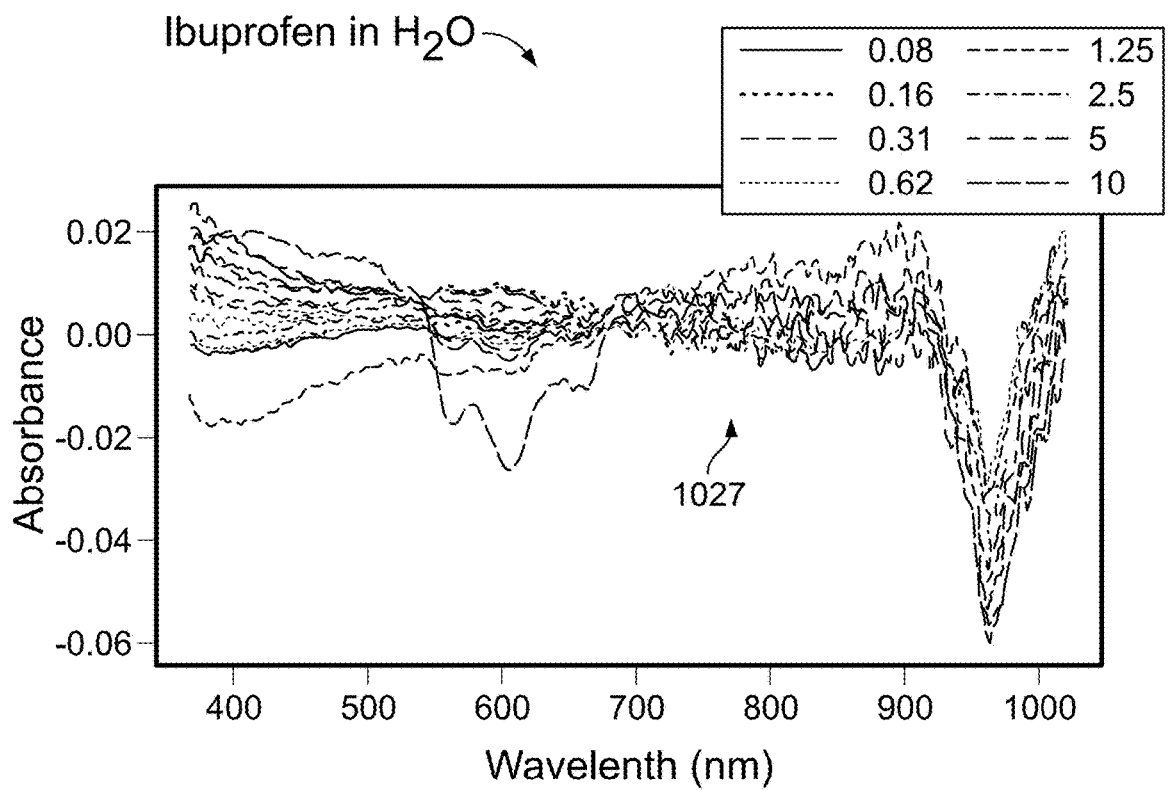
Figure 38C:
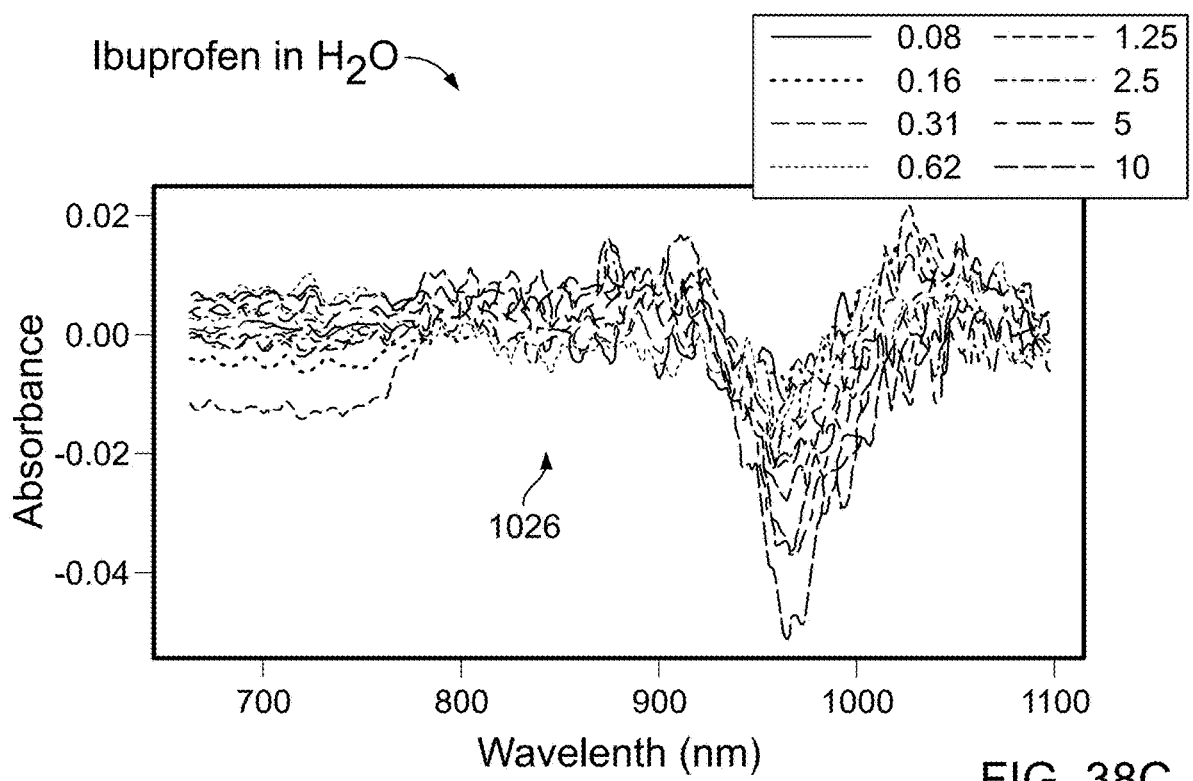
Figure 38D:
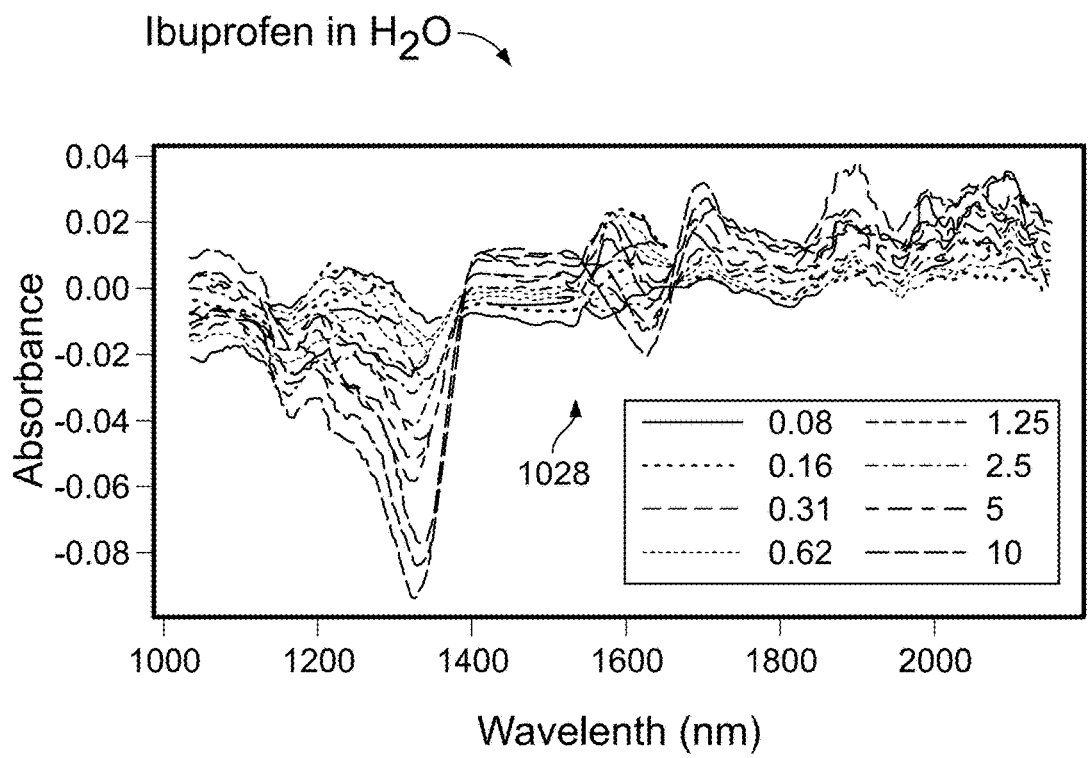
Figures 39A, 39B, 39C, 39D:
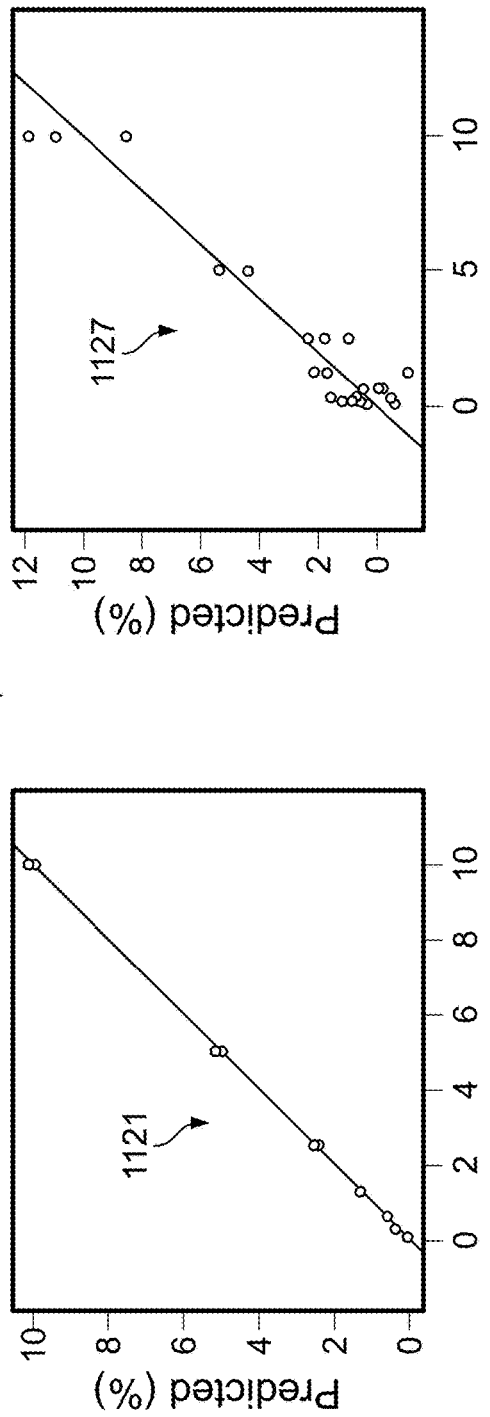
FIGS. 39A-39D illustrate results of predictions based on a model.
Figure 40A:
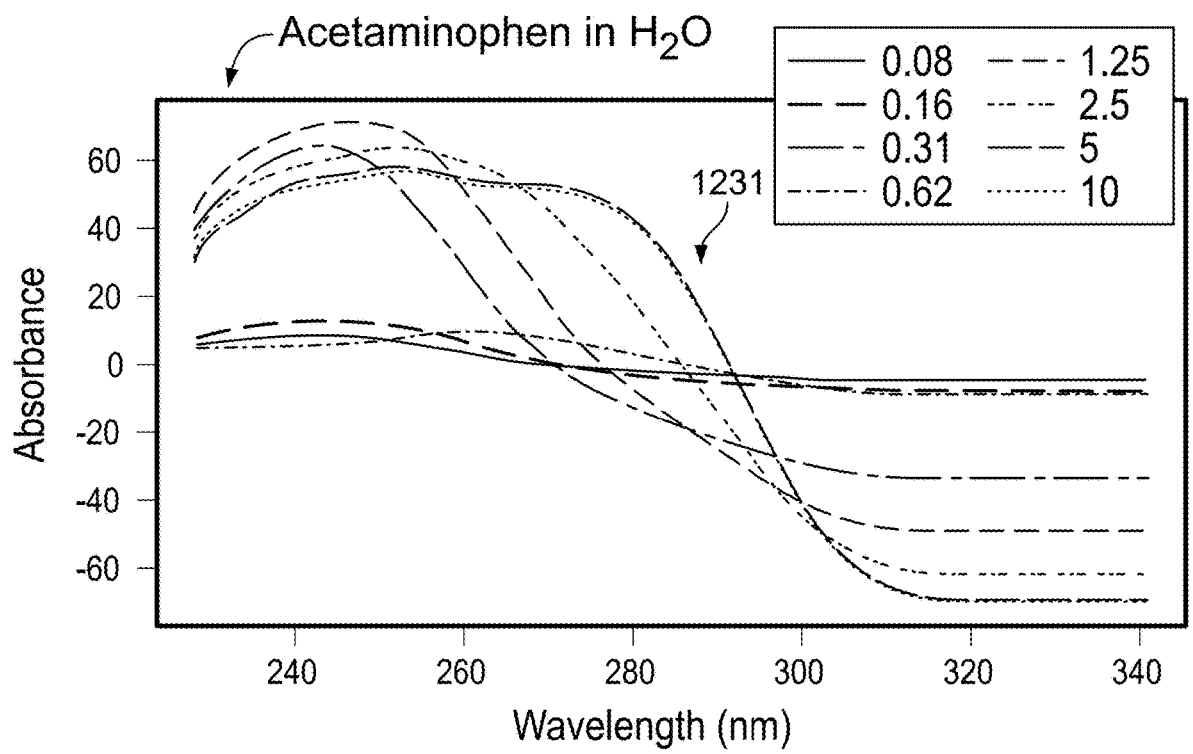
FIGS. 40A-40D show spectra.
Figure 40B:
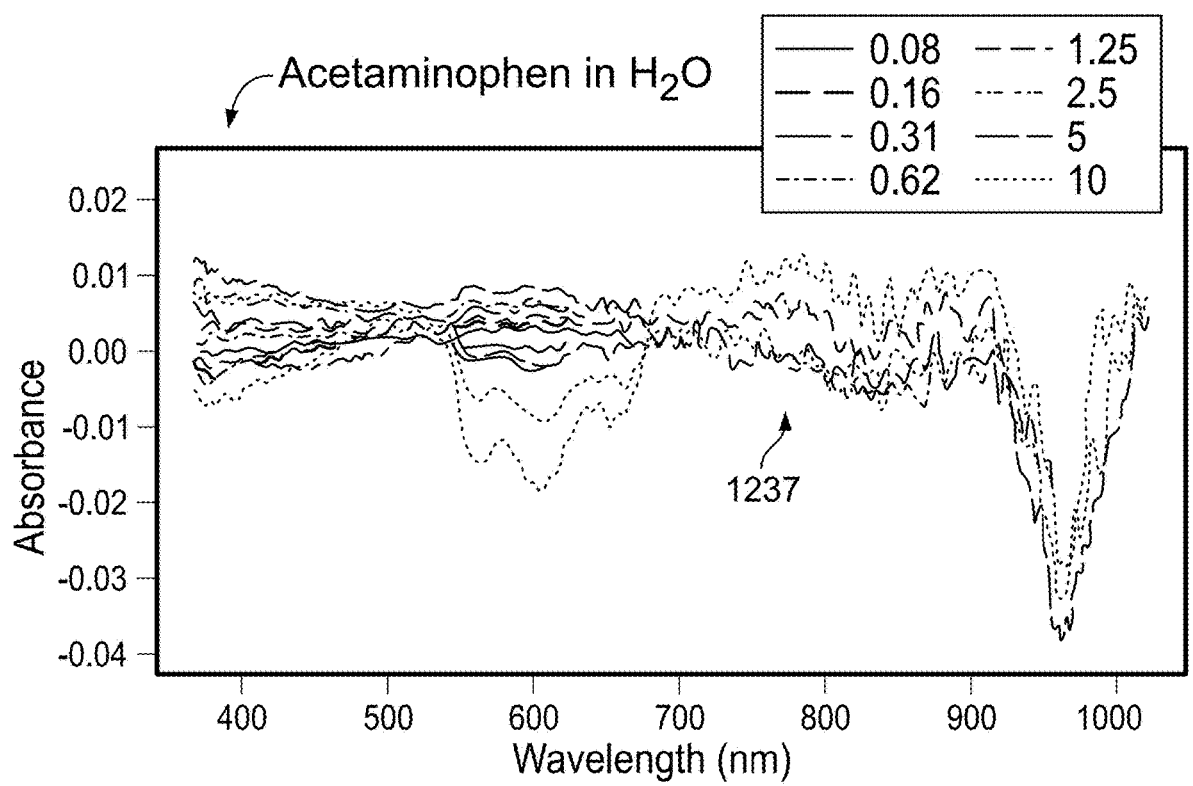
Figure 40C:
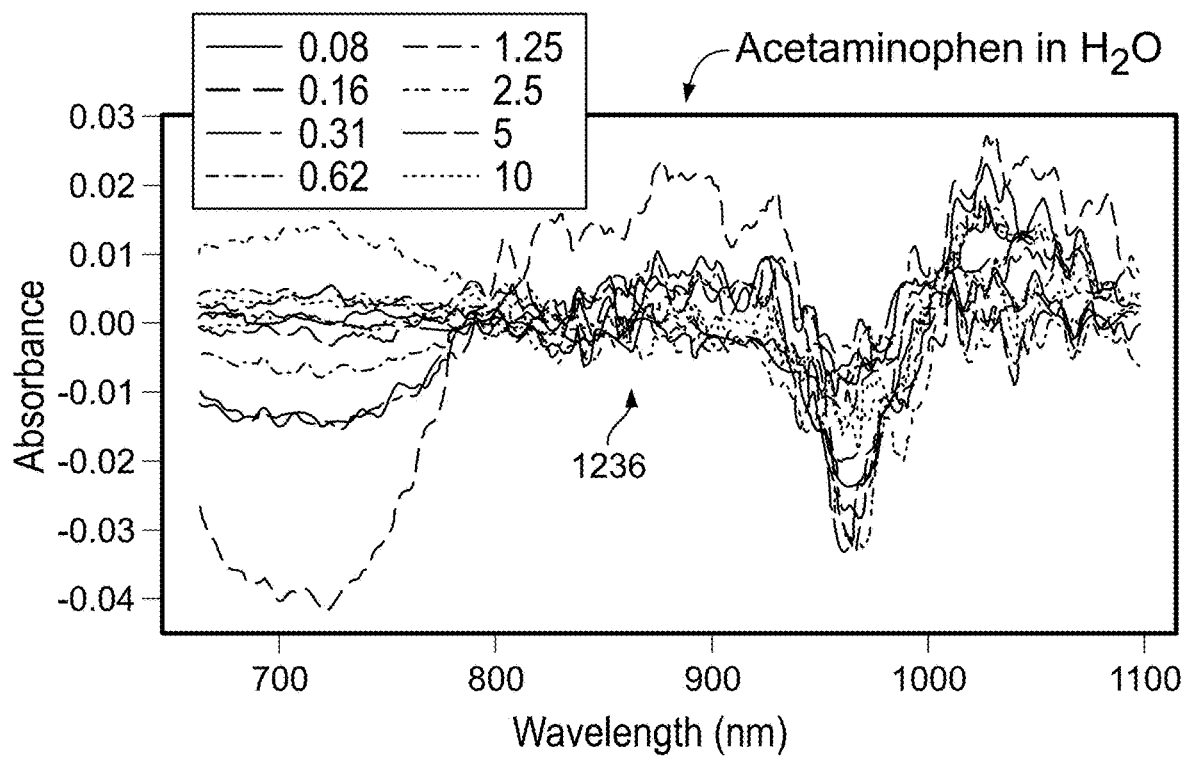
Figure 40D:
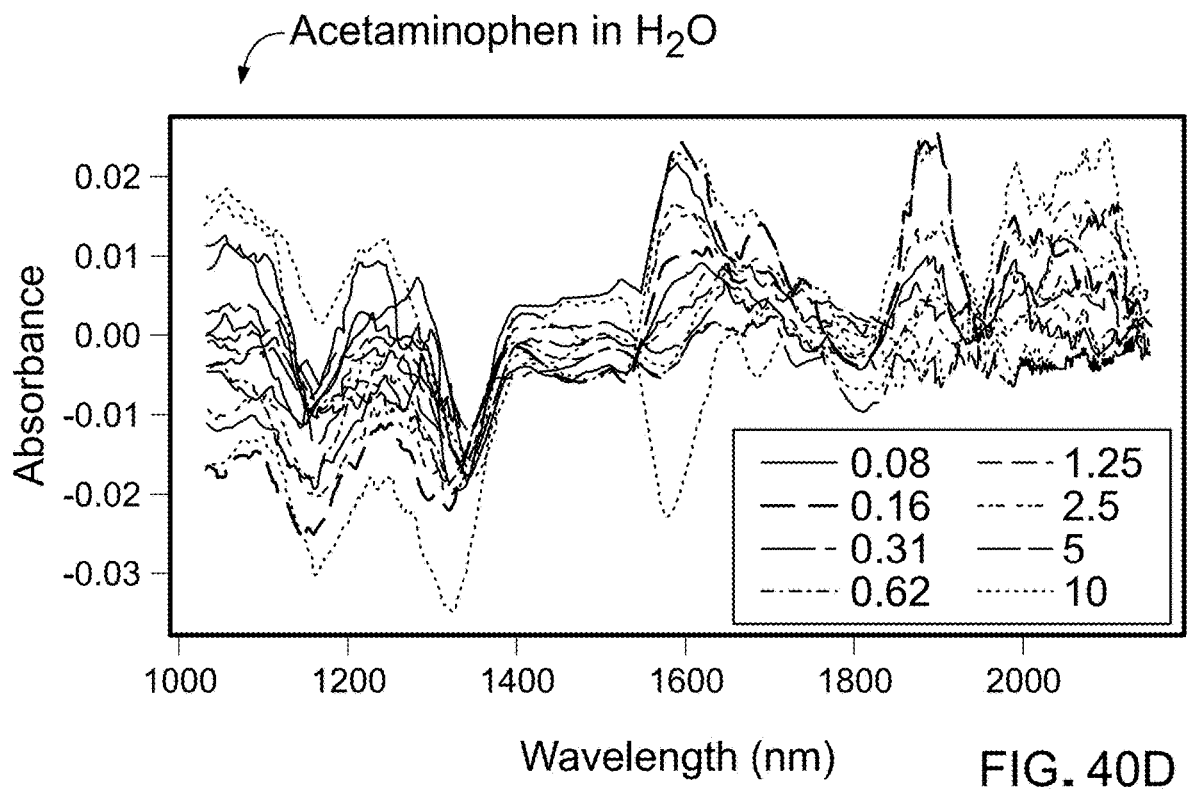
Figure 42A:
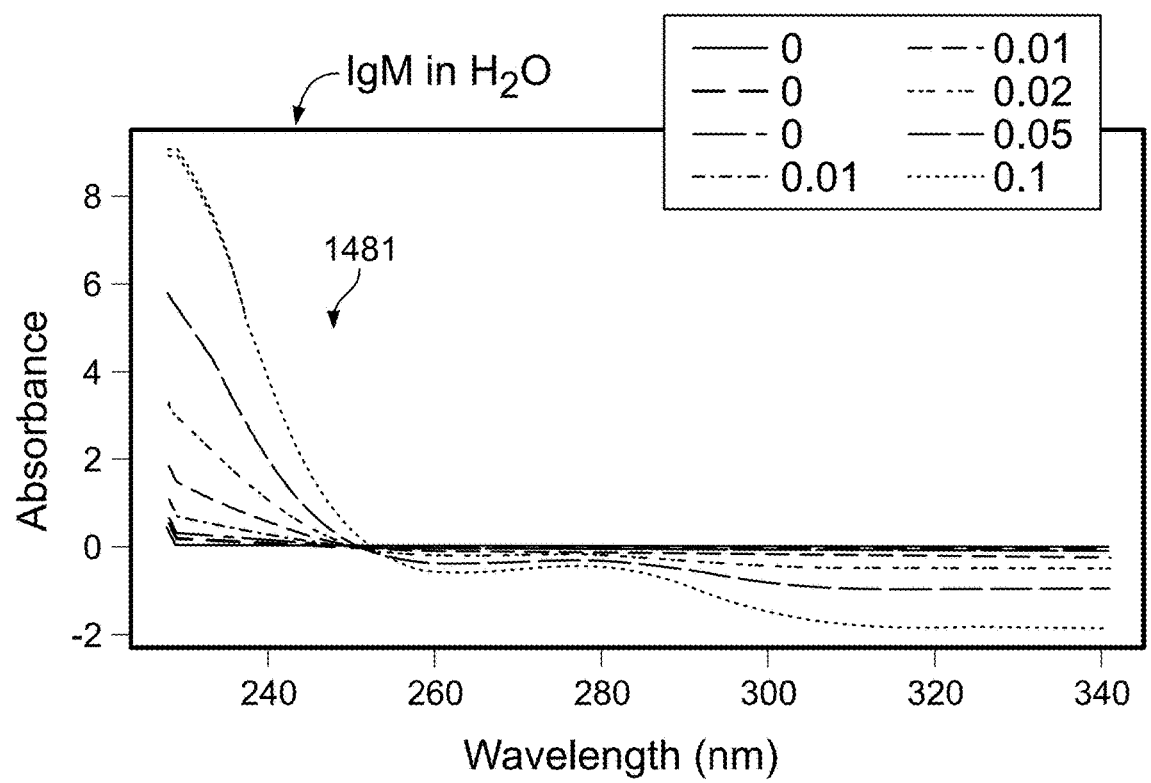
FIGS. 42A-42D show spectra.
Figure 42B:
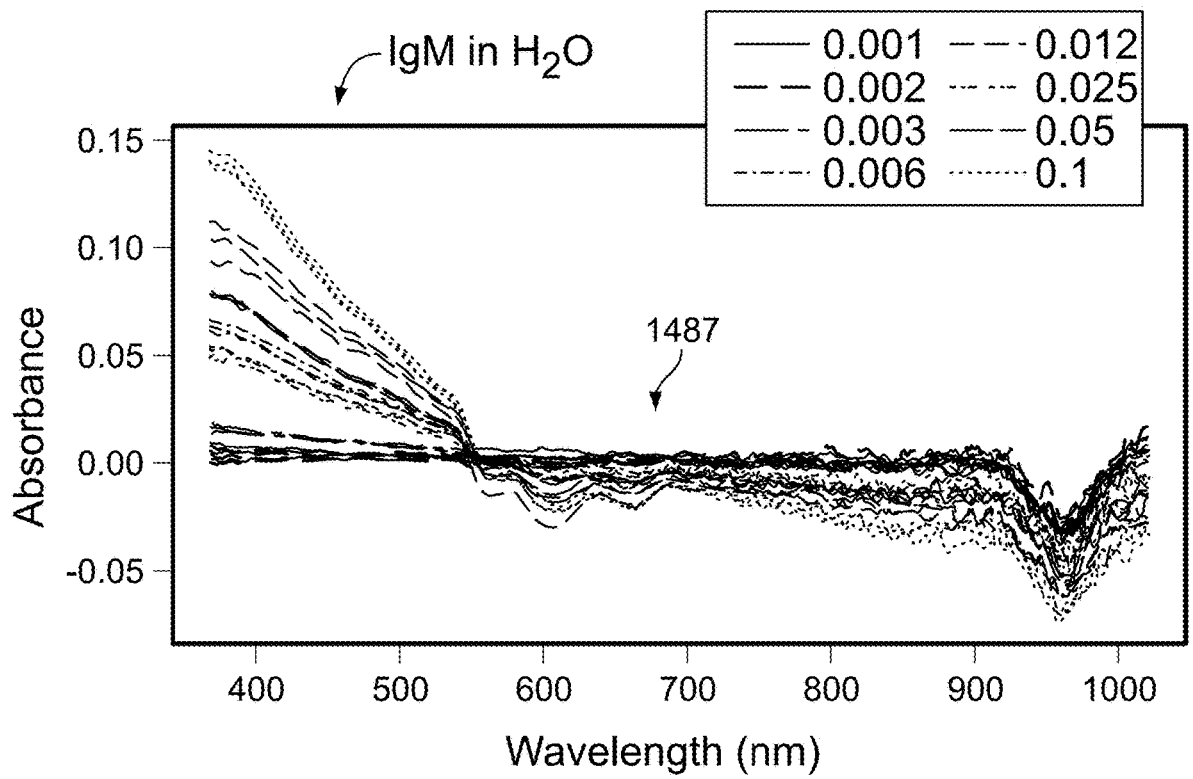
Figure 42C:
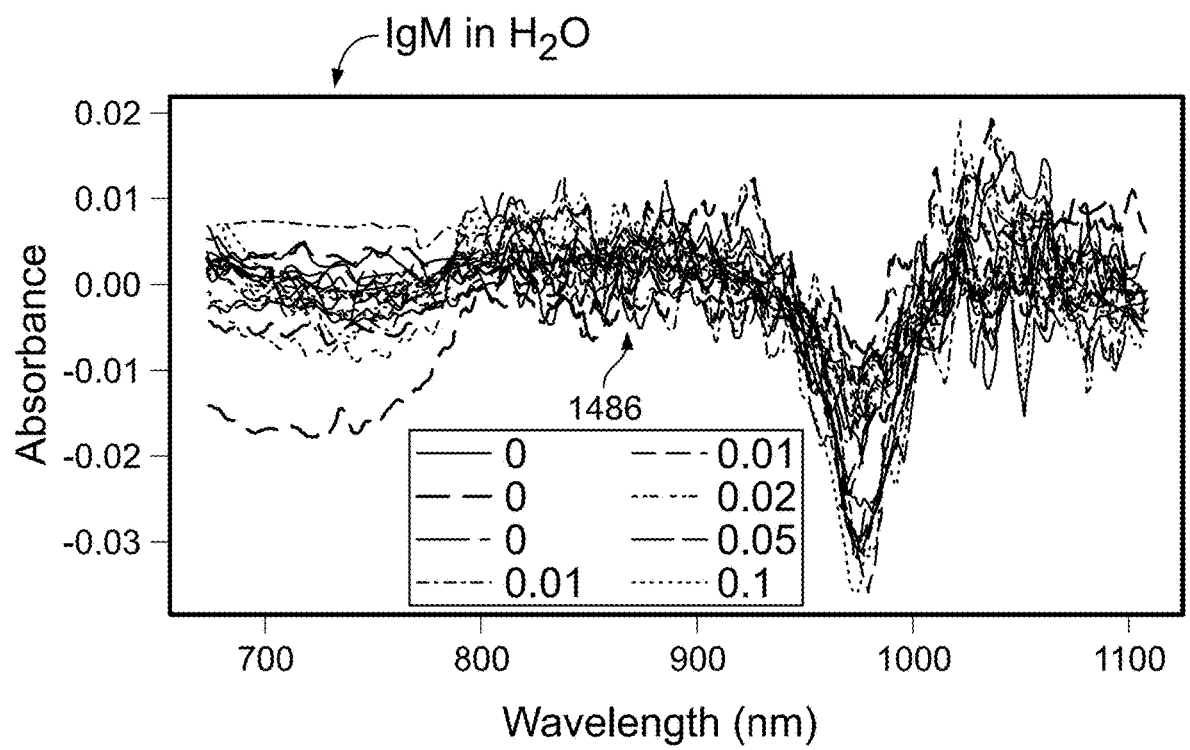
Figure 42D:
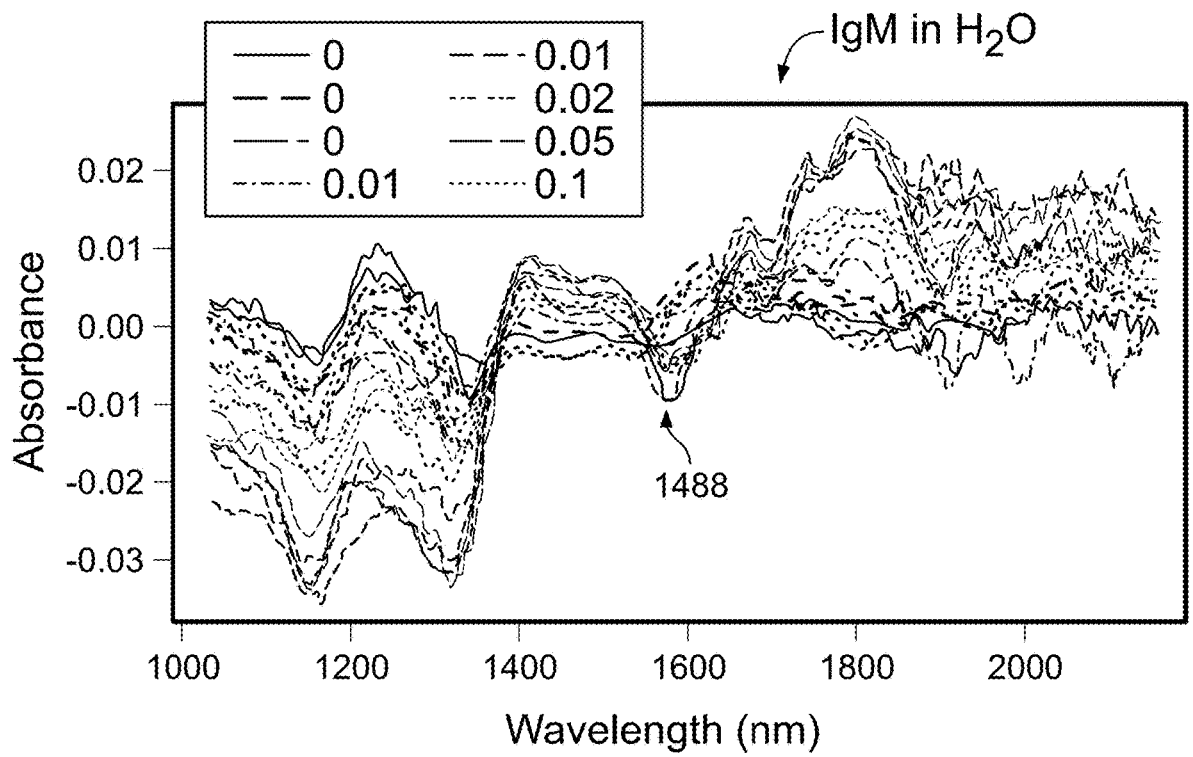
Figure 43A:
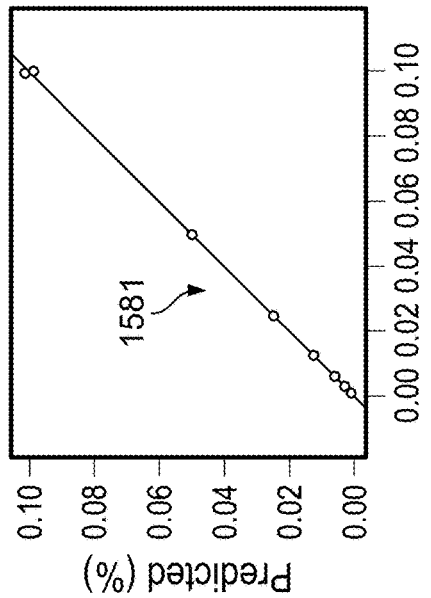
FIGS. 43A-43D illustrate results of predictions based on a model.
Figure 43B:
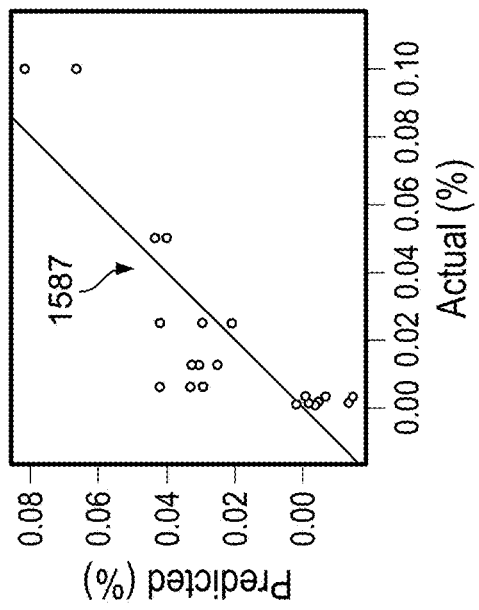
Figure 43C:
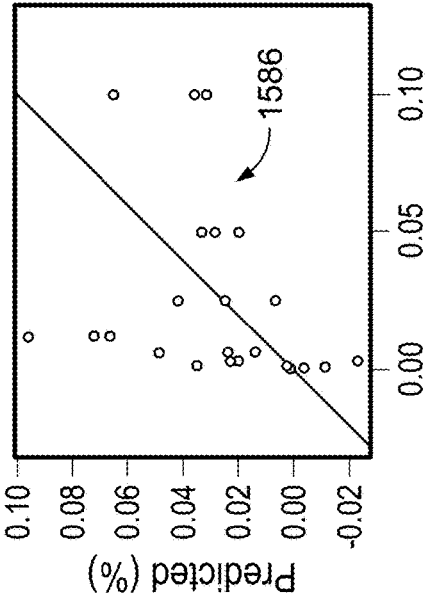
Figure 43D:
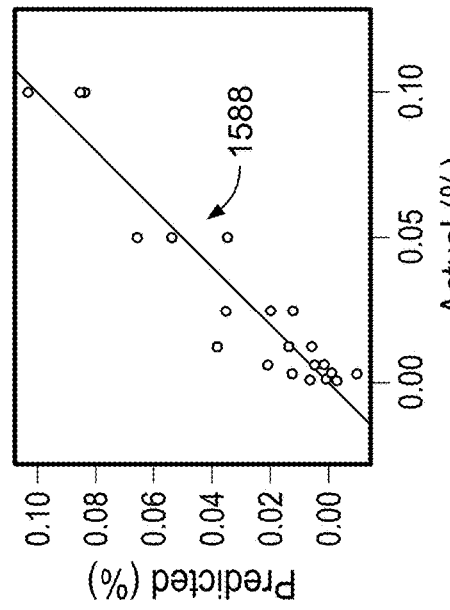
Figure 44A:
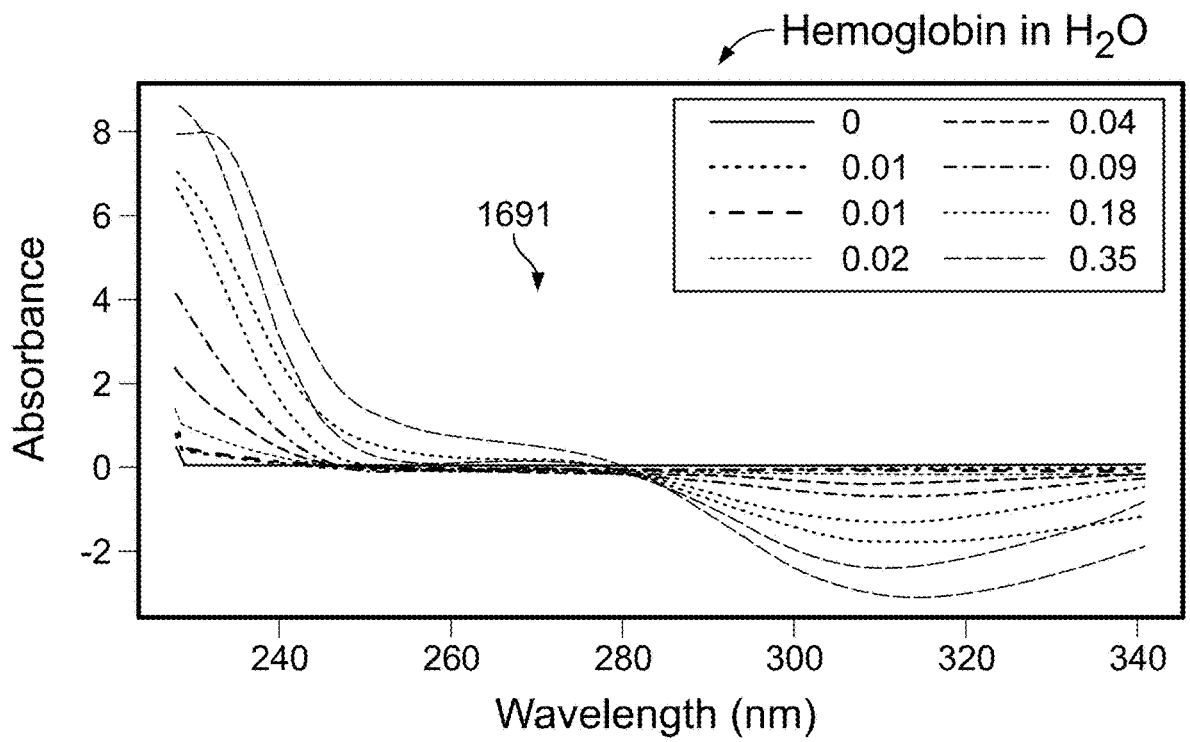
FIGS. 44A-44D show spectra.
Figure 44B:
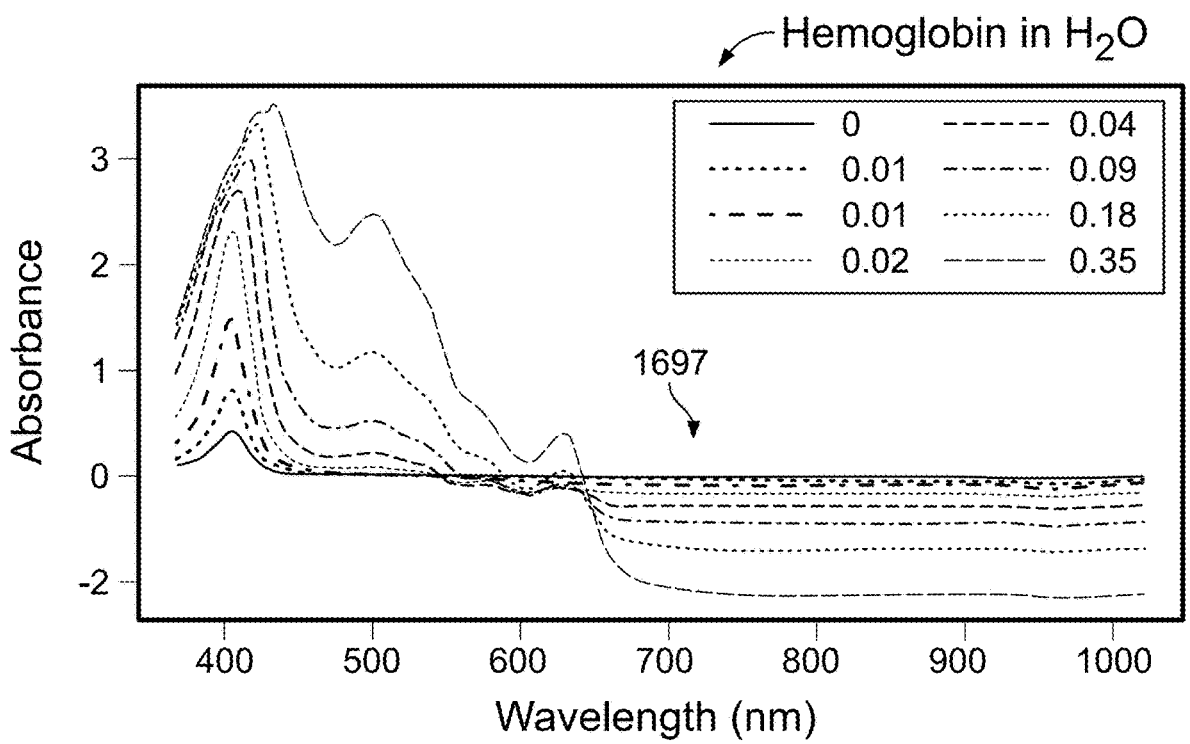
Figure 44C:
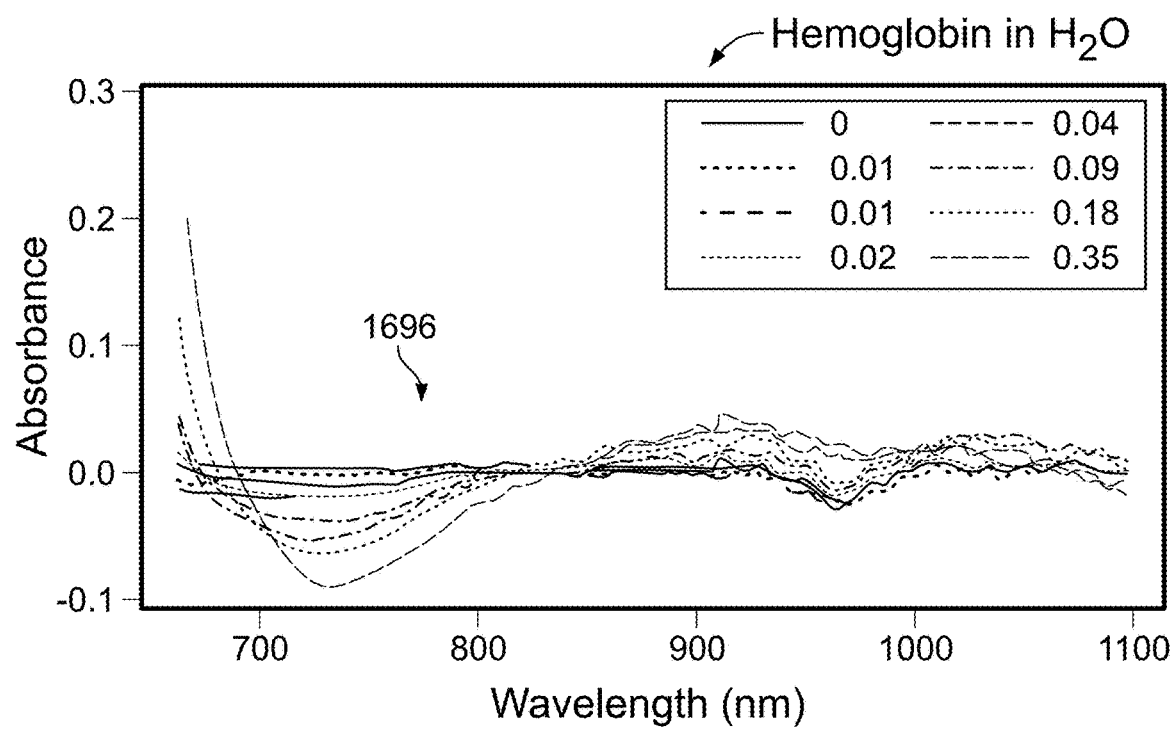
Figure 44D:
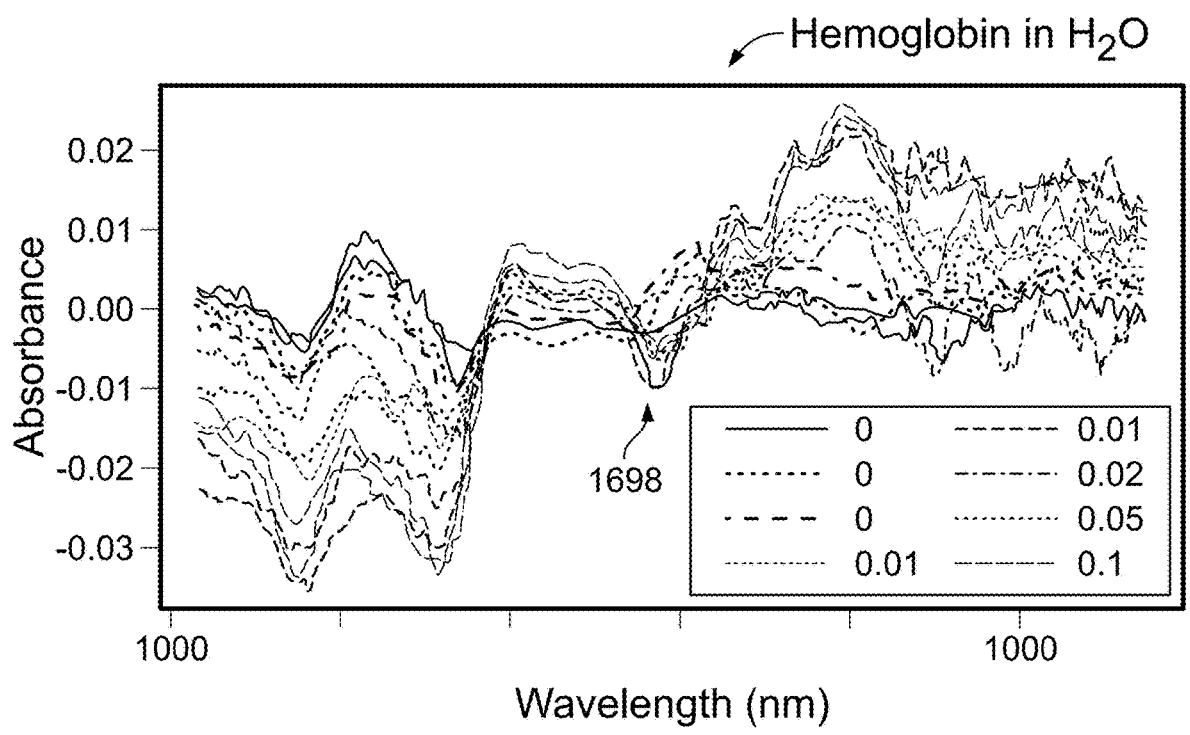
Figure 45A:
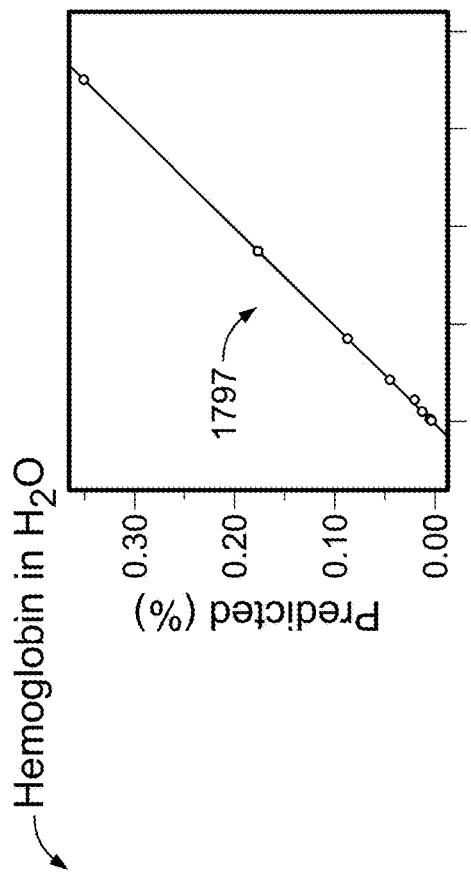
Figure 45B:
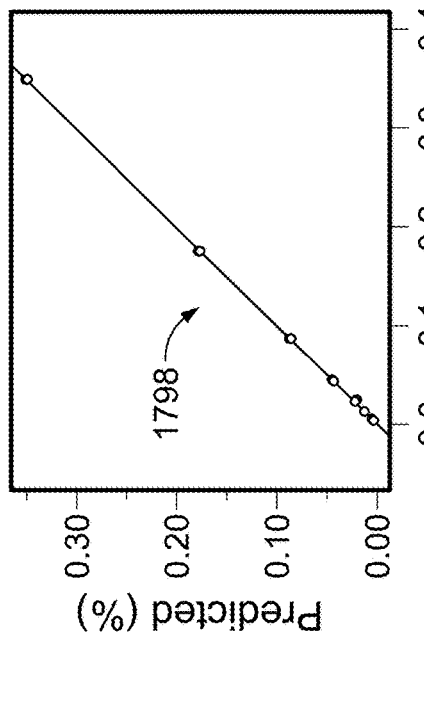
Figure 45C:
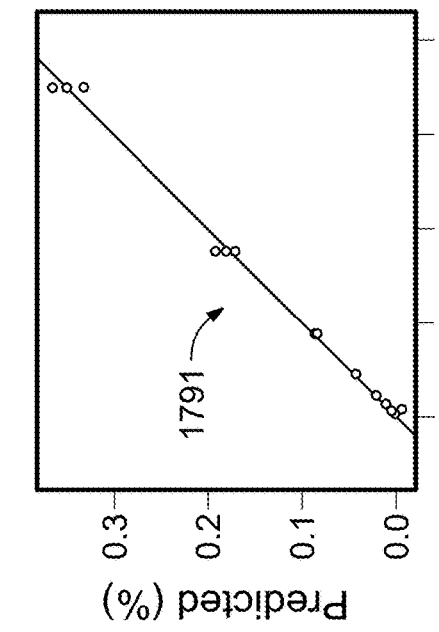
Figure 45D:
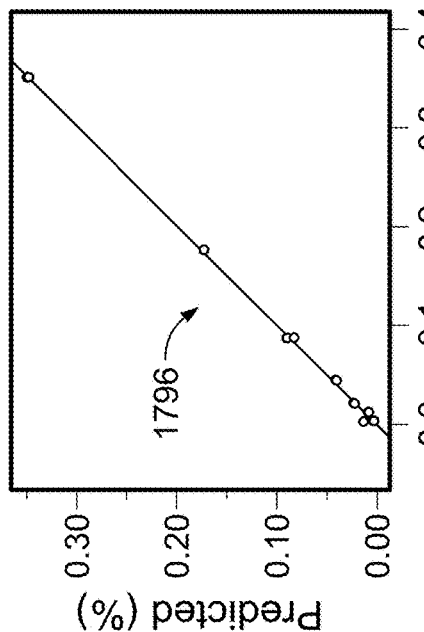

FIGS. 37A-37D show sets of spectra of light transmitted through solutions of coated and uncoated Ibuprofen, Acetaminophen and ACE inhibitor in water, where each set of transmission spectra corresponds to a respective drug. FIG. 37D shows sets of spectra of light transmitted through solutions of coated and uncoated Ibuprofen, and Acetaminophen in water, where each set of transmission spectra corresponds to a respective drug. The transmission spectra shown in FIG. 37A were acquired with Benchtop spectrometer #4. The transmission spectra shown in FIG. 37B were acquired with Benchtop spectrometer #5. The transmission spectra shown in FIG. 37C were acquired with Benchtop spectrometer #2. The transmission spectra shown in FIG. 37D were acquired with Benchtop spectrometer #3. The transmission spectra shown in FIGS. 37B-37D correspond to nine spectra per analyte, in the following manner: three spectra per sample, and three samples per analyte.

Note that as the transmission spectroscopy was performed with the Benchtop spectrometer #4 is over the UV spectral range, each of the sample holding cuvettes had an optical path thickness of 1 mm. Also note that in addition to acquiring the transmission spectra corresponding to the above-noted solutions of coated and uncoated Ibuprofen, Acetaminophen, and ACE inhibitor in water, spectra of light transmitted through plain water were also acquired. The transmission spectra corresponding to the water samples also are shown in FIG. 36A for reference purposes. The transmission spectra shown in FIG. 36A correspond to three spectra per analyte, in the following manner: three spectra per sample, and one sample per analyte.

Preprocessing methods included (i) mean correction (MC), (ii) standard normal variate (SNV), and (iii) Savitzy-Golay 1st derivative (SG), to smooth the raw spectral data to obtain the spectra used to perform classification analyses. For example, the reflection spectra shown in FIGS. 36A-36C was preprocessed using the mean correction method. As another example, the transmission spectra shown in FIGS. 37A-37D was preprocessed using the SNV method.

The above-noted analytes, i.e., drugs, cellulose, and water, were identified (see below) by performing classification analyses on the reflection spectra shown in FIGS. 36A-36C, and separately on the transmission spectra shown in FIGS. 37A-37D. Examples of classification analyses that were been performed as part of this study are k-means clustering analysis, k-nearest neighbors analysis, principal component analysis (PCA), and support vector machine (SVM) analysis. It was found that the best classification performance was provided by the k-nearest neighbors analysis.

Figure 35C:
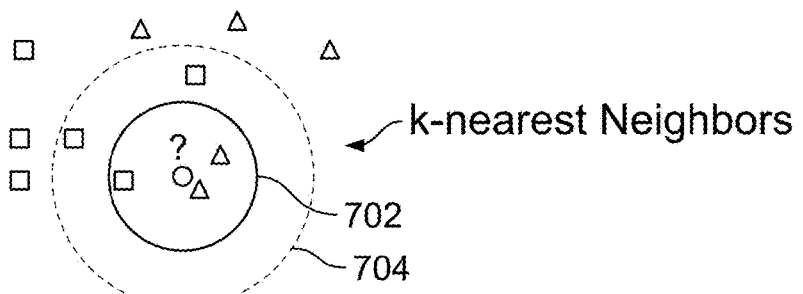
FIG. 35C illustrates a nearest neighbors analysis.

Referring now to FIG. 35C, an example of k-nearest neighbors analysis is shown in which a spectrum corresponding to an unknown analyte has a particular "location" in the analysis' parameter space. The particular location of the spectrum corresponding to the unknown analyte is represented here by a full circle. This spectrum has similar parameters with k other spectra (referred to as the k nearest-neighbor spectra), some of which corresponding to analytes known to be of a first type (or first class), and the remaining of which corresponding to an analyte known to be of a second type (or second class). Here, a location of a spectrum corresponding to an analyte of the first type is represented by a square, and a location of a spectrum corresponding to an analyte of the second type is represented by a triangle. The degree of similarity is represented by a radius of a "k nearest-neighbor circle" in the analysis' parameter space, which is centered at the location of the spectrum corresponding to an unknown analyte and encompasses k nearest-neighbor spectra. As such, the unknown analyte will be classified as (i) an analyte of the first type if the k nearest-neighbor circle encompasses more squares than triangles, or (ii) an analyte of the second type if the k nearest-neighbor circle encompasses more triangles than squares. Note that the outcome of the classification of an unknown analyte depends on the value of k, i.e., the actual number spectra being considered to be similar to the spectrum of the unknown analyte. In the example illustrated in FIG. 35C, the unknown analyte will be classified as an analyte of the first type if 3-nearest neighbors are used for classification, as bound by the inner circle 702. However, the unknown analyte will be classified as an analyte of the second type if 5-nearest neighbors are used for classification, as bound by the inner circle 704.

As part of the training stage of a classification analysis, the number k of nearest neighbors can be optimized to obtain a most accurate classification of a training set of spectra of analytes of known types. For example, the reflection spectra shown in FIGS. 36A-36C and the transmission spectra shown in FIGS. 37B-37D were used to perform a 4-nearest neighbors analysis. Analyses based on different numbers of nearest neighbors were explored using the foregoing spectra, however, k=4 was found to provide the best performance. As another example, the transmission spectra shown in FIG. 37A were used to perform a 1-nearest neighbor analysis. Analyses based on different numbers of nearest neighbors were explored using the transmission spectra shown in FIG. 37A, however, k=1 was found to provide the best performance.

Referring again to the reflection spectra shown in FIGS. 36A-36C, the first out of eight total spectra corresponding to water was used as a reference spectrum of the 4-nearest neighbors classification analysis. The first 18 out of a total of 30 spectra corresponding to each drug, and the next 5 out of 8 total spectra corresponding to water were used as a training set of the 4-nearest neighbors classification analysis. The last 12 out of the total of 30 spectra corresponding to each drug, and the last 2 out of 8 total spectra corresponding to water were used as a test set of the 4-nearest neighbors classification analysis. The results of the classification analysis performed using the reflection spectra shown in FIGS. 36A-36C are summarized in Table 16.

TABLE 16

| Benchtop spectrometer # | Pre-Processing | Analytes | | | | | |
|---|---|---|---|---|---|---|---|
| | | Coated ibuprofen | Uncoated ibuprofen | Acetaminophen | Cellulose | ACE inhibitor | Water |
| 5 | MC | 12/12 | 12/12 | 11/12 | 12/12 | 12/12 | 6/6 |
| | SNV | 10/12 | 12/12 | 12/12 | 12/12 | 12/12 | 5/6 |
| | SG | 5/12 | 8/12 | 11/12 | 12/12 | 12/12 | 6/6 |

TABLE 16-continued

| Benchtop spectrometer # | Pre-Processing | Analytes | | | | | |
|---|---|---|---|---|---|---|---|
| | | Coated ibuprofen | Uncoated ibuprofen | Acetaminophen | Cellulose | ACE inhibitor | Water |
| 2 | MC | 5/12 | 9/12 | 12/12 | 10/12 | 12/12 | 6/6 |
| | SNV | 2/12 | 6/12 | 11/12 | 11/12 | 12/12 | 4/6 |
| | SG | 2/12 | 5/12 | 12/12 | 1/12 | 12/12 | 6/6 |
| 3 | MC | 11/12 | 7/12 | 12/12 | 10/12 | N/A | 4/6 |
| | SNV | 11/12 | 5/12 | 12/12 | 10/12 | N/A | 1/6 |
| | SG | 8/12 | 10/12 | 12/12 | 11/12 | N/A | 6/6 |

In Table 16, 11/12 means 11 out of 12 spectra produced correct classification results. The above results suggest that reflectance spectra shown in FIG. 36A, which were acquired using the Benchtop spectrometer #5, produce the most accurate classifications, and reflectance spectra shown in FIG. 36B, which were acquired using the Benchtop spectrometer #2, produce the least accurate classifications. Also note that the classifications that used reflectance spectra shown in FIG. 36C, which were acquired using the Benchtop spectrometer #3, cannot differentiate between coated and uncoated ibuprofen. The latter result could be because the difference caused by the reddish brown coating is only notable in visible wavelengths available to the Benchtop spectrometer #5. The results summarized in Table 16 also suggest that the reflectance spectra produced by smoothing raw spectral data based on a mean correction preprocessing technique can be used to perform more accurate classification analyses that if spectra produced based on the other two preprocessing techniques were applied to the raw spectral data.

As such, the results summarized in Table 16 also indicate that the reflectance spectra shown in FIGS. 36A-36C can be used in classification analyses to accurately classify Acetaminophen, ACE Inhibitor and Microcrystalline cellulose. In general, a larger training set can make such classification analyses even more robust. However, the less accurate classification of the coated and uncoated ibuprofen can be because their corresponding spectral data is representative of filler materials in the drugs, particularly dyes, as the drug itself is a fraction of the total pill mass. This explanation also suggests that the classification of these drugs could be manufacturing dependent.

It was shown in Table 16 that drugs and other related analytes can be correctly classified based on analyses that use reflectance spectra, like the ones shown in FIGS. 36A-36C, which span a wavelength range that is accessible to a Si detector. Such a Si detector could be used as the sensor of an inexpensive, miniature spectrometer to be integrated in an ingestible device as described herein. Moreover, additional experiments may be performed to determine how well classification analyses would perform if they were to use reflectance spectra corresponding to mixtures having drugs and other components as would be seen in the small intestine or with a wider range of drugs.

Referring now to the transmission spectra shown in FIGS. 37B-37D, the first out of 3 total spectra corresponding to water was used as a reference spectrum of the 4-nearest neighbors classification analysis. The first 6 out of a total of 9 spectra corresponding to each drug were used as a training set of the 4-nearest neighbors classification analysis. The last 3 out of the total of 9 spectra corresponding to each drug were used as a test set of the 4-nearest neighbors classification analysis. The results of the classification analysis performed using the transmission spectra shown in FIGS. 37B-37D are summarized in Table 17.

TABLE 17

| Benchtop spectrometer # | Pre-processing | Drugs | | | |
|---|---|---|---|---|---|
| | | Coated ibuprofen | Uncoated ibuprofen | Acetaminophen | ACE inhibitor |
| 5 | MC | 3/3 | 3/3 | 3/3 | 2/3 |
| | SNV | 3/3 | 3/3 | 3/3 | 3/3 |
| | SG | 3/3 | 3/3 | 3/3 | 2/3 |
| 2 | MC | 3/3 | 3/3 | 3/3 | 3/3 |
| | SNV | 3/3 | 3/3 | 3/3 | 3/3 |
| | SG | 1/3 | 2/3 | 0/3 | 2/3 |
| 3 | MC | 3/3 | 3/3 | 3/3 | N/A |
| | SNV | 2/3 | 3/3 | 3/3 | N/A |
| | SG | 3/3 | 3/3 | 3/3 | N/A |

In Table 17, 2/3 means 2 out of 3 spectra produced correct classification results.

Referring now to the transmission spectra shown in FIG. 37A, the first out of 3 total spectra corresponding to water was used as a reference spectrum of the 1-nearest neighbor classification analysis. The first 2 out of a total of 3 spectra corresponding to each analyte were used as a training set of the 1-nearest neighbors classification analysis. The last 1 or 2 out of the total of 3 spectra corresponding to each drug were used as a test set of the 1-nearest neighbors classification analysis. The results of the classification analysis performed using the transmission spectra shown in FIG. 37A are summarized in Table 18.

TABLE 18

| Benchtop spectrometer # | Pre-Processing | Analytes | | | | |
| --- | --- | --- | --- | --- | --- | --- |
| | | Coated ibuprofen | Uncoated ibuprofen | Acetaminophen | ACE inhibitor | Water |
| 4 | MC | 1/1 | 1/1 | 1/1 | 1/2 | 1/1 |
| | SNV | 1/1 | 1/1 | 1/1 | 1/1 | 1/1 |
| | SG | 1/1 | 1/1 | 1/1 | 1/2 | 1/1 |

In Table 18, 1/2 means 1 out of 2 spectra produced correct classification results.

The results summarized above in Tables 17 and 18 suggest that transmission spectra which were acquired with any one of the Benchtop spectrometers #4, #5, #2 and #3 can be used to produce accurate classification analysis results. The results summarized in Tables 17 and 18 also suggest that the transmission spectra produced by smoothing raw spectral data based on both the mean correction preprocessing technique and the SNV preprocessing technique can be used to perform accurate classification analyses. As such, the results summarized in Tables 17 and 18 also indicate that the transmission spectra shown in FIGS. 37A-37D can be used in classification analyses to accurately classify the above noted drugs.

Although the above drug-classification analyses used spectroscopic data acquired with benchtop spectrometers, these results demonstrate feasibility of performing similarly accurate classification analyses that use spectra acquired with an ingestible device as described herein, which includes a low-cost, miniature spectrometer, to identify certain drugs in the GI tract. Determining concentration of at least some of the identified drugs will be described next.

Example 12: Spectroscopy Used for Quantifying Drugs

Spectroscopy was performed with benchtop spectrometers from Tables 2, 10 and 13 in transmission mode, for determining the concentration of various anti-inflammatory drugs dissolved in water.

Some test samples included solutions of Ibuprofen having various concentrations. Ibuprofen powder (Sigma 11892) was dissolved in water directly in cuvettes having an optical path thickness of 10 mm. These solutions had Ibuprofen concentrations varying in the range of 0.1-10% (w/v). Other test samples included solutions of Acetaminophen having various concentrations. Acetaminophen powder (Sigma A5000) was dissolved in water directly in cuvettes having an optical path thickness of 10 mm. These solutions had Acetaminophen concentrations varying in the range of 0.1-10% (w/v). Note that Acetaminophen appears to have limited solubility in water. The foregoing Ibuprofen and Acetaminophen samples were used for transmission-mode spectroscopy performed on each one of the Benchtop spectrometers #5, #2 and #3. Solutions of the same drugs were transferred to cuvettes having an optical path thickness of 1 mm when transmission-mode spectroscopy has been performed on the Benchtop spectrometers #4.

FIGS. 38A-38D show spectra of light transmitted through solutions of Ibuprofen in water, where each transmission spectrum corresponds to a respective Ibuprofen concentration (in % w/v). The transmission spectra 1021 shown in FIG. 38A was acquired with Benchtop spectrometer #4. The transmission spectra 1027 shown in FIG. 38B was acquired with Benchtop spectrometer #5. The transmission spectra 1026 shown in FIG. 38C was acquired with Benchtop spectrometer #2. The transmission spectra 1028 shown in FIG. 38D was acquired with Benchtop spectrometer #3. Note that at least the transmission spectra 1021 that cover the UV wavelength range and the transmission spectra 1028 that cover the long-NIR wavelength range have spectral features that are concentration dependent.

The transmission spectra shown in FIGS. 38A-38D corresponding to Ibuprofen solutions were preprocessed using a moving average filter and a mean correction. Moreover, a subset of the acquired transmission spectra shown in FIGS. 38A-38D were used as training inputs for machine learning modeling, e.g., machine learning modeling that uses a partial least squares (PLS) algorithm. Once this PLS-based model is trained in this manner, it can be used to predict the concentration of Ibuprofen of a solution to which one of the acquired spectra corresponds. As such, an unknown Ibuprofen concentration for a solution having an acquired spectrum can be determined by (i) identifying one of a number of spectra corresponding to solutions having known concentrations of Ibuprofen that best matches the acquired spectrum, and (ii) assigning to the unknown concentration a value of the Ibuprofen concentration for the solution to which the identified spectrum corresponds.

FIGS. 39A-39D show results 1121, 1127, 1126, 1128 of a PLS-based model for predicting concentration of Ibuprofen in water. Here, the result 1121/1127/1126/1128 represents a correlation between the estimated and known concentrations of Ibuprofen, where the spectra used to determine this correlation were acquired with the respective Benchtop spectrometer #4/#5/#2/#3, as listed in Tables 2, 10 and 13.

Respective values of model performance metrics for Ibuprofen concentration-prediction models having results summarized in FIGS. 39A-39D are listed in Table 19.

TABLE 19

| | Ibuprofen | |
| --- | --- | --- |
| Spectrometer | Result | RMSECV (%) |
| Benchtop #4 | 1121 | 0.1 |
| Benchtop #5 | 1127 | 1 |
| Benchtop #2 | 1126 | 1 |
| Benchtop #3 | 1128 | 0.2 |

Here, a performance metric called root mean square error of cross-validation (RMSECV) is a measure of model performance. The closer the points are disposed to the line with slope=1, i.e., the smaller the spread of the points relative to the line with slope=1, the smaller the RMSECV value and the better the model performance. The model performance summarized in Table 19 indicates that transmission spectra 1021, 1028 shown in FIG. 38A, FIG. 38D, respectively, when used with the above-noted PLS-based model, cause more accurate predictions for unknown Ibuprofen concentrations than if the model uses the transmission spectra 1027, 1026 shown in FIGS. 38B, 38C, respectively. This may be due to the fact that there were more distinct spectral differences in the UV and long-NIR wavelength range for the noted Ibuprofen concentration range.

FIGS. 40A-40D show spectra of light transmitted through solutions of Acetaminophen in water, where each transmission spectrum corresponds to a respective Acetaminophen concentration (in % w/v). The transmission spectra 1231 shown in FIG. 40A were acquired with Benchtop spectrometer #4. The transmission spectra 1237 shown in FIG. 40B were acquired with Benchtop spectrometer #5. The transmission spectra 1236 shown in FIG. 40C were acquired with Benchtop spectrometer #2. The transmission spectra 1238 shown in FIG. 40D were acquired with Benchtop spectrometer #3.

The transmission spectra shown in FIGS. 40A-40D corresponding to Acetaminophen solutions were preprocessed using a moving average filter and a mean correction. Moreover, a subset of the acquired transmission spectra shown in FIGS. 40A-40D were used as training inputs for machine learning modeling, e.g., machine learning modeling that uses a PLS algorithm. Once this PLS-based model is trained in this manner, it can be used to predict the concentration of Acetaminophen of a solution to which one of the acquired spectra corresponds. As such, an unknown Acetaminophen concentration for a solution having an acquired spectrum can be determined by (i) identifying one of a number of spectra corresponding to solutions having known concentrations of Acetaminophen that best matches the acquired spectrum, and (ii) assigning to the unknown concentration a value of the Acetaminophen concentration for the solution to which the identified spectrum corresponds.

FIGS. 41A-41D show results 1331, 1337, 1336, 1338 of a PLS-based model for predicting concentration of Acetaminophen in water. Here, the result 1331/1337/1336/1338 represents a correlation between the estimated and known concentrations of Acetaminophen, where the spectra used to determine this correlation were acquired with the respective Benchtop spectrometer #4/#5/#2/#3, as listed in Tables 2, 10 and 13.

Respective values of model performance metrics for the Acetaminophen concentration-prediction models having results summarized in FIGS. 41A-41D are listed in Table 20.

TABLE 20

| Acetaminophen | | |
|---|---|---|
| Spectrometer | Result | RMSECV (%) |
| Benchtop #4 | 1331 | 1.6 |
| Benchtop #5 | 1337 | 2.3 |
| Benchtop #2 | 1336 | 4 |
| Benchtop #3 | 1338 | 1.6 |

Here, the metric RMSECV was used as a measure of model performance. The model performance summarized in Table 20 indicates that transmission spectra corresponding to Acetaminophen solutions shown in FIGS. 40A-40D was used by PLS-based models to predict unknown Acetaminophen concentrations. This may be due to the above-noted poor solubility of Acetaminophen in water.

The experiments summarized as part of Example 12 demonstrate feasibility of using an ingestible device as described herein, which includes a low-cost, miniature spectrometer for acquiring, within the GI tract of a subject, transmission spectra corresponding to anti-inflammatory drugs ingested by the subject. As such, the transmission spectra can be used to determine the concentration of the anti-inflammatory drugs in the water present in the GI tract of the subject.

Other analytes can be quantified using the techniques described above in Example 12. For instance, quantifying particular proteins, which are typically found in serum, will be described next.

Example 13: Spectroscopy Used for Quantifying Serum-Based Proteins

Spectroscopy was performed with benchtop spectrometers from Tables 2, 10 and 13 in transmission mode, for determining the concentration of various proteins dissolved in water. Specifically, the proteins quantified in Example 13 were Immunoglobulin M (IgM) and Hemoglobin, which typically are found in serum.

Some test samples included solutions of IgM having various concentrations. IgM (Sigma 18135) was dissolved in water directly in cuvettes having an optical path thickness of 10 mm. These solutions had IgM concentrations varying in the range of 0.01-0.1% (w/v). Other test samples include solutions of Hemoglobin having various concentrations. Hemoglobin (Sigma H4131) was dissolved in water directly in cuvettes having an optical path thickness of 10 mm. These solutions had Hemoglobin concentrations varying in the range of 0.01-0.35% (w/v). The foregoing IgM and Hemoglobin samples were used for transmission-mode spectroscopy performed on each one of the Benchtop spectrometers #5, #2 and #3. Solutions of the same serum-based proteins were transferred to cuvettes having an optical path thickness of 1 mm when transmission-mode spectroscopy has been performed on the Benchtop spectrometers #4.

FIGS. 42A-42D show spectra of light transmitted through solutions of IgM in water, where each transmission spectrum corresponds to a respective IgM concentration (in % w/v). The transmission spectra 1481 shown in FIG. 42A were acquired with Benchtop spectrometer #4. The transmission spectra 1487 shown in FIG. 42B were acquired with Benchtop spectrometer #5. The transmission spectra 1486 shown in FIG. 42C were acquired with Benchtop spectrometer #2. The transmission spectra 1488 shown in FIG. 42D were acquired with Benchtop spectrometer #3. Note that the transmission spectra 1481, 1487 have spectral features that are concentration dependent over the UV wavelength range. Additionally, the transmission spectra 1488 also have some spectral features that are concentration dependent over the long-NIR wavelength range.

A subset of the acquired transmission spectra corresponding to IgM solutions shown in FIGS. 42A-42D were used as training inputs for machine learning modeling, e.g., machine learning modeling that uses a PLS algorithm. Once this PLS-based model is trained in this manner, it can be used to predict the concentration of IgM of a solution to which one of the acquired spectra corresponds. As such, an unknown IgM concentration for a solution having an acquired spectrum can be determined by (i) identifying one of a number of spectra corresponding to solutions having known concentrations of IgM that best matches the acquired spectrum, and (ii) assigning to the unknown concentration a value of the IgM concentration for the solution to which the identified spectrum corresponds.

FIGS. 43A-43D show results 1581, 1587, 1586, 1588 of a PLS-based model for predicting concentration of IgM in water. Here, the result 1581/1587/1586/1588 represents a correlation between the estimated and known concentrations of IgM, where the spectra used to determine this correlation were acquired with the respective Benchtop spectrometer #4/#5/#2/#3, as listed in Tables 2, 10 and 13.

Respective values of model performance metrics for IgM concentration-prediction models having results summarized in FIGS. 43A-43D are listed in Table 21.

TABLE 21

| IgM | | |
|---|---|---|
| Spectrometer | Result | RMSECV (%) |
| Benchtop #4 | 1581 | 0 |
| Benchtop #5 | 1587 | 0.02 |
| Benchtop #2 | 1586 | 0.04 |
| Benchtop #3 | 1588 | 0.01 |

Here, the metric RMSECV was used as a measure of model performance. The model performance summarized in Table 21 indicates that transmission spectra 1481, 1488 shown in FIG. 42A, FIG. 42D, respectively, when used with the above-noted PLS-based model, cause more accurate predictions for unknown IgM concentrations than if the model uses the transmission spectra 1487, 1486 shown in FIGS. 42B, 42C, respectively. This may be due to the fact that there are more distinct spectral differences in the UV and long-NIR wavelength range for the noted IgM concentration range.

FIGS. 44A-44D show spectra of light transmitted through solutions of Hemoglobin in water, where each transmission spectrum corresponds to a respective Hemoglobin concentration (in % w/v). The transmission spectra 1691 shown in FIG. 44A were acquired with Benchtop spectrometer #4, the transmission spectra 1697 shown in FIG. 44B were acquired with Benchtop spectrometer #5, the transmission spectra 1696 shown in FIG. 44C were acquired with Benchtop spectrometer #2, and the transmission spectra 1698 shown in FIG. 44D were acquired with Benchtop spectrometer #3. Note that all transmission spectra 1691, 1697, 1696, 1698 have spectral features that are concentration dependent over their respective wavelength ranges. These concentration-dependent spectral features correspond to a chromophore that is part of the Hemoglobin's structure.

A subset of the acquired transmission spectra corresponding to Hemoglobin solutions shown in FIGS. 44A-44D were used as training inputs for machine learning modeling, e.g., machine learning modeling that uses a PLS algorithm. Once this PLS-based model is trained in this manner, it can be used to predict the concentration of Hemoglobin of a solution to which one of the acquired spectra corresponds. As such, an unknown Hemoglobin concentration for a solution having an acquired spectrum can be determined by (i) identifying one of a number of spectra corresponding to solutions having known concentrations of Hemoglobin that best matches the acquired spectrum, and (ii) assigning to the unknown concentration a value of the Hemoglobin concentration for the solution to which the identified spectrum corresponds.

FIGS. 45A-45D show results 1791, 1797, 1796, 1798 of a PLS-based model for predicting concentration of Hemoglobin in water. Here, the result 1791/1797/1796/1798 represents a correlation between the estimated and known concentrations of Hemoglobin, where the spectra used to determine this correlation were acquired with the respective Benchtop spectrometer #4/#5/#2/#3, as listed in Tables 2, 10 and 13.

Respective values of model performance metrics for Hemoglobin concentration-prediction models having results summarized in FIGS. 45A-45D are listed in Table 22.

TABLE 22

| Hemoglobin | | |
|---|---|---|
| Spectrometer | Result | RMSECV (%) |
| Benchtop #4 | 1791 | 0.006 |
| Benchtop #5 | 1797 | 0.001 |
| Benchtop #2 | 1796 | 0.003 |
| Benchtop #3 | 1798 | 0.001 |

Here, the metric RMSECV was used as a measure of model performance. The model performance summarized in Table 22 indicates that that transmission spectra 1691, 1697, 1696, 1698 shown in FIGS. 44A-44D, respectively, when used with the above-noted PLS-based model, cause accurate predictions for unknown Hemoglobin concentrations.

The experiments summarized as part of Example 13 demonstrate feasibility of using an ingestible device as described herein, which includes a low-cost, miniature spectrometer for acquiring, within the GI tract of a subject, transmission spectra corresponding to proteins of the subject's serum. As such, the transmission spectra can be used to determine the concentration of a serum-based protein in the water present in the GI tract of the subject.

Example 14: Mapping Spectral Data Relating to Tissue Excised from GI Tract and Excision Location Spectral analysis was performed, by using spectra of light reflected off tissue samples, the spectra acquired with spectrometers from among the spectrometers from Table 2 or obtained from images acquired with a hyperspectral camera (e.g., the one described in connection with Example 3), for identifying spectral features corresponding to locations of the GI tract from where the tissue has been excised.

Figure 46:
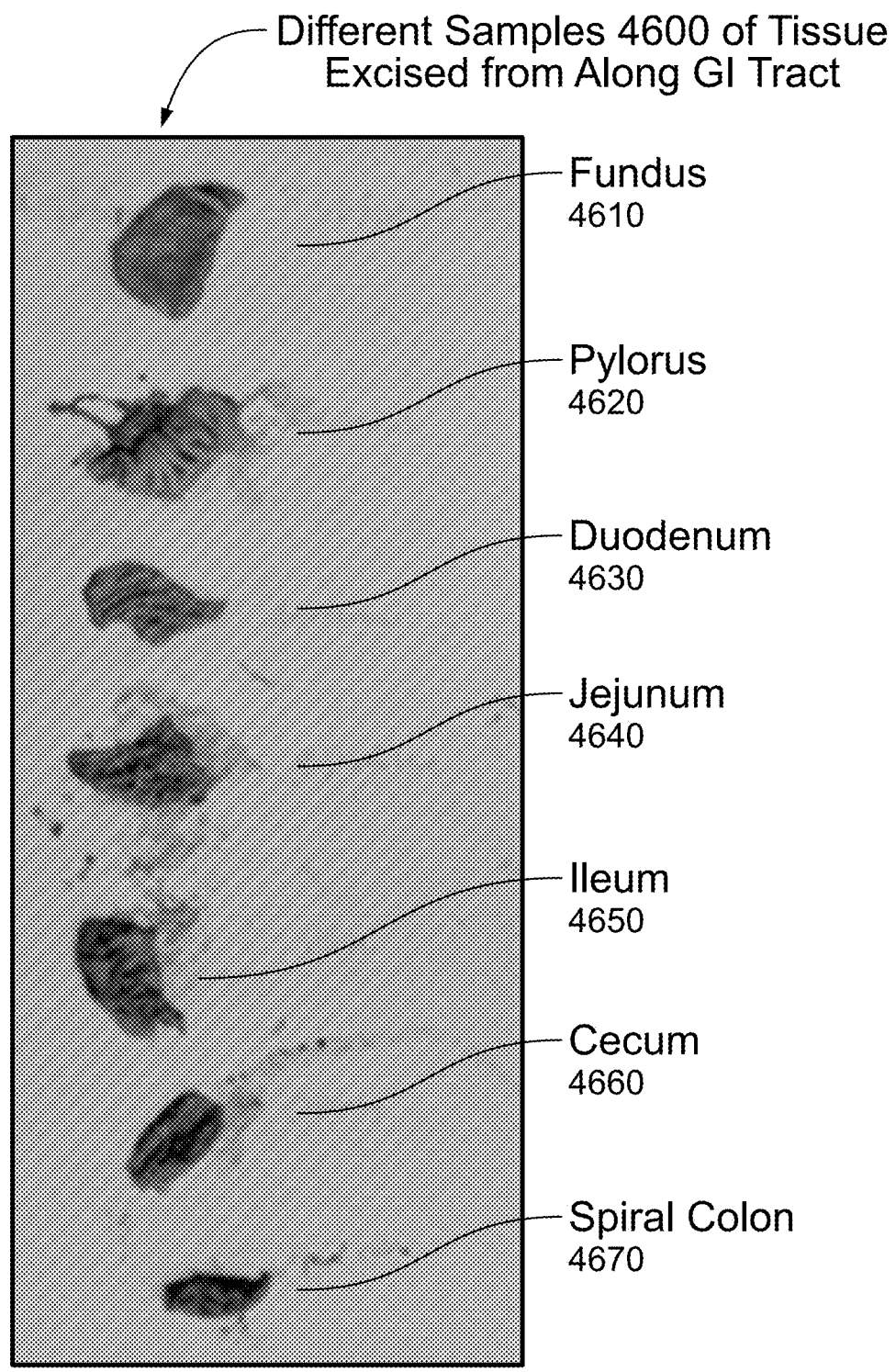
FIG. 46 shows tissue samples for which the tissue has been excised from different regions of the GI tract.

FIG. 46 is a photograph of tissue samples 4600 for which the tissue has been excised from different locations of the GI tract of a live pig. For example, from the stomach, tissue samples included fundus tissue 4610 and pylorus tissue 4620. As another example, from the small intestine, tissue samples included duodenum tissue 4630, jejunum tissue 4640 and ileum tissue 4650. As yet another example, from the large intestine, tissue samples included cecum tissue 4660, spiral colon tissue 4670. Colon tissue was not imaged in FIG. 46. The tissue samples 4600 were prepared from normal tissue. Here, "normal" represents a health condition of the tissue that is different from inflamed or necrotic.

For example, the tissue samples 4600 were used to produce corresponding spectra by performing reflection-mode spectroscopy using Benchtop spectrometers #2 and #3.

Figure 47A:
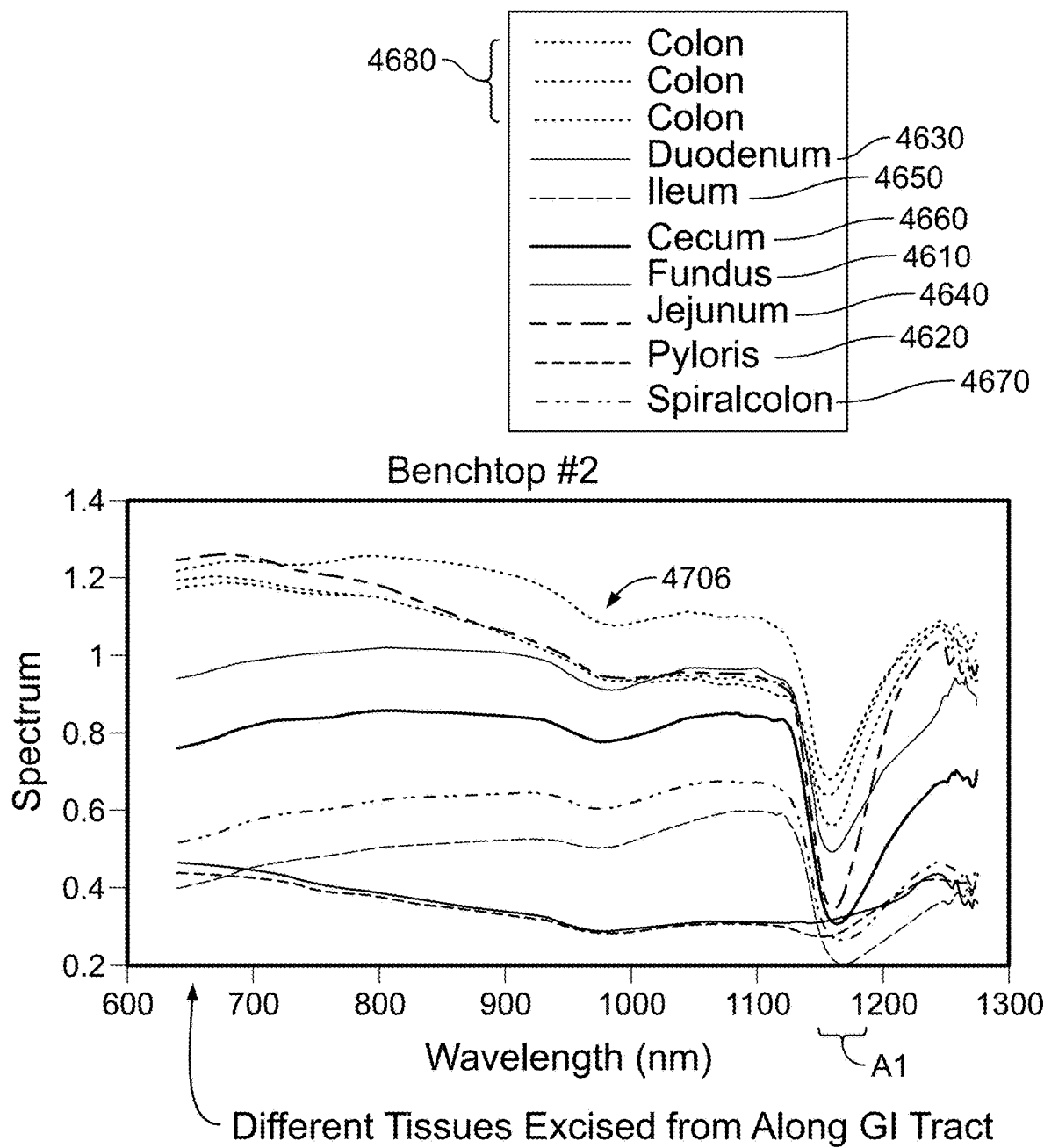
FIG. 47A shows first spectra of light reflected from some of the tissue samples shown in FIG. 46, where the first spectra have been acquired over a first spectral range.

FIG. 47A shows first spectra 4706 of light reflected off the tissue samples 4600, where each of the first spectra corresponds to a tissue sample from a respective location along the GI tract. The first spectra 4706 were acquired using Benchtop spectrometer #2. The numerical references associated with the legend of FIG. 47A correspond to the numerical references used in FIG. 46. Note that numerical reference 4680 corresponds to colon tissue.

Figure 47B:
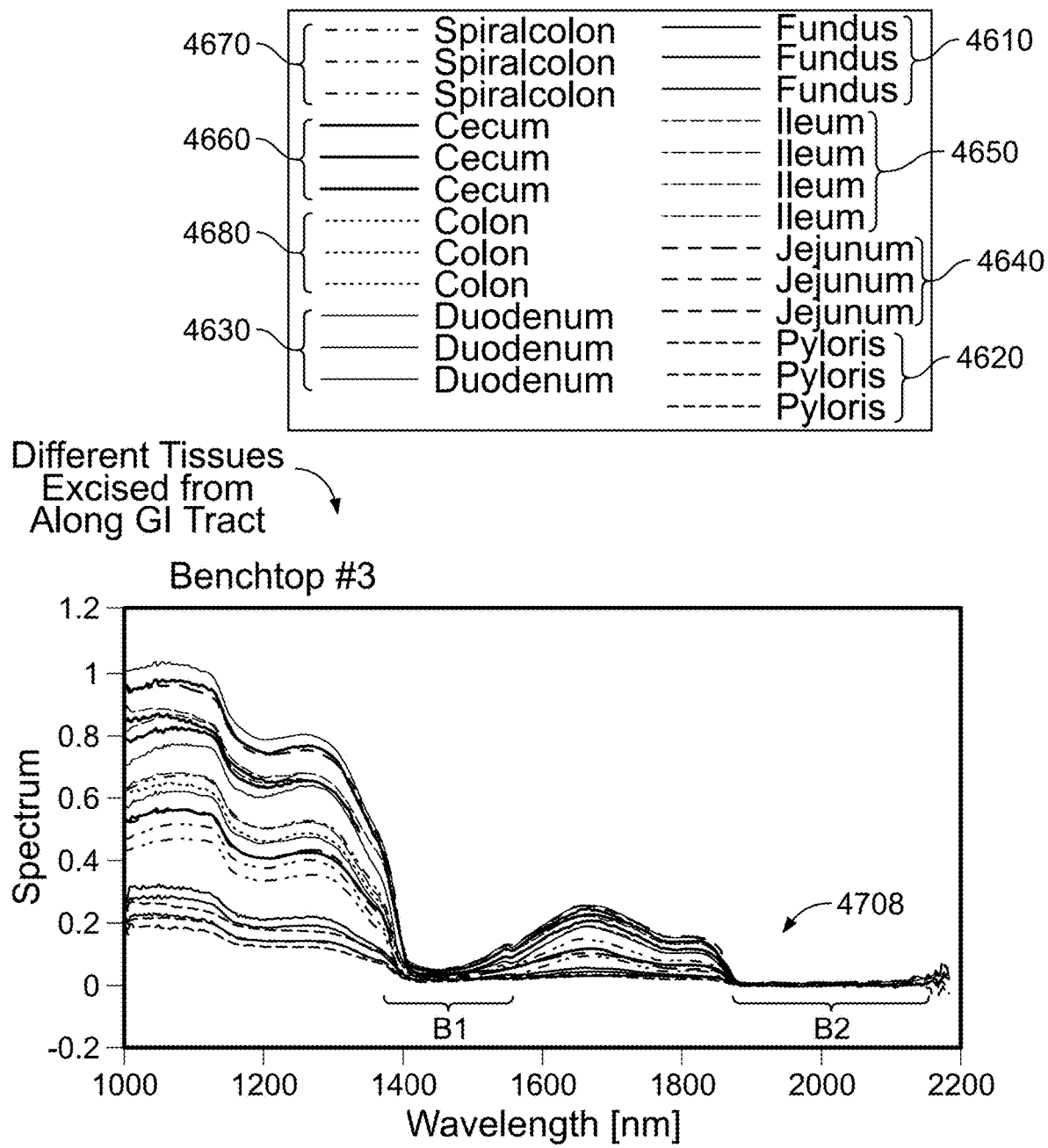
FIG. 47B shows second spectra of light reflected from some of the tissue samples shown in FIG. 46, where the second spectra have been acquired over a second spectral range.

FIG. 47B shows second spectra 4708 of light reflected off the tissue samples 4600, where each of the second spectra corresponds to a tissue sample from a respective location along the GI tract. The first spectra 4708 were acquired using Benchtop spectrometer #3. The numerical references associated with the legend of FIG. 47B correspond to the numerical references used in FIG. 46.

The spectra 4706, 4708 obtained for different samples were preprocessed to account for illumination non-uniformities and other sources of noise. The preprocessing included subtracting a dark background spectrum from a raw ("as-measured") spectrum, and then normalizing the difference spectrum by a white reference spectrum.

Note that, over the spectral ranges of the Benchtop spectrometers #2 and #3, a first subset of spectra 4706, 4708, which corresponds to fundus tissue 4610 and pylorus tissue 4620 has overall magnitudes that are lower than overall magnitudes of a second subset of spectra 4706, 4708, which corresponds to duodenum tissue 4630, jejunum tissue 4640 and ileum tissue 4650 or a third subset of spectra 4706, 4708, which corresponds to cecum tissue 4660, spiral colon tissue 4670 and colon tissue 4680. This suggests that the tissues excised from the stomach are less reflecting (e.g., more absorbent) than tissues excised from the small intestine or large intestine. By extension, a location of an ingestible device within the stomach or the small intestine or the large intestine of a subject could be determined by (i) acquiring, with a spectrometer carried by the ingestible device, a spectrum of light reflected off the GI tract tissue, and (ii) comparing magnitudes of the acquired spectrum and reference spectra (e.g., 4706, 4708) corresponding to stomach tissue (e.g., 4610 or 4620), small intestine tissue (e.g., 4630, 4640 and 4650), and large intestine tissue (e.g., 4660, 4670 and 4680).

Additionally, the spectra corresponding to tissues excised from the small intestine appear to share spectral features with the spectra corresponding to tissues excised from the large intestine, while neither of the foregoing spectra appear to share spectral features with the spectra corresponding to tissues excised from the stomach. By extension, a location of an ingestible device within the stomach or the small/large intestine of a subject could be determined by (i) acquiring, with a spectrometer carried by the ingestible device, a spectrum of light reflected off the GI tract tissue, and (ii) comparing spectral features of the acquired spectrum and reference spectra (e.g., 4706, 4708) corresponding to stomach tissue (e.g., 4610 or 4620) and small/large intestine tissue (e.g., 4630, 4640, 4650, 4660, 4670 and 4680).

Moreover, note that dips in the reflection spectra 4706, 4708, in the spectral ranges denoted A1 in FIG. 47A and B1, B2 in FIG. 47B, correspond to absorption peaks of the water that is lodged in the excised tissue samples 4600.

As another example, the tissue samples 4600 were used to produce corresponding spectra by performing hyperspectral imaging. Here, the tissue samples 4600 were illuminated with a halogen light source (e.g., Olympus CLK-4), and one or more images of each of the tissue samples 4600 were acquired with the hyperspectral camera. For instance, different exposure times were used to acquire the hyperspectral images of each of the tissue samples 4600. Then, spectra were produced for up to three regions of interest (ROIs) of the acquired images. Note that the ROIs were chosen from portions of an image that is uniform and not saturated.

Figure 48A:
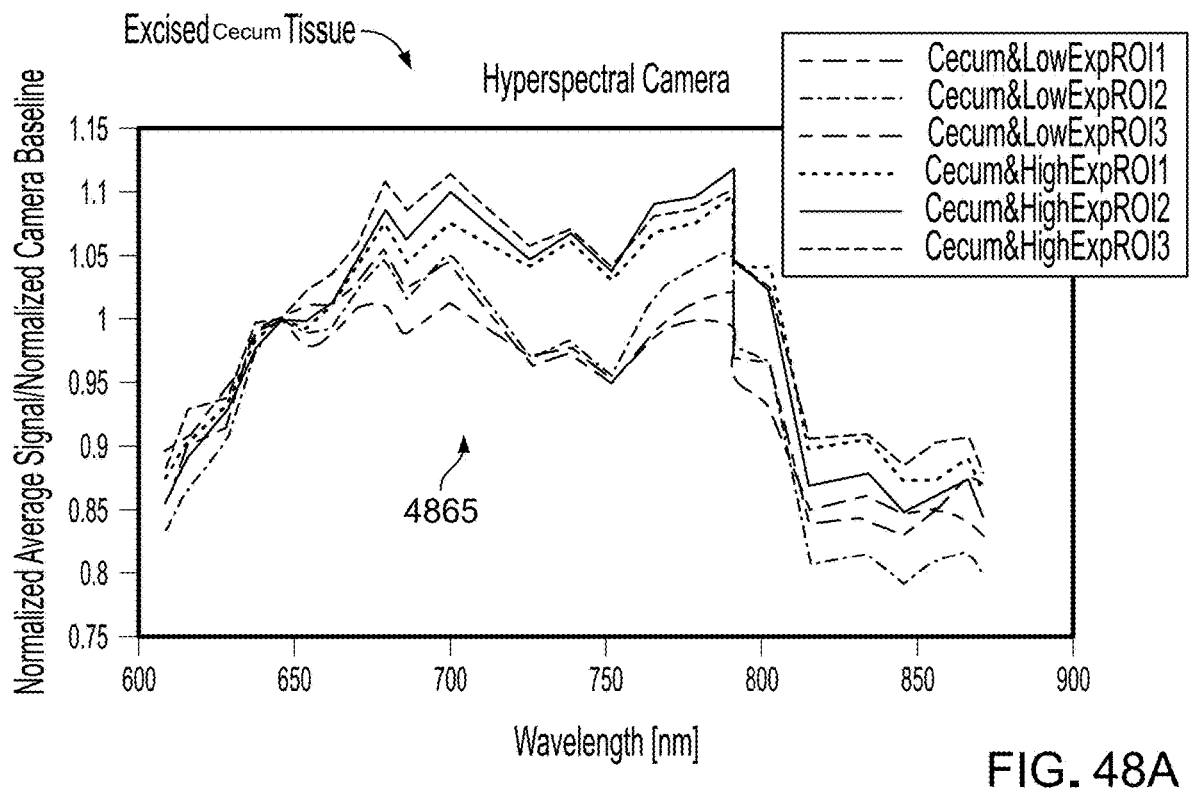
FIG. 48A shows spectra obtained from hyperspectral images of tissue samples including tissue excised from the cecum.
Figure 48B:
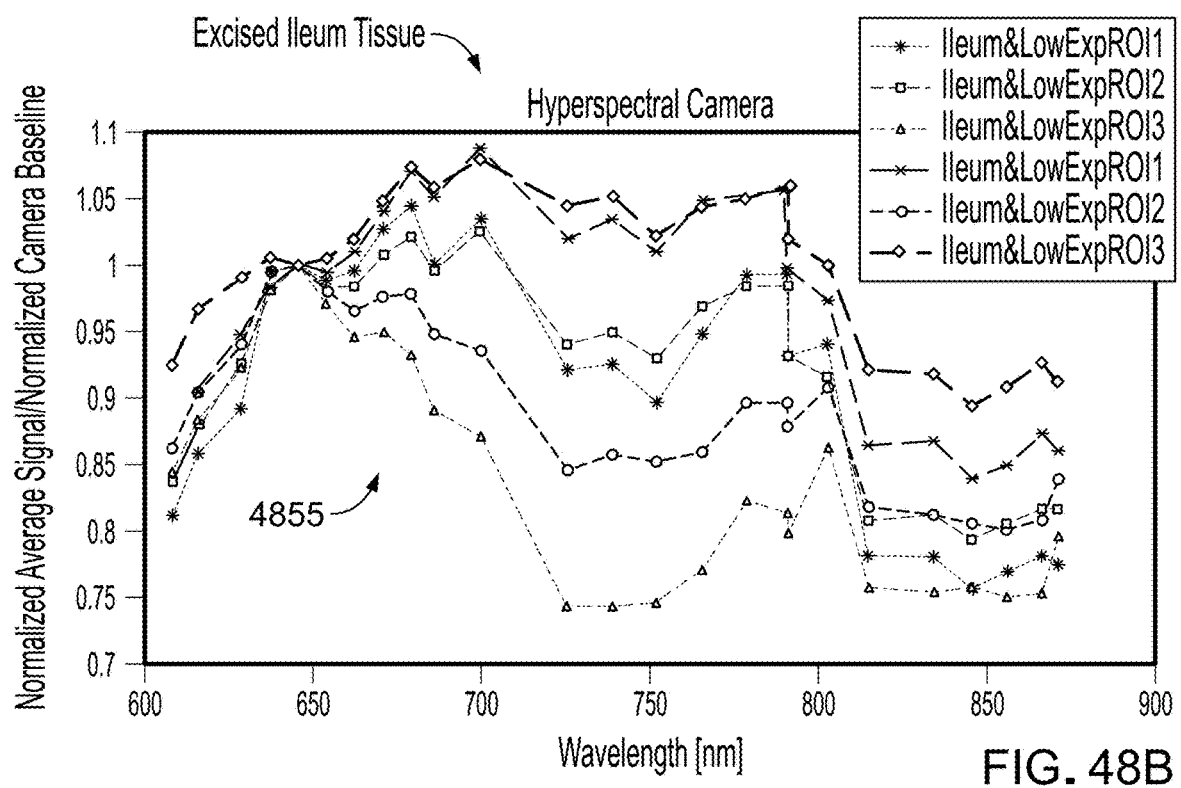
FIG. 48B shows spectra obtained from hyperspectral images of tissue samples including tissue excised from the ileum.

FIG. 48A shows spectra 4865 obtained from hyperspectral images of the cecum tissue samples 4660. FIG. 48B shows spectra 4855 obtained from hyperspectral images of the ileum tissue samples 4650. To account for illumination non-uniformities and other sources of noise, each of the raw ("as-acquired") images has been normalized against a camera baseline. Each of the spectra 4865 corresponds to a respective ROI of the same image of a cecum tissue sample 4660. Also, each of the spectra 4855 corresponds to a respective ROI of the same image of an ileum tissue sample 4650. Moreover, for each of the spectra 4865, 4855, the respective image has been acquired using a first exposure time or a second exposure time longer than the first exposure time. Note that the spectra 4865 are similar across different ROIs, which indicates that the image of the cecum tissue sample 4660 is quite uniform (and most likely was unsaturated). However, the spectra 4855 are quite dissimilar across different ROIs, which indicates that the image of the ileum tissue sample 4650 is non-uniform (and most likely had saturated portions).

Figure 49:
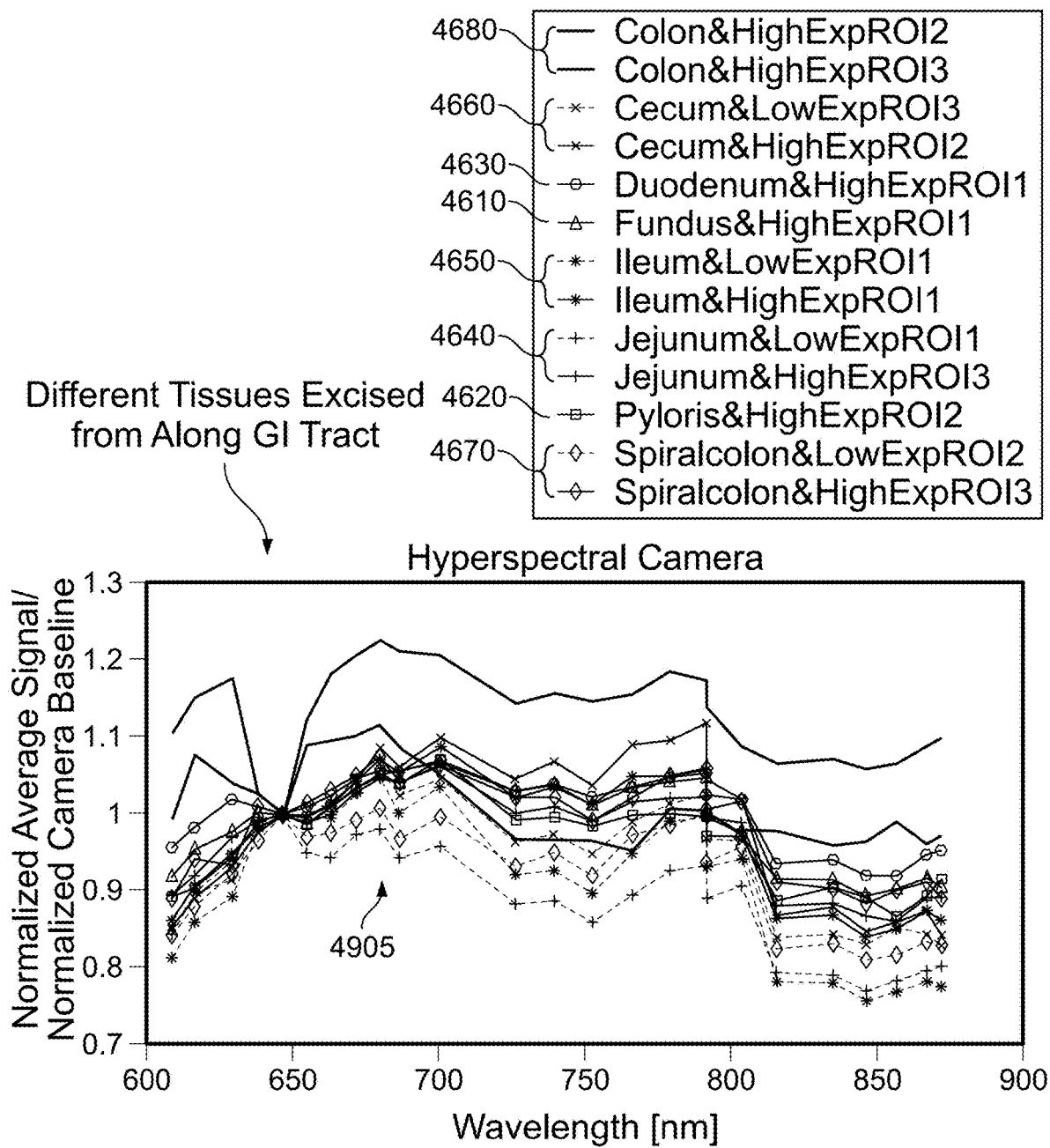
FIG. 49 shows spectra obtained from hyperspectral images of the tissue samples shown in FIG. 46.

FIG. 49 shows spectra 4905 obtained from hyperspectral images of the tissue samples 4600. These images were normalized as described above in connection with FIGS. 48A-48B. As in the case of the foregoing figures, the numerical references associated with the legend of FIG. 47A correspond to the numerical references used in FIG. 46. Moreover, each of the spectra 4905 corresponds to an ROI of a respective image of a tissue sample from a respective location along the GI tract. Here, like in the images used for producing the spectra 4865, 4855, the respective image has been acquired using either a short exposure time or a long exposure time.

Note that the spectra from among the all the spectra 4865, 4855, 4905 corresponding to the longer exposure time, which are shown as solid lines, have higher magnitudes than the magnitudes of the ones from among the spectra 4865, 4855, 4905 corresponding to the shorter exposure time, which are shown as dash lines.

Further note that, over the spectral range of the hyperspectral camera, the spectra corresponding to tissues excised from the stomach, the spectra corresponding to tissues excised from the small intestine, and the spectra corresponding to tissues excised from the large intestine appear to be similar with each other. This makes it hard to differentiate, over the spectral range of the hyperspectral camera, between spectra corresponding to tissues excised at different locations of the GI tract. However, as demonstrated, for example, in connection with FIGS. 47A and 47B, this can be addressed with the use of spectrometers operating in different spectral ranges.

Example 15: Mapping Spectral Data Relating to Excised Colon Tissue and Colon Tissue's Health Condition Spectral analysis was performed, by using spectra of light reflected off portions of excised colon tissue, the spectra acquired with spectrometers from among the spectrometers from Table 2 or obtained from images acquired with a hyperspectral camera (e.g., the one described in connection with Example 3), for identifying spectral features corresponding to health conditions of the portions of the excised colon tissue.

FIGS. 50A-50O show views of a sample 5080 that includes tissue excised from the colon of a live pig. In this example, the colon-tissue sample 5080 has at least one normal portion 4680, at least one inflamed portion 5090, and at least one necrotic portion 5070. Note that the necrotic portion 5070 of the colon-tissue sample 5080 can be exposed by scraping off a scab portion (not shown in FIGS. 50A-50O) of the colon-tissue sample 5080.

As such, a normal portion 4680, an inflamed portion 5090, a scab portion and a necrotic portion 5070 of the colon-tissue sample 5050 were used to produce corresponding spectra by performing reflection-mode spectroscopy using Benchtop spectrometers #2 and #3. Note that three spectra were acquired for each of the foregoing portions of the colon tissue-sample 5080, by exposing different locations within each of the portions of interest.

Figure 51A:
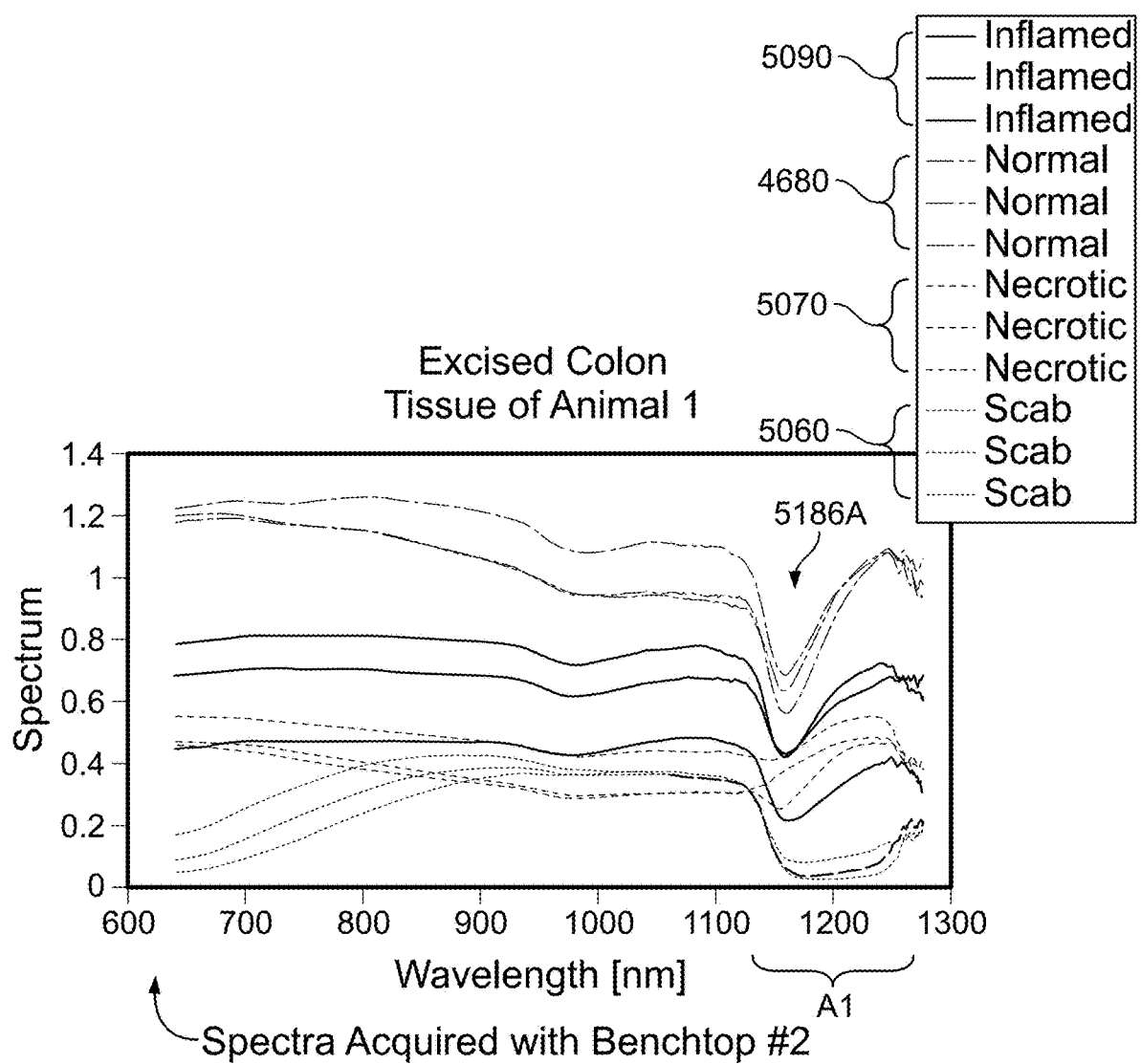
FIGS. 51A-51B show spectra of light reflected from some of the tissue samples shown in FIGS. 50A-50C, where the spectra have been acquired over a first spectral range.
Figure 51B:
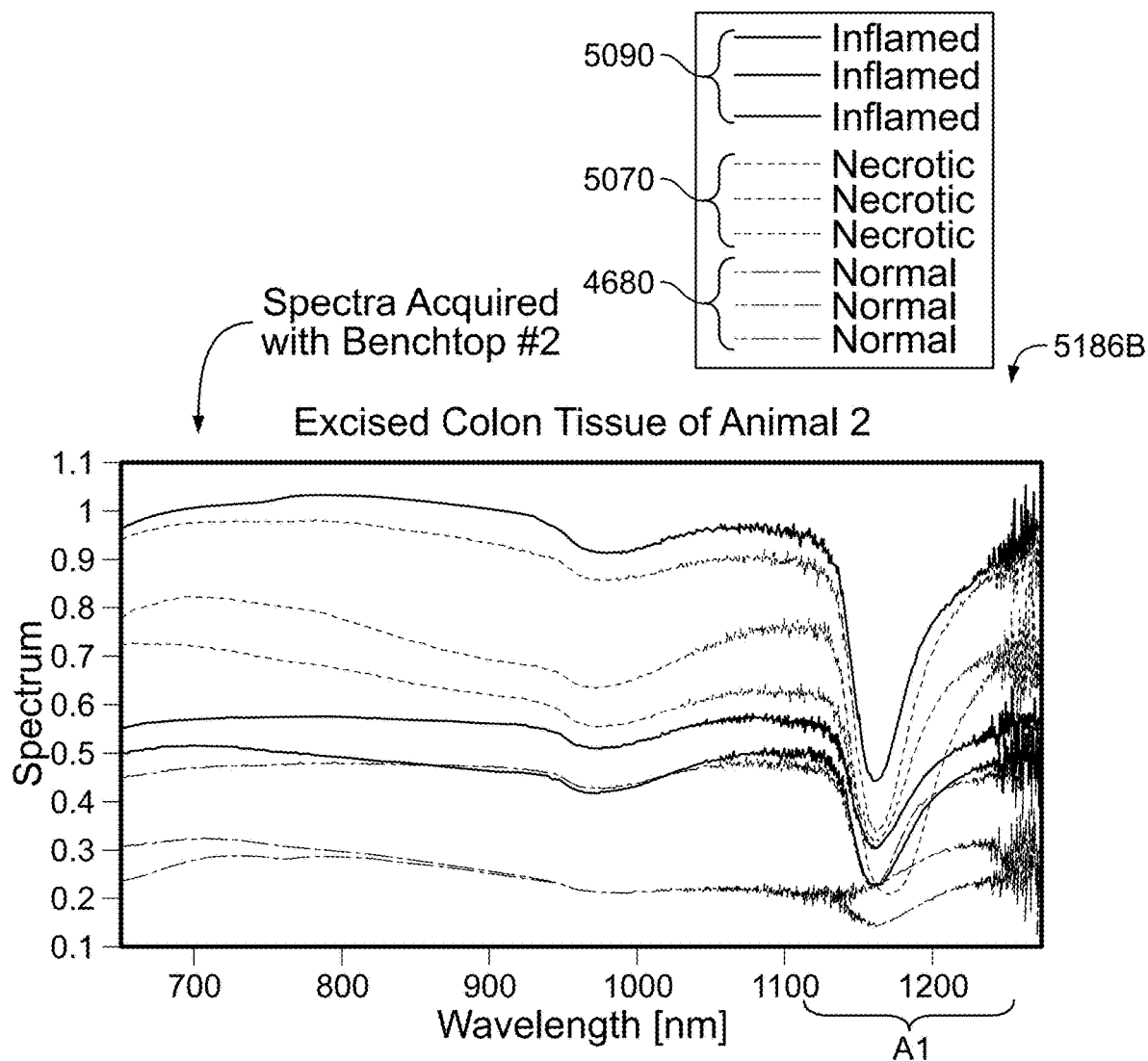

FIG. 51A shows a first set of spectra 5186A of light reflected off portions of the colon-tissue sample 5080. As noted above, the colon-tissue sample 5080 has been harvested from a first live pig. FIG. 51B shows a second set of spectra 5186B of light reflected off portions of a colon-tissue sample (not shown in FIGS. 50A-50C) harvested from a second live pig. In FIGS. 51A-51B, each spectrum of the first set of spectra 5186A and of the second set of spectra 5186B corresponds to a colon-tissue portion that has a respective health condition from among the health conditions noted above: normal, inflamed, necrotic or scab. Note that the numerical references associated with the legends of FIGS. 51A-51B correspond to the numerical references used in FIGS. 50A-50C. In addition, the numerical reference 5060 corresponds to a scab portion of colon tissue. All the spectra in the first and second sets of spectra 5186A, 5186B were acquired using Benchtop spectrometer #2.

Figure 52A:
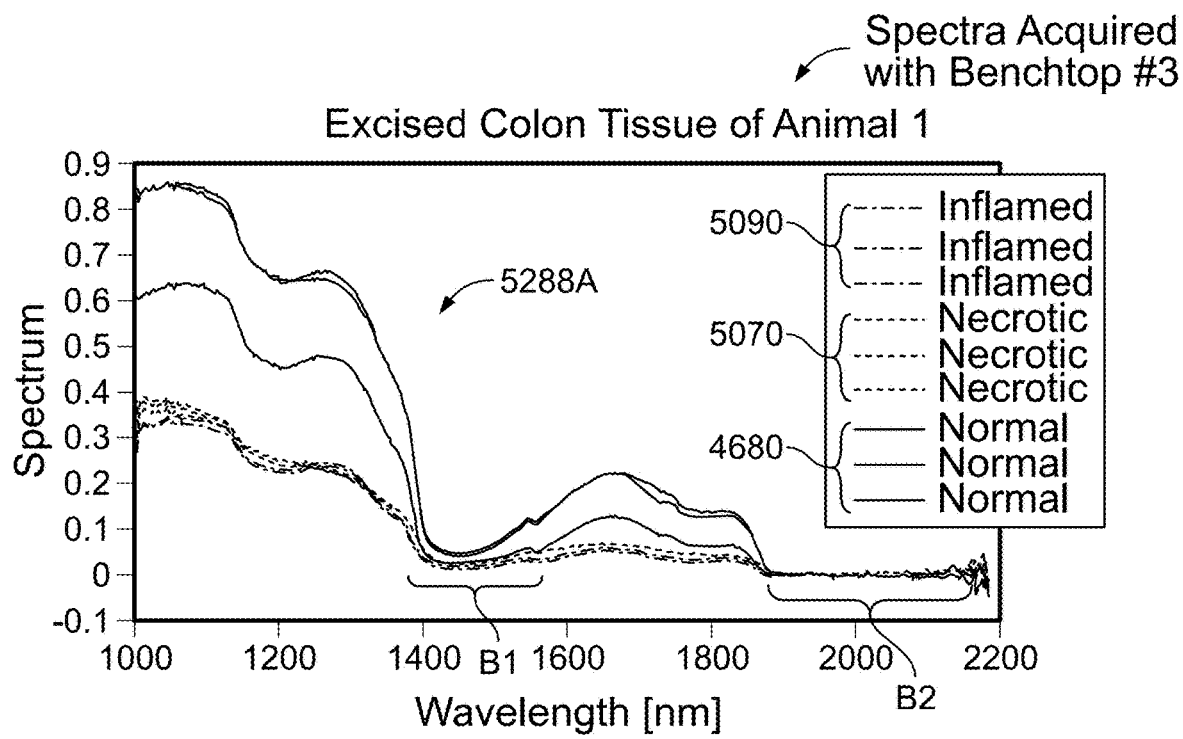
FIGS. 52A-52B show spectra of light reflected from some of the tissue samples shown in FIGS. 50A-50C, where the spectra have been acquired over a second spectral range.
Figure 52B:
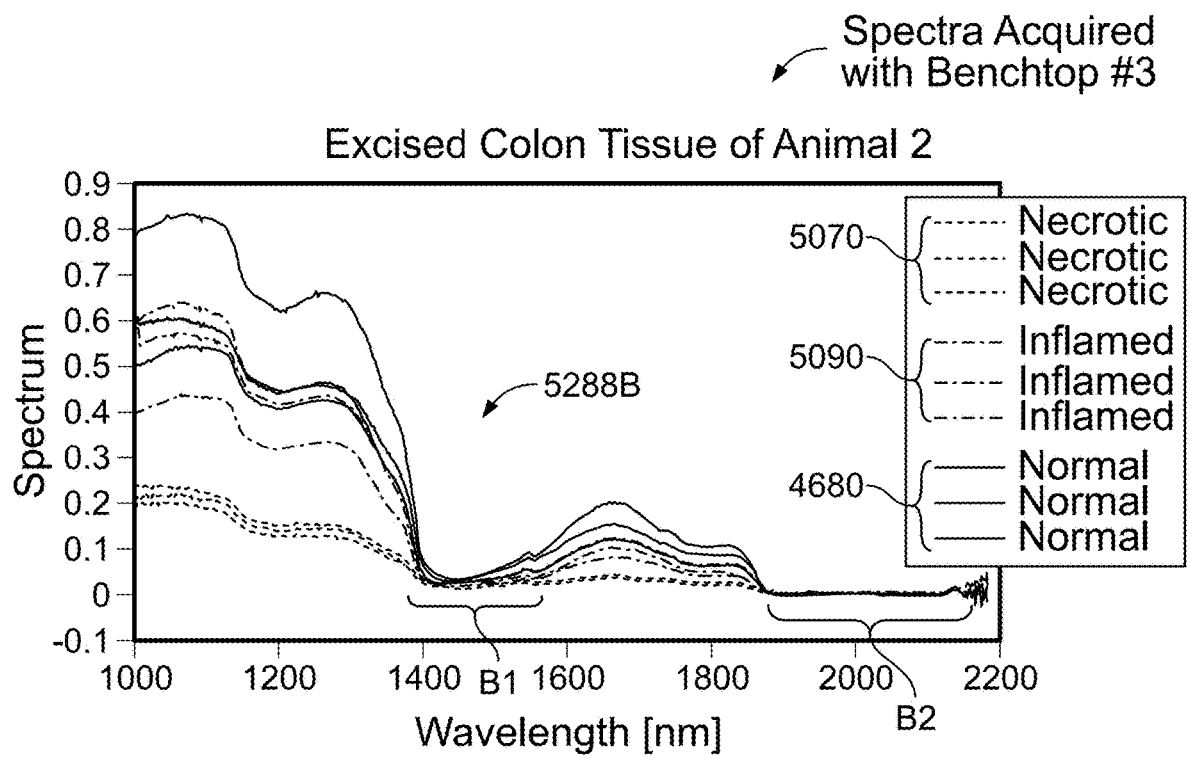

FIG. 52A shows a third set of spectra 5288A of light reflected off portions of the colon tissue sample 5080. FIG. 52B shows a fourth set of spectra 5288B of light reflected off portions of the same colon-tissue sample used to acquire the first spectra 5186B. In FIGS. 52A-52B, each spectrum of the third set of spectra 5288A and of the fourth set of spectra 5288B corresponds to a colon-tissue portion that has a respective health condition from among the health conditions noted above: normal, inflamed, necrotic or scab. Note that the numerical references associated with the legends of FIGS. 52A-52B correspond to the numerical references used in FIGS. 50A-50C. All the spectra in the first and second sets of spectra 5288A, 5288B were acquired using Benchtop spectrometer #3.

The spectra 5186A, 5186B and the spectra 5288A, 5288B obtained for the above-noted different portions of the colon-tissue samples were preprocessed to account for illumination non-uniformities and other sources of noise. The preprocessing included subtracting a dark background spectrum from a raw ("as-measured") spectrum, and then normalizing the difference spectrum by a white reference spectrum.

Note that, over the spectral ranges of the Benchtop spectrometers #2 and #3, a first subset of spectra 5186A, 5186B, 5288A, 5288B, which corresponds to normal colon tissue 4680, has overall magnitudes that are larger than overall magnitudes of a second subset of the spectra 5186A, 5186B, 5288A, 5288B, which corresponds to inflamed colon tissue 5090. And, a third subset of spectra 5186A, 5186B, 5288A, 5288B, which corresponds to necrotic colon tissue 5070 and scabbed colon tissue 5060, has overall magnitudes that are smaller than the overall magnitudes of the second subset of the spectra 5186A, 5186B, 5288A, 5288B, which corresponds to inflamed colon tissue 5090. This suggests that the inflamed portions of the excised colon tissues are less reflecting (e.g., more absorbent) than the normal portions of the excised colon tissues, while they are more reflecting (e.g., less absorbent) than the necrotic/scabbed portions of the excised colon tissues. In fact, the difference between the spectra corresponding to the inflamed colon tissue 5090 and normal colon tissue 4680 or the necrotic/scabbed colon tissue 5070/5060 appears to depend on the degree of inflammation. Thus, a degree of inflammation of a colon tissue could be determined, in-vivo, by (i) acquiring, with a spectrometer of an ingestible device, a spectrum of light reflected off the colon tissue, and (ii) comparing magnitudes of the acquired spectrum and reference spectra corresponding to normal colon tissue and necrotic/scabbed colon tissue.

Also note that dips in the reflection spectra 5186A, 5186B, in the spectral range denoted A1 in FIGS. 51A-51B, and in the reflection spectra 5288A, 5288B, in the spectral ranges denoted B1, B2 in FIGS. 52A-52B, correspond to absorption peaks of the water that is lodged in the excised colon tissue samples. For instance, the fact that the subset of the spectra 5186A corresponding to the scabbed colon tissue 5060 shows no significant magnitude change in the spectral range A1, which corresponds to water absorption, indicates that less water was present in a scabbed portion of colon tissue 5060 compared to normal, inflamed or even necrotic portions of the colon tissue 4680, 5090, 5070.

As another example, excised colon tissue samples like 5080 were used to produce corresponding spectra by performing hyperspectral imaging. Here, the colon tissue samples were illuminated with a halogen light source (e.g., Olympus CLK-4), and one or more images of each of normal, inflamed and necrotic portions of each colon-tissue sample were acquired with the hyperspectral camera. Then, spectra were produced for three or more regions of interest (ROIs) of the acquired images. Note that the ROIs were chosen from portions of an image that were uniform and not saturated.

Figure 53A:
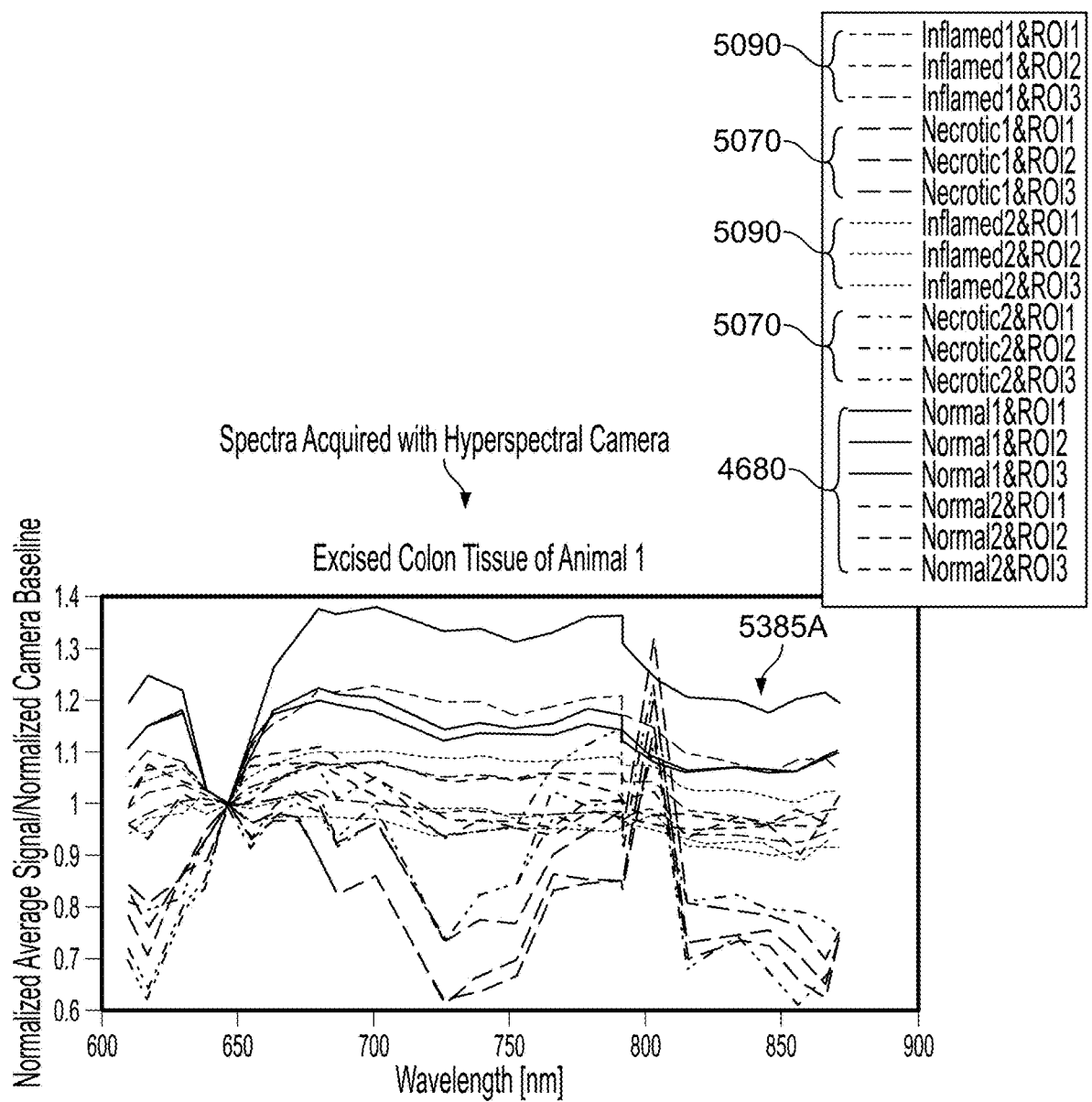
FIGS. 53A-53B show spectra obtained from hyperspectral images of the tissue samples shown in FIGS. 50A-500.

FIG. 53A shows spectra 5385A obtained from hyperspectral images of portions of interest of the colon-tissue sample 5080. To account for illumination non-uniformities and other sources of noise, each of the raw ("as-acquired") images were normalized against a camera baseline. Each of the spectra 5385A corresponds to a respective ROI of an image corresponding to a particular portion of the colon-tissue sample 5080, where the particular portion is one of a normal portion 4680, an inflamed portion 5090 or a necrotic portion 5070.

Note that, over the spectral range of the hyperspectral camera, a first subset of spectra 5385A, and which corresponds to different normal portions 4680, has overall magnitudes that are larger than overall magnitudes of a second subset of the spectra 5385A, which corresponds to different inflamed portions 5090; and, a third subset of spectra 5385A, which corresponds to different necrotic portions 5070 has overall magnitudes that are smaller than the overall magnitudes of the second subset of the spectra 5385A. For the colon-tissue sample 5080, a peak around 800 nm has been observed in the spectral corresponding to each of two necrotic portions 5070, for each of the ROIs used to produce the respective spectrum. However, this spectral feature of the necrotic colon tissue has not been observed in colon tissue, whether necrotic or not, excised from three other pigs, as described below.

Figure 53B:
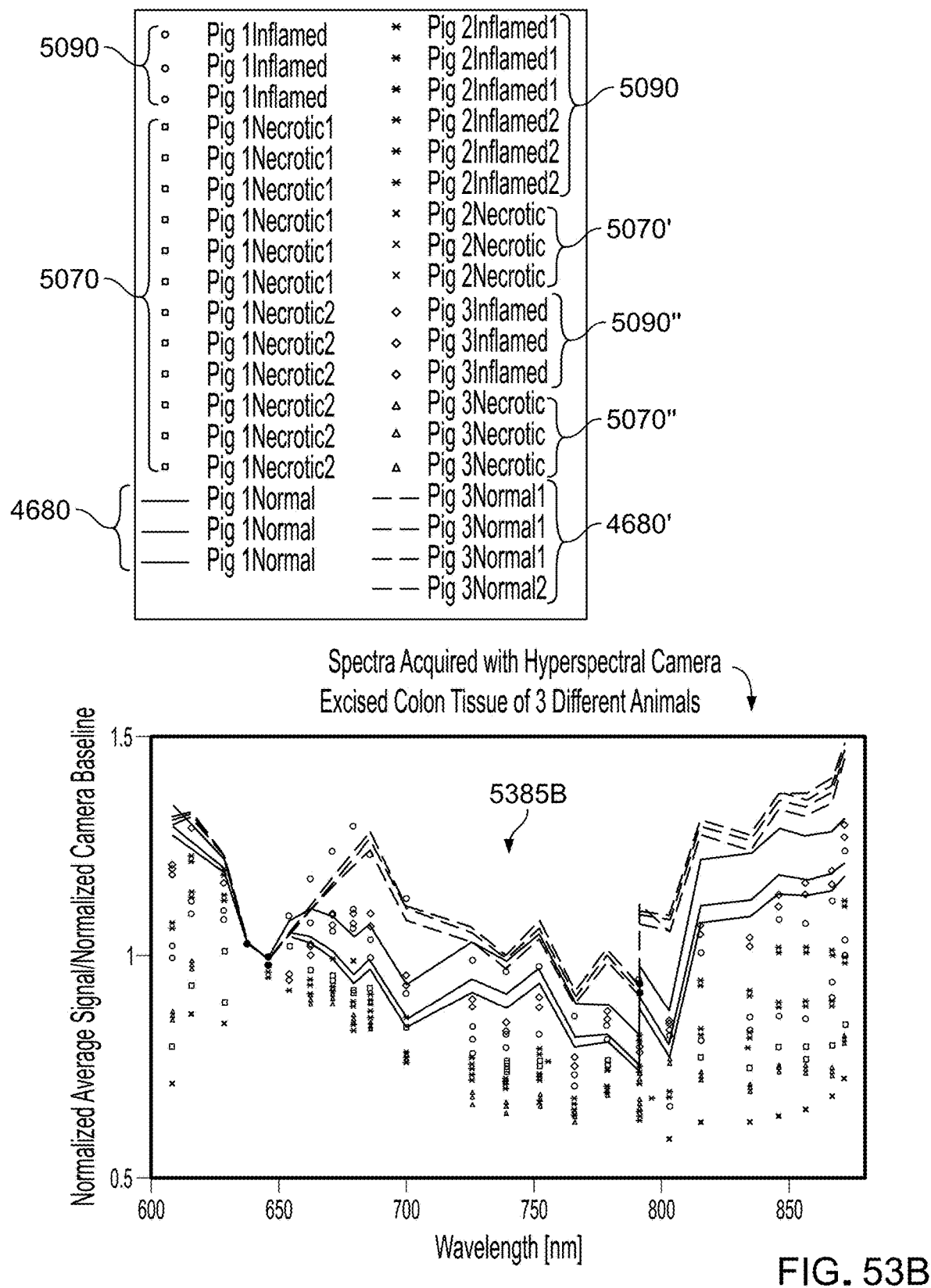

FIG. 53B shows spectra 5385B obtained from hyperspectral images of portions of interest of colon-tissue samples excised from three different pigs. These images were normalized as described above in connection with FIG. 53A. Each of the spectra 5385B corresponds to a respective ROI of an image corresponding to a particular portion of a colon tissue excised from a given pig, where the particular portion is one of a normal portion 4680, 4680', an inflamed portion 5090, 5090', 5090", or a necrotic portion 5070, 5070', 5070", and the given pig is one of the three different pigs.

Note that, over the spectral range of the hyperspectral camera, spectra corresponding to different necrotic portions 5070 of the colon tissue excised from the first pig, the second pig and the third pig are similar to each other. Additionally, as in the case of the spectra 5385A, the magnitudes of the spectra 5385B decrease from a largest magnitude for the spectra corresponding to normal portions 4680, 4680', to intermediary magnitude for the spectra corresponding to inflamed portions 5090, 5090', 5090", and to smallest magnitude for the spectra corresponding to necrotic portions 5070, 5070', 5070".

Moreover, for both examples illustrated in FIGS. 53A-53B, the difference between the spectra 5385A, 5385B corresponding to the inflamed colon tissue 5090, 5090', 5090" and normal colon tissue 4680, 4680' or the necrotic/scabbed colon tissue 5070, 5070', 5070"/5060 appears to depend on the degree of inflammation. Thus, a degree of inflammation of a colon tissue could be determined, in-vivo, by (i) acquiring, with a hyperspectral camera of an ingestible device, an image of the colon tissue, (ii) producing at least one spectrum corresponding to the colon tissue from the acquired image, and (iii) comparing magnitudes of the produced spectrum and reference spectra corresponding to normal colon tissue and necrotic/scabbed colon tissue.

Example 16: Mapping Spectral Data Relating to Formalin-Fixed Colon Tissue and Colon Tissue's Health Condition Spectral analysis was performed, by using spectra obtained from images of formalin-fixed colon tissue, the images acquired with a hyperspectral camera (e.g., the one described in connection with Example 3). The spectral analysis can be used for identifying spectral features corresponding to health conditions of the portions of the formalin-fixed colon tissue.

Figure 54A:
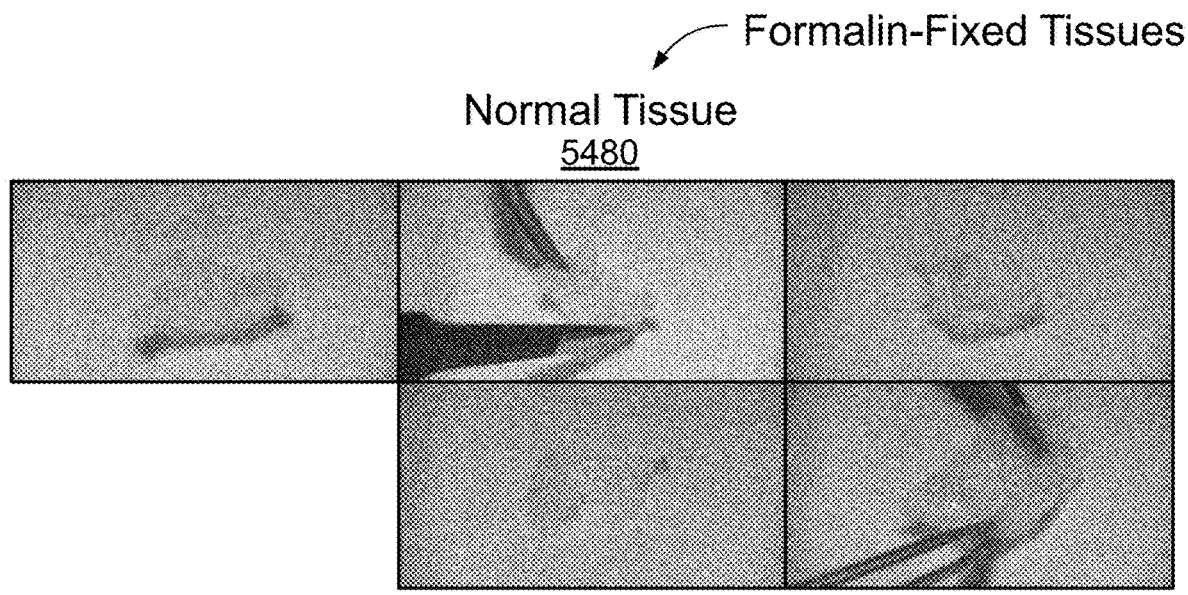
FIG. 54A shows formalin-fixed tissue samples including normal tissue excised from the colon.
Figure 54B:
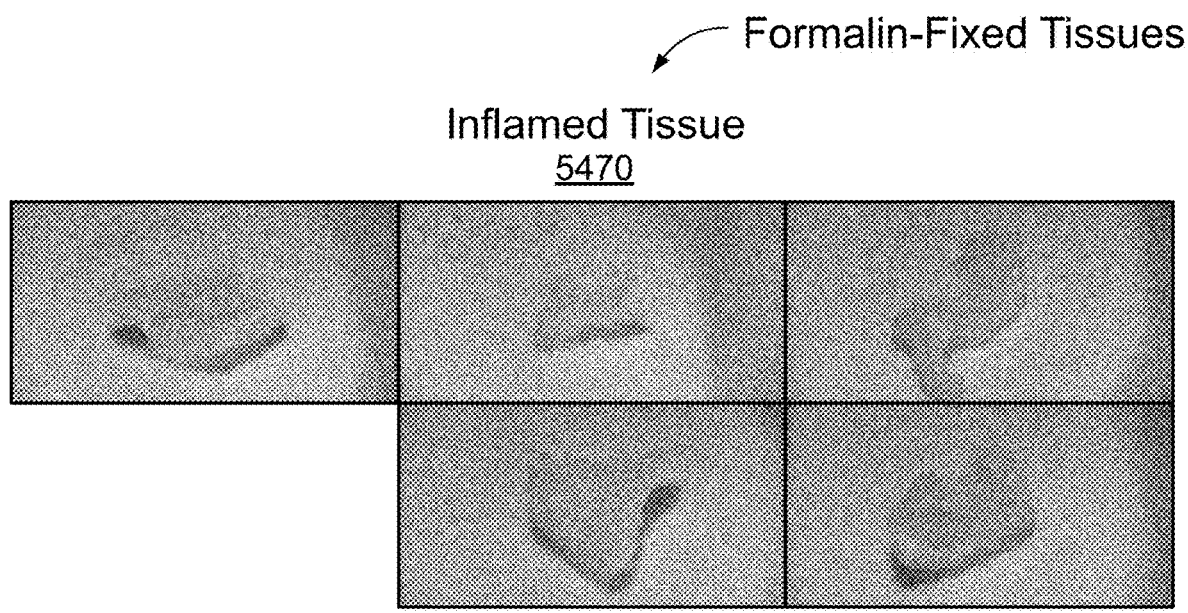
FIG. 54B shows formalin-fixed tissue samples including inflamed tissue excised from the colon.

FIG. 54A shows photographs of samples including normal tissue 5480 of five different pigs that had been excised from the respective pig's colon, and has been fixed in formalin. FIG. 54B shows photographs of samples including inflamed tissue 5470 of five different pigs that had been excised from the pig's colon, and has been fixed in formalin. The formalin-fixed normal colon tissue 5480 and the formalin-fixed inflamed colon tissue 5470 were used to produce corresponding spectra by performing hyperspectral imaging. Here, the formalin-fixed colon-tissue samples were illuminated with a halogen light source, and one or more images of each of the formalin-fixed normal colon tissue 5480 and the formalin-fixed inflamed colon tissue 5470 were acquired with the hyperspectral camera. Then, spectra were produced for at least one region of interest (ROI) of the acquired images. Note that the ROIs were chosen from portions of an image that are uniform and not saturated.

Figure 55A:
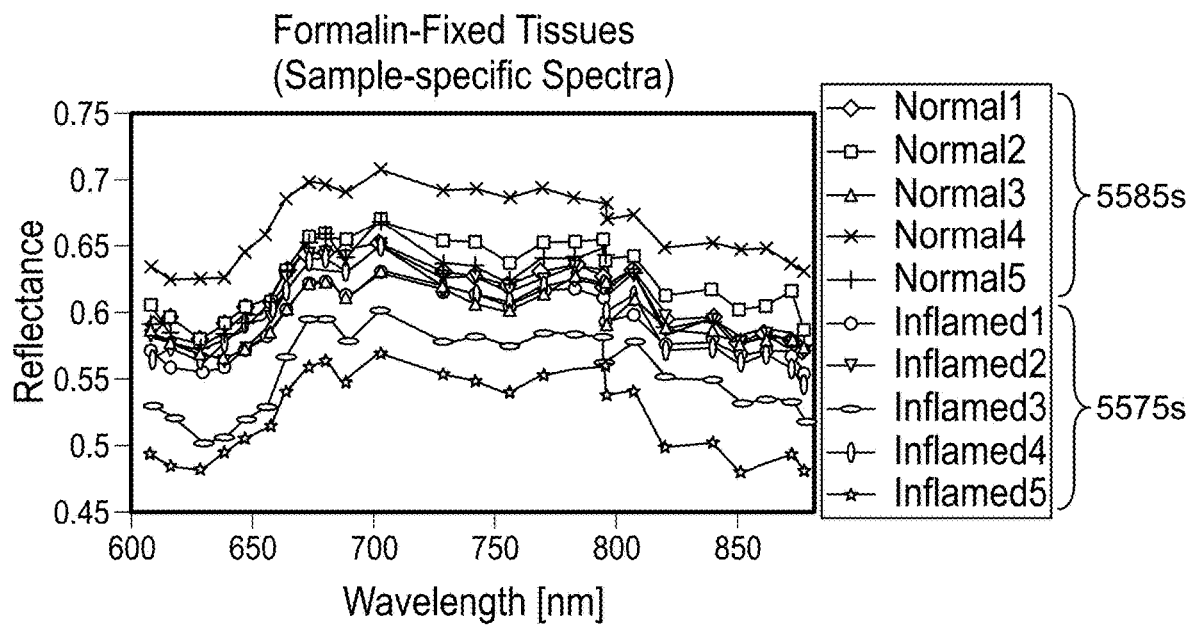
FIGS. 55A/55B show raw/average spectra obtained from hyperspectral images of the tissue samples shown in FIG. 54A-54B.
Figure 55B:
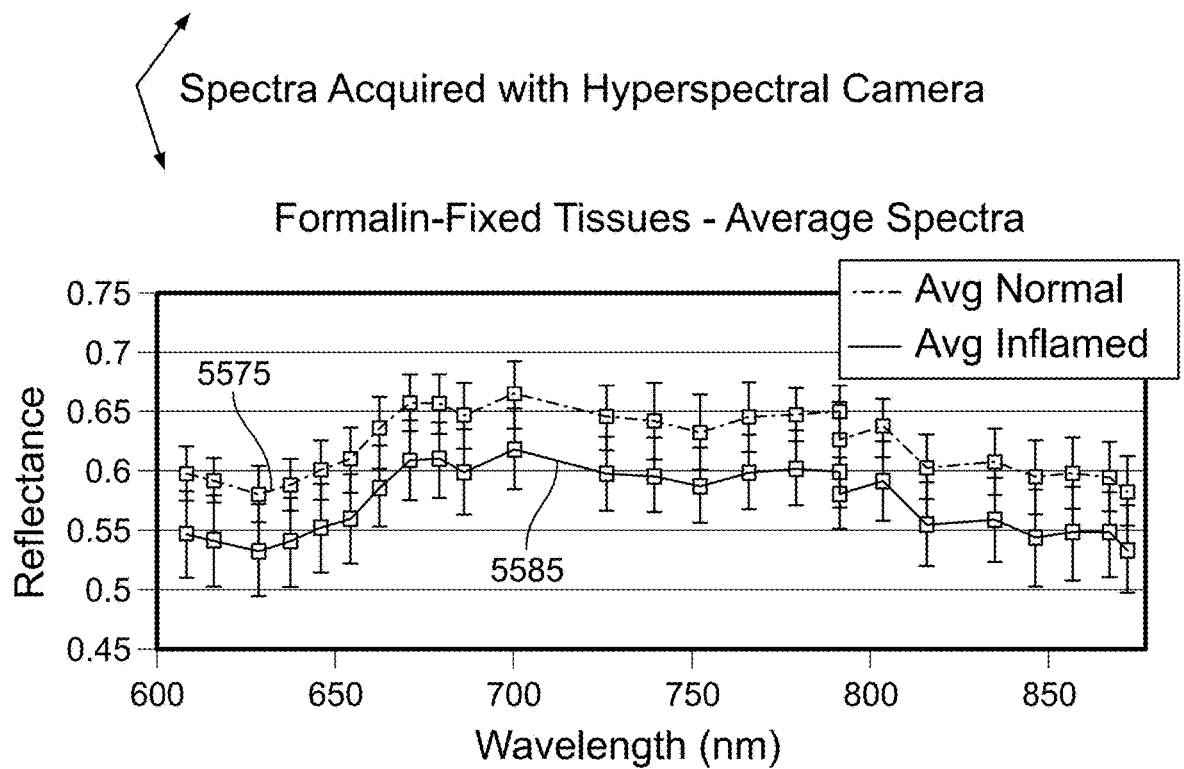

FIG. 55A shows a set of spectra 5585s obtained from hyperspectral images of respective samples of formalin-fixed normal colon tissue 5480 and a set of spectra 5575s obtained from hyperspectral images of respective samples of formalin-fixed inflamed colon tissue 5470. To account for illumination non-uniformities and other sources of noise, including to factor out the spectrum of the halogen light source, each of the raw ("as-acquired") images were normalized against a camera baseline. Each of the spectra from the set 5585s corresponds to an ROI of an image of a formalin-fixed normal colon tissue 5480 of a particular pig, and each of the spectra from the set 5575s corresponds to an ROI of an image of a formalin-fixed inflamed colon tissue 5470 of the particular pig. FIG. 55B shows a spectrum 5585 that corresponds to formalin-fixed normal colon tissue 5480, as the average of the spectra of set 5585s, and a spectrum 5575 that corresponds to formalin-fixed inflamed colon tissue 5470, as the average of the spectra of set 5575s.

Note that, over the spectral range of the hyperspectral camera, the spectrum 5585 that corresponds to formalin-fixed normal colon tissue 5480 has magnitudes that are larger than corresponding magnitudes of the spectrum 5575 that corresponds to formalin-fixed inflamed colon tissue 5470. As such, it could be determined whether a colon tissue fixed in formalin was inflamed at excision time by (i) acquiring, with a hyperspectral camera, an image of the formalin-fixed colon tissue, (ii) producing one or more spectra corresponding to the formalin-fixed colon tissue from the acquired image, and (iii) comparing magnitudes of the produced spectrum and reference spectra corresponding to formalin-fixed normal colon tissues.

Example 17: Mapping Spectral Data Relating to Live Colon Tissue and Colon Tissue's Health Condition Spectral analysis was performed, by using spectra of light reflected off portions of live colon tissue, the spectra acquired with Benchtop spectrometer #2 (from Table 2) optically coupled inside a live pig through an optical fiber, or obtained from images acquired with a hyperspectral camera (e.g., the one described in connection with Example 3) disposed inside the live pig, for identifying spectral features corresponding to health conditions of the portions of the live colon tissue.

As both spectroscopy and hyperspectral imaging were carried out in live pigs, the animals were prepared according to the protocol "Non-GLP (good laboratory practice) Transit Time of a Drug Dispensing System (DDS) Capsule after Endoscopic Placement into the Colon in a Porcine trinitrobenzene sulfonic acid (TNBS) Colitis Model." For example, a colonofiberscope (e.g., Olympus CF 10LIM OES) was inserted inside the colon of a live pig to perform either spectroscopy or hyperspectral imaging.

For example, when spectroscopy was performed, an optical fiber was placed down the working channel of the colonofiberscope. A first end of the optical fiber was coupled at the Benchtop spectrometer #2, while the other, second end of the optical fiber reached inside the colon of the live pig to illuminate a portion of colon tissue and collect light reflected from the portion of the colon tissue. The illumination source can be a halogen light source (e.g., Olympus CLK-4), and the integration time of the Benchtop spectrometer #2 can be variable (e.g., 0.04 s). Note that the second end of the optical fiber could be brought adjacent to a portion of interest, e.g., a portion of normal colon tissue, a portion of inflamed colon tissue, or a portion of necrotic colon tissue, such that light collected by the optical fiber at the second end was reflected only by the portion of interest. Further note that, as part of these experiments, a portion of interest was identified using real-time images provided by a camera of the colonofiberscope. For example, when the real-time images provided by the colonofiberscope camera indicated that the second end of the optical fiber was located adjacent normal/inflamed/necrotic colon tissue, acquisition of two or more images of the normal/inflamed/necrotic colon tissue by the hyperspectral camera was triggered. In this manner, two or more spectra were acquired for each of the portions of interest of the colon tissue, e.g., the acquired spectra corresponding to different locations within a respective portion of interest.

Figure 56:
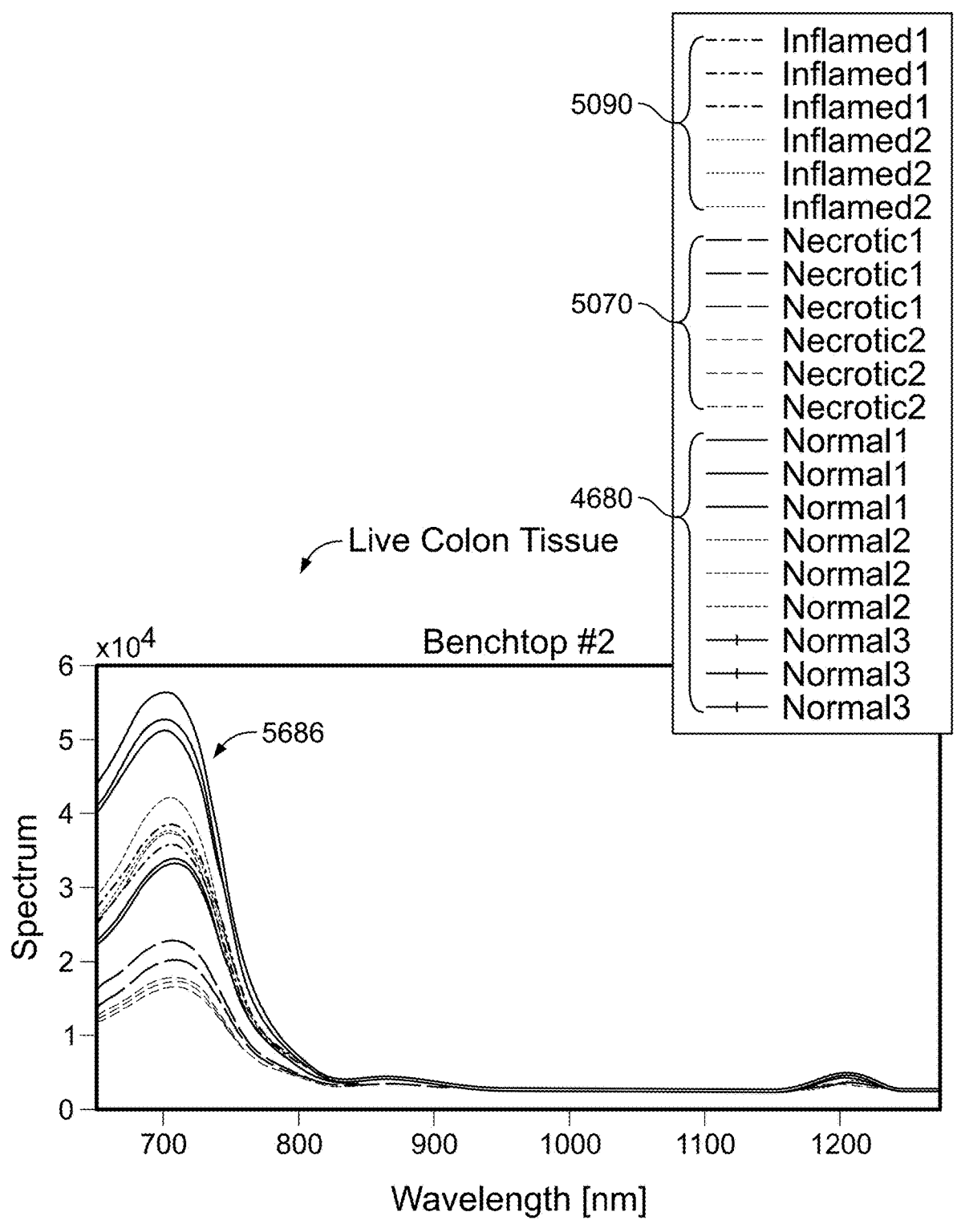
FIG. 56 shows spectra of light reflected from corresponding normal, inflamed or necrotic portions of live colon tissue.

FIG. 56 shows spectra 5686 of light reflected from corresponding normal, inflamed or necrotic portions of live colon tissue. Note that the numerical references associated with the legend of FIG. 56 correspond to the numerical references used in FIGS. 50A-50O. The spectra 5686 are raw spectra, i.e., no normalization has been performed.

Note that, over the spectral ranges of the Benchtop spectrometer #2, a first subset of spectra 5686, which corresponds to normal portions of live colon tissue 4680, has overall magnitudes that are larger than overall magnitudes of a second subset of the spectra 5686, which corresponds to inflamed portions of live colon tissue 5090; and, a third subset of spectra 5686, which corresponds to necrotic portions of live colon tissue 5070 has overall magnitudes that are smaller than the overall magnitudes of the second subset of the spectra 5686, which corresponds to inflamed portions of live colon tissue 5090. This suggests that the inflamed portions of the live colon tissue 5090 are less reflecting (e.g., more absorbent) than the normal portions of the live colon tissue 4680, while they are more reflecting (e.g., less absorbent) than the necrotic portions of the live colon tissue 5070. In fact, the difference between the spectra corresponding to the inflamed portions of live colon tissue 5090 and normal portions of live colon tissue 4680 appears to depend on the degree of inflammation. Thus, a degree/level of inflammation of live colon tissue could be determined, in-vivo, by (i) acquiring, with a spectrometer of an ingestible device, a spectrum of light reflected off the live colon tissue, and (ii) comparing magnitudes of the acquired spectrum and reference spectra corresponding to normal portions of colon tissue 4680 and reference spectra corresponding to inflamed portions of colon tissue 5090.

As another example, when hyperspectral imaging was performed, a hyperspectral camera was coupled to the colonofiberscope to image inside the colon of a live pig. Here, the hyperspectral camera was coupled to the colonofiberscope through a zoom coupler (e.g., a Precision Optics 5197-801 17.5 zoom coupler). An illumination source (e.g., a halogen light source) can illuminate the inside of the live colon through an optical fiber placed down the working channel of the colonofiberscope. Note that the end of the optical fiber could be brought adjacent to a portion of interest, e.g., a portion of normal colon tissue, a portion of inflamed colon tissue, or a portion of necrotic colon tissue, such that the hyperspectral camera images mostly the portion of interest.

Figure 57:
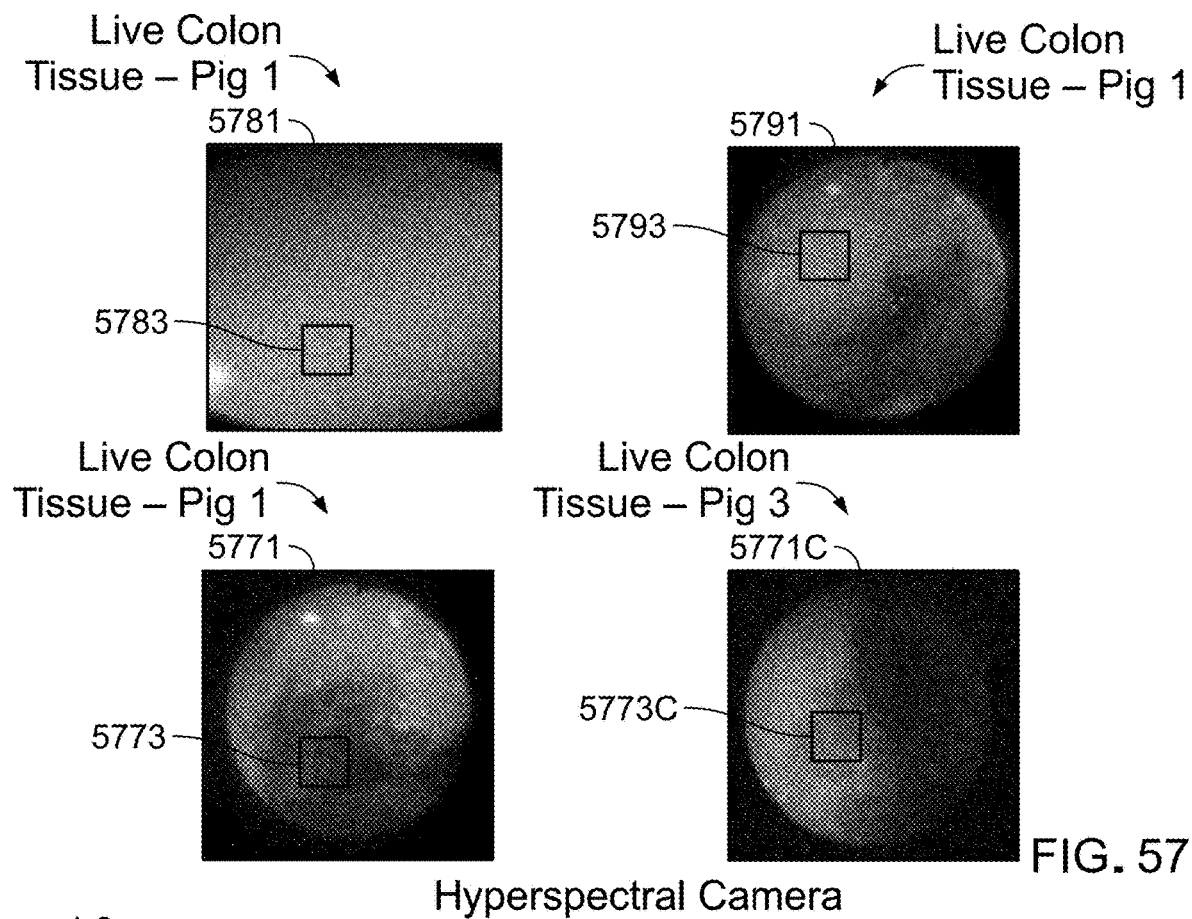
FIG. 57 shows raw images acquired with a hyperspectral camera of respective portions of a live colon that have normal, inflamed or necrotic tissue.

FIG. 57 shows raw images acquired with a hyperspectral camera of respective portions of a live colon that have normal, inflamed or necrotic tissue. For example, a first image 5781 of colon tissue of a first live pig has a region of interest (ROI) 5783 corresponding to a normal portion of the live colon tissue. As another example, a second image 5791 of the colon tissue of the first live pig has an ROI 5793 corresponding to an inflamed portion of the live colon tissue. As yet another example, a third/a fourth image 5771/5771C of the colon tissue of the first live pig/a third live pig has an ROI 5773/5773C corresponding to a necrotic portion of the live colon tissue. Note that each of the ROIs 5783, 5793, 5773, 5773C can have a total of 1, 3×3, 5×5 or 10×10 pixels, for instance, depending on the spread of the portion of tissue having the particular health condition. Further note that the foregoing ROIs were chosen from portions of each image that are uniform and not saturated. To account for illumination non-uniformities and other sources of noise, including to factor out the spectrum of the halogen light source, each of the raw ("as-acquired") images 5781, 5791, 5771, and 5771C has been normalized against a camera baseline. Moreover, a spectrum corresponding to a particular ROI represents the average of the spectra corresponding to each pixel of the particular ROI, and a spectrum corresponding to a respective pixel can be represented mathematically by a spectrum vector Y having N coefficients. Here, the number N of coefficients is the number of wavelength bins, e.g., N=25, of the hyperspectral camera used to acquire the images 5781, 5791, 5771, and 5771C, and the spectrum vector can be represented as a matrix $(Y)_{N \times 1}$ with N rows and 1 column. Furthermore, the spectrum corresponding to a respective pixel is normalized to its own peak.

Figure 58:
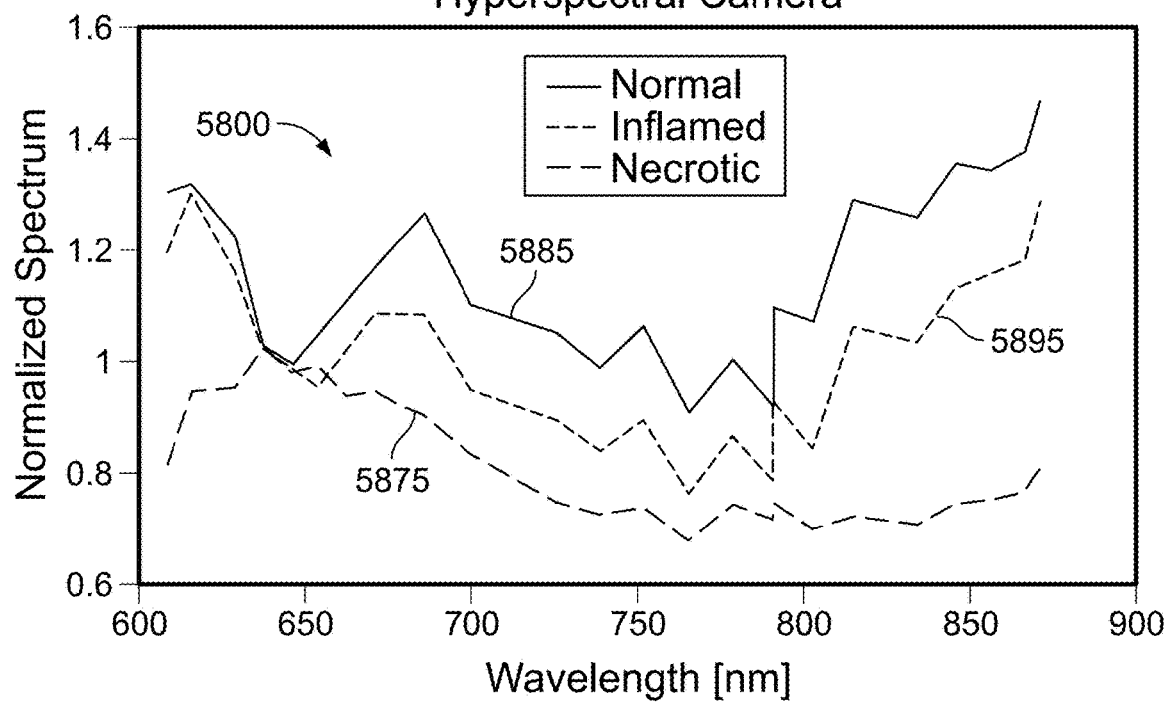
FIG. 58 shows spectra obtained from the raw images of FIG. 57 and corresponding to normal, inflamed or necrotic portions of live colon tissue.

FIG. 58 shows spectra 5800 corresponding to various health conditions of the live colon tissue. The spectra 5800 were obtained from the raw images 5781, 5791, 5771, and 5771C as part of a training stage of a classification model for predicting a health condition of live colon tissue based on its image(s) acquired with a hyperspectral camera. In the example shown in FIG. 58, the spectra 5800 include a first spectrum 5885 corresponding to ROI 5783 which images a normal portion of the live colon tissue, a second spectrum 5895 corresponding to ROI 5793 which images an inflamed portion of the live colon tissue, and a third spectrum 5875 corresponding to ROIs 5773 and 5773C, which image respective necrotic portions of different live colon tissues. Note that the first spectrum 5885 corresponding to normal colon tissue, the second spectrum 5895 corresponding to inflamed colon tissue, and the third spectrum 5875 corresponding to necrotic colon tissue have spectral features that are different from each other. As such, the spectra 5800 can be used as a set of basis spectra of the classification model. The set 5800 of basis spectra of the classification model can be represented mathematically by a matrix $(A)_{N \times 3}$ with N rows and 3 columns, where the first column is the first spectrum 5885, the second column is the second spectrum 5895, and the third column is the third spectrum 5875.

In this manner, for an image of a live colon tissue acquired by the hyperspectral camera, the image having $N_1 \times N_2$ pixels, a spectrum Y(i,j) of a pixel P(i,j), where i=1 . . . $N_1$, 4=1 . . . $N_2$, can be represented mathematically by a linear combination of the first spectrum 5885, the second spectrum 5895, and the third spectrum 5875, in accordance with the following equation:

$$Y(i,j) = x_1(i,j)S_{5885} + x_2(i,j)S_{5895} + x_3(i,j)S_{5875}, (Y(i,j))_{N \times 1} = (A)_{N \times 3}(X(i,j))_{3 \times 1} \quad (4).$$

In EQ. (4), the coefficients $x_1(i,j)$, $x_2(i,j)$, $x_3(i,j)$ of the first spectrum 5885, the second spectrum 5895, and the third spectrum 5875, respectively, are unique for the pixel P(i,j) and form a pixel-dependent matrix $(X(i,j))_{3 \times 1}$ having 3 rows and 1 column. In this manner, the set 5800 of basis spectra of the classification model can be used to determine a health condition of live colon tissue with a spatial resolution corresponding to a pixel of an image of the live colon tissue acquired with the hyperspectral camera. The determination is performed, for each pixel of the acquired image, by inverting EQ. (4) to solve for the pixel-dependent matrix X corresponding to the "acquired" spectrum Y of the pixel, based on the set 5800 of basis spectra of the classification model.

Thus, extent of an inflamed portion within a normal portion of colon tissue, or of necrotic portion within an inflamed portion of colon tissue could be determined, in-vivo, by (i) acquiring, with a hyperspectral camera of an ingestible device, an image of the colon tissue, (ii) producing at least one spectrum corresponding to the colon tissue from the acquired image, and (iii) comparing values of coefficients of a linear combination of the spectra 5800 that matches the produced spectrum. For example, if for an ROI of an image of colon tissue, coefficients of the set of coefficients X(ROI) satisfy the conditions $x_1 > x_2$ and $x_2 \gg x_3$, then this is due to the fact that the ROI corresponds to imaged colon tissue having (a) a normal portion larger than an inflamed portion, and (b) only traces of a necrotic portion. As another example, if for an ROI of an image of colon tissue, coefficients of the set of coefficients X(ROI) satisfy the conditions $x_1 \ll x_2$ and $x_2 \approx x_3$, then this is due to the fact that the ROI corresponds to imaged colon tissue having (a) an inflamed portion about equal to a necrotic portion, and (b) only traces of a normal portion.

Figure 59:
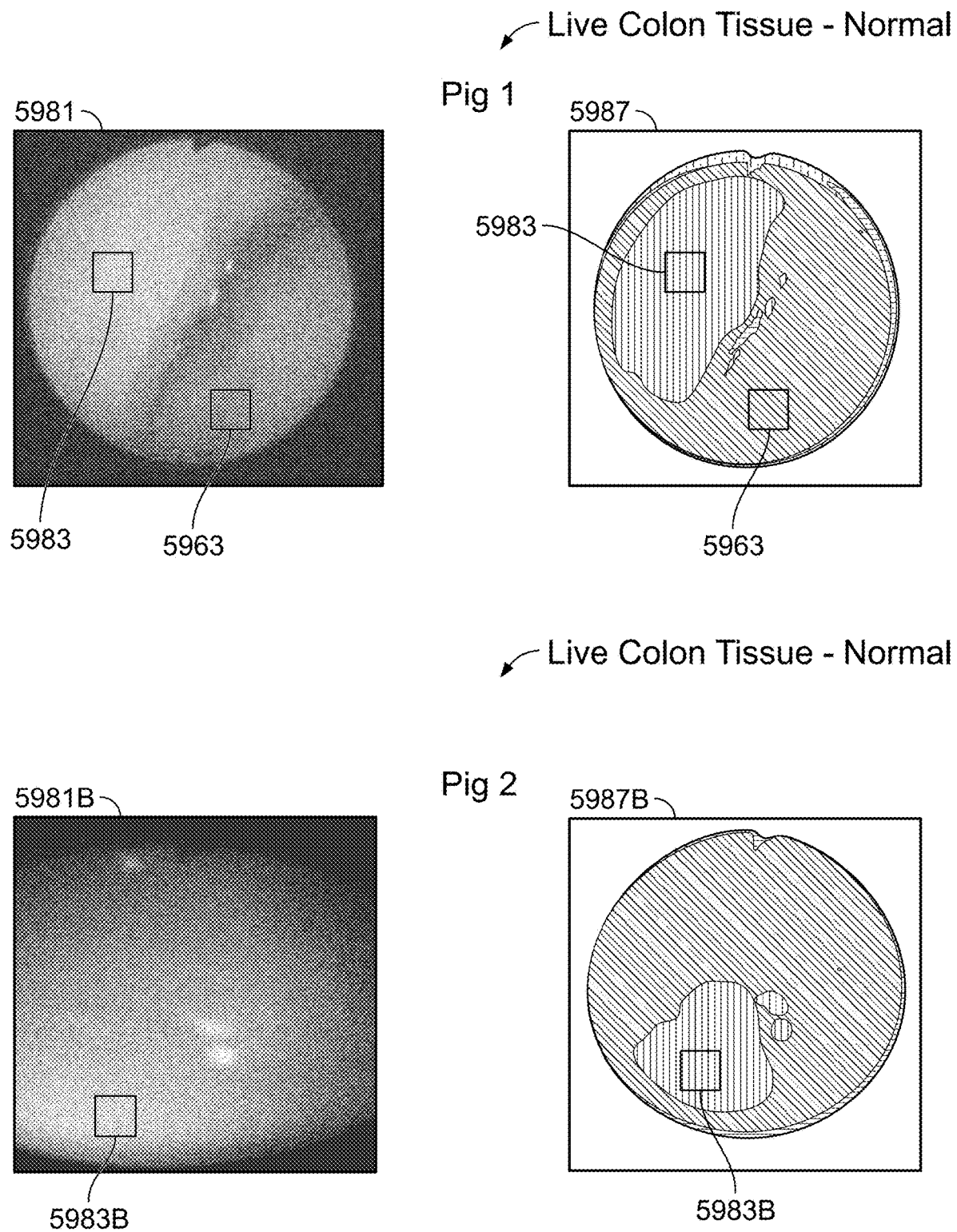
FIG. 59 shows raw images of normal portions of live colon and their corresponding health-condition images obtained based on the spectra of FIG. 58.

FIG. 59 shows a raw image 5981 of colon tissue of a first live pig and a raw image 5981B of colon tissue of a second live pig, each acquired with the hyperspectral camera used to produce the set 5800 of basis spectra of the classification model. FIG. 59 also shows a health-condition image 5987 corresponding to the raw image 5981 and a health-condition image 5987B corresponding to the raw image 5981B. In each of the health-condition images 5987, 5987B, each pixel represents, in accordance with EQ. (4), the respective set of three coefficients X of the linear combination of the set 5800 of basis spectra of the classification model that is equal to the spectrum Y corresponding the pixel. For example, as each of the ROIs 5983, 5983B corresponds to a portion of normal colon tissue, the respective spectrum Y(5983), Y(5983B) acquired for ROI 5983, 5983B matches the first spectrum 5885 of the set 5800 of basis spectra of the classification model, so each of the sets of coefficients X(5983), X(5983B) will be $x_1 \approx 1$, $x_2 \approx 0$, $x_3 \approx 0$. As another example, as the ROI 5963 corresponds to a portion of colon tissue that is partially inflamed and partially necrotic, the spectrum Y(5963) acquired for ROI 5963 is a linear combination of mostly the second spectrum 5895 and the third spectrum 5875 of the set 5800 of basis spectra of the classification model, so the set of coefficients X(5963) will be $x_1 \approx 0$, $x_2 \neq 0$, $x_3 \neq 0$. Also, because here $x_2 > x_3$, the ROI 5963 includes more inflamed colon tissue than necrotic colon tissue. In this manner, health-condition images 5987, 5987B can be used to classify each of the live colon tissue of pig 1 imaged in image 5981 and the live colon tissue of pig 2 imaged in image 5981B as containing a normal portion surrounded by a combination of inflamed and necrotic portions.

Figure 60:
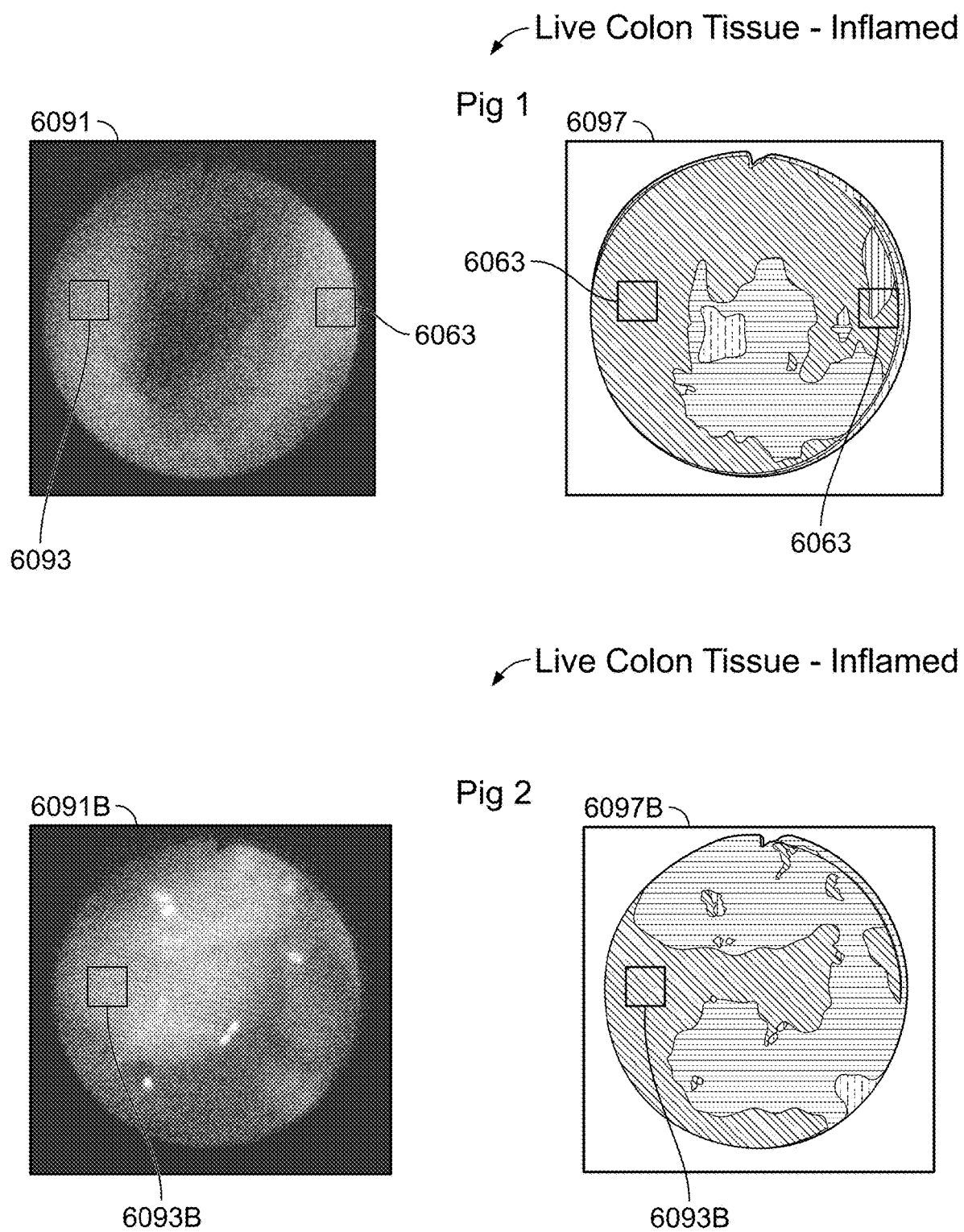
FIG. 60 shows raw images of inflamed portions of live colon and their corresponding health-condition images obtained based on the spectra of FIG. 58.

FIG. 60 shows a raw image 6091 of colon tissue of a first live pig and a raw image 6091B of colon tissue of a second live pig, each acquired with the hyperspectral camera used to produce the set 5800 of basis spectra of the classification model. FIG. 60 also shows a health-condition image 6097 corresponding to the raw image 6091 and a health-condition image 6097B corresponding to the raw image 6091B. In each of the health-condition images 6097, 6097B, each pixel represents, in accordance with EQ. (4), the respective set of three coefficients X of the linear combination of the set 5800 of basis spectra of the classification model that is equal to the spectrum Y corresponding the pixel. For example, as each of the ROIs 6093, 6093B corresponds to a portion of inflamed colon tissue, the respective spectrum Y(6093), Y(6093B) acquired for ROI 6093, 6093B matches the second spectrum 5895 of the set 5800 of basis spectra of the classification model, so each of the sets of coefficients X(6093), X(6093B) will be $x_1 \approx 0$, $x_2 \approx 1$, $x_3 \approx 0$. As another example, as the ROI 6063 corresponds to a portion of colon tissue that is partially normal and partially inflamed, the spectrum Y(6063) acquired for ROI 6063 is a linear combination of mostly the first spectrum 5885 and the second spectrum 5895 of the set 5800 of basis spectra of the classification model, so the set of coefficients X(6063) will be $x_1 \neq 0$, $x_2 \neq 0$, $x_3 \approx 0$. Also, because here $x_1 \approx x_2$, the ROI 6063 includes about as much inflamed colon tissue as normal colon tissue. In this manner, health-condition images 6097, 6097B can be used to classify each of the live colon tissue of pig 1 imaged in image 6091 and the live colon tissue of pig 2 imaged in image 6091B as containing inflamed portions adjacent to combinations of normal and inflamed portions and combinations of inflamed and necrotic portions.

FIG. 61 shows a raw image 6171 of colon tissue of a first live pig and a raw image 6171B of colon tissue of a second live pig, each acquired with the hyperspectral camera used to produce the set 5800 of basis spectra of the classification model. FIG. 61 also shows a health-condition image 6177 corresponding to the raw image 6171 and a health-condition image 6177B corresponding to the raw image 6171B. In each of the health-condition images 6177, 6177B, each pixel represents, in accordance with EQ. (4), the respective set of three coefficients X of the linear combination of the set 5800 of basis spectra of the classification model that is equal to the spectrum Y corresponding the pixel. For example, as each of the ROIs 6173, 6173B corresponds to a portion of necrotic colon tissue, the respective spectrum Y(6173), Y(6173B) acquired for ROI 6173, 6173B matches the third spectrum 5875 of the set 5800 of basis spectra of the classification model, so each of the sets of coefficients X(6173), X(6173B) will be $x_1 \approx 0$, $x_2 \approx 0$, $x_3 \approx 1$. As another example, as the ROI 6163B corresponds to a portion of colon tissue that is partially inflamed and partially necrotic, the spectrum Y(6163B) acquired for ROI 6163B is a linear combination of mostly the second spectrum 5895 and the third spectrum 5875 of the set 5800 of basis spectra of the classification model, so the set of coefficients X(6163B) will be $x_1 \approx 0$, $x_2 \neq 0$, $x_3 \neq 0$. Also, because here $x_2 \approx x_3$, the ROI 6163B includes about as much inflamed colon tissue as necrotic colon tissue. In this manner, health-condition images 6177, 6177B can be used to classify each of the live colon tissue of pig 1 imaged in image 6171 and the live colon tissue of pig 2 imaged in image 6171B as containing necrotic portions adjacent to normal portions or combinations of inflamed and necrotic portions.

Example 18: Hyperspectral Imaging for Quantifying Blood Oxygenation

Spectral analysis was performed, by using spectra obtained from images of blood samples acquired with a hyperspectral camera (e.g., the one described in connection with Example 3), for determining a level of oxygenation of the blood samples.

Figure 62:
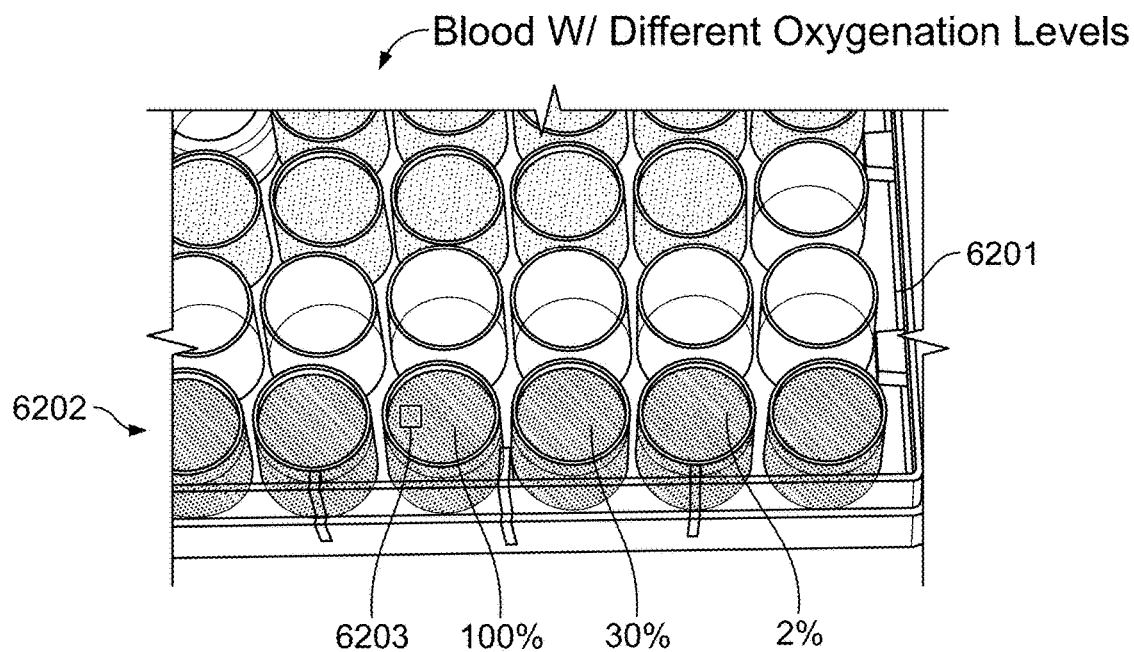
FIG. 62 shows samples of blood having different oxygenation levels.

FIG. 62 shows samples of blood 6202 having different oxygenation levels, e.g., 2%, 30% or 100% oxygenation, as tested on a co-oximeter. The blood samples 6202 were disposed in a 24-well plate 6201. Images of the well plate 6201 were acquired with the hyperspectral camera while illuminating the well plate with a halogen light source.

An image of the well plate 6201, acquired as it was holding N blood samples 6202 in respective N wells, was processed in the following manner. To correct for non-uniform illumination of the N blood samples 6202 held by the well plate 6201, an image of a uniform white calibration surface was used to normalize the image of the well plate holding the N blood samples 6202 via pixel-by-pixel division. A respective region of interest (ROI) 6203 of the acquired image, for each well of the N well plates holding the blood samples 6202, was defined to have 3×3 pixels, for instance. The spectral signature of light corresponding to each ROI was averaged to obtain a respective spectrum of light that reflected off the respective blood sample held by the well associated with the ROI.

Figure 63:
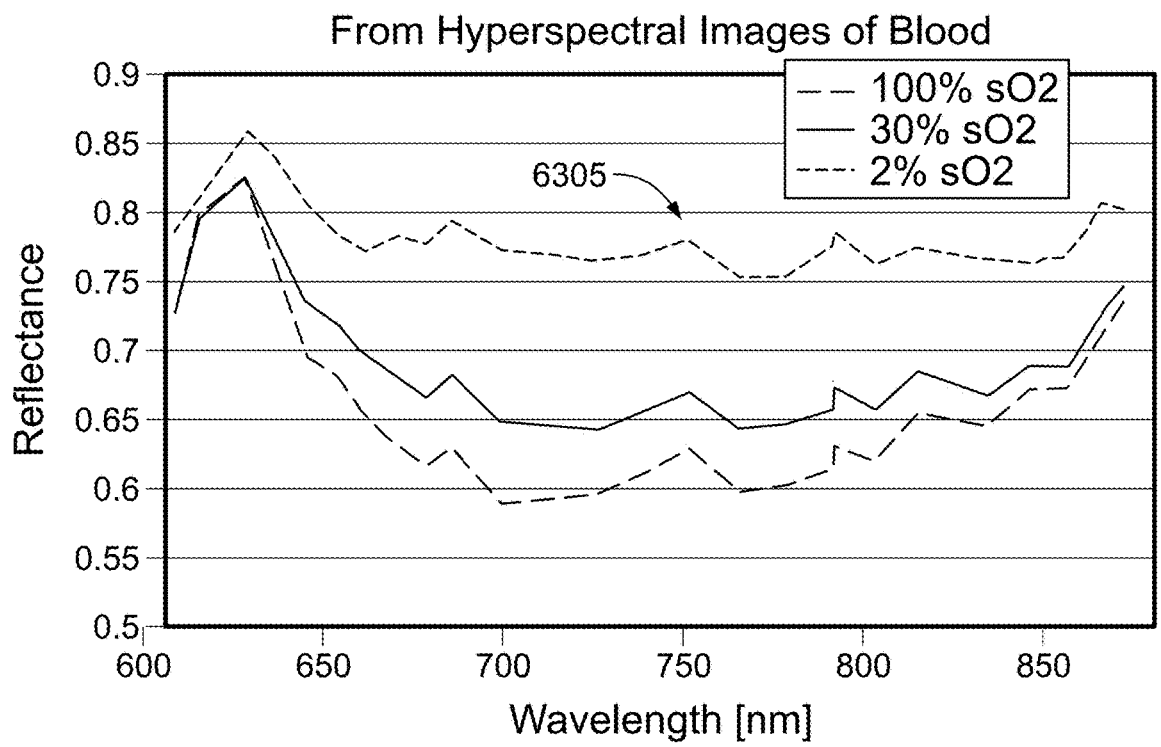
FIG. 63 shows spectra obtained from hyperspectral images of the samples shown in FIG. 62.

FIG. 63 shows spectra 6305 obtained from hyperspectral images of the blood samples 6202. Here, each of the spectra 6305 corresponds to a blood sample have a respective oxygenation level. Note that, over the spectral range of the hyperspectral camera, the spectra 6305 corresponding to samples having different oxygenation levels have different spectral features. This suggests that the level of oxygenation of a blood sample can be determined based on spectral features of a spectrum obtained from a hyperspectral image of the blood sample.

As such, the spectra 6305 can be used as inputs for machine learning modeling, e.g., based on partial least squares (PLS), to predict the oxygenation level of a blood sample to which one of the spectra 6305 corresponds. In this manner, an unknown oxygenation level of a blood sample having a spectrum obtained from a hyperspectral image can be determined by (i) identifying one of the spectra 6305, corresponding to blood samples 6202 having known oxygenation levels, that best matches the obtained spectrum, and (ii) assigning to the unknown oxygenation level a value of the oxygenation level of the blood sample to which the identified spectrum corresponds.

Note that tissue of the GI tract includes a large number of blood vessels. As the results discussed in Example 18 suggest that it is possible to differentiate between oxygenation levels of blood based on differences in spectra obtained from hyperspectral images of the blood, by extension, it may be possible to differentiate between oxygenated and de-oxygenated GI tract tissue using reference spectra obtained from hyperspectral images of GI tract tissue having different oxygenation levels, or even using reference the spectra corresponding to blood samples having different oxygenation levels, e.g., like the spectra 6305. As such, in some implementations, it could be determined, in-vivo, whether a GI tract tissue is oxygenated or de-oxygenated by (i) acquiring, with a hyperspectral camera of an ingestible device, an image of the GI tract tissue, (ii) producing one or more spectra corresponding to the GI tract tissue from the acquired image, and (iii) comparing spectral features of the produced spectrum and reference spectra corresponding to oxygenated GI tract tissue and de-oxygenated GI tract tissue. In other implementations, the foregoing comparing operation (iii) may be replaced with comparing the spectral features of the spectrum produced at (ii) and reference spectra (e.g., like the spectra 6305) corresponding to blood samples having different oxygenation levels.

Example 19: Localization

An ingestible medical device according to the disclosure ("TLC1") was tested on 20 subjects to investigate its localization ability. TLC1 was a biocompatible polycarbonate capsule that contained a power supply, electronics and software. An onboard software algorithm used time, temperature and reflected light spectral data to determine the location of the capsule as it traveled the GI tract. The capsule is 0.51×1.22 inches which is larger than a vitamin pill which is 0.4×0.85 inches. The subjects fasted overnight before participating in the study. Computerized tomography ("CT") were used as a basis for determining the accuracy of the localization data collected with TLC1. One of the 20 subjects did not follow the fasting rule. CT data was lacking for another one of the 20 subjects. Thus, these two subjects were excluded from further analysis. TLC1 sampled RGB data (radially transmitted) every 15 seconds for the first 14 hours after it entered the subject's stomach, and then samples every five minutes after that until battery dies. TLC1 did not start to record optical data until it reached the subject's stomach. Thus, there was no RGB-based data for the mouth-esophagus transition for any of the subjects.

In addition, a PillCam® SB (Given Imaging) device was tested on 57 subjects. The subjects fasted overnight before joining the study. PillCam videos were recorded within each subject. The sampling frequency of PillCam is velocity dependent. The faster PillCam travels, the faster it would sample data. Each video is about seven to eight hours long, starting from when the capsule was administrated into the subject's mouth. RGB optical data were recorded in a table. A physician provided notes on where stomach-duodenum transition and ileum-cecum transition occurred in each video. Computerized tomography ("CT") was used as a basis for determining the accuracy of the localization data collected with PillCam.

Esophagus-Stomach Transition

For TLC1, it was assumed that this transition occurred one minute after the patient ingested the device. For PillCam, the algorithm was as follows:
1. Start mouth-esophagus transition detection after capsule is activated/administrated
2. Check whether Green <102.3 and Blue <94.6
    a. If yes, mark as mouth-esophagus transition
    b. If no, continue to scan the data
3. After detecting mouth-esophagus transition, continue to monitor Green and Blue signals for another 30 seconds, in case of location reversal
    a. If either Green >110.1 or Blue >105.5, mark it as mouth-esophagus location reversal
    b. Reset the mouth-esophagus flag and loop through step 2 and 3 until the confirmed mouth-esophagus transition detected
4. Add one minute to the confirmed mouth-esophagus transition and mark it as esophagus-stomach transition For one of the PillCam subjects, there was not a clear cut difference between the esophagus and stomach, so this subject was excluded from future analysis of stomach localization. Among the 56 valid subjects, 54 of them have correct esophagus-stomach transition localization. The total agreement is 54/56=96%. Each of the two failed cases had prolonged esophageal of greater than one minute. Thus, adding one minute to mouth-esophagus transition was not enough to cover the transition in esophagus for these two subjects.

Stomach-Duodenum

For both TLC1 and PillCam, a sliding window analysis was used. The algorithm used a dumbbell shape two-sliding-window approach with a two-minute gap between the front (first) and back (second) windows. The two-minute gap was designed, at least in part, to skip the rapid transition from stomach to small intestine and capture the small intestine signal after capsule settles down in small intestine. The algorithm was as follows:
1. Start to check for stomach-duodenum transition after capsule enters stomach
2. Setup the two windows (front and back)
    a. Time length of each window: 3 minutes for TLC1; 30 seconds for PillCam
    b. Time gap between two windows: 2 minutes for both devices
    c. Window sliding step size: 0.5 minute for both devices 3. Compare signals in the two sliding windows
   a. If difference in mean is higher than 3 times the standard deviation of Green/Blue signal in the back window
      i. If this is the first time ever, record the mean and standard deviation of signals in the back window as stomach reference
      ii. If mean signal in the front window is higher than stomach reference signal by a certain threshold (0.3 for TLC1 and 0.18 for PillCam), mark this as a possible stomach-duodenum transition
   b. If a possible pyloric transition is detected, continue to scan for another 10 minutes in case of false positive flag
      i. If within this 10 minutes, location reversal is detected, the previous pyloric transition flag is a false positive flag. Clear the flag and continue to check
      ii. If no location reversal has been identified within 10 minutes following the possible pyloric transition flag, mark it as a confirmed pyloric transition
   c. Continue monitoring Green/Blue data for another 2 hours after the confirmed pyloric transition, in case of location reversal
      i. If a location reversal is identified, flag the timestamp when reversal happened and then repeat steps a-c to look for the next pyloric transition
      ii. If the capsule has not gone back to stomach 2 hours after previously confirmed pyloric transition, stops location reversal monitoring and assume the capsule would stay in intestinal area For TLC1, one of the 18 subjects had too few samples (<3 minutes) taken in the stomach due to the delayed esophagus-stomach transition identification by previously developed localization algorithm. Thus, this subject was excluded from the stomach-duodenum transition algorithm test. For the rest of the TLC1 subjects, CT images confirmed that the detected pyloric transitions for all the subjects were located somewhere between stomach and jejunum. Two out of the 17 subjects showed that the capsule went back to stomach after first the first stomach-duodenum transition. The total agreement between the TLC1 algorithm detection and CT scans was 17/17=100%.

For one of the PillCam subjects, the capsule stayed in the subject's stomach all the time before the video ended. For another two of the PillCam subjects, too few samples were taken in the stomach to run the localization algorithm. These three PillCam subjects were excluded from the stomach-duodenum transition localization algorithm performance test. The performance summary of pyloric transition localization algorithm for PillCam was as follows:
1. Good cases (48 subjects):
   a. For 25 subjects, our detection matches exactly with the physician's notes
   b. For 19 subjects, the difference between the two detections is less than five minutes
   c. For four subjects, the difference between the two detections is less than 10 minutes (The full transition could take up to 10 minutes before the G/B signal settled)
2. Failed cases (6 subjects):
   a. Four subjects had high standard deviation of Green/Blue signal in the stomach
   b. One subject had bile in the stomach, which greatly affected Green/Blue in stomach
   c. One subject had no Green/Blue change at pyloric transition The total agreement for the PillCam stomach-duodenum transition localization algorithm detection and physician's notes was 48/54=89%.

Duodenum-Jejunum Transition

For TLC1, it was assumed that the device left the duodenum and entered the jejunum three minutes after it was determined that the device entered the duodenum. Of the 17 subjects noted above with respect to the TLC1 investigation of the stomach-duodenum transition, 16 of the subjects mentioned had CT images that confirmed that the duodenum-jejunum transition was located somewhere between stomach and jejunum. One of the 17 subjects had a prolonged transit time in duodenum. The total agreement between algorithm detection and CT scans was 16/17=94%.

For PillCam, the duodenum-jejunum transition was not determined.

Jejunum-Ileum Transition

It is to be noted that the jejunum is redder and more vascular than ileum, and that the jejunum has a thicker intestine wall with more mesentery fat. These differences can cause various optical responses between jejunum and ileum, particularly for the reflected red light signal. For both TLC1 and PillCam, two different approaches were explored to track the change of red signal at the jejunum-ileum transition. The first approach was a single-sliding-window analysis, where the window is 10 minutes long, and the mean signal was compared with a threshold value while the window was moving along. The second approach was a two-sliding-window analysis, where each window was 10 minutes long with a 20 minute spacing between the two windows. The algorithm for the jejunum-ileum transition localization was as follows:
1. Obtain 20 minutes of Red signal after the duodenum-jejunum transition, average the data and record it as the jejunum reference signal
2. Start to check the jejunum-ileum transition 20 minutes after the device enters the jejunum
   a. Normalize the newly received data by the jejunum reference signal
   b. Two approaches:
      i. Single-sliding-window analysis
         Set the transition flag if the mean of reflected red signal is less than 0.8
      ii. Two-sliding-window analysis:
         Set the transition flag if the mean difference in reflected red is higher than 2× the standard deviation of the reflected red signal in the front window For TLC1, 16 of the 18 subjects had CT images that confirmed that the detected jejunum-ileum transition fell between jejunum and cecum. The total agreement between algorithm and CT scans was 16/18=89%. This was true for both the single-sliding-window and double-sliding-window approaches, and the same two subjects failed in both approaches.

The performance summary of the jejunum-ileum transition detection for PillCam is listed below:
1. Single-sliding-window analysis:
   a. 11 cases having jejunum-ileum transition detected somewhere between jejunum and cecum
   b. 24 cases having jejunum-ileum transition detected after cecum c. 19 cases having no jejunum-ileum transition detected
d. Total agreement: 11/54=20%
2. Two-sliding-window analysis:
   a. 30 cases having jejunum-ileum transition detected somewhere between jejunum and cecum
   b. 24 cases having jejunum-ileum transition detected after cecum
   c. Total agreement: 30/54=56%

Ileum-Cecum Transition

Data demonstrated that, for TLC1, mean signal of reflected red/green provided the most statistical difference before and after the ileum-cecum transition. Data also demonstrated that, for TLC1, the coefficient of variation of reflected green/blue provided the most statistical contrast at ileum-cecum transition. The analysis based on PillCam videos showed very similar statistical trends to those results obtained with TLC1 device. Thus, the algorithm utilized changes in mean value of reflected red/green and the coefficient of variation of reflected green/blue. The algorithm was as follows:
1. Start to monitor ileum-cecum transition after the capsule enters the stomach
2. Setup the two windows (front (first) and back (second))
   a. Use a five-minute time length for each window
   b. Use a 10-minute gap between the two windows
   c. Use a one-minute window sliding step size
3. Compare signals in the two sliding windows
   a. Set ileum-cecum transition flag if
      i. Reflected red/green has a significant change or is lower than a threshold
      ii. Coefficient of variation of reflected green/blue is lower than a threshold
   b. If this is the first ileum-cecum transition detected, record average reflected red/green signal in small intestine as small intestine reference signal
   c. Mark location reversal (i.e. capsule returns to terminal ileum) if
      i. Reflected red/green is statistically comparable with small intestine reference signal
      ii. Coefficient of variation of reflected green/blue is higher than a threshold
   d. If a possible ileum-cecum transition is detected, continue to scan for another 10 minutes for TLC1 (15 minutes for PillCam) in case of false positive flag
      i. If within this time frame (10 minutes for TLC1, 15 minutes for PillCam), location reversal is detected, the previous ileum-cecum transition flag is a false positive flag. Clear the flag and continue to check
      ii. If no location reversal has been identified within this time frame (10 minutes for TLC1, 15 minutes for PillCam) following the possible ileum-cecum transition flag, mark it as a confirmed ileum-cecum transition
   e. Continue monitoring data for another 2 hours after the confirmed ileum-cecum transition, in case of location reversal
      i. If a location reversal is identified, flag the timestamp when reversal happened and then repeat steps a-d to look for the next ileum-cecum transition
      ii. If the capsule has not gone back to small intestine 2 hours after previously confirmed ileum-cecum transition, stop location reversal monitoring and assume the capsule would stay in large intestinal area The flag setting and location reversal criteria particularly designed for TLC1 device were as follows:
1. Set ileum-cecum transition flag if
   a. The average reflected red/Green in the front window is less than 0.7 or mean difference between the two windows is higher than 0.6
   b. And the coefficient of variation of reflected green/blue is less than 0.02
2. Define as location reversal if
   a. The average reflected red/green in the front window is higher than small intestine reference signal
   b. And the coefficient of variation of reflected green/blue is higher than 0.086

For TLC1, 16 of the 18 subjects had CT images that confirmed that the detected ileum-cecum transition fell between terminal ileum and colon. The total agreement between algorithm and CT scans was 16/18=89%. Regarding those two subject where the ileum-cecum transition localization algorithm failed, for one subject the ileum-cecum transition was detected while TLC1 was still in the subject's terminal ileum, and for the other subject the ileum-cecum transition was detected when the device was in the colon.

Among the 57 available PillCam endoscopy videos, for three subjects the endoscopy video ended before PillCam reached cecum, and another two subjects had only very limited video data (less than five minutes) in the large intestine. These five subjects were excluded from ileum-cecum transition localization algorithm performance test. The performance summary of ileum-cecum transition detection for PillCam is listed below:
1. Good cases (39 subjects):
   a. For 31 subjects, the difference between the PillCam detection and the physician's notes was less than five minutes
   b. For 3 subjects, the difference between the PillCam detection and the physician's notes was less than 10 minutes
   c. For 5 subjects, the difference between the PillCam detection and the physician's notes was less than 20 minutes (the full transition can take up to 20 minutes before the signal settles)
2. Marginal/bad cases (13 subjects):
   a. Marginal cases (9 subjects)
      i. The PillCam ileum-cecum transition detection appeared in the terminal ileum or colon, but the difference between the two detections was within one hour
   b. Failed cases (4 subjects)
      i. Reasons of failure:
         1. The signal already stabilized in the terminal ileum
         2. The signal was highly variable from the entrance to exit
         3. There was no statistically significant change in reflected red/green at ileum-cecum transition The total agreement between ileocecal transition localization algorithm detection and the physician's notes is 39/52=75% if considering good cases only. Total agreement including possibly acceptable cases is 48/52=92.3%

Cecum-Colon Transition

Data demonstrated that, for TLC1, mean signal of reflected red/green provided the most statistical difference before and after the cecum-colon transition. Data also demonstrated that, for TLC1, the coefficient of variation of reflected blue provided the most statistical contrast at cecum-colon transition. The same signals were used for PillCam. The cecum-colon transition localization algorithm was as follows:
1. Obtain 10 minutes of reflected red/green and reflected blue signals after ileum-cecum transition, average the data and record it as the cecum reference signals
2. Start to check cecum-colon transition after capsule enters cecum (The cecum-colon transition algorithm is dependent on the ileum-cecum transition flag)
   a. Normalize the newly received data by the cecum reference signals
   b. Two-sliding-window analysis:
      i. Use two adjacent 10 minute windows
      ii. Set the transition flag if any of the following criteria were met
         The mean difference in reflected red/green was more than 4× the standard deviation of reflected red/green in the back (second) window
         The mean of reflected red/green in the front (first) window was higher than 1.03
         The coefficient of variation of reflected blue signal in the front (first) window was greater than 0.23

The threshold values above were chosen based on a statistical analysis of data taken by TLC1.

For TLC1, 15 of the 18 subjects had the cecum-colon transition detected somewhere between cecum and colon. One of the subjects had the cecum-colon transition detected while TLC1 was still in cecum. The other two subjects had both wrong ileum-cecum transition detection and wrong cecum-colon transition detection. The total agreement between algorithm and CT scans was 15/18=83%.

For PillCam, for three subjects the endoscopy video ended before PillCam reached cecum, and for another two subjects there was very limited video data (less than five minutes) in the large intestine. These five subjects were excluded from cecum-colon transition localization algorithm performance test. The performance summary of cecum-colon transition detection for PillCam is listed below:
1. 27 cases had the cecum-colon transition detected somewhere between the cecum and the colon
2. one case had the cecum-colon transition detected in the ileum
3. 24 cases had no cecum-colon transition localized The total agreement: 27/52=52%.

The following table summarizes the localization accuracy results.

| Transition | TLC1 | PillCam |
| --- | --- | --- |
| Stomach-Duodenum | 100% (17/17) | 89% (48/54) |
| Duodenum-Jejunum | 94% (16/17) | N/A |
| Ileum-Cecum | 89% (16/18) | 75% (39/52) |
| Ileum-terminal ileum/cecum/colon | 100% (18/18) | 92% (48/52) |

OTHER EMBODIMENTS

While certain aspects of ingestible devices have been described, the disclosure is not limited in this sense. FIGS. 64-99 illustrate additional nonlimiting examples of ingestible devices that can be implemented with the technology described herein. FIGS. 100-112 illustrate nonlimiting examples of localization information collection and analysis that can be performed with an ingestible device disclosed herein. FIG. 113 illustrates a nonlimiting example of a system for collecting, communicating and/or analyzing data about a subject, using an ingestible device as disclosed herein. It is to be understood that the technology, including ingestible devices, described with respect to FIGS. 64-113, can include componentry as discussed above, such as, for example, one or more spectrometers (e.g., to collect hyperspectral data).

Figure 64:
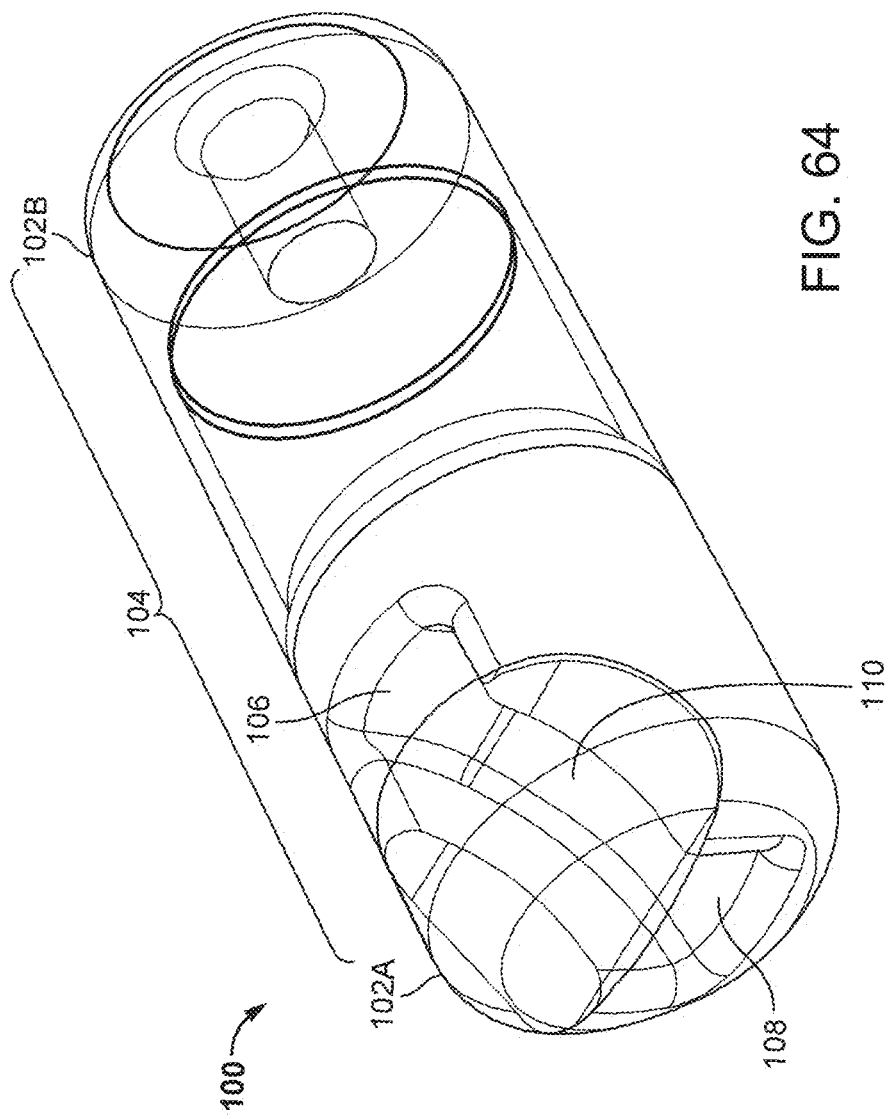
FIG. 64 shows an illustrative embodiment of an ingestible device.

FIG. 64 illustrates an example ingestible device 100 with multiple openings in the housing. The ingestible device 100 has an outer housing with a first end 102A, a second end 102B, and a wall 104 extending longitudinally from the first end 102A to the second end 102B. Ingestible device 100 has a first opening 106 in the housing, which is connected to a second opening 108 in the housing. The first opening 106 of the ingestible device 100 is oriented substantially perpendicular to the second opening 108, and the connection between the first opening 106 and the second opening 108 forms a curved chamber 110 within the ingestible device 100.

The overall shape of the ingestible device 100, or any of the other ingestible devices discussed in this disclosure, may be similar to an elongated pill or capsule. This may make the ingestible device 100 easy to consume, and allow it to travel easily through the GI tract. As used herein, the term "gastrointestinal tract" or "GI tract" refers to all portions of an organ system responsible for consuming and digesting foodstuffs, absorbing nutrients, and expelling waste. This includes orifices and organs such as the mouth, throat, esophagus, stomach, small intestine, large intestine, rectum, anus, and the like, as well as the various passageways and sphincters connecting the aforementioned parts. In certain portions of the GI tract, such as the stomach, the ingestible device 100 may be free to move or rotate in any direction. In other portions of the GI tract, the movement of the ingestible device 100 may be restricted. For example, in the relatively narrow confines of the small intestine, the walls of the small intestine may squeeze down on the ingestible device, forcing the ingestible device 100 to orient itself longitudinally along the length of the small intestine. In this case, the walls of the small intestine wrap around the longitudinally extending wall 104 of the ingestible device 100, and the ingestible device 100 travels through the small intestine with one of the ends 102A or 102B in front.

For illustrative purposes, the ingestible device 100 of FIG. 64 shows the first opening 106 located in a portion of the wall 104 and oriented radially, and the second opening 108 located near the first end 102A and oriented longitudinally. However, in some embodiments, the exact location and orientation of the first opening 106 and the second opening 108 may be different from that shown in FIG. 64. During transit through the GI Tract, natural contractions within the small intestine may apply pressure radially to different portions of the wall 104 of the ingestible device 100, which may force solids or fluids into the first opening 106. As new material (e.g., fluid and solid particulates from the small intestine or other portions of the GI tract) enters the curved chamber 110 through the first opening 106, older material already located in the curved chamber 110 may be naturally forced out of the curved chamber 110 through the second opening 108.

In some embodiments, a portion of the curved chamber 110 may be used as a sampling chamber, which may hold samples obtained from the GI tract. In some embodiments the curved chamber 110 is subdivided into sub-chambers, each of which may be separated by a series of one or more valves or interlocks. For example, sub-chambers may be used to retain multiple samples within different portions of the curved chamber 110. In some embodiments, the curved chamber 110 is connected to other chambers within the ingestible device 100, or other openings located on the housing of the ingestible device 100. This may allow new samples to be acquired in the curved chamber 110 while older samples of interest are still stored within the ingestible device 100. In some embodiments, the ingestible device 100 is equipped with sensors to detect the properties a sample contained in the sampling chamber, or the results of an assay technique applied to the sample. In some embodiments, the ingestible device 100 is configured to obtain and retain a sample within the sampling chamber, which may be retrieved at a later time.

In some embodiments, the first opening 106, the second opening 108, or the curved chamber 110 include one or more of a hydrophilic or hydrophobic material, a sponge, a valve, or an air permeable membrane. For example, a one-way valve may prevent material from entering the curved chamber 110 through the second opening 108. As an alternate example, placing an air permeable membrane within the curved chamber 110 near the second opening 108 may allow unwanted gasses and air bubbles to pass through the air permeable membrane and exit the curved chamber 110, while solid or liquid samples may be prevented from passing through the air permeable membrane, and are retained within the curved chamber 110. The air permeable membrane may also prevent solid or liquid samples from entering the curved chamber 110 through the second opening 108.

The use of a hydrophilic material or sponge may allow samples to be retained within the curved chamber 110, and may reduce the amount of pressure needed for fluid to enter through the first opening 106 and dislodge air or gas in the curved chamber 110. Examples of hydrophilic materials that may be incorporated into the ingestible device 100 include hydrophilic polymers such as polyvinyl alcohol, polyvinyl pyrrolidone, and the like. Similarly, materials that have undergone various types of treatments, such as plasma treatments, may have suitable hydrophilic properties, and may be incorporated into the investible device 100. Sponges may be made of any suitable material or combination of materials, such as fibers of cotton, rayon, glass, polyester, polyethylene, polyurethane, and the like. Sponges generally may be made from commercially available materials, such as those produced by Porex®.

In some embodiments, the sponges may be treated in order to change their absorbency or to help preserve samples. Examples of materials which may be used to treat the sponges, alone or in combination, include sorbic acid, propyl parabene, citric acid, surfactants such as Tween® (polysorbate), DNA inhibitors and stabilizers, RNA inhibitors and stabilizers, protein inhibitors and stabilizers, and the like. In some embodiments, the sponges may be cut or abraded to change their absorbency or other physical properties.

Hydrophobic materials located near the second opening 108 may repel liquids, discouraging liquid samples from entering or exiting the curved chamber 110 through the second opening 108. This may serve a similar function as an air permeable membrane. Examples of hydrophobic materials which may be incorporated into the ingestible device 100 include polycarbonate, acrylics, fluorocarbons, styrenes, certain forms of vinyl, and the like.

The various materials listed above are provided as examples, and are not limiting. In practice, any type of suitable hydrophilic, hydrophobic, or sample preserving material may be used in an ingestible device described herein, and the teachings discussed in relation to such an ingestible device may be incorporated into any of the other ingestible devices described in this disclosure. Various methods for taking samples, controlling the movement of samples, or removing unwanted gasses, are discussed in detail in relation to FIGS. 64-97, and any of the various structures or techniques described in connection with FIGS. 64-97 may be incorporated into any ingestible device described herein.

Figure 65:
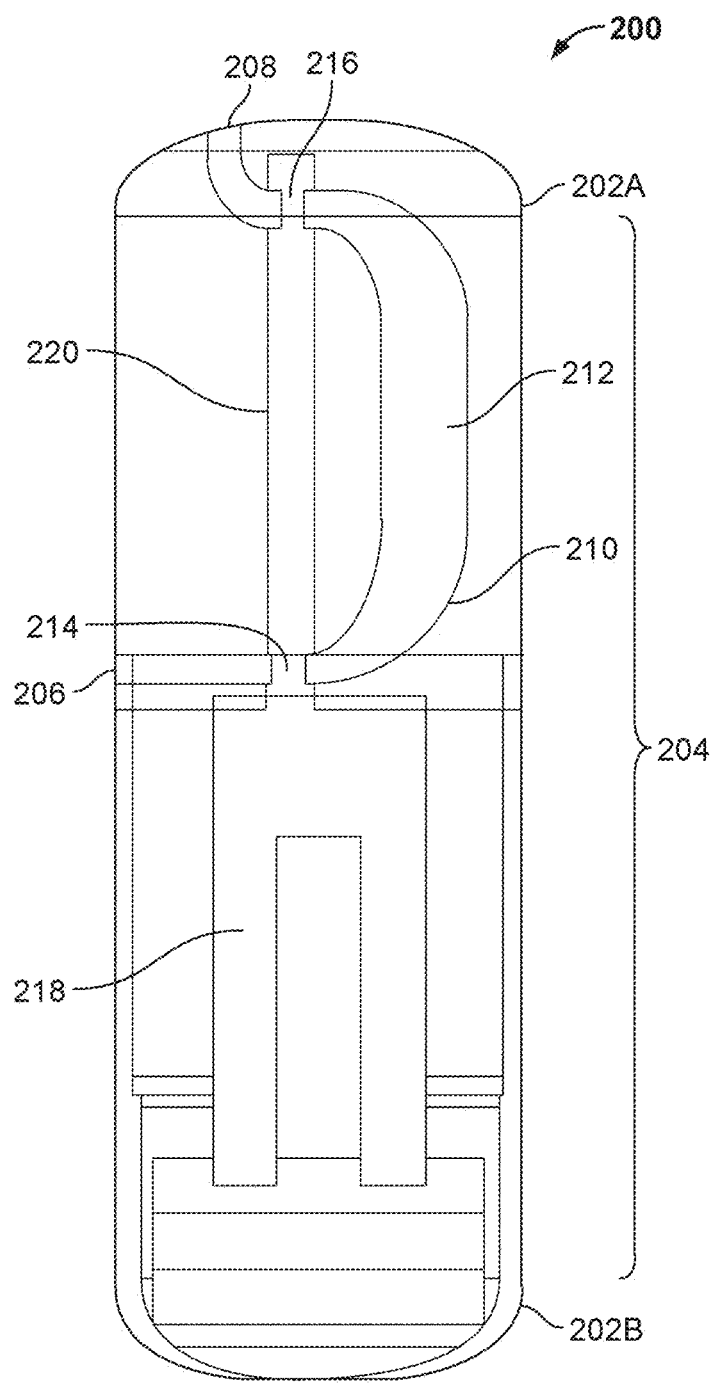
FIG. 65 shows another illustrative embodiment of an ingestible device.

FIG. 65 illustrates an example ingestible device 200 with multiple openings in the housing and various modifications that may be made to the ingestible device 100. Similar to the ingestible device 100, the ingestible device 200 has an outer housing with a first end 202A, a second end 202B, and a wall 204 extending longitudinally from the first end 202A to the second end 202B. Also similar to the ingestible device 100, the ingestible device 200 has a first opening 206 in the housing, which is connected to a second opening 208 in the housing. The connection between the first opening 206 and the second opening 208 forms a curved chamber 210 within the ingestible device 200.

In the ingestible device 200, a portion of the curved chamber 210 forms a sampling chamber 212. In some embodiments, the ingestible device 200 may include a sensor (not shown) within or proximate to the sampling chamber. This sensor may be used to detect a property of the sample. In some embodiments, an assay technique is applied to a sample within the sampling chamber, and the sensor may be used to detect the results of the assay technique. A first valve 214 is located between the first opening 206 and the sampling chamber 212. Similarly, a second valve 216 is located between the second opening 208 and the sampling chamber 212. In some embodiments, the valves 214 and 216 prevent a fluid from entering or exiting the sampling chamber 212, or may be used to isolate a sample within the sampling chamber 212.

The ingestible device 200 includes a mechanical actuator 218 coupled to the valves 214 and 216. In some embodiments, the mechanical actuator 218 is used to move one or both of the valves 214 and 216 between an open and a closed position. In some embodiments, the mechanical actuator 218 is controlled by a microcontroller, microprocessor, or other circuitry inside the ingestible device 200. In an open position, the first valve 214 may allow a sample to pass in and out of the sampling chamber 212 through the portion of the curved chamber 210 connected to the first opening 206. Similarly, in an open position, the second valve 216 may allow a sample to pass in and out of the sampling chamber 212 from the portion of the curved chamber 210 connected to the second opening 208. When the valves 214 and 216 are in the closed positions, they may not allow a sample to pass into or out of the sampling chamber 212.

In some embodiments, the valves 214 and 216 are rotary valves, pin valves, flap valves, butterfly valves, ball valves, plug valves, or any other suitable type of one-way or two-way valves, and may be the same or different types of valves. In some embodiments, one or both of the valves 214 and 216 are automatic valves that reseal themselves after a sample has been obtained, similar to the osmotic valve mechanism discussed in relation to FIG. 66. In some embodiments, one or both of the valves 214 and 216 include a pumping mechanism, such as the pumping mechanism discussed in relation to FIG. 72. For illustrative purposes, the ingestible device 200 is depicted with both of the valves 214 and 216 as moveable two-way valves coupled to the mechanical actuator 218. However, in some embodiments, the mechanical actuator 218 is coupled to only one of the valves, and the other valve may be replaced with a passive one-way valve. For example, the mechanical actuator 218 may be coupled to only the first valve 214, and the second valve 216 may be replaced with a passive one-way valve that allows gases, fluids, or solids to exit the sampling chamber 212 through the portion of the curved chamber 210 connected to the second opening 208. This may restrict fluid from entering the sampling chamber 212 from the second opening 208, but allow unwanted material to be removed from the sampling chamber 212 as the sample is obtained.

In some embodiments, the ingestible device 200 may be able to detect the approximate location of the ingestible device 200 within the GI tract. For example, it may be possible to use various combinations of light emitting diodes and sensors positioned along the ingestible device 200 to determine whether the device is in the stomach, small intestine, or large intestine. Methods for determining the location of an ingestible device within a gastrointestinal tract are described in greater detail in PCT Application No. PCT/US15/52500 filed 25 Sep. 2015, which is hereby incorporated by reference herein in its entirety. In these embodiments, the ingestible device 200 may be configured to use the mechanical actuator 218 to move the valves 214 and 216 into an open position in response to determining that the ingestible device 200 has reached a predetermined location within the GI tract. For example, a microcontroller on board the ingestible device 200 may be configured to open the valves 214 and 216 only when the ingestible device 200 is within the small intestine, thereby obtaining a sample from within the small intestine.

For illustrative purposes, the ingestible device 200 is depicted with the mechanical actuator 218, the first valve 214, and the second valve 216 oriented in a substantially straight line, with a single shaft 220 being used to couple the mechanical actuator 218 to the valves 214 and 216. However, in some embodiments, the orientation and/or positioning of the valves 214 and 216 relative to the position of the mechanical actuator 218 may be different than that shown, and the coupling of the mechanical actuator 218 to the valves 214 and 216 may also be different. In some embodiments, the mechanical actuator 218 simultaneously moves the valves 214 and 216. For example, in some embodiments the valves 214 and 216 are rotary valves, and they may be simultaneously opened and closed by rotating the shaft 220 that extends from the mechanical actuator 218 along the length of the ingestible device 200. As an alternate example, the valves 214 and 216 may be pin valves, and the pins may be attached to the shaft 220 that extends from the mechanical actuator 218 along the length of the ingestible device 200. In this case, the mechanical actuator 218 may open and close the valves by moving the shaft 220 linearly. This may be accomplished either by configuring mechanical actuator 218 to be a linear actuator, such as a solenoid. Alternately, the mechanical actuator 218 may be a rotary actuator, and the rotation may be converted into a linear motion. One skilled in the art will understand that this may be done any number of ways, for example, by coupling the mechanical actuator 218 to a ball screw mechanism, a threaded lead nut and lead screw mechanism, a rack and pinion mechanism, or the like.

In some embodiments, the ingestible device 200 does not include the second valve 216 at all. In this case, fluids and solids contained within the sampling chamber 212 may be free to exit through the second opening 208. Alternately, the second valve 216 near the second opening 208 may be replaced by an air-permeable membrane, which may allow gasses and unwanted air bubbles to exit the sampling chamber 212 through the second opening 208, while still retaining fluids and/or solids within the sampling chamber 212. Alternately, the second valve 216 near the second opening 208 may be replaced with a hydrophobic material. Similar to an air permeable membrane, an appropriately positioned hydrophobic material may be used to line the walls of the curved chamber 210 proximate to the second opening 208, which may allow gasses or unwanted air bubbles to exit the sampling chamber 212 through the second opening 208, while restricting some fluids from entering or exiting the sampling chamber 212 through the second opening 208. In some embodiments, one or more of the above described mechanisms may be combined in the same ingestible device. For example, the ingestible device 200 may implement the second valve 216 as a two-way valve, and also have hydrophobic material and an air-permeable membrane located near the second opening 208.

In some embodiments, the curved chamber 210 is connected to one or more sub-chambers (not shown). Each of these sub-chambers may be configured to hold one or more samples, and isolate the samples from both the sampling chamber 212, and the other sub-chambers. For example, each sub-chamber may be connected to the curved chamber 210 through a one-way valve, allowing samples to enter the sub-chamber from the curved chamber 210, but preventing the obtained samples from exiting the sub-chamber and re-entering either the curved chamber 210 or the sampling chamber 212. In general, any type of valve or other suitable mechanism may be used to isolate samples contained in the sub-chambers. In some embodiments, the ingestible device 200 distributes different samples into different sub-chambers at different times, or from different locations of the GI tract. For example, the ingestible device 200 may obtain a sample from the duodenum and distribute it into a first sub-chamber, and the ingestible device 200 may later obtain a sample from the ileum and distribute it into a second sub-chamber. In some embodiments, different types of assay techniques or diagnostics are applied to some of the samples contained in the different sub-chambers.

Figure 66:
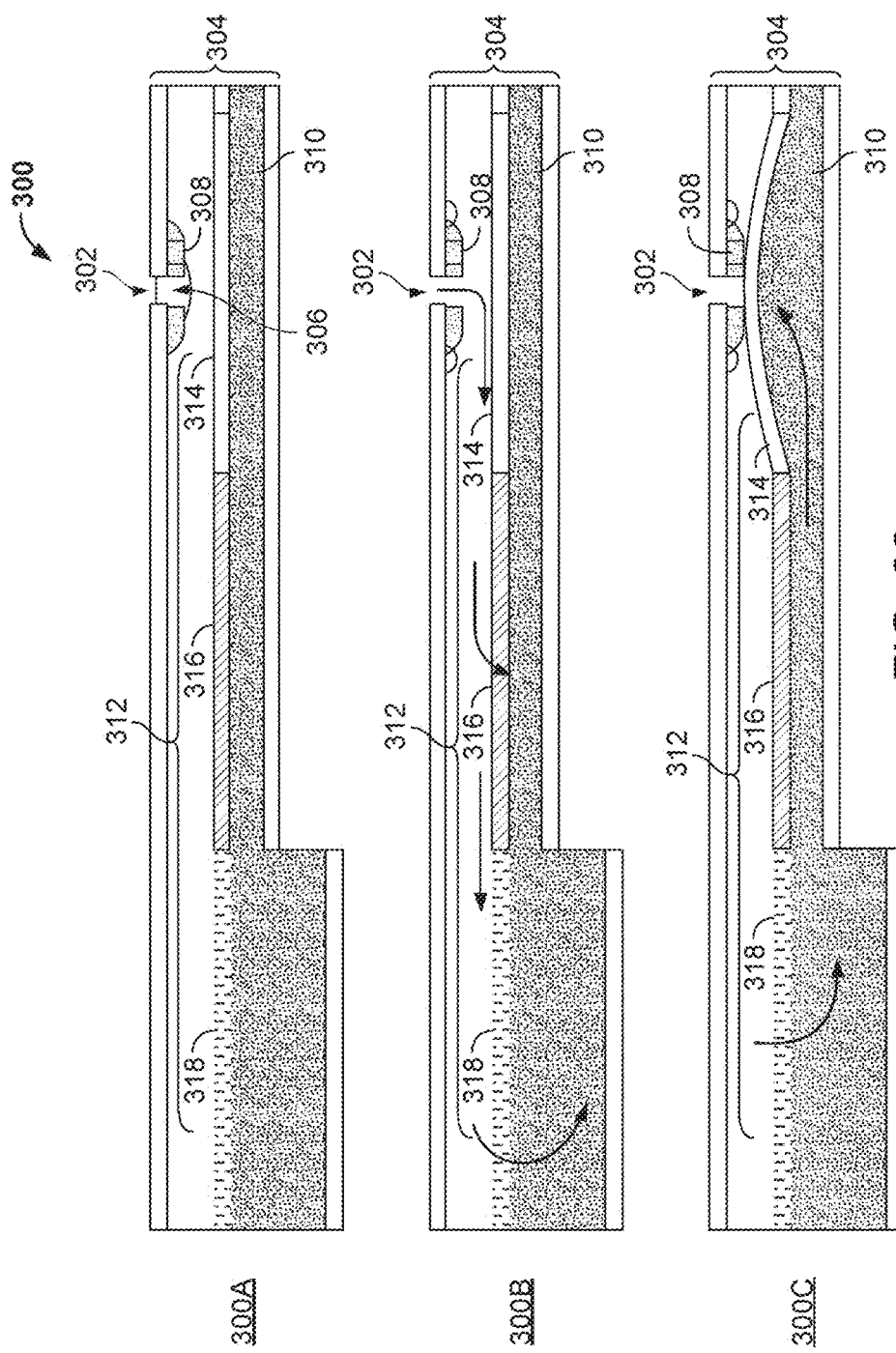
FIG. 66 shows an illustrative valve design that may be used to obtain a sample with an ingestible device.

FIG. 66 illustrates an example of an osmotic valve mechanism 300, which may be incorporated into an ingestible device in order to obtain samples. The osmotic valve mechanism 300 may be used in an ingestible device that features a first end, a second end, and a wall extending longitudinally between the first end and the second end, similar to the shape of the ingestible devices 100 and 200.

The osmotic valve mechanism 300 includes an inlet port 302, which is connected to a sampling chamber 304. In some embodiments, the inlet port 302 connects sampling chamber 304 directly or indirectly to an opening in the housing of an ingestible device.

The initial state of the osmotic valve mechanism 300 is shown in diagram 300A. As shown in diagram 300A, the inlet port 302 of the osmotic valve mechanism 300 is sealed using a single use sealing device 306 positioned within the inlet port 302. The single use sealing device 306 is positioned adjacent to a heating element 308. When it is time for the osmotic valve mechanism 300 to be opened (which may be determined by a localization mechanism that determines the ingestible device is located in a desirable region of the GI tract), the heating element 308 applies heat to the sealing device 306, causing the sealing device 306 to deform and unseal the inlet port 302.

Figure 67:
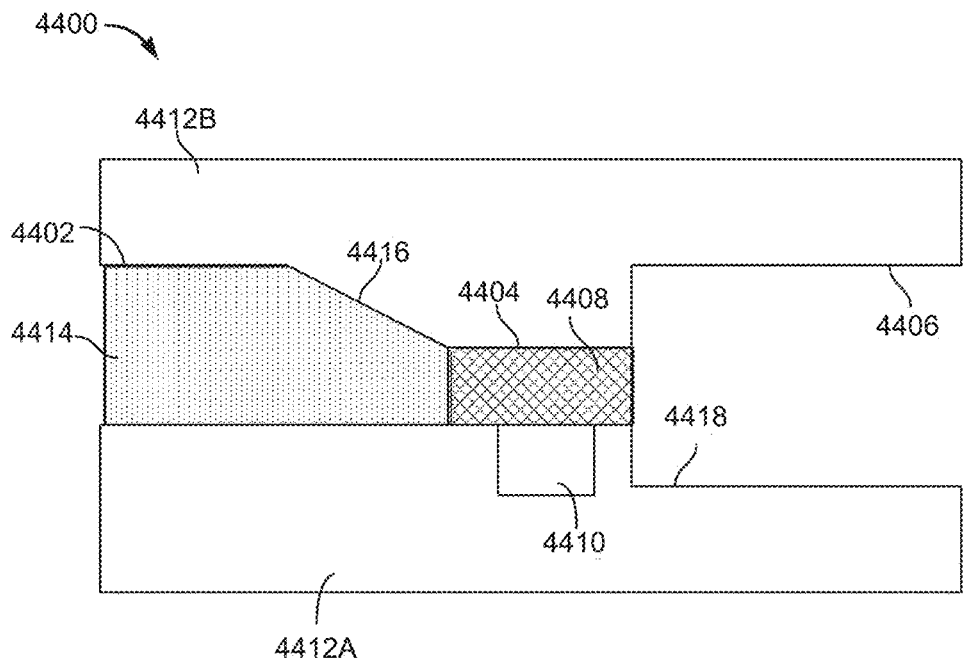
FIGS. 67 and 68 illustrate how the valve in FIG. 66 may be operated in order to obtain a sample.
Figure 68:
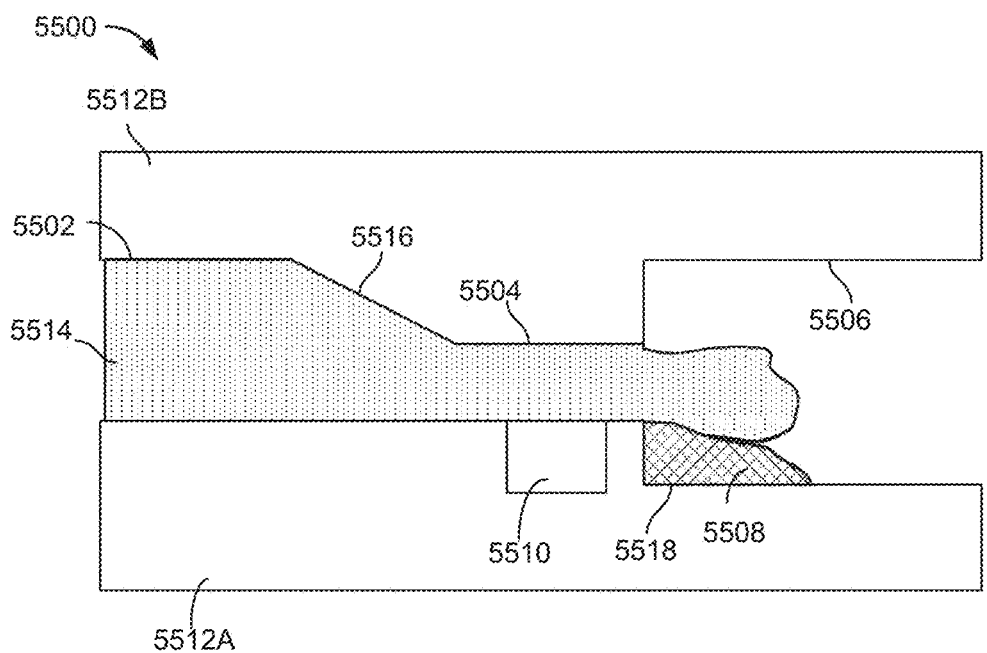

In some embodiments, the sealing device 306 may be a plug made out of a material that is meltable, deformable, and/or destroyable through the use of the heating element 308, such as wax. For example, in some embodiments, the heating element 308 may be a resistive heater that undergoes ohmic heating as an electrical current is passed through it, and the sealing device 306 is a wax plug. In some embodiments, the type of wax used to form the wax plug has a melting point between 38 degrees and 80 degrees Celsius, which is above the ambient temperature of a human body, but which may be easily achieved using the heating element 308. Some embodiments of the osmotic valve mechanism 300 may use a sealing device 306 that is melted or deformed at temperatures outside of the range described above, but practical considerations may be made to ensure that the osmotic valve mechanism 300 does not cause unwanted damage or burning to the GI tract. In some embodiments, a microprocessor is configured to control the heating element 308, causing it to generate heat. For example, the microprocessor may be configured to activate the heating element 308 once the ingestible device reaches a particular location within the GI tract. An example mechanism for unsealing the inlet port 302 is described in greater detail in relation to FIGS. 67 and 68. Although FIGS. 66, 67, and 68 depict the sealing device 306 as a type of plug, any type of suitable sealing device may be used. For example, in some embodiments, the sealing device includes a breakable membrane, which may be destroyed when heat is applied to the membrane. In some embodiments, the osmotic valve mechanism 300 does not include a heating element 308, and the sealing device 306 is melted, deformed, destroyed, or dislodged from the inlet port 302 by a mechanical actuator, or through electromagnetic fields. For example, the sealing device 306 may be a membrane that will rupture when a sufficiently large electrical current or magnetic field is applied to the membrane.

Inside the sampling chamber 304 of the osmotic valve mechanism 300 is an absorptive material 310, and at least a portion of the absorptive material 310 is located near the inlet port 302. The absorptive material 310 may include any suitable sponge material or hydrophilic material, such as any of the materials described in relation to FIG. 64. The portion of the absorptive material 310 located near the inlet port 302 may have a tendency to expand when it comes into contact with fluids. The osmotic valve mechanism 300 has a barrier 312 inside the sampling chamber 304, which is divided into three portions. The first portion of the barrier 312 is a flexible membrane 314, the second portion of the barrier 312 adjacent to the flexible membrane 314 is a rigid portion 316, and the third portion of the barrier 312 adjacent to the rigid portion 316 is a semi-permeable membrane 318.

The barrier 312 within the sampling chamber 304 is positioned between the inlet port 302 and the absorptive material 310, covering a surface of the absorptive material 310. When the inlet port 302 is unsealed, a sample (e.g., a fluid sample containing solid particulates taken from the GI tract) enters the sampling chamber 304 through the inlet port 302, and begins to fill the sampling chamber 304. The absorptive material 310 may have a natural tendency to expand when it comes into contact with a fluid sample. However, by covering a surface of the absorptive material 310, the barrier 312 may allow only certain portions of absorptive material 310 to expand. The barrier 312 may also direct the flow of a fluid sample as it enters the sampling chamber 304, and allow the fluid sample to come into contact with only certain parts of the absorptive material 310.

Diagram 300B shows the osmotic valve mechanism 300 shortly after the inlet port 302 is unsealed. Once the inlet port 302 is unsealed, the sampling chamber 304 may be opened, and a sample may enter the sampling chamber 304 through the inlet port 302. In some embodiments, the sample cannot cross the flexible membrane 314 and contact the absorptive material 310. As a result, the flexible membrane 314 may be used to guide the sample as it enters the sampling chamber 304. Similarly, in some embodiments the sample cannot cross the rigid portion 316 of the barrier 312, and the rigid portion 316 may also be used to guide the sample as it enters the sampling chamber 304. The semi-permeable membrane 318 allows at least a portion of the sample to pass through the semi-permeable membrane and contact the absorptive material 310. This may allow the sample to be absorbed by the absorptive material 310 after the sample has filled the top portion of the sampling chamber 304, which in turn may cause the absorptive material 310 to begin to expand.

Diagram 300C shows the state of the osmotic valve mechanism 300 after the absorptive material 310 has absorbed a portion of the sample. The portion of the absorptive material 310 under the flexible membrane 314 expands when the absorptive material 310 absorbs the sample. As the absorptive material 310 expands, the flexible membrane 314 is forced up against the inlet port 302, effectively sealing the inlet port 302 from the sampling chamber 304. In some embodiments, the rigid portion 316 prevents the portion of the absorptive material 310 under the rigid portion 316 from expanding. In some embodiments, the semi-permeable membrane 318 may be rigid, and prevent the portion of the absorptive material 310 adjacent to the semi-permeable membrane 318 from expanding.

After the absorptive material 310 expands, causing the inlet port 302 to be resealed, a portion of the sample may be confined within the sampling chamber 304. Once a sample has been properly confined, it may be possible to apply a wide range of assay techniques or diagnostics to the sample. In some embodiments, the portion of the sampling chamber 304 between the rigid portion 316 and the wall of the sampling chamber forms a testing area. For example, a sensor may be placed within or proximate to the sampling chamber 304 in order to study the portion of the sample contained within the testing area located above the rigid portion 316. This sensor may be used to study properties of the sample, or it may be used to detect the results of an assay technique applied to the sample.

Diagram 300C is shown for illustrative purposes only, and is not limiting. In some embodiments, the osmotic valve mechanism 300 does not include the barrier 312, or one or more portions of the barrier 312 are excluded or rearranged within the sampling chamber 304. For example, the location of the rigid portion 316 and the semi-permeable membrane 318 may be reversed, or the rigid portion 316 may be removed and the semi-permeable membrane 318 extended so that it connects directly with the flexible membrane 314. When the osmotic valve mechanism 300 does not include a barrier 312 or does not include the flexible membrane 314, a portion of the absorptive material 310 near the inlet port 302 may expand and clog the inlet port 302, effectively resealing the inlet port 302.

In some embodiments, the material used to form the absorptive material 310 expands at a controlled rate, which may ensure that sufficient time has passed for the sample to enter the sampling chamber 304 and for the sampling chamber 304 to be filled before the inlet port 302 is resealed. This may be particularly useful for embodiments where the osmotic valve mechanism 300 does not include a flexible membrane 314 and/or the semi-permeable membrane 318. In some embodiments, a portion of the absorptive material 310 is covered by a dissolvable film or membrane, which may prevent the absorptive material 310 from expanding until a sufficient amount of time has passed for the film to dissolve.

In some embodiments, the sampling chamber 304 is connected to one or more sub-chambers (not shown). Each of these sub-chambers may be configured to hold samples, and isolate the samples from both the sampling chamber 304, and the other sub-chambers. For example, each sub-chamber may be connected to the sampling chamber 304 through a one-way valve, allowing samples to enter the sub-chamber from the sampling chamber, but preventing the obtained samples from exiting the sub-chamber. As an alternate example, each of the sub-chambers may employ a sealing device, heating element, and absorptive material arranged similar to osmotic valve mechanism 300. In these embodiments, each of the sub-chambers may be opened by activating their respective heating elements, and may be automatically sealed off from the sampling chamber 304 after a sufficient amount of the sample has been obtained. In general, any type of valve or other suitable mechanism may be used to isolate samples contained in the sub-chambers. In some embodiments, similar to ingestible device 200, an ingestible device employing multiple sub-chambers in conjunction with the osmotic valve mechanism 300 may distribute different samples into different sub-chambers at different times, or from different locations of the GI tract.

It will be understood by one skilled in the art that variations of the osmotic valve mechanism 300 may be combined with any of the other ingestible devices described in this disclosure. For example, in some embodiments of the ingestible device 200 shown and described in relation to FIG. 65, one or both of the valves 214 and 216 may be replaced with certain embodiments of the osmotic valve mechanism 300. One or both of the valves 214 and 216 may include a sealing device that can be destroyed or deformed (e.g., by the mechanical actuator 218 or through a heating element), and one or both of the valves 214 and 216 may be automatically resealed by the expansion of absorptive material located within the sampling chamber 212.

FIGS. 67 and 68 illustrate in detail how some embodiments of the osmotic valve mechanism 300 may be operated in order to obtain a sample.

FIG. 67 shows a detailed view of an inlet port 4400, which may be incorporated into osmotic valve mechanism 300, prior to being unsealed. The inlet port 4400 features an exterior portion 4402, which is separated by a middle portion 4404 from an interior portion 4406. The middle portion 4404 of the inlet port 4400 contains a sealing device 4408, which may be the same as sealing device 306 shown and described in relation to FIG. 66. A heating element 4410 is located near the middle portion 4404, and adjacent to the sealing device 4408. The sides of the inlet port 4412A and 4412B form the shape of the inlet port 4400, and may be constructed from an insulating material, such as insulating ceramic, or polymers such as polyamide-imide, polyphenylene sulfide, polyphenylene oxide, and the like. For illustrative purposes, the exterior portion 4402 of the inlet port 4400 is depicted as being filled with a sample 4414, which may be a fluid sample obtained from the GI tract. However, in some embodiments, the inlet port 4400 may be operated regardless of whether a sample 4414 is actually contained in the exterior portion 4402. The exterior portion 4402 and the interior portion 4406 are wider than the middle portion 4404. A sloped wall 4416 gradually reduces the width of the exterior portion 4402, to transition from the wider width of the exterior portion 4402 to the narrower width of the middle portion 4404. This configuration may reduce the overall volume of the sealing device 4408 (compared to a configuration with a wider middle portion 4404), and reduce the surface area of the sealing device 4408 exposed to the sample 4414, which may reduce the amount of heat lost from the sealing device 4408 to the sample 4414. In turn, this may make it easier to raise the temperature of the sealing device 4408 using the heating element 4410. In some embodiments, the geometry of the inlet port 4400 may allow an air pocket (not shown) to form in the exterior portion 4402, separating the sealing device 4408 from fluid contained within the GI tract. This may act as an insulating barrier around the sealing device 4408, and also make it easier to raise the temperature of the sealing device 4408 using the heating element 4410. Moreover, the larger width of the interior portion 4406 relative to the middle portion 4404 forms a remnant capture area 4418, which may hold the remnants of the sealing device 4408 after the inlet port 4400 is unsealed.

In some embodiments, the exterior portion 4402 of the inlet port 4400 may be connected directly or indirectly to an opening in the housing of an ingestible device. In some embodiments, there is nothing to restrict a sample from entering the opening, and, at any given time, the exterior portion 4402 of the inlet port 4400 may be filled with a fluid sample 4414 gathered from whatever region of the GI tract the ingestible device is located within.

Sealing device 4408 prevents the fluid sample 4414 contained within the exterior portion 4402 of the inlet port 4400 from entering the interior portion 4406 of the inlet port 4400. For simplicity, FIGS. 67 and 68 depict the sealing device 4408 as a plug, which forms a seal that may be broken by using a heating element 4410. However, in some embodiments the sealing device 4408 may be any other type of breakable seal or valve used within the middle portion 4404 to separate the exterior portion 4402 of the inlet port 4400 and the interior portion 4406 of the inlet port 4400.

In some embodiments, the heating element 4410 may be operated by a microcontroller. For example, the microcontroller may be configured to operate the heating element 4410 and unseal the inlet port 4400 when the ingestible device is in a certain region of the GI tract. The sides of the inlet port 4412A and 4412B may be formed from an insulating material, which may shield the ingestible device and the fluid sample 4414 from the heat generated by the heating element 410. This may also help to focus the heat produced by heating element 4410 in the direction of the sealing device 4408, and may reduce the total amount of power required to drive the heating element 4410 to melt, deform, or destroy the sealing device 4408.

In some embodiments, the dimensions of the inlet port 4400 are chosen such that a fluid sample 4414 is naturally drawn into the exterior portion 4402, and ultimately through the middle portion 4404 into the interior portion 4406, through capillary action. Typically, the cross-section of the exterior portion 4402, the middle portion 4404, and the interior portion 4406 will be square, circular, or rectangular, but any type of cross-section may be used. The overall cross-sectional area of the exterior portion 4402, the middle portion 4404, and the interior portion 4406 of the inlet port 4400 is typically less than 50 square millimeters given the size constraints of the ingestible device, with 0.2 to 2 square millimeters being common. However, the cross-sectional areas listed above are only examples, and any cross-sectional area may be chosen in order to better draw in samples from the different portions of the GI tract. One skilled in the art will understand that the exact shape and dimensions will depend on the physical properties of the sample to be acquired, and some embodiments may use cross-sections other than the ones mentioned above.

FIG. 68, shows a detailed view of an inlet port 5500, which may be incorporated into osmotic valve mechanism 300, after it has been unsealed.

After the heating element 5510 has heated the sealing device 5508 sufficiently, the sealing device 5508 may deform, melt, or otherwise be destroyed, effectively unsealing the inlet port 5500. Once the inlet port 5500 is unsealed, the fluid sample 5514 is able to flow naturally from the exterior portion 5502 of the inlet port 5500 to the interior portion 5506 of the inlet port 5500 through the middle portion 5504. Similar to the embodiments described in relation to FIG. 67, the sides 5512A and 5512B of the inlet port may be made of an appropriate insulating material, and form the shape of the inlet port 5500, the exterior portion 5502 with the sloped wall 5516, the middle portion 5504, and the interior portion 5506 along with the remnant capture area 5518. As the fluid sample 5514 enters the interior portion 5506 of the inlet port 5500, the natural flow of the fluid sample 5514 may carry any of the remnants of the sealing device 5508 into the remnant capture area 5518 located within the interior portion 5506. In some embodiments, once the melted or deformed remnants of the sealing device 5508 cease to be in contact with the heating element 5510 and instead come into contact with the insulating material that make up the walls of the remnant capture area 5518, the remnants of the sealing device 5508 re-solidifies or re-forms along the walls of the remnant capture area 5518. As a result, the remnant capture area 5518 may provide a location for the re-solidified remnants of the sealing device 5508 to be stored, and may prevent the remnants of the sealing device 5508 from impeding the flow of the sample 5514.

In some embodiments, electromagnetic forces are used to attract the remnants of the sealing device 5508 to the remnant capture area 5518. For example, the sealing device (e.g., the sealing device 4408) may be made from a magnetic material, and an induced or permanent magnetic field may be used to attract the remnants of the sealing device 5508 to the remnant capture area 5518. This magnetic field may be applied after the heating element 5510 is activated, and until the remnants of the sealing device 5508 re-solidify or re-form within the remnant capture area 5518.

It will be understood that the embodiments described by FIGS. 66, 67, and 68, are merely illustrative, and they may be modified and combined with other techniques for drawing in or pumping fluid samples without departing from the spirit and scope of this disclosure. For example, to encourage samples to be drawn into the sampling chamber 304, the sampling chamber 304 may contain a low-pressure vacuum, and samples may be forcibly drawn into the sampling chamber 304 when the inlet port 302 is unsealed. A similar effect may also be produced by connecting the sampling chamber 304 to a sub-chamber containing a low-pressure vacuum, or by using by using a mechanical actuator to either pump the fluid samples or to increase the volume of the sampling chamber 304. In some embodiments, the geometry and relative size of the exterior portions 4402 and 5502, the middle portions 4404 and 5504, and interior portions 4406 and 5506, may be different from those depicted in FIGS. 67 and 68. For example, the different portions 4402, 4404, 4406, 5502, 5504, and 5506 may have a uniform width, and the sloped walls 4416 and 5516 and/or the remnant capture areas 4418 and 5518 are not included. As another example, a sloped wall may be used to form the remnant capture areas 4518 and 5518.

Figure 69:
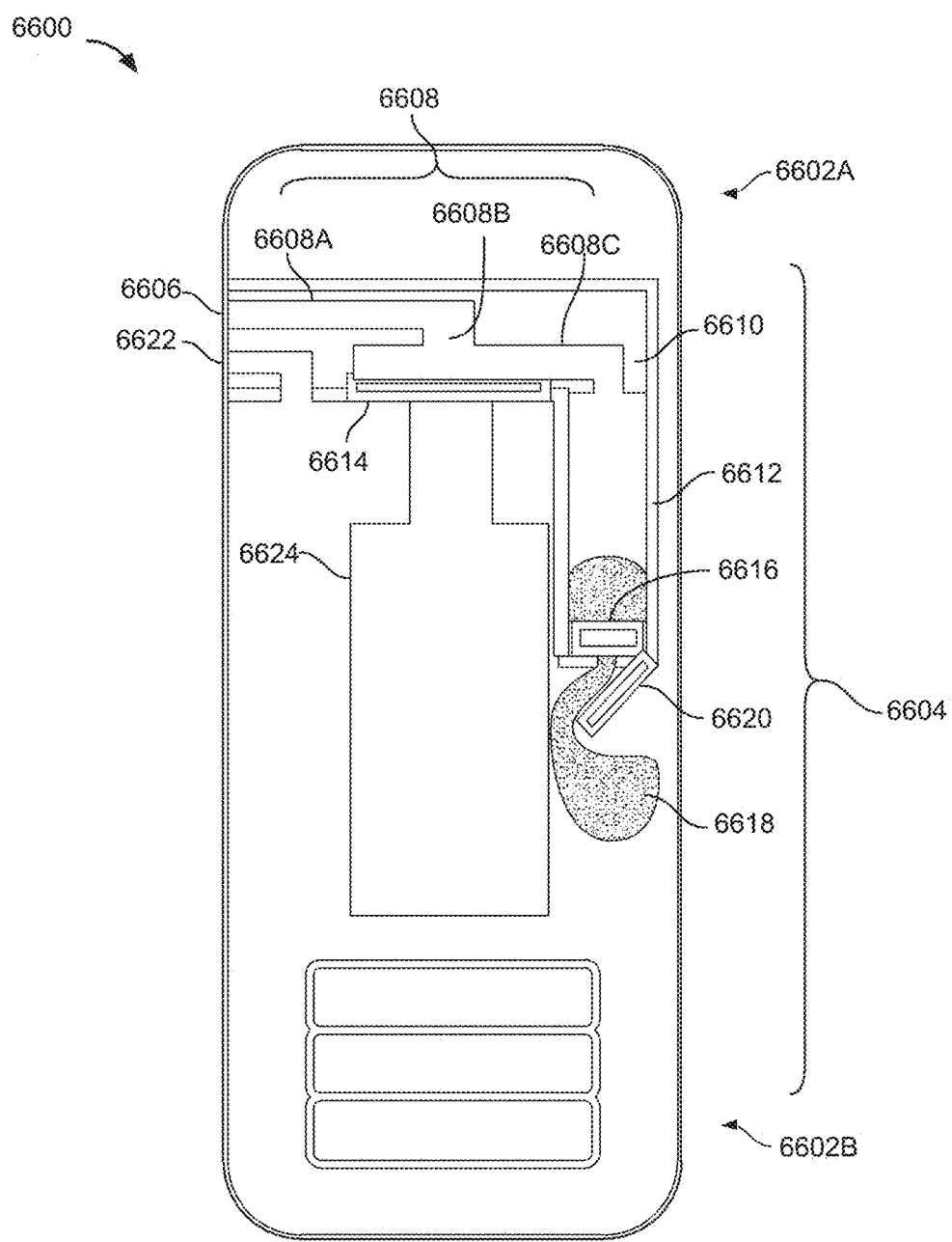
FIG. 69 shows an illustrative embodiment of an ingestible device.

FIG. 69 illustrates another example of an ingestible device 6600 with a sampling chamber that includes an exit port. Similar to the ingestible devices 100 and 200, the ingestible device 6600 is designed to have an outer housing with a first end 6602A, a second end 6602B, and a wall 6604 extending longitudinally from the first end 6602A to the second end 6602B. The ingestible device 6600 has an opening 6606 in the housing, which allows samples to enter the ingestible device 6600 from the surrounding environment. The ingestible device 6600 has an inlet region 6608 connected to the opening 6606. The inlet region 6608 is connected to an entry port 6610 of a sampling chamber 6612. The inlet region 6608 is divided into three portions. A first portion 6608A of the inlet region 6608 is connected to the opening 6606 and a second portion 6608B, and a third portion 6608C is connected to the entry port 6610 of the sampling chamber 6612. The second portion 6608B connects the first portion 6608A to the third portion 6608C, and may contain a moveable valve 6614 that is used to prevent samples from flowing through the inlet region 6608, and isolate the first portion 6608A of the inlet region 6608 from the third portion 6608C of the inlet region 6608.

The ingestible device 6600 has a mechanical actuator 6624 coupled to the moveable valve 6614. In some embodiments, a microprocessor or microcontroller is configured to control the mechanical actuator 6624 and move the moveable valve 6614 between an open and a closed position. For example, the microcontroller may be configured to move the moveable valve 6614 into an open position after the ingestible device reaches a particular location within the GI tract. In some embodiments, the mechanical actuator may be driven by a set of batteries or other power source located within the ingestible device 6600. When the moveable valve 6614 is moved into an open position, a sample may be allowed to flow through the inlet region 6608, and enter the sampling chamber 6612 through the entry port 6610. When the moveable valve 6614 is in a closed position, the sample is prevented from flowing through the inlet region 6608 and reaching the sampling chamber 6612 from the opening 6606.

For illustrative purposes, FIG. 69 depicts the moveable valve 6614 as a diaphragm valve, which uses a mechanical actuator 6624 to move a flexible diaphragm in order to seal or unseal an aperture in the second portion 6608B of the inlet region 6608, which may effectively block or unblock the inlet region 6608. However, it will be understood that, in some embodiments, the moveable valve 6614 may be a different type of valve. For example, in some embodiments the moveable valve 6614 may be replaced by a pumping mechanism, such as the pumping mechanism described in relation to FIG. 72. As another example, in some embodiments the moveable valve 6614 is replaced with an osmotic valve, similar to the embodiments described in relation to FIGS. 66, 67, and 68. Several examples of other different valve types are described in relation to FIG. 70.

The sampling chamber 6612 of the ingestible device 6600 has an exit port 6616 located on the opposite end of the sampling chamber 6612 from the entry port 6610. In general, the exit port 6616 may be located anywhere within the sampling chamber 6612. The exit port 6616 is configured to allow air or gas 6618 to exit the sampling chamber 6612, while preventing at least a portion of the sample obtained by the ingestible device 6600 from exiting the sampling chamber 6612. For example, the exit port 6616 may include a gas-permeable membrane, which allows the gas 6618 to exit the sampling chamber 6612, but which would prevent a liquid or solid sample from leaving the sampling chamber 6612 through the exit port 6616. Allowing the gas 6618 to exit the sampling chamber 6612 may prevent pressure from building up within the sampling chamber 6612 as the sample enters through the entry port 6610. This may result in the sample being drawn into the sampling chamber 6612 more easily, and result in increasing the overall volume of the sample able to be collected by the ingestible device 6600, and increasing the ease with which the sample is brought into the sampling chamber 6612.

The ingestible device 6600 includes a one-way valve 6620 as part of the exit port 6616. This valve may prevent the gas 6618 from re-entering the sampling chamber 6612. However, in some embodiments the one-way valve 6620 may be excluded from the ingestible device 6600. In some embodiments, the exit port 6616 includes a gas permeable membrane. This gas permeable membrane may lose its permeability when it is placed in contact with the sample. For example, the gas permeable membrane may include a spongy material that allows the gas 6618 to exit the sampling chamber 6612 through the exit port 6616. Once the spongy material becomes moist through contact with the sample, it may become no longer gas permeable, or the permeability may be greatly reduced, thereby preventing the gas 6618 from reentering the sampling chamber 6612. In some embodiments, the gas permeable membrane may include expanded polytetrafluorethylene, polypropylene, or the like. In some embodiments, the material used to make the gas permeable membrane may be filter-like, as opposed to sponge-like materials. Generally, the gas permeable membrane may be made of any material that allow gas to permeate, but which prevents liquid from flowing through the membrane due to sufficient resistance or surface tension effects.

In the ingestible device 6600, the exit port 6616 is connected to a volume within the housing of ingestible device 6600 outside of the sampling chamber. Depending on the manufacturing process used to produce the ingestible device 6600, the volume within the housing of the ingestible device 6600 may contain air or some other type of gas.

The ingestible device 6600 includes an outlet port 6622, which is connected to the volume within housing of the ingestible device 6600. The outlet port 6622 may provide a path for the gas 6618 to exit the ingestible device 6600 and be released into the environment surrounding the ingestible device 6600. This may be advantageous when the volume of gas 6618 is relatively large, since it may prevent pressure from building up within the housing of the ingestible device 6600. In some embodiments, the ingestible device 6600 does not include an outlet port 6622, and the gas 6618 stays inside the volume of the ingestible device 6600. In some embodiments, the outlet port 6622 is directly or indirectly connected to the exit port 6616, for example, by a tube or channel. In some embodiments, the exit port 6616 leads directly from the sampling chamber 6612 to an opening in the ingestible device 6600, and the exit port 6616 may effectively replace the outlet port 6622. In some embodiments, the outlet port 6622 may contain a gas permeable membrane, a one-way valve, a hydrophobic channel, or some other mechanism to avoid unwanted material, (e.g., fluids and solid particulates from within the GI tract), from entering the ingestible device 6600 through the outlet port 6622.

In some embodiments, the ingestible device 6600 may include a sensor within or proximate to the sampling chamber 6612. For example, this sensor may be used to detect various properties of a sample contained within the sampling chamber 6612, or this sensor may be used to detect the results of an assay technique applied to the sample contained within the sampling chamber 6612.

In some embodiments, a hydrophilic sponge is located within the sampling chamber 6612, and the hydrophilic sponge may be configured to absorb the sample as the sample enters the sampling chamber 6612. In some embodiments, the hydrophilic sponge fills a substantial portion of the sampling chamber 6612, and holds the sample for an extended period of time. This may be particularly advantageous if the sample is collected from the ingestible device 6600 after the ingestible device 6600 exits the body. In some embodiments, the hydrophilic sponge is placed on only certain surfaces or fills only certain portions of the sampling chamber 6612. For example, it may be possible to line certain walls (or all walls) of the sampling chamber 6612 with a hydrophilic sponge to assist in drawing in the sample, while leaving some (or none) of the walls of the sampling chamber 6612 uncovered. Leaving walls uncovered may allow the use of diagnostics or assay techniques that require a relatively un-obscured optical path. An example of such an embodiment is described in detail in relation to FIG. 71. In some embodiments, the sponge material may be placed on all walls of the sampling chamber 6612. This may prevent unwanted ambient light from entering the sampling chamber 6612, which may be useful for certain types of low light detection assays. In some embodiments, an opaque material is used to cover some or all sides of the sampling chamber 6612. This may also prevent unwanted ambient light from entering the sampling chamber 6612.

In some embodiments, the ingestible device 6600 may include a sealed vacuum chamber connected to the exit port 6616, or connected directly or indirectly to the sampling chamber 6612. The sealed vacuum chamber may have an internal pressure that is substantially lower than ambient pressure of the sampling chamber 6612 and/or the inlet region 6608. In these embodiments, the ingestible device 6600 unseals the vacuum chamber in order to reduce the pressure within the sampling chamber. This change in pressure may force the sample to be sucked into the sampling chamber, or allow the sample to be drawn into the sampling chamber quickly.

For simplicity, FIG. 69 depicts only a single sampling chamber 6612, but it will be understood that the inlet region 6608 may be connected to multiple sampling chambers arranged throughout the device, each of which may be controlled independently through the use of one or more valves. For example, in some embodiments there may be one or more sub-chambers connected to the inlet region 6608. Each of the sub-chambers may be configured to hold samples gathered from within the GI tract, and keep those samples isolated. In general, any type of valve or other suitable mechanism may be used to isolate samples contained in the sub-chambers, including any of the valves or mechanisms described in relation to FIGS. 64-69. In some embodiments, the ingestible device 6600 distributes different samples into each of the different sub-chambers at different times, or from different locations within the GI tract. For example, the ingestible device 6600 may accomplish this by opening up a valve to connect the interior of inlet region 6608 to the appropriate sub-chamber before opening up the inlet region 6608 to draw in the sample from the opening 6606 in the housing.

Figure 70:
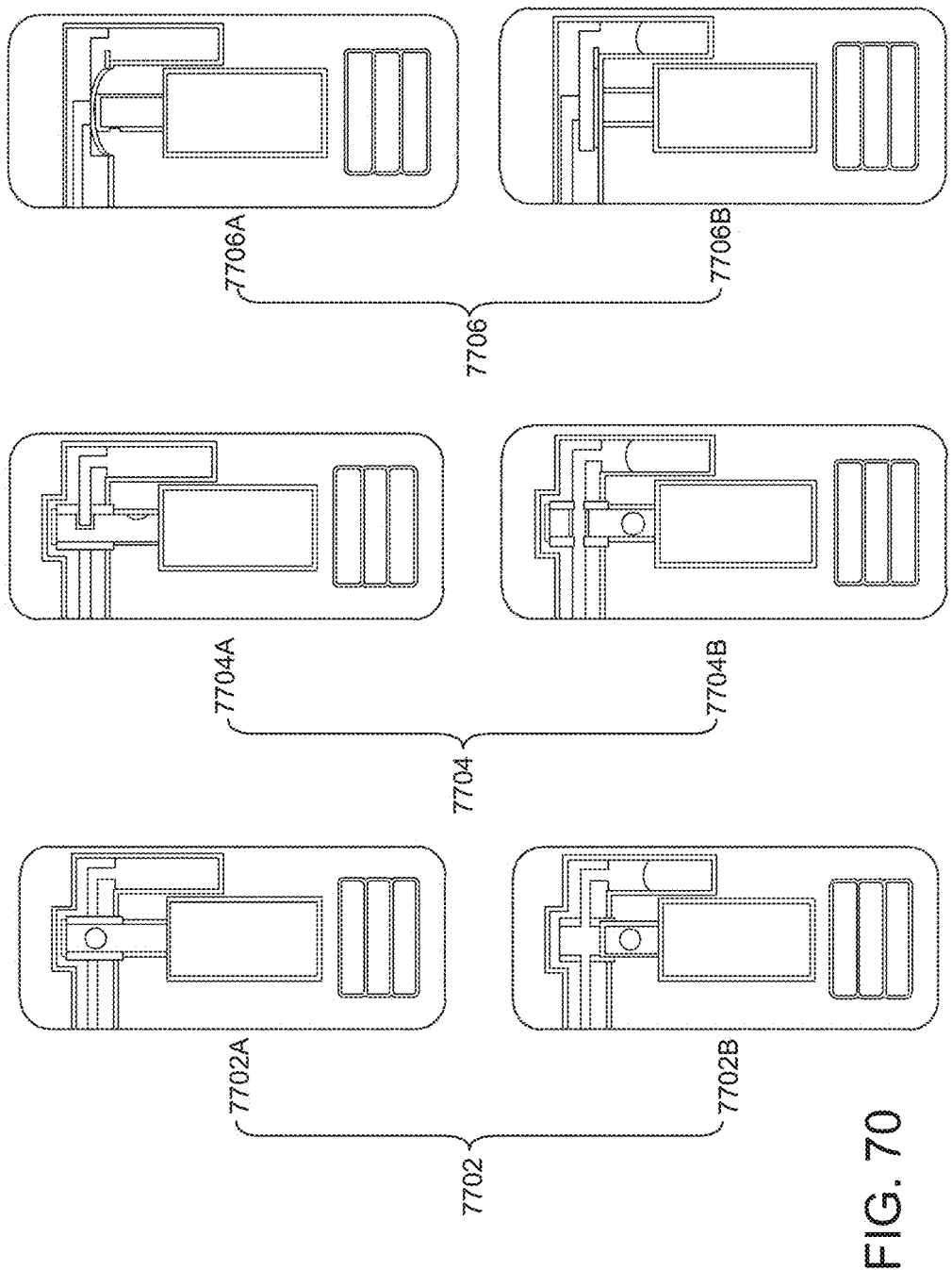
FIG. 70 shows different illustrative valve designs that may be incorporated into an ingestible device.

FIG. 70 depicts different types of moveable valves that may be incorporated into an ingestible device, such as the ingestible devices 100, 200 or 600. The ingestible device 7702 illustrates how a pin valve may be used as a moveable valve (e.g., as moveable valve 6614 of ingestible device 6600), with diagram 7702A showing the pin valve in a closed position, and diagram 77026 showing the pin valve in an open position. In the ingestible device 7702, a mechanical actuator may be configured to move the pin valve linearly in order to switch between an open position and a closed position. For example, in diagram 7702A, the ingestible device 7702 has a pin inserted into the inlet port, thereby preventing the sample from flowing into the sampling chamber from the opening in the ingestible device 7702. In diagram 7702B, the ingestible device 7702 has a pin that has been removed from the inlet port, allowing the sample to flow freely into the sampling chamber from the opening in the ingestible device 7702. In order to generate linear motion, the mechanical actuator may be a linear actuator, such as a solenoid. Alternately, the mechanical actuator may be a rotatory actuator, and the rotation may be converted into a linear motion. One skilled in the art will understand that this may be done any number of ways, for example, by coupling the mechanical actuator to a ball screw mechanism, a threaded lead nut and lead screw mechanism, a rack and pinion mechanism, or the like.

Ingestible device 7704 illustrates how a rotary valve may be used as a moveable valve (e.g., as moveable valve 6614 of ingestible device 6600), with diagram 7704A showing the rotary valve in a closed position, and diagram 7704B showing the rotary valve in an open position. In diagram 7704A, the ingestible device 7704 has a rotary pin oriented such that the sample is prevented from entering the sampling chamber from the opening in the ingestible device 7704. In diagram 7704B, the ingestible device 7704 has a rotary pin that has been rotated into an orientation where the sample is free to flow into the sampling chamber from the opening in the ingestible device 7704. In order to operate the rotary valve, the mechanical actuator in ingestible device 7704 may be a rotatory actuator, which is capable of rotating the rotary pin to switch between the open position and the closed position.

Ingestible device 7706 illustrates how a flexible diaphragm, or diaphragm valve, may be used as a moveable valve (e.g., as moveable valve 6614 of ingestible device 6600), with diagram 7706A showing the diaphragm valve in a closed position, and diagram 7706B showing the diaphragm valve in an open position. In diagram 7706A, the ingestible device 7706 has a diaphragm valve in a closed position, with the flexible diaphragm being pressed against an aperture in the inlet region due to the pressure generated by the mechanical actuator against the flexible diaphragm. This may effectively block a sample from flowing through the inlet region, and thereby preventing a sample from entering the sampling chamber from the opening in the ingestible device 7706. In diagram 7706B, the ingestible device 7706 has a diaphragm valve in an open position, with the pressure removed from the flexible diaphragm. The diaphragm returns to a position away from the aperture in the inlet region, allowing a sample to flow freely into the sampling chamber from the opening the in ingestible device 7706.

In some embodiments, ingestible device 7706 has a spring mechanism near the diaphragm or in direct contact with the diaphragm. The spring mechanism may apply pressure to the diaphragm to oppose the pressure applied by the mechanical actuator, which may cause the flexible diaphragm to be moved into an open position when the mechanical actuator is not applying pressure to the flexible diaphragm. Additionally, this may ensure that the diaphragm valve remains open when the mechanical actuator is not applying pressure across the flexible diaphragm.

In some embodiments, moving the mechanical actuator from a closed position to an open position causes a volume of the inlet region within the ingestible device to increase. This may cause the pressure within the inlet region to be reduced, generating suction to draw a sample into the inlet region. Similarly, moving the mechanical actuator from an open position to a closed position may cause the volume of the inlet region to be reduced. This may cause the pressure within the inlet region to be increased, pushing the sample out of the inlet region. Depending on the design of the inlet region, the mechanical actuator, and the moveable valve, this may push the sample into the sampling chamber rather than pushing the sample back through the opening in the ingestible device. An example of such a design is described in greater detail in relation to FIG. 72.

Figure 71:
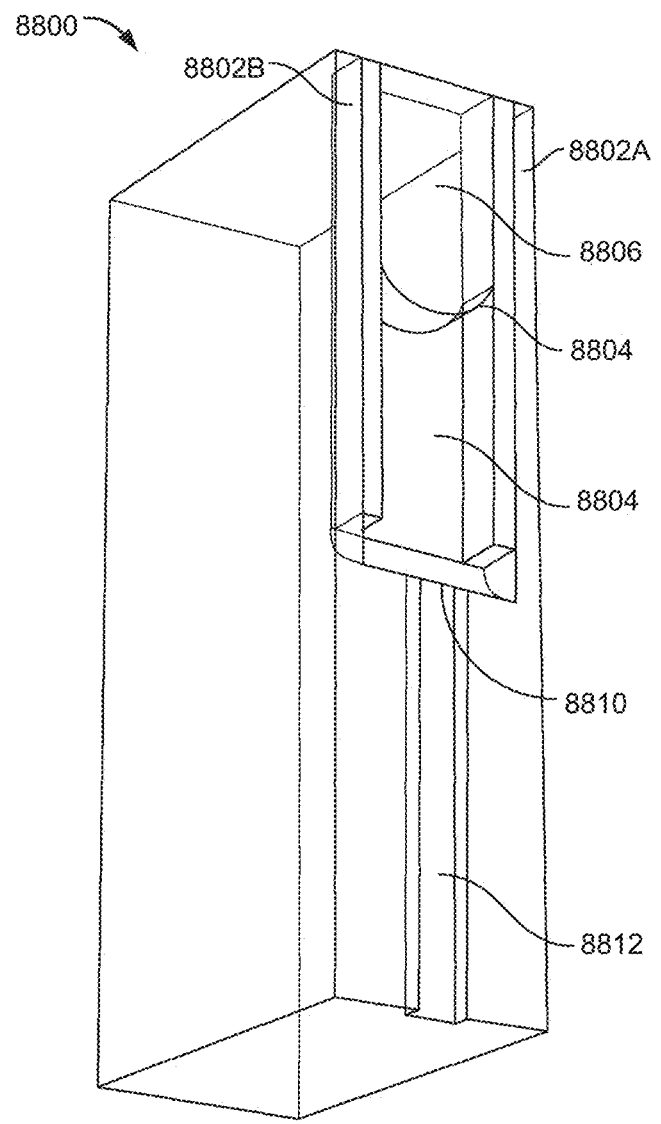
FIG. 71 shows an illustrative sampling chamber that may be incorporated into an ingestible device.

FIG. 71 illustrates an example of a sampling mechanism that may be incorporated into an ingestible device, such as the ingestible devices 100, 200, 6600, and 7702-7706. The sampling mechanism 8800 is partially lined with hydrophilic sponges 8802A and 8802B. In between the hydrophilic sponges 8802A and 8802B is a testing region 8804 within the sampling mechanism 8800. The hydrophilic sponges 8802A and 8802B attract a liquid or fluid sample 8806, and may draw the sample 8806 into the sampling mechanism 8800. As the hydrophilic sponges 8802A and 8802B are saturated with the sample 8806, a meniscus 8808 is formed at the end of the sample 8806, between the hydrophilic sponges 8802A and 8802B. This system may be useful for acquiring particularly viscous samples, which may have difficulty flowing into the sampling mechanism 800 naturally.

The sampling mechanism 8800 includes an exit port 8810 connected to a channel 8812. As the sample 8806 is drawn into the sampling mechanism 800, air or gas contained in the sampling mechanism 8800 may be pushed out of the sampling mechanism 8800 through the exit port 8810 and into the channel 8812. This may avoid gas being trapped within the sampling mechanism 8800, which in turn may avoid pressure building inside of the sampling mechanism 8800 and preventing the sample 8806 from being drawn into the testing region 8804.

In some embodiments, the sampling mechanism 8800 may not include an exit port 8810 or a channel 812, and any air or gas in the sampling mechanism 8800 may be allowed to remain within the sampling mechanism 8800. In some embodiments, the sampling mechanism 8800 may be filled with a low pressure vacuum, attached to a pump or other mechanism to create a vacuum, or attached to a sealed chamber containing a low pressure vacuum that may be unsealed. The use of a vacuum may allow the sampling mechanism 8800 to forcibly draw in a sample.

In some embodiments, an ingestible device may include sensors or diagnostics to study the sample 8806 contained within the sampling mechanism 8800. Because there is no sponge material on the front and back walls of the testing region 8804, information about the sample 8806 contained within the testing region 8804 may be gathered by using sensors and/or assay techniques that require a clear optical path, which would otherwise be obscured by a sponge (e.g., the hydrophilic sponges 8802A and 8802B). For example, light sources and/or optical sensors may be placed near the front and/or back walls in order to test optical properties of the sample, or to detect the results of certain assay techniques.

It will be understood by those skilled in the art that the sampling mechanism 8800 depicted in FIG. 71 is merely illustrative, and the general techniques described in relation to FIG. 71 may be applied to a wide range of different chambers, channels, and fluid pathways, and incorporated into a wide range of different ingestible devices. Furthermore, in some embodiments, the overall geometry of FIG. 71 and the positioning of the sponges and the testing area may be altered. For example, the sponge may be formed in the shape of hollow tubes, with testing areas located in the middle of each tube. In this case, there would be a clear optical path from one end of the tube to the other.

Figure 72:
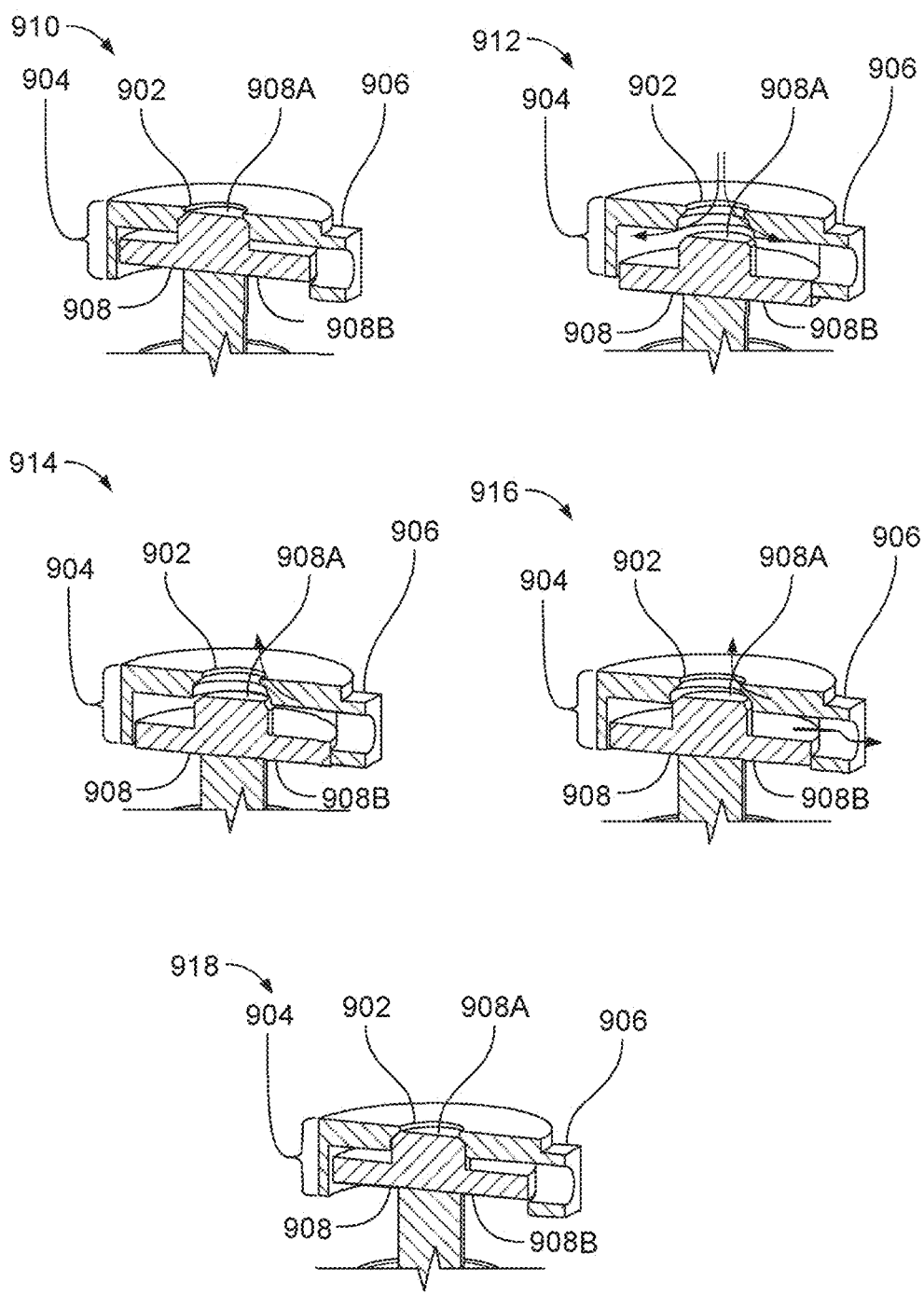
FIG. 72 shows an illustrative pumping mechanism that may be incorporated into an ingestible device.

FIG. 72 illustrates a pumping mechanism 900 that may be incorporated into an ingestible device, including certain embodiments of ingestible devices 100, 200, 6600, and 7702-7706. For illustrative purposes, the pumping mechanism 900 may be described in the context of an ingestible device similar to ingestible device 6600. When it is incorporated into an ingestible device similar to ingestible device 6600, the pumping mechanism 900 may function as a moveable valve (e.g., moveable valve 6614 of ingestible device 6600), and control the ability of samples to flow between the opening 6606 in the housing and the entry port 6610 of the sampling chamber 6612. Additionally, the pumping chamber 904 of the pumping mechanism 900 may form part of the second portion 6608B of the inlet region 6608. However, the general structure and principles of pumping mechanism 900 are not limited to the ingestible devices described in this disclosure, and they may be applied to a wide range of ingestible devices.

Pumping mechanism 900 is designed to draw in a sample through a first opening 902 into a pumping chamber 904, and push a portion of the sample out of the pumping chamber 904 through a second opening 906. In some embodiments, the first opening 902 may be connected directly or indirectly to an opening in the housing of an ingestible device. For example, an inlet region (e.g., the first portion 6608A of the inlet region 6608 of the ingestible device 6600) may connect an opening in the housing of an ingestible device (e.g., the opening 6606 in the housing of ingestible device 6600) to the first opening 902. In some embodiments, the second opening 906 is connected directly or indirectly to a sampling chamber of an ingestible device. For example, the second opening 906 may be connected to an entry port of a sampling chamber (e.g., connected via the third portion 6608C of the inlet region 6608 to the entry port 610 of the sampling chamber 6612 of the ingestible device 6600).

The pumping mechanism 900 features a moveable pump head 908 contained within the pumping chamber 904. The protrusion 908A of the moveable pump head 908 is shaped to fit within the first opening 902, or otherwise block the first opening 902. The base 908B of the moveable pump head 908 is able to cover the second opening 906 or otherwise block the second opening 906. Moreover, the protrusion 908A and the base 908B of the moveable pump head 908 are sized and oriented from each other in such a manner such that when the protrusion 908A blocks the first opening 902, the base 908B may simultaneously block the second opening 906 or leave the second opening 906 unblocked. Furthermore, when the base 908B blocks the second opening 906, the protrusion 908A may always be configured to also block the first opening 902.

As the moveable pump head 908 is moved up and down, the openings 902 and 906 may be sealed or unsealed, switching the pumping mechanism 900 across an open position, a partially closed position, and a closed position. In the open position (as is shown in the diagram 912), both the first opening 902 and the second opening 906 are unsealed or open. In the partially closed position (as is shown in the diagram 914, the moveable pump head 908 is positioned to only seal the first opening 902, while leaving the second opening 906 open. Finally, in the closed position (as is shown in the diagrams 910 and 918), both the first opening 902 and the second opening 906 are sealed.

In some embodiments, the moveable pump head 908 may be connected to a mechanical actuator (e.g., the mechanical actuator 6624 of the ingestible device 6600), which may be configured to move the moveable pump head 908 linearly up and down. For example, the moveable pump head 908 may be located on the end of a shaft that is attached to the mechanical actuator. In some embodiments, the mechanical actuator and the positioning of the moveable pump head 908 may be controlled by a microcontroller or microprocessor located within the ingestible device. For example, a microcontroller may be configured to move the pump head 908 and begin pumping a sample through the pumping chamber 904 only after the ingestible device has reached a particular location within the GI tract.

Diagram 910 depicts the pumping mechanism 900 in a fully closed position. When the pumping mechanism 900 is in the fully closed position, the protrusion 908A of the moveable pump head 908 may be positioned within the first opening 902, and the base 908B of the moveable pump head 908 may be positioned adjacent to the second opening 906. In the fully closed position, the positioning of the moveable pump head 908 may effectively prevent a sample from entering or exiting the pumping chamber 904 from the openings 902 or 906.

Diagram 912 depicts the pumping mechanism 900 in an open position. When the pumping mechanism 900 is in the open position, the moveable pump head 908 is moved away from the first opening 902, moving the protrusion 908A of the moveable pump head 908 out of the first opening 902, and moving the base 908B of the moveable pump away from the second opening 906. In this position, the pumping mechanism 900 may allow one or more samples to enter the pumping chamber 904 through the first opening 902, and exit the pumping chamber 904 through the second opening 906. Because the effective volume of the pumping chamber 904 increases when the moveable pump head 908 is moved away from the first opening 902, the pumping mechanism 900 may draw a sample into the sampling chamber through the first opening 902 when transitioning from a closed position depicted in the diagram 910 to an open position depicted in the diagram 912. In some embodiments, a one-way valve may be incorporated into an ingestible device to prevent samples from being drawn into the pumping chamber 904 through the second opening 906 when the pumping mechanism 900 transitions between the closed position and the open position. This may ensure that the only sample entering the pumping chamber 904 is drawn in through the first opening 902.

Diagram 914 depicts the pumping mechanism 900 in a partially closed position. When the pumping mechanism 900 is in the partially closed position, the protrusion 908A of the moveable pump head 908 is positioned adjacent to the first opening 902, or just inside the first opening 902. In this position, the protrusion 908A of the moveable pump head 908 effectively seals off the first opening 902, preventing any of the sample remaining in the pumping chamber 904 from exiting pumping chamber 904 via the first opening 902. In this position, the base 908B of the moveable pump head 908 is positioned away from the second opening 906. This may allow any sample remaining in the pumping chamber 904 to exit the pumping chamber 904 through the second opening 906. For example, if the second opening 906 is connected to an entry port of a sampling chamber (e.g., connected via the third portion 6608C of the inlet region 6608 to the entry port 6610 of the sampling chamber 6612 of the ingestible device 6600), this may allow the sample to flow freely from the pumping mechanism 900 into the sampling chamber via the entry port.

Diagram 916 depicts the pumping mechanism 900 as it transitions between the partially closed position to the fully closed position. As the pumping mechanism 900 moves into the fully closed position, the moveable pump head 908 forces any of remaining sample contained within the pumping chamber 904 out of the pumping chamber 904 through the second opening 906. As this happens, the protrusion 908A of the moveable pump head 908 remains within the first opening 902, blocking it off and preventing the sample from exiting the pumping chamber 904 through first opening 902. By comparison, the base 908B of the moveable pump head 908 does not fully cover the second opening 906, and the sample is free to exit the pumping chamber 904 through the second opening 906. In combination, this may result in a majority of the sample remaining in the sampling chamber being forced through the second opening 906 as the pumping mechanism 900 moves from the partially closed position depicted in diagram 914 to the fully closed position depicted in diagram 918.

Diagram 918 depicts the pumping mechanism 900 in the fully closed position, similar to diagram 910. As noted before, in the fully closed position the moveable pump head 908 is positioned to seal off the openings 902 and 906, which may prevent a sample from entering or exiting the pumping chamber 904 from the openings 902 or 904. In general, the pumping mechanism 900 may cycle between the closed position depicted in diagrams 910 and 918 and the open position depicted in diagram 912 any number of times in order to draw additional samples into the pumping chamber 904 through the first opening 902, and force the samples out of the pumping chamber 904 through the second opening 906.

Although FIG. 72 depicts the protrusion 908A of the moveable pump head 908 located in the center of the moveable pump head 908, the location of the protrusion 908A may be anywhere on the moveable pump head 908. For example, the protrusion 908A of the moveable pump head 908 and the first opening 902 may be positioned on the side of the pumping chamber 904. In some embodiments, the moveable pump head 908 is split into two pieces, which may be controlled by one or more actuators. For example, the protrusion 908A and the base 908B may be two separate pieces, each of which is moved using a different actuator. This may allow the first opening 902 to be sealed and unsealed independently from the volume of the pumping mechanism 900 being increased or decreased.

For illustrative purposes, the diagrams 910-918 depict the base 908B of the moveable pump head 908 being used to cover or otherwise block the second opening 906. However, in some embodiments, the moveable pump head 908 may not cover, fit within, or otherwise block the second opening 906, and it will be understood by one skilled in the art that the second opening 906 does not need to be partially or fully blocked in order to push a sample through the second opening 906. For example, the moveable pump head 908 may not include a base 908B at all. Instead, the moveable pump head 908 may be made of a flexible material that forms a seal with the underside of the pumping chamber 904. In this case, the moveable pump head 908 may be moved up and down in a manner similar to a plunger in order to change the effective volume of the pumping chamber 904. When the volume decreases, the sample is at least partially forced out of the pumping chamber 904 through the second opening 906.

In general, incorporating the pumping mechanism 900 into an ingestible device may not impair the function of the openings, ports, valves, membranes, sampling chambers, or other structures of the ingestible device, and any of the teachings or embodiments described in conjunction with the ingestible devices 100, 200, 6600, or 7702-7706 may be combined in different embodiments of an ingestible device along with the pumping mechanism 900. For example, the pumping mechanism 900 may replace the first valve 214 in the ingestible device 200, and may be used to force the sample into the sampling chamber 212. As an alternate example, the pumping mechanism 900 may be used to force samples into the sampling chamber 304 of the osmotic valve mechanism 300. As another example, the pumping mechanism 900 may be incorporated into an embodiment of the ingestible device 6600 where the exit port 6616 is not included, and the pumping mechanism 900 may be used to force the sample into the sampling chamber 6612 despite the pressure that may result from air or gas 6618 being trapped within the sampling chamber 6612.

For illustrative purposes, the examples provided by this disclosure focus primarily on a number of different example embodiments of an ingestible device, such as the ingestible devices 100, 200, 6600, and 7702-7706. However, it is understood that variations in the general shape and design of one or more embodiments of the ingestible devices described in relation to FIGS. 64-72 may be made without significantly changing the functions and operations of the device. Furthermore, it should be noted that the features and limitations described in any one embodiment may be applied to any other embodiment herein, and the descriptions and examples relating to one embodiment may be combined with any other embodiment in a suitable manner. For example, any of the valves described in relation to FIG. 70 may be used as the valves 214 and 216. As an alternate example, the absorptive material 310 and flexible membrane 314 may be incorporated into any of the various sampling chambers described in various embodiments of ingestible devices 100, 200, 6600, and 7702-7706 in order to automatically seal the sampling chamber. Moreover, the figures and examples provided in disclosure are intended to be only exemplary, and not limiting. Only the claims that follow are meant to set bounds as to what the present invention includes. It should also be noted that the systems and/or methods described above may be applied to, or used in accordance with, other systems and/or methods, including systems and/or methods that may or may not be directly related to ingestible devices.

Figure 73:
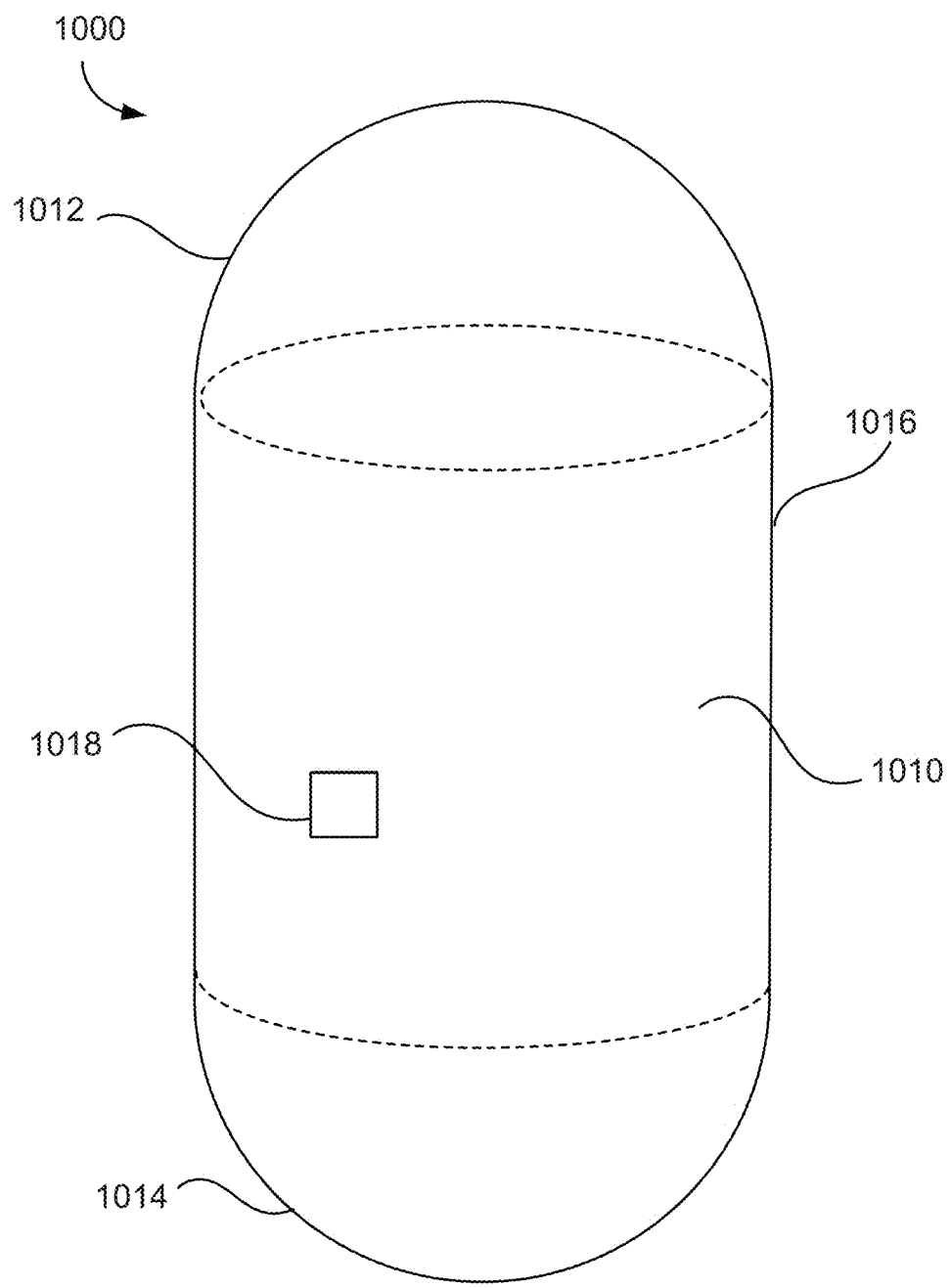
FIG. 73 shows a highly schematic representation of an ingestible device.

FIG. 73 illustrates, in a highly schematic fashion, an ingestible device 1000 having a housing 1010 that includes a first end 1012 and a second end 1014 opposite first end 1012. Housing 1010 also includes a wall 1016 that connects first end 1012 and second end 1014. Wall 1016 has an opening 1018 that allows fluid from an exterior of the ingestible device 1000 (e.g., from the GI tract) and into an interior of ingestible device 1000.

Figure 74:
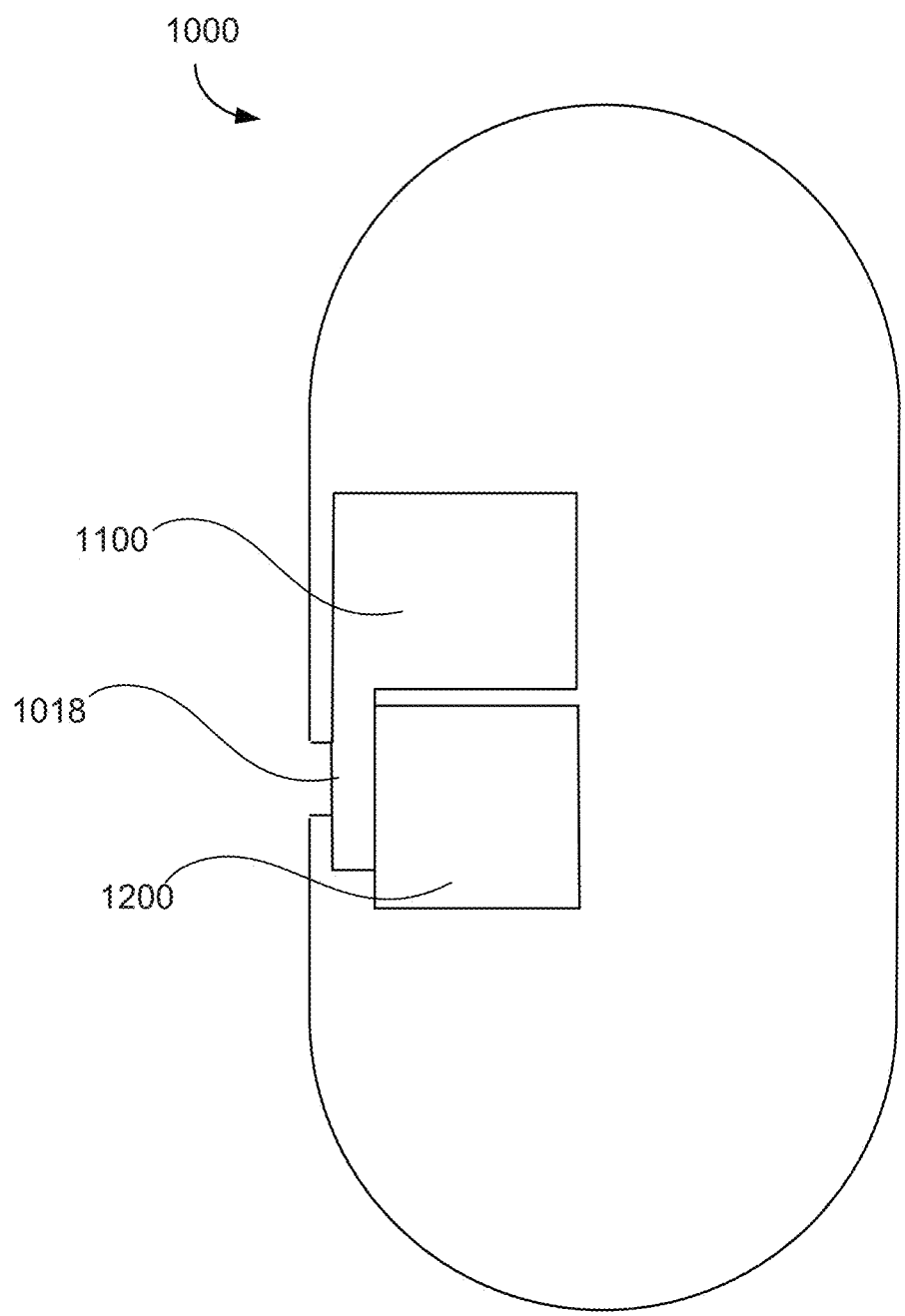
FIG. 74 shows a highly cross-section of an ingestible device including a valve system and a sampling system.

FIG. 74 depicts a cross-sectional view of a portion of the interior of ingestible device 1000. The interior of ingestible device 1000 includes a valve system 1100 and a sampling system 1200. Valve system 1100 is depicted as having a portion that is flush with the opening 1018 so that valve system 1100 prevents fluid exterior to ingestible device 1000 from entering sampling system 1200. However, as described in more detail below, valve system 1100 can change position so that valve system 1100 allows fluid exterior to ingestible device 1000 to enter sampling system 1200.

Figure 75:
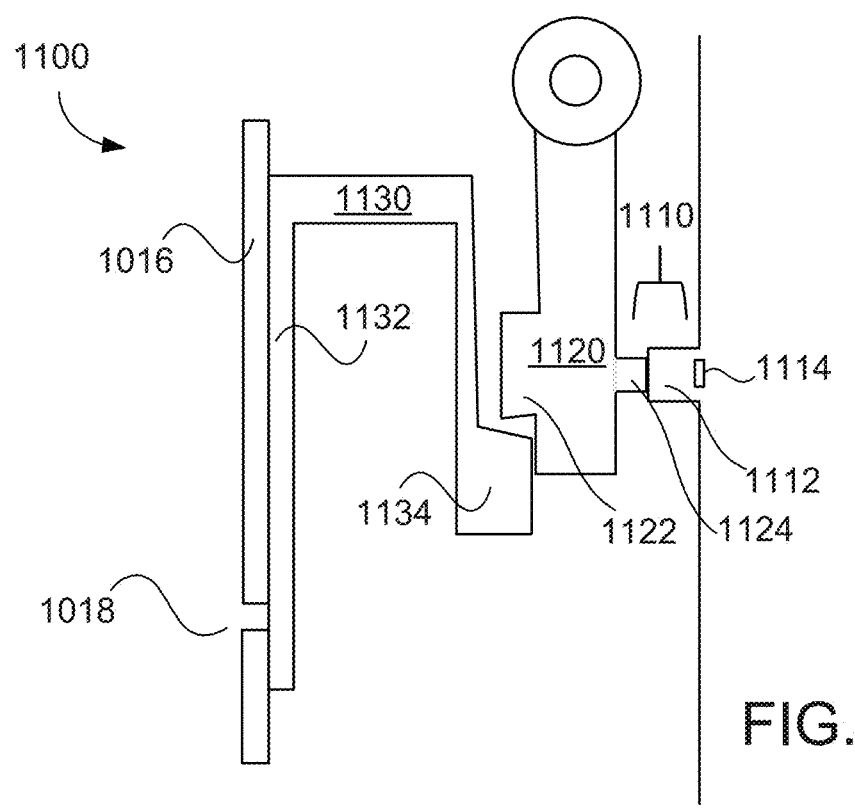
FIG. 75 illustrates a valve system.
Figure 78B:
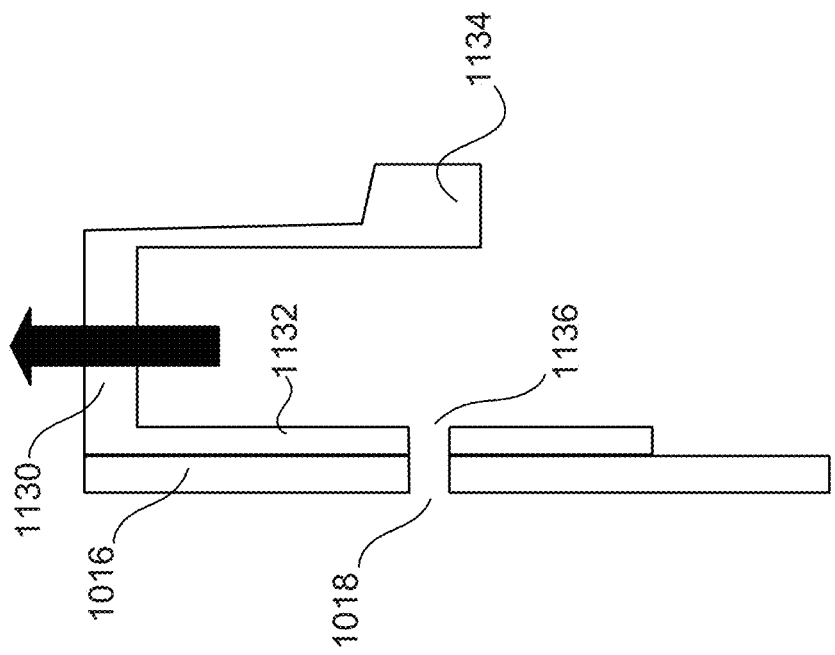
FIGS. 78A and 78B illustrate a portion of a two-stage valve system in its first and second stages, respectively.
Figure 78A:
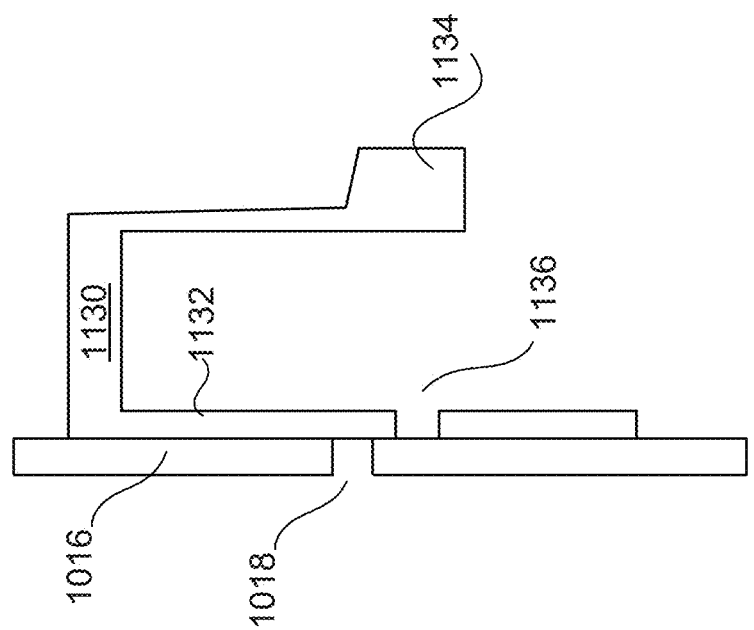
Figure 79:
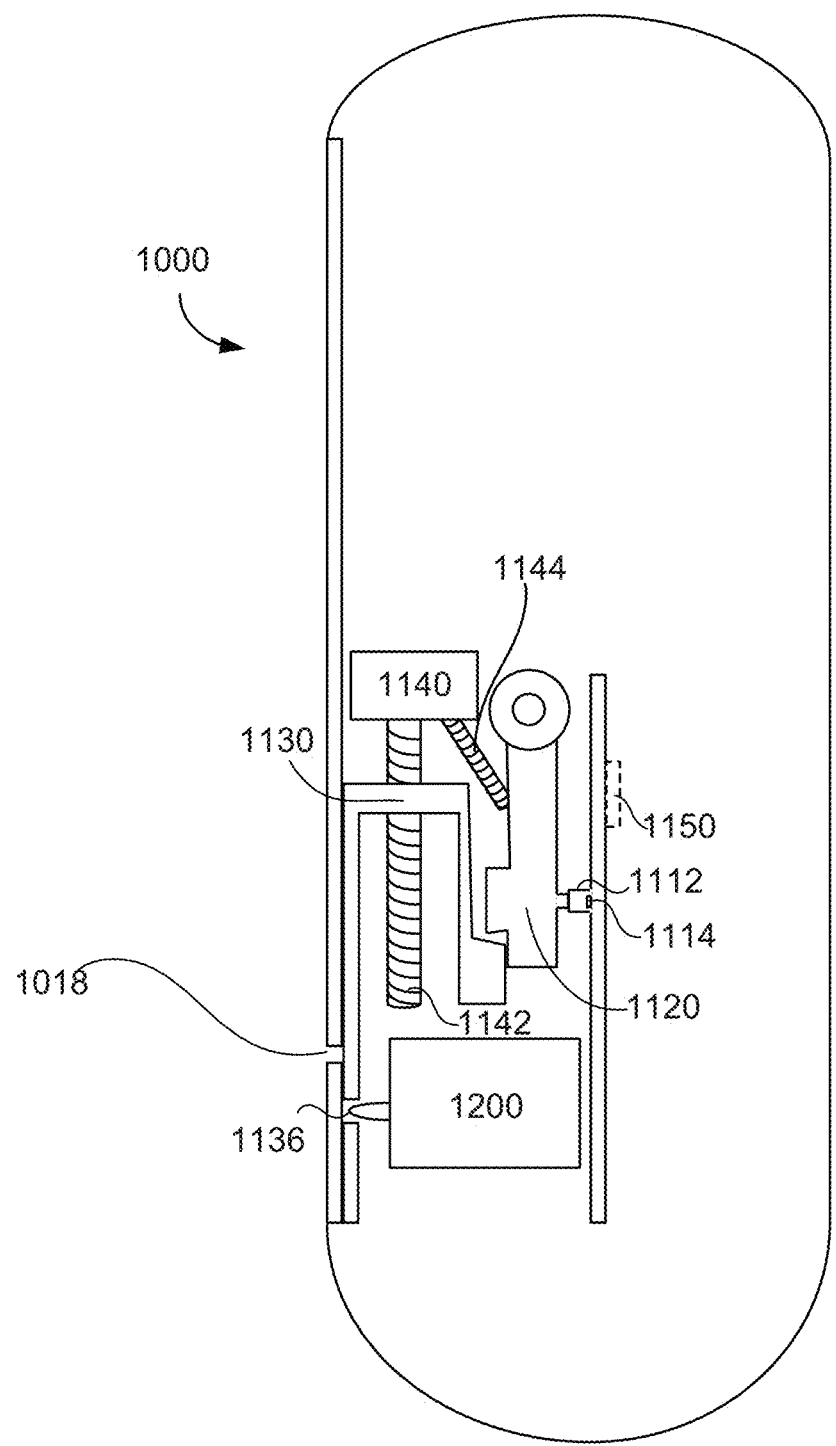
FIG. 79 illustrates a more detailed view of an ingestible device including a valve system and a sampling system.

FIGS. 75-79 illustrate valve system 1100 in more detail. As shown in FIG. 75, valve system 1100 includes an actuation mechanism 1110, a trigger 1120, and a gate 1130. A leg 1132 of gate 1130 is flush against, and parallel with, housing wall 1016 so that gate leg 1132 covers opening 1018 to prevent fluid exterior to ingestible device 1000 (e.g., fluid in the GI tract) from entering the interior of ingestible device 1000. A protrusion 1134 of gate 1130 engages a lip 1122 of trigger 1120. A peg 1124 of trigger 1120 engages a wax pot 1112 of actuation mechanism 1110. Referring to FIG. 79, a biasing mechanism 1140 includes a compression spring 1142 that applies an upward force on gate 1130. Biasing mechanism 1140 also includes a torsion spring 1144 that applies a force on trigger 1120 in the counter-clockwise direction. The force applied by torsion spring 1144 is counter-acted by the solid wax in pot 1112, and the force applied by compression spring 1142 is counter-acted by lip 1122.

Figure 76A:
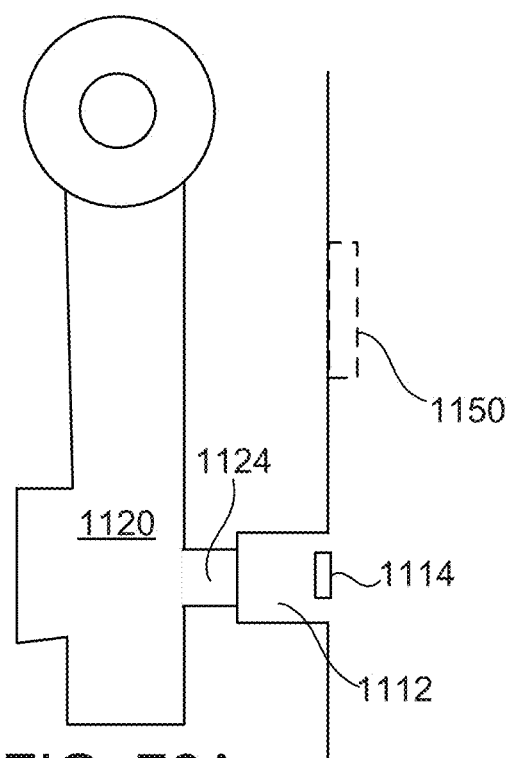
FIGS. 76A and 76B illustrate a portion of a two-stage valve system in its first and second stages, respectively.
Figure 76B:
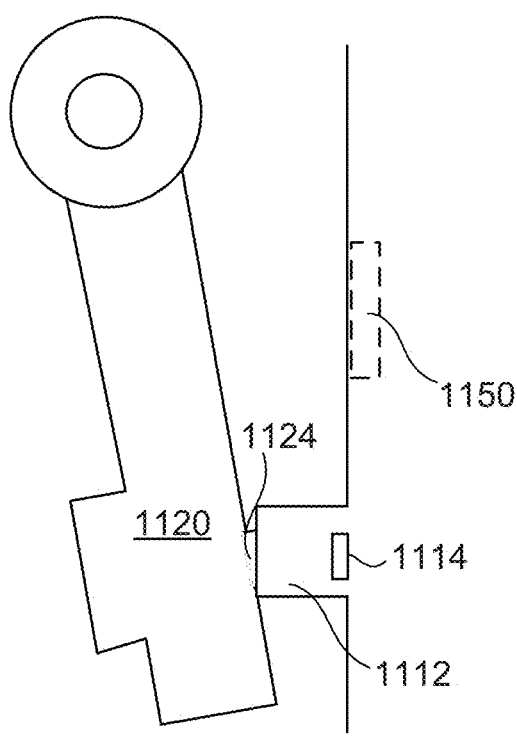

FIG. 76A and FIG. 76B show an embodiment of the manner in which actuation mechanism 1110 actuates movement of trigger 1120. FIG. 76A shows a configuration in which peg 1124 applies a force against solid wax pot 1112 due to torsion spring 1144, and in which the solid nature of wax pot 1112 resists the force applied by peg 1124. A control unit 1150 is in signal communication with valve system 1100. During use of ingestible device 1000, a control unit 1150 receives a signal, indicating that the position of valve system 1100 should change, e.g., so that ingestible device 1000 can take a sample of a fluid in the GI tract. Control unit 1150 sends a signal that causes a heating system 1114 of actuation system 1100 to heat the wax in pot 1112 so that the wax melts. As shown in FIG. 76B, the melted wax is not able to resist the force applied by peg 1124 so that, under the force of torsion spring 1144, trigger 1120 moves in a counter-clockwise fashion.

Figures 77A, 77B:
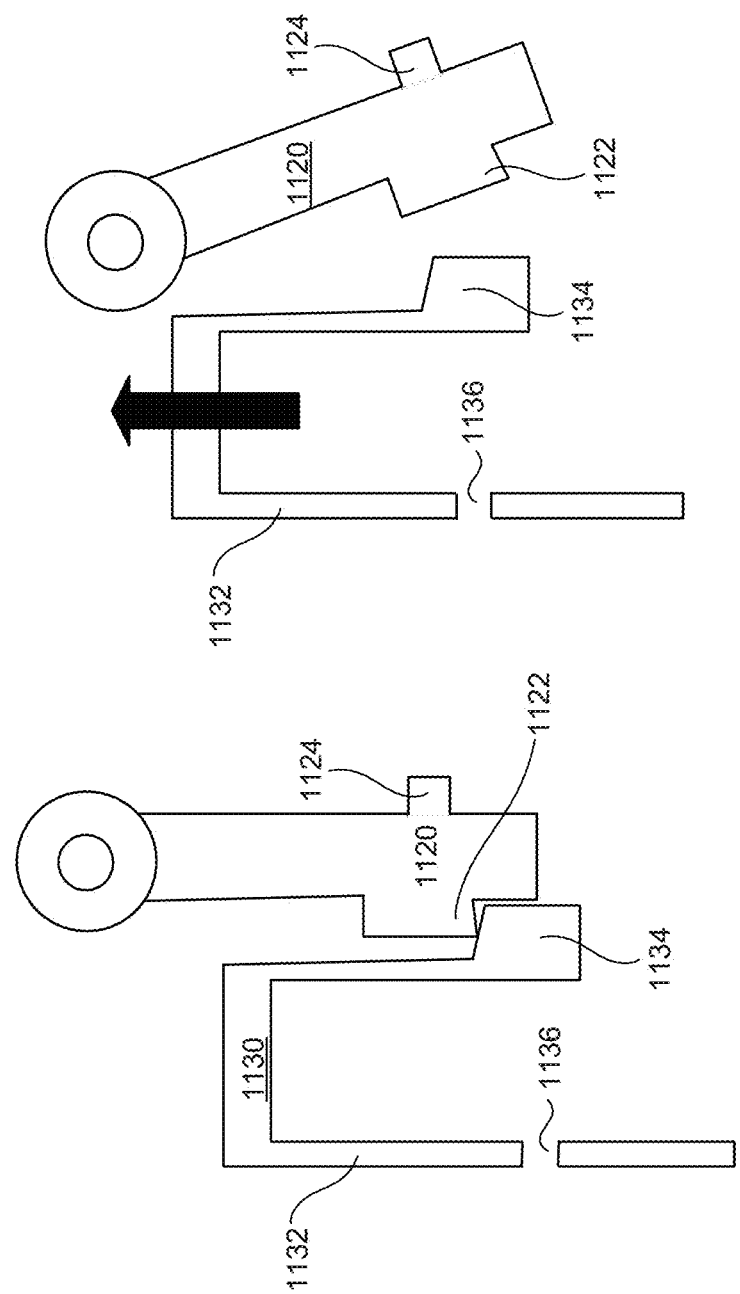
FIGS. 77A and 77B illustrate a portion of a two-stage valve system in its first and second stages, respectively.

FIGS. 77A and 77B illustrate the interaction of trigger 1120 and gate 1130 before and after actuation. As shown in FIG. 77A, when wax pot 1112 is solid (corresponding to the configuration shown in FIG. 76A), protrusion 1134 engages lip 1122, which prevents the force of compression spring 1142 from moving gate 1130 upward. As shown in FIG. 77B, when the wax in pot 1112 melts (FIG. 76B), trigger 1120 moves counter-clockwise, and lip 1122 disengages from protrusion 1134. This allows the force of compression spring 1142 to move gate 1130 upward. As seen by comparing FIG. 77A to FIG. 77B, the upward movement of gate 1130 results in an upward movement of an opening 1136 in gate leg 1132.

FIGS. 78A and 78B illustrate the impact of the upward movement of opening 1136 on the ability of ingestible device 1000 to obtain a sample. As shown in FIG. 77A, when the wax in pot 1112 is solid (FIGS. 76A and 77A), opening 1136 in is not aligned with opening 1018 in wall 1016 of ingestible device 1000. Instead, gate leg 1132 covers opening 1018 and blocks fluid from entering the interior of ingestible device 1000. As shown in FIG. 78B, when the wax in pot 1112 is melted and trigger 1120 and gate 1130 have moved (FIGS. 76B and 77B), opening 1136 in gate 1130 is aligned with opening 1018 in wall 1016. In this configuration, fluid that is exterior to ingestible device 1000 (e.g., in the GI tract) can enter the interior of ingestible device 1000 via openings 1018 and 1036.

Figure 80A:
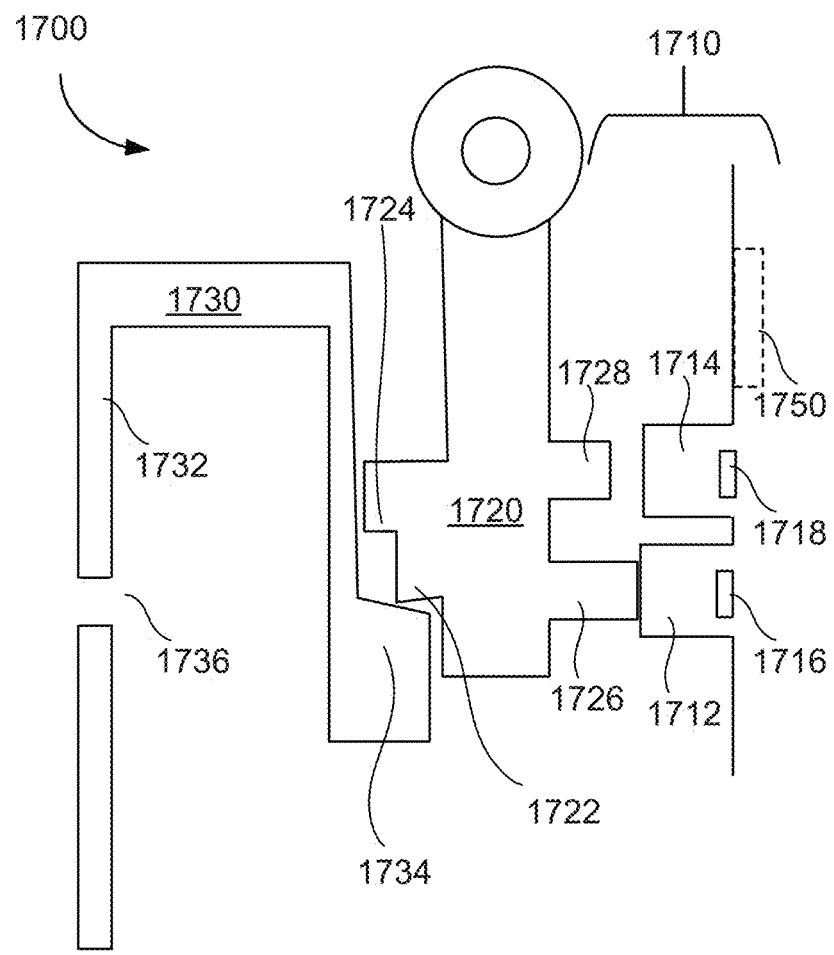
FIGS. 80A-80C illustrate a portion of a three-stage valve system in its first, second and third stages, respectively.
Figure 80C:
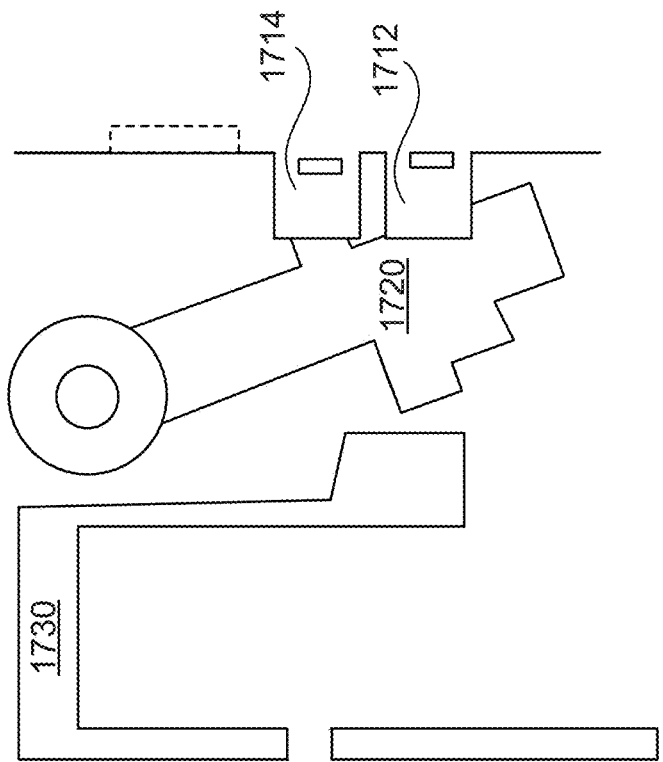
Figure 80B:
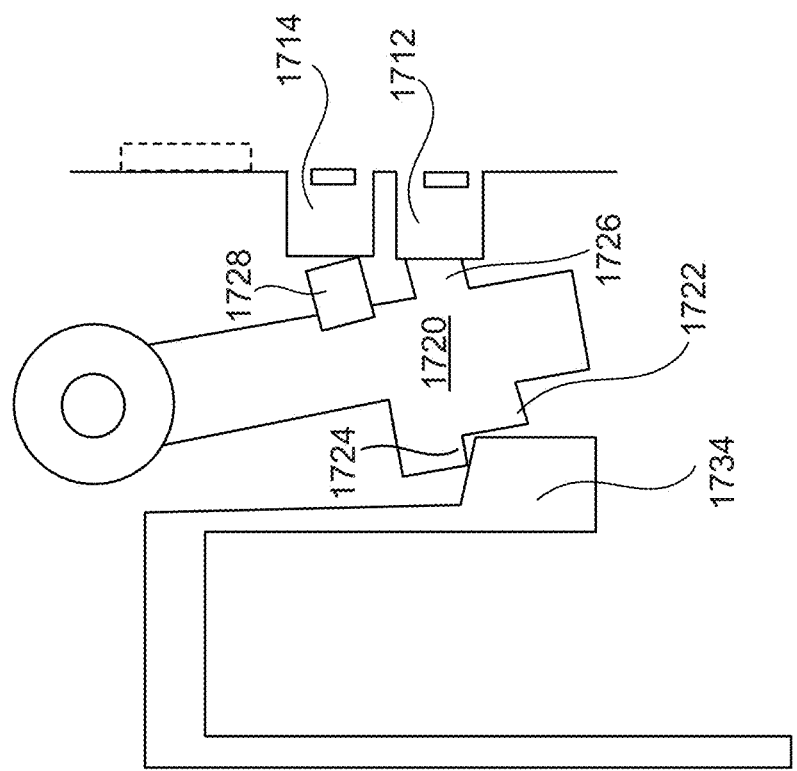
Figure 81C:
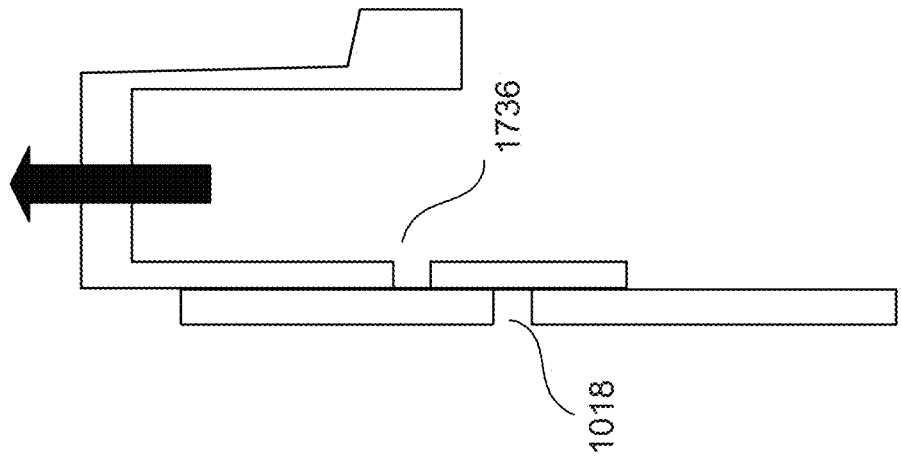
FIGS. 81A-81C illustrate a portion of a three-stage valve system in its first, second and third stages, respectively.
Figure 81B:
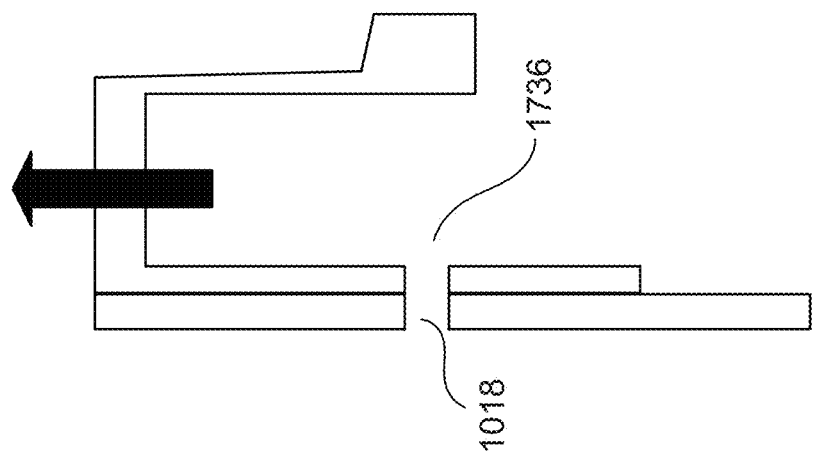
Figure 81A:
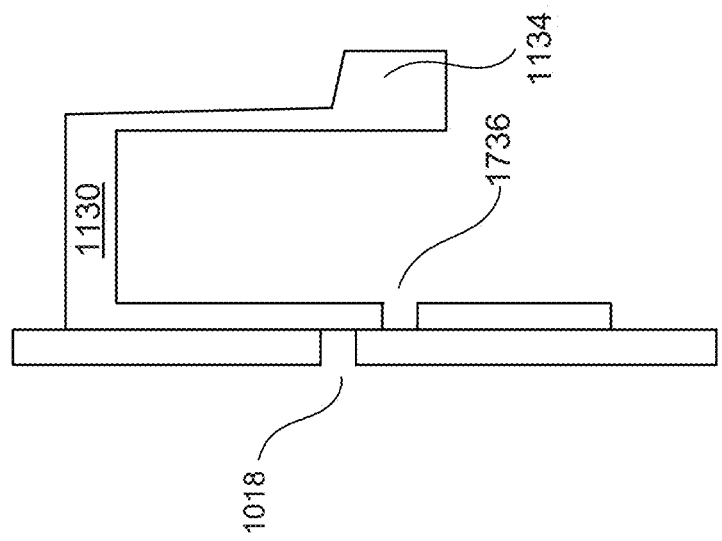
Figure 82A:
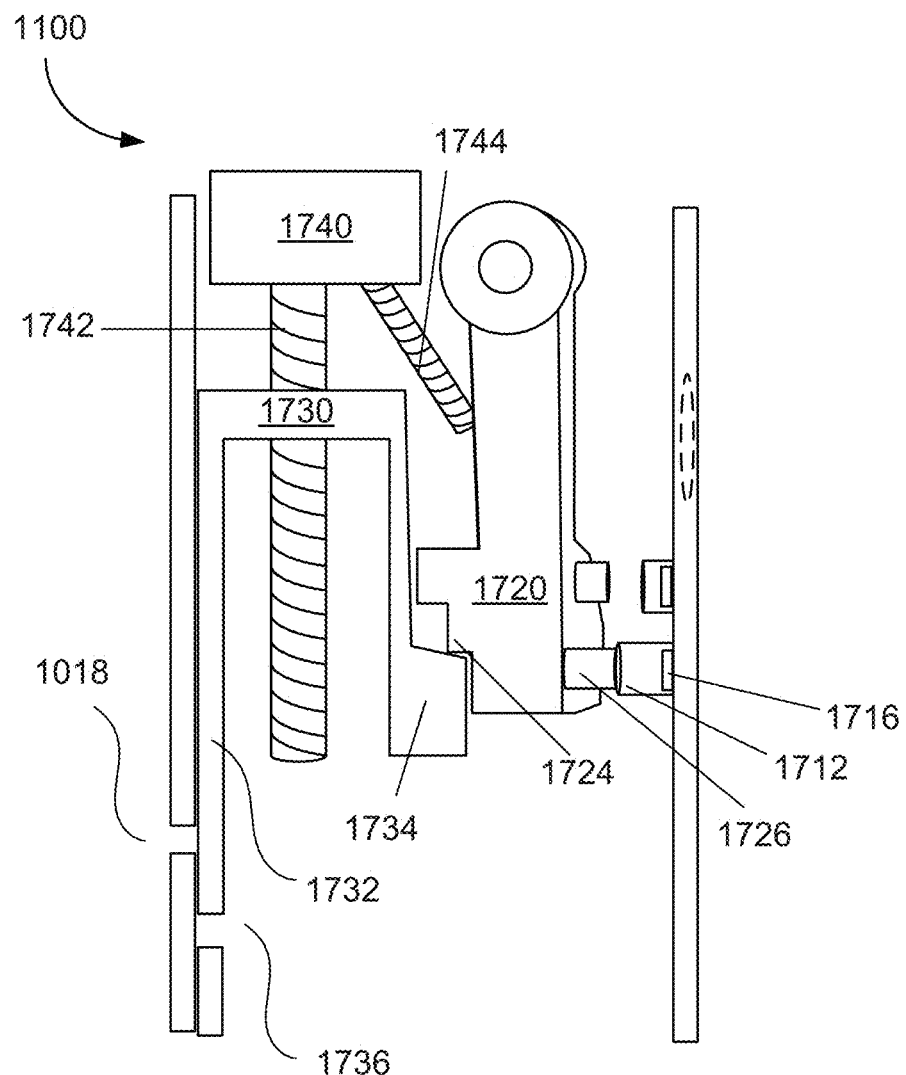
FIGS. 82A-82C illustrate a portion of a three-stage valve system in its first, second and third stages, respectively.
Figure 82B:
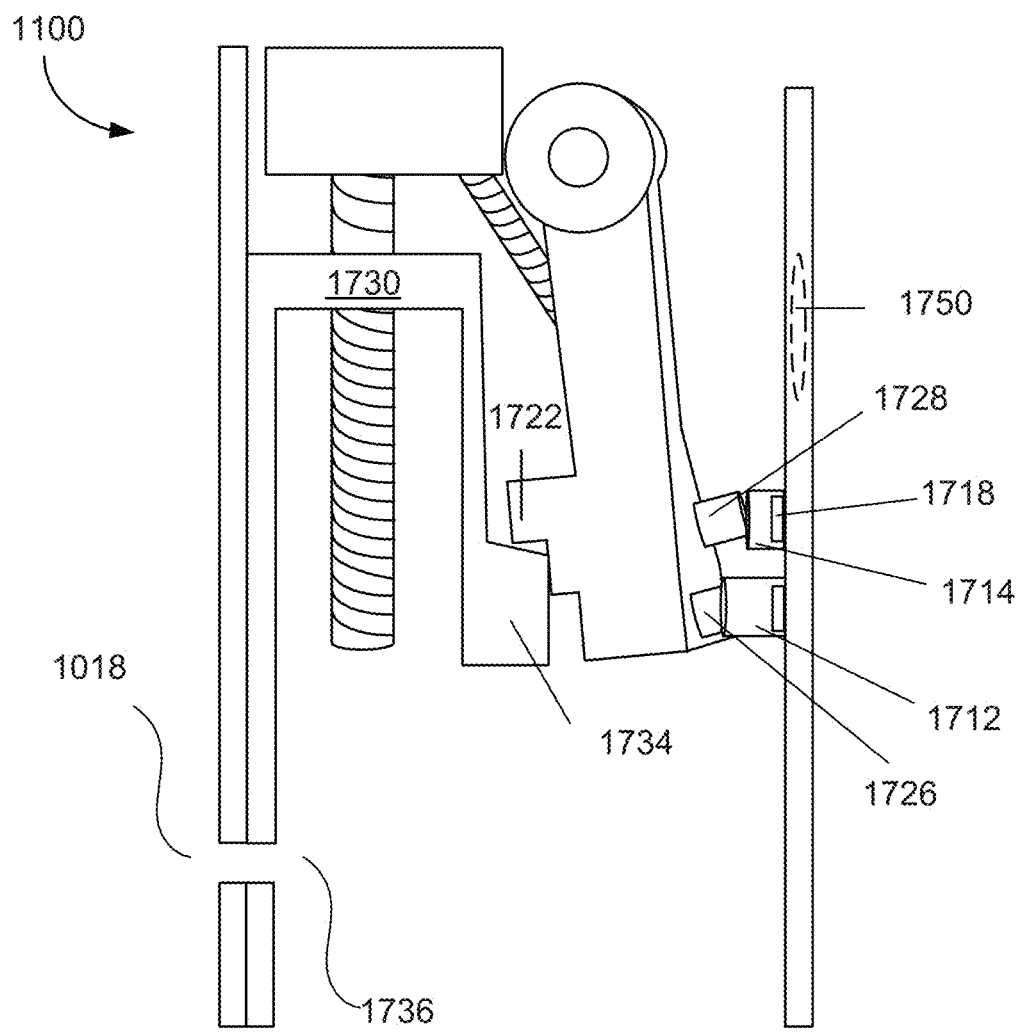
Figure 82C:
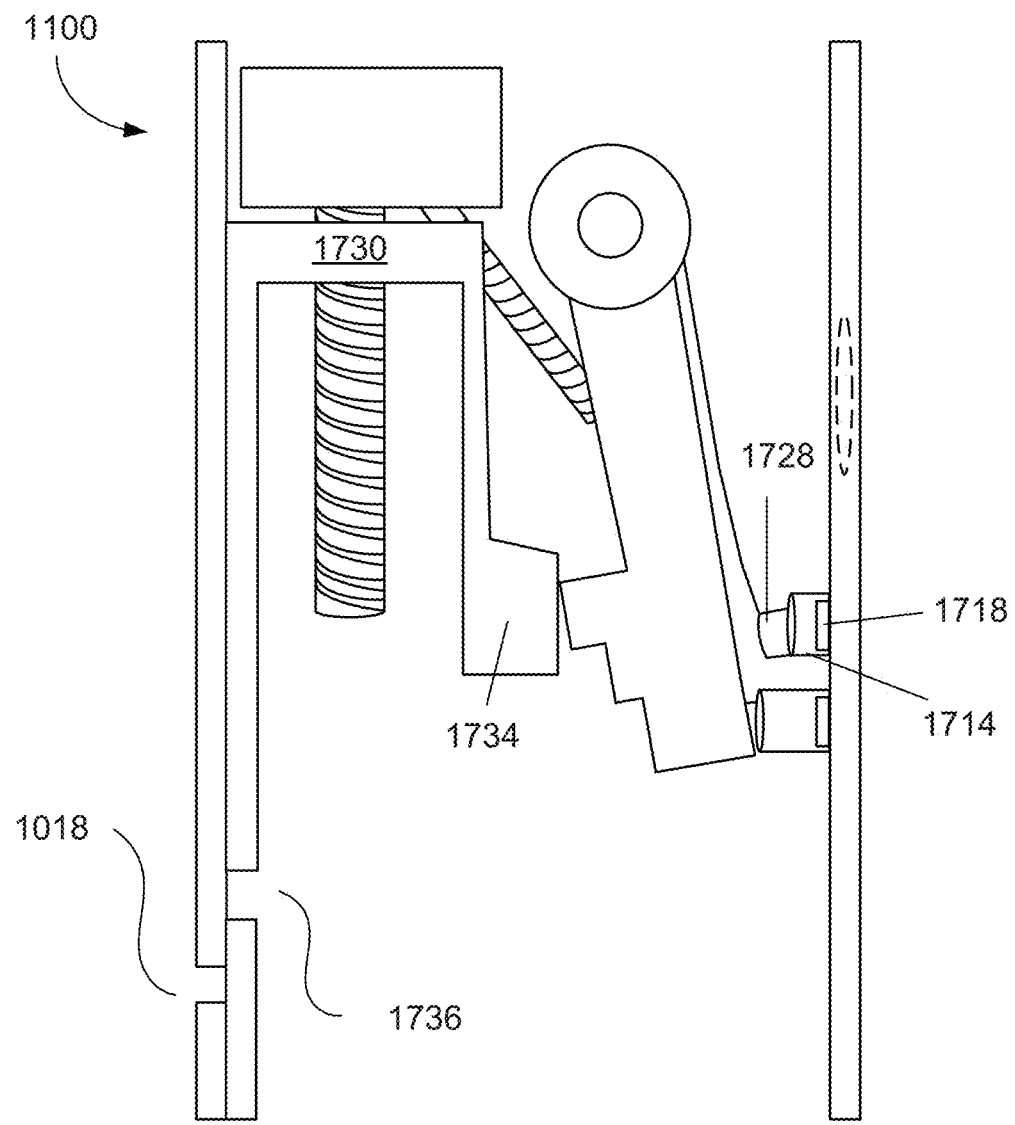

While the foregoing description is made with regard to a valve system having one open position and one closed position (e.g., a two-stage valve system), the disclosure is not limited in this sense. Rather, the concepts described above with regard to a two stage valve system can be implemented with a valve system have more than two stages (e.g., three stages, four stages, five stages, etc.). For example, FIGS. 80A-820 illustrate cross-sectional views of a three-stage valve system 1700. FIGS. 80A, 81A and 82A illustrate different views of components of valve system 1700 in the same position. FIGS. 80B, 81B and 82B illustrate different views of components of valve system 1700 in the same position. FIGS. 80C, 81C and 82C illustrate different views of components of valve system 1700 in the same position.

As shown in FIGS. 80A-82C, valve system 1700 includes an actuation system 1710, a trigger 1720, a gate 1730 and a biasing system 1740. Actuation system 1710 includes a first wax pot 1712, a second wax pot 1714, a first heating system 1716 and a second heating system 1718. Trigger 1720 includes a first lip 1722, a second lip 1724, a first peg 1726 and a second peg 1728. Gate 1730 includes a gate leg 1732 and a protrusion 1734. Gate leg 1732 has an opening 1736. Biasing system 1740 includes a compression spring 1742 and a torsion spring 1744. In addition, the ingestible device includes a control unit 1750.

As shown in FIGS. 80A, 81A and 82A, in the first stage, protrusion 1734 engages first lip 1722, and first peg 1726 engages first wax pot 1712. Compression spring 1742 applies an upward force on gate 1730, and torsion spring 1744 applies a force on trigger 1720 in the counter-clockwise direction. The force applied by torsion spring 1744 is counter-acted by the solid wax in first pot 1712, and the force applied by compression spring 1742 is counter-acted by first lip 1722. Opening 1736 is not aligned with opening 1018.

FIGS. 80B, 81B and 82B illustrate the configuration in a second stage, after control unit 1750 sends a signal to first heating system 1716 to melt the wax in first pot 1712. In the second stage, trigger 1720 has moved counter-clockwise relative to its position in the first stage. First peg 1726 is positioned in first pot 1712 because the melted wax cannot prevent this movement. Further counter-clockwise movement of trigger 1720 is prevented by the engagement of second peg 1728 with the solid wax in second pot 1714. With the counter-clockwise movement of trigger 1720, first lip 1722 disengages from protrusion 1734, and gate 1730 moves upward so that opening 1736 in leg 1732 is aligned with opening 1018. Further upward movement of gate 1730 is prevented by the engagement of protrusion 1734 with second lip 1724.

FIGS. 80C, 81C and 82C illustrate the configuration in a third stage, after control unit 1750 sends a signal to second heating system 1718 to melt the wax in second pot 1714. In the third stage, trigger 1720 has moved counter-clockwise relative to its position in the second stage. Second peg 1728 is positioned in second pot 1714 because the melted wax cannot prevent this movement. Further counter-clockwise rotation is prevented by the engagement of first and second pegs 1726 and 1728, respectively with first and second pots 1712 and 1714, respectively. Protrusion 1734 is disengaged from second lip 1724, allowing the force of compression spring 1742 to move gate 1730 upward so that opening 1736 is no longer aligned with opening 1018.

Figure 83:
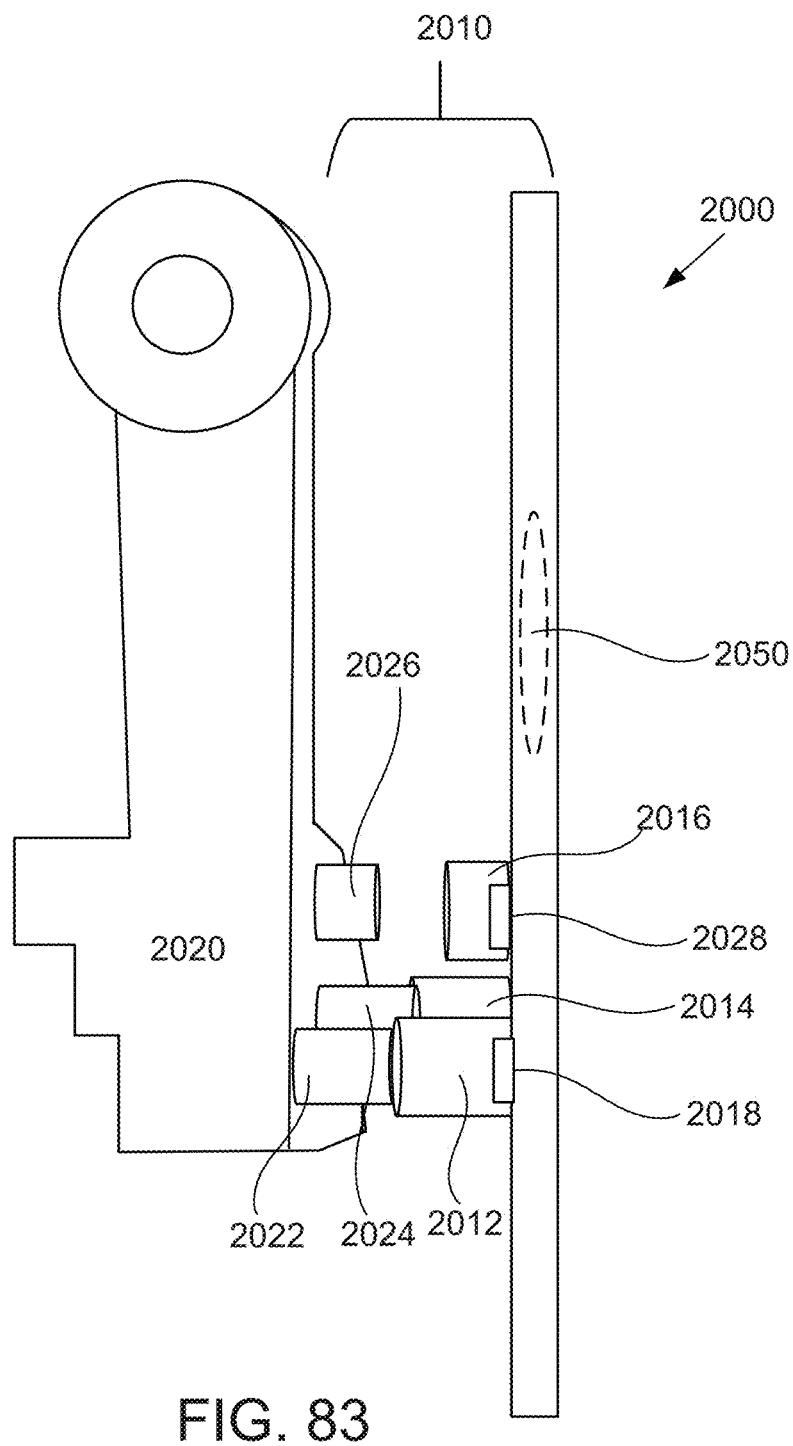
FIG. 83 illustrates a three-stage valve system in its first stage.

FIG. 83 illustrates another embodiment of a three stage valve system 2000 that can be used in an ingestible device. Valve system 2000 that is similar to valve system 1700 except that actuation system 2010 includes three includes wax pots 2012, 2014 and 2016, respectively, that define a triangle, and trigger 2020 includes three pegs 2022, 2024 and 2026, respectively, that define a corresponding triangle. Actuation system 2010 is controlled using a control unit 2050. Actuation system 2010 also includes a first heating system 2018 that heats the wax in pots 2012 and 2014 and so that pegs 2022 and 2024 enters their corresponding pot, causing valve system 2000 to move from its first stage to its second stage. Actuation system 2010 also includes a second heating system 2028 that heats the wax in pot 2016 so that pegs 2026 enters pot 2016, causing valve system 2000 to move from its second stage to its third stage.

In the foregoing discussion, embodiments actuating systems are described that include one or more wax pots and corresponding heating systems. But the disclosure is not limited to such actuating systems. Generally, any actuating system can be used that will provide an appropriate force to resist counter-clockwise movement of the trigger when desired and to remove that force when desired. Examples of such actuation systems include a pot with a silicon or wax seal. A control unit may be used to rupture the seal and allow counter clock-wise movement of the trigger. Additionally, or alternatively, the actuation mechanism may use dissolvable coating to that dissolves over time or in the presence of a substance. As the coating dissolves, the trigger may move further in the counter clock-wise direction. Other actuation mechanisms may also apply an attractive force rather than remove a resistive force. For example, the actuation mechanism may include magnetic pegs and slidable magnets The magnets may be located behind the pots or may slide to a position behind the pots when the valve system should change stages. As the magnets behind the pots slide into range of the magnetic trigger pegs, the trigger moves in the counterclockwise direction due to the attractive force between the magnetic peg and the magnets. The sliding mechanism to move the slidable magnets may be powered by an osmotic pump, a pressurized chamber, or any other applicable method of movement previously described in other embodiments.

In the discussion above, embodiments of triggers are disclosed that include one or more lips and one or more pegs. However, the disclosure is not limited to such triggers. In general, for example, any trigger design can be used that is capable of providing the step-wise movement of the trigger. Such trigger designs include, for example, a releasable latch coupling or a saw toothed engagement wall. A different embodiment may utilize a ball in socket joint to engage the trigger and gate, in which the "socket" is located on the trigger. It is to be noted that such designs need not be based on counter-clockwise movement and may be, for example, designed for the controlled movement of the trigger in one or more of various degrees of freedom. For example, rather than rotate, the trigger may be configured to slide laterally to push a peg of the trigger into a melted wax pot.

The discussion above describes embodiments of gates that include a protrusion and a leg with an opening. The disclosure is not limited to such designs. Generally, any appropriate arrangement can be used so long as it provides the desired step-wise controlled movement of an opening to the interior of the ingestible device. Exemplary designs include a gate that is capable of responding to or applying magnetic forces on the trigger. A saw toothed pattern may also provide a step-wise gate movement. Additionally, embodiments include a latch designed to releasably couple the gate to the trigger. A different embodiment may utilize a ball in socket joint in which the "ball" is located on the gate. Optionally, a gate can include one or regions that include one or more appropriate sealing materials positioned to cover the opening in the housing of the ingestible device when the gate is positioned to prevent fluid exterior to the ingestible device from entering the interior of the device via the opening in the housing of the ingestible device.

In the foregoing discussion, embodiments of biasing systems are described that include a compression spring and a biasing spring. However, the disclosure is not limited in this sense. In general, any biasing elements can be used to provide the counter-clockwise force to the trigger and/or to provide the upward force to the gate. Exemplary biasing elements include elastic bands, wherein a stretched elastic band acts similar to a stretched compression spring as described. Additional basing mechanisms may include magnets and/or magnetic forces to induce trigger or gate movement. For example, a magnet may be located above the gate, where, like the constant force of the stretched compression spring, the magnet also applies a constant attractive force on the gate.

Figure 84A:
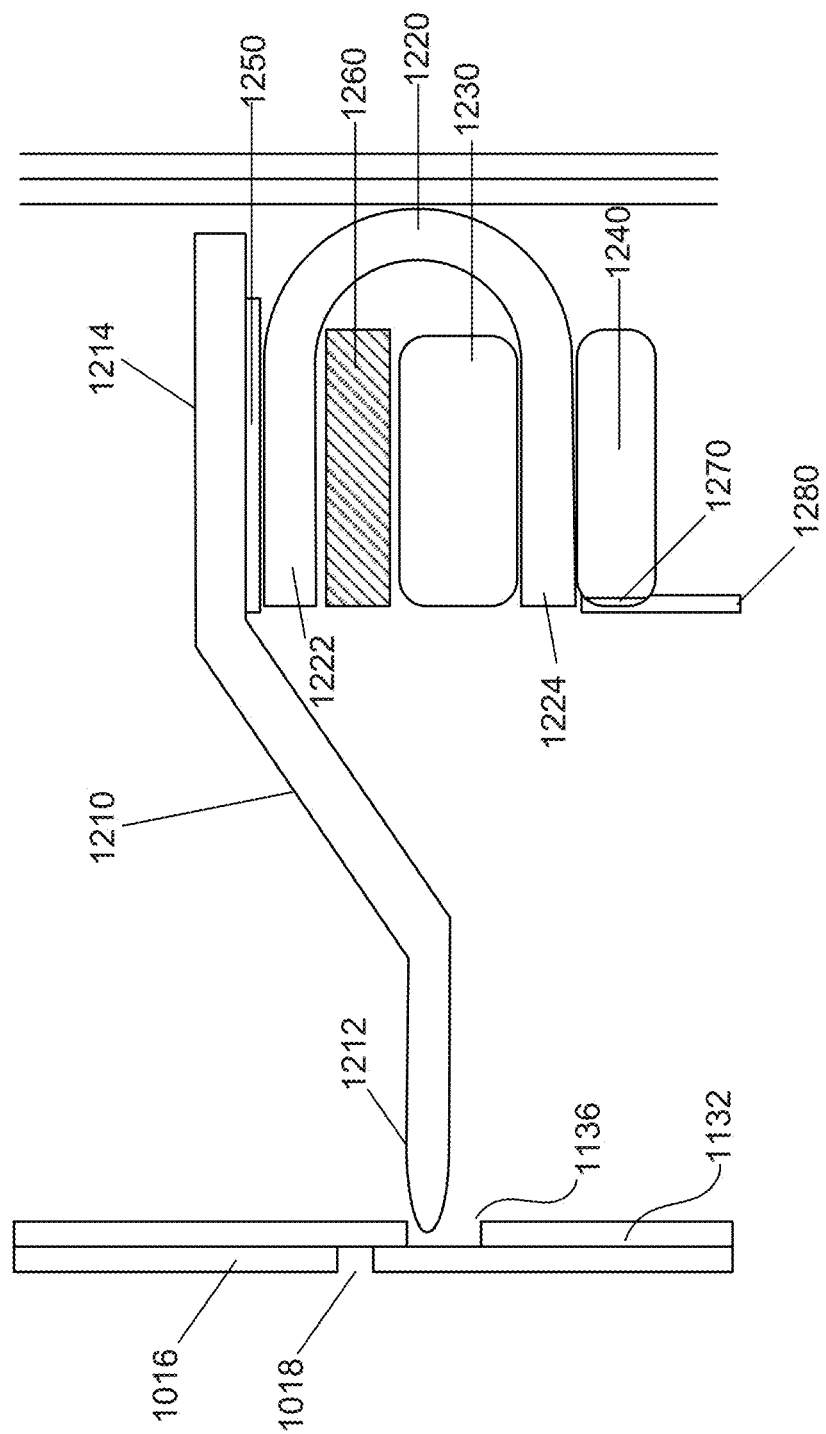
FIG. 84A illustrates a portion of an ingestible device including a sampling system and a two-stage valve system in its first stage.
Figure 84B:
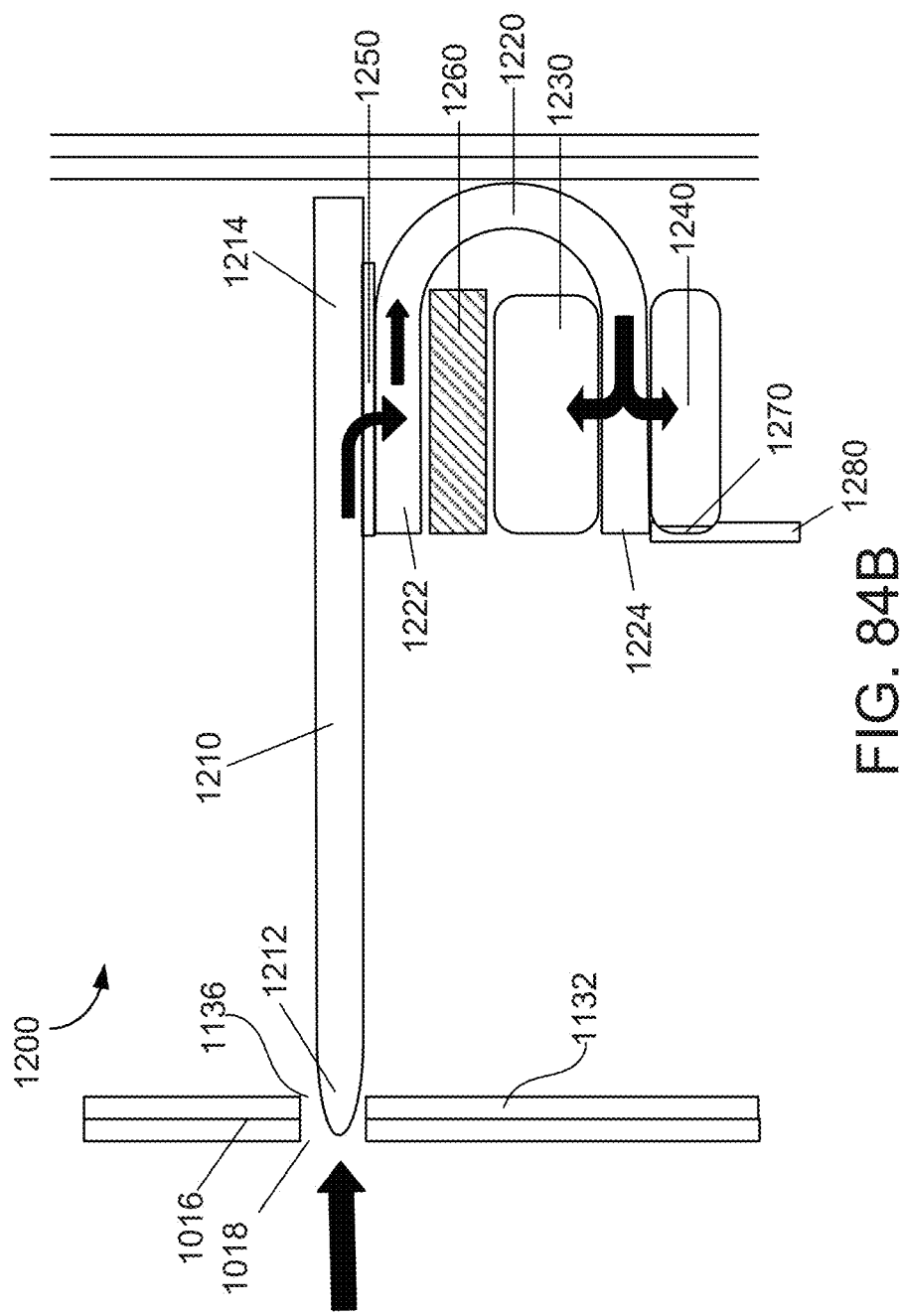
FIG. 84B illustrates a portion of an ingestible device including a sampling system and a two-stage valve system in its second stage.

As noted above in addition to a valve system, an ingestible device includes a sampling system. FIGS. 84A and 84B illustrate a partial cross sectional view of ingestible device 1000 with sampling system 1200 and certain components of valve system 1100. Sampling system 1200 includes a series of sponges configured to absorb fluid from an opening, move the fluid to a location within the housing, and prepare the fluid for testing. Preparation for testing may include filtering the fluid and combining the fluid with a chemical assay. The assay may be configured to dye cells in the filtered sample. The series of sponges includes a wicking sponge 1210, a transfer sponge 1220, a volume sponge 1230, and an assay sponge 1240.

Wicking sponge 1210 absorbs the fluid form the opening in the housing when the valve is open i.e. when the inlet and the housing are aligned. The wicking sponge transfers the fluid from the opening to a filter. Wicking sponge 1210 includes a wicking tongue 1212 extended towards the housing 1016. As shown in FIG. 84A, before actuation of the actuation system (FIGS. 76A, 77A, 78A), wicking tongue 1212 is not adjacent opening 1018 in wall 1016 of ingestible device 1000 so that wicking tongue 1212 does not absorb fluid exterior to ingestible device 1000. However, as shown in FIG. 84B, after actuation of the actuation system (FIGS. 76B, 77B, 78B), wicking tongue 1212 is adjacent opening 1018 so that wicking sponge 1212 absorbs fluid that passes through opening 1018, e.g., fluid from the GI tract. Fluid absorbed by wicking tongue 1212 can travel through wicking sponge 1210 to a distal end 1214 of wicking sponge 1210. The wicking sponge 1210 and wicking tongue 1212 may be made of a VF2 sponge, an Ahlstrom M13 sponge, MF/F material, a Carwild Ivalon Polyvinyl Alcohol material, or another suitable absorptive material. Optionally, the dimensions of the sponge material may be selected to enable all its desired functions while remaining precisely packaged within the capsule. In some embodiments, Carwild Ivalon Polyvinyl Alcohol material is cut to the dimensions 1.4 millimeters (height)×6 millimeters (width)×8.5 millimeters (length). In certain embodiments, one or more of the following parameters can be considered when selecting an appropriate material and/or its dimension: ability to load one more preservative materials; desired preservative material(s) to be loaded; capacity to hold one or more dried preservatives; ability to facilitate hydration of one or more dried preservative materials upon contact with one or more GI fluids; capacity to capture fluid (e.g., GI fluid); and swelling properties upon fluid uptake (generally, it is desirable to have little or no swelling upon fluid uptake).

A cell filter 1250 is located between distal end 1214 of wicking sponge 1210 and a first end 1222 of transfer sponge 1220. The cell filter 1250 is configured to prevent undesired cells, such as Hela cells, from entering one or more downstream sponges in sampling system 1200, particularly sponges used in testing. Excluding such undesired cells enhances the accuracy of various analytical results.

Fluid that passes from wicking sponge 1210 and through cell filter 1250 can enter transfer sponge 1220 via its first end first end 1222. Transfer sponge 1220 is configured to move the filtered fluid from cell filter 1250 to volume sponge 1230 and/or assay sponge 1240.

To allow transfer sponge 1220 to absorb a relatively large volume of fluid, transfer sponge 1220 is shaped (e.g., arc-shaped) to provide a relatively long distance between first end 1222 of transfer sponge 1220 and a second end 1224 of transfer sponge 1220. Second end 1224 contacts both volume sponge 1230 and assay sponge 1240 while preventing volume sponge 1230 and assay sponge 1240 from directly contacting each other. A barrier 1260 is located between first end 1222 and volume sponge 1230 to ensure that fluid absorbed in transfer sponge 1220 at first end 1222 travels to second end 1224 before being absorbed by volume sponge 1230. Although depicted as being arc-shaped, transfer sponge 1220 can have one or more different configurations, such as, for example, an extended straight line or multiple curves, depending, for example, on the desired volume of sample and/or desired transfer speed. In general, the shorter and/or thinner the path of transfer sponge 1220, the quicker the transfer speed from first end 1222 to second end 1224. The transfer sponge 1220 may be made of a VF2 sponge, an Ahlstrom M13 sponge, MF/F material, or another suitable absorptive material.

Volume sponge 1230 absorbs additional fluid for testing and is in fluid communication with assay sponge 1240 via second end 1224 of transfer sponge 1220. Volume sponge 1230 can be particularly useful when fluorescent or optical testing is used. In some embodiments, assay sponge 1240 and transfer sponge 1224 may not individually contain a sufficient volume of the sample to attain a confident test result. The volume of volume sponge 1230, assay sponge 1240, and second end 1224 of the transfer sponge 1220 sum to a sufficient testing volume for optical, and other, tests. Assay sponge 1240 contains a chemical assay that is used to test the sample or to prepare the sample for a test. Once assay sponge 1240 is saturated, the assay chemicals are free to flow from assay sponge 1240 and interact with sample absorbed by transfer sponge 1220 and volume sponge 1230. Volume sponge 1230 and the assay sponge 1240 may be made of a VF2 sponge, an Ahlstrom M13 sponge, MF/F material, or another suitable absorptive material. Preferably, the wicking sponge, wicking tongue, transfer sponge, and assay sponge are Ahlstrom M13 sponges, and the volume sponge is a VF2 sponge.

Cell filter 1250 can be made from any appropriate material and have any appropriate dimensions. Exemplary materials include polycarbonate (PCTE), polyethersulfone (PES), polyester (PETE) and polytetrafluoroethylene (PTFE). In some embodiments, the dimensions of cell filter 1250 can be about 9.5 millimeters by about 6.5 millimeters by about 0.05 millimeter.

Sampling system 1200 also includes a membrane 1270 located between assay sponge 1240 and a vent 1280 for gases to leave sampling system 1200. Membrane 1270 is configured to allow one or more gases to leave sampling system 1200 via an opening 1280, while maintaining liquid in sampling system 1200.

Figure 85:
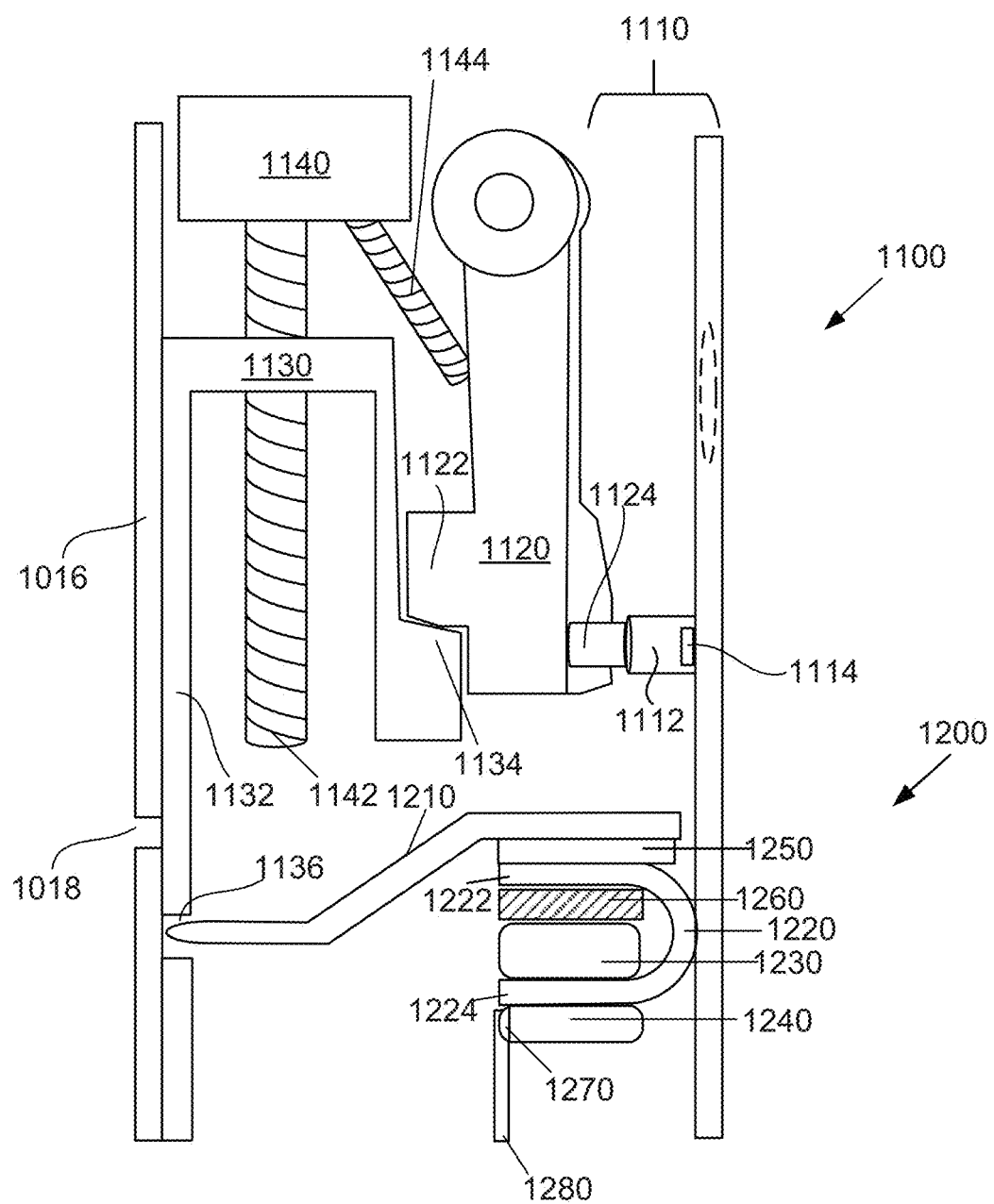
FIG. 85 illustrates an ingestible device including a sampling system and a two-stage valve system in its first stage.

FIG. 85 illustrates an embodiment of ingestible device 1000 with a relatively detailed view of both valve system 1100 and sampling system 1200. FIG. 85 shows valve system 1100 positioned prior to actuation of actuation system 1110 (e.g., when configured as shown in FIGS. 76A, 77A, 78A and 80A).

Figure 86:
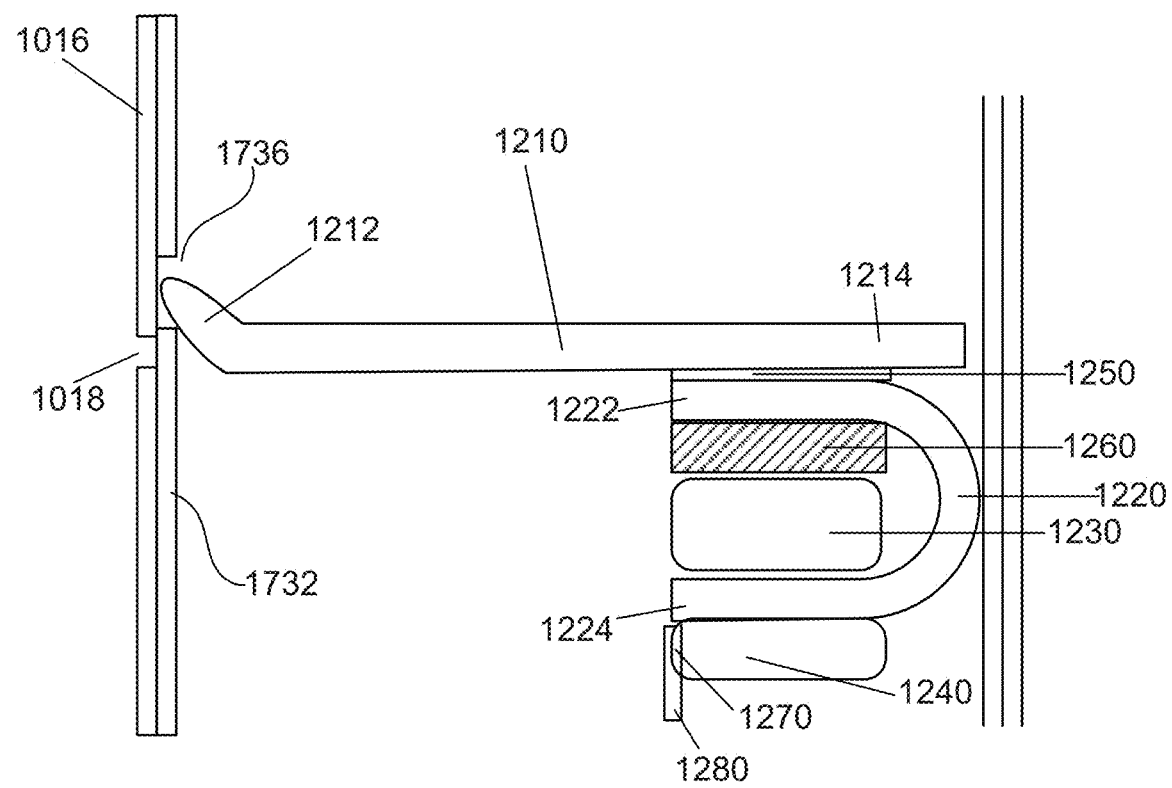
FIG. 86 illustrates an ingestible device including a sampling system and a portion of a three-stage valve system in third stage.

FIG. 86 illustrates an embodiment of an ingestible device including sampling system 1200 and three-stage valve system 1700 positioned in its third stage.

Figure 87:
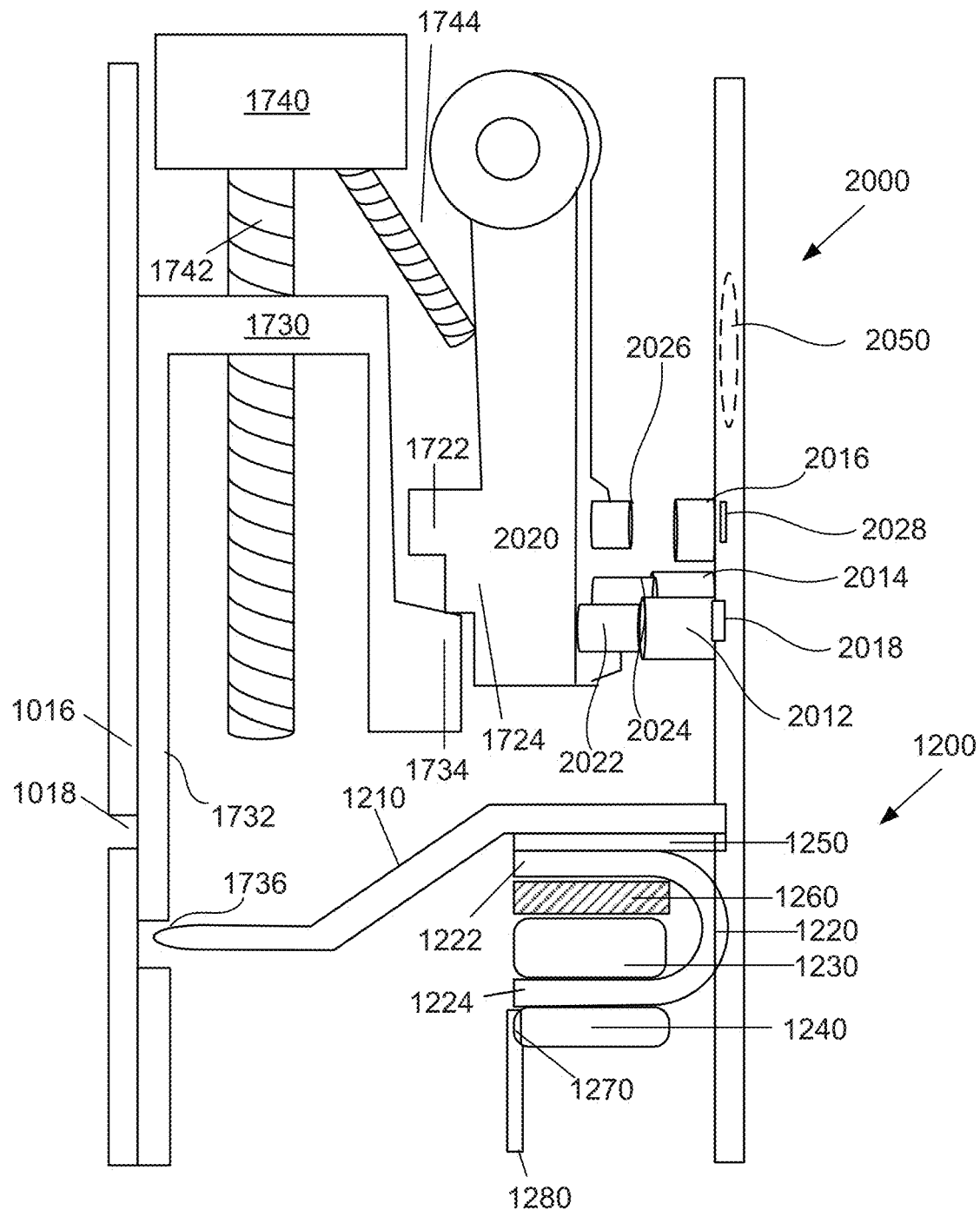
FIG. 87 illustrates an ingestible device including a sampling system and a three-stage valve system in third first stage.

FIG. 87 illustrates an embodiment of an ingestible device 1000 including sampling system 1200 and valve system 2000 positioned in its third stage.

Figure 88:
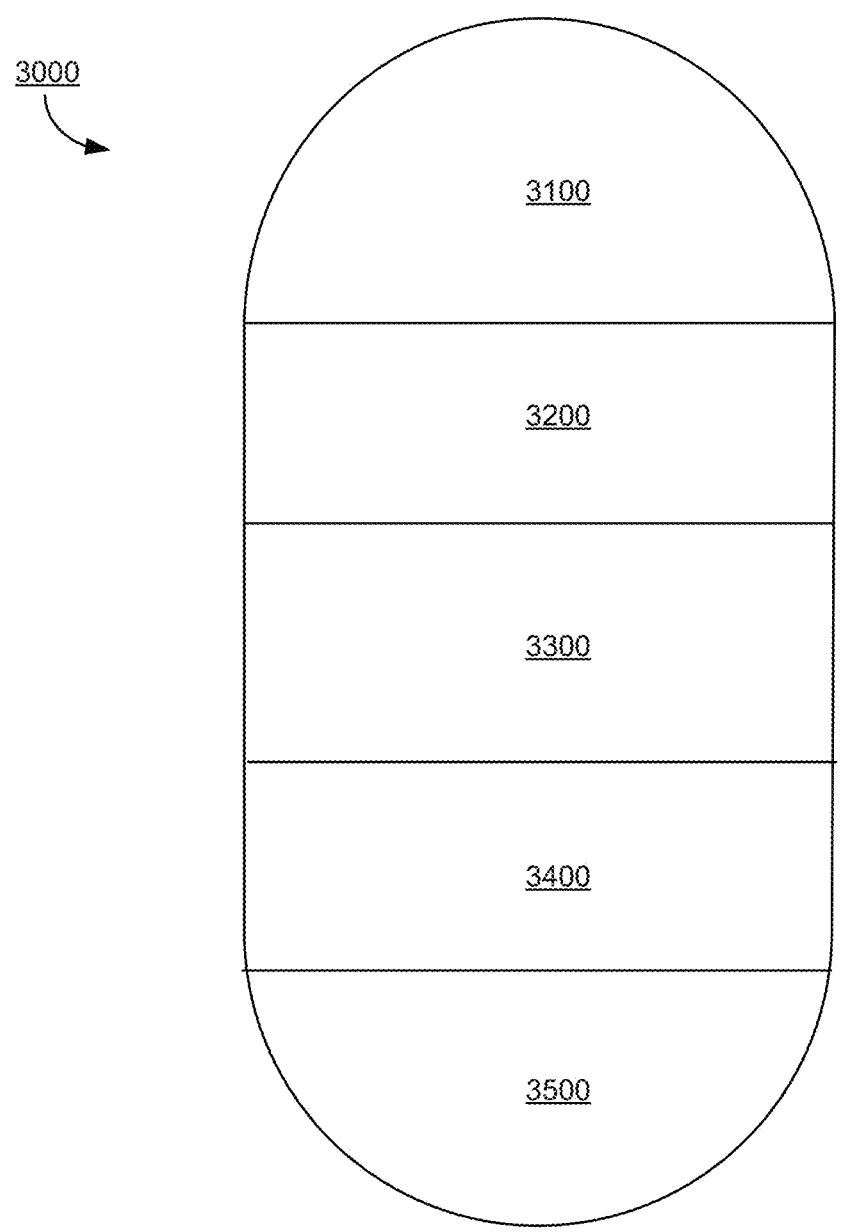
FIG. 88 is a highly schematic illustrate of an ingestible device.

FIG. 88 is a highly schematic illustration of an ingestible device 3000 that contains multiple different systems that cooperate for obtaining a sample and analyzing a sample, e.g., within the GI tract of a subject. Ingestible device 3000 includes a power system 3100 (e.g., one or more batteries), configured to power an electronics system 3200 (e.g., including a control system, optionally in signal communication with an external base station), and an analytic system 3500.

Exemplary analytical systems include assay systems, such as, for example, optical systems containing one or more sources of radiation and/or one or more detectors. Such systems may use, for example, a light source that illuminates and a sample and a detector configured to detect light that is emitted by the sample (e.g., fluorescence spectroscopy), optical density (e.g., the portion of light that passes through the sample), and/or light that is diffracted by sample (e.g., diffraction optics). An analytical system may use, for example, ELISA (enzyme-linked immunosorbent assay). An analytical system may use, for example, LOCI (luminescent oxygen channeling). An analytical technique may involve incubating and/or diluting a sample before or during the analysis/assaying of the sample. An analytical technique may involve the use of staining/dyeing a live cell.

Ingestible device 3000 also includes a sampling system 3400 for taking in a sample from the environment exterior to ingestible device 3000, and a valve system 3300 that regulates the ability of a fluid to access sampling system 3400.

Figure 89:
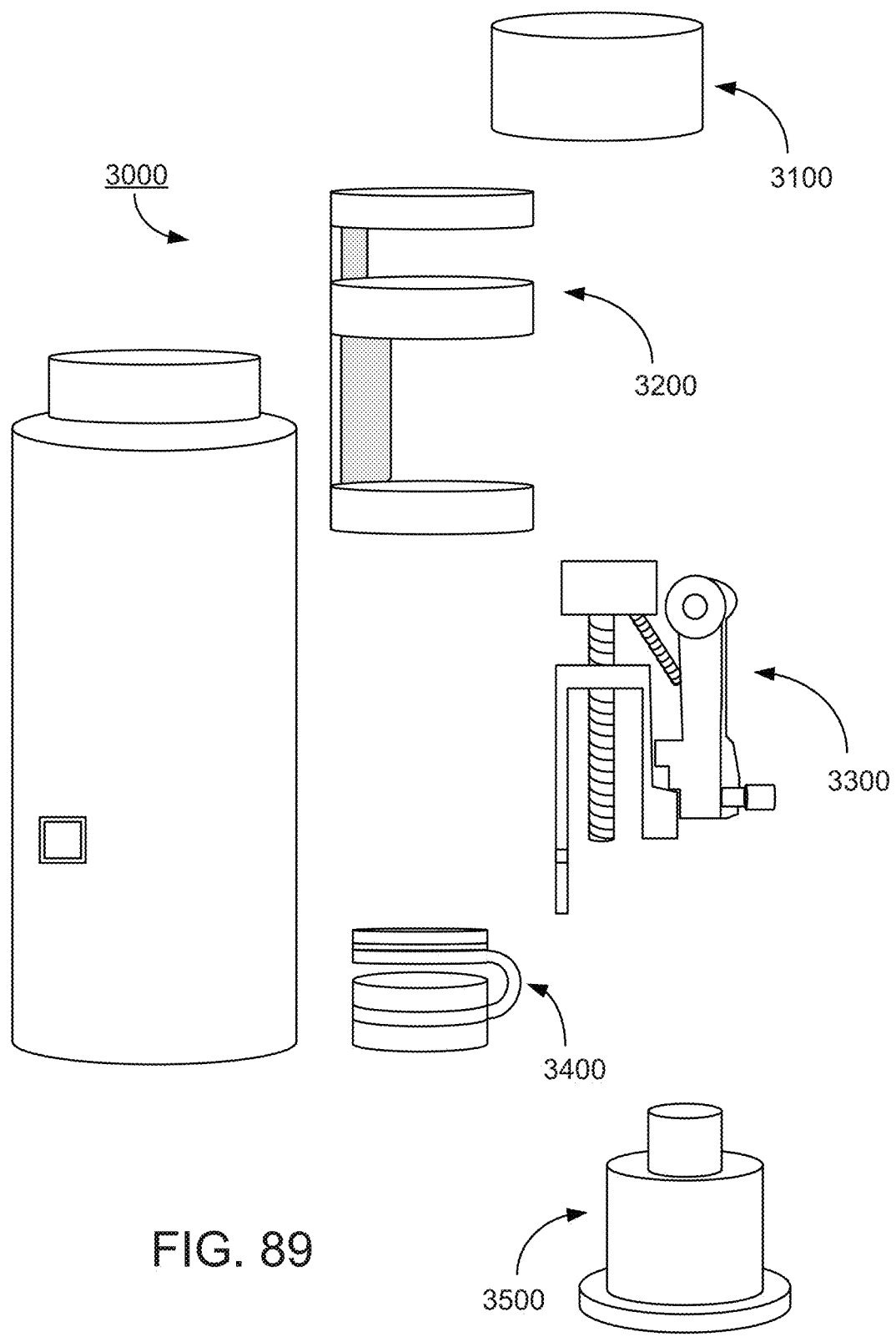
FIG. 89 is an exploded view of an ingestible device.

FIG. 89 provides an exploded view of the ingestible device 3000. FIG. 89 includes an exploded view of ingestible device 3000, showing a general configuration of the systems in FIG. 88. FIG. 89 includes power system 3100 (e.g., a stack of batteries), electronic system 3200 (e.g., a PCB and associated wiring), valve system 3300, sampling system 3400, and analytic system 3500.

Figure 90:
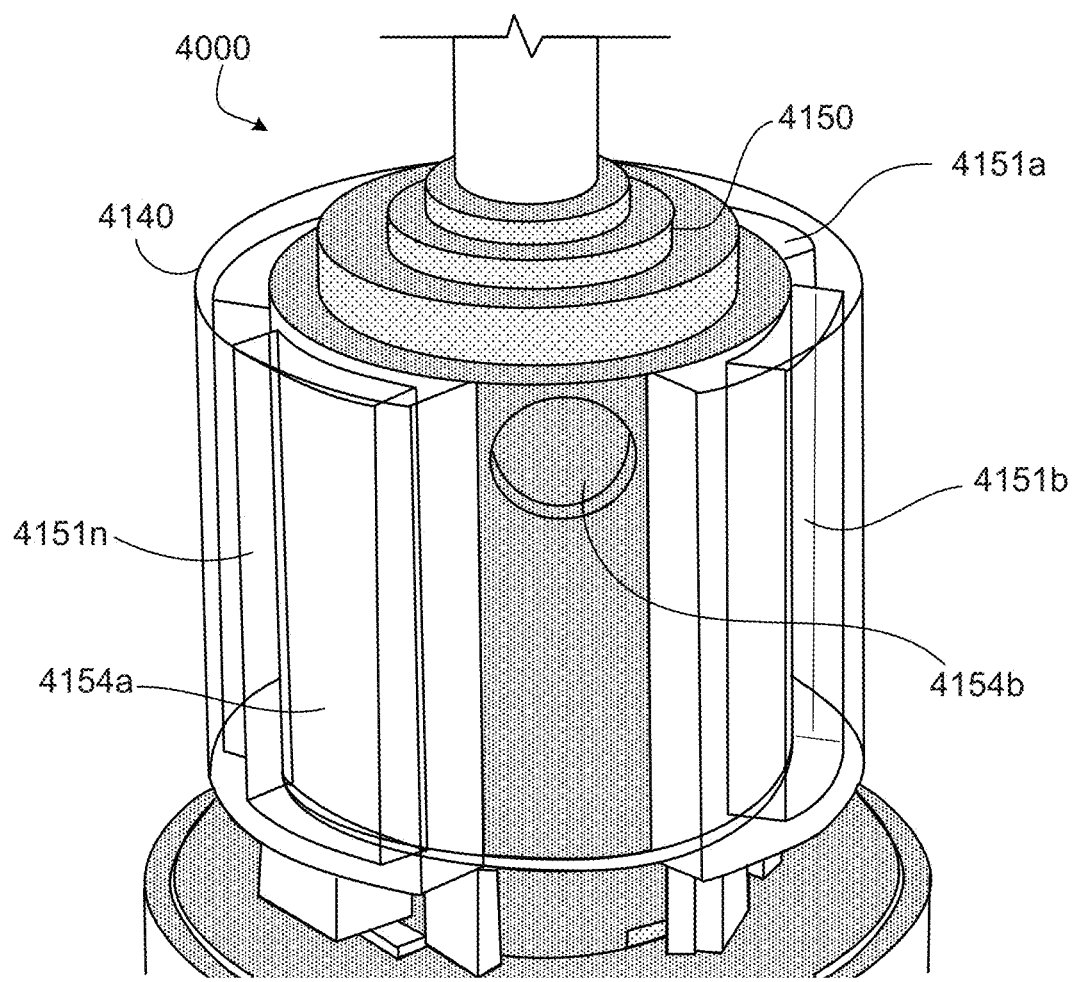
FIG. 90 illustrates a portion of an ingestible device with a port in an open position exposed to the exterior of device.

FIG. 90 illustrates a portion of an ingestible device 4000 with a port 4154b in an open position to the exterior of the ingestible device 4000. The ingestible device 4000 may include a cylinder-shaped rotatable element 4150 that includes sampling ports 4154a-b on the wall of the rotatable element 4150. The sampling chamber 4150 is wrapped by a shell element 4140 with dividers to form a series of dilution chambers 4151a-n between the shell element 4140 and the rotatable element 4150. In operation, when the ingestible device 4000 determines the device itself arrives at a target location within the GI tract, the rotatable element 4150 may be rotated into an open position such that an aperture of the shell element 4140 is aligned with the port 4154b on the wall of the rotatable element 4150 and the port 4154b is exposed to the exterior of the ingestible device 4000 through the aperture. In this way, fluid from the GI tract can enter the port 4154b and occupy the volume defined by the port 154b. In the embodiment shown in FIG. 90, the port 4154b may be a depression on the surface of a rotatable element 4150 and a number of dilution chambers 4151a-n are positioned circumferentially around the axis of rotation of the rotatable element 4150. As previously discussed, each of the dilution chambers 4151*a-n* may store a dilution fluid. In some embodiments, the depression is a cylindrical depression. Optionally, the depression may be a rectangular depression, or any concave depression forming a regular or irregular shape. In another embodiment, the port 4154*b* may be connected to a chamber (not shown) within the rotatable element 4150 to create an enlarged space to store the GI fluid sample from the external environment of the ingestible device.

In some embodiments, the ingestible device 4000 may further include a controller and an actuator. The controller may determine that the ingestible device 4000 is located at a target location of the GI tract, and then the actuator may trigger the rotation of the rotatable element 4150 to align the port 4154*b* at the open position to initiate the sampling. For example, the housing of ingestible device 4000 may have a pH-sensitive enteric coating to detect or otherwise be sensitive to a pH level of the environment external to the ingestible device 4000, based on which the controller may determine whether the ingestible device has arrived at a target location. For another example, the ingestible device 4000 may include an optical sensing unit that transmits an illumination to the environment and collects a reflectance, based on which, the regio-specific location of the ingestible device 4000 may be identified based on optical characteristics of the reflectance.

Figure 91:
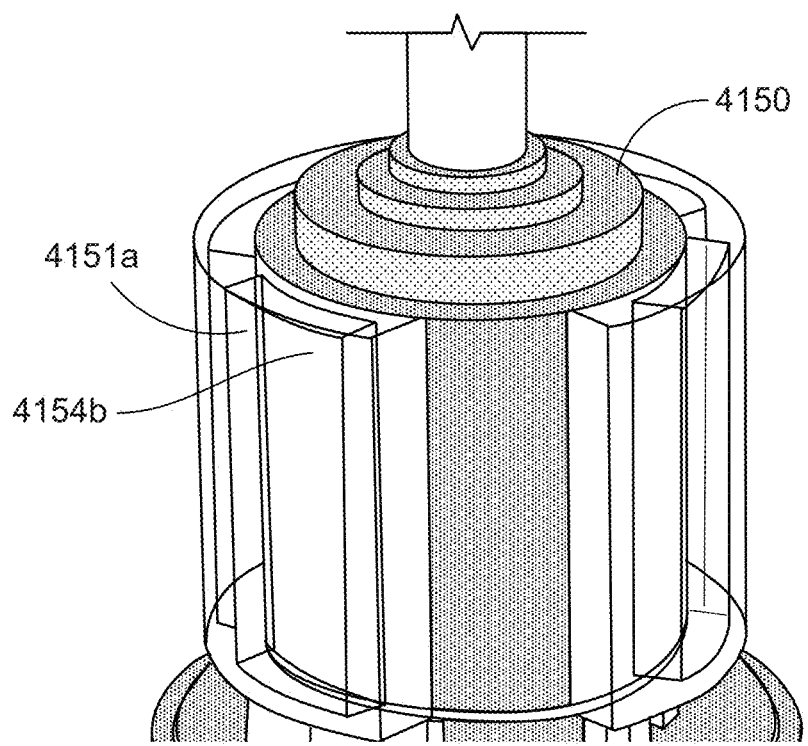
FIG. 91 illustrates a portion of an ingestible device with a port in a first position in fluid communication with a first incubation chamber.

FIG. 91 shows an embodiment of a portion of an ingestible device with a port 4154*b* at a first position aligned with a first dilution chamber 4151*a*. In operation, the rotatable element 4150 may be rotated to align the sampling port 4154*b* and the first dilution chamber 4151*a* such that the fluid sample from the GI tract stored within the volume of the sampling port 4154*b* can be combined with dilution fluid in the first dilution chamber to form a first dilution. The first dilution may then occupy the combined volume of the port 4154*b* and first dilution chamber 4151*a*. Optionally, the rotatable element 4150 may be subsequently rotated to a second position such that the port 4154*b* containing a portion of the first dilution is then moved to be aligned and in fluid communication with another dilution chamber, e.g., a second dilution chamber that is next to the first dilution chamber along the rotational direction. In this way, the first dilution stored within the port 4154*b* may then again be diluted with the dilution fluid stored within the second dilution chamber. Similarly, if the rotatable element 4150 keeps rotating and allows the port 4154*b* to be serially aligned with each dilution chamber, then the original GI fluid sample may be diluted serially and each dilution chambers 4151*a-n* may be left with a diluted GI fluid sample at a different dilution ratio.

Figure 92:
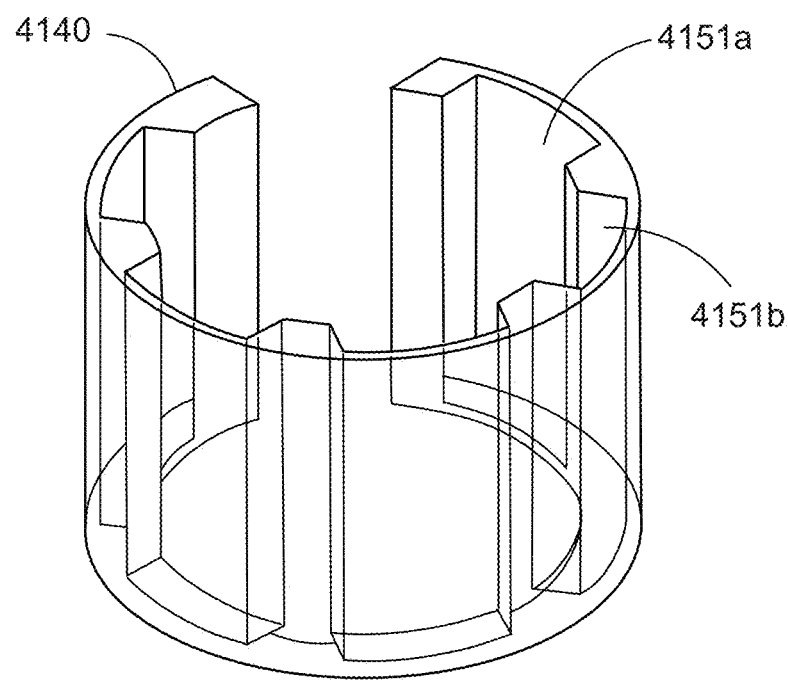
FIG. 92 illustrates a member forming part of a set of five incubation chambers suitable for an ingestible device.
Figure 93:
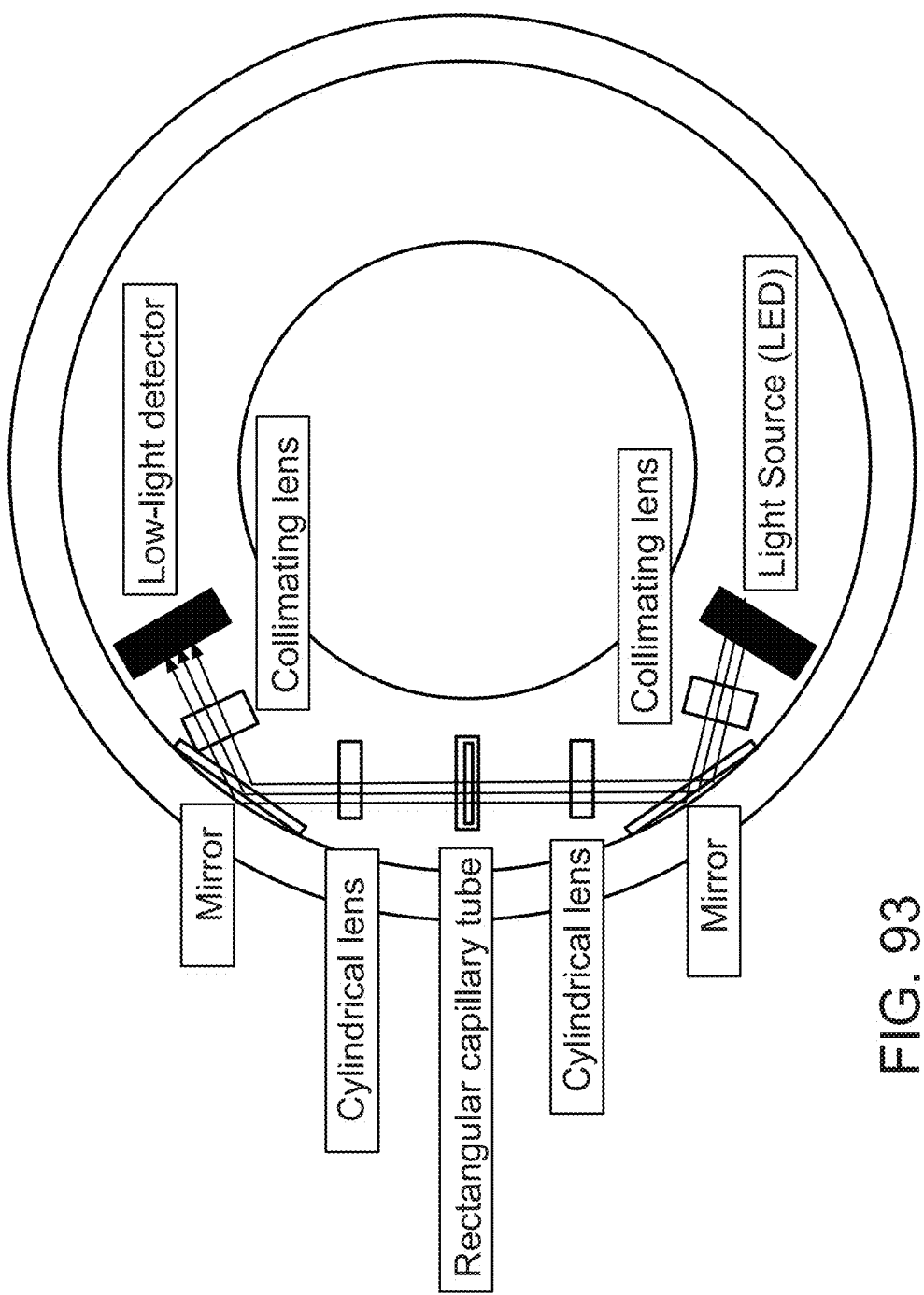
FIG. 93 illustrates a partial cross-sectional view of optics in an ingestible device.

FIG. 92 shows an embodiment of an element 4140 forming part of a set of five dilution chambers (e.g., including 4151*a-b*) for surrounding a rotatable element (e.g., 4150) in an ingestible device as described herein. In some embodiments, the device may contain a single dilution chamber. Alternatively, the device may contain 2, 3, 4, 5, 6, 7, 8 or greater than 8 dilution chambers.

In some embodiments, each dilution chamber 4151*a-n* may be filled with a dilution fluid prior to the ingestible device 4000 being administered. In another embodiment, the dilution fluid may be stored in a separate reservoir (not shown) within the ingestible device 4000. At the time when the ingestible device 4000 is determined to be at a target location within the GI tract, a pumping mechanism may pump the dilution fluid into one or more dilution chambers 4151*a-b* via one or more outlet (not shown) of the reservoir.

In some embodiments, the shell element 4140 may have valves or pumps (not shown) between the dilution chambers 4151*a-n*. For example, the diluted fluid from a first dilution chamber may be pumped into a second dilution chamber via a valve between the two chambers.

Devices of the type depicted in FIGS. 90-92 optionally can include a sampling system as disclosed herein.

In certain embodiments, an ingestible device includes a microscopic evaluation system. In some embodiments, bacterial cells in a sample may be first labeled with fluorescent dyes (such as those described herein), and the fluorescently-labeled cells may be imaged and counted by the microscopic evaluation using an ingestible device as described herein. In other embodiments, the fluorescently-labeled cells are counted as they pass through an onboard flow system (e.g., microfluidic single cell channeling). Examples of flow cytometry systems include hydrodynamic focusing, small diameter capillary tube flow, and rectangular capillary tube flow. As described herein, live bacteria cells are labeled, and the principles of flow cytometry are used to quantify labeled cells. Generally speaking, the photons from an incident laser beam are absorbed by the fluorophore and raised to a higher, unstable energy level. Within less than a nanosecond, the fluorophore re-emits the light at a longer representative wavelength where it is passed through a series of dichroic filters. This reemitted light can be collected and interpreted as proportional to the number of labeled bacteria cells. In some embodiments, a sheath fluid is not used as part of the flow system to help accommodate the volume restrictions of the device. In some embodiments, a rectangular capillary tube is used to achieve a sufficiently large cross-sectional area and relatively thin inspection area. The flow cytometry optical system operates parallel to the fluidics system and serves to observe the redirection of light passing through the cell and delivers information about the bacterial cells. In some embodiments, rather than using a conventional laser and spherical lenses to focus the light to a point, an LED and cylindrical lenses are used to focus the light to a line across a rectangular capillary tube. In other embodiments, collimating lenses are used to make the light source parallel, while cylindrical lenses are used to refine the inspection area. An exemplary optical configuration for this arrangement can be seen in FIG. 93. In some embodiments, optical filters can be added to permit the use of fluorophores. The characteristic wavelength of reemitted light from the fluorophores can be isolated and detected with the use of dichroic, bandpass, and short or long wave pass filters. Generally, multiple dichroic lenses and photomultipliers are used, however, due to space limitations, only a single side-scatter detector and forward scatter detector may be used in certain embodiments.

One of the design challenges of integrating flow cytometry into the device is to provide a pumping mechanism. Without moving fluid, individual bacteria cells cannot be identified and accounted for by flow cytometry within a fixed volume of fluid. In some embodiments, a gear motor is to move fluid through the device. For example, a micromotor comprising a planetary gearhead (e.g., with a 25:1 reduction) can provide the desired amount of torque to create fluid flow. In another embodiment, a series of piezoelectric resistors embedded in the surface of a microfabricated plate is used to create flow. In yet another embodiment, a micropump that includes a pair of one-way valves and uses a magnetic pump membrane actuated by an external magnetic field is used to create flow.

Figure 94:
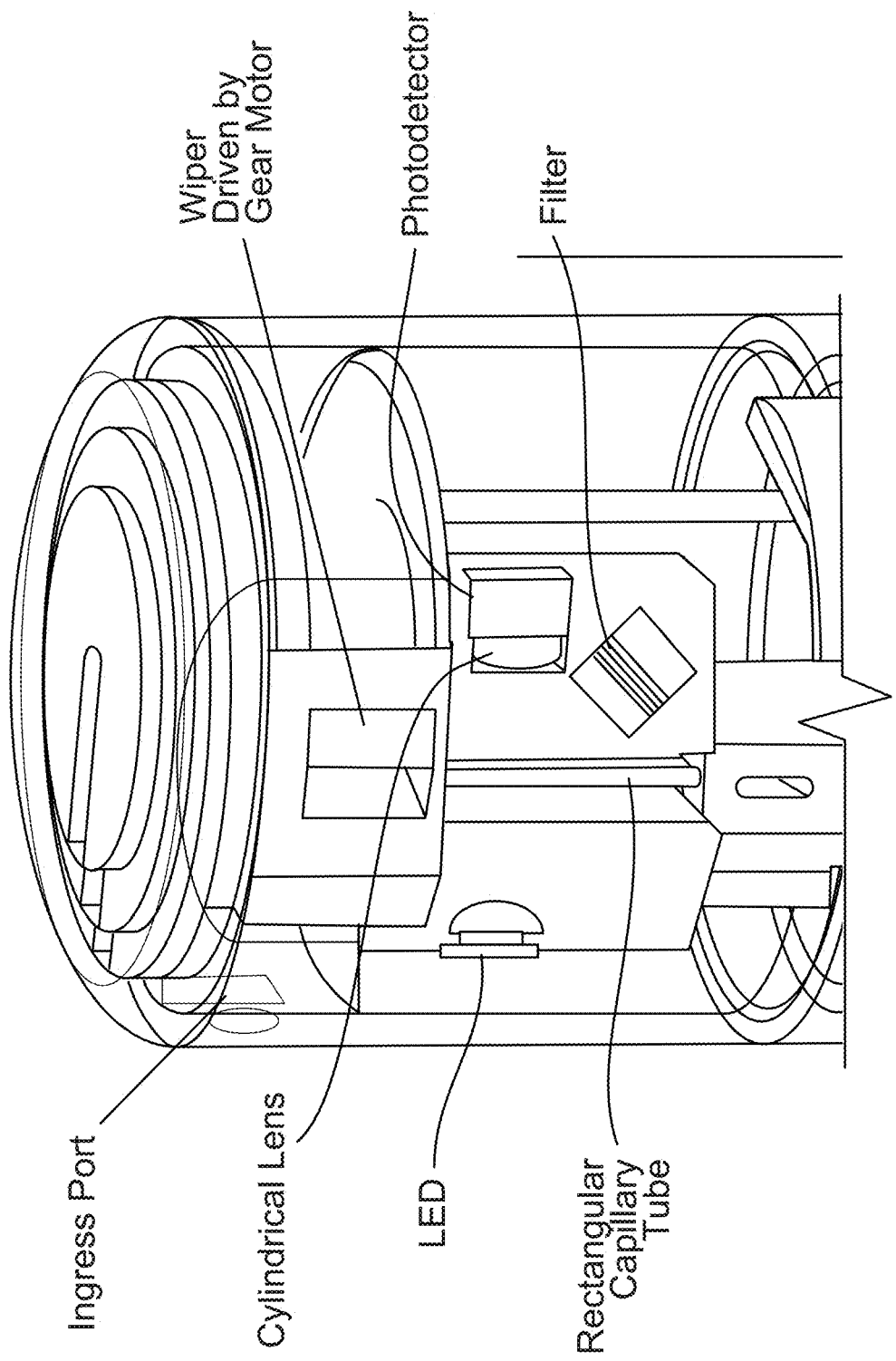
FIG. 94 illustrates components of the optics and flow chamber systems in an ingestible device.
Figure 95:
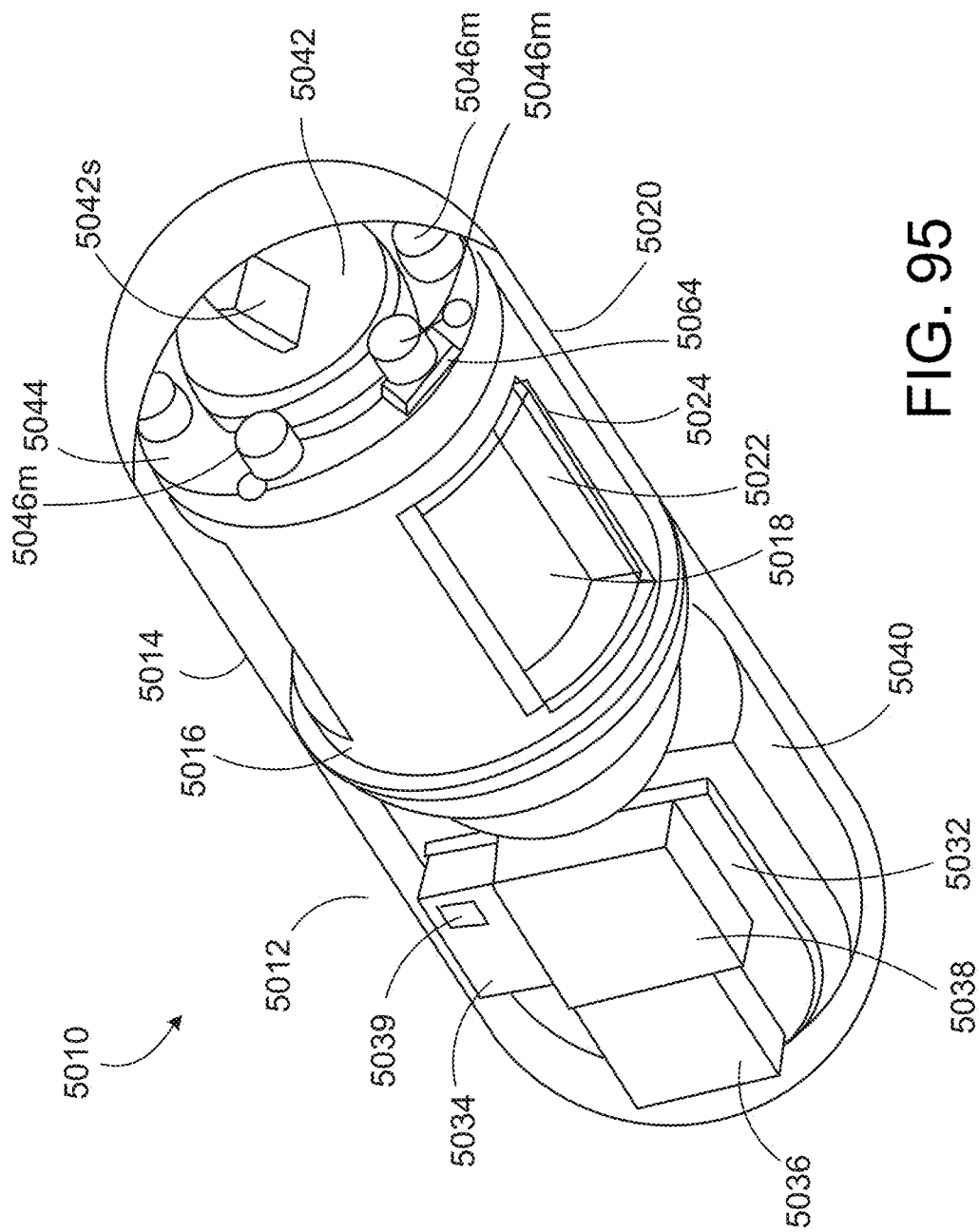
FIG. 95 shows a partial view of an ingestible device

In some embodiments, the system architecture comprises an opening and sealing mechanism combined with a rotary wiper which creates a pressure driven flow via a gear motor. The gear motor can be used for other functions in the device. As shown in FIG. 94, the components of the optics and flow chamber systems fit within the device. In some embodiments, the sample fluid is absorbed via a flexible membrane at the top of the capsule. In some embodiments, the gear motor has 270° of permissible travel which serves to open and fill the fluid chamber. During closure, the motor closes the ingress port while simultaneously pushing the fluid through the rectangular capillary tube where the optical system is located. The threaded component allows the flexible membrane to close and seal the ingress channel without changing the wiper height. In some embodiments, the volume of the sample chamber is 25 µL, 50 µL, 75 µL or more. In some embodiments, two or more samples are taken from the GI tract to procure a sufficient sample size. Referring to FIG. 95, an LED on the left side of the capillary tube and the two low-light detectors on the right for capturing forward and side scatter are shown. Once the fluid passes through the capillary tube, it exits the capsule via a one-way valve. In certain embodiments, the flow system allows for the detection of cell size and internal cell complexity, in addition to cell quantitation.

The foregoing discussion is not exhaustive with respect to various ingestible device designs, either with respect to sampling componentry or absorbent (sponge) design.

As an example, while ingestible devices have been described that include one or more optical systems incorporated into the ingestible device, in some embodiments, an ingestible device does not include an optical system. Optionally, such ingestible devices may also not include any other analytical componentry. In embodiments of an ingestible device which do not include an optical system and/or other analytical componentry, there may be more room inside the ingestible device to store one or more samples.

Exemplary ingestible devices are provided in U.S. Ser. No. 14/460,893, which is incorporated by reference herein.

FIG. 95 shows a partial view of an exemplary embodiment of an ingestible device 5010 in which a portion of the enclosure of ingestible device 5010 has been removed. Ingestible device 5010 may be used for collecting substances. Ingestible device 5010 may generally be in the shape of a capsule, like a conventional pill. Accordingly, the shape of ingestible device 5010 provides for easier ingestion and is also familiar to healthcare practitioners and patients.

The structure of ingestible device 5010 includes first portions and second portions 5012 and 5014. First portion 5012 includes control electronics, a power supply, and a communication system. Second portion 5014 is generally configured to interact with the GI tract, such as, for example but not limited to, sample collection, substance delivery and environmental monitoring. Second portion 5014 includes a storage sub-unit 5016 with one or more chambers 5018 and a chamber enclosure 5020 that encloses or overlays a storage sub-unit 5016. Each chamber 5018 has a corresponding chamber opening 5022. Chamber enclosure 5020 has an access port 5024. In this example embodiment, ingestible device 5010 includes three chambers 5018, but there can be other embodiments that have one, two or more than three chambers 5018.

FIGS. 96A-96C illustrate operation of ingestible device 5010. Generally, chamber enclosure 5020 operates as a "closed-loop" revolver mechanism. Chamber enclosure 5020 rotates, in a controlled manner, to align the access port 5024 with each of chamber openings 5022 for collecting, at targeted locations, samples of the contents in the GI into corresponding chamber 5018, and/or for delivering substances stored in chambers 5018 to targeted locations within the body.

Generally, during collection of samples, the rotation of chamber enclosure 5020 may be described as a "closed-loop" revolver mechanism because each chamber opening 5022 is exposed only once during the passage of ingestible device 5010 within the body in order to avoid cross-contamination of the collected samples. In other words, in some embodiments, chamber enclosure 5020 ideally rotates only once when collecting samples during each usage of ingestible device 5010 so that access port 5024 aligns with each of chamber openings 5022 serially and only once. That is, during collection of samples, access port 2224 does not bypass any chamber opening 5022 and also does not return to a previous chamber opening 5022 during its rotation.

In some embodiments, chamber enclosure 5020 can rotate in a bidirectional motion before completing one revolution and/or perform multiple revolutions during one usage of the ingestible device 5010 so that at least one chamber opening 5022 is exposed multiple times. A chamber opening 5022 may need to be exposed multiple times if its corresponding chamber stores solids or semi-solid reagents, sensors or cleaning agents for cleaning the GI tract.

As illustrated in FIG. 96A, shown therein generally is ingestible device 5010 in an open position 5010a in which access port 5024 on chamber enclosure 5020 is aligned with a chamber opening 5022. In this configuration, ingestible device 5010 may collect substances through chamber opening 5022. In other words, the contents of the GI tract may be forced into exposed chamber 5018 through muscular contractions (e.g., peristalsis).

Thereafter, chamber enclosure 5020 may rotate to seal chamber opening 5022. FIG. 96B shows ingestible device 5010 with a partially open/partially closed position 5010b in which access port 5024 has been rotated such that chamber enclosure 5020 partially seals chamber opening 5022.

FIG. 96C shows ingestible device 5010 in a closed position 5010c, in which the chamber enclosure 5020 has been rotated a distance such that access port 5024 completely seals chamber opening 5022. If chamber enclosure 5020 has not rotated one revolution, chamber enclosure 5020 may continue to rotate in the same direction in order to align access port 5024 with another chamber opening 5022 depending if ingestible device 5010 has been configured to perform another operation (i.e. sampling or distribution).

In another example embodiment, chamber enclosure 5020 may be stationary and storage sub-unit 5016 may instead rotate to align its one or more chamber openings 5022 with access port 5024. Rotating storage sub-unit 5016 instead of chamber enclosure 5020 may provide greater control over the rotation motion and a more constant motion since storage sub-unit 5016 would not be subjected to a varying viscosity arising from the contents in the GI tract. This arrangement, however, may limit a volume of at least one of chambers 5018.

In some embodiments, chamber enclosure 5020 or storage sub-unit 5016 may rotate in a predetermined sequence of bidirectional rotational motions. As described above, when storage sub-unit 5016 is configured to rotate instead of chamber enclosure 5020, the volume of at least one of chambers 5018 can be limited. In order to avoid having to limit the volume of the chambers 5018, non-recess areas that may be used to separate different chambers 5018 in storage sub-unit 5016 may be minimized in volume or removed. Ingestible device 5010 can rotate in a first direction for aligning access port 5024 with one of the two adjacent chambers. Ingestible device 5010 can be configured to rotate in a second direction that is opposite to the first direction in order to avoid cross contamination between samples collected into or substances released from those two adjacent chambers.

Ingestible device 5010 may be used for collecting usable samples from the contents of the GI tract (e.g., 100 μL sized samples) and maintaining each sample in isolation from one another until the samples are extracted.

In some embodiments, ingestible device 5010 may also be configured to conduct in-vivo measurements. Ingestible device 5010 is introduced into the body with some of chambers 5018 being empty and some of chambers 5018 carrying at least one reagents. At a predefined location in the body, ingestible device 5010 is configured to collect a sample from the GI tract and to store the sample into a chamber carrying at least one reagent. After collection, in-vivo analysis may be conducted based on how the collected sample interacts with the reagent inside chamber 5018. For example, ingestible device 5010 may use a biochemistry assay, such as an enzyme-linked immunosorbent assay (ELISA), for performing in-situ experiments on collected samples. Alternatively, peripherals can be included into chambers 5018 for changing the dynamics of several in-vivo analysis and measurements. The peripherals may include a light source, a receiver, a transducer, a heater, and the like. In general, the in-vivo experiments vary according to the type of information that is being sought.

FIG. 97 illustrates an exploded view of the components of ingestible device 5010 in one example embodiment. First portion 5012 of ingestible device 5010 includes an end closure 5030, and electronic components embedded on a main printed circuit board (PCB) 5032 including a communication subsystem having communication peripherals 5034 and a transceiver 5036, a main microcontroller (i.e. processor) 5038, a power supply 5040 and other peripheral components described in further detail below. Second portion 5014 of ingestible device 5010 generally includes a motor 5042, storage sub-unit 5016, a secondary PCB 5044, an encoding magnet arrangement 5046m and the chamber enclosure 5020. Generally, by placing main PCB 5032 and secondary PCB 5044 in distinct regions inside ingestible device 5010, they may be prevented from experiencing the same electrical or physical hazards. Motor 42 is inserted into a motor compartment 5054 that is located in the center of storage sub-unit 5016. PCB 5044 is annular and includes one or more peripheral electronic components (e.g., a capacitor 5062 and a resistor 4060, which can be used as a pull-up resistor), and a sensor 5064. 5039 is a magnetic switch. 5042s is a shaft. 5056 are access holes.

End enclosure 5030 provides a hollow space defined by an inner wall 5048 that is cylindrical with a domed end portion. End enclosure 5030 also includes engagement members 5050 for aligning and releasably engaging with storage sub-unit 5016 to releasably lock end enclosure 5030 in place during operation. In particular, engagement members 5050 releasably engage complementary structures 5052 in storage sub-unit 5016. When end enclosure 5030 locks with storage sub-unit 5016, end enclosure 5030 overlaps with a rear of storage sub-unit 5016 and creates a seal. In some embodiments, the overlap between end enclosure 5030 and storage sub-unit 5016 may span a width of 3 millimeters.

Some or all of the sponges of the above-described sampling systems may contain one or more preservatives (see discussion above). Typically, the assay sponge and/or the volume sponge 1230 and/or the transfer sponge contain one or more preservatives. Typically, the preservative(s) are selected based on the analyte of interest, e.g., an analyte (such as a nucleic acid or protein biomarker) for a GI disorder.

As noted above, an ingestible device as disclosed herein can be used to determine the location of the device with the GI tract of a subject. FIGS. 98-112 illustrate nonlimiting examples of such ingestible devices and related methods. It is to be understood that such ingestible device include componentry as discussed above, such as, for example, one or more spectrometers. In some embodiments, aspects of devices and methods described with regard to FIGS. 1-63 may be implemented with localization technology described with respect to FIGS. 98-112.

In some embodiments, the location of the ingestible device within the GI tract of the subject can be determined to an accuracy of at least 85%, e.g., at least 90%, at least 95%, at least 97%, at least 98%, at least 99%, 100%. In such embodiments, the region of the GI tract of the subject can include, for example, the esophagus, the stomach, duodenum, the jejunum, and/or the terminal ileum, cecum and colon.

In certain embodiments, the location of the ingestible device within the esophagus of the subject can be determined to an accuracy of at least 85%, e.g., at least 90%, at least 95%, at least 97%, at least 98%, at least 99%, 100%.

In some embodiments, the location of the ingestible device within the stomach of the subject can be determined to an accuracy of at least 85%, e.g., at least 90%, at least 95%, at least 97%, at least 98%, at least 99%, 100%.

In certain embodiments, the location of the ingestible device within the duodenum of the subject can be determined to an accuracy of at least 85%, e.g., at least 90%, at least 95%, at least 97%, at least 98%, at least 99%, 100%.

In some embodiments, the location of the ingestible device within the jejunum of the subject can be determined to an accuracy of at least 85%, e.g., at least 90%, at least 95%, at least 97%, at least 98%, at least 99%, 100%.

In certain embodiments, the location of the ingestible device within the terminal ileum, cecum and colon of the subject can be determined to an accuracy of at least 85%, e.g., at least 90%, at least 95%, at least 97%, at least 98%, at least 99%, 100%.

In some embodiments, the location of the ingestible device within the cecum of the subject can be determined to an accuracy of at least 85%, e.g., at least 90%, at least 95%, at least 97%, at least 98%, at least 99%, 100%.

As used herein, the term "reflectance" refers to a value derived from light emitted by the device, reflected back to the device, and received by a detector in or on the device. For example, in some embodiments this refers to light emitted by the device, wherein a portion of the light is reflected by a surface external to the device, and the light is received by a detector located in or on the device.

As used herein, the term "illumination" refers to any electromagnetic emission. In some embodiments, an illumination may be within the range of Infrared Light (IR), the visible spectrum and ultraviolet light (UV), and an illumination may have a majority of its power centered at a particular wavelength in the range of 100 nm to 1000 nm. In some embodiments, it may be advantageous to use an illumination with a majority of its power limited to one of the infrared (750 nm-1000 nm), red (600 nm-750 nm), green (495 nm-600 nm), blue (400 nm-495 nm), or ultraviolet (100 nm-400 nm) spectrums. In some embodiments a plurality of illuminations with different wavelengths may be used. For illustrative purposes, the embodiments described herein may refer to the use of green or blue spectrums of light. However, it is understood that these embodiments may use any suitable light having a wavelength that is substantially or approximately within the green or blue spectra defined above, and the localization systems and methods described herein may use any suitable spectra of light.

Figure 98:
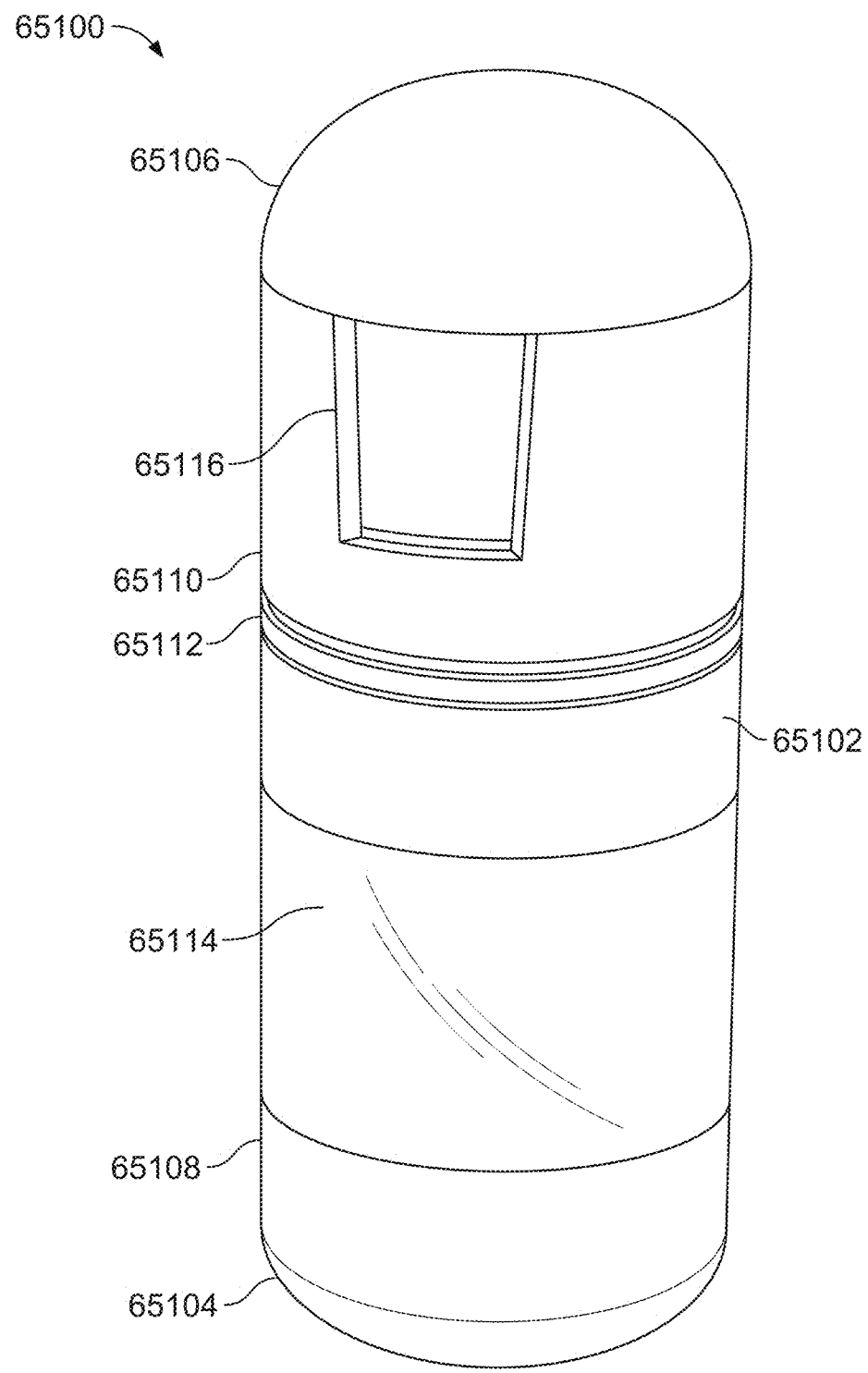
FIG. 98 is a view of an example embodiment of an ingestible device, in accordance with some embodiments of the disclosure.

Referring now to FIG. 98, shown therein is a view of an example embodiment of an ingestible device 65100, which may be used to identify a location within a gastrointestinal (GI) tract. It is to be understood that certain details regarding the design of ingestible device 65100 are not shown in FIG. 98 and the following figures, and that, in general, various aspect of ingestible devices described elsewhere herein can be implemented in ingestible device 65100 and the ingestible devices shown in the following figures.

In some embodiments, ingestible device 65100 may be configured to autonomously determine whether it is located in the stomach, a particular portion of the small intestine such as a duodenum, jejunum, or ileum, or the large intestine by utilizing sensors operating with different wavelengths of light. Additionally, ingestible device 65100 may be configured to autonomously determine whether it is located within certain portions of the small intestine or large intestine, such as the duodenum, the jejunum, the cecum, or the colon.

Ingestible device 65100 may have a housing 65102 shaped similar to a pill or capsule. The housing 65102 of ingestible device 65100 may have a first end portion 65104, and a second end portion 65106. The first end portion 65104 may include a first wall portion 65108, and second end portion 65106 may include a second wall portion 65110. In some embodiments, first end portion 65104 and second end portion 65106 of ingestible device 65100 may be manufactured separately, and may be affixed together by a connecting portion 65112.

In some embodiments, ingestible device 65100 may include an optically transparent window 65114. Optically transparent window 65114 may be transparent to various types of illumination in the visible spectrum, infrared spectrum, or ultraviolet light spectrum, and ingestible device 65100 may have various sensors and illuminators located within the housing 65102, and behind the transparent window 65114. This may allow ingestible device 65100 to be configured to transmit illumination at different wavelengths through transparent window 65114 to an environment external to housing 65102 of ingestible device 65100, and to detect a reflectance from a portion of the illumination that is reflected back through transparent window 65114 from the environment external to housing 65102. Ingestible device 65100 may then use the detected level of reflectance in order to determine a location of ingestible device 65100 within a GI tract. In some embodiments, optically transparent window 65114 may be of any shape and size, and may wrap around the circumference of ingestible device 65100. In this case, ingestible device 65100 may have multiple sets of sensors and illuminators positioned at different locations azimuthally behind window 65114.

In some embodiments, ingestible device 65100 may optionally include an opening 65116 in the second wall portion 65110. In some embodiments, the second wall portion 65110 may be configured to rotate around the longitudinal axis of ingestible device 65100 (e.g., via a suitable motor or other actuator housed within ingestible device 65100). This may allow ingestible device 65100 to obtain a fluid sample from the GI tract, or release a substance into the GI tract, through opening 65116.

Figure 99:
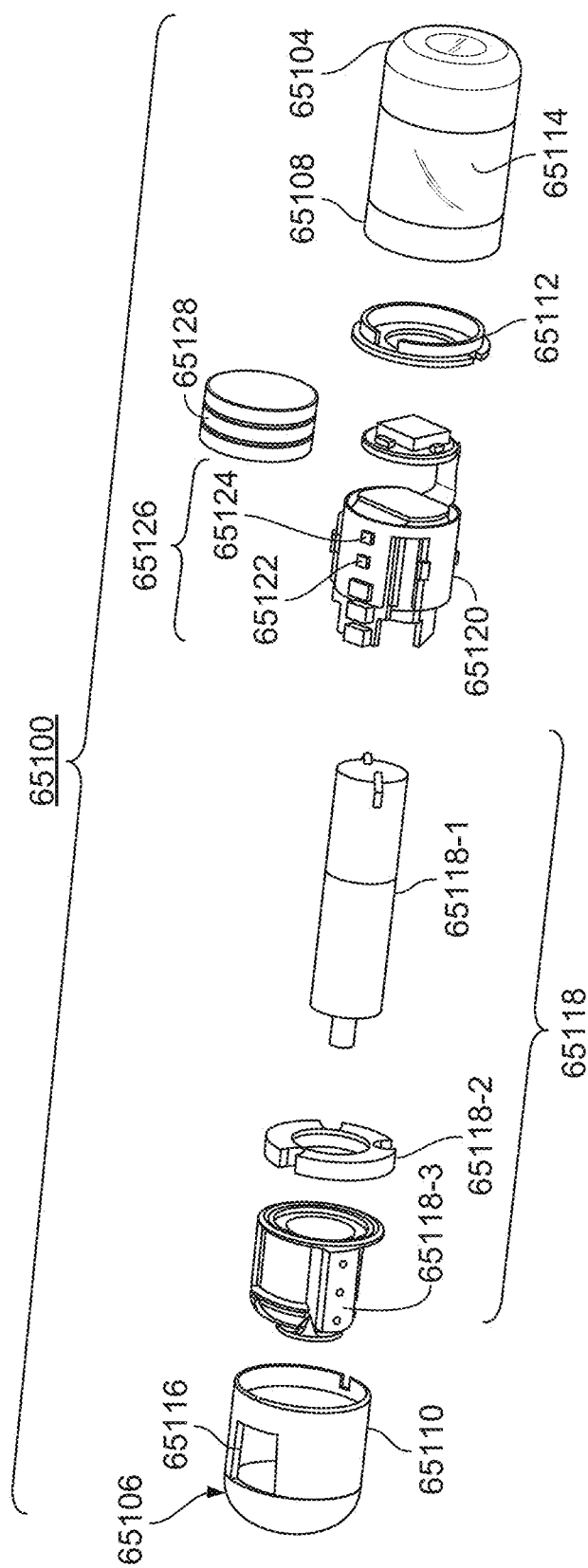
FIG. 99 is an exploded view of the ingestible device of FIG. 87, in accordance with some embodiments of the disclosure.

FIG. 99 shows an exploded view of ingestible device 65100. In some embodiments, ingestible device 65100 may optionally include a rotation assembly 65 118. Optional rotation assembly 65118 may include a motor 65118-1 driven by a microcontroller (e.g., a microcontroller coupled to printed circuit board 65120), a rotation position sensing ring 65118-2, and a storage sub-unit 65118-3 configured to fit snugly within the second end portion 65104. In some embodiments, rotation assembly 65118 may cause second end portion 65104, and opening 65116, to rotate relative to the storage sub-unit 65118-3. In some embodiments, there may be cavities on the side of storage sub-unit 65118-3 that function as storage chambers. When the opening 65116 is aligned with a cavity on the side of the storage sub-unit 65118-3, the cavity on the side of the storage sub-unit 65118-3 may be exposed to the environment external to the housing 65102 of ingestible device 65100. In some embodiments, the storage sub-unit 65118-3 may be loaded with a medicament or other substance prior to the ingestible device 65100 being administered to a subject. In this case, the medicament or other substance may be released from the ingestible device 65100 by aligning opening 65116 with the cavity within storage sub-unit 65118-3. In some embodiments, the storage sub-unit 65118-3 may be configured to hold a fluid sample obtained from the GI tract. For example, ingestible device 65100 may be configured to align opening 65116 with the cavity within storage sub-unit 65118-3, thus allowing a fluid sample from the GI tract to enter the cavity within storage sub-unit 65118-3. Afterwards, ingestible device 65100 may be configured to seal the fluid sample within storage sub-unit 65118-3 by further rotating the second end portion 65106 relative to storage sub-unit 65118-3. In some embodiments, storage sub-unit 118-3 may also contain a hydrophilic sponge, which may enable ingestible device 65100 to better draw certain types of fluid samples into ingestible device 65100. In some embodiments, ingestible device 65100 may be configured to either obtain a sample from within the GI tract, or to release a substance into the GI tract, in response to determining that ingestible device 65100 has reached a predetermined location within the GI tract. For example, ingestible device 65100 may be configured to obtain a fluid sample from the GI tract in response to determining that the ingestible device has entered the jejunum portion of the small intestine (e.g., as determined by process 65900). Other ingestible devices capable of obtaining samples or releasing substances are discussed in commonly-assigned PCT Application No. PCT/CA2013/000133 filed Feb. 15, 2013, commonly-assigned U.S. Provisional Application No. 62/385,553, and commonly-assigned U.S. Provisional Application No. 62/376,688, which each are hereby incorporated by reference herein in their entirety. It is understood that any suitable method of obtaining samples or releasing substances may be incorporated into some of the embodiments of the ingestible devices disclosed herein, and that the systems and methods for determining a location of an ingestible device may be incorporated into any suitable type of ingestible device.

Ingestible device 65100 may include a printed circuit board (PCB) 65120, and a battery 65128 configured to power PCB 65120. PCB 65120 may include a programmable microcontroller, and control and memory circuitry for holding and executing firmware or software for coordinating the operation of ingestible device 65100, and the various components of ingestible device 65100. For example, PCB 65120 may include memory circuitry for storing data, such as data sets of measurements collected by sensing sub-unit 65126, or instructions to be executed by control circuitry to implement a localization process, such as, for example, one or more of the processes, discussed herein, including those discussed below in connection with one or more of the associated flow charts. PCB 65120 may include a detector 65122 and an illuminator 65124, which together form sensing sub-unit 65126. In some embodiments, control circuitry within PCB 65120 may include processing units, communication circuitry, or any other suitable type of circuitry for operating ingestible device 65100. For illustrative purposes, only a single detector 65122 and a single illuminator 65124 forming a single sensing sub-unit 65126 are shown. However, it is understood that in some embodiments there may be multiple sensing sub-units, each with a separate illuminator and detector, within ingestible device 65100. For example, there may be several sensing sub-units spaced azimuthally around the circumference of the PCB 65120, which may enable ingestible device 65100 to transmit illumination and detect reflectances or ambient light in all directions around the circumference of the device. In some embodiments, sensing sub-unit 65126 may be configured to generate an illumination using illuminator 65124, which is directed through the window 65114 in a radial direction away from ingestible device 65100. This illumination may reflect off of the environment external to ingestible device 65100, and the reflected light coming back into ingestible device 65100 through window 65114 may be detected as a reflectance by detector 65122.

In some embodiments, window 65114 may be of any suitable shape and size. For example, window 65114 may extend around a full circumference of ingestible device 65100. In some embodiments there may be a plurality of sensing sub-units (e.g., similar to sensing sub-unit 65126) located at different positions behind the window. For example, three sensing sub-units may be positioned behind the window at the same longitudinal location, but spaced 120 degrees apart azimuthally. This may enable ingestible device 65100 to transmit illuminations in all directions radially around ingestible device 65100, and to measure each of the corresponding reflectances.

In some embodiments, illuminator 65124 may be capable of producing illumination at a variety of different wavelengths in the ultraviolet, infrared, or visible spectrum. For example, illuminator 65124 may be implemented by using Red-Green-Blue Light-Emitting diode packages (RGB-LED). These types of RGB-LED packages are able to transmit red, blue, or green illumination, or combinations of red, blue, or green illumination. Similarly, detector 65122 may be configured to sense reflected light of the same wavelengths as the illumination produced by illuminator 65124. For example, if illuminator 65124 is configured to produce red, blue, or green illumination, detector 65122 may be configured to detect different reflectances produced by red, blue, or green illumination (e.g., through the use of an appropriately configured photodiode). These detected reflectances may be stored by ingestible device 65100 (e.g., within memory circuitry of PCB 65120), and may then be used by ingestible device 65100 in determining a location of ingestible device 65100 within the GI tract (e.g., through the use of process 65500, process 65600, or process 65900).

It is understood that ingestible device 65100 is intended to be illustrative, and not limiting. It will be understood that modifications to the general shape and structure of the various devices and mechanisms described in relation to FIGS. 98 and 99 may be made without significantly changing the functions and operations of the devices and mechanisms. For example, ingestible device 65100 may have a housing formed from a single piece of molded plastic, rather than being divided into a first end portion 65104 and a second end portion 65106. As an alternate example, the location of window 65114 within ingestible device 65100 may be moved to some other location, such as the center of ingestible device 65100, or to one of the ends of ingestible device 65100. Moreover, the systems and methods discussed in relation to FIGS. 98-112 may be implemented on any suitable type of ingestible device, provided that the ingestible device is capable of detecting reflectances or levels of illumination in some capacity. For example, in some embodiments ingestible device 65100 may be modified to replace detector 65122 with an image sensor, and the ingestible device may be configured to measure relative levels of red, blue, or green light by decomposing a recorded image into its individual spectral components. Other examples of ingestible devices with localization capabilities, which may be utilized in order to implement the devices, systems and methods discussed in relation to FIGS. 98-112, are discussed in co-owned U.S. patent application Ser. No. 14/460,893, which is incorporated by reference herein in its entirety. Furthermore, it should be noted that the features and limitations described in any one embodiment may be applied to any other embodiment herein, and the descriptions and examples relating to one embodiment may be combined with any other embodiment in a suitable manner.

Figure 100:
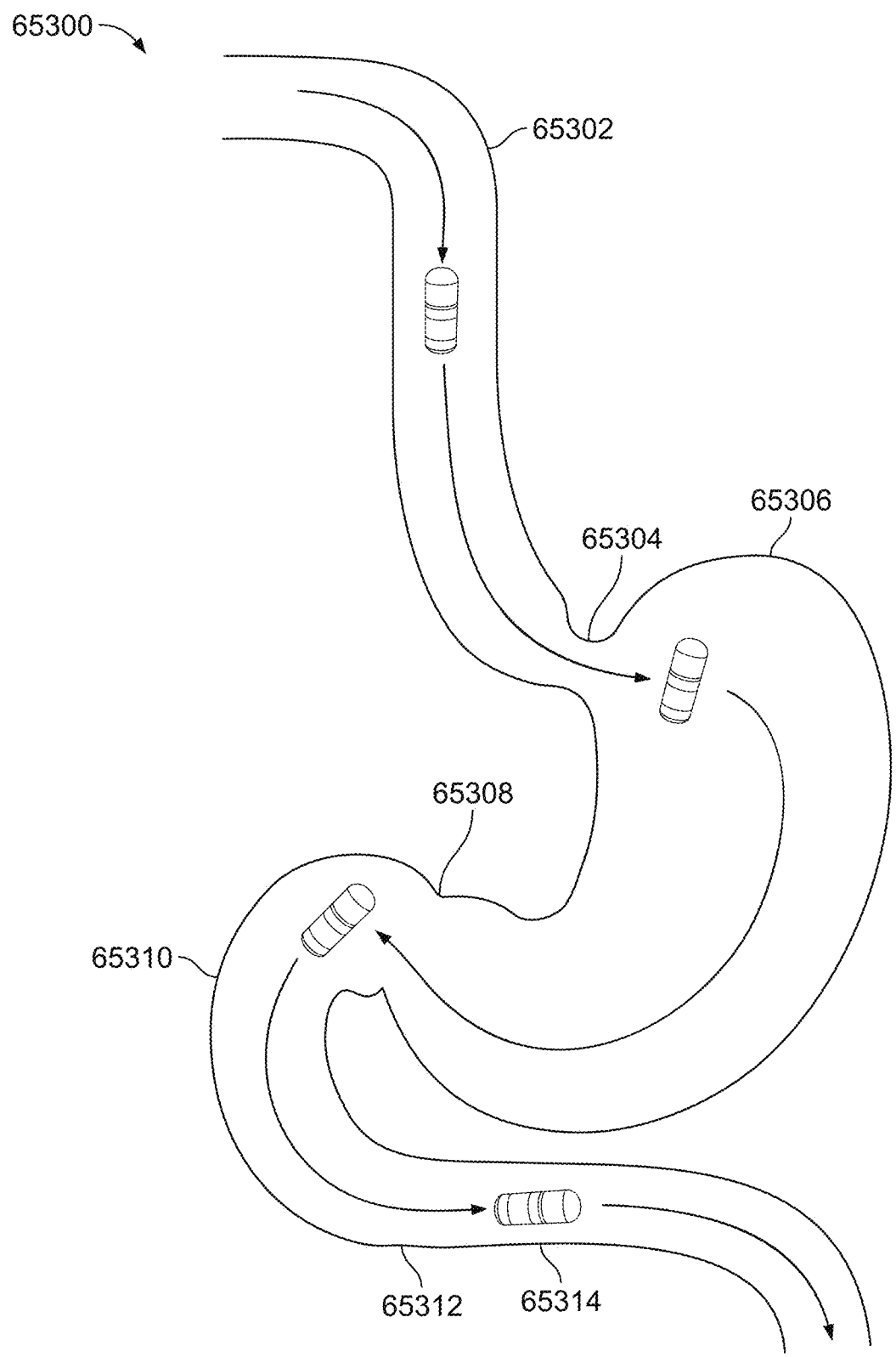
FIG. 100 is a diagram of an ingestible device during an example transit through a GI tract, in accordance with some embodiments of the disclosure.

FIG. 100 is a diagram of an ingestible device during an example transit through a gastrointestinal (GI) tract, in accordance with some embodiments of the disclosure. Ingestible device 65300 may include any portion of any other ingestible device discussed in this disclosure (e.g., ingestible device 65100), and may be any suitable type of ingestible device with localization capabilities. For example, ingestible device 65300 may be an embodiment of ingestible device 65100 without the optional opening 65116 or optional rotation assembly 65118). In some embodiments, ingestible device 65300 may be ingested by a subject, and as ingestible device 65300 traverses the GI tract, ingestible device 65300 may be configured to determine its location within the GI tract. For example, the movement of ingestible device 65300 and the amount of light detected by ingestible device 65300 (e.g., via detector 65112) may vary substantially depending on the location of ingestible device 65300 within the GI tract, and ingestible device 65300 may be configured to use this information to determine a location of ingestible device 65300 within the GI tract. For instance, ingestible device 65300 may detect ambient light from the surrounding environment, or reflectances based on illumination generated by ingestible device 65300 (e.g., generated by illuminator 65124), and use this information to determine a location of ingestible device 65300 through processes, such as described herein. The current location of ingestible device 65300, and the time that ingestible device 65300 detected each transition between the various portions of the GI tract, may then be stored by ingestible device 65300 (e.g., in memory circuitry of PCB 65120), and may be used for any suitable purpose.

Shortly after ingestible device 65300 is ingested, ingestible device will traverse the esophagus 65302, which may connect the subject's mouth to a stomach 65306. In some embodiments, ingestible device 65300 may be configured to determine that it has entered the esophagus portion GI tract by measuring the amount and type of light (e.g., via detector 65122) in the environment surrounding the ingestible device 65300. For instance, ingestible device 65300 may detect higher levels of light in the visible spectrum (e.g., via detector 65122) while outside the subject's body, as compared to the levels of light detected while within the GI tract.

In some embodiments, ingestible device 65300 may have previously stored data (e.g., on memory circuitry of PCB 65120) indicating a typical level of light detected when outside of the body, and the ingestible device 65300 may be configured to determine that entry to the body has occurred when a detected level of light (e.g., detected via detector 6512) has been reduced beyond a threshold level (e.g., at least a 20-30% reduction) for a sufficient period of time (e.g., 5.0 seconds).

In some embodiments, ingestible device 65300 may be configured to detect a transition from esophagus 65302 to stomach 65306 by passing through sphincter 65304. In some embodiments, ingestible device 65300 may be configured to determine whether it has entered stomach 65306 based at least in part on a plurality of parameters, such as but not limited to the use of light or temperature measurements (e.g., via detector 65122 or via a thermometer within ingestible device 65300), pH measurements (e.g., via a pH meter within ingestible device 65300), time measurements (e.g., as detected through the use of clock circuitry included within PCB 65120), or any other suitable information. For instance, ingestible device 65300 may be configured to determine that ingestible device 65300 has entered stomach 65306 after detecting that a measured temperature of ingestible device 65300 exceeds 31 degrees Celsius. Additionally, or alternately, ingestible device 65300 may be configured to automatically determine it has entered stomach 65306 after one minute (or another pre-set time duration parameter, 80 seconds, 90 seconds, etc.) has elapsed from the time that ingestible device 65300 was ingested, or one minute (or another pre-set time duration parameter, 80 seconds, 90 seconds, etc.) from the time that ingestible device 65300 detected that it has entered the GI tract.

Stomach 65306 is a relatively large, open, and cavernous organ, and therefore ingestible device 65300 may have a relatively large range of motion. By comparison, the motion of ingestible device 65300 is relatively restricted within the tube-like structure of the duodenum 65310, the jejunum 65314, and the ileum (not shown), all of which collectively form the small intestine. Additionally, the interior of stomach 65306 has distinct optical properties from duodenum 65310 and jejunum 65314, which may enable ingestible device 65300 to detect a transition from stomach 65306 to duodenum 65310 through the appropriate use of measured reflectances (e.g., through the use of reflectances measured by detector 65122), as used in conjunction with process 65600).

In some embodiments, ingestible device 65300 may be configured to detect a pyloric transition from stomach 65306 to duodenum 65310 through the pylorus 65308. For instance, in some embodiments, ingestible device 65300 may be configured to periodically generate illumination in the green and blue wavelengths (e.g., via illuminator 65124), and measure the resulting reflectances (e.g., via detector 65122). Ingestible device 65300 may be configured to then use a ratio of the detected green reflectance to the detected blue reflectance to determine whether ingestible device 65300 is located within the stomach 65306, or duodenum 65310 (e.g., via process 65600). In turn, this may enable ingestible device 65300 to detect a pyloric transition from stomach 65306 to duodenum 65310, examples of which is discussed below.

Similarly, in some embodiments, ingestible device 65300 may be configured to detect a reverse pyloric transition from duodenum 65310 to stomach 65306. Ingestible device 65300 will typically transition naturally from stomach 65306 to duodenum 65310, and onward to jejunum 65314 and the remainder of the GI tract. However, similar to other ingested substances, ingestible device 65300 may occasionally transition from duodenum 65310 back to stomach 65306 as a result of motion of the subject, or due to the natural behavior of the organs with the GI tract. To accommodate this possibility, ingestible device 65300 may be configured to continue to periodically generate illumination in the green and blue wavelengths (e.g., via illuminator 65124), and measure the resulting reflectances (e.g., via detector 65122) to detect whether or not ingestible device 65300 has returned to stomach 65306. Exemplary detection processes are described in additional detail below.

After entering duodenum 65310, ingestible device 65300 may be configured to detect a transition to the jejunum 65314 through the duodenojejunal flexure 65312. For example, ingestible device 65300 may be configured to use reflectances to detect peristaltic waves within the jejunum 65314, caused by the contraction of the smooth muscle tissue lining the walls of the jejunum 65314. In particular, ingestible device 65300 may be configured to begin periodically transmitting illumination (and measuring the resulting reflectances (e.g., via detector 65122 and illuminator 65124 of sensing sub-unit 65126) at a sufficiently high frequency in order to detect muscle contractions within the jejunum 65314. Ingestible device 65300 may then determine that it has entered the jejunum 65314 in response to having detected either a first muscle contraction, or a predetermined number of muscle contractions (e.g., after having detected three muscle contractions in sequence). The interaction of ingestible device 65300 with the walls of jejunum 65314 is also discussed in relation to FIG. 101, and exemplary detection processes are described in additional detail below.

Figure 101:
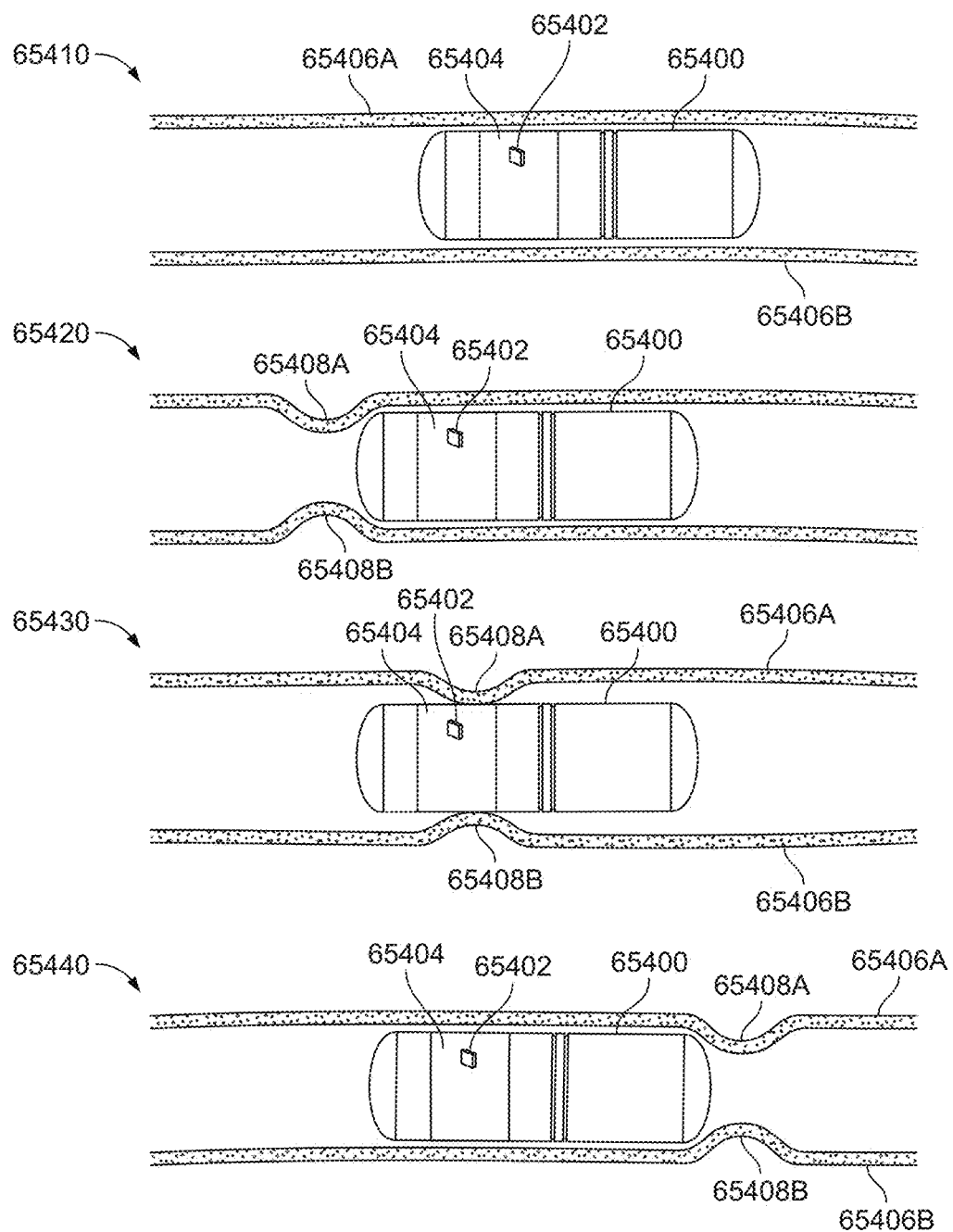
FIG. 101 is a diagram of an ingestible device during an example transit through a jejunum, in accordance with some embodiments of the disclosure.

FIG. 101 is a diagram of an ingestible device during an example transit through a jejunum, in accordance with some embodiments of the disclosure. Diagrams 65410, 65420, 65430, and 65440 depict ingestible device 65400 as it traverses through a jejunum (e.g., jejunum 65314), and how ingestible device 65400 interacts with peristaltic waves formed by walls 65406A and 65406B (collectively, walls 65406) of the jejunum. In some implementations, ingestible device 65400 may include any portion of any other ingestible device discussed in this disclosure (e.g., ingestible device 65100 or ingestible device 65300), and may be any suitable type of ingestible device with localization capabilities. For example, ingestible device 65400 may be substantially similar to the ingestible device 65300 or ingestible device 65100, with window 65404 being the same as window 65114, and sensing sub-unit 65402 being the same as sensing sub-unit 65126.

Diagram 65410 depicts ingestible device 65400 within the jejunum, when the walls 65406 of the jejunum are relaxed. In some embodiments, the confined tube-like structure of the jejunum naturally causes ingestible device 65400 to be oriented longitudinally along the length of the jejunum, with window 65404 facing walls 65406. In this orientation, ingestible device 65400 may use sensing sub-unit 65402 to generate illumination (e.g., via illuminator 65124) oriented towards walls 65406, and to detect the resulting reflectances (e.g., via detector 65122) from the portion of the illumination reflected off of walls 65406 and back through window 65404. In some embodiments, ingestible device 65400 may be configured to use sensing sub-unit 65402 to generate illumination and measure the resulting reflectance with sufficient frequency to detect peristaltic waves within the jejunum. For instance, in a healthy human subject, peristaltic waves may occur at a rate of approximately 0.05 Hz to 0.33 Hz. Therefore, the ingestible device 65400 may be configured to generate illumination and measure the resulting reflectance at least once every 2.5 seconds (i.e., potentially minimum rate to detect a 0.2 Hz signal), and preferably at a higher rate, such as once every 0.5 seconds, which may improve the overall reliability of the detection process due to more data points being available. It is understood that the ingestible device 65400 need not gather measurements at precise intervals, and in some embodiments the ingestible device 65400 may be adapted to analyze data gathered at more irregular intervals, provided that there are still a sufficient number of appropriately spaced data points to detect 0.05 Hz to 0.33 Hz signals.

Diagram 65420 depicts ingestible device 65400 within the jejunum, when the walls 65406 of the jejunum begin to contract and form a peristaltic wave. Diagram 65420 depicts contracting portion 65408A of wall 65406A and contracting portion 65408B of wall 65406B (collectively, contracting portion 65408 of wall 65406) that form a peristaltic wave within the jejunum. The peristaltic wave proceeds along the length of the jejunum as different portions of wall 65406 contract and relax, causing it to appear as if contracting portions 65408 of wall 65406 proceed along the length of the jejunum (i.e., as depicted by contracting portions 65408 proceeding from left to right in diagrams 65410-65430). While in this position, ingestible device 65400 may detect a similar level of reflectance (e.g., through the use of illuminator 65124 and detector 65122 of sensing sub-unit 65126) as detected when there is no peristaltic wave occurring (e.g., as detected when ingestible device 65400 is in the position indicated in diagram 65410).

Diagram 65430 depicts ingestible device 65400 within the jejunum, when the walls 65406 of the jejunum continue to contract, squeezing around ingestible device 65400. As the peristaltic wave proceeds along the length of the jejunum, contracting portions 65408 of wall 65406 may squeeze tightly around ingestible device 65400, bringing the inner surface of wall 65406 into contact with window 65404. While in this position, ingestible device 65400 may detect a change in a reflectance detected as a result of illumination produced by sensing sub-unit 65402. The absolute value of the change in the measured reflectance may depend on several factors, such as the optical properties of the window 65404, the spectral components of the illumination, and the optical properties of the walls 65406. However, ingestible device 65400 may be configured to store a data set with the reflectance values over time, and search for periodic changes in the data set consistent with the frequency of the peristaltic waves (e.g., by analyzing the data set in the frequency domain, and searching for peaks between 0.05 Hz to 0.33 Hz). This may enable ingestible device 65400 to detect muscle contractions due to peristaltic waves without foreknowledge of the exact changes in reflectance signal amplitude that may occur as a result of detecting the muscle contractions of the peristaltic wave. Exemplary procedures for detecting muscle contractions and exemplary procedures for gathering reflectance data set(s) while ingestible device 65400 is located within the jejunum are discussed further below.

Diagram 65440 depicts ingestible device 65400 within the jejunum, when the peristaltic wave has moved past ingestible device 65400. Diagram 65440 depicts contracting portions 65408 that form the peristaltic wave within the jejunum having moved past the end of ingestible device 65400. The peristaltic wave proceeds along the length of the jejunum as different portions of wall 65406 contract and relax, causing it to appear as if contracting portions 65408 of wall 65406 proceed along the length of the jejunum (i.e., as depicted by contracting portions 65408 proceeding from left to right in diagrams 65410-65430). While in this position, ingestible device 65400 may detect a similar level of reflectance (e.g., through the use of illuminator 65124 and detector 65122 of sensing sub-unit 65126) as detected when there is no peristaltic wave occurring (e.g., as detected when ingestible device 65400 is in the position indicated in diagram 65410, or diagram 65420).

Depending on the species of the subject, peristaltic waves may occur with relatively predictable regularity. After the peristaltic wave has passed over ingestible device 65400 (e.g., as depicted in diagram 65440), the walls 65406 of the jejunum may relax again (e.g., as depicted in diagram 65410), until the next peristaltic wave begins to form. In some embodiments, ingestible device 65400 may be configured to continue to gather reflectance value data while it is within the GI tract, and may store a data set with the reflectance values over time. This may allow ingestible device 65400 to detect each of the muscle contractions as the peristaltic wave passes over ingestible device 65400 (e.g., as depicted in diagram 65430), and may enable ingestible device 65400 to both count the number of muscle contractions that occur, and to determine that a current location of the ingestible device 65400 is within the jejunum. For example, ingestible device 65400 may be configured to monitor for possible muscle contractions while is inside either the stomach or the duodenum, and may determine that ingestible device 65400 has moved to the jejunum in response to detecting a muscle contraction consistent with a peristaltic wave.

Figure 102:
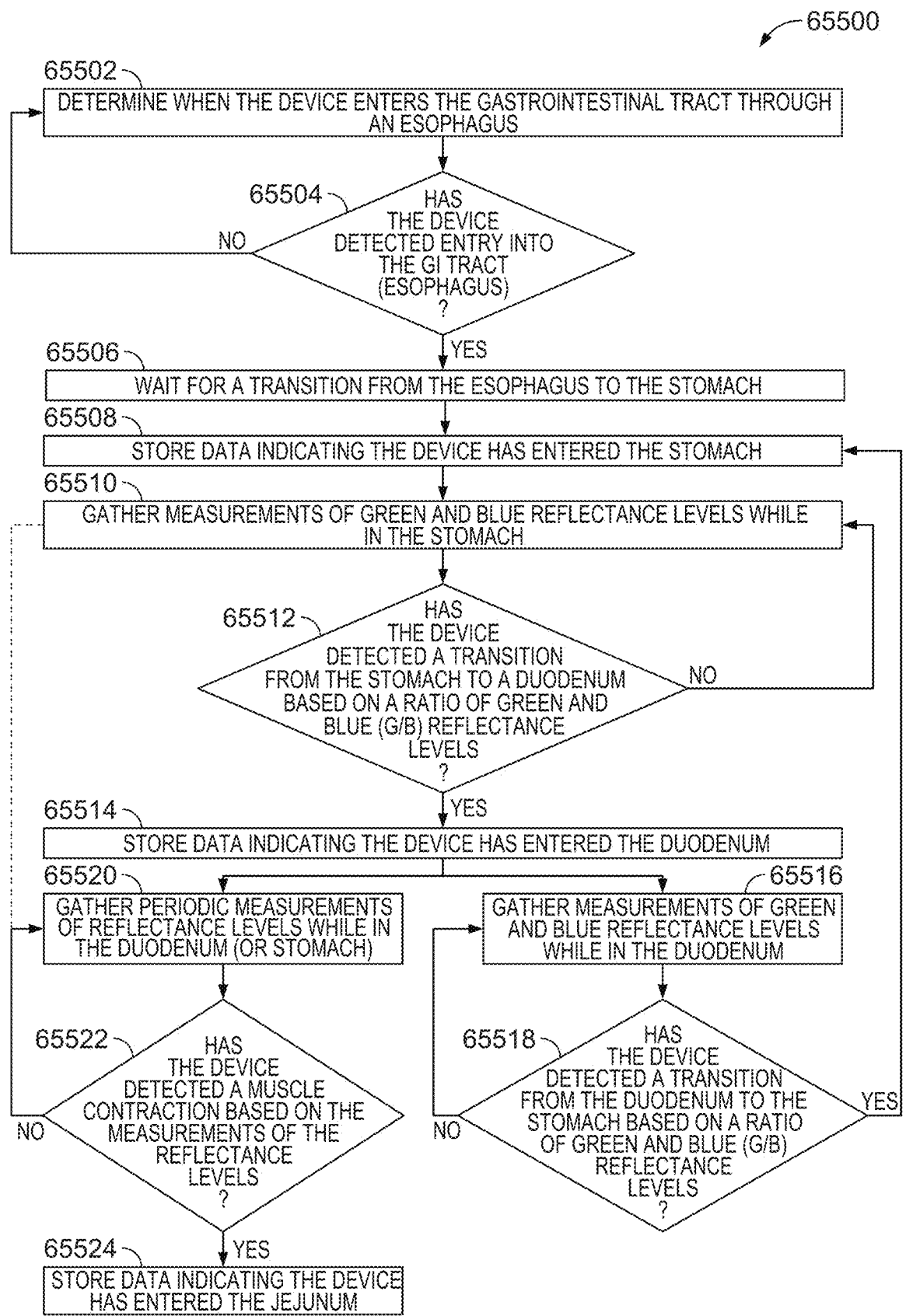
FIG. 102 is a flowchart of illustrative steps for determining a location of an ingestible device as it transits through a GI tract, in accordance with some embodiments of the disclosure.

FIG. 102 is a flowchart illustrating some aspects of a localization process used by the ingestible device. Although FIG. 102 may be described in connection with the ingestible device 65100 for illustrative purposes, this is not intended to be limiting, and either portions or the entirety of the localization procedure 65500 described in FIG. 102 may be applied to any device discussed in this application (e.g., the ingestible devices 65100, 65300, and 65400), and any of the ingestible devices may be used to perform one or more parts of the process described in FIG. 102. Furthermore, the features of FIG. 102 may be combined with any other systems, methods or processes described in this application. For example, portions of the process in FIG. 102 may be integrated into or combined with the pyloric transition detection procedure described by FIG. 103, or the jejunum detection processes described elsewhere herein.

At 65502, the ingestible device (e.g., ingestible device 65100, 65300, or 65400) gathers measurements (e.g., through detector 65122) of ambient light. For example, ingestible device 65100 may be configured to periodically measure (e.g., through detector 65122) the level of ambient light in the environment surrounding ingestible device 65100. In some embodiments, the type of ambient light being measured may depend on the configuration of detector 65122 within ingestible device 65100. For example, if detector 65122 is configured to measure red, green, and blue wavelengths of light, ingestible device 65100 may be configured to measure the ambient amount of red, green, and blue light from the surrounding environment. In some embodiments, the amount of ambient light measured by ingestible device 65100 will be larger in the area external to the body (e.g., a well-lit room where ingestible device 65100 is being administered to a subject) and in the oral cavity of the subject, as compared to the ambient level of light measured by ingestible device 65100 when inside of an esophagus, stomach, or other region of the GI tract (e.g., esophagus 65302, stomach 65306, duodenum 65310, or jejunum 65314).

At 65504, the ingestible device (e.g., ingestible device 65100, 65300, or 65400) determines (e.g., via control circuitry within PCB 65120 whether the ingestible device has detected entry into the GI tract. For example, ingestible device 65100 may be configured to determine when the most recent measurement of ambient light (e.g., the measurement gathered at 65502) indicates that the ingestible device has entered the GI tract. For instance, the first time that ingestible device 65100 gatherers a measurement of ambient light at 65502, ingestible device 65100 may store that measurement (e.g., via storage circuitry within PCB 65120) as a typical level of ambient light external to the body. Ingestible device 65100 may be configured to then compare the most recent measurement of ambient light to the typical level of ambient light external to the body (e.g., via control circuitry within PCB 65120), and determine that ingestible device 65100 has entered the GI tract when the most recent measurement of ambient light is substantially smaller than the typical level of ambient light external to the body. For example, ingestible device 65100 may be configured to detect that it has entered the GI tract in response to determining that the most recent measurement of ambient light is less than or equal to 20% of the typical level of ambient light external to the body. If ingestible device 65100 determines that it has detected entry into the GI tract (e.g., that ingestible device 65100 has entered at least the esophagus 65302), process 65500 proceeds to 65506. Alternately, if ingestible device 65100 determines that it has not detected entry into the GI tract (e.g., as a result of the most recent measurement being similar to the typical level of ambient light external to the body), process 65500 proceeds back to 65502 where the ingestible device 65100 gathers further measurements. For instance, ingestible device 65100 may be configured to wait a predetermined amount of time (e.g., five seconds, ten seconds, etc.), and then gather another measurement of the level of ambient light from the environment surrounding ingestible device 65100.

At 65506, the ingestible device (e.g., ingestible device 65100, 65300, or 65400) waits for a transition from the esophagus to the stomach (e.g., from esophagus 65302 to stomach 65306). For example, ingestible device 65100 may be configured to determine that it has entered the stomach (e.g., stomach 65306) after waiting a predetermined period of time after having entered the GI tract. For instance, a typical esophageal transit time in a human patient may be on the order of 15-30 seconds. In this case, after having detected that ingestible device 65100 has entered the GI tract at 65504 (i.e., after detecting that ingestible device 65100 has reached at least esophagus 65302), ingestible device 65100 may be configured to wait one minute, or a similar amount of time longer than the typical esophageal transit time (e.g., ninety-seconds), before automatically determining that ingestible device 65100 has entered at least the stomach (e.g., stomach 65306).

In some embodiments, the ingestible device (e.g., ingestible device 65100, 65300, or 65400) may also determine it has entered the stomach based on measurements of pH or temperature. For example, ingestible device 65100 may be configured to determine that it has entered the stomach if a temperature of ingestible device 65100 has increased to at least 31 degrees Celsius (i.e., consistent with the temperature inside the stomach), or if a measured pH of the environment surrounding ingestible device 65100 is sufficiently acidic (i.e., consistent with the acidic nature of gastric juices that may be found inside the stomach).

At 65508, the ingestible device (e.g., ingestible device 65100, 65300, or 65400) stores data indicating the ingestible device has entered the stomach (e.g., stomach 65306). For example, after having waited a sufficient amount of time at 65506, ingestible device 65100 may store data (e.g., within storage circuitry of PCB 65120) indicative of ingestible device 65100 having entered at least the stomach. Once ingestible device 65100 reaches at least the stomach, process 65500 proceeds to 65510 where ingestible device 65100 may be configured to gather data to detect entry into the duodenum (e.g., duodenum 65310).

In some embodiments, process 65500 may also simultaneously proceed from 65508 to 65520, where ingestible device 65100 may be configured to gather data in order to detect muscle contractions and detect entry into the jejunum (e.g., jejunum 65314). In some embodiments, ingestible device 65100 may be configured to simultaneously monitor for entry into the duodenum at 65516-65518, as well as detect for entry into the jejunum at 65520-65524. This may allow ingestible device 65100 to determine when it has entered the jejunum (e.g., as a result of detecting muscle contractions), even when it fails to first detect entry into the duodenum (e.g., as a result of very quick transit times of the ingestible device through the duodenum).

At 65510, the ingestible device (e.g., ingestible device 65100, 65300, or 65400) gathers measurements of green and blue reflectance levels (e.g., through the use of illuminator 65124 and detector 65122 of sensing sub-unit 65126) while in the stomach (e.g., stomach 65306). For example, ingestible device 65100 may be configured to periodically gather measurements of green and blue reflectance levels while in the stomach. For instance, ingestible device 65100 may be configured to transmit a green illumination and a blue illumination (e.g., via illuminator 65124) every five to fifteen seconds, and measure the resulting reflectance (e.g., via detector 65122). Every time that ingestible device 65100 gathers a new set of measurements, the measurements may be added to a stored data set (e.g., stored within memory circuitry of PCB 65120). The ingestible device 65100 may then use this data set to determine whether or not ingestible device 65100 is still within a stomach (e.g., stomach 65306), or a duodenum (e.g., duodenum 65310).

In some embodiments, the ingestible device (e.g., ingestible device 65100, 65300, or 65400) may be configured to detect a first reflectance based on generating an illumination of a first wavelength in approximately the green spectrum of light (between 495-600 nm), and detecting a second reflectance based on generating an illumination of the second wavelength in approximately the blue spectrum of light (between 400-495 nm). In some embodiments, the ingestible device may ensure that the illumination in the green spectrum and the illumination in the blue spectrum have wavelengths separated by at least 50 nm. This may enable ingestible device 65100 to sufficiently distinguish between the two wavelengths when detecting the reflectances (e.g., via detector 65122). It is understood that the separation of 50 nm is intended to be illustrative, and not limiting, and depending on the accuracy of the detectors within ingestible device 65100, smaller separations may be possible to be used.

At 65512, the ingestible device (e.g., ingestible device 65100, 65300, or 65400) determines (e.g., using control circuitry within PCB 65120) whether the ingestible device has detected a transition from the stomach (e.g., stomach 65306) to a duodenum (e.g., duodenum 65310) based on a ratio of green and blue (G/B) reflectance levels. For example, ingestible device 65100 may obtain (e.g., from memory circuitry of PCB 65120) a data set containing historical data for the respective ratio of the green reflectance to the blue reflectance as measured at a respective time. Generally speaking, a duodenum (e.g., duodenum 65310) of a human subject reflects a higher ratio of green light to blue light, as compared to the ratio of green light to blue light that is reflected by a stomach (e.g., stomach 65306). Based on this, ingestible device 65100 may be configured to take a first set of ratios from the data set, representing the result of recent measurements, and compare them to a second set of ratios from the data set, representing the results of past measurements. When the ingestible device 65100 determines that the mean value of the first set of ratios is substantially larger than the mean value of the second set of ratios (i.e., that the ratio of reflected green light to reflected blue light has increased), the ingestible device 65100 may determine that it has entered the duodenum (e.g., duodenum 65310) from the stomach (e.g., stomach 65306). If the ingestible device 65100 detects a transition from the stomach (e.g., stomach 65306) to a duodenum (e.g., duodenum 65310), process 65500 proceeds to 65514, where ingestible device 65100 stores data indicating that the ingestible device 65100 has entered the duodenum (e.g., duodenum 65310). Alternatively, if the ingestible device determines that the ingestible device has not transitioned from the stomach (e.g., stomach 65306) to the duodenum (e.g., duodenum 65310), process 65500 proceeds back to 65510 to gather more measurements of green and blue reflectance levels while still in the stomach (e.g., stomach 65306). An example procedure for using measurements of green and blue reflectances to monitor for transitions between the stomach and the duodenum is discussed in greater detail in relation to FIG. 103.

In some embodiments, the first time that ingestible device 65100 detects a transition from the stomach (e.g., stomach 65306) to the duodenum (e.g., duodenum 65310), ingestible device 65100 may be configured to take a mean of the second set of data, (e.g., the set of data previously recorded while in stomach 65306) and store this as a typical ratio of green light to blue light detected within the stomach (e.g., stomach 65306) (e.g., within memory circuitry of PCB 65120. This stored information may later be used by ingestible device 65100 to determine when ingestible device 65100 re-enters the stomach (e.g., stomach 65306) from the duodenum (e.g., duodenum 65310) as a result of a reverse pyloric transition.

At 65514, the ingestible device (e.g., ingestible device 65100, 65300, or 65400) stores data indicating that the ingestible device has entered the duodenum (e.g., duodenum 65310). For example, ingestible device 65100 may store a flag within local memory (e.g., memory circuitry of PCB 65120) indicating that the ingestible device 65100 is currently in the duodenum. In some embodiments, the ingestible device 65100 may also store a timestamp indicating the time when ingestible device 65100 entered the duodenum. Once ingestible device 65100 reaches the duodenum, process 65500 proceeds to 65520 where ingestible device 65100 may be configured to gather data in order to detect muscle contractions and detect entry into the jejunum (e.g., jejunum 65314). Process 65500 also proceeds from 65514 to 65516, where ingestible device 65100 may be configured to gather data additional data in order to detect re-entry into the stomach (e.g., stomach 65306) from the duodenum (e.g., duodenum 65310).

At 65516, the ingestible device (e.g., ingestible device 65100, 65300, or 65400) gathers measurements (e.g., via sensing sub-unit 65126) of green and blue reflectance levels while in the duodenum (e.g., duodenum 65310). For example, ingestible device 65100 may be configured to periodically gather measurements (e.g., via sensing sub-unit 65126) of green and blue reflectance levels while in the duodenum, similar to the measurements made at 65510 while in the stomach. For instance, ingestible device 65100 may be configured to transmit a green illumination and a blue illumination (e.g., via illuminator 65124) every five to fifteen seconds, and measure the resulting reflectance (e.g., via detector 65122). Every time that ingestible device 65100 gathers a new set of measurements, the measurements may be added to a stored data set (e.g., stored within memory circuitry of PCB 65120). The ingestible device 65100 may then use this data set to determine whether or not ingestible device 65100 is still within the duodenum (e.g., duodenum 65310), or if the ingestible device 65100 has transitioned back into the stomach (e.g., stomach 65306).

At 65518, the ingestible device (e.g., ingestible device 65100, 65300, or 65400) determines a transition from the duodenum (e.g., duodenum 65310) to the stomach (e.g., stomach 65306) based on a ratio of the measured green reflectance levels to the measured blue reflectance levels. In some embodiments, ingestible device 65100 may compare the ratio of the measured green reflectance levels to the measured blue reflectance levels recently gathered by ingestible device 65100 (e.g., measurements gathered at 65516), and determine whether or not the ratio of the measured green reflectance levels to the measured blue reflectance levels is similar to the average ratio of the measured green reflectance levels to the measured blue reflectance levels seen in the stomach (e.g., stomach 65306). For instance, ingestible device 65100 may retrieve data (e.g., from memory circuitry of PCB 65120) indicative of the average ratio of the measured green reflectance levels to the measured blue reflectance levels seen in the stomach, and determine that ingestible device 65100 has transitioned back to the stomach if the recently measured ratio of the measured green reflectance levels to the measured blue reflectance levels is sufficiently similar to the average level in the stomach (e.g., within 20% of the average ratio of the measured green reflectance levels to the measured blue reflectance levels seen in the stomach, or within any other suitable threshold level). If the ingestible device detects a transition from the duodenum (e.g., duodenum 65310) to the stomach (e.g., stomach 65306, process 65500 proceeds to 65508 to store data indicating the ingestible device has entered the stomach (e.g., stomach 65306), and continues to monitor for further transitions. Alternatively, if the ingestible device does not detect a transition from the duodenum (e.g., duodenum 65310) to the stomach (e.g., stomach 65306), process 65500 proceeds to 65516 to gather additional measurements of green and blue reflectance levels while in the duodenum (e.g., duodenum 65310), which may be used to continuously monitor for possible transitions back into the stomach. An example procedure for using measurements of green and blue reflectances to monitor for transitions between the stomach and the duodenum are discussed in greater detail below.

At 65520, the ingestible device (e.g., ingestible device 65100, 65300, or 65400) gathers periodic measurements of the reflectance levels (e.g., via sensing sub-unit 65126) while in the duodenum (e.g., duodenum 65310). In some embodiments, the ingestible device (e.g., ingestible device 65100, 65300, or 65400) may gather similar periodic measurements while in the stomach as well. In some embodiments, these periodic measurements may enable ingestible device 65100 to detect muscle contractions (e.g., muscle contractions due to a peristaltic wave as discussed elsewhere herein), which may be indicative of entry into a jejunum (e.g., jejunum 65314). Ingestible device 65100 may be configured to gather periodic measurements using any suitable wavelength of illumination (e.g., by generating illumination using illuminator 65124, and detecting the resulting reflectance using detector 65122), or combinations of wavelengths of illumination. For example, in some embodiments, ingestible device 65100 may be configured to generate red, green, and blue illumination, store separate data sets indicative of red, green, and blue illumination, and analyze each of the data sets separately to search for frequency components in the recorded data indicative of detected muscle contractions. In some embodiments, the measurements gathered by ingestible device 65100 at 65520 may be sufficiently fast as to detect peristaltic waves in a subject. For instance, in a healthy human subject, peristaltic waves may occur at a rate of approximately 0.05 Hz to 0.33 Hz. Therefore, the ingestible device 65400 may be configured to generate illumination and measure the resulting reflectance at least once every 2.5 seconds (i.e., potentially minimum rate to detect a 0.2 Hz signal), and preferably at a higher rate, such as once every 0.5 seconds or faster, and store values indicative of the resulting reflectances in a data set (e.g., within memory circuitry of PCB 65120). After gathering additional data (e.g., after gathering one new data point, or a predetermined number of new data points), process 65500 proceeds to 65522, where ingestible device 65100 determines whether or not a muscle contraction has been detected.

At 65522, the ingestible device (e.g., ingestible device 65100, 65300, or 65400) determines (e.g., via control circuitry within PCB 65120) whether the ingestible device detects a muscle contraction based on the measurements of reflectance levels (e.g., as gathered by sensing sub-unit 65126). For example, ingestible device 65100 may obtain a fixed amount of data stored as a result of measurements made at 65520 (e.g., retrieve the past minute of data from memory circuitry within PCB 65120). Ingestible device 65100 may then convert the obtained data into the frequency domain, and search for peaks in a frequency range that would be consistent with peristaltic waves. For example, in a healthy human subject, peristaltic waves may occur at a rate of approximately 0.05 Hz to 0.33 Hz, and an ingestible device 65100 may be configured to search for peaks in the frequency domain representation of the data between 0.05 Hz to 0.33 Hz above a threshold value. If the ingestible device 65100 detects a contraction based on the reflectance levels (e.g., based on detecting peaks in the frequency domain representation of the data between 0.05 Hz to 0.33 Hz), process 65500 proceeds to 65524 to store data indicating that the device has entered the jejunum. Alternatively, if the ingestible device 65100 does not detect a muscle contraction, process 65500 proceeds to 65520 to gather periodic measurements of the reflectance levels while in the duodenum (e.g., duodenum 65310). In some embodiments, the ingestible device (e.g., ingestible device 65100, 65300, or 65400) may store data (e.g., within memory circuitry of PCB 65120) indicating that a muscle contraction was detected, and process 65500 will not proceed from 65522 to 65524 until a sufficient number of muscle contractions have been detected.

At 65524, the ingestible device (e.g., ingestible device 65100, 65300, or 65400) stores data (e.g., within memory circuitry of PCB 65120) indicating that the device has entered the jejunum (e.g., jejunum 65314). For example, in response to detecting that muscle contraction has occurred at 65522, ingestible device 65100 may determine that it has entered the jejunum 65314, and is no longer inside of the duodenum (e.g., duodenum 65310) or the stomach (e.g., stomach 65306). In some embodiments, the ingestible device 65100 may continue to measure muscle contractions while in the jejunum, and may store data indicative of the frequency, number, or strength of the muscle contractions over time (e.g., within memory circuitry of PCB 65120). In some embodiments, the ingestible device 65100 may also be configured to monitor for one or more transitions. Such transitions can include a transition from the jejunum to the ileum, an ileoceacal transition from the ileum to the cecum, a transition from the cecum to the colon, or detect exit from the body (e.g., by measuring reflectances, temperature, or levels of ambient light).

In some embodiments, the ingestible device (e.g., ingestible device 65100, 65300, or 65400) may also determine that it has entered the jejunum (e.g., jejunum 65314) after a pre-determined amount of time has passed after having detected entry into the duodenum (e.g., duodenum 65310). For example, barring a reverse pyloric transition from the duodenum (e.g., duodenum 65310) back to the stomach (e.g., stomach 65306), the typical transit time for an ingestible device to reach the jejunum from the duodenum in a healthy human subject is less than three minutes. In some embodiments, the ingestible device (e.g., ingestible device 65100, 65300, or 65400) may therefore be configured to automatically determine that it has entered the jejunum after spending at least three minutes within the duodenum. This determination may be made separately from the determination made based on measured muscle contractions (e.g., the determination made at 65522), and in some embodiments, ingestible device 65100 may determine that it has entered the jejunum in response to either detecting muscle contractions, or after three minutes has elapsed from having entered the duodenum (e.g., as determined by storing data at 65514 indicative of the time that ingestible device entered the duodenum).

For illustrative purposes, 65512-65518 of process 65500 describe the ingestible device (e.g., ingestible device 65100, 65300, or 65400) measuring green reflectances and blue reflectances, calculating a ratio of the two reflectances, and using this information to determine when the ingestible device has transitioned between the duodenum and stomach. However, in some embodiments, other wavelengths of light may be used other than green and blue, provided that the wavelengths of light chosen have different reflective properties within the stomach and the duodenum (e.g., as a result of different reflection coefficients of the stomach tissue and the tissue of the duodenum).

It will be understood that the steps and descriptions of the flowcharts of this disclosure, including FIG. 102, are merely illustrative. Any of the steps and descriptions of the flowcharts, including FIG. 102, may be modified, omitted, rearranged, and performed in alternate orders or in parallel, two or more of the steps may be combined, or any additional steps may be added, without departing from the scope of the present disclosure. For example, the ingestible device 65100 may calculate the mean and the standard deviation of multiple data sets in parallel in order to speed up the overall computation time. As another example, ingestible device 65100 may gather data periodic measurements and detect possible muscle contractions (e.g., at 65520-65522) while simultaneously gathering green and blue reflectance levels to determine transitions to and from the stomach and duodenum (e.g., at 65510-65518). Furthermore, it should be noted that the steps and descriptions of FIG. 102 may be combined with any other system, device, or method described in this application, including processes 65600 and 65900, and any of the ingestible devices or systems discussed in this application (e.g., ingestible devices 65100, 65300, or 65400) could be used to perform one or more of the steps in FIG. 102.

Figure 103:
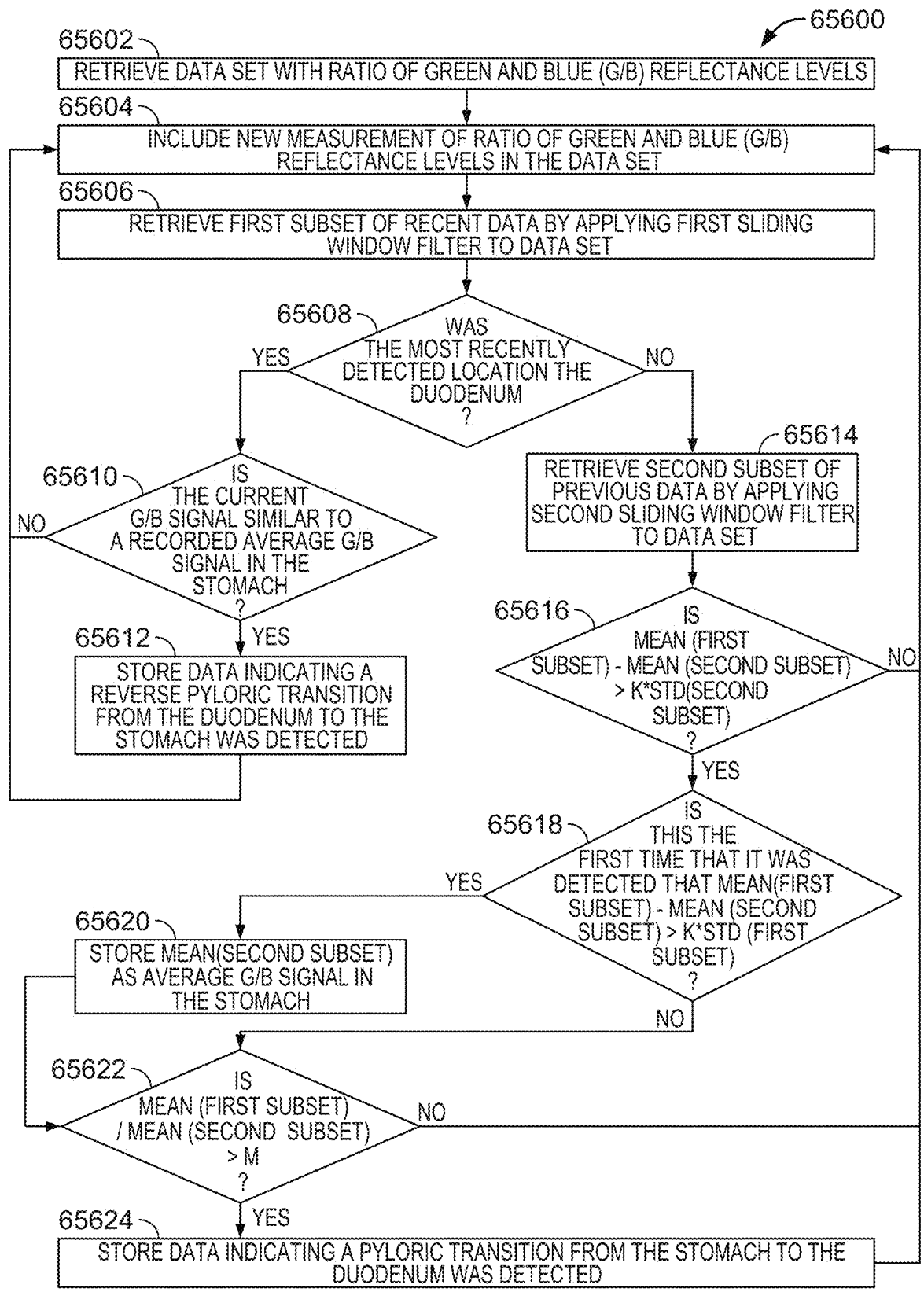
FIG. 103 is a flowchart of illustrative steps for detecting transitions from a stomach to a duodenum and from a duodenum back to a stomach, which may be used when determining a location of an ingestible device as it transits through a GI tract, in accordance with some embodiments of the disclosure.

FIG. 103 is a flowchart illustrating some aspects of a process for detecting transitions from a stomach to a duodenum and from a duodenum back to a stomach, which may be used when determining a location of an ingestible device as it transits through a gastrointestinal (GI) tract, in accordance with some embodiments of the disclosure. In some embodiments, process 65600 may begin when an ingestible device first detects that it has entered the stomach, and will continue as long as the ingestible device determines that it is within the stomach or the duodenum. In some embodiments, process 65600 may only be terminated when an ingestible device determines that it has entered the jejunum, or otherwise progressed past the duodenum and the stomach. Although FIG. 103 may be described in connection with the ingestible device 65100 for illustrative purposes, this is not intended to be limiting, and either portions or the entirety of the duodenum detection process 65600 described in FIG. 103 may be applied to any device discussed in this application (e.g., the ingestible devices 65100, 65300, or 65400), and any of the ingestible devices may be used to perform one or more parts of the process described in FIG. 103. Furthermore, the features of FIG. 85 may be combined with any other systems, methods or processes described in this application. For example, portions of the process described by the process in FIG. 103 may be integrated into process 65500.

At 65602, the ingestible device (e.g., ingestible device 65100, 65300, or 65400) retrieves a data set (e.g., from memory circuitry within PCB 65120) with ratios of the measured green reflectance levels to the measured blue reflectance levels over time. For example, ingestible device 65100 may retrieve a data set from PCB 65120 containing recently recorded ratios of the measured green reflectance levels to the measured blue reflectance levels (e.g., as recorded at 65510 or 65516 of process 65500). In some embodiments, the retrieved data set may include the ratios of the measured green reflectance levels to the measured blue reflectance levels over time. Example plots of data sets of ratios of the measured green reflectance levels to the measured blue reflectance levels are discussed further in relation to FIG. 104 and FIG. 105.

At 65604, the ingestible device (e.g., ingestible device 65100, 65300, or 65400) includes a new measurement (e.g., as made with sensing sub-unit 65126) of a ratio of the measured green reflectance level to the measured blue reflectance level in the data set. For example, ingestible device 65100 may be configured to occasionally record new data by transmitting green and blue illumination (e.g., via illuminator 65124), detecting the amount of reflectance received due to the green and blue illumination (e.g., via detector 65122), and storing data indicative of the amount of the received reflectance (e.g., in memory circuitry of PCB 65120). The ingestible device 65100 may be configured to record new data every five to fifteen seconds, or at any other convenient interval of time. For illustrative purposes, ingestible device 65100 is described as storing and retrieving the ratio of the measured green reflectance levels to the measured blue reflectance levels (e.g., if the amount of detected green reflectance was identical to the amount of detected blue reflectance at a given time, the ratio of the green and blue reflectances would be "1.0" at that given time); however, it is understood that the green reflectance data and the blue reflectance data may be stored separately within the memory of ingestible device 65100 (e.g., stored as two separate data sets within memory circuitry of PCB 65120).

At 65606, the ingestible device (e.g., ingestible device 65100, 65300, or 65400) retrieves a first subset of recent data by applying a first sliding window filter to the data set. For example, ingestible device 65100 may use a sliding window filter to obtain a predetermined amount of the most recent data within the data set, which may include any new values of the ratio of the measured green reflectance level to the measured blue reflectance level obtained at 65604. For instance, the ingestible device may be configured to select between ten and forty data points from the data set, or ingestible device 65100 may be configured to select a predetermined range of data values between fifteen seconds of data and five minutes of data. In some embodiments, other ranges of data may be selected, depending on how frequently measurements are recorded, and the particular application at hand. For instance, any suitable amount of data may be selected in the sliding window, provided that it is sufficient to detect statistically significant differences between the data selected in a second sliding window (e.g., the second subset of data selected at 65614).

In some embodiments, the ingestible device (e.g., ingestible device 65100, 65300, or 65400) may also be configured to remove outliers from the data set, or to smooth out unwanted noise in the data set. For example, ingestible device 65100 may select the first subset of data, or any other subset of data, by first obtaining a raw set of values by applying a window filter to the data set (e.g., selecting a particular range of data to be included). Ingestible device 65100 may then be configured to identify outliers in the raw set of values; for instance, by identifying data points that are over three standard deviations away from the mean value of the raw set of values, or any other suitable threshold. Ingestible device 65100 may then determine the subset of data by removing outliers from the raw set of values. This may enable ingestible device 65100 to avoid spurious information when determining whether or not it is located within the stomach or the duodenum.

At 65608, the ingestible device (e.g., ingestible device 65100, 65300, or 65400) determines whether the most recently detected location was the duodenum (e.g., duodenum 65310). In some embodiments, ingestible device 65100 may store a data flag (e.g., within memory circuitry of PCB 65120) indicating the most recent region of the GI tract that the ingestible device 65100 detected itself to be within. For instance, every time ingestible device 65100 detects entry to the stomach (e.g., detects entry into stomach 65306 as a result of the decision made at 65610), a flag is stored in memory indicating the ingestible device 65100 is in the stomach (e.g., as part of storing data at 65612). If ingestible device 65100 subsequently detects entry into the duodenum (e.g., detects entry into duodenum 65310 as a result of a decision made at 65624), another different flag is stored in memory indicating that the ingestible device 65100 is in the duodenum (e.g., as part of storing data at 65624). In this case, ingestible device 65100 may retrieve the most recently stored flag at 65608, and determine whether or not the flag indicates that the ingestible device 65100 was most recently within the duodenum. If ingestible device 65100 detects that it was most recently in the duodenum, process 65600 proceeds to 65610 where the ingestible device compares the recent measurements of the ratios of the measured green reflectance levels to the measured blue reflectance levels (e.g., measurements that include the recent measurement made at 65606) to the typical ratios measured within the stomach, and uses this information to determine whether a reverse pyloric transition from the duodenum back to the stomach has occurred. Alternately, if ingestible device 65100 detects that it was not most recently in the duodenum (e.g., because it was in the stomach instead), process 65600 proceeds to 65614 where the ingestible device compares the recent measurements of the ratios of the measured green reflectance levels to the measured blue reflectance levels (e.g., measurements that include the recent measurement made at 65606) to past measurements, and uses this information to determine whether a pyloric transition from the stomach to the duodenum has occurred.

Process 65600 proceeds from 65608 to 65610 when the ingestible device determined that it was most recently in the duodenum. At 65610, the ingestible device (e.g., ingestible device 65100, 65300, or 65400) determines (e.g., via control circuitry within PCB 65120) whether the current G/B signal is similar to a recorded average G/B signal in the stomach. For example, ingestible device 65100 may be configured to have previously stored data (e.g., within memory circuitry of PCB 65120) indicative of the average ratio of the measured green reflectance levels to the measured blue reflectance levels measured in the stomach. Ingestible device 65100 may then retrieve this stored data indicative of the average ratio of the measured green reflectance levels to the measured blue reflectance levels in the stomach, and compare this against the recent measurements in order to determine whether or not ingestible device 65100 has returned back to the stomach from the duodenum. For instance, ingestible device 65100 may determine if the mean value of the first subset of recent data (i.e., the average value of the recently measured ratios of the measured green reflectance levels to the measured blue reflectance levels) is less than the average ratio of the measured green reflectance levels to the measured blue reflectance levels within the stomach, or less that the average ratio measured within the stomach plus a predetermined number times the standard deviation of the ratios measured within the stomach. For instance, if the average ratio of the measured green reflectance levels to the measured blue reflectance levels in the stomach was "1," with a standard deviation of "0.2," ingestible device 65100 may determine whether or not the mean value of the first subset of data is less than "1.0+k*0.2," where "k" is a number between zero and five. It is understood that, in some embodiments, the ingestible device 65100 may be configured to use a different threshold level to determine whether or not the mean value of the first subset of recent data is sufficiently similar to the average ratio of the measured green reflectance levels to the measured blue reflectance levels within the stomach. In response to determining that the recent ratio of the measured green reflectance levels to the measured blue reflectance levels is similar to the average ratio of measured green and blue reflectance levels seen in the stomach, process 65600 proceeds to 65612 where ingestible device 65100 stores data indicating that it has re-entered the stomach from the duodenum. Alternately, in response to determining that the recent ratio of measured green and blue reflectance levels is sufficiently different from the average ratio of measured green and blue reflectance levels seen in the stomach, ingestible device 65100 proceeds directly to 65604, and continues to obtain new data on an ongoing basis.

At 65612, the ingestible device (e.g., ingestible device 65100, 65300, or 65400) stores data indicating a reverse pyloric transition from the duodenum to the stomach was detected. For example, ingestible device 65100 may store a data flag (e.g., within memory circuitry of PCB 65120) indicating that the ingestible device 65100 most recently detected itself to be within the stomach region of the GI tract (e.g., stomach 65306). In some embodiments, ingestible device 65100 may also store data (e.g., within memory circuitry of PCB 65120) indicating a time that ingestible device 65100 detected the reverse pyloric transition from the duodenum to the stomach. This information may be used by ingestible device 65100 at 65608, and as a result process 65600 may proceed from 65608 to 65614, rather than proceeding from 65618 to 65610. After ingestible device 65100 stores the data indicating a reverse pyloric transition from the duodenum to the stomach was detected, process 65600 proceeds to 65604 where ingestible device 65100 continues to gather additional measurements, and continues to monitor for further transitions between the stomach and the duodenum.

Process 65600 proceeds from 65608 to 65614 when the ingestible device determined that it was not most recently in the duodenum (e.g., as a result of having most recently been in the stomach instead). At 65614, the ingestible device (e.g., ingestible device 65100, 65300, or 65400) retrieves a second subset of previous data by applying a second sliding window filter to the data set. For example, ingestible device 65100 may use a sliding window filter to obtain a predetermined amount of older data from a past time range, which may be separated from recent time range used to select the first subset of data gathered at 65606 by a predetermined period of time. In some embodiments, any suitable amount of data may be selected by the first and second window filters, and the first and second window filters may be separated by any appropriate predetermined amount of time. For example, in some embodiments, the first window filter and the second window filter may each be configured to select a predetermined range of data values from the data set, the predetermined range being between fifteen seconds of data and five minutes of data. In some embodiments, the recent measurements and the past measurements may then be separated by a predetermined period of time that is between one to five times the predetermined range of data values. For instance, ingestible device 65100 may select the first subset of data and the second subset of data to each be one minute of data selected from the dataset (i.e., selected to have a predetermined range of one minute), and the first subset of data and the second subset of data are selected from recorded measurements that are at least two minutes apart (i.e., the predetermined period of time is two minutes, which is twice the range used to select the subsets of data using the window filters). As another example, ingestible device 65100 may select the first subset of data and the second subset of data to each be five minutes of data selected from the dataset (i.e., selected to have a predetermined range of five minutes), and the first subset of data and the second subset of data are selected from recorded measurements that are at least 10 minutes apart (i.e., the predetermined period of time is two minutes, which is twice the range used to select the subsets of data using the window filters).

In some embodiments, if ingestible device 65100 recently transitioned to the stomach from the duodenum (e.g., as determined by checking for recent data stored within ingestible device 65100 at 65612), ingestible device 65100 may select the second subset of data at 65614 from a time frame when ingestible device 65100 is known to be within the stomach. In some embodiments, ingestible device 65100 may alternately select a previously recorded average and standard deviation for ratios of green reflectances and blue reflectances within the stomach (e.g., an average and standard deviation typical of data recorded within the stomach, as previously recorded within memory circuitry of PCB 65120 at 65620) in place of the second subset of data. In this case, ingestible device 65100 may simply use the previously recorded average and previously recorded standard deviation when making a determination at 65616, rather than expending resources to calculate the mean and standard deviation of the second subset.

At 65616, the ingestible device (e.g., ingestible device 65100, 65300, or 65400) determines whether the difference between the mean of the second subset and the mean of the first subset is greater than a predetermined multiple of the standard deviation of the first subset. For example, ingestible device 65100 may compute a difference between a mean of the first subset of recent data and a mean of a second subset of past data, and determine whether this difference is greater than three times the standard deviation of the second subset of past data. In some embodiments, it is understood that any convenient threshold level may be used other than three times the standard deviation, such as any value between one and five times the standard deviation. Also, in some embodiments, the ingestible device may instead set the threshold level based on the standard deviation of the second subset instead of the first subset. In response to determining that the difference between the mean of the first subset and the mean of the second subset is greater than a predetermined multiple of the standard deviation of the second subset, process 65600 proceeds to 65618. Otherwise, process 65600 proceeds back to 65604, where the ingestible device 65604 continues to gather new data to be used in monitoring for transitions between the stomach (e.g., stomach 65306) and the duodenum (e.g., duodenum 65310).

At 65618, the ingestible device (e.g., ingestible device 65100, 65300, or 65400) determines (e.g., via control circuitry within PCB 65120) whether the determination made at 65616 is the first time that the difference between the mean of the first subset of recent data and the mean of the second subset of past data is calculated to be greater than the standard deviation of the second subset. If the ingestible device determines that this is the first time that the difference between the mean of the first subset and the mean of the second subset is calculated to be greater than the standard deviation of the second subset, process 65600 proceeds to 65620 to store the mean of the second subset of past data as an average G/B signal in the stomach. Alternatively, if the ingestible device determines that the immediately preceding determination made at 65616 is not the first time that the difference between the mean of the first subset of recent data and the mean of the second subset of past data is calculated to be greater than the standard deviation of the second subset, process 65600 proceeds directly to 65622.

At 65620, the ingestible device (e.g., ingestible device 65100, 65300, or 65400) stores the mean of the second subset as an average G/B signal in the stomach. For example, ingestible device 65100 may be configured to store the mean of the second subset of past data (e.g., store within memory circuitry of PCB 65120) as the average ratio of the measured green reflectance levels to the measured blue reflectance levels measured in the stomach. In some embodiments, ingestible device 65100 may also store the standard deviation of the second subset of past data as a typical standard deviation of the ratios of the measured green reflectance levels to the measured blue reflectance levels detected within the stomach. This stored information may be used by the ingestible device later on (e.g., at 65610) to compare against future data, which may enable the ingestible device to detect reverse pyloric transitions from the duodenum (e.g., duodenum 65310) back to the stomach (e.g., stomach 65306), and may generally be used in place of other experimental data gathered from the stomach (e.g., in place of the second subset of data at 65616). After storing the mean of the second subset as an average G/B signal in the stomach, process 65600 proceeds to 65622.

At 65622, the ingestible device (e.g., ingestible device 65100, 65300, or 65400) determines whether a difference of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable ingestible device 65100 to ensure that it detected an actual transition to the duodenum. This may be particularly advantageous when the determination made at 65616 is potentially unreliable due to the standard deviation of the second subset of past data being abnormally small. For example, a typical value of the predetermined threshold "M," may be on the order of 0.1 to 0.5. If ingestible device 65100 determines that the difference of the mean of the first subset of recent data to the second subset of past data is greater than a predetermined threshold, process 65600 proceeds to 65624 to store data indicating that a pyloric transition from the stomach to the duodenum (e.g., from stomach 65306 to duodenum 65310) was detected. Alternatively, if the ingestible device determines that the ratio of the mean of the first subset to the second subset is less than or equal to the predetermined threshold, "M" (i.e., determines that a transition to the duodenum has not occurred), process 65600 proceeds directly to 65604 where ingestible device 65100 continues to make new measurements and monitor for possible transitions between the stomach and the duodenum.

In some embodiments, instead of using a difference of the mean of the first subset of recent data to the mean of the second subset of past data, the ingestible device (e.g., ingestible device 65100, 65300, or 65400) determines whether the ratio of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable ingestible device 65100 to ensure that it detected an actual transition to the duodenum. This may be particularly advantageous when the determination made at 65616 is potentially unreliable due to the standard deviation of the second subset of past data being abnormally small. For example, a typical value of the predetermined threshold "M," may be on the order of 1.2 to 2.0. It is understood any convenient type of threshold or calculation may be used to determine whether or not the first subset of data and the second subset of data are both statistically distinct from one another, and also substantially different from one another in terms of overall average value.

At 65624, the ingestible device (e.g., ingestible device 65100, 65300, or 65400) stores data indicating a pyloric transition from the stomach to the duodenum was detected. For example, ingestible device 65100 may store a data flag (e.g., within memory circuitry of PCB 65120) indicating that the ingestible device 65100 most recently detected itself to be within the duodenum region of the GI tract (e.g., duodenum 65310). In some embodiments, ingestible device 65100 may also store data (e.g., within memory circuitry of PCB 65120) indicating a time that ingestible device 65100 detected the pyloric transition from the stomach to the duodenum. This information may be used by ingestible device 65100 at 65608, and as a result process 65600 may proceed from 65608 to 65610, rather than proceeding from 65618 to 65614. After ingestible device 65100 stores the data indicating a pyloric transition from the stomach to the duodenum was detected, process 65600 proceeds to 65604 where ingestible device 65100 continues to gather additional measurements, and continues to monitor for further transitions between the stomach and the duodenum.

It will be understood that the steps and descriptions of the flowcharts of this disclosure, including FIG. 103, are merely illustrative. Any of the steps and descriptions of the flowcharts, including FIG. 103, may be modified, omitted, rearranged, and performed in alternate orders or in parallel, two or more of the steps may be combined, or any additional steps may be added, without departing from the scope of the present disclosure. For example, the ingestible device 65100 may calculate the mean and the standard deviation of multiple data sets in parallel in order to speed up the overall computation time. Furthermore, it should be noted that the steps and descriptions of FIG. 103 may be combined with any other system, device, or method described in this application, and any of the ingestible devices or systems discussed in this application could be used to perform one or more of the steps in FIG. 103. For example, portions of process 65600 may be incorporated into 65508-65516 of process 65500, and may be part of a more general process for determining a location of the ingestible device. As another example, the ratio of detected blue and green light (e.g., as measured and added to the data set at 65604) may continue even outside of the stomach or duodenum, and similar information may be recorded by the ingestible device throughout its transit in the GI tract. Example plots of data sets of ratios of measured green and blue reflectance levels, which may be gathered throughout the GI tract, are discussed further in relation to FIG. 104 and FIG. 105 below.

Figure 104:
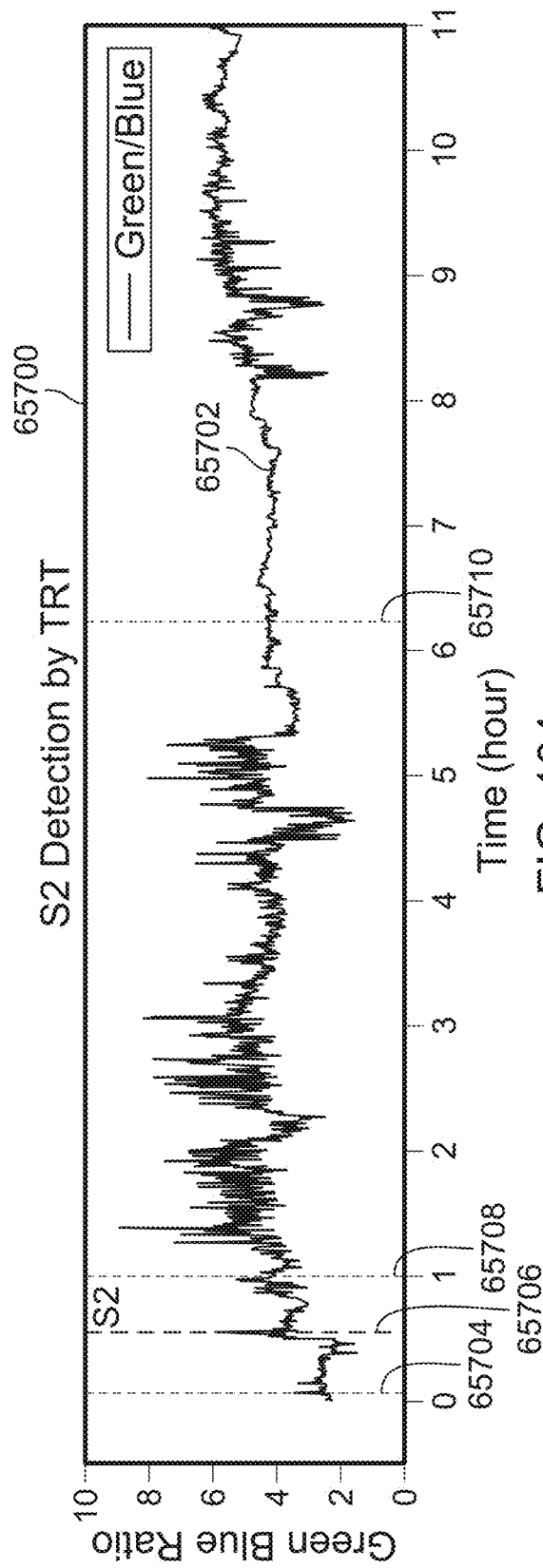
FIG. 104 is a plot illustrating data collected during an example operation of an ingestible device, which may be used when determining a location of an ingestible device as it transits through a GI tract, in accordance with some embodiments of the disclosure.

FIG. 104 is a plot illustrating data collected during an example operation of an ingestible device (e.g., ingestible device 65100, 65300, or 65400), which may be used when determining a location of an ingestible device as it transits through a gastrointestinal (GI) tract, in accordance with some embodiments of the disclosure.

Although FIG. 104 may be described in connection with ingestible device 65100 for illustrative purposes, this is not intended to be limiting, and plot 65700 and data set 65702 may be typical of data gathered by any device discussed in this application. Plot 65700 depicts the ratios of the measured green reflectance levels to the measured blue reflectance levels over time. For example, ingestible device 65100 may have computed the value for each point in the data set 65702 by transmitting green and blue illumination at a given time (e.g., via illuminator 65124), measuring the resulting green and blue reflectances (e.g., via detector 65122), calculating the ratio of the resulting reflectances, and storing the ratio in the data set along with a timestamp indicating the time that the reflectances were gathered.

At 65704, shortly after ingestible device 65100 begins operation, ingestible device 65100 determines that it has reached at least the stomach (e.g., as a result of making a determination similar to the determination discussed in relation to 65506 in process 65500). Ingestible device 65100 continues to gather additional measurements of green and blue reflectance levels, and at 65706 ingestible device 65100 determines that a pyloric transition has occurred from the stomach to the duodenum (e.g., as a result of making a determination similar to the determinations discussed in relation to 65616-65624 of process 65600). Notably, the values in data set 65702 around 65706 jump up precipitously, which is indicative of the higher ratios of measured green reflectance levels to measured blue reflectance levels typical of the duodenum.

The remainder of the data set 65702 depicts the ratios of the measured green reflectance levels to the measured blue reflectance levels throughout the remainder of the GI tract. At 65708, ingestible device 65100 has reached the jejunum (e.g., as determined through measurements of muscle contractions, as discussed in relation to, and by 65710, ingestible device 65100 has reached the cecum. It is understood that, in some embodiments, the overall character and appearance of data set 65702 changes within the small intestine (i.e., the duodenum, jejunum, and ileum) versus the cecum. Within the jejunum and ileum, there may typically be a wide variation in the ratios of the measured green reflectance levels to the measured blue reflectance levels, resulting in relatively noisy data with a high standard deviation. By comparison, within the cecum ingestible device 65100 may measure a relatively stable ratio of the measured green reflectance levels to the measured blue reflectance levels. In some embodiments, ingestible device 65100 may be configured to determine transitions from the small intestine to the cecum based on these differences. For example, ingestible device 65100 may compare recent windows of data to past windows of data, and detect a transition to the cecum in response to determining that the standard deviation of the ratios in the recent window of data is substantially less than the standard deviation of the ratios in the past window of data.

Figure 105:
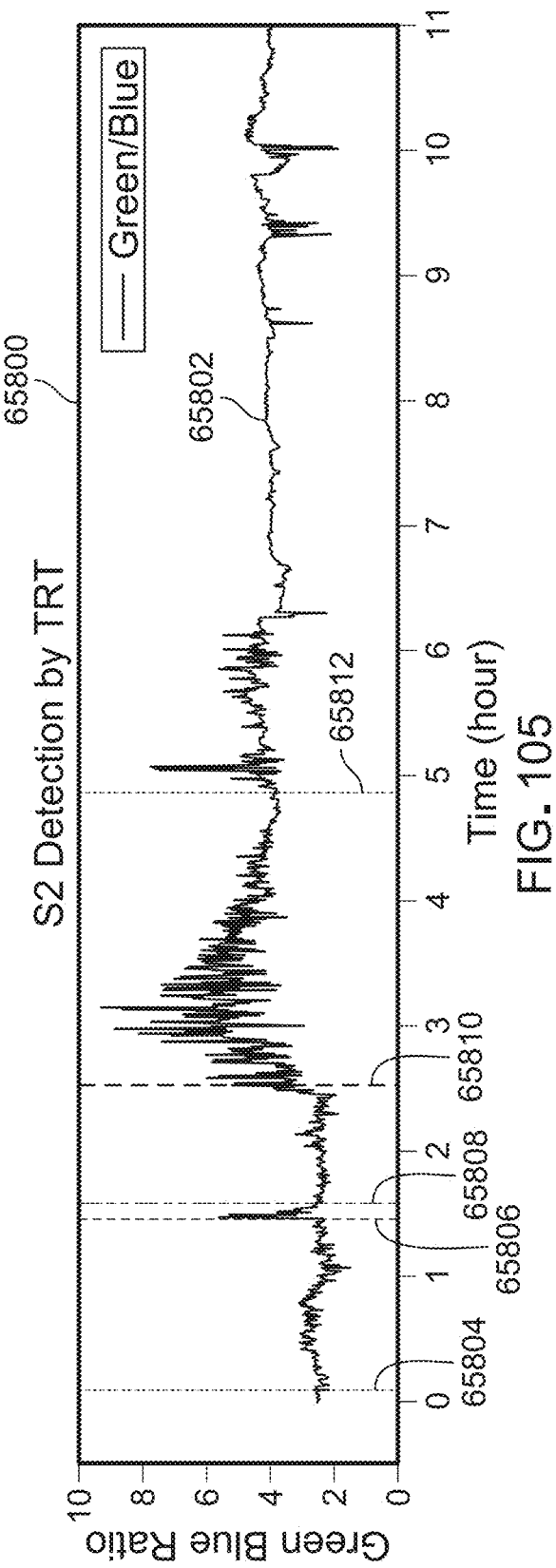
FIG. 105 is another plot illustrating data collected during an example operation of an ingestible device, which may be used when determining a location of an ingestible device as it transits through a GI tract, in accordance with some embodiments of the disclosure.

FIG. 105 is another plot illustrating data collected during an example operation of an ingestible device, which may be used when determining a location of an ingestible device as it transits through a gastrointestinal (GI) tract, in accordance with some embodiments of the disclosure. Similar to FIG. 104, FIG. 105 may be described in connection with the ingestible device 65100 for illustrative purposes. However, this is not intended to be limiting, and plot 65800 and data set 65802 may be typical of data gathered by any device discussed in this application.

At 65804, shortly after ingestible device 65100 begins operation, ingestible device 65100 determines that it has reached at least the stomach (e.g., as a result of making a determination similar to the determination discussed in relation to 65506 in process 65500). Ingestible device 65100 continues to gather additional measurements of green and blue reflectance levels (e.g., via sensing sub-unit 65126), and at 65806 ingestible device 65100 determines that a pyloric transition has occurred from the stomach to the duodenum (e.g., as a result of making a determination similar to the determinations discussed in relation to 65616-65624 of process 65600). Notably, the values in data set 65802 around 65806 jump up precipitously, which is indicative of the higher ratios of measured green reflectance levels to measured blue reflectance levels typical of the duodenum, before falling shortly thereafter. As a result of the reduced values in data set 65802, ingestible device 65100 determines that a reverse pyloric transition has occurred from the duodenum back to the stomach at 65808 (e.g., as a result of making a determination similar to the determinations discussed in relation to 65610-65612 of process 65600). At 65810, as a result of the values in data set 65802 increasing again, ingestible device 65100 determines that another pyloric transition has occurred from the stomach to the duodenum, and shortly thereafter ingestible device 65100 proceeds onwards to the jejunum, ileum, and cecum.

The remainder of the data set 65802 depicts the ratios of the measured green reflectance levels to the measured blue reflectance levels throughout the remainder of the GI tract. Notably, at 65812, ingestible device reaches the transition point between the ileum and the cecum. As discussed above in relation to FIG. 104, the transition to the cecum is marked by a reduced standard deviation in the ratios of measured green reflectances and measured blue reflectances over time, and ingestible device 65100 may be configured to detect a transition to the cecum based on determining that the standard deviation of a recent set of measurements is substantially smaller than the standard deviation of past measurements taken from the jejunum or ileum.

Figure 106:
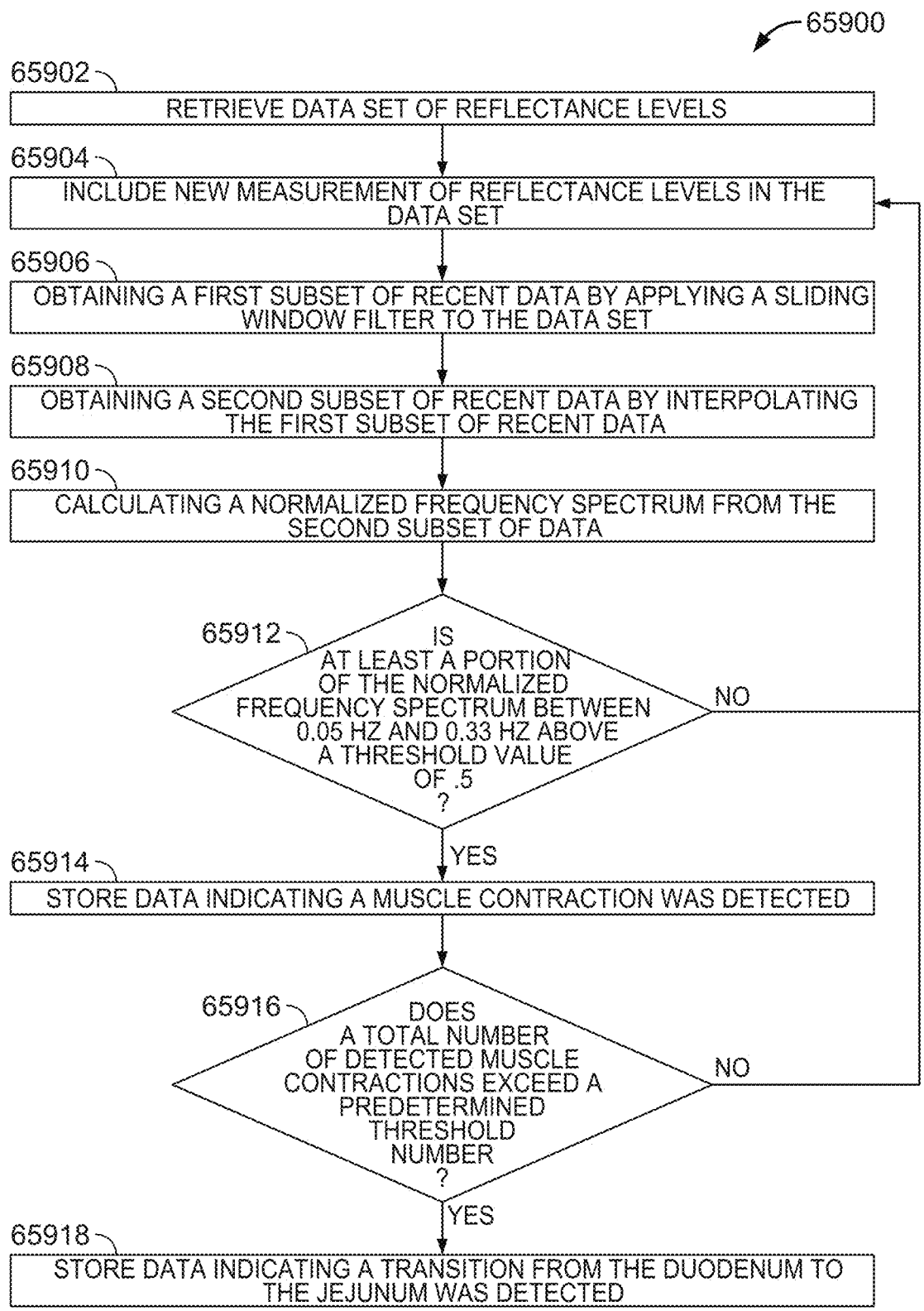

FIG. 106 is a flowchart of illustrative steps for detecting a transition from a duodenum to a jejunum, which may be used when determining a location of an ingestible device as it transits through a gastrointestinal (GI) tract, in accordance with some embodiments of the disclosure. Although FIG. 106 may be described in connection with the ingestible device 65100 for illustrative purposes, this is not intended to be limiting, and either portions or the entirety of process 65900 described in FIG. 106 may be applied to any device discussed in this application (e.g., the ingestible devices 65100, 65300, and 65400), and any of these ingestible devices may be used to perform one or more parts of the process described in FIG. 106. Furthermore, the features of FIG. 106 may be combined with any other systems, methods or processes described in this application. For example, portions of the process described by the process in FIG. 106 may be integrated into the localization process described by FIG. 102 (e.g., as part of 65520-65524 of process 65500). In some embodiments, an ingestible device 65100 may perform process 65900 while in the duodenum, or in response to detecting entry to the duodenum. In other embodiments, an ingestible device 65100 may perform process 65900 while in the stomach, or in response to detecting entry into the GI tract. It is also understood that process 65900 may be performed in parallel with any other process described in this disclosure (e.g., process 65600), which may enable ingestible device 65100 to detect entry into various portions of the GI tract, without necessarily detecting entry into a preceding region of the GI tract.

For illustrative purposes, FIG. 106 may be discussed in terms of ingestible device 65100 generating and making determinations based on a single set of reflectance levels generated at a single wavelength by a single sensing sub-unit (e.g., sensing sub-unit 65126). However, it is understood that ingestible device 65100 may generate multiple wavelengths of illumination from multiple different sensing sub-units positioned around the circumference of ingestible device (e.g., multiple sensing sub-units positioned at different locations behind window 65114 of ingestible device 65100, and each of the resulting reflectances may be stored as a separate data set. Moreover, each of these sets of reflectance levels may be used to detect muscle contractions by running multiple versions of process 65900, each one of which processes data for a different set of reflectances corresponding to data sets obtained from measurements of different wavelengths or measurements made by different sensing sub-units.

At 65902, the ingestible device (e.g., ingestible device 65100, 65300, or 65400) retrieves a set of reflectance levels. For example, ingestible device 65100 may retrieve a data set of previously recorded reflectance levels from memory (e.g., from memory circuitry of PCB 65120). Each of the reflectance levels may correspond to reflectances previously detected by ingestible device 65100 (e.g., via detector 65122) from illumination generated by ingestible device 65100 (e.g., via illuminator 65124), and may represent a value indicative of an amount of light detected in a given reflectance. However, it is understood that any suitable frequency of light may be used, such as light in the infrared, visible, or ultraviolet spectrums. In some embodiments, the reflectance levels may correspond to reflectances previously detected by ingestible device 65100 at periodic intervals.

At 904, the ingestible device (e.g., ingestible device 65100, 65300, or 65400) includes new measurements of reflectance levels in the data set. For example, ingestible device 65100 may be configured to detect a new reflectance (e.g., transmit illumination and detect the resulting reflectance using sensing sub-unit 65126) at regular intervals, or with sufficient speed as to detect peristaltic waves. For example, ingestible device 65100 may be configured to generate illumination and measure the resulting reflectance once every three seconds (i.e., potentially minimum rate to detect a 0.17 Hz signal), and preferably at a higher rate, as fast at 0.1 second or even faster. It is understood that the periodic interval between measurements may be adapted as needed based on the species of the subject, and the expected frequency of the peristaltic waves to be measured. Every time ingestible device 65100 makes a new reflectance level measurement at 65904, the new data is included to the data set (e.g., a data set stored within memory circuitry of PCB 65120).

At 65906, the ingestible device (e.g., ingestible device 65100, 65300, or 65400) obtains a first subset of recent data by applying a sliding window filter to the data set. For example, ingestible device 65100 may retrieve a one-minute worth of data from the data set. If the data set includes values for reflectances measured every second, this would be approximately 60 data points worth of data. Any suitable type of window size may be used, provided that the size of the window is sufficiently large to detect peristaltic waves (e.g., fluctuations on the order of 0.05 Hz to 0.33 Hz for healthy human subjects). In some embodiments, ingestible device 65100 may also clean the data, for example, by removing outliers from the first subset of data obtained through the use of the sliding window filter.

At 65908, the ingestible device (e.g., ingestible device 65100, 65300, or 65400) obtains a second subset of recent data by interpolating the first subset of recent data. For example, ingestible device 65100 may interpolate the first subset of data in order to generate a second subset of data with a sufficient number of data points (e.g., data points spaced every 0.5 seconds or greater). In some embodiments, this may enable ingestible device 65100 to also replace any outlier data points that may have been removed as part of applying the window filter at 65906.

At 65910, the ingestible device (e.g., ingestible device 65100, 65300, or 65400) calculates a normalized frequency spectrum from the second subset of data. For example, ingestible device 65100 may be configured to perform a fast Fourier transform to convert the second subset of data from a time domain representation into a frequency domain representation. It is understood that depending on the application being used, and the nature of the subset of data, any number of suitable procedures (e.g., Fourier transform procedures) may be used to determine a frequency spectrum for the second subset of data. For example, the sampling frequency and size of the second subset of data may be known in advance, and ingestible device 65100 may be configured to have pre-stored values of a normalized discreet Fourier transform (DFT) matrix, or the rows of the DFT matrix corresponding to the 0.05 Hz to 0.33 Hz frequency components of interest, within memory (e.g., memory circuitry of PCB 65120). In this case, the ingestible device may use matrix multiplication between the DFT matrix and the data set to generate an appropriate frequency spectrum. An example data set and corresponding frequency spectrum that may be obtained by the ingestible device is discussed in greater detail below.

At 65912, the ingestible device (e.g., ingestible device 65100, 65300, or 65400) determines whether at least a portion of the normalized frequency spectrum is between 00.05 Hz to 0.33 Hz above a threshold value of 0.5 Hz. Peristaltic waves in a healthy human subject occur at a rate between 0.05 Hz to 0.33 Hz, and an ingestible device experiencing peristaltic waves (e.g., ingestible device 65400 detecting contractions in walls 65406 of the jejunum) may detect sinusoidal variations in the amplitude of detected reflectances levels that follow a similar 0.05 Hz to 0.33 Hz frequency. If the ingestible device determines that a portion of the normalized frequency spectrum between 0.05 Hz to 0.33 Hz is above a threshold value of 0.5 Hz, this measurement may be consistent with peristaltic waves in a healthy human subject, and process 65900 proceeds to 65914 where ingestible device 65100 stores data indicating a muscle contraction was detected. Alternatively, if the ingestible device determines that no portion of the normalized frequency spectrum between 0.05 Hz to 0.33 Hz above a threshold value of 0.5, process 65900 proceeds directly to 65904 to make new measurements and to continue to monitor for new muscle contractions. It is understood that a threshold value other than 0.5 may be used, and that the exact threshold may depend on the sampling frequency and type of frequency spectrum used by ingestible device 65100.

At 65914, the ingestible device (e.g., ingestible device 65100, 65300, or 65400) stores data indicating a muscle contraction was detected. For example, ingestible device 65100 may store data in memory (e.g., memory circuitry of PCB 65120) indicating that a muscle contraction was detected, and indicating the time that the muscle contraction was detected. In some embodiments, ingestible device 65100 may also monitor the total number of muscle contractions detected, or the number of muscle contractions detected in a given time frame. In some embodiments, detecting a particular number of muscle contractions may be consistent with ingestible device 65100 being within the jejunum (e.g., jejunum 65314) of a healthy human subject. After detecting a muscle contraction, process 65900 proceeds to 65916.

At 65916, the ingestible device (e.g., ingestible device 65100, 65300, or 65400) determines whether a total number of muscle contractions exceeds a predetermined threshold number. For example, ingestible device 65100 may retrieve the total number of muscle contractions detected from memory (e.g., from memory circuitry of PCB 65120), and compare the total number to a threshold value. In some embodiments, the threshold value may be one, or any number larger than one. The larger the threshold value, the more muscle contractions need to be detected before ingestible device 65100 stores data indicating that it has entered the jejunum. In practice, setting the threshold value as three or higher may prevent the ingestible device from detecting false positives (e.g., due to natural movement of the GI tract organs, or due to movement of the subject). If the total number of contractions exceeds the predetermined threshold number, process 65900 proceeds to 65918 to store data indicating detection of a transition from the duodenum to the jejunum. Alternatively, if the total number of contractions does not exceed a predetermined threshold number, process 65900 proceeds to 65904 to include new measurements of reflectance levels in the data set. An example plot of the muscle contractions detected over time is discussed in greater detail below.

At 65918, the ingestible device (e.g., ingestible device 65100, 65300, or 65400) stores data indicating detection of a transition from the duodenum to the jejunum. For example, ingestible device 65100 may store data in memory (e.g., from memory circuitry of PCB 65120) indicating that the jejunum has been reached. In some embodiments, if ingestible device 65100 is configured to perform all or part of process 65900 while in the stomach, ingestible device 65100 may store data at 65918 indicating detection of a transition from the stomach directly to the jejunum (e.g., as a result of transitioning too quickly through the duodenum for the pyloric transition to be detected using process 65600).

In some embodiments, the ingestible device (e.g., ingestible device 65100, 65300, or 65400) may be configured to obtain a fluid sample from the environment external to a housing of the ingestible device in response to identifying a change in the location of the ingestible device. For example, ingestible device 65100 may be configured to obtain a fluid sample from the environment external to the housing of ingestible device 65100 (e.g., through the use of optional opening 65116 and optional rotating assembly 65118) in response to determining that the ingestible device is located within the jejunum (e.g., jejunum 65314). In some embodiments, ingestible device 65100 may also be equipped with appropriate diagnostics to detect certain medical conditions based on the retrieved fluid sample, such as small intestinal bacterial overgrowth (SIBO).

In some embodiments, the ingestible device (e.g., ingestible device 65100, 65300, or 65400) may be configured to deliver a dispensable substance that is pre-stored within the ingestible device from the ingestible device into the gastrointestinal tract in response to identifying the change in the location of the ingestible device. For example, ingestible device 65100 may have a dispensable substance pre-stored within the ingestible device 65100 (e.g., within a storage chamber or cavity on optional storage sub-unit 65118-3), and ingestible device 65100 may be configured to dispense the substance into the gastrointestinal tract (e.g., through the use of optional opening 65116 and optional rotating assembly 65118) when the ingestible device 65100 detects that the ingestible device 65100 is located within the jejunum (e.g., jejunum 65314 ( ). In some embodiments, this may enable ingestible device 65100 to deliver substances (e.g., therapeutics and medicaments) at targeted locations within the GI tract.

In some embodiments, the ingestible device (e.g., ingestible device 65100, 65300, or 65400) may be configured to perform an action based on the total number of detected muscle contractions. For example, ingestible device 65100 may be configured to retrieve data indicative of the total number of muscle contractions (e.g., from memory circuitry of PCB 65120), and compare that to an expected number of muscle contractions in a healthy individual. In response, the ingestible device may either dispense a substance into the gastrointestinal tract (e.g., through the use of optional opening 65116 and optional rotating assembly 65118), or may obtain a fluid sample from the environment external to the housing of ingestible device 65100 (e.g., through the use of optional opening 65116 and optional rotating assembly 65118). For instance, ingestible device 65100 may be configured to obtain a sample in response to determining that a number of detected muscle contractions is abnormal, and differs greatly from the expected number. As another example, ingestible device 65100 may be configured to deliver a substance into the GI tract (such as a medicament), in response to determining that the detected muscle contractions are consistent with a functioning GI tract in a healthy individual.

It will be understood that the steps and descriptions of the flowcharts disclosed herein are merely illustrative. Any of the steps and descriptions of the flowcharts may be modified, omitted, rearranged, and/or performed in alternate orders or in parallel, two or more of the steps may be combined, or any additional steps may be added, without departing from the scope of the present disclosure. For example, the ingestible device 65100 may calculate the mean and the standard deviation of multiple data sets in parallel (e.g., multiple data sets, each one corresponding to a different wavelength of reflectance or different sensing sub-unit used to detect the reflectance) in order to speed up the overall computation time. Furthermore, it should be noted that the steps and descriptions of any given system, device or method disclosed herein may be combined with any other system, device, or method described herein, and any of the ingestible devices or systems discussed in this application could be used to perform one or more of the steps in any of the methods disclosed herein.

Figure 107:
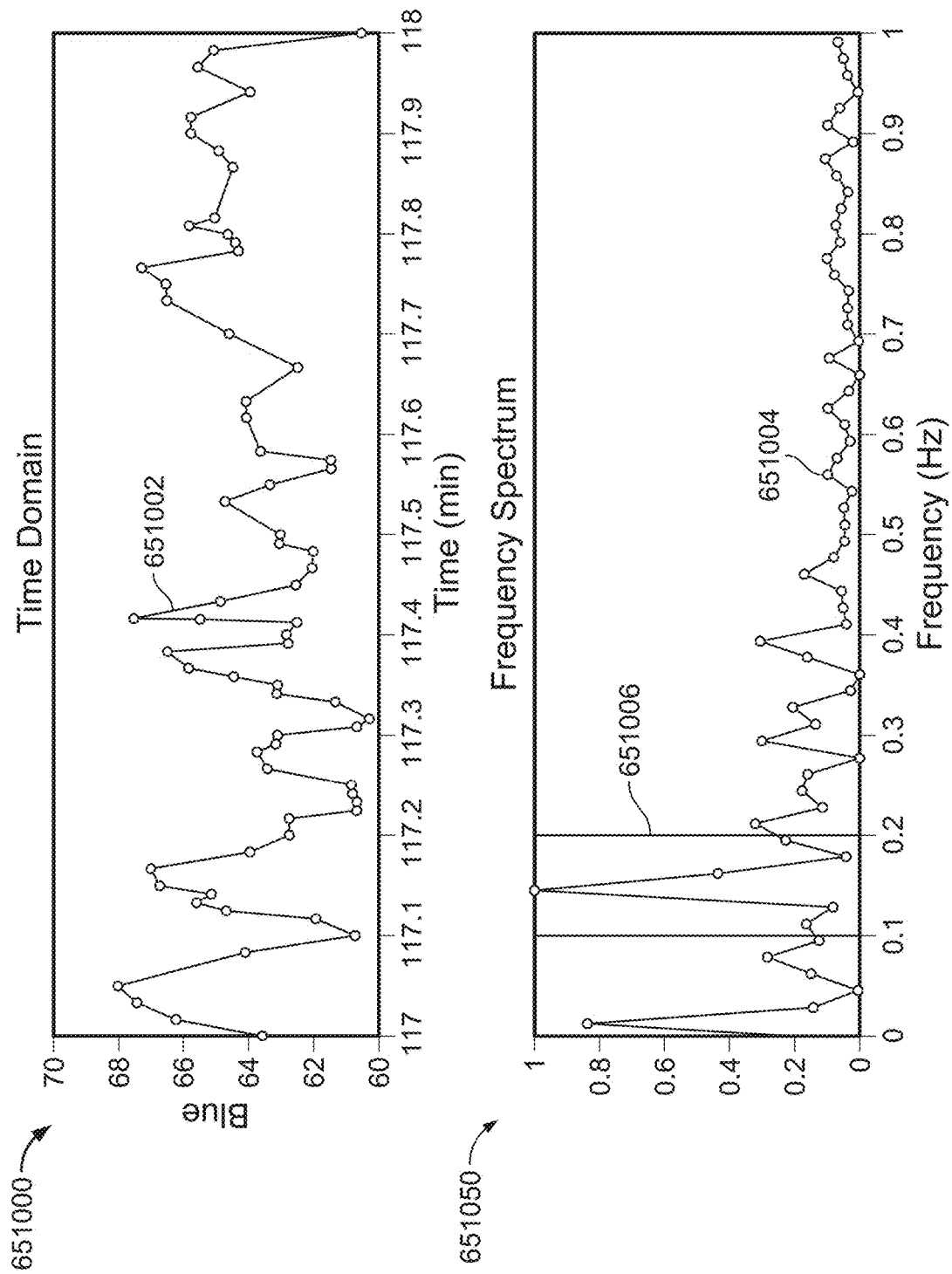

FIG. 107 is a plot illustrating data collected during an example operation of an ingestible device, which may be used when detecting a transition from a duodenum to a jejunum, in accordance with some embodiments of the disclosure. Diagram 651000 depicts a time domain plot 651002 of a data set of reflectance levels measured by an ingestible device (e.g., the second subset of data discussed in relation to 65908). In some embodiments, ingestible device 65100 may be configured to gather data points at semi-regular intervals approximately 0.5 seconds apart. By comparison, diagram 651050 depicts a frequency domain plot 651004 of the same data set of reflectance levels measured by an ingestible device (e.g., as a result of ingestible device 65100 calculating a frequency spectrum at 65910). In some embodiments, ingestible device 65100 may be configured to calculate the frequency spectrum through any convenient means.

In diagram 651050, the range of frequencies 651006 between 0.05 Hz to 0.33 Hz may be the range of frequencies that ingestible device 65100 searches in order to detect muscle contractions. As shown in diagram 651050, there is a strong peak in the frequency domain plot 651004 around 0.14 Hz, which is consistent with the frequency of peristaltic motion in a healthy human individual. In this case, an ingestible device 65100 analyzing frequency domain plot 651004 may be configured to determine that the data is consistent with a detected muscle contraction (e.g., using a process similar to 65912 of process 65900), and may store data (e.g., in memory circuitry of PCB 65120) indicating that a muscle contraction has been detected. Because the muscle contraction was detected from the one-minute window of data ending at 118 minutes, ingestible device 65100 may also store data indicating that the muscle contraction was detected at the 118-minute mark (i.e., which may indicate that the ingestible device 65100 was turned on and ingested by the subject 118 minutes ago).

Figure 108:
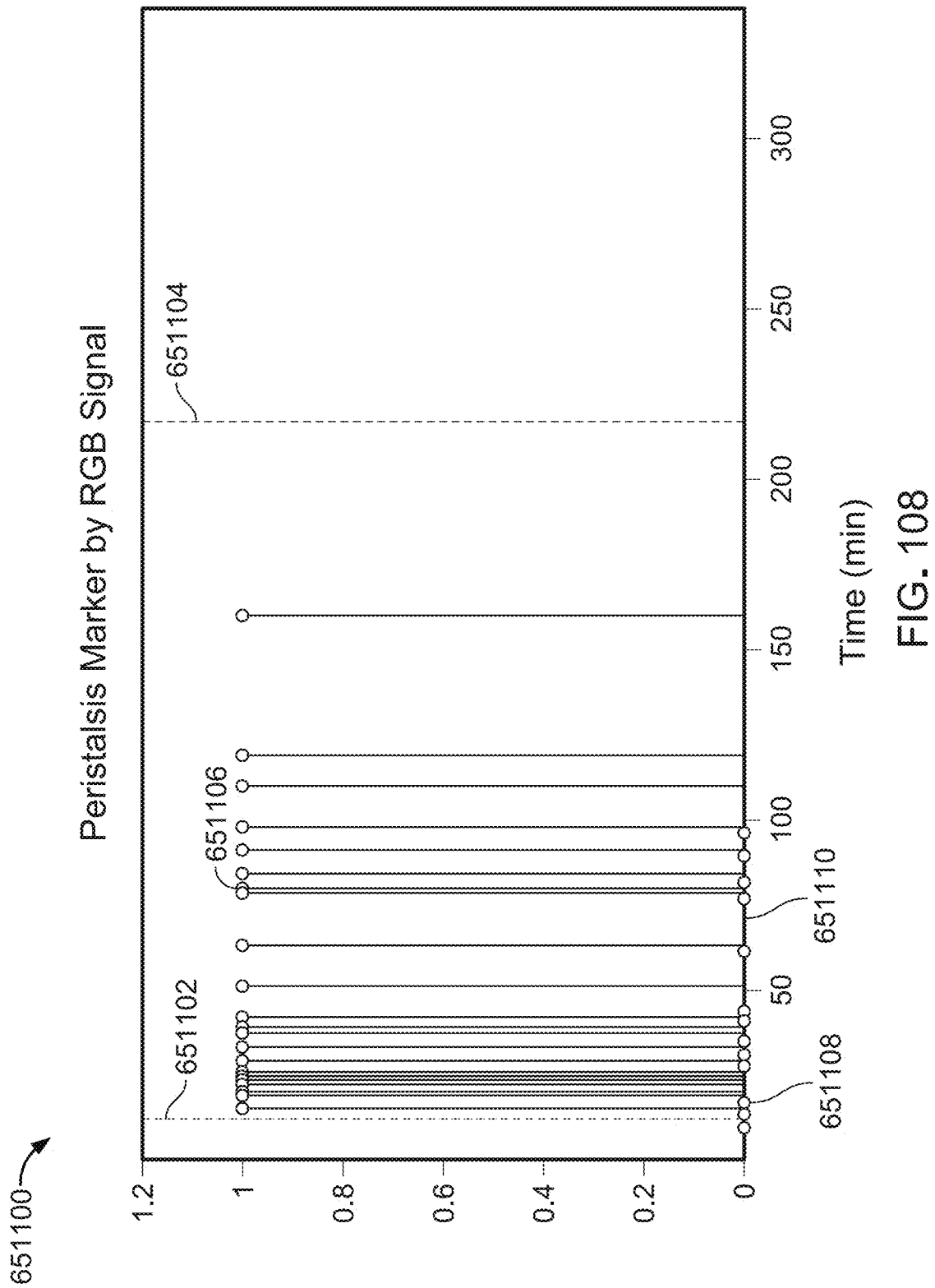

FIG. 108 is a plot illustrating muscle contractions detected by an ingestible device over time, which may be used when determining a location of an ingestible device as it transits through a gastrointestinal (GI) tract, in accordance with some embodiments of the disclosure. In some embodiments, ingestible device 65100 may be configured to detect muscle contractions, and store data indicative of when each muscle contraction is detected (e.g., as part of 65914 of process 65900). Plot 651100 depicts the detected muscle contractions 651106 over time, with each muscle contraction being represented by a vertical line reaching from "0" to "1" on the y-axis.

At 651102, around the 10-minute mark, ingestible device 65100 first enters the duodenum (e.g., as determined by ingestible device 65100 performing process 65600). Shortly thereafter, at 651108, ingestible device 65100 begins to detect several muscle contractions 651106 in quick succession, which may be indicative of the strong peristaltic waves that form in the jejunum (e.g., jejunum 65314). Later, around 651110, ingestible device 65100 continues to detect intermittent muscle contractions, which may be consistent with an ingestible device 65100 within the ileum. Finally, at 651104, ingestible device 65100 transitions out of the small intestine, and into the cecum. Notably, ingestible device 65100 detects more frequent muscle contractions in the jejunum portion of the small intestine as compared to the ileum portion of the small intestine, and ingestible device 65100 does not measure any muscle contractions after having exited the small intestine. In some embodiments, ingestible device 65100 may incorporate this information into a localization process. For example, ingestible device 65100 may be configured to detect a transition from a jejunum to an ileum in response to determining that a frequency of detected muscle contractions (e.g., the number of muscle contractions measured in a given 10-minute window) has fallen below a threshold number. As another example, ingestible device 65100 may be configured to detect a transition from an ileum to a cecum in response to determining that no muscle contractions have been detected for a threshold period of time. It is understood that these examples are intended to be illustrative, and not limiting, and that measurements of muscle contractions may be combined with any of the other processes, systems, or methods discussed in this disclosure.

Figure 109:
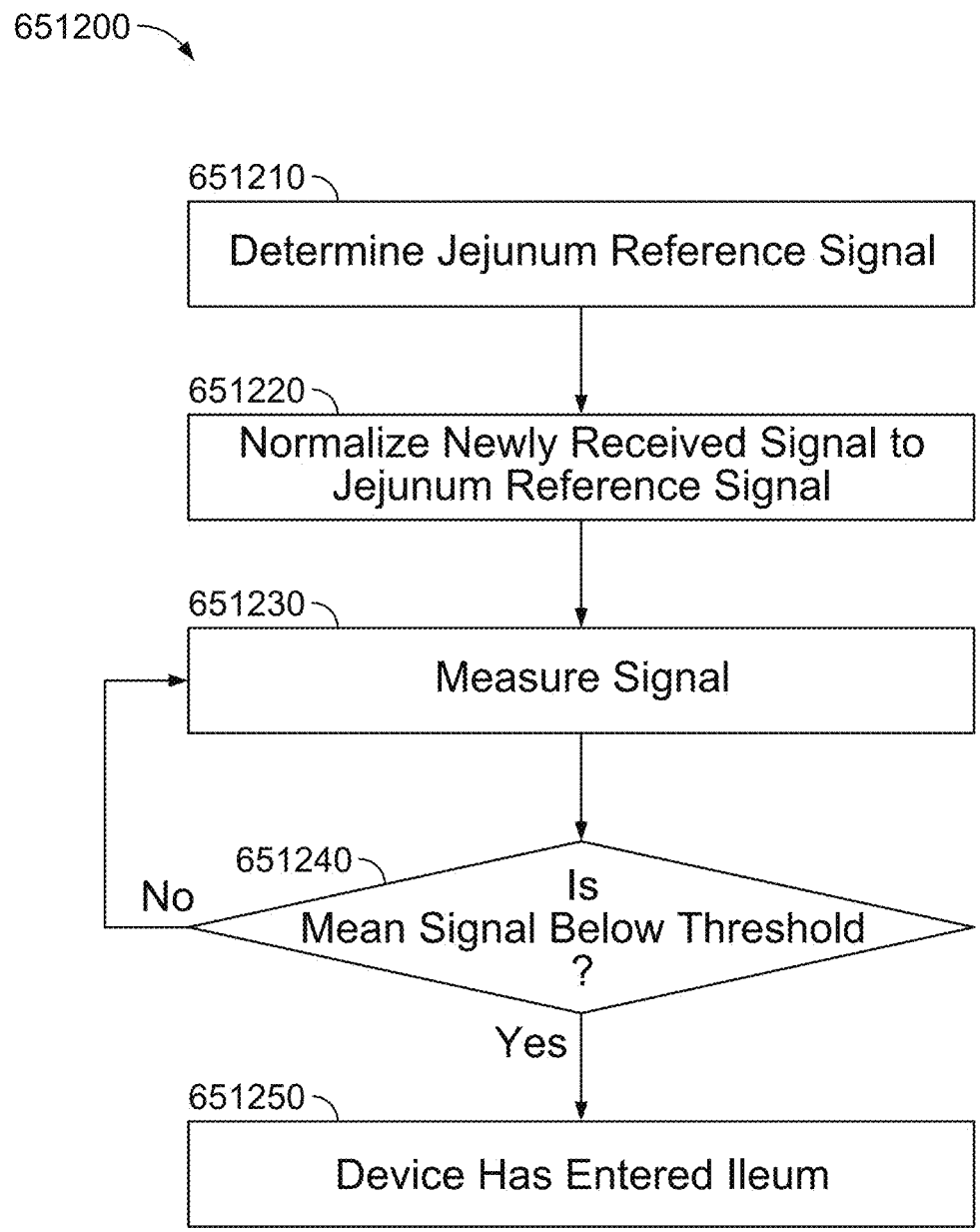

FIG. 109 is a flowchart 651200 for certain embodiments for determining a transition of the device from the jejunum to the ileum. It is to be noted that, in general, the jejunum is redder and more vascular than the ileum. Moreover, generally, in comparison to the ileum, the jejunum has a thicker intestine wall with more mesentery fat. These differences between the jejunum and the ileum are expected to result in differences in optical responses in the jejunum relative to the ileum. Optionally, one or more optical signals may be used to investigate the differences in optical responses. For example, the process can include monitoring a change in optical response in reflected red light, blue light, green light, ratio of red light to green light, ratio of red light to blue light, and/or ratio of green light to blue light. In some embodiments, reflected red light is detected in the process.

Flowchart 651200 represents a single sliding window process. In step 651210, the jejunum reference signal is determined based on optical reflection. Typically, this signal is as the average signal (e.g., reflected red light) over a period of time since the device was determined to enter the jejunum. The period of time can be, for example, from five minutes to 40 minutes (e.g., from 10 minutes to 30 minutes, from 15 minutes to 25 minutes). In step 651220, the detected signal (e.g., reflected red light) just after the period of time used in step 651210 is normalized to the reference signal determined in step 651210. In step 651230, the signal (e.g., reflected red light) is detected. In step 651240, the mean signal detected based on the single sliding window is compared to a signal threshold. The signal threshold in step 651240 is generally a fraction of the reference signal of the jejunum reference signal determined in step 651210. For example, the signal threshold can be from 60% to 90% (e.g., from 70% to 80%) of the jejunum reference signal. If the mean signal exceeds the signal threshold, then the process determines that the device has entered the ileum at step 651250. If the mean signal does not exceed the signal threshold, then the process returns to step 651230.

Figure 110:
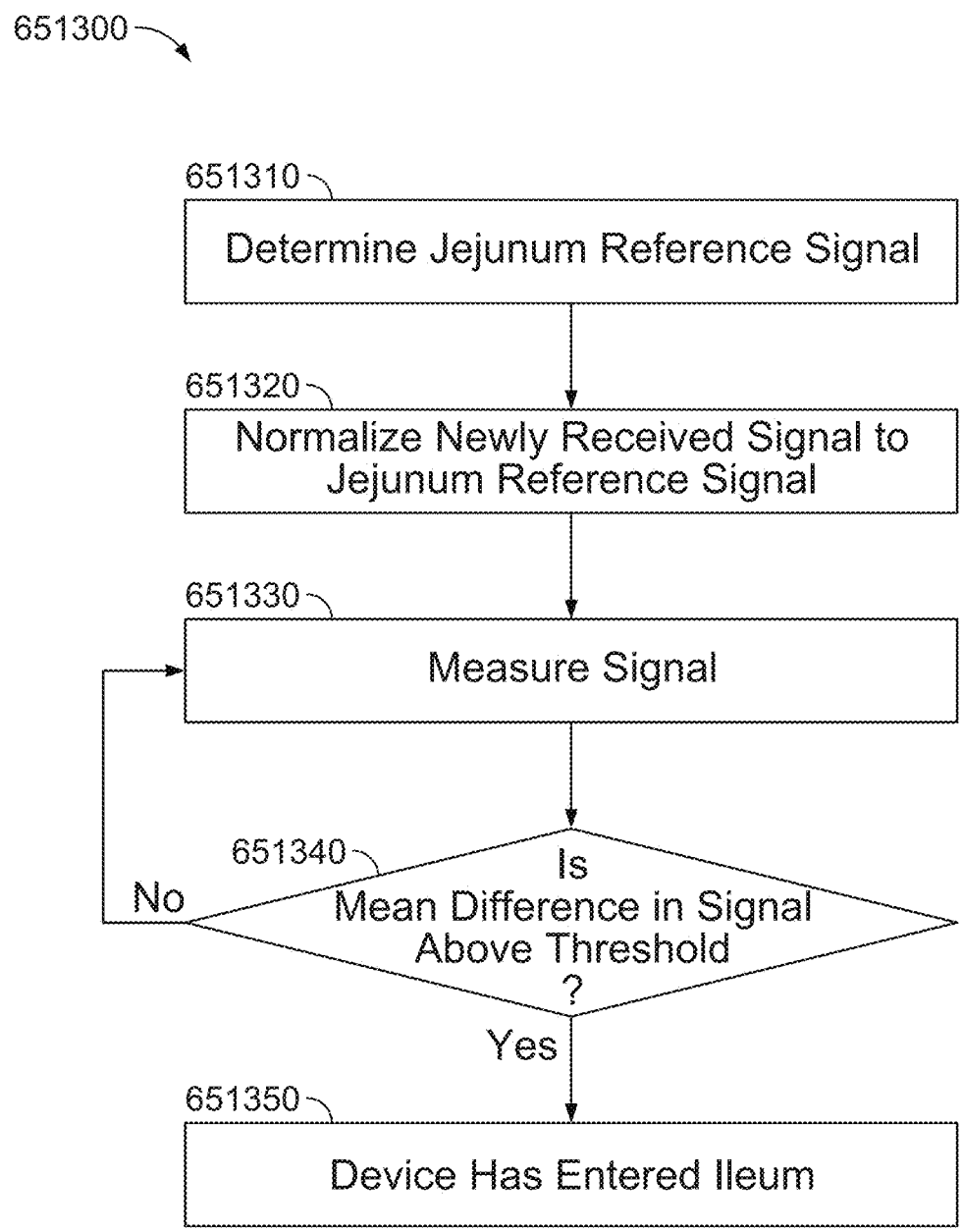

FIG. 110 is a flowchart 651200 for certain embodiments for determining a transition of the device from the jejunum to the ileum using a two sliding window process. In step 651310, the jejunum reference signal is determined based on optical reflection. Typically, this signal is as the average signal (e.g., reflected red light) over a period of time since the device was determined to enter the jejunum. The period of time can be, for example, from five minutes to 40 minutes (e.g., from 10 minutes to 30 minutes, from 15 minutes to 25 minutes). In step 651320, the detected signal (e.g., reflected red light) just after the period of time used in step 651310 is normalized to the reference signal determined in step 651310. In step 651330, the signal (e.g., reflected red light) is detected. In step 651340, the mean difference in the signal detected based on the two sliding windows is compared to a signal threshold. The signal threshold in step 651340 is based on whether the mean difference in the detected signal exceeds a multiple (e.g., from 1.5 times to five times, from two times to four times) of the detected signal of the first window. If signal threshold is exceeded, then the process determines that the device has entered the ileum at step 651350. If the signal threshold is not exceeded, then the process returns to step 651330.

Figure 111:
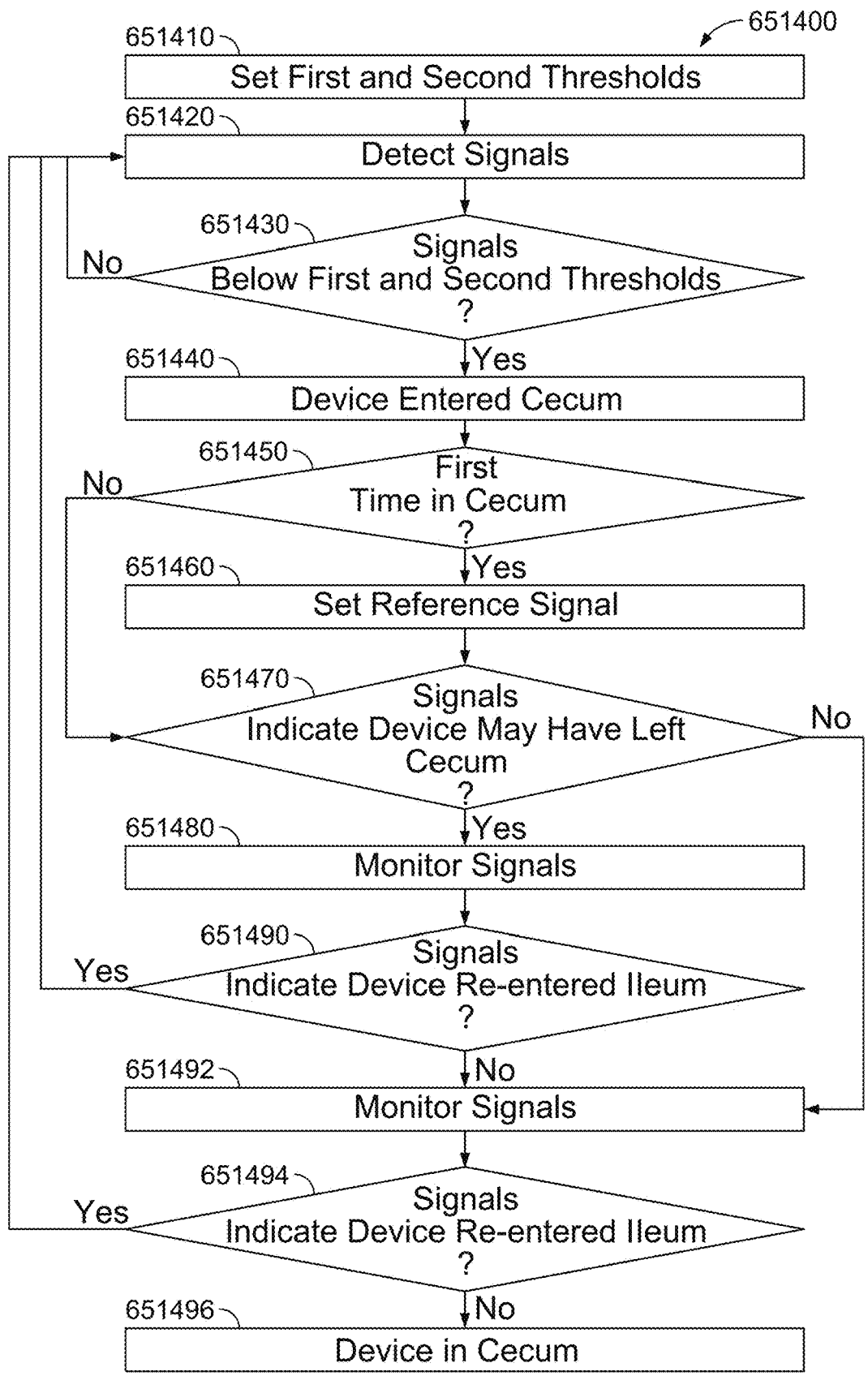

FIG. 111 is a flowchart 651400 for a process for certain embodiments for determining a transition of the device from the ileum to the cecum. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected green light to reflected blue light. Generally, in the process 651400, the sliding window analysis (first and second windows) discussed with respect to process 65600 is continued.

Step 651410 includes setting a first threshold in a detected signal, e.g., ratio of detected red light to detected green light, and setting a second threshold for the coefficient of variation for a detected signal, e.g., the coefficient of variation for the ratio of detected green light to detected blue light. The first threshold can be set to a fraction (e.g., from 0.5 to 0.9, from 0.6 to 0.8) of the average signal (e.g., ratio of detected red light to detected green light) in the first window, or a fraction (e.g., from 0.4 to 0.8, from 0.5 to 0.7) of the mean difference between the detected signal (e.g., ratio of detected red light to detected green light) in the two windows. The second threshold can be set to 0.1 (e.g., 0.05, 0.02).

Step 651420 includes detecting the signals in the first and second windows that are to be used for comparing to the first and second thresholds.

Step 651430 includes comparing the detected signals to the first and second thresholds. If the corresponding value is not below the first threshold or the corresponding value is not below the second threshold, then it is determined that the device has not left the ileum and entered the cecum, and the process returns to step 651420. If the corresponding value is below the first threshold and the corresponding value is below the second threshold, then it is determined that the device has left the ileum and entered the cecum, and the proceeds to step 651440.

Step 651450 includes determining whether it is the first time that that the device was determined to leave the ileum and enter the cecum. If it is the first time that the device was determined to leave the ileum and enter the cecum, then the process proceeds to step 651460. If it is not the first time that the device has left the ileum and entered the cecum, then the process proceeds to step 651470.

Step 651460 includes setting a reference signal. In this step the optical signal (e.g., ratio of detected red light to detected green light) as a reference signal.

Step 651470 includes determining whether the device may have left the cecum and returned to the ileum. The device is determined to have left the cecum and returned to the ileum if the corresponding detected signal (e.g., ratio of detected red light to detected green light) is statistically comparable to the reference signal (determined in step 651460) and the coefficient of variation for the corresponding detected signal (e.g., ratio of detected green light to detected blue light) exceeds the second threshold. If it is determined that the device may have left the cecum and returned to the ileum, the process proceeds to step 651480.

Step 651480 includes continuing to detect the relevant optical signals for a period of time (e.g., at least one minute, from five minutes to 15 minutes).

Step 651490 includes determining whether the signals determined in step 651480 indicate (using the methodology discussed in step 651470) that the device re-entered the ileum. If the signals indicate that the device re-entered the ileum, the process proceeds to step 651420. If the signals indicate that the device is in the cecum, the process proceeds to step 651492.

Step 651492 includes continuing to monitor the relevant optical signals for a period of time (e.g., at least 30 minutes, at least one hour, at least two hours).

Step 651494 includes determining whether the signals determined in step 651492 indicate (using the methodology discussed in step 651470) that the device re-entered the ileum. If the signals indicate that the device re-entered the ileum, the process proceeds to step 651420. If the signals indicate that the device is in the cecum, the process proceeds to step 651496.

At step 651496, the process determines that the device is in the cecum.

Figure 112:
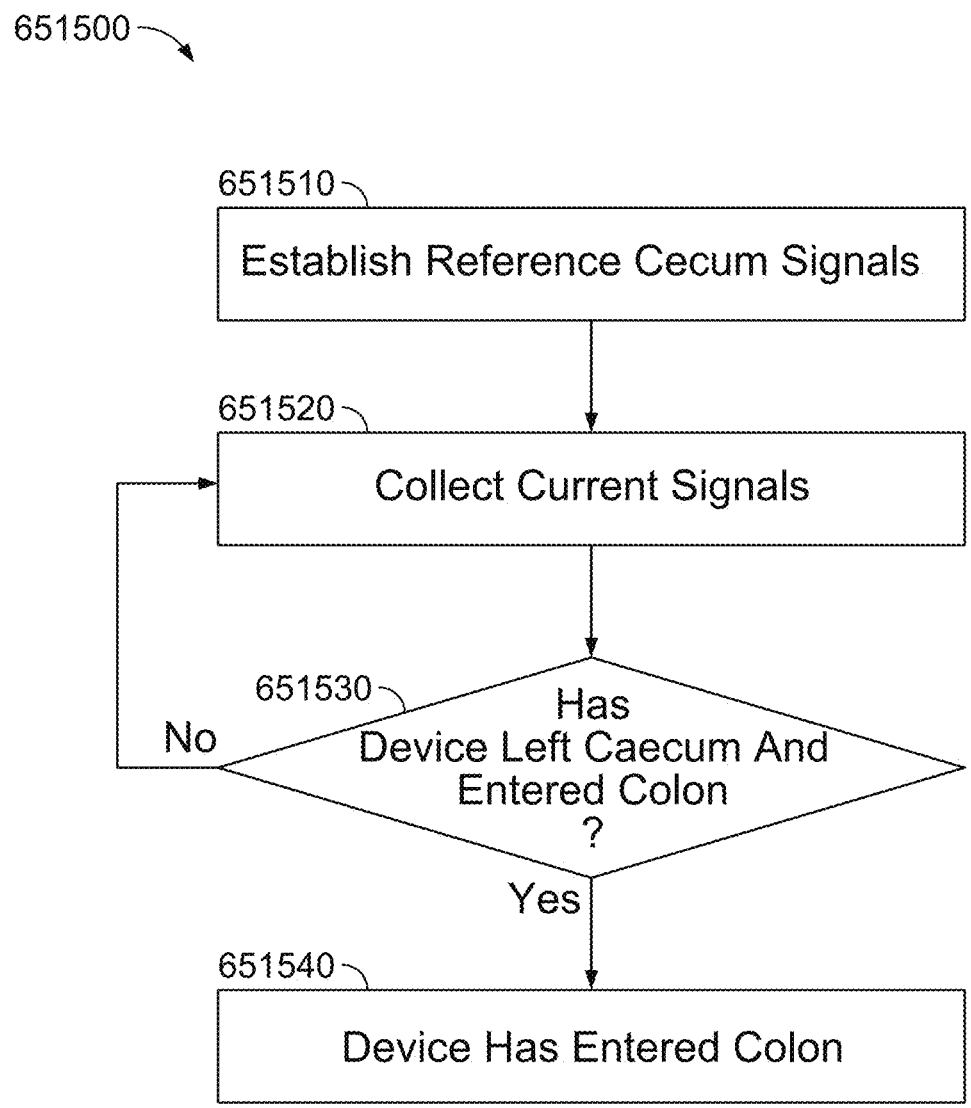
Figure 113:
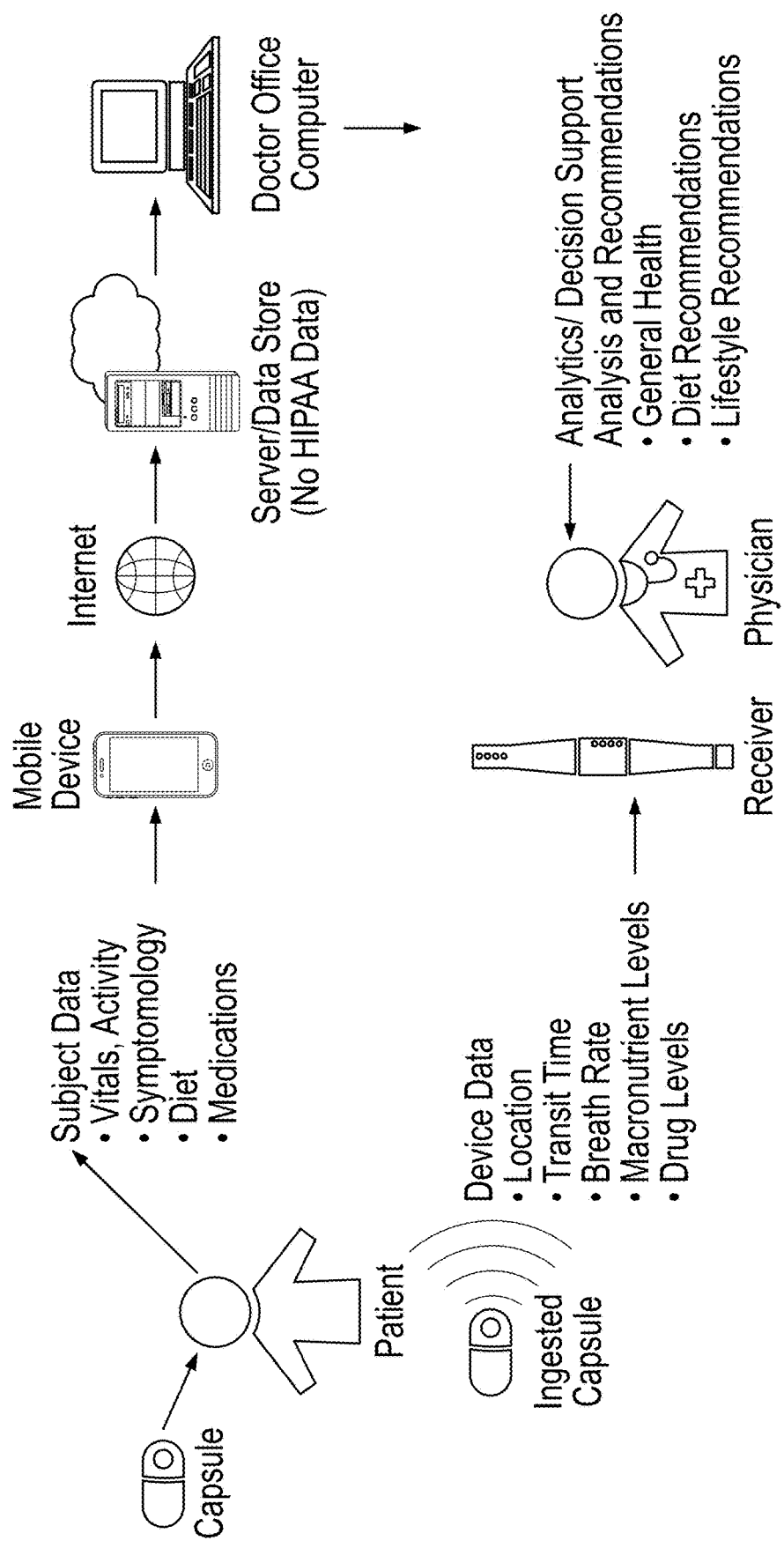

FIG. 112 is a flowchart 651500 for a process for certain embodiments for determining a transition of the device from the cecum to the colon. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected blue light. Generally, in the process 651500, the sliding window analysis (first and second windows) discussed with respect to process 651400 is continued.

In step 651510, optical signals (e.g., the ratio of reflected red signal to reflected green signal, and reflected blue signal) are collected for a period of time (e.g., at least one minute, at least five minutes, at least 10 minutes) while the device is in the cecum (e.g., during step 651480). The average values for the recorded optical signals (e.g., the ratio of reflected red signal to reflected green signal, and reflected blue signal) establish the cecum reference signals.

In step 651520, the optical signals are detected after it has been determined that the device entered the cecum (e.g., at step 651440). The optical signals are normalized to the cecum reference signals.

Step 651530 involves determining whether the device has entered the colon. This includes determining whether any of three different criteria are satisfied. The first criterion is satisfied if the mean difference in the ratio of a detected optical signal (e.g., ratio of detected red signal to the detected green) is a multiple greater than one (e.g., 2×, 3×, 4×) the standard deviation of the corresponding signal (e.g., ratio of detected red signal to the detected green) in the second window. The second criterion is satisfied if the mean of a detected optical signal (e.g., a ratio of detected red light to detected green light) exceeds a given value (e.g., exceeds one). The third criterion is satisfied if the coefficient of variation of an optical signal (e.g., detected blue light) in the first window exceeds a given value (e.g., exceeds 0.2). If any of the three criteria are satisfied, then the process proceeds to step 651540. Otherwise, none of the three criteria are satisfied, the process returns to step 651520.

For illustrative purposes the disclosure focuses primarily on a number of different example embodiments of an ingestible device, and example embodiments of methods for determining a location of an ingestible device within a GI tract. However, the possible ingestible devices that may be constructed are not limited to these embodiments, and variations in the shape and design may be made without significantly changing the functions and operations of the device. Similarly, the possible procedures for determining a location of the ingestible device within the GI tract are not limited to the specific procedures and embodiments discussed (e.g., process 65500, process 65600, process 65900, process 651200, process 651300, process 651400 and process 651500). Also, the applications of the ingestible devices described herein are not limited merely to gathering data, sampling and testing portions of the gastrointestinal tract, or delivering medicament. For example, in some embodiments the ingestible device may be adapted to include a number of chemical, electrical, or optical diagnostics for diagnosing a number of diseases. Similarly, a number of different sensors for measuring bodily phenomenon or other physiological qualities may be included on the ingestible device. For example, the ingestible device may be adapted to measure elevated levels of certain chemical compounds or impurities in the gastrointestinal tract, or the combination of localization, sampling, and appropriate diagnostic and assay techniques incorporated into a sampling chamber may be particularly well suited to determine the presence of small intestinal bacterial overgrowth (SIBO).

At least some of the elements of the various embodiments of the ingestible device described herein that are implemented via software (e.g., software executed by control circuitry within PCB 65120) may be written in a high-level procedural language such as object oriented programming, a scripting language or both. Accordingly, the program code may be written in C, $C^{++}$ or any other suitable programming language and may comprise modules or classes, as is known to those skilled in object oriented programming. Alternatively, or in addition, at least some of the elements of the embodiments of the ingestible device described herein that are implemented via software may be written in assembly language, machine language or firmware as needed. In either case, the language may be a compiled or an interpreted language.

At least some of the program code used to implement the ingestible device can be stored on a storage media or on a computer readable medium that is readable by a general or special purpose programmable computing device having a processor, an operating system and the associated hardware and software to implement the functionality of at least one of the embodiments described herein. The program code, when read by the computing device, configures the computing device to operate in a new, specific and predefined manner in order to perform at least one of the methods described herein.

Furthermore, at least some of the programs associated with the systems, devices, and methods of the example embodiments described herein are capable of being distributed in a computer program product comprising a computer readable medium that bears computer usable instructions for one or more processors. The medium may be provided in various forms, including non-transitory forms such as, but not limited to, one or more diskettes, compact discs, tapes, chips, and magnetic and electronic storage. In some embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The techniques described above can be implemented using software for execution on a computer. For instance, the software forms procedures in one or more computer programs that execute on one or more programmed or programmable computer systems (which may be of various architectures such as distributed, client/server, or grid) each including at least one processor, at least one data storage system (including volatile and non-volatile memory and/or storage elements), at least one input device or port, and at least one output device or port.

The software may be provided on a storage medium, such as a CD-ROM, readable by a general or special purpose programmable computer or delivered (encoded in a propagated signal) over a communication medium of a network to the computer where it is executed. All of the functions may be performed on a special purpose computer, or using special-purpose hardware, such as coprocessors. The software may be implemented in a distributed manner in which different parts of the computation specified by the software are performed by different computers. Each such computer program is preferably stored on or downloaded to a storage media or device (e.g., solid state memory or media, or magnetic or optical media) readable by a general or special purpose programmable computer, for configuring and operating the computer when the storage media or device is read by the computer system to perform the procedures described herein. The inventive system may also be considered to be implemented as a computer-readable storage medium, configured with a computer program, where the storage medium so configured causes a computer system to operate in a specific and predefined manner to perform the functions described herein.

For illustrative purposes the examples given herein focus primarily on a number of different example embodiments of an ingestible device. However, the possible ingestible devices that may be constructed are not limited to these embodiments, and variations in the general shape and design may be made without significantly changing the functions and operations of the device. For example, some embodiments of the ingestible device may feature a sampling chamber substantially towards the middle of the device, along with two sets of axial sensing sub-units, each located on substantially opposite ends of the device. In addition, the applications of the ingestible device are not limited merely to gathering data, sampling and testing portions of the gastrointestinal tract, or delivering medicament. For example, in some embodiments the ingestible device may be adapted to include a number of chemical, electrical, or optical diagnostics for diagnosing a number of diseases. Similarly, a number of different sensors for measuring bodily phenomenon or other physiological qualities may be included on the ingestible device. For example, the ingestible device may be adapted to measure elevated levels of certain analytes, chemical compounds or impurities in the gastrointestinal tract, or the combination of localization, sampling, and appropriate diagnostic and assay techniques incorporated into a sampling chamber may be particularly well suited to determine the presence of small intestinal bacterial overgrowth (SIBO). It is also noted that although embodiments described herein focus on an ingestible device in the GI tract, such ingestible device described in FIGS. 1-63 may be used for delivering substances including medicaments and therapeutics in other parts of the body, such as but not limited to the female reproductive tract, and/or the like.

The various embodiments of systems, processes and apparatuses have been described herein by way of example only. It is contemplated that the features and limitations described in any one embodiment may be applied to any other embodiment herein, and flowcharts or examples relating to one embodiment may be combined with any other embodiment in a suitable manner, done in different orders, or done in parallel. It should be noted, the systems and/or methods described above may be applied to, or used in accordance with, other systems and/or methods. Various modifications and variations may be made to these example embodiments without departing from the spirit and scope of the embodiments, which is limited only by the appended embodiments. The appended embodiments should be given the broadest interpretation consistent with the description as a whole.

Implementations of the subject matter and the operations described in this specification can be implemented by digital electronic circuitry, or via computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus.

A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, discs, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., a FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical discs, or optical discs. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic discs, e.g., internal hard discs or removable discs; magneto optical discs; and CD ROM and DVD-ROM discs. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Implementations of the subject matter described in this specification can be implemented in a computing system that includes a back end component, e.g., as a data server, or that includes a middleware component, e.g., an application server, or that includes a front end component, e.g., a user computer having a graphical display or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some implementations, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary implementations, and that such variations are intended to be encompassed by the present disclosure. It is recognized that features of the disclosed implementations can be incorporated into other disclosed implementations.

As noted above, an ingestible device may be configured to communicate with an external base station. For example, FIGS. 1 and 2 illustrate exemplary an ingestible device 10 having a communications unit 30 that communicates with base station 40 having a communications unit 30'. FIG. 113 illustrates exemplary implementation of such an ingestible device. As shown in FIG. 113, a subject ingests the capsule (e.g., an ingestible device as disclosed herein). Certain data about the subject (e.g., vitals, activity, symptomology, diet, medications) is collected or otherwise available and provided to a mobile device, which then forwards the data via the internet and a server/data store to a physician's office computer. The capsule collects data about the subject (e.g., location of the device in the GI tract, transit time of the device, breath rate, macronutrient level, drug level). The information collected by the capsule is communicated to a receiver, such as, for example, a watch or other object worn by the subject. The information is then communicated from the receiver to the mobile device which then forwards the data via the internet and a server/data store to a physician's office computer. The physician is then able to analyze some or all of the data about the subject to provide recommendations, such as, for example, general health recommendations, dietary health recommendations and/or lifestyle recommendations. While FIG. 113 shows a particular approach to collecting and transferring data about a subject, the disclosure is not limited. As an example, one or more of the receiver, mobile device, internet, and/or server/data store can be excluded from the data communication channel. For example, a mobile device can be used as the receiver of the device data, e.g., by using a dongle. In such embodiments, the item worn by the subject need not be part of the communication chain. As another example, one or more of the items in the data communication channel can be replaced with an alternative item. For example, rather than be provided to a physician's office computer, data may be provided to a service provider network, such as a hospital network, an HMO network, or the like. In some embodiments, subject data may be collected and/or stored in one location (e.g., a server/data store) while device data may be collected and/or stored in a different location (e.g., a different server/data store).

Moreover, one or more aspects of the foregoing disclosure may be combined with one or more aspects of the disclosure relating to FIGS. 114-134.

Figure 114:
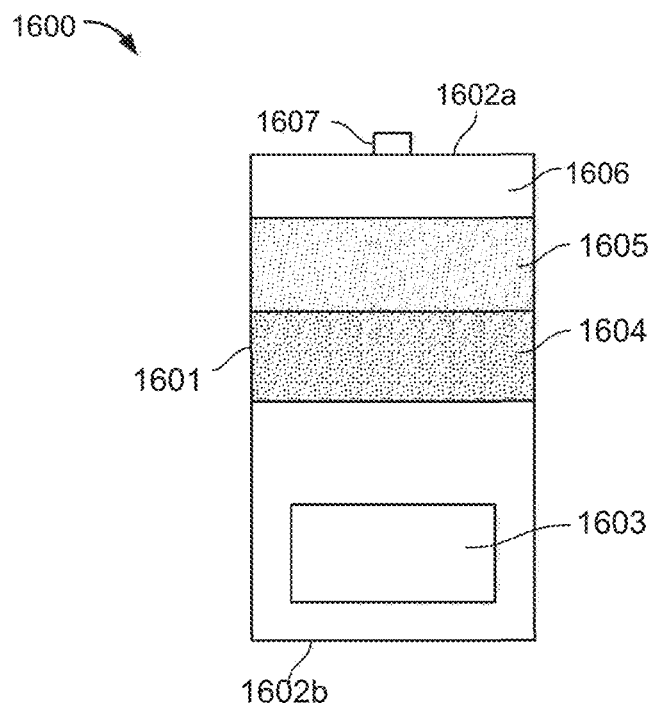

FIG. 114 provides an example mock-up diagram illustrating aspects of a structure of an ingestible device 1600 for delivering a dispensable substance, according to some embodiments described herein. In some embodiments, the ingestible device 1600 may generally be in the shape of a capsule, a pill or any swallowable form that may be orally consumed by an individual. In this way, the ingestible device 1600 may be ingested by a patient and may be prescribed by healthcare practitioners and patients.

The ingestible device 1600 includes a housing 1601 that may take a shape similar to a capsule, a pill, and/or the like, which may include two ends 1602*a*-*b*. The housing 1601 may be designed to withstand the chemical and mechanical environment of the GI tract (e.g., effects of muscle contractile forces and concentrated hydrochloric acid in the stomach). A broad range of materials that may be used for the housing 1601. Examples of these materials include, but are not limited to, thermoplastics, fluoropolymers, elastomers, stainless steel and glass complying with ISO 10993 and USP Class VI specifications for biocompatibility; and any other suitable materials and combinations thereof.

In some embodiment, the wall of the housing 1601 may have a thickness of 0.5 mm-1 mm, which is sufficient to sustain an internal explosion (e.g., caused by hydrogen ignition or over pressure inside the housing).

The housing 1601 may or may not have a pH-sensitive enteric coating to detect or otherwise be sensitive to a pH level of the environment external to the ingestible device. As discussed elsewhere in the application in more detail, the ingestible device 1600 may additionally or alternatively include one more sensors, e.g., temperature sensor, optical sense.

The housing 1601 may be formed by coupling two enclosure portions together. The ingestible device 1600 may include an electronic component within the housing 1600. The electronic component may be placed proximally to an end 1602*b* of the housing, and includes a printed circuit board (PCB), a battery, an optical sensing unit, and/or the like.

The ingestible device 1600 further includes a gas generating cell 1603 that is configured to generate gas and thus cause an internal pressure within the housing 1601. In some embodiments, the gas generating cell may include or be connected to a separate channel or valve of the ingestible device such that gas may be release through the channel or valve to create a motion to alter the position of the ingestible device within the GI tract. Such gas release can also be used to position the ingestible device relative to the intestinal lining. In another embodiment, gas may be released through the separate channel or valve to alter the surface orientation of the intestinal tissue prior to delivery of the dispensable substance.

A traveling plunger 1604 may be placed on top of the gas generating cell 1603 within the housing 1601. The traveling plunger 1604 is a membrane that separates the gas generating cell 1603 and a storage reservoir that stores the dispensable substance 1605. In some embodiments, the traveling plunger 1604 may be a movable piston. In some embodiments, the traveling plunger 1604 may instead be a flexible membrane such as but not limited to a diaphragm. In some embodiments, the traveling plunger 1604, which may have the form of a flexible diaphragm, may be placed along an axial direction of the housing 1601, instead of being placed on top of the gas generating cell 1603. The traveling plunger or the membrane 1604 may move (when the membrane 1604 is a piston) or deform (when the membrane 1604 is a diaphragm) towards a direction of the end 1602*a* of the housing, when the gas generating cell 1603 generates gas to create an internal pressure that pushes the membrane 1604. In this way, the membrane or traveling plunger 1604 may push the dispensable substance 1605 out of the housing via a dispensing outlet 1607.

The housing 1601 may include a storage reservoir storing one or more dispensable substances 1605 adjacent to the traveling plunger 1604. The dispensable substance 1605 may take the form of a powder, a compressed powder, a fluid, a semi-liquid gel, or any other dispensable or deliverable form. The delivery of the dispensable substance 1605 may take a form such as but not limited to bolus, semi-bolus, continuous, systemic, burst delivery, and/or the like.

In some embodiments, the storage reservoir may include multiple chambers, and each chamber stores a different dispensable substance. For example, the different dispensable substances can be released at the same time via the dispensing outlet 1607. Alternatively, the multiple chambers may take a form of different layers within the storage reservoir such that the different dispensable substance from each chamber is delivered sequentially in an order. In one example, each of the multiple chambers is controlled by a separate traveling plunger, which may be propelled by gas generation. The electronic component may control the gas generating cell 1603 to generate gas to propel a specific traveling plunger, e.g., via a separate gas generation chamber, etc., to delivery the respective substance. In some embodiments, the content of the multiple chambers may be mixed or combined prior to release.

The ingestible device 1600 may include a dispensing outlet 1607 at one end 1602*a* of the housing 1601 to direct the dispensable substance 105 out of the housing. The dispensing outlet 1607 may include an exit valve, a slit or a hole, a jet injection nozzle with a syringe, and/or the like. When the traveling plunger 1604 moves towards the end 1602*a* of the housing 1601, an internal pressure within the storage reservoir may increase and push the dispensing outlet to be open to let the dispensable substance 1605 be released out of the housing 1601.

In an embodiment, a pressure relief device 1606 may be placed within the housing 1601, e.g., at the end 1602*a* of the housing 1601.

In some embodiments, the housing 1601 may include small holes (e.g., with a diameter smaller than 2 mm), e.g., on the side of the housing 1601, or at the end 1602*a* to facilitate loading the dispensable substance into the storage reservoir.

In some embodiments, a feedback control circuit (e.g., a feedback resistor, etc.) may be added to send feedback from the gas generating cell 1603 to the electronic component such that when the internal pressure reaches a threshold level, the electronic component may control the gas generating cell 1603 to turn off gas generation, or to activate other safety mechanism (e.g., feedback-controlled release valve, etc.). For example, an internal pressure sensor may be used to measure the internal pressure within the ingestible device and generate feedback to the feedback control circuit.

Figure 115:
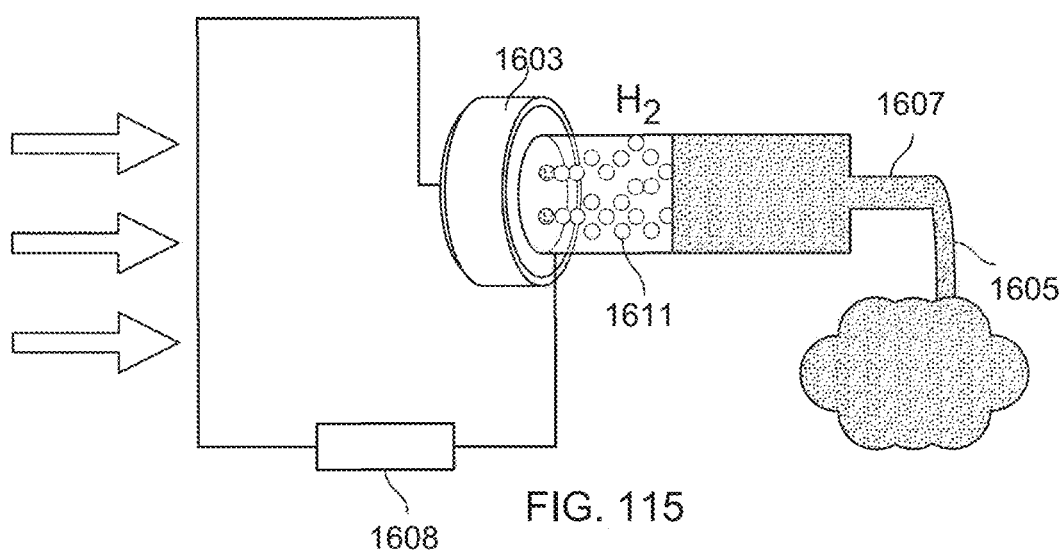

FIG. 115 provides an example diagram illustrating aspects of a mechanism for a gas generating cell 1603 configured to generate a gas to dispense a substance, according to some embodiments described herein. As shown in FIG. 115, the gas generating cell 1603 generates a gas 1611 which can propel the dispensable substance 1605 out of the dispensing outlet 1607. A variable resistor 1608 may be connected to a circuit with the gas generating cell 1603 such that the variable resistor 1608 may be used to control an intensity and/or an amount of gas 1611 (e.g., hydrogen) generated by the cell 1603. Specifically, the gas generating cell 1603 may be a battery form factor cell that is capable of generating hydrogen when a resistor is applied. In this way, as the gas generating cell 1603 only needs the use of a resistor only without any active power requirements, the gas generating cell 1603 may be integrated into an ingestible device such as a capsule with limited energy/power available. For example, the gas generating cell 1603 may be compatible with a capsule at a size of 26 mm×13 mm or smaller.

In some embodiments, based on the elution rate of gas from the cell, and an internal volume of the ingestible device, it may take time to generate sufficient gas 1611 to deliver the substance 1605, and the time required may be 30 seconds or longer. For example, the time to generate a volume of hydrogen equivalent to 500 μL of fluid would be approximately 5 minutes. A longer period of time may be needed based upon non-ideal conditions within the ingestible device, such as friction, etc. Thus, given that the production of gas (e.g., hydrogen) may take time, gas generation may need to start prior to the ingestible device arriving at the site of delivery to build pressure up within the device. The ingestible device may then need to know when it is approaching the site of delivery. For example, the device may start producing gas on an "entry transition," which is determined by temperature, so as to produce enough gas to be close to the pressure high enough to deliver the dispensable substance. The ingestible device may then only start producing gas again when it arrives at the site of delivery, which will cause the internal pressure within the ingestible device to reach a level required by the dispensing outlet to release the dispensable substance. Also, for regio-specific delivery, the ingestible device may estimate the time it takes to build up enough pressure to deliver the dispensable substance before the ingestible device arrives at a specific location, to activate gas generation.

Figure 116:
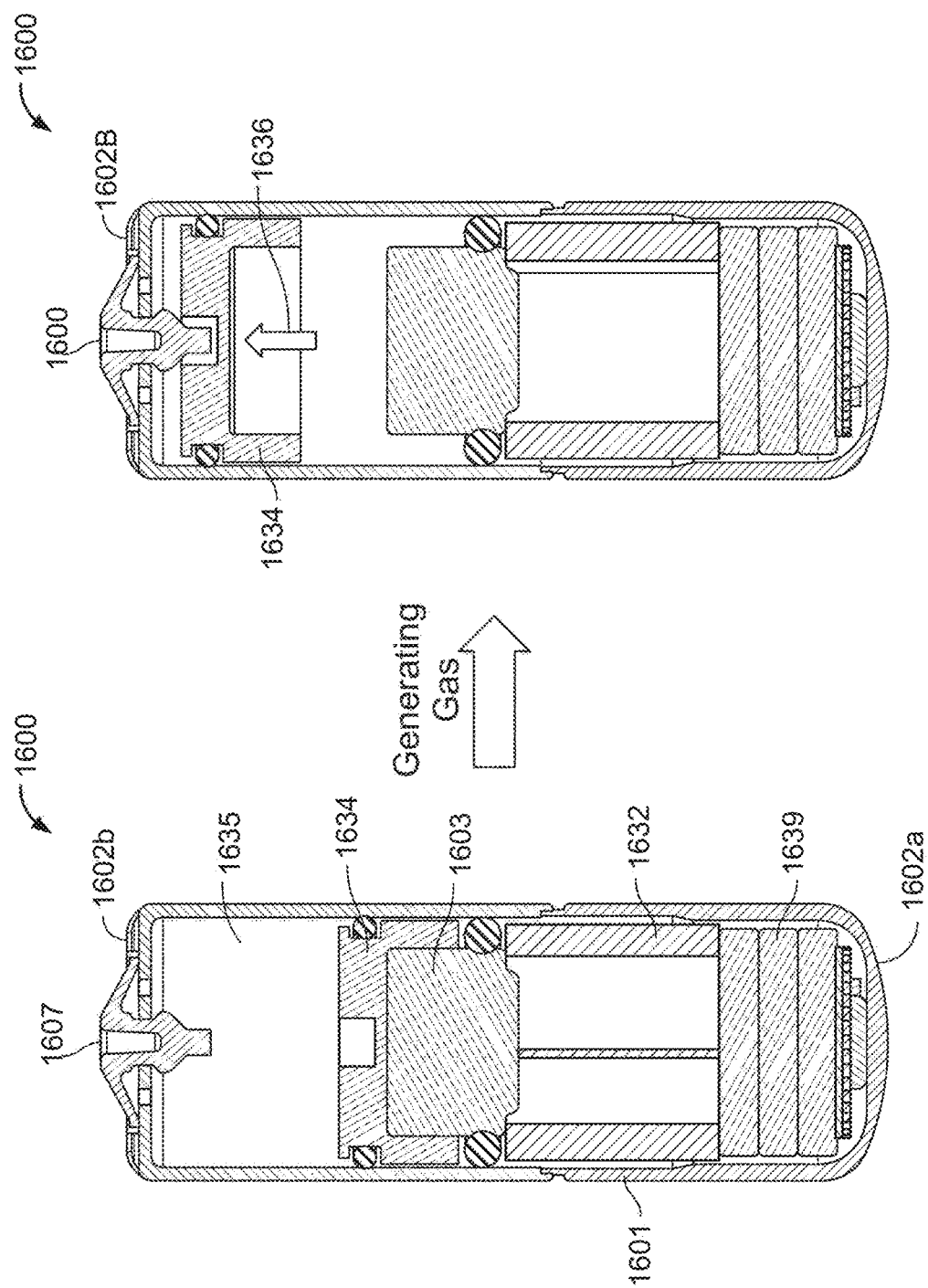
Figure 117:
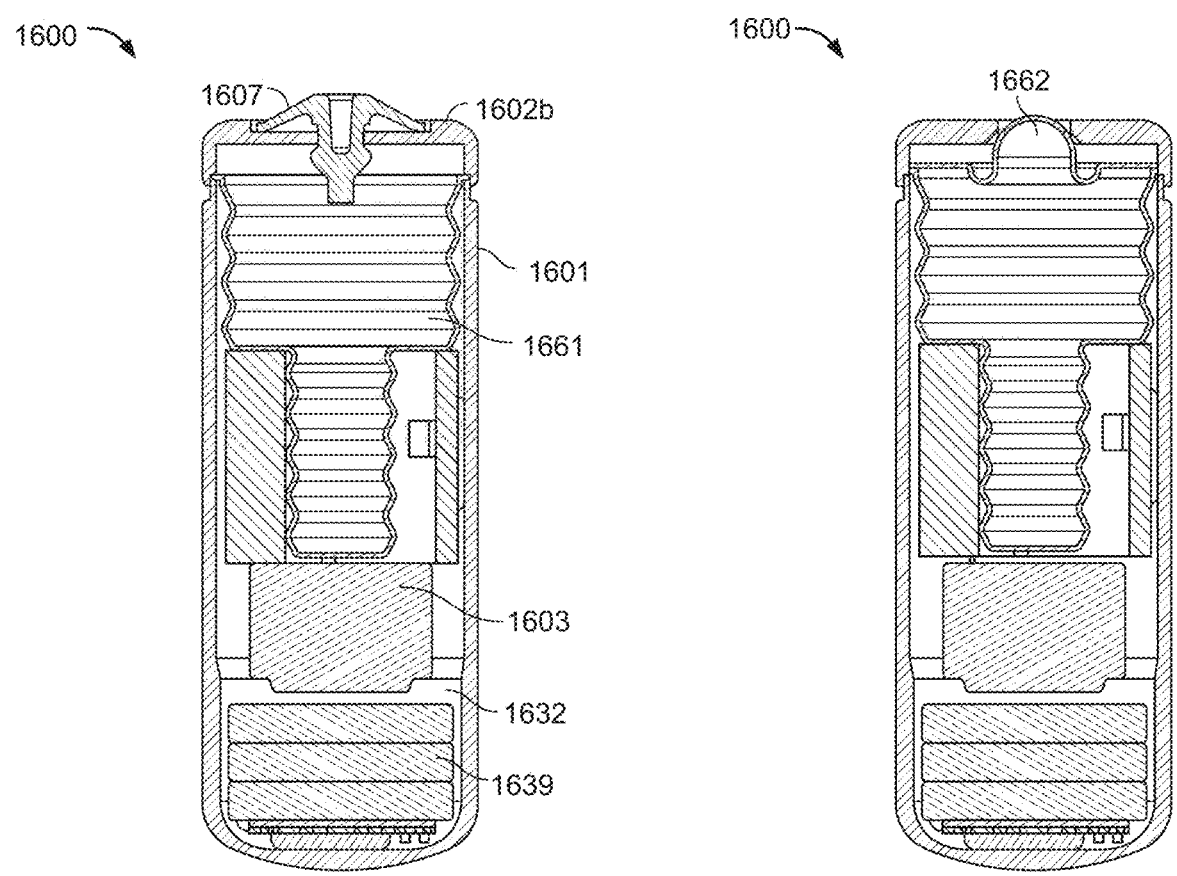

FIGS. 116 and 117, disclosed in U.S. Provisional Application No. 62/385,553, incorporated by reference herein in its entirety, illustrates an example of an ingestible device for localized delivery of a dispensable substance. The ingestible device 1600 includes a piston or drive element 1634 to push for substance delivery, in accordance with particular implementations described herein. The ingestible device 1600 may have one or more batteries 1639 placed at one end 1602a of a housing 1601 to provide power for the ingestible device 1600. A printed circuit board (PCB) 1632 may be placed adjacent to a battery or other power source 1639, and a gas generating cell 1603 may be mounted on or above the PCB 1632. The gas generating cell 1603 may be sealed from the bottom chamber (e.g., space including 1639 and 1632) of the ingestible device 1600. A movable piston 1634 may be placed adjacent to the gas generating cell 1603. In this way, gas generation from the gas generating cell 1603 may propel a piston 1634 to move towards another end 1602b of the housing 1601 such that the dispensable substance in a reservoir compartment 1635 can be pushed out of the housing through a dispensing outlet 1607, e.g., the movement is shown at 1636, with the piston 1634 at a position after dispensing the substance. The dispensing outlet 1607 may comprise a plug. The reservoir compartment 1635 can store the dispensable substance, or alternatively the reservoir compartment can house a storage reservoir 1661 which comprises the dispensable substance. The reservoir compartment 1635 or storage reservoir 1661 may have a volume of approximately 600 μL or even more dispensable substance, which may be dispensed in a single bolus, or gradually over a period of time.

FIGS. 119-121 provide example structural diagrams illustrating aspects of anchoring mechanisms of an ingestible device to anchor the ingestible device to the intestine for dispensable substance delivery. As shown in FIG. 119, the ingestible device 101100 can be anchored within the intestine by extending hooks 101203a-d from the ingestible device 101100 after it has entered the region of interest. At 101201, as the ingestible device 101100 travels along the GI tract, the hooks 101203a-d are contained within the ingestible device. At 101202, when the ingestible device 101100 determines it has arrived at a location within the GI tract, the hooks 101203a-d can be actuated to extend outside of the ingestible device 101100 to catch in the intestinal wall and hold the ingestible device 101100 in the respective location. The hooks 101203a-d can be oriented to catch the intestinal wall regardless of the instant orientation of the ingestible device 101100. The hooks 101203a-d can also retract, dissolve, or detach from the intestinal wall after the dispensable substance has been delivered at the anchored location.

As shown in FIG. 120, the hooks 101203a-d could also extend radially from the ingestible device, and pierce into the intestinal wall to hold the ingestible device 101100 in place. As shown in FIG. 121, if the extending hooks (e.g., 101203a-b) are hollow, the hooks can be used to both anchor the ingestible device and inject the dispensable substance into the intestinal wall.

FIG. 122 illustrates an ingestible device 4500 including a pre-pressurized actuator chamber 4503 and a sliding piston 4504, according to some embodiments described herein.

Ingestible device 4500 includes a device housing 4501. The device housing 4501 is composed of a cap portion 4502a and a base portion 4502b in the illustrated embodiments. Ingestible device 4500 also includes a pre-pressurized actuator chamber 4503 that is pressurized to a target pressure, for example during manufacture or via air fill port 4506 prior to ingestion. The capsule incorporates an active release mechanism that activates as the capsule reaches the target location. As the release mechanism activates, sliding piston 4504 will rapidly move to the left, pushing a high pressure jet of dispensable substance through the nozzle.

Depending on the material used to form the walls of the device housing 4501, the material could diffuse the compressed gas in the pre-pressurized actuator chamber 4503 over time, decreasing the internal pressure. To ensure that pressure is maintained in the ingestible device 4500 over a period between fabrication and patient use, packaging could be pressurized to equal the internal pressure of the pill in certain embodiments; therefore, preventing the permeation of compressed gas from the ingestible device 4500. Assuming the gas expansion within the capsule occurs very fast and an adiabatic polytropic process takes place, gas laws are used to correlate the initial and final pressure of the gas with its volume change ratio.

FIG. 123A illustrates a burst disc 4608 with an in line nozzle 4509. FIG. 123B illustrates a partial sectional view of a burst disc holder 4610, according to some embodiments described herein. A burst disc 4608 may enable the release of a dispensable substance, (for example from reservoir 4505) by purposefully fracturing at a targeted pressure allowing the dispensable substance to exit a nozzle 4509 to a target location within the GI tract. A burst disc 4608 can be used as the sole occlusion component in certain embodiments and can be used to provide isolation between upstream contamination and the dispensable substance payload in embodiments including another occlusion component. The burst disc 4608 can be held in place via clamped outer rings 4611 of disc holder 4610 as demonstrated in FIG. 123B.

FIG. 124 illustrates an ingestible device 4900 including a magnetic occlusion component 4908b, a burst disc 4608, and a pre-pressurized actuator chamber 4903, according to some embodiments described herein. FIG. 125 illustrates an ingestible device 5000 including a magnetic occlusion component, a pre-pressurized actuator chamber 4903 and a bioabsorbable plug 5008, according to some embodiments described herein. A magnetic stack (as shown FIG. 124 and FIG. 125), which upon peristaltic or osmotic pressure application releases pneumatic pressure, allowing for the delivery of a jet of dispensable substance through a conduit 4509. As shown by FIG. 124 and FIG. 125, osmotic pressure may be used to reconfigure the occlusion component that includes magnets 4908*a* and 4908*b* in FIGS. 124 and 125. The enteric coating 4908*c* dissolves when exposed to luminal fluid, exposing the membrane 4908*d* and osmogen 4908*e*. The membrane 4908*d* and osmogen 4908*e* facilitate the movement of liquid to create osmotic pressure on the magnet 4908*a*. As the osmotic pressure builds up, magnet 4908*a* will be pushed up in proximity to magnet 4908*b*. Magnet 4908*b* will be pulled down providing a flow through path for a gas from pressurized chamber 4905 to interact with the reservoir 4905 via connecting conduit 4911. The advantage of this system is that the mechanism may be completely sealed from the exterior of the capsule, allowing for pressure to only project into the chamber 4905. Note that an enteric coating/membrane stack 4908*c*, 4908*d* could be replaced by a method of leveraging peristalsis for pushing magnet 4908*a*. FIG. 124 is implemented with a burst disc 4608 as the sealing/release mechanism once the chamber 4905 is exposed to the pressurized chamber 4903. FIG. 125 is implemented with a bioabsorbable plug 5008 (e.g. enteric coating) that is dissolved and expelled once the reservoir 4905 is exposed to the pressurized actuator chamber 4903.

FIG. 126 illustrates an ingestible device 5100 including enteric sliding occlusion component 5102, a pre-pressurized actuator chamber 4903 and a sliding component 5108, according to some embodiments described herein. An osmotic drive 4908, including an enteric coating 5102 and semipermeable membrane 5104, is configured to move a sliding component 5108. The sliding component 5108, once pushed by the osmotic drive 4908, will allow a flow-through port 4911 to connect the pressurized actuator chamber 4903 to the reservoir 4905, providing dispensable substance delivery through the nozzle 5108.

FIG. 127 illustrates an ingestible device 5200 including dissolvable pin occlusion component, a chamber 5202, a pre-pressurized chamber 5204 and a sliding piston 5206, according to some embodiments described herein. In another embodiment, an enteric coating 5208*b* is dissolved, exposing a structural pin 5208*a* (such as a glucose spike or hydrogel) that dissolves in the presence of intestinal luminal fluid. With this design, as long as the pin 5208*a* is in place, the force exerted on the piston 5206 and the chamber 5202 is not large enough for the burst disk 4608 to rupture. The enteric coating 5208*b* and pin 5208*a* will dissolve as the capsule 5200 is ingested and as a result, the pressure force on the piston 5206 will increase. The full force of the pre-pressurized chamber 5204 translated onto the chamber 5202 via the piston 5206 is large enough to rupture the burst disk 4608. The rupture of the burst disk 4608 results in a pressurized jet of liquid being delivered from the chamber 5202 through the nozzle 4509.

FIG. 128 illustrates an ingestible device 5300 including wax plug 5308*a* with wire lead activators 5308*b*, according to some embodiments described herein. In this method, the dispensing site is identified based on collected reflected light. The reflectance of light in green and red spectrums (with iterations to this methodology and algorithm actively being pursued) are measured and an algorithm is used to correlate the measured reflectance with the location in the Gastrointestinal (GI) tract. This method provides a non-pH based system to determine the anatomical locations of the capsule during fasted transit. As the capsule 5300 reaches the target location, a signal is generated which will be used to activate an alternative release mechanism.

FIG. 129 illustrates an ingestible 5500 device including a spring actuator 5503 and a sliding piston 5504, according to some embodiments described herein. Ingestible device 5500 uses the potential energy stored in a spring 5503 when compressed as the driving or actuating mechanism for jet delivery of the dispensable substance. The occlusion component or release mechanism consists of bioabsorbable plug 5508*a* separated from the reservoir 5505 by a protectant layer 5508*b*. In this embodiment, the inner volume of the capsule 5500 is divided into two sections separated by a sliding piston 5504. The left section (e.g., reservoir 5505) is filled with dispensable substance and a spring 5503 is mounted in the right section. The piston 5504 can freely move to the right or left depending on the net force exerted on the piston 5504 (FIG. 129). An O-ring 5511 is used to provide the sealing required between the two sections, with alternative sealing means possible. Compressed spring 5503 applies a force on the piston 5504 and the piston 5504 transfers this force to the liquid dispensable substance in form of pressure. The same pressure will be transferred to the plug 5508*a* sealing the nozzle 5513. However, this pressure acts on a small area (area of the plug 5508*a*). Therefore, the large force exerted by the spring 5503 translates into a small force on the sealing plug 5508*a*. As the capsule 5500 is digested, it moves through GI tract and the bioabsorbable sealing plug 5508*a* will start dissolving. After certain amount of time, the plug will weaken or fully dissolve in GI fluid. As soon as the plug 5508*a* weakens to the design threshold, the pressure inside the reservoir 5503 drops, the spring 5503 will expand delivering dispensable substance (e.g., in the form of a high-pressure jet of fluid) through the opening.

FIG. 130 illustrates an ingestible device 5600 including a spring actuated slidable housing portion 5602*b*, according to some embodiments described herein. Ingestible device 5600 consists of a pressurized actuator 5603 chamber, a reservoir 5605 separated from the pressure actuator chamber 5603 by a deformable body 5604 such as bellows and a spring/enteric coating release mechanism The spring 5608*a* is mounted on the polycarbonate cap 5602*a* from one end and to a sliding cap 5602*b* on the other end (FIG. 130). The stainless steel top slider 5602*b* can slide to the left and right opening and closing the nozzle 5611. An enteric ring 5608*b* is used to keep the top slider closed. An O-ring and a bioabsorbable plug 5609 are used to provide the required sealing. An adhesive seal 5612 is located on the housing, on the opposite end of the capsule 5600 from the spring 5608*a*. Compressed gas applies a force on the bellows 5604 and the bellows 5604 transfer this force to the liquid dispensable substance in form of pressure. The same pressure will be transferred to the slider 5602*b* in form of a radial force. However, this pressure acts on a small area (area of the exit orifice 5607). Therefore, the transverse load on the slider 5602*b* is relatively small. When the capsule 5600 is assembled, the spring 5608*a* is compressed (slider 5602*b* in closed mode), and the enteric coating 5608*b* keeps the slider 5602*b* in position. As the capsule 5600 is digested, it moves through GI tract. The enteric coating 5608*b* will dissolve when the capsule 5600 passes through the intestinal fluid. With the dissolution of the enteric coating 5608*b*, the spring 5608*a* will push the slider 5602*b* back away from the capsule 5600 (open mode). As a result, the exit orifice 5607 becomes concentric with the nozzle 5611 and the jet of fluid will be released.

FIG. 131 illustrates an ingestible device 5700 with another spring actuated slidable housing portion 5712, according to some embodiments described herein. Ingestible device 5700 uses a compressed spring (spring 5703) as the drive mechanism and a compressed spring 5708a (spring with sliding top cap 5712 as the release mechanism. A piston 5704 separates the reservoir 5705 from the spring chamber and an enteric coating 5708b is used to initiate the release mechanism. An O-ring 5710 is used to provide sealing between the piston 5704 and cylinder. Compressed spring 5703 applies a force on the piston 5704 and the piston 5704 transfers this force to the liquid dispensable substance in the form of pressure. The same pressure will be transferred to the top cap slider 5712 in form of a radial force. However, this pressure acts on a small area (area of the exit orifice 5714) resulting in a small transverse force on the top slider 5712. When the capsule 5700 is assembled, spring 5703 is left in compressed mode (slider 5712 in closed position). As the capsule 5700 is digested, it moves through GI tract. The enteric coating 5708b will dissolve when the capsule 5700 passes through the intestinal fluid. With the dissolution of the enteric coating 5708b, the spring 5708a will push the slider 5712 back away from the capsule 5700 (open mode). As a result, the exit orifice 5714 becomes concentric with the nozzle 5716 and the jet of fluid will be released.

FIG. 132 illustrates an ingestible device 5800 including a melt away occlusion component 5808a and a pressurized chamber 5803, according to some embodiments described herein. Ingestible device 5800 consists of two chambers, one chamber is filled with dispensable substance and the other chamber is filled with pressurized gas. A wax valve 5808a actuated by localization board 5822 is used as the occlusion component. A large section of the pressure chamber 5803 is occupied by the release mechanism and the required batteries 5821. Wax valve wires 5808b are connected to the wax valve 5808a and will melt the wax using an electric current. The timing of this operation is controlled by the localization board 5822. In this embodiment, a fully controlled release mechanism is used. As the capsule 5800 reaches target area, the localization kit will activate and direct a predetermined electric current toward the wax valve 5808a. A heating element will receive this current and will melt or weaken the wax valve 5808a. With weakening or removal of the wax from the nozzle 5810, gas pressure from the pressurized chamber 5803 will push the bellows 5804 resulting in a pressurized jet of liquid dispensable substance exiting the nozzle 5810, thus delivering the dispensable substance.

FIG. 133 illustrates an ingestible device 5900 including a dissolvable pin occlusion component 5908 and a spring actuated sliding piston 5914, according to some embodiments described herein. One of the main challenges of designing an effective capsule is the sealing between the two chambers inside the capsule since there is a significant pressure difference between the two chambers, the dispensable substance tends to move from the dispensable substance chamber into the pressure or spring chamber. Certain embodiments address this by reducing the pressure difference between the two chambers during the shelf life and before jet delivery. For example, ingestible device 5900 includes a compressed spring 5903 is retained using a dissolvable pin 5908. Additionally, an O-ring 5912 is used to provide sealing between the piston 5914 and housing. With this design, as long as the pin 5908 is in place, there is no force exerted on the piston 5904 and the liquid in chamber 5906. The force exerted by the spring 5903 will result in shear stress on the pin 5908. The pin 5908 will dissolve as the capsule 5900 is ingested and as a result, the spring force will translate into a pressurized jet of liquid. An enteric coating on the ends of the pin 5908 could further enhance the specificity of the triggering location. During the shelf life and before ingestion of the capsule 5900, there is not a significant amount of pressure acting on the dispensable substance and consequently, sealing challenges are easier to address. With a 200-psi design pressure, the pin would be expected to hold approximately 20 lbf, and would involve design consideration to the shear strength of the dissolvable pin. As the capsule 5900 passes through the GI tract, the pin 5908 will start dissolving. As the pin 5908 dissolves, there is no support for the piston 5904 to keep the piston 5904 in place. The force of the spring 5903 will result in a significant pressure in the fluid. At a certain point the pin 5908 will fail and the piston 5904 will move to the left releasing a high-pressure jet of fluid through the nozzle 5910.

FIG. 134 illustrates an ingestible device 6000 including shuttle slider occlusion component 6012 and a pressurized chamber 6010, according to some embodiments described herein. Ingestible device 6000 includes two chambers separated by a wall 6002 made of polycarbonate. The right chamber is an adhesive seal 6028 and a pressurized chamber 6010, pressurized with gas, and a bellows 6006 is installed in the left chamber. There are no openings connecting the two chambers 6006, 6010. An osmotic release mechanism is used to connect the two chambers 6006, 6010 through a sliding valve 6012. As shown in FIG. 134, osmogen 6014 is contained within a small container below the sliding valve 6012. Osmogen 6014 is separated from the GI fluid by a water permeable membrane 6016 covered with enteric coating 6018. On the top of the osmogen 6014, a shuttle slider 6012 is mounted. The slider 6012 has an opening 6020 in the middle. The slider shuttle 6012 is sandwiched between two slabs of polycarbonate with a pressure through port 6022. When the slider shuttle 6012 is in closed form, the holes on the polycarbonate slabs are not concentric with the hole on the slider shuttle 6012. When the slider shuttle 6012 is in open mode, the holes of the slider and polycarbonate slabs surrounding it all will be concentric letting gas and pressure exchange between the two chambers 6006, 6010.

While the disclosure has been described with reference to what are presently considered to be the preferred examples, it is to be understood that the disclosure is not limited to the disclosed examples. On the contrary, the applicant's teachings described and illustrated herein encompass various alternatives, modifications, and equivalents, without departing from the embodiments described herein, the general scope of which is defined in the appended listing of embodiments.

What is claimed is:
1. A device, comprising:
   a spectrometer configured to generate spectral data of gastrointestinal (GI) tract tissue of a subject in vivo; and
   a processing unit configured to produce a GI tract tissue health profile for the GI tract tissue based on the spectral data,
   wherein the processing unit is configured:
   i) to access a plurality of reference spectra corresponding to tissue having a specific health condition or a specific oxygenation level; and
   ii) to compare the spectral data with the plurality of reference spectra to determine the health condition of the GI tract tissue, and
   wherein the device is an ingestible device and the comparison comprises:
   i) comparing a magnitude of one or more spectra produced from the spectral data with a magnitude of each reference spectrum within the plurality of reference spectra; and ii) identifying the health condition of the GI tract tissue by matching the magnitude of the acquired spectrum to the magnitude of a reference spectrum corresponding to tissue having a specific health condition.

2. The device of claim 1, wherein the spectrometer comprises a hyperspectral camera, and the spectral data comprise a hyperspectral image of the GI tract tissue.

3. The device of claim 2, wherein the hyperspectral camera is configured to use the hyperspectral image to produce one or more spectra corresponding to the tissue.

4. The device of claim 1, further comprising a communications unit configured to transmit data to and/or receive operating parameters from a base station.

5. The device of claim 1, wherein the processing unit is within the device.

6. The device of claim 1, wherein the device is configured to communicate with a processing unit within a base station that is external to the device.

7. The device of claim 1, wherein the device and/or the base station comprises memory configured to store the spectral data and/or the GI tract tissue health profile.

8. The device of claim 1, wherein the specific health condition comprises one or more of normal issue, inflamed tissue, scabbed tissue, and necrotic tissue.

9. The device of claim 1, wherein the specific health condition comprises a specific oxygenation level of the GI tract tissue.

10. The device of claim 9, wherein the oxygenation level is from about 1% to about 100%.

11. The device of claim 9, wherein the comparison comprises:
i) comparing a spectral feature of the one or more spectra with a spectral feature of each reference spectrum within the plurality of reference spectra; and
ii) identifying the oxygenation level of the GI tract tissue by matching the spectral features of the one or more spectra to the spectral features of a reference spectrum corresponding to tissue having a specific oxygenation level.

12. The device of claim 1, wherein the spectrometer is configured to acquire a spectrum corresponding to a GI tract tissue.

13. The device of claim 1, wherein the device is configured to generate the spectral data at a predetermined region within the GI tract of the subject.

14. The device of claim 1, wherein the device is operable to generate the spectral data at a plurality of time points as the device travels through the GI tract of the subject.

15. The device of claim 1, wherein the spectrometer is configured to generate at least one member selected from the group consisting of absorbance spectral data, transmission spectral data, reflectance spectral data, Fourier transform spectral data, and Raman spectral data.

16. The device of claim 1, wherein the device comprises a plurality of spectrometers configured to generate different types of spectral data.

17. The device of claim 1, wherein the spectrometer comprises a light source and a photodetector positioned on the exterior of the device.

18. The device of claim 1, wherein the light source is configured to transmit light radially towards an environment external to the device, and the photodetector is configured to detect a radial reflectance from the environment external to the device.

19. The device of claim 1, wherein the spectral data comprises at least one member selected from the group consisting of ultraviolet spectral data, visible spectral data, near-infrared (NIR) spectral data, and mid-infrared (MIR) spectral data.

20. The device of claim 1, wherein the spectrometer comprises a 2-dimensional array of photodetectors.

21. The device of claim 1, wherein the device further comprises one or more environmental sensors for measuring environmental data external to the device.

22. The device of claim 1, wherein the processing unit is configured to identify a location of the device within the GI tract of the subject based on the spectral data.

23. The device of claim 1, wherein the device is configured to attach to the GI tract of the subject in vivo.

24. A method, comprising:
using a spectrometer to generate in situ spectral data of a gastrointestinal (GI) tract of a subject; and
generating a GI tract tissue health profile for the subject based on the in situ spectral data of the GI tract tissue by:
accessing a plurality of reference spectra corresponding to tissue having a specific health condition or a specific oxygenation level; and
comparing the spectral data with the plurality of reference spectra to determine the health condition of the GI tract tissue by:
comparing a magnitude of one or more spectra produced from the spectral data with a magnitude of each reference spectrum within the plurality of reference spectra; and
identifying the health condition of the GI tract tissue by matching the magnitude of the acquired spectrum to the magnitude of a reference spectrum corresponding to tissue having a specific health condition,
wherein the spectral data indicate whether a bleed is present in the GI tract.

25. The method of claim 24, wherein the spectral data indicate whether hemoglobin and/or a red blood cell is present in the GI tract.

26. The method of claim 24, wherein the spectral data comprise wavelengths in a range of 400 nm to 680 nm.

27. The method of claim 24, wherein the spectral data comprise wavelengths in a range of 500 nm to 650 nm.

28. The method of claim 24, wherein the spectral data comprise wavelengths of 545 nm to 580 nm.

29. The method of claim 24, the spectral data indicate a concentration of blood in the GI tract of from 0 to 3.5%.

30. A device, comprising:
a spectrometer configured to generate spectral data of gastrointestinal (GI) tract tissue of a subject in vivo; and
a processing unit configured to determine, based on the spectral data, whether blood in meals is present in the GI tract by:
accessing a plurality of reference spectra corresponding to blood in meals being present in the GI tract; and
comparing the spectral data with the plurality of reference spectra to determine blood in meals being present in the GI tract by:
comparing a magnitude of one or more spectra produced from the spectral data with a magnitude of each reference spectrum within the plurality of reference spectra; and
identifying blood in meals being present in the GI tract by matching the magnitude of the acquired spectrum to the magnitude of a reference spectrum corresponding to to blood in meals being present in the GI tract,
wherein the device is an ingestible device.

31. The ingestible device of claim 30, wherein the processing unit is configured to determine whether hemoglobin is present in the GI tract based on features below 600 nm in the spectral data.

32. The ingestible device of claim 30, wherein the processing unit is configured to differentiate between oxygenated hemoglobin and deoxygenated hemoglobin based on features of from 600 nm to 1000 nm in the spectral data.

33. A device, comprising:
a spectrometer configured to generate spectral data of gastrointestinal (GI) tract tissue of a subject in vivo; and
a processing unit configured to produce a GI tract tissue health profile for the GI tract tissue based on the spectral data,
wherein the processing unit is configured:
  i) to access a plurality of reference spectra corresponding to tissue having a specific health condition or a specific oxygenation level; and
  ii) to compare the spectral data with the plurality of reference spectra to determine the health condition of the GI tract tissue, and
wherein the device is an ingestible device and determination of the health condition of the GI tract tissue comprises:
  i) determining coefficients of a linear combinations of the plurality of reference spectra that match one or more spectra produced from the spectral data; and
  ii) identifying the health condition of the GI tract tissue as a combination of health conditions corresponding to the determined coefficients.

34. A method, comprising:
using a spectrometer to generate in situ spectral data of a gastrointestinal (GI) tract of a subject; and
generating a GI tract tissue health profile for the subject based on the in situ spectral data of the GI tract tissue by:
  accessing a plurality of reference spectra corresponding to tissue having a specific health condition or a specific oxygenation level; and
  comparing the spectral data with the plurality of reference spectra to determine the health condition of the GI tract tissue by:
    determining coefficients of a linear combinations of the plurality of reference spectra that match one or more spectra produced from the spectral data; and
    identifying the health condition of the GI tract tissue as a combination of health conditions corresponding to the determined coefficients,
wherein the spectral data indicate whether a bleed is present in the GI tract.

35. A device, comprising:
a spectrometer configured to generate spectral data of gastrointestinal (GI) tract tissue of a subject in vivo; and
a processing unit configured to determine, based on the spectral data, whether blood in meals is present in the GI tract by:
  accessing a plurality of reference spectra corresponding to blood in meals being present in the GI tract; and
  comparing the spectral data with the plurality of reference spectra to determine blood in meals being present in the GI tract by:
    determining coefficients of a linear combinations of the plurality of reference spectra that match one or more spectra produced from the spectral data; and
    identifying the health condition of the GI tract tissue as a combination of health conditions corresponding to the determined coefficients,
wherein the device is an ingestible device.

* * * * *